United States Patent
Levin et al.

(10) Patent No.: US 8,242,072 B2
(45) Date of Patent: Aug. 14, 2012

(54) METHODS OF TREATING INFLAMMATION USING SOLUBLE IL-17RA/RC FUSION PROTEINS

(75) Inventors: Steven D. Levin, Seattle, WA (US); Mark W. Rixon, Issaquah, WA (US); Zeren Gao, Redmond, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 13/293,384

(22) Filed: Nov. 10, 2011

(65) Prior Publication Data

US 2012/0082668 A1 Apr. 5, 2012

Related U.S. Application Data

(62) Division of application No. 12/828,041, filed on Jun. 30, 2010, now Pat. No. 8,084,231, which is a division of application No. 12/055,597, filed on Mar. 26, 2008, now Pat. No. 7,790,676.

(60) Provisional application No. 60/908,554, filed on Mar. 28, 2007, provisional application No. 60/983,822, filed on Oct. 30, 2007.

(51) Int. Cl.
*A61K 38/00* (2006.01)

(52) U.S. Cl. ...... 514/1.1; 530/350; 530/351; 530/387.3; 435/69.7

(58) Field of Classification Search .................. None
See application file for complete search history.

(56) References Cited

U.S. PATENT DOCUMENTS

| | | | |
|---|---|---|---|
| 5,684,032 A | 11/1997 | Elliott et al. | |
| 6,072,033 A * | 6/2000 | Yao et al. ................ | 530/350 |
| 6,569,645 B2 | 5/2003 | Chen et al. | |
| 6,579,520 B2 | 6/2003 | Chen et al. | |
| 7,115,398 B2 | 10/2006 | Chen et al. | |
| 7,247,442 B1 | 7/2007 | Ruben et al. | |
| 7,619,071 B2 | 11/2009 | Presnell et al. | |
| 7,622,116 B2 | 11/2009 | Kuestner et al. | |
| 7,790,676 B2 | 9/2010 | Levin et al. | |
| 7,842,665 B2 | 11/2010 | Levin et al. | |
| 7,910,540 B2 | 3/2011 | Levin et al. | |
| 7,910,701 B2 | 3/2011 | Presnell et al. | |
| 8,084,231 B2 | 12/2011 | Levin et al. | |
| 8,093,355 B2 | 1/2012 | Kuestner et al. | |
| 2002/0119130 A1 | 8/2002 | Eaton et al. | |
| 2002/0177188 A1 | 11/2002 | Chen et al. | |
| 2002/0182673 A1 | 12/2002 | Chen et al. | |
| 2003/0008815 A1 | 1/2003 | Chen et al. | |
| 2003/0040471 A1 | 2/2003 | Watson et al. | |
| 2003/0046196 A1 | 3/2003 | Kelly | |
| 2003/0073623 A1 | 4/2003 | Drmanac et al. | |
| 2003/0092881 A1 | 5/2003 | Gorman | |
| 2003/0100051 A1 | 5/2003 | Ruben et al. | |
| 2003/0180857 A1 | 9/2003 | Eaton et al. | |
| 2003/0181669 A1 | 9/2003 | Eaton et al. | |
| 2003/0199041 A1 | 10/2003 | Presnell et al. | |
| 2003/0203451 A1 * | 10/2003 | Chen et al. ................ | 435/69.1 |
| 2004/0009479 A1 | 1/2004 | Wohlgemuth et al. | |
| 2004/0048249 A1 | 3/2004 | Tang et al. | |
| 2004/0091959 A1 | 5/2004 | Baker et al. | |
| 2004/0097447 A1 | 5/2004 | Dobie | |
| 2006/0002925 A1 | 1/2006 | Presnell et al. | |
| 2007/0036763 A1 | 2/2007 | Presnell et al. | |
| 2007/0036791 A1 | 2/2007 | Presnell et al. | |
| 2007/0037968 A1 | 2/2007 | Presnell et al. | |
| 2007/0048257 A1 | 3/2007 | Presnell et al. | |
| 2007/0048824 A1 | 3/2007 | Presnell et al. | |
| 2007/0048826 A1 | 3/2007 | Presnell et al. | |
| 2007/0238658 A1 | 10/2007 | Levin et al. | |
| 2007/0249533 A1 | 10/2007 | Levin et al. | |

OTHER PUBLICATIONS

Yao, Zhengbin et al., "Human IL-17: A Novel Cytokine Derived from T Cells," The Journal of Immunology, vol. 155:5483-5486 (1995).
Yao, Zhengbin et al., "Molecular Characterization of the Human Interleukin (IL)-17 Receptor," Cytokine, vol. 9 (11):794-800 (1997).
Ye, Peng et al., "Interleukin-17 and Lung Host Defense against *Klebsiella pneumoniae* Infection," Am. J. Respir. Cell Mol. Biol., vol. 25:335-340 (2001).
Zabarovsky, E. et al., "Shot-gun sequencing strategy for long range genome mapping: first results," Accession No. Z22374 (1995).
Zabarovsky, E. et al., "Shot-gun sequencing strategy for long range genome mapping first results," Accession No. Z22384 (1995).

* cited by examiner

*Primary Examiner* — Dong Jiang
(74) *Attorney, Agent, or Firm* — Nelson Mullins Riley & Scarborough LLP; Jane E. Remillard, Esq.; Jill Gorny Sloper, Esq.

(57) ABSTRACT

Disclosed are antagonists of IL-17A and IL-17F. The antagonists are based on soluble IL-17RA and IL-17RC fusion proteins, including hybrid soluble receptors comprising portions of both IL-17RC and IL-17RA ("IL-17RC/IL-17RA"). Such antagonists serve to block, inhibit, reduce, antagonize or neutralize the activity of IL-17F, IL-17A, or both IL-17A and IL-17F. Also disclosed are methods of using such antagonists for treating disease, particularly inflammatory diseases mediated at least in part by IL-17A and/or IL-17F.

14 Claims, 9 Drawing Sheets

```
                                10                   20        25
IL17RCx1   M P V P W F L L S L A L G R S P V V L S L E R L V
                     Signal sequence           exon 1

IL17RCx1   G P Q D A T H C S P | G L S C R L W | D S D I L C L P
                                      exon 2

IL17RCx1   G D I V P A P G P V L A P T H L Q T E L V L R C Q
                                  exon 3

100
IL17RCx1   K E T D C D L C L R V A V H L A V H | G H W E E P E

IL17RCx1   D E E K F G G A A D S G V E E P R N | A S L Q A Q V
                                  exon 4

IL17RCx1   V L S F Q A Y P T A R C V L L E V Q V P A A L V Q
                                  exon 5

IL17RCx1   F G Q S V | G S V V Y D C F E A A L G S E V R I W S
                                  exon 6 exon 7 (spliced out)
                                              ▼
IL17RCx1   Y T Q P R Y E K E L N H T Q Q L P | A L P W L N V S
                                                   exon 8

IL17RCx1   A D G D N V H L V L N V S E E Q H F G L S L Y W N

IL17RCx1   Q V Q G P P K P R W H K N L | T G P Q I I T L N H T
                                            exon 9

IL17RCx1   D L V P C L C I Q | V W P L E P D S V R T N I C P F
                                   exon 10

IL17RCx1   R | E D P R A H Q N L W Q A A R L R L L T L Q S W L

IL17RCx1   L D A P C S L P A E A A L C W R A P G G D P C Q P
                                  exon 11

IL17RCx1   L V P P L S W E N V T V D | K V L E F P L L K G H P
                                           exon 12
```

Figure 1A

```
IL17RCx1  N L C V Q|V N S S E K L Q L Q E C L W A|D S L G P
                                  exon 13

IL17RCx1  L K D D V L L E T R G P Q D N R S L C A L E P S
                                  exon 14

IL17RCx1  G C T S L P S K A S T|R A A R L G E Y L L Q D L Q
                                  exon 15

IL17RCx1  S G Q C L Q|L W D D D L G A L W A C P M D K|Y I H
                                  exon 16

IL17RCx1  K R  W A L V W L A C L L F A A A L S L L L L L  K K
                         TMD         exon 17 exon 18 (spliced out)
                     ▼
IL17RCx1  D H A K|A A A R G R A A L L L Y S A D D S G F E R IL17RCx1  L V G A L A S A L C Q L P L R V A V D L W S R R E IL17RCx1  L S A Q G P V A W F H A Q R R Q T L Q E G G V V V IL17RCx1  L L F S P G A V A L C S E W L Q D G V S G P G A H
                                  exon 19

IL17RCx1  G P H D A F R A S L S C V L P D F L Q G R A P G S

IL17RCx1  Y V G A C F D R L L H P D A V P A L F R T V P V F

IL17RCx1  T L P S Q L P D F L G A L Q Q P R A P R S G R L Q

IL17RCx1  E R A E Q V S R A L Q P A L D S Y F H P P G T P A

IL17RCx1  P G R G V G P G A G P G A G D G T
```

Figure 1B

```
                      10                  20        25
IL17RCx4    M P V P W F L L S L A L G R S P V V L S L E R L V
                  Signal sequence             exon 1

IL17RCx4    G P Q D A T H C S P│G L S C R L W│D S D I L C L P
                                    exon 2

IL17RCx4    G D I V P A P G P V L A P T H L Q T E L V L R C Q
                                    exon 3
                                                          100
IL17RCx4    K E T D C D L C L R V A V H L A V H│G H W E E P E IL17RCx4    D E E K F G G A A D S G V E E P R N│A S L Q A Q V
                                    exon 4

IL17RCx4    V L S F Q A Y P T A R C V L L E V Q V P A A L V Q
                                    exon 5

IL17RCx4    F G Q S V│G S V V Y D C F E A A L G S E V R I W S
                                    exon 6
                                                          200
IL17RCx4    Y T Q P R Y E K E L N H T Q Q L P│D C R G L E V W 215
IL17RCx4    N S I P S C W│A L P W L N V S
            exon 7
                                                          240
IL17RCx4    A D G D N V H L V L N V S E E Q H F G L S L Y W N
                                    exon 8
                                          265
IL17RCx4    Q V Q G P P K P R W H K N L│T G P Q I I T L N H T
                                  │ exon 9
                                                          290
IL17RCx4    D L V P C L C I Q│V W P L E P D S V R T N I C P F
                                    exon 10

315
IL17RCx4    R│E D P R A H Q N L W Q A A R L R L L T L Q S W L

340
IL17RCx4    L D A P C S L P A E A A L C W R A P G G D P C Q P
                                    exon 11
```

Figure 2A

```
                                        |                              365
IL17RCx4    L V P P L S W E N V T V D K V L E F P L L K G H P
                                        |      exon 12

|                               |       390
IL17RCx4    N L C V Q V N S S E K L Q L Q E C L W A D S L G P
                      |          exon 13              |
                                                              415
IL17RCx4    L K D D V L L L E T R G P Q D N R S L C A L E P S
                              exon 14

|                           440
IL17RCx4    G C T S L P S K A S T R A A R L G E Y L L Q D L Q
                                  | exon 15

|                                 |     465
IL17RCx4    S G Q C L Q L W D D D L G A L W A C P M D K Y I H
                      |          exon 16                |
                                                              490
IL17RCx4    K R W A L V W L A C I I P A A A L S L I L L L K K
                   TMB              exon 17 exon 18
               ▼                                              515
IL17RCx4    D H A K A A A R G R A A L L L Y S A D D S G F E R
                  |

IL17RCx4    L V G A L A S A L C Q L P L R V A V D L W S R R E

IL17RCx4    L S A Q G P V A W F H A Q R R Q T L Q E G G V V V

IL17RCx4    L L F S P G A V A L C S E W L Q D G V S G P G A H
                              exon 19

IL17RCx4    G P H D A F R A S L S C V L P D F L Q G R A P G S

IL17RCx4    Y V G A C F D R L L H P D A V P A L F R T V P V F

IL17RCx4    T L P S Q L P D F L G A L Q Q P R A P R S G R L Q

IL17RCx4    E R A E Q V S R A L Q P A L D S Y F H P P G T P A
                                                   707
IL17RCx4    P G R G V G P G A G P G A G D G T
```

Figure 2B

```
                        10                  20        25
IL17RA    M G A A R S P P S A V P G P L L G L L L L L L G V
                         Signal Sequence IL17RA    L A P G G A S L R L L D H R A L V C S Q P|G L N C
                              exon 1              | exon 2

IL17RA    T V K N|S T C L D D S W I H P R N L T P S S P K D
                 |
                                                        100
IL17RA    L Q I Q L H F A H T Q Q G D L F P V A H I E W T L
                              exon 3

IL17RA    Q T D|A S I L Y L E G A E L S V L Q L N T N E R L
                              exon 4

IL17RA    C V R F E F L S K L R H H H R R|W R F T F S H F V

IL17RA    V D P D Q E Y E V T V H H L P K P I P D G D P N H
                              exon 5
                                                        200
IL17RA    Q S K N F L V P|D C E H A R M K V T T P C M S S|G
                         |    exon 6                    |

IL17RA    S L W D P N I T V E T L E A H Q L R V S F T L W N
                              exon 7

IL17RA    E S T H Y Q I L L T S F P H M E N H S C F E H M H

IL17RA    H I P A|P R P E E F H Q R S N V T L T L R N L K G
                              exon 8
                                                        300
IL17RA    C C R H Q V Q|I Q P F F S S C L N D C L R H S A T
                              exon 9

IL17RA    V S C P E M P D T P|E P I P D Y M P L W . . . . .
                             |    exon 10           TMD
```

Figure 3

```
                         10                    20        25
IL17RA     M G A A R S P P S A V P G P L L G L L L L L G V
                          Signal Sequence IL17RA     L A P G G A S L R L L D H R A L V C S Q P|G L N C
                              exon 1              | exon 2

IL17RA     T V K N|S T C L D D S W I H P R N L T P S S P K D
                 |

100
IL17RA     L Q I Q L H F A H T Q Q G D L P P V A H I E W T L
                              exon 3

IL17RA     Q T D|A S I L Y L E G A E L S V L Q L N T N E R L
              |                   exon 4

IL17RA     C V R F E P L S K L R H H H R R|W R F T F S H F V
                                         |

IL17RA     V D P D Q E Y E V T V H L P K P I P D G D P N H
                              exon 5
                                                      199
IL17RA     Q S K N F L V P|D C E H A R M K V T T P C M S S|
                         |      exon 6                   |

215
IL17RC    |A L P W L N V S
          |
                                                      240
IL17RC     A D G D N V H L V L N V S E E Q H F G L S L Y W N
                              exon 8
                                                      265
IL17RC     Q V Q G P P K P R W H K N L|T G P Q I I T L N H T
                                     |    exon 9
                                                      290
IL17RC     D L V P C L C I Q|V W P L E P D S V R T N I C P F
                            |         exon 10

315
IL17RC     R|E D P R A H Q N L W Q A A R L R L L T L Q S W L
            |
                                                      340
IL17RC     L D A P C S L P A E A A L C W R A P G G D P C Q P
                              exon 11
                                                      365
IL17RC     L V P P L S W E N V T V D|K V L E F P L L K G H P
                                    |    exon 12
```

Figure 4A

```
                              |                                     |     390
IL17RC    N L C V Q|V N S S E K L Q L Q E C L W A|D S L G P
                   |              exon 13         |
                                                              415
IL17RC    L K D D V L L E T R G P Q D N R S L C A L E P S
                              exon 14

|                              440
IL17RC    G C T S L P S K A S T|R A A R L G E Y L L Q D L Q
                               |      exon 15

|                                     |  465
IL17RC    S G Q C L Q|L W D D D L G A L W A C P M D K|Y I H
                    |             exon 16            |
          |
IL17RC    K| . . . .
          |
```

Figure 4B

* Mean BW's are significantly different (p < 0.05)

SEQUENCE LISTING

```
<160> NUMBER OF SEQ ID NOS: 190

<210> SEQ ID NO 1
<211> LENGTH: 2255
<212> TYPE: DNA
<213> ORGANISM: Homo sapiens
<220> FEATURE:
<221> NAME/KEY: CDS
<222> LOCATION: (154)...(2229)
<220> FEATURE:
<223> OTHER INFORMATION: Optimized tissue Plasminogen Activator (otPA)
      pre-pro signal sequence and exons 7-10 of human
      IL-17RC, and Fc5

<400> SEQUENCE: 1
aactacccag cacagccccc tccgcccccct ctggaggctg aagagggatt ccagccccctg         60 ccacccacag acacgggctg actggggtgt ctgcccccct tggggggggg cagcacaggg        120
cctcaggcct gggtgccacc tggcacctag aag atg cct gtg ccc tgg ttc ttg        174
                                    Met Pro Val Pro Trp Phe Leu
                                      1               5 ctg tcc ttg gca ctg ggc cga agc cca gtg gtc ctt tct ctg gag agg         222
Leu Ser Leu Ala Leu Gly Arg Ser Pro Val Val Leu Ser Leu Glu Arg
         10                  15                  20 ctt gtg ggg cct cag gac gct acc cac tgc tct ccg ggc ctc tcc tgc         270
Leu Val Gly Pro Gln Asp Ala Thr His Cys Ser Pro Gly Leu Ser Cys
     25                  30                  35 cgc ctc tgg gac agt gac ata ctc tgc ctg ggg gac atc gtg cct         318
Arg Leu Trp Asp Ser Asp Ile Leu Cys Leu Pro Gly Asp Ile Val Pro
 40                  45                  50                  55 gct ccg ggc ccc gtg ctg gcg cct acg cac ctg cag aca gag ctg gtg         366
Ala Pro Gly Pro Val Leu Ala Pro Thr His Leu Gln Thr Glu Leu Val
                 60                  65                  70 ctg agg tgc cag aag gag acc gac tgt gac ctc tgt ctg cgt gtg gct         414
Leu Arg Cys Gln Lys Glu Thr Asp Cys Asp Leu Cys Leu Arg Val Ala
             75                  80                  85 gtc cac ttg gcc gtg cat ggg cac tgg gaa gag cct gaa gat gag gaa         462
```

|   |   |   |   |   |   |   |   |   |   |   |   |   |   |   |   |      |
|---|---|---|---|---|---|---|---|---|---|---|---|---|---|---|---|------|
|   | Val | His | Leu | Ala | Val | His | Gly | His | Trp | Glu | Pro | Glu | Asp | Glu |   |      |
|   |     | 90  |     |     |     | 95  |     |     |     | 100 |     |     |     |     |   |      |

```
aag ttt gga gga gca gct gac tca ggg gtg gag gag cct agg aat gcc     510
Lys Phe Gly Gly Ala Ala Asp Ser Gly Val Glu Glu Pro Arg Asn Ala
    105             110                 115 tct ctc cag gcc caa gtc gtg ctc tcc ttc cag gcc tac cct act gcc     558
Ser Leu Gln Ala Gln Val Val Leu Ser Phe Gln Ala Tyr Pro Thr Ala
120             125                 130                 135 cgc tgc gtc ctg ctg gag gtg caa gtg cct gct gcc ctt gtg cag ttt     606
Arg Cys Val Leu Leu Glu Val Gln Val Pro Ala Ala Leu Val Gln Phe
                140                 145                 150 ggt cag tct gtg ggc tct gtg gta tat gac tgc ttc gag gct gcc cta     654
Gly Gln Ser Val Gly Ser Val Val Tyr Asp Cys Phe Glu Ala Ala Leu
            155                 160                 165 ggg agt gag gta cga atc tgg tcc tat act cag ccc agg tac gag aag     702
Gly Ser Glu Val Arg Ile Trp Ser Tyr Thr Gln Pro Arg Tyr Glu Lys
        170                 175                 180 gaa ctc aac cac aca cag cag ctg cct gcc ctg ccc tgg ctc aac gtg     750
Glu Leu Asn His Thr Gln Gln Leu Pro Ala Leu Pro Trp Leu Asn Val
    185                 190                 195 tca gca gat ggt gac aac gtg cat ctg gtt ctg aat gtc tct gag gag     798
Ser Ala Asp Gly Asp Asn Val His Leu Val Leu Asn Val Ser Glu Glu
200                 205                 210                 215 cag cac ttc ggc ctc tcc ctg tac tgg aat cag gtc cag ggc ccc cca     846
Gln His Phe Gly Leu Ser Leu Tyr Trp Asn Gln Val Gln Gly Pro Pro
                220                 225                 230 aaa ccc cgg tgg cac aaa aac ctg act gga ccg cag atc att acc ttg     894
Lys Pro Arg Trp His Lys Asn Leu Thr Gly Pro Gln Ile Ile Thr Leu
            235                 240                 245 aac cac aca gac ctg gtt ccc tgc ctc tgt att cag gtg tgg cct ctg     942
Asn His Thr Asp Leu Val Pro Cys Leu Cys Ile Gln Val Trp Pro Leu
        250                 255                 260 gaa cct gac tcc gtt agg acg aac atc tgc ccc ttc agg gag gac ccc     990
Glu Pro Asp Ser Val Arg Thr Asn Ile Cys Pro Phe Arg Glu Asp Pro
    265                 270                 275 cgc gca cac cag aac ctc tgg caa gcc gcc cga ctg cga ctg ctg acc    1038
Arg Ala His Gln Asn Leu Trp Gln Ala Ala Arg Leu Arg Leu Leu Thr
280                 285                 290                 295 ctg cag agc tgg ctg ctg gac gca ccg tgc tcg ctg ccc gca gaa gcg    1086
Leu Gln Ser Trp Leu Leu Asp Ala Pro Cys Ser Leu Pro Ala Glu Ala
                300                 305                 310 gca ctg tgc tgg cgg gct ccg ggt ggg gac ccc tgc cag cca ctg gtc    1134
Ala Leu Cys Trp Arg Ala Pro Gly Gly Asp Pro Cys Gln Pro Leu Val
            315                 320                 325 cca ccg ctt tcc tgg gag aac gtc act gtg gac aag gtt ctc gag ttc    1182
Pro Pro Leu Ser Trp Glu Asn Val Thr Val Asp Lys Val Leu Glu Phe
        330                 335                 340 cca ttg ctg aaa ggc cac cct aac ctc tgt gtt cag gtg aac agc tcg    1230
Pro Leu Leu Lys Gly His Pro Asn Leu Cys Val Gln Val Asn Ser Ser
    345                 350                 355 gag aag ctg cag ctg cag gag tgc ttg tgg gct gac tcc ctg ggc cct    1278
Glu Lys Leu Gln Leu Gln Glu Cys Leu Trp Ala Asp Ser Leu Gly Pro
360                 365                 370                 375 ctc aaa gac gat gtg cta ctg ttg gag aca cga ggc ccc cag gac aac    1326
Leu Lys Asp Asp Val Leu Leu Leu Glu Thr Arg Gly Pro Gln Asp Asn
                380                 385                 390 aga tcc ctc tgt gcc ttg gaa ccc agt ggc tgt act tca cta ccc agc    1374
Arg Ser Leu Cys Ala Leu Glu Pro Ser Gly Cys Thr Ser Leu Pro Ser
            395                 400                 405 aaa gcc tcc acg agg gca gct cgc ctt gga gag tac tta cta caa gac    1422
```

|  |  |  |  |  |  |  |  |  |  |  |  |  |
|---|---|---|---|---|---|---|---|---|---|---|---|---|
| Lys | Ala | Ser | Thr | Arg | Ala | Ala | Arg | Leu | Gly | Glu | Tyr | Leu | Leu | Gln | Asp |
|  |  | 410 |  |  |  | 415 |  |  |  | 420 |  |  |

```
ctg cag tca ggc cag tgt ctg cag cta tgg gac gat gac ttg gga gcg      1470
Leu Gln Ser Gly Gln Cys Leu Gln Leu Trp Asp Asp Asp Leu Gly Ala
425                 430                 435 cta tgg gcc tgc ccc atg gac aaa tac atc cac aag cgc tgg gcc ctc      1518
Leu Trp Ala Cys Pro Met Asp Lys Tyr Ile His Lys Arg Trp Ala Leu
440                 445                 450                 455 gtg tgg ctg gcc tgc cta ctc ttt gcc gct gcg ctt tcc ctc atc ctc      1566
Val Trp Leu Ala Cys Leu Leu Phe Ala Ala Leu Ser Leu Ile Leu
            460                 465                 470 ctt ctc aaa aag gat cac gcg aaa gcg gcc gcc agg ggc cgc gcg gct      1614
Leu Leu Lys Lys Asp His Ala Lys Ala Ala Ala Arg Gly Arg Ala Ala
        475                 480                 485 ctg ctc ctc tac tca gcc gat gac tcg ggt ttc gag cgc ctg gtg ggc      1662
Leu Leu Leu Tyr Ser Ala Asp Asp Ser Gly Phe Glu Arg Leu Val Gly
            490                 495                 500 gcc ctg gcg tcg gcc ctg tgc cag ctg ccg ctc cgc gtg gcc gta gac      1710
Ala Leu Ala Ser Ala Leu Cys Gln Leu Pro Leu Arg Val Ala Val Asp
505                 510                 515 ctg tgg agc cgt cgt gaa ctg agc gcg cag ggg ccc gtg gct tgg ttt      1758
Leu Trp Ser Arg Arg Glu Leu Ser Ala Gln Gly Pro Val Ala Trp Phe
520                 525                 530                 535 cac gcg cag cgg cgc cag acc ctg cag gag ggc ggc gtg gtg gtc ttg      1806
His Ala Gln Arg Arg Gln Thr Leu Gln Glu Gly Gly Val Val Val Leu
                540                 545                 550 ctc ttc tct ccc ggt gcg gtg gcg ctg tgc agc gag tgg cta cag gat      1854
Leu Phe Ser Pro Gly Ala Val Ala Leu Cys Ser Glu Trp Leu Gln Asp
            555                 560                 565 ggg gtg tcc ggg ccc ggg gcg cac ggc ccg cac gac gcc ttc cgc gcc      1902
Gly Val Ser Gly Pro Gly Ala His Gly Pro His Asp Ala Phe Arg Ala
        570                 575                 580 tcg ctc agc tgc gtg ctg ccc gac ttc ttg cag ggc cgg gcg ccc ggc      1950
Ser Leu Ser Cys Val Leu Pro Asp Phe Leu Gln Gly Arg Ala Pro Gly
585                 590                 595 agc tac gtg ggg gcc tgc ttc gac agg ctg ctc cac ccg gac gcc gta      1998
Ser Tyr Val Gly Ala Cys Phe Asp Arg Leu Leu His Pro Asp Ala Val
600                 605                 610                 615 ccc gcc ctt ttc cgc acc gtg ccc gtc ttc aca ctg ccc tcc caa ctg      2046
Pro Ala Leu Phe Arg Thr Val Pro Val Phe Thr Leu Pro Ser Gln Leu
                620                 625                 630 cca gac ttc ctg ggg gcc ctg cag cag cct cgc gcc ccg cgt tcc ggg      2094
Pro Asp Phe Leu Gly Ala Leu Gln Gln Pro Arg Ala Pro Arg Ser Gly
            635                 640                 645 cgg ctc caa gag aga gcg gag caa gtg tcc cgg gcc ctt cag cca gcc      2142
Arg Leu Gln Glu Arg Ala Glu Gln Val Ser Arg Ala Leu Gln Pro Ala
        650                 655                 660 ctg gat agc tac ttc cat ccc ccg ggg act ccc gcg ccg gga cgc ggg      2190
Leu Asp Ser Tyr Phe His Pro Pro Gly Thr Pro Ala Pro Gly Arg Gly
665                 670                 675 gtg gga cca ggg gcg gga cct ggg gcg ggg gac ggg act taaataaagg      2239
Val Gly Pro Gly Ala Gly Pro Gly Ala Gly Asp Gly Thr
680                 685                 690 cagacgctgt ttttct                                                    2255

<210> SEQ ID NO 2
<211> LENGTH: 692
<212> TYPE: PRT
<213> ORGANISM: Homo sapiens

<400> SEQUENCE: 2
```

```
Met Pro Val Pro Trp Phe Leu Leu Ser Leu Ala Leu Gly Arg Ser Pro
 1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
 50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
                100                 105                 110

Val Glu Glu Pro Arg Asn Ala Ser Leu Gln Ala Gln Val Val Leu Ser
            115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
                180                 185                 190

Ala Leu Pro Trp Leu Asn Val Ser Ala Asp Gly Asp Asn Val His Leu
            195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
                260                 265                 270

Cys Pro Phe Arg Glu Asp Pro Arg Ala His Gln Asn Leu Trp Gln Ala
            275                 280                 285

Ala Arg Leu Arg Leu Leu Thr Leu Gln Ser Trp Leu Leu Asp Ala Pro
    290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Lys Val Leu Glu Phe Pro Leu Leu Lys Gly His Pro Asn Leu
            340                 345                 350

Cys Val Gln Val Asn Ser Ser Glu Lys Leu Gln Leu Gln Glu Cys Leu
    355                 360                 365

Trp Ala Asp Ser Leu Gly Pro Leu Lys Asp Asp Val Leu Leu Leu Glu
    370                 375                 380

Thr Arg Gly Pro Gln Asp Asn Arg Ser Leu Cys Ala Leu Glu Pro Ser
385                 390                 395                 400

Gly Cys Thr Ser Leu Pro Ser Lys Ala Ser Thr Arg Ala Ala Arg Leu
                405                 410                 415

Gly Glu Tyr Leu Leu Gln Asp Leu Gln Ser Gly Gln Cys Leu Gln Leu
```

-continued

```
            420                 425                 430
Trp Asp Asp Asp Leu Gly Ala Leu Trp Ala Cys Pro Met Asp Lys Tyr
        435                 440                 445
Ile His Lys Arg Trp Ala Leu Val Trp Leu Ala Cys Leu Leu Phe Ala
    450                 455                 460
Ala Ala Leu Ser Leu Ile Leu Leu Lys Lys Asp His Ala Lys Ala
465                 470                 475                 480
Ala Ala Arg Gly Arg Ala Ala Leu Leu Leu Tyr Ser Ala Asp Asp Ser
                485                 490                 495
Gly Phe Glu Arg Leu Val Gly Ala Leu Ala Ser Ala Leu Cys Gln Leu
            500                 505                 510
Pro Leu Arg Val Ala Val Asp Leu Trp Ser Arg Arg Glu Leu Ser Ala
        515                 520                 525
Gln Gly Pro Val Ala Trp Phe His Ala Gln Arg Arg Gln Thr Leu Gln
    530                 535                 540
Glu Gly Gly Val Val Leu Leu Phe Ser Pro Gly Ala Val Ala Leu
545                 550                 555                 560
Cys Ser Glu Trp Leu Gln Asp Gly Val Ser Gly Pro Ala His Gly
                565                 570                 575
Pro His Asp Ala Phe Arg Ala Ser Leu Ser Cys Val Leu Pro Asp Phe
            580                 585                 590
Leu Gln Gly Arg Ala Pro Gly Ser Tyr Val Gly Ala Cys Phe Asp Arg
        595                 600                 605
Leu Leu His Pro Asp Ala Val Pro Ala Leu Phe Arg Thr Val Pro Val
    610                 615                 620
Phe Thr Leu Pro Ser Gln Leu Pro Asp Phe Leu Gly Ala Leu Gln Gln
625                 630                 635                 640
Pro Arg Ala Pro Arg Ser Arg Leu Gln Glu Arg Ala Glu Gln Val
                645                 650                 655
Ser Arg Ala Leu Gln Pro Ala Leu Asp Ser Tyr Phe His Pro Pro Gly
            660                 665                 670
Thr Pro Ala Pro Gly Arg Gly Val Gly Pro Gly Ala Gly Pro Gly Ala
        675                 680                 685
Gly Asp Gly Thr
    690

<210> SEQ ID NO 3
<211> LENGTH: 432
<212> TYPE: PRT
<213> ORGANISM: Homo sapiens

<400> SEQUENCE: 3

Leu Glu Arg Leu Val Gly Pro Gln Asp Ala Thr His Cys Ser Pro Gly
1               5                   10                  15
Leu Ser Cys Arg Leu Trp Asp Ser Asp Ile Leu Cys Leu Pro Gly Asp
            20                  25                  30
Ile Val Pro Ala Pro Gly Pro Val Leu Ala Pro Thr His Leu Gln Thr
        35                  40                  45
Glu Leu Val Leu Arg Cys Gln Lys Glu Thr Asp Cys Asp Leu Cys Leu
    50                  55                  60
Arg Val Ala Val His Leu Ala Val His Gly His Trp Glu Glu Pro Glu
65                  70                  75                  80
Asp Glu Glu Lys Phe Gly Gly Ala Ala Asp Ser Gly Val Glu Glu Pro
                85                  90                  95
Arg Asn Ala Ser Leu Gln Ala Gln Val Val Leu Ser Phe Gln Ala Tyr
```

```
                     100                 105                 110
Pro Thr Ala Arg Cys Val Leu Leu Glu Val Gln Val Pro Ala Ala Leu
            115                 120                 125

Val Gln Phe Gly Gln Ser Val Gly Ser Val Val Tyr Asp Cys Phe Glu
        130                 135                 140

Ala Ala Leu Gly Ser Glu Val Arg Ile Trp Ser Tyr Thr Gln Pro Arg
145                 150                 155                 160

Tyr Glu Lys Glu Leu Asn His Thr Gln Gln Leu Pro Ala Leu Pro Trp
                165                 170                 175

Leu Asn Val Ser Ala Asp Gly Asp Asn Val His Leu Val Leu Asn Val
            180                 185                 190

Ser Glu Glu Gln His Phe Gly Leu Ser Leu Tyr Trp Asn Gln Val Gln
        195                 200                 205

Gly Pro Pro Lys Pro Arg Trp His Lys Asn Leu Thr Gly Pro Gln Ile
    210                 215                 220

Ile Thr Leu Asn His Thr Asp Leu Val Pro Cys Leu Cys Ile Gln Val
225                 230                 235                 240

Trp Pro Leu Glu Pro Asp Ser Val Arg Thr Asn Ile Cys Pro Phe Arg
                245                 250                 255

Glu Asp Pro Arg Ala His Gln Asn Leu Trp Gln Ala Ala Arg Leu Arg
            260                 265                 270

Leu Leu Thr Leu Gln Ser Trp Leu Asp Ala Pro Cys Ser Leu Pro
        275                 280                 285

Ala Glu Ala Ala Leu Cys Trp Arg Ala Pro Gly Gly Asp Pro Cys Gln
    290                 295                 300

Pro Leu Val Pro Pro Leu Ser Trp Glu Asn Val Thr Val Asp Lys Val
305                 310                 315                 320

Leu Glu Phe Pro Leu Leu Lys Gly His Pro Asn Leu Cys Val Gln Val
                325                 330                 335

Asn Ser Ser Glu Lys Leu Gln Leu Gln Glu Cys Leu Trp Ala Asp Ser
            340                 345                 350

Leu Gly Pro Leu Lys Asp Asp Val Leu Leu Leu Glu Thr Arg Gly Pro
        355                 360                 365

Gln Asp Asn Arg Ser Leu Cys Ala Leu Glu Pro Ser Gly Cys Thr Ser
    370                 375                 380

Leu Pro Ser Lys Ala Ser Thr Arg Ala Ala Arg Leu Gly Glu Tyr Leu
385                 390                 395                 400

Leu Gln Asp Leu Gln Ser Gly Gln Cys Leu Gln Leu Trp Asp Asp Asp
                405                 410                 415

Leu Gly Ala Leu Trp Ala Cys Pro Met Asp Lys Tyr Ile His Lys Arg
            420                 425                 430

<210> SEQ ID NO 4
<211> LENGTH: 1753
<212> TYPE: DNA
<213> ORGANISM: Homo sapiens
<220> FEATURE:
<221> NAME/KEY: CDS
<222> LOCATION: (2)...(1726)

<400> SEQUENCE: 4 g gag gag cct agg aat gcc tct ctc cag gcc caa gtc gtg ctc tcc ttc       49
  Glu Glu Pro Arg Asn Ala Ser Leu Gln Ala Gln Val Val Leu Ser Phe
  1               5                   10                  15 cag gcc tac cct act gcc cgc tgc gtc ctg ctg gag gtg caa gtg cct       97
Gln Ala Tyr Pro Thr Ala Arg Cys Val Leu Leu Glu Val Gln Val Pro
            20                  25                  30
```

```
gct gcc ctt gtg cag ttt ggt cag tct gtg ggc tct gtg gta tat gac     145
Ala Ala Leu Val Gln Phe Gly Gln Ser Val Gly Ser Val Val Tyr Asp
        35                  40                  45 tgc ttc gag gct gcc cta ggg agt gag gta cga atc tgg tcc tat act     193
Cys Phe Glu Ala Ala Leu Gly Ser Glu Val Arg Ile Trp Ser Tyr Thr
 50                  55                  60 cag ccc agg tac gag aag gaa ctc aac cac aca cag cag ctg cct gcc     241
Gln Pro Arg Tyr Glu Lys Glu Leu Asn His Thr Gln Gln Leu Pro Ala
 65                  70                  75                  80 ctg ccc tgg ctc aac gtg tca gca gat ggt gac aac gtg cat ctg gtt     289
Leu Pro Trp Leu Asn Val Ser Ala Asp Gly Asp Asn Val His Leu Val
                 85                  90                  95 ctg aat gtc tct gag gag cag cac ttc ggc ctc tcc ctg tac tgg aat     337
Leu Asn Val Ser Glu Glu Gln His Phe Gly Leu Ser Leu Tyr Trp Asn
                100                 105                 110 cag gtc cag ggc ccc cca aaa ccc cgg tgg cac aaa aac ctg act gga     385
Gln Val Gln Gly Pro Pro Lys Pro Arg Trp His Lys Asn Leu Thr Gly
            115                 120                 125 ccg cag atc att acc ttg aac cac aca gac ctg gtt ccc tgc ctc tgt     433
Pro Gln Ile Ile Thr Leu Asn His Thr Asp Leu Val Pro Cys Leu Cys
    130                 135                 140 att cag gtg tgg cct ctg gaa cct gac tcc gtt agg acg aac atc tgc     481
Ile Gln Val Trp Pro Leu Glu Pro Asp Ser Val Arg Thr Asn Ile Cys
145                 150                 155                 160 ccc ttc agg gag gac ccc cgc gca cac cag aac ctc tgg caa gcc gcc     529
Pro Phe Arg Glu Asp Pro Arg Ala His Gln Asn Leu Trp Gln Ala Ala
                165                 170                 175 cga ctg cga ctg ctg acc ctg cag agc tgg ctg ctg gac gca ccg tgc     577
Arg Leu Arg Leu Leu Thr Leu Gln Ser Trp Leu Leu Asp Ala Pro Cys
            180                 185                 190 tcg ctg ccc gca gaa gcg gca ctg tgc tgg cgg gct ccg ggt ggg gac     625
Ser Leu Pro Ala Glu Ala Ala Leu Cys Trp Arg Ala Pro Gly Gly Asp
        195                 200                 205 ccc tgc cag cca ctg gtc cca ccg ctt tcc tgg gag aac gtc act gtg     673
Pro Cys Gln Pro Leu Val Pro Pro Leu Ser Trp Glu Asn Val Thr Val
    210                 215                 220 gac gtg aac agc tcg gag aag ctg cag ctg cag gag tgc ttg tgg gct     721
Asp Val Asn Ser Ser Glu Lys Leu Gln Leu Gln Glu Cys Leu Trp Ala
225                 230                 235                 240 gac tcc ctg ggg cct ctc aaa gac gat gtg cta ctg ttg gag aca cga     769
Asp Ser Leu Gly Pro Leu Lys Asp Asp Val Leu Leu Leu Glu Thr Arg
                245                 250                 255 ggc ccc cag gac aac aga tcc ctc tgt gcc ttg gaa ccc agt ggc tgt     817
Gly Pro Gln Asp Asn Arg Ser Leu Cys Ala Leu Glu Pro Ser Gly Cys
            260                 265                 270 act tca cta ccc agc aaa gcc tcc acg agg gca gct cgc ctt gga gag     865
Thr Ser Leu Pro Ser Lys Ala Ser Thr Arg Ala Ala Arg Leu Gly Glu
        275                 280                 285 tac tta cta caa gac ctg cag tca ggc agt gtc tg cag cta tgg gac     913
Tyr Leu Leu Gln Asp Leu Gln Ser Gly Gln Cys Leu Gln Leu Trp Asp
    290                 295                 300 gat gac ttg gga gcg cta tgg gcc tgc ccc atg gac aaa tac atc cac     961
Asp Asp Leu Gly Ala Leu Trp Ala Cys Pro Met Asp Lys Tyr Ile His
305                 310                 315                 320 aag cgc tgg gcc ctc gtg tgg ctg gcc tgc cta ctc ttt gcc gct gcg    1009
Lys Arg Trp Ala Leu Val Trp Leu Ala Cys Leu Leu Phe Ala Ala Ala
                325                 330                 335 ctt tcc ctc atc ctc ctt ctc aaa aag gat cac gcg aaa ggg tgg ctg    1057
Leu Ser Leu Ile Leu Leu Leu Lys Lys Asp His Ala Lys Gly Trp Leu
            340                 345                 350
```

```
agg ctc ttg aaa cag gac gtc cgc tcg ggg gcg gcc agg ggc cgc      1105
Arg Leu Leu Lys Gln Asp Val Arg Ser Gly Ala Ala Arg Gly Arg
            355                 360                 365 gcg gct ctg ctc ctc tac tca gcc gat gac tcg ggt ttc gag cgc ctg  1153
Ala Ala Leu Leu Leu Tyr Ser Ala Asp Asp Ser Gly Phe Glu Arg Leu
    370                 375                 380 gtg ggc gcc ctg gcg tcg gcc ctg tgc cag ctg ccg ctg cgc gtg gcc  1201
Val Gly Ala Leu Ala Ser Ala Leu Cys Gln Leu Pro Leu Arg Val Ala
385                 390                 395                 400 gta gac ctg tgg agc cgt cgt gaa ctg agc gcg cag ggc ccc gtg gct  1249
Val Asp Leu Trp Ser Arg Arg Glu Leu Ser Ala Gln Gly Pro Val Ala
                405                 410                 415 tgg ttt cac gcg cag cgg cgc cag acc ctg cag gag ggc ggc gtg gtg  1297
Trp Phe His Ala Gln Arg Arg Gln Thr Leu Gln Glu Gly Gly Val Val
            420                 425                 430 gtc ttg ctc ttc tct ccc ggt gcg gtg gcg ctg tgc agc gag tgg cta  1345
Val Leu Leu Phe Ser Pro Gly Ala Val Ala Leu Cys Ser Glu Trp Leu
        435                 440                 445 cag gat ggg gtg tcc ggg ccc ggg gcg cac ggc ccg cac gac gcc ttc  1393
Gln Asp Gly Val Ser Gly Pro Gly Ala His Gly Pro His Asp Ala Phe
    450                 455                 460 cgc gcc tcg ctc agc tgc gtg ctg ccc gac ttc ttg cag ggc cgg gcg  1441
Arg Ala Ser Leu Ser Cys Val Leu Pro Asp Phe Leu Gln Gly Arg Ala
465                 470                 475                 480 ccc ggc agc tac gtg ggg gcc tgc ttc gac agg ctg ctc cac ccg gac  1489
Pro Gly Ser Tyr Val Gly Ala Cys Phe Asp Arg Leu Leu His Pro Asp
                485                 490                 495 gcc gta ccc gcc ctt ttc cgc acc gtg ccc gtc ttc aca ctg ccc tcc  1537
Ala Val Pro Ala Leu Phe Arg Thr Val Pro Val Phe Thr Leu Pro Ser
            500                 505                 510 caa ctg cca gac ttc ctg ggg gcc ctg cag cag cct cgc gcc ccg cgt  1585
Gln Leu Pro Asp Phe Leu Gly Ala Leu Gln Gln Pro Arg Ala Pro Arg
        515                 520                 525 tcc ggg cgg ctc caa gag aga gcg gag caa gtg tcc cgg gcc ctt cag  1633
Ser Gly Arg Leu Gln Glu Arg Ala Glu Gln Val Ser Arg Ala Leu Gln
    530                 535                 540 cca gcc ctg gat agc tac ttc cat ccc ccg ggg act ccc gcg ccg gga  1681
Pro Ala Leu Asp Ser Tyr Phe His Pro Pro Gly Thr Pro Ala Pro Gly
545                 550                 555                 560 cgc ggg gtg gga cca ggg gcg gga cct ggg gcg ggg gac ggg act      1726
Arg Gly Val Gly Pro Gly Ala Gly Pro Gly Ala Gly Asp Gly Thr
                565                 570                 575 taaataaagg cagacgctgt ttttcta                                    1753

<210> SEQ ID NO 5
<211> LENGTH: 575
<212> TYPE: PRT
<213> ORGANISM: Homo sapiens

<400> SEQUENCE: 5

Glu Glu Pro Arg Asn Ala Ser Leu Gln Ala Gln Val Val Leu Ser Phe
1               5                   10                  15

Gln Ala Tyr Pro Thr Ala Arg Cys Val Leu Glu Val Gln Val Pro
            20                  25                  30

Ala Ala Leu Val Gln Phe Gly Gln Ser Val Gly Ser Val Val Tyr Asp
        35                  40                  45

Cys Phe Glu Ala Ala Leu Gly Ser Glu Val Arg Ile Trp Ser Tyr Thr
    50                  55                  60

Gln Pro Arg Tyr Glu Lys Glu Leu Asn His Thr Gln Gln Leu Pro Ala
```

```
                65                  70                  75                  80
Leu Pro Trp Leu Asn Val Ser Ala Asp Gly Asp Asn Val His Leu Val
                    85                  90                  95

Leu Asn Val Ser Glu Glu Gln His Phe Gly Leu Ser Leu Tyr Trp Asn
                    100                 105                 110

Gln Val Gln Gly Pro Pro Lys Pro Arg Trp His Lys Asn Leu Thr Gly
                    115                 120                 125

Pro Gln Ile Ile Thr Leu Asn His Thr Asp Leu Val Pro Cys Leu Cys
                    130                 135                 140

Ile Gln Val Trp Pro Leu Glu Pro Asp Ser Val Arg Thr Asn Ile Cys
145                 150                 155                 160

Pro Phe Arg Glu Asp Pro Arg Ala His Gln Asn Leu Trp Gln Ala Ala
                    165                 170                 175

Arg Leu Arg Leu Leu Thr Leu Gln Ser Trp Leu Leu Asp Ala Pro Cys
                    180                 185                 190

Ser Leu Pro Ala Glu Ala Ala Leu Cys Trp Arg Ala Pro Gly Gly Asp
                    195                 200                 205

Pro Cys Gln Pro Leu Val Pro Pro Leu Ser Trp Glu Asn Val Thr Val
                    210                 215                 220

Asp Val Asn Ser Ser Glu Lys Leu Gln Leu Gln Glu Cys Leu Trp Ala
225                 230                 235                 240

Asp Ser Leu Gly Pro Leu Lys Asp Val Leu Leu Leu Glu Thr Arg
                    245                 250                 255

Gly Pro Gln Asp Asn Arg Ser Leu Cys Ala Leu Glu Pro Ser Gly Cys
                    260                 265                 270

Thr Ser Leu Pro Ser Lys Ala Ser Thr Arg Ala Ala Arg Leu Gly Glu
                    275                 280                 285

Tyr Leu Leu Gln Asp Leu Gln Ser Gly Gln Cys Leu Gln Leu Trp Asp
                    290                 295                 300

Asp Asp Leu Gly Ala Leu Trp Ala Cys Pro Met Asp Lys Tyr Ile His
305                 310                 315                 320

Lys Arg Trp Ala Leu Val Trp Leu Ala Cys Leu Leu Phe Ala Ala Ala
                    325                 330                 335

Leu Ser Leu Ile Leu Leu Leu Lys Lys Asp His Ala Lys Gly Trp Leu
                    340                 345                 350

Arg Leu Leu Lys Gln Asp Val Arg Ser Gly Ala Ala Ala Arg Gly Arg
                    355                 360                 365

Ala Ala Leu Leu Leu Tyr Ser Ala Asp Asp Ser Gly Phe Glu Arg Leu
                    370                 375                 380

Val Gly Ala Leu Ala Ser Ala Leu Cys Gln Leu Pro Leu Arg Val Ala
385                 390                 395                 400

Val Asp Leu Trp Ser Arg Arg Glu Leu Ser Ala Gln Gly Pro Val Ala
                    405                 410                 415

Trp Phe His Ala Gln Arg Arg Gln Thr Leu Gln Glu Gly Gly Val Val
                    420                 425                 430

Val Leu Leu Phe Ser Pro Gly Ala Val Ala Leu Cys Ser Glu Trp Leu
                    435                 440                 445

Gln Asp Gly Val Ser Gly Pro Gly Ala His Gly Pro His Asp Ala Phe
                    450                 455                 460

Arg Ala Ser Leu Ser Cys Val Leu Pro Asp Phe Leu Gln Gly Arg Ala
465                 470                 475                 480

Pro Gly Ser Tyr Val Gly Ala Cys Phe Asp Arg Leu Leu His Pro Asp
                    485                 490                 495
```

```
Ala Val Pro Ala Leu Phe Arg Thr Val Pro Val Phe Thr Leu Pro Ser
            500                 505                 510

Gln Leu Pro Asp Phe Leu Gly Ala Leu Gln Gln Pro Arg Ala Pro Arg
        515                 520                 525

Ser Gly Arg Leu Gln Glu Arg Ala Glu Gln Val Ser Arg Ala Leu Gln
    530                 535                 540

Pro Ala Leu Asp Ser Tyr Phe His Pro Pro Gly Thr Pro Ala Pro Gly
545                 550                 555                 560

Arg Gly Val Gly Pro Gly Ala Gly Pro Gly Ala Gly Asp Gly Thr
                565                 570                 575

<210> SEQ ID NO 6
<211> LENGTH: 1725
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(1725)
<223> OTHER INFORMATION: n = A,T,C or G

<400> SEQUENCE: 6
gargarccnm gnaaygcnws nytncargcn cargtngtny tnwsnttyca rgcntayccn      60
acngcnmgnt gygtnytnyt ngargtncar gtnccngcng cnytngtnca rttyggncar    120
wsngtnggnw sngtngtnta ygaytgytty gargcngcny tnggnwsnga rgtnmgnath    180
tggwsntaya cncarccnmg ntaygaraar garytnaayc ayacncarca rytnccngcn    240
ytnccntggy tnaaygtnws ngcngayggn gayaaygtnc ayytngtnyt naaygtnwsn    300
gargarcarc ayttyggnyt nwsnytntay tggaaycarg tncarggncc ccnaarccn     360 mgntggcaya araayytnac nggnccncar athathacny tnaaycayac ngayytngtn    420
ccntgyytnt gyathcargt ntggccnytn garccngayw sngtnmgnac naayathtgy    480
ccnttymgng argayccnmg ngcncaycar aayytntggc argcngcnmg nytnmgnytn    540
ytnacnytnc arwsntggyt nytngaygcn ccntgywsny tnccgcnga rgcngcnytn    600 tgytggmgng cnccnggngg ngayccntgy carccnytng tnccnccnyt nwsntgggar    660
aaygtnacng tngaygtnaa ywsnwsngar aarytncary tncargartg yytntgggcn    720
gaywsnytng gnccnytnaa rgaygaygtn ytnytnytng aracnmgngg nccncargay    780
aaymgnwsny tntgygcnyt ngarccnwsn ggntgyacnw snytnccnws naargcnwsn    840
acnmgngcng cnmgnytngg ngartayytn ytncargayy tncarwsngg ncartgyytn    900
carytntggg aygaygayyt nggngcnytn tgggcntgyc cnatggayaa rtayathcay    960
aarmgntggg cnytngtntg gytngcntgy ytnytnttyg cngcngcnyt nwsnytnath   1020
ytnytnytna araargayca ygcnaarggn tggytnmgny tnytnaarca rgaygtnmgn   1080
wsnggngcng cngcnmgngg nmgncngcn ytnytnytnt aywsngcnga ygaywsnggn    1140
ttygarmgny tngtnggngc nytngcnwsn gcnytntgyc arytnccnyt nmgngtngcn   1200
gtngayytnt ggwsnmgnmg ngarytnwsn gcncarggnc cngtngcntg gttycaygcn   1260
carmgnmgnc aracnytnca rgarggnggn gtngtngtny tnytnttyws nccnggngcn   1320
gtngcnytnt gywsngartg gytncargay gggntnwsng gnccnggngc ncayggnccn   1380
caygaygcnt tymgngcnws nytnwsntgy gtnytnccng ayttyytnca rggnmgngcn   1440
ccnggnwsnt aygtngggnc ntgyttygay mgnytnytnc ayccngaygc ngtnccngcn   1500
ytnttymgna cngtnccngt nttyacnytn ccnwsncary tnccngaytt yytnggngcn   1560
```

| | |
|---|---|
| ytncarcarc cnmgngcncc nmgnwsnggn mgnytncarg armgngcnga rcargtnwsn | 1620 |
| mgngcnytnc arccngcnyt ngaywsntay ttycayccnc cnggnacncc ngcncngg n | 1680 |
| mgnggngtng gnccnggngc nggnccnggn gcnggngayg gnacn | 1725 |

```
<210> SEQ ID NO 7
<211> LENGTH: 2076
<212> TYPE: DNA
<213> ORGANISM: Artificial Sequence
<220> FEATURE:
<223> OTHER INFORMATION: degenerate sequence
<220> FEATURE:
<221> NAME/KEY: misc_feature
<222> LOCATION: (1)...(2076)
<223> OTHER INFORMATION: n = A,T,C or G
```

<400> SEQUENCE: 7

| | |
|---|---|
| atgccngtnc cntggttyyt nytnwsnytn gcnytnggnm gnwsnccngt ngtnytnwsn | 60 |
| ytngarmgny tngtnggncc ncargaygcn acncaytgyw snccnggnyt nwsntgymgn | 120 |
| ytntgggayw sngayathyt ntgyytnccn ggngayathg tnccngcncc nggnccngtn | 180 |
| ytngcnccna cncayytnca racngarytn gtnytnmgnt gycaraarga racngaytgy | 240 |
| gayytntgyy tnmgngtngc ngtncayytn gcngtncayg gncaytggga rgarccngar | 300 |
| gaygargara arttyggngg ngcngcngay wsnggngtng argarccnmg naaygcnwsn | 360 |
| ytncargcnc argtngtnyt nwsnttycar gcntayccna cngcnmgntg ygtnytnytn | 420 |
| gargtncarg tnccngcngc nytngtncar ttyggncarw sngtnggnws ngtngtntay | 480 |
| gaytgyttyg argcngcnyt nggnwsngar gtnmgnatht ggwsntayac ncarccnmgn | 540 |
| taygaraarg arytnaayca yacncarcar ytnccngcny tnccntggyt naaygtnwsn | 600 |
| gcngayggng ayaaygtnca yytngtnytn aaygtnwsng argarcarca yttyggnytn | 660 |
| wsnytntayt ggaaycargt ncarggnccn ccnaarccnm gntggcayaa raayytnacn | 720 |
| ggnccncara thathacnyt naaycayacn gayytngtnc cntgyytntg yathcargtn | 780 |
| tggccnytng arccngayws ngtnmgnacn aayathtgyc cnttymgnga rgayccnmgn | 840 |
| gcncaycara ayytntggca rgcngcnmgn ytnmgnytny tnacnytnca rwsntggytn | 900 |
| ytngaygcnc cntgywsnyt nccngcngar gcngcnytnt gytggmgngc nccnggnggn | 960 |
| gayccntgyc arccnytngt nccnccnytn wsntgggara aygtnacngt ngayaargtn | 1020 |
| ytngarttyc cnytnytnaa rggncayccn aayytntgyg tncargtnaa ywsnwsngar | 1080 |
| aarytncary tncargartg yytntgggcn gaywsnytng gnccnytnaa rgaygaygtn | 1140 |
| ytnytnytng aracnmgngg nccncargay aaymgnwsny tntgygcnyt ngarccnwsn | 1200 |
| ggntgyacnw snytnccnws naargcnwsn acnmgngcng cnmgnytngg ngartayytn | 1260 |
| ytncargayy tncarwsngg ncartgyytn carytntggg aygaygayyt nggngcnytn | 1320 |
| tgggcntgyc cnatggayaa rtayathcay aarmgntggg cnytngtntg gytngcntgy | 1380 |
| ytnytntttyg cngcngcnyt nwsnytnath ytnytnytna araargayca ygcnaargcn | 1440 |
| gcngcmgng gnmgngcngc nytnytnytn taywsngcng aygaywsngg nttygarmgn | 1500 |
| ytngtnggng cnytngcnws ngcnytntgy carytnccny tnmgngtngc ngtngayytn | 1560 |
| tggwsnmgnm gngarytnws ngcncarggn ccngtngcnt ggttycaygc ncarmgnmgn | 1620 |
| caracnytnc argarggngg ngtngtngtn ytnytnttyw snccnggngc ngtngcnytn | 1680 |
| tgywsngart ggytncarga yggngtnwsn ggnccngggn cncayggncc ncaygaygcn | 1740 |
| ttymgngcnw snytnwsntg ygtnytnccn gayttyytnc arggnmgngc nccnggnwsn | 1800 |

-continued

```
taygtnggng cntgyttyga ymgnytnytn cayccngayg cngtnccngc nytnttymgn    1860
acngtnccng tnttyacnyt nccnwsncar ytnccngayt tyytnggngc nytncarcar    1920
ccnmgngcnc cnmgnwsngg nmgnytncar garmgngcng arcargtnws nmgngcnytn    1980
carccngcny tngaywsnta yttycayccn ccnggnacnc cngcccngg nmgnggngtn     2040 ggnccnggng cnggnccngg ngcnggngay ggnacn                              2076
```

<210> SEQ ID NO 8
<211> LENGTH: 21
<212> TYPE: DNA
<213> ORGANISM: Artificial Sequence
<220> FEATURE:
<223> OTHER INFORMATION: PCR primer

<400> SEQUENCE: 8
cggcgtggtg gtcttgctct t     21

<210> SEQ ID NO 9
<211> LENGTH: 16
<212> TYPE: PRT
<213> ORGANISM: Artificial Sequence
<220> FEATURE:
<223> OTHER INFORMATION: peptide linker

<400> SEQUENCE: 9

```
Gly Gly Ser Gly Gly Ser Gly Gly Gly Gly Ser Gly Gly Gly Gly Ser
  1               5                  10                  15
```

<210> SEQ ID NO 10
<211> LENGTH: 688
<212> TYPE: PRT
<213> ORGANISM: Artificial Sequence
<220> FEATURE:
<223> OTHER INFORMATION: Chimeric Zcytor14 protein

<400> SEQUENCE: 10

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
                 20                  25                  30

Cys Ser Pro Gly Leu Ser Cys Arg Leu Trp Asp Ser Asp Ile Leu Cys
             35                  40                  45

Leu Pro Gly Asp Ile Val Pro Ala Pro Gly Pro Val Leu Ala Pro Thr
         50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
```

```
                180             185             190
Ala Leu Pro Trp Leu Asn Val Ser Ala Asp Gly Asp Asn Val His Leu
            195                 200             205
Val Leu Asn Val Ser Glu Glu Gln His Phe Gly Leu Ser Leu Tyr Trp
210                 215                 220
Asn Gln Val Gln Gly Pro Lys Pro Arg Trp His Lys Asn Leu Thr
225                 230                 235                 240
Gly Pro Gln Ile Ile Thr Leu Asn His Thr Asp Leu Val Pro Cys Leu
                245                 250                 255
Cys Ile Gln Val Trp Pro Leu Glu Pro Asp Ser Val Arg Thr Asn Ile
            260                 265                 270
Cys Pro Phe Arg Glu Asp Pro Arg Ala His Gln Asn Leu Trp Gln Ala
            275                 280                 285
Ala Arg Leu Arg Leu Leu Thr Leu Gln Ser Trp Leu Leu Asp Ala Pro
            290                 295                 300
Cys Ser Leu Pro Ala Glu Ala Ala Leu Cys Trp Arg Ala Pro Gly Gly
305                 310                 315                 320
Asp Pro Cys Gln Pro Leu Val Pro Pro Leu Ser Trp Glu Asn Val Thr
                325                 330                 335
Val Asp Val Asn Ser Ser Glu Lys Leu Gln Leu Gln Glu Cys Leu Trp
            340                 345                 350
Ala Asp Ser Leu Gly Pro Leu Lys Asp Asp Val Leu Leu Leu Glu Thr
            355                 360                 365
Arg Gly Pro Gln Asp Asn Arg Ser Leu Cys Ala Leu Glu Pro Ser Gly
            370                 375                 380
Cys Thr Ser Leu Pro Ser Lys Ala Ser Thr Arg Ala Ala Arg Leu Gly
385                 390                 395                 400
Glu Tyr Leu Leu Gln Asp Leu Gln Ser Gly Gln Cys Leu Gln Leu Trp
                405                 410                 415
Asp Asp Asp Leu Gly Ala Leu Trp Ala Cys Pro Met Asp Lys Tyr Ile
            420                 425                 430
His Lys Arg Trp Ala Leu Val Trp Leu Ala Cys Leu Leu Phe Ala Ala
            435                 440                 445
Ala Leu Ser Leu Ile Leu Leu Lys Lys Asp His Ala Lys Gly Trp
450                 455                 460
Leu Arg Leu Leu Lys Gln Asp Val Arg Ser Gly Ala Ala Ala Arg Gly
465                 470                 475                 480
Arg Ala Ala Leu Leu Leu Tyr Ser Ala Asp Asp Ser Gly Phe Glu Arg
                485                 490                 495
Leu Val Gly Ala Leu Ala Ser Ala Leu Cys Gln Leu Pro Leu Arg Val
            500                 505                 510
Ala Val Asp Leu Trp Ser Arg Arg Glu Leu Ser Ala Gln Gly Pro Val
            515                 520                 525
Ala Trp Phe His Ala Gln Arg Arg Gln Thr Leu Gln Glu Gly Gly Val
            530                 535                 540
Val Val Leu Leu Phe Ser Pro Gly Ala Val Ala Leu Cys Ser Glu Trp
545                 550                 555                 560
Leu Gln Asp Gly Val Ser Gly Pro Gly Ala His Gly Pro His Asp Ala
                565                 570                 575
Phe Arg Ala Ser Leu Ser Cys Val Leu Pro Asp Phe Leu Gln Gly Arg
            580                 585                 590
Ala Pro Gly Ser Tyr Val Gly Ala Cys Phe Asp Arg Leu Leu His Pro
            595                 600                 605
```

-continued

Asp Ala Val Pro Ala Leu Phe Arg Thr Val Pro Val Phe Thr Leu Pro
           610                 615                 620

Ser Gln Leu Pro Asp Phe Leu Gly Ala Leu Gln Gln Pro Arg Ala Pro
625                 630                 635                 640

Arg Ser Gly Arg Leu Gln Glu Arg Ala Glu Gln Val Ser Arg Ala Leu
                645                 650                 655

Gln Pro Ala Leu Asp Ser Tyr Phe His Pro Pro Gly Thr Pro Ala Pro
               660                 665                 670

Gly Arg Gly Val Gly Pro Gly Ala Gly Pro Gly Ala Gly Asp Gly Thr
                675                 680                 685

<210> SEQ ID NO 11
<211> LENGTH: 705
<212> TYPE: PRT
<213> ORGANISM: Artificial Sequence
<220> FEATURE:
<223> OTHER INFORMATION: Chimeric Zcytor14 protein

<400> SEQUENCE: 11

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
                20                  25                  30

Cys Ser Pro Gly Leu Ser Cys Arg Leu Trp Asp Ser Asp Ile Leu Cys
            35                  40                  45

Leu Pro Gly Asp Ile Val Pro Ala Pro Gly Pro Val Leu Ala Pro Thr
        50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro

```
            290                 295                 300
Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Lys Val Leu Glu Phe Pro Leu Leu Lys Gly His Pro Asn Leu
                340                 345                 350

Cys Val Gln Val Asn Ser Ser Glu Lys Leu Gln Leu Gln Glu Cys Leu
                355                 360                 365

Trp Ala Asp Ser Leu Gly Pro Leu Lys Asp Asp Val Leu Leu Leu Glu
                370                 375                 380

Thr Arg Gly Pro Gln Asp Asn Arg Ser Leu Cys Ala Leu Glu Pro Ser
385                 390                 395                 400

Gly Cys Thr Ser Leu Pro Ser Lys Ala Ser Thr Arg Ala Ala Arg Leu
                405                 410                 415

Gly Glu Tyr Leu Leu Gln Asp Leu Gln Ser Gly Gln Cys Leu Gln Leu
                420                 425                 430

Trp Asp Asp Asp Leu Gly Ala Leu Trp Ala Cys Pro Met Asp Lys Tyr
                435                 440                 445

Ile His Lys Arg Trp Ala Leu Val Trp Leu Ala Cys Leu Leu Phe Ala
                450                 455                 460

Ala Ala Leu Ser Leu Ile Leu Leu Leu Lys Lys Asp His Ala Lys Gly
465                 470                 475                 480

Trp Leu Arg Leu Leu Lys Gln Asp Val Arg Ser Gly Ala Ala Ala Arg
                485                 490                 495

Gly Arg Ala Ala Leu Leu Leu Tyr Ser Ala Asp Asp Ser Gly Phe Glu
                500                 505                 510

Arg Leu Val Gly Ala Leu Ala Ser Ala Leu Cys Gln Leu Pro Leu Arg
                515                 520                 525

Val Ala Val Asp Leu Trp Ser Arg Arg Glu Leu Ser Ala Gln Gly Pro
                530                 535                 540

Val Ala Trp Phe His Ala Gln Arg Arg Gln Thr Leu Gln Glu Gly Gly
545                 550                 555                 560

Val Val Val Leu Leu Phe Ser Pro Gly Ala Val Ala Leu Cys Ser Glu
                565                 570                 575

Trp Leu Gln Asp Gly Val Ser Gly Pro Gly Ala His Gly Pro His Asp
                580                 585                 590

Ala Phe Arg Ala Ser Leu Ser Cys Val Leu Pro Asp Phe Leu Gln Gly
                595                 600                 605

Arg Ala Pro Gly Ser Tyr Val Gly Ala Cys Phe Asp Arg Leu Leu His
                610                 615                 620

Pro Asp Ala Val Pro Ala Leu Phe Arg Thr Val Pro Val Phe Thr Leu
625                 630                 635                 640

Pro Ser Gln Leu Pro Asp Phe Leu Gly Ala Leu Gln Gln Pro Arg Ala
                645                 650                 655

Pro Arg Ser Gly Arg Leu Gln Glu Arg Ala Glu Gln Val Ser Arg Ala
                660                 665                 670

Leu Gln Pro Ala Leu Asp Ser Tyr Phe His Pro Pro Gly Thr Pro Ala
                675                 680                 685

Pro Gly Arg Gly Val Gly Pro Gly Ala Gly Pro Gly Ala Gly Asp Gly
                690                 695                 700

Thr
705
```

```
<210> SEQ ID NO 12
<211> LENGTH: 675
<212> TYPE: PRT
<213> ORGANISM: Artificial Sequence
<220> FEATURE:
<223> OTHER INFORMATION: Chimeric Zcytor14 protein

<400> SEQUENCE: 12

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
    290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Val Asn Ser Ser Glu Lys Leu Gln Leu Gln Glu Cys Leu Trp
            340                 345                 350

Ala Asp Ser Leu Gly Pro Leu Lys Asp Asp Val Leu Leu Leu Glu Thr
        355                 360                 365

Arg Gly Pro Gln Asp Asn Arg Ser Leu Cys Ala Leu Glu Pro Ser Gly
```

```
                370             375             380
Cys Thr Ser Leu Pro Ser Lys Ala Ser Thr Arg Ala Ala Arg Leu Gly
385                 390                 395                 400

Glu Tyr Leu Leu Gln Asp Leu Gln Ser Gly Gln Cys Leu Gln Leu Trp
                405                 410                 415

Asp Asp Asp Leu Gly Ala Leu Trp Ala Cys Pro Met Asp Lys Tyr Ile
            420                 425                 430

His Lys Arg Trp Ala Leu Val Trp Leu Ala Cys Leu Leu Phe Ala Ala
        435                 440                 445

Ala Leu Ser Leu Ile Leu Leu Lys Lys Asp His Ala Lys Ala Ala
450                 455                 460

Ala Arg Gly Arg Ala Ala Leu Leu Leu Tyr Ser Ala Asp Asp Ser Gly
465                 470                 475                 480

Phe Glu Arg Leu Val Gly Ala Leu Ala Ser Ala Leu Cys Gln Leu Pro
                485                 490                 495

Leu Arg Val Ala Val Asp Leu Trp Ser Arg Arg Glu Leu Ser Ala Gln
                500                 505                 510

Gly Pro Val Ala Trp Phe His Ala Gln Arg Arg Gln Thr Leu Gln Glu
                515                 520                 525

Gly Gly Val Val Leu Leu Phe Ser Pro Gly Ala Val Ala Leu Cys
530                 535                 540

Ser Glu Trp Leu Gln Asp Gly Val Ser Gly Pro Ala His Gly Pro
545                 550                 555                 560

His Asp Ala Phe Arg Ala Ser Leu Ser Cys Val Leu Pro Asp Phe Leu
                565                 570                 575

Gln Gly Arg Ala Pro Gly Ser Tyr Val Gly Ala Cys Phe Asp Arg Leu
            580                 585                 590

Leu His Pro Asp Ala Val Pro Ala Leu Phe Arg Thr Val Pro Val Phe
        595                 600                 605

Thr Leu Pro Ser Gln Leu Pro Asp Phe Leu Gly Ala Leu Gln Gln Pro
    610                 615                 620

Arg Ala Pro Arg Ser Gly Arg Leu Gln Glu Arg Ala Glu Gln Val Ser
625                 630                 635                 640

Arg Ala Leu Gln Pro Ala Leu Asp Ser Tyr Phe His Pro Pro Gly Thr
                645                 650                 655

Pro Ala Pro Gly Arg Gly Val Gly Pro Gly Ala Gly Pro Gly Ala Gly
            660                 665                 670

Asp Gly Thr
        675

<210> SEQ ID NO 13
<211> LENGTH: 1874
<212> TYPE: DNA
<213> ORGANISM: Homo sapiens

<400> SEQUENCE: 13
gaattccggc aggcacaaac tcatccatcc ccagttgatt ggaagaaaca acgatgactc    60
ctgggaagac ctcattggtg tcactgctac tgctgctgag cctggaggcc atagtgaagg   120
caggaatcac aatcccacga aatccaggat gcccaaattc tgaggacaag aacttccccc   180
ggactgtgat ggtcaacctg aacatccata accggaatac caataccaat cccaaaaggt   240
cctcagatta ctacaaccga tccacctcac cttggaatct ccaccgcaat gaggaccctg   300
agagatatcc ctctgtgatc tgggaggcaa agtgccgcca cttgggctgc atcaacgctg   360
atgggaacgt ggactaccac atgaactctg tccccatcca gcaagagatc ctggtcctgc   420
```

```
gcagggagcc tccacactgc cccaactcct tccggctgga gaagatactg gtgtccgtgg    480
gctgcacctg tgtcaccccg attgtccacc atgtggccta agagctctgg ggagcccaca    540
ctccccaaag cagttagact atggagagcc gacccagccc ctcaggaacc ctcatccttc    600
aaagacagcc tcatttcgga ctaaactcat tagagttctt aaggcagttt gtccaattaa    660
agcttcagag gtaacacttg gccaagatat gagatctgaa ttaccttttcc ctctttccaa    720
gaaggaaggt ttgactgagt accaatttgc ttcttgttta cttttttaag ggctttaagt    780
tatttatgta tttaatatgc cctgagataa ctttgggggta taagattcca ttttaatgaa    840
ttacctactt tattttgttt gtcttttttaa agaagataag attctgggct tgggaatttt    900
attatttaaa aggtaaaacc tgtatttatt tgagctattt aaggatctat ttatgtttaa    960
gtatttagaa aaaggtgaaa aagcactatt atcagttctg cctaggtaaa tgtaagatag   1020
aattaaatgg cagtgcaaaa tttctgagtc tttacaacat acggatatag tatttcctcc   1080
tctttgtttt taaaagttat aacatggctg aaaagaaaga ttaaacctac tttcatatgt   1140
attaatttaa attttgcaat ttgttgaggt tttacaagag atacagcaag tctaactctc   1200
tgttccatta aacccttata ataaaatcct tctgtaataa taaagtttca aaagaaaatg   1260
tttatttgtt ctcattaaat gtattttagc aaactcagct cttccctatt gggaagagtt   1320
atgcaaattc tcctataagc aaaacaaagc atgtctttga gtaacaatga cctgaaaata   1380
cccaaaattc caagttctcg atttcacatg ccttcaagac tgaacaccga ctaaggtttt   1440
catactatta gccaatgctg tagacagaag cattttgata ggaatagagc aaataagata   1500
atggccctga ggaatggcat gtcattatta aagatcatat ggggaaaatg aaaccctccc   1560
caaaatacaa gaagttctgg gaggagacat tgtcttcaga ctacaatgtc cagtttctcc   1620
cctagactca ggcttccttt ggagattaag gcccctcaga gatcaacaga ccaacatttt   1680
tctcttcctc aagcaacact cctagggcct ggcttctgtc tgatcaaggc accacacaac   1740
ccagaaagga gctgatgggg cagaatgaac tttaagtatg agaaaagttc agcccaagta   1800
aaataaaaac tcaatcacat tcaattccag agtagtttca agtttcacat cgtaaccatt   1860
ttcgcccgga attc                                                     1874
```

<210> SEQ ID NO 14
<211> LENGTH: 155
<212> TYPE: PRT
<213> ORGANISM: Homo sapiens

<400> SEQUENCE: 14

```
Met Thr Pro Gly Lys Thr Ser Leu Val Ser Leu Leu Leu Leu Ser
  1               5                  10                  15

Leu Glu Ala Ile Val Lys Ala Gly Ile Thr Ile Pro Arg Asn Pro Gly
                 20                  25                  30

Cys Pro Asn Ser Glu Asp Lys Asn Phe Pro Arg Thr Val Met Val Asn
             35                  40                  45

Leu Asn Ile His Asn Arg Asn Thr Asn Thr Pro Lys Arg Ser Ser
         50                  55                  60

Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110
```

```
Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
        130                 135                 140

Thr Cys Val Thr Pro Ile Val His His Val Ala
145                 150                 155

<210> SEQ ID NO 15
<211> LENGTH: 923
<212> TYPE: DNA
<213> ORGANISM: Homo sapiens

<400> SEQUENCE: 15
ggcttcagtt actagctagg ctactgagtt tagttctcag tttggcacct tgatacctttt      60
aggtgtgagt gttcccattt ccaggtgagg aactgaggtg caaagagaag ccctgatccc     120
ataaaaggac aggaatgctg agttccgcca gaccatgcat ctcttgctag taggtgaggc     180
gagtctctaa ctgattgcag cgtcttctat tttccaggtc aagtacttgc tgctgtcgat     240
attggggctt gcctttctga gtgaggcggc agctcggaaa atccccaaag taggacatac     300
ttttttccaa aagcctgaga gttgcccgcc tgtgccagga ggtagtatga agcttgacat     360
tggcatcatc aatgaaaacc agcgcgtttc catgtcacgt aacatcgaga gccgctccac     420
ctcccccctgg aattacactg tcacttggga ccccaaccgg taccctcgg aagttgtaca     480
ggcccagtgt aggaacttgg gctgcatcaa tgctcaagga aaggaagaca tctccatgaa     540
ttccgttccc atccagcaag agaccctggt cgtccgagg aagcaccaag gctgctctgt     600
ttcttttccag ttggagaagg tgctggtgac tgttggctgc acctgcgtca ccctgtcat     660
ccaccatgtg cagtaagagg tgcatatcca ctcagctgaa gaagctgtag aaatgccact     720
ccttacccag tgctctgcaa caagtcctgt ctgaccccca attccctcca cttcacagga     780
ctcttaataa gacctgcacg gatggaaaca taaaatattc acaatgtatg tgtgtatgta     840
ctacacttta tatttgatat ctaaaatgtt aggagaaaaa ttaatatatt cagtgctaat     900
ataataaagt attaataatg tta                                              923

<210> SEQ ID NO 16
<211> LENGTH: 153
<212> TYPE: PRT
<213> ORGANISM: Homo sapiens

<400> SEQUENCE: 16

Met Val Lys Tyr Leu Leu Leu Ser Ile Leu Gly Leu Ala Phe Leu Ser
  1               5                  10                  15

Glu Ala Ala Ala Arg Lys Ile Pro Lys Val Gly His Thr Phe Phe Gln
         20                  25                  30

Lys Pro Glu Ser Cys Pro Pro Val Pro Gly Gly Ser Met Lys Leu Asp
         35                  40                  45

Ile Gly Ile Ile Asn Glu Asn Gln Arg Val Ser Met Ser Arg Asn Ile
     50                  55                  60

Glu Ser Arg Ser Thr Ser Pro Trp Asn Tyr Thr Val Thr Trp Asp Pro
 65                  70                  75                  80

Asn Arg Tyr Pro Ser Glu Val Val Gln Ala Gln Cys Arg Asn Leu Gly
                 85                  90                  95

Cys Ile Asn Ala Gln Gly Lys Glu Asp Ile Ser Met Asn Ser Val Pro
             100                 105                 110

Ile Gln Gln Glu Thr Leu Val Val Arg Arg Lys His Gln Gly Cys Ser
        115                 120                 125
```

```
Val Ser Phe Gln Leu Glu Lys Val Leu Val Thr Val Gly Cys Thr Cys
        130                 135                 140

Val Thr Pro Val Ile His His Val Gln
145                 150
```

<210> SEQ ID NO 17
<211> LENGTH: 1172
<212> TYPE: DNA
<213> ORGANISM: Mus musculus

<400> SEQUENCE: 17

```
gatccacctc acacgaggca caagtgcacc cagcaccagc tgatcaggac gcgcaaacat    60
gagtccaggg agagcttcat ctgtgtctct gatgctgttg ctgctgctga gcctggcggc   120
tacagtgaag gcagcagcga tcatccctca agctcagcg tgtccaaaca ctgaggccaa   180
ggacttcctc cagaatgtga aggtcaacct caaagtcttt aactcccttg gcgcaaaagt   240
gagctccaga aggccctcag actacctcaa ccgttccacg tcaccctgga ctctccaccg   300
caatgaagac cctgatagat atccctctgt gatctgggaa gctcagtgcc gccaccagcg   360
ctgtgtcaat gcggagggaa agctggacca ccacatgaat tctgttctca tccagcaaga   420
gatcctggtc ctgaagaggg agcctgagag ctgccccttc actttcaggg tcgagaagat   480
gctggtgggt gtgggctgca cctgcgtggc ctcgattgtc cgccaggcag cctaaacaga   540
gacccgcggc tgaccccta gaaacccca cgtttctcag caaacttact tgcattttta   600
aaacagttcg tgctattgat tttcagcaag gaatgtggat tcagaggcag attcagaatt   660
gtctgccctc cacaatgaaa agaaggtgta aggggtccc aaactgcttc gtgtttgttt   720
ttctgtggac tttaaattat ttgtgtattt acaatatccc aagatagctt tgaagcgtaa   780
cttatttaa tgaagtatct acattattat tatgtttctt tctgaagaag acaaaattca   840
agactcagaa attttattat ttaaaaggta aagcctatat ttatatgagc tatttatgaa   900
tctatttatt tttcttcagt atttgaagta ttaagaacat gattttcaga tctacctagg   960
gaagtcctaa gtaagattaa atattaatgg aaatttcagc tttactattt gtttatttaa  1020
ggttctctcc tctgaatggg gtgaaaacca aacttagttt tatgtttaat aacttttttaa  1080
attattgaag attcaaaaaa ttggataatt tagctcccta ctctgtttta aaaaaaaatt  1140
gtaacaatat cactgtaata ataaagtttt gg                                 1172
```

<210> SEQ ID NO 18
<211> LENGTH: 158
<212> TYPE: PRT
<213> ORGANISM: Mus musculus

<400> SEQUENCE: 18

```
Met Ser Pro Gly Arg Ala Ser Ser Val Ser Leu Met Leu Leu Leu Leu
1               5                   10                  15

Leu Ser Leu Ala Ala Thr Val Lys Ala Ala Ile Ile Pro Gln Ser
            20                  25                  30

Ser Ala Cys Pro Asn Thr Glu Ala Lys Asp Phe Leu Gln Asn Val Lys
        35                  40                  45

Val Asn Leu Lys Val Phe Asn Ser Leu Gly Ala Lys Val Ser Ser Arg
    50                  55                  60

Arg Pro Ser Asp Tyr Leu Asn Arg Ser Thr Ser Pro Trp Thr Leu His
65                  70                  75                  80

Arg Asn Glu Asp Pro Asp Arg Tyr Pro Ser Val Ile Trp Glu Ala Gln
                85                  90                  95
```

```
Cys Arg His Gln Arg Cys Val Asn Ala Glu Gly Lys Leu Asp His His
            100                 105                 110

Met Asn Ser Val Leu Ile Gln Gln Glu Ile Leu Val Leu Lys Arg Glu
        115                 120                 125

Pro Glu Ser Cys Pro Phe Thr Phe Arg Val Glu Lys Met Leu Val Gly
    130                 135                 140

Val Gly Cys Thr Cys Val Ala Ser Ile Val Arg Gln Ala Ala
145                 150                 155

<210> SEQ ID NO 19
<211> LENGTH: 462
<212> TYPE: DNA
<213> ORGANISM: Mus musculus

<400> SEQUENCE: 19
atggtcaagt ctttgctact gttgatgttg ggacttgcca ttctgaggga ggtagcagct     60
cggaagaacc ccaaagcagg ggttcctgcc ttgcagaagg ctgggaactg tcctcccctg    120
gaggataaca ctgtgagagt tgacattcga atcttcaacc aaaaccaggg catttctgtc    180
ccacgtgaat tccagaaccg ctccagttcc ccatgggatt acaacatcac tcgagacccc    240
caccggttcc cctcagagat cgctgaggcc cagtgcagac actcaggctg catcaatgcc    300
cagggtcagg aagacagcac catgaactcc gtcgccattc agcaagaaat cctggtcctt    360
cggagggagc cccagggctg ttctaattcc ttcaggttgg agaagatgct cctaaaagtt    420
ggctgcacct gtgtcaagcc cattgtccac caagcggcct ga                      462

<210> SEQ ID NO 20
<211> LENGTH: 153
<212> TYPE: PRT
<213> ORGANISM: Mus musculus

<400> SEQUENCE: 20

Met Val Lys Ser Leu Leu Leu Met Leu Gly Leu Ala Ile Leu Arg
 1               5                  10                  15

Glu Val Ala Ala Arg Lys Asn Pro Lys Ala Gly Val Pro Ala Leu Gln
            20                  25                  30

Lys Ala Gly Asn Cys Pro Pro Leu Glu Asp Asn Thr Val Arg Val Asp
        35                  40                  45

Ile Arg Ile Phe Asn Gln Asn Gln Gly Ile Ser Val Pro Arg Glu Phe
    50                  55                  60

Gln Asn Arg Ser Ser Ser Pro Trp Asp Tyr Asn Ile Thr Arg Asp Pro
65                  70                  75                  80

His Arg Phe Pro Ser Glu Ile Ala Glu Ala Gln Cys Arg His Ser Gly
                85                  90                  95

Cys Ile Asn Ala Gln Gly Gln Glu Asp Ser Thr Met Asn Ser Val Ala
            100                 105                 110

Ile Gln Gln Glu Ile Leu Val Leu Arg Arg Glu Pro Gln Gly Cys Ser
        115                 120                 125

Asn Ser Phe Arg Leu Glu Lys Met Leu Leu Lys Val Gly Cys Thr Cys
    130                 135                 140

Val Lys Pro Ile Val His Gln Ala Ala
145                 150

<210> SEQ ID NO 21
<211> LENGTH: 320
<212> TYPE: PRT
<213> ORGANISM: Homo sapien
```

<400> SEQUENCE: 21

Met Gly Ala Ala Arg Ser Pro Pro Ser Ala Val Gly Pro Leu Leu
1               5                   10                  15

Gly Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
130                 135                 140

Thr Phe Ser His Phe Val Val Asp Pro Asp Gln Glu Tyr Glu Val Thr
145                 150                 155                 160

Val His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

<210> SEQ ID NO 22
<211> LENGTH: 221
<212> TYPE: PRT
<213> ORGANISM: Homo sapien

<400> SEQUENCE: 22

Lys Pro Arg Trp His Lys Asn Leu Thr Gly Pro Gln Ile Ile Thr Leu
1               5                   10                  15

Asn His Thr Asp Leu Val Pro Cys Leu Cys Ile Gln Val Trp Pro Leu
            20                  25                  30

Glu Pro Asp Ser Val Arg Thr Asn Ile Cys Pro Phe Arg Glu Asp Pro
        35                  40                  45

```
Arg Ala His Gln Asn Leu Trp Gln Ala Ala Arg Leu Arg Leu Leu Thr
 50                  55                  60

Leu Gln Ser Trp Leu Leu Asp Ala Pro Cys Ser Leu Pro Ala Glu Ala
 65                  70                  75                  80

Ala Leu Cys Trp Arg Ala Pro Gly Gly Asp Pro Cys Gln Pro Leu Val
                 85                  90                  95

Pro Pro Leu Ser Trp Glu Asn Val Thr Val Asp Lys Val Leu Glu Phe
            100                 105                 110

Pro Leu Leu Lys Gly His Pro Asn Leu Cys Val Gln Val Asn Ser Ser
            115                 120                 125

Glu Lys Leu Gln Leu Gln Glu Cys Leu Trp Ala Asp Ser Leu Gly Pro
130                 135                 140

Leu Lys Asp Asp Val Leu Leu Glu Thr Arg Gly Pro Gln Asp Asn
145                 150                 155                 160

Arg Ser Leu Cys Ala Leu Glu Pro Ser Gly Cys Thr Ser Leu Pro Ser
                165                 170                 175

Lys Ala Ser Thr Arg Ala Ala Arg Leu Gly Glu Tyr Leu Leu Gln Asp
            180                 185                 190

Leu Gln Ser Gly Gln Cys Leu Gln Leu Trp Asp Asp Leu Gly Ala
            195                 200                 205

Leu Trp Ala Cys Pro Met Asp Lys Tyr Ile His Lys Arg
210                 215                 220

<210> SEQ ID NO 23
<211> LENGTH: 2180
<212> TYPE: DNA
<213> ORGANISM: Homo sapien

<400> SEQUENCE: 23
aactacccag cacagccccc tccgcccccct ctggaggctg aagagggatt ccagcccctg      60
ccacccacag acacgggctg actggggtgt ctgcccccct tggggggggg cagcacaggg     120
cctcaggcct gggtgccacc tggcacctag aagatgcctg tgccctggtt cttgctgtcc     180
ttggcactgg gccgaagccc agtggtcctt tctctggaga ggcttgtggg gcctcaggac     240
gctacccact gctctccggg cctctcctgc cgcctctggg acagtgacat actctgcctg     300
cctggggaca tcgtgcctgc tccgggcccc gtgctggcgc tacgcacct gcagacagag      360 ctggtgctga ggtgccagaa ggagaccgac tgtgacctct gtctgcgtgt ggctgtccac     420
ttggccgtgc atgcctctct ccaggcccaa gtcgtgctct ccttccaggc ctaccctact     480
gcccgctgcg tcctgctgga ggtgcaagtg cctgctgccc ttgtgcagtt tggtcagtct     540
gtgggctctg tggtatatga ctgcttcgag gctgccctag ggagtgaggt acgaatctgg     600
tcctatactc agcccaggta cgagaaggaa ctcaaccaca cacagcagct gcctgccctg     660
ccctggctca acgtgtcagc agatggtgac aacgtgcatc tggttctgaa tgtctctgag     720
gagcagcact tcggcctctc cctgtactgg aatcaggtcc agggcccccc aaaaccccgg     780
tggcacaaaa acctgactgg accgcagatc attaccttga ccacacaga cctggttccc     840 tgcctctgta ttcaggtgtg gcctctgaa cctgactccg ttaggacgaa catctgcccc      900 ttcaggagg accccgcgc acaccagaac ctctggcaag ccgcccgact gcgactgctg       960
accctgcaga gctggctgct ggacgcaccg tgctcgctgc ccgcagaagc ggcactgtgc    1020
tggcgggctc cgggtgggga ccctgccag ccactggtcc accgcttc ctgggagaac      1080 gtcactgtgg acaaggttct cgagttccca ttgctgaaag gccaccctaa cctctgtgtt    1140
caggtgaaca gctcggagaa gctgcagctg caggagtgct gtgtgggctga ctccctgggg    1200
```

-continued

```
cctctcaaag acgatgtgct actgttggag acacgaggcc cccaggacaa cagatccctc    1260
tgtgccttgg aacccagtgg ctgtacttca ctacccagca aagcctccac gagggcagct    1320
cgccttggag agtacttact acaagacctg cagtcaggcc agtgtctgca gctatgggac    1380
gatgacttgg gagcgctatg ggcctgcccc atggacaaat acatccacaa gcgctgggcc    1440
ctcgtgtggc tggcctgcct actctttgcc gctgcgcttt ccctcatcct ccttctcaaa    1500
aaggatcacg cgaaagcggc cgccaggggc cgcgcggctc tgctcctcta ctcagccgat    1560
gactcgggtt tcgagcgcct ggtgggcgcc ctggcgtcgg ccctgtgcca gctgccgctg    1620
cgcgtggccg tagacctgtg gagccgtcgt gaactgagcg cgcaggggcc cgtggcttgg    1680
tttcacgcgc agcggcgcca gaccctgcag gagggcggcg tggtggtctt gctcttctct    1740
cccggtgcgg tggcgctgtg cagcgagtgg ctacaggatg gggtgtccgg gcccggggcg    1800
cacggcccgc acgacgcctt ccgcgcctcg ctcagctgcg tgctgcccga cttcttgcag    1860
ggccgggcgc ccggcagcta cgtggggggcc tgcttcgaca ggctgctcca cccggacgcc    1920
gtacccgccc ttttccgcac cgtgcccgtc ttcacactgc cctcccaact gccagacttc    1980
ctgggggccc tgcagcagcc tcgcgccccg cgttccgggc ggctccaaga gagagcggag    2040
caagtgtccc gggcccttca gccagccctg gatagctact ccatccccc ggggactccc    2100 gcgccgggac gcggggtggg accagggggcg ggacctgggg cggggacgg gacttaaata    2160 aaggcagacg ctgttttct                                                 2180
```

<210> SEQ ID NO 24
<211> LENGTH: 667
<212> TYPE: PRT
<213> ORGANISM: Homo sapien

<400> SEQUENCE: 24

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
                 20                  25                  30

Cys Ser Pro Gly Leu Ser Cys Arg Leu Trp Asp Ser Asp Ile Leu Cys
             35                  40                  45

Leu Pro Gly Asp Ile Val Pro Ala Pro Gly Pro Val Leu Ala Pro Thr
         50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Ala Ser Leu
                 85                  90                  95

Gln Ala Gln Val Val Leu Ser Phe Gln Ala Tyr Pro Thr Ala Arg Cys
            100                 105                 110

Val Leu Leu Glu Val Gln Val Pro Ala Ala Leu Val Gln Phe Gly Gln
        115                 120                 125

Ser Val Gly Ser Val Val Tyr Asp Cys Phe Glu Ala Ala Leu Gly Ser
    130                 135                 140

Glu Val Arg Ile Trp Ser Tyr Thr Gln Pro Arg Tyr Glu Lys Glu Leu
145                 150                 155                 160

Asn His Thr Gln Gln Leu Pro Ala Leu Pro Trp Leu Asn Val Ser Ala
                165                 170                 175

Asp Gly Asp Asn Val His Leu Val Leu Asn Val Ser Glu Glu Gln His
            180                 185                 190

Phe Gly Leu Ser Leu Tyr Trp Asn Gln Val Gln Gly Pro Pro Lys Pro
```

-continued

```
            195                 200                 205
Arg Trp His Lys Asn Leu Thr Gly Pro Gln Ile Ile Thr Leu Asn His
    210                 215                 220

Thr Asp Leu Val Pro Cys Leu Cys Ile Gln Val Trp Pro Leu Glu Pro
225                 230                 235                 240

Asp Ser Val Arg Thr Asn Ile Cys Pro Phe Arg Glu Asp Pro Arg Ala
                245                 250                 255

His Gln Asn Leu Trp Gln Ala Ala Arg Leu Arg Leu Leu Thr Leu Gln
            260                 265                 270

Ser Trp Leu Leu Asp Ala Pro Cys Ser Leu Pro Ala Glu Ala Ala Leu
    275                 280                 285

Cys Trp Arg Ala Pro Gly Gly Asp Pro Cys Gln Pro Leu Val Pro Pro
    290                 295                 300

Leu Ser Trp Glu Asn Val Thr Val Asp Lys Val Leu Glu Phe Pro Leu
305                 310                 315                 320

Leu Lys Gly His Pro Asn Leu Cys Val Gln Val Asn Ser Ser Glu Lys
                325                 330                 335

Leu Gln Leu Gln Glu Cys Leu Trp Ala Asp Ser Leu Gly Pro Leu Lys
            340                 345                 350

Asp Asp Val Leu Leu Glu Thr Arg Gly Pro Gln Asp Asn Arg Ser
    355                 360                 365

Leu Cys Ala Leu Glu Pro Ser Gly Cys Thr Ser Leu Pro Ser Lys Ala
    370                 375                 380

Ser Thr Arg Ala Ala Arg Leu Gly Glu Tyr Leu Leu Gln Asp Leu Gln
385                 390                 395                 400

Ser Gly Gln Cys Leu Gln Leu Trp Asp Asp Leu Gly Ala Leu Trp
                405                 410                 415

Ala Cys Pro Met Asp Lys Tyr Ile His Lys Arg Trp Ala Leu Val Trp
            420                 425                 430

Leu Ala Cys Leu Leu Phe Ala Ala Ala Leu Ser Leu Ile Leu Leu Leu
    435                 440                 445

Lys Lys Asp His Ala Lys Ala Ala Ala Arg Gly Arg Ala Ala Leu Leu
    450                 455                 460

Leu Tyr Ser Ala Asp Asp Ser Gly Phe Glu Arg Leu Val Gly Ala Leu
465                 470                 475                 480

Ala Ser Ala Leu Cys Gln Leu Pro Leu Arg Val Ala Val Asp Leu Trp
                485                 490                 495

Ser Arg Arg Glu Leu Ser Ala Gln Gly Pro Val Ala Trp Phe His Ala
            500                 505                 510

Gln Arg Arg Gln Thr Leu Gln Glu Gly Gly Val Val Val Leu Leu Phe
    515                 520                 525

Ser Pro Gly Ala Val Ala Leu Cys Ser Glu Trp Leu Gln Asp Gly Val
530                 535                 540

Ser Gly Pro Gly Ala His Gly Pro His Asp Ala Phe Arg Ala Ser Leu
545                 550                 555                 560

Ser Cys Val Leu Pro Asp Phe Leu Gln Gly Arg Ala Pro Gly Ser Tyr
                565                 570                 575

Val Gly Ala Cys Phe Asp Arg Leu Leu His Pro Asp Ala Val Pro Ala
            580                 585                 590

Leu Phe Arg Thr Val Pro Val Phe Thr Leu Pro Ser Gln Leu Pro Asp
    595                 600                 605

Phe Leu Gly Ala Leu Gln Gln Pro Arg Ala Pro Arg Ser Gly Arg Leu
    610                 615                 620
```

| Gln | Glu | Arg | Ala | Glu | Gln | Val | Ser | Arg | Ala | Leu | Gln | Pro | Ala | Leu | Asp |
| 625 | | | | 630 | | | | | 635 | | | | | 640 | |

| Ser | Tyr | Phe | His | Pro | Pro | Gly | Thr | Pro | Ala | Pro | Gly | Arg | Gly | Val | Gly |
| | | | | 645 | | | | | 650 | | | | | 655 | |

| Pro | Gly | Ala | Gly | Pro | Gly | Ala | Gly | Asp | Gly | Thr |
| | 660 | | | | | 665 | | | | |

<210> SEQ ID NO 25
<211> LENGTH: 2269
<212> TYPE: DNA
<213> ORGANISM: Mus musculus

<400> SEQUENCE: 25

| aaatcgaaag cactccagct gaaactgggc ctggagtcca ggctcactgg agtggggaag | 60 |
| catggctgga gaggaattct agcccttgct ctctcccagg acacggggc tgattgtcag | 120 |
| caggggcgag gggtctgccc ccccttgggg gggcaggacg gggcctcagg cctgggtgct | 180 |
| gtccggcacc tggaagatgc ctgtgtcctg gttcctgctg tccttggcac tgggccgaaa | 240 |
| ccctgtggtc gtctctctgg agagactgat ggagcctcag acactgcac gctgctctct | 300 |
| aggcctctcc tgccacctct gggatggtga cgtgctctgc ctgcctggaa gcctccagtc | 360 |
| tgccccaggc cctgtgctag tgcctacccg cctgcagacg gagctggtgc tgaggtgtcc | 420 |
| acagaagaca gattgcgccc tctgtgtccg tgtggtggtc cacttggccg tgcatgggca | 480 |
| ctgggcagag cctgaagaag ctggaaagtc tgattcagaa ctccaggagt ctaggaacgc | 540 |
| ctctctccag gcccaggtgg tgctctcctt ccaggcctac cccatcgccc gctgtgccct | 600 |
| gctggaggtc caggtgcccg ctgacctggt gcagcctggt cagtccgtgg gttctgcggt | 660 |
| atttgactgt ttcgaggcta gtcttggggc tgaggtacag atctggtcct acacgaagcc | 720 |
| caggtaccag aaagagctca acctcacaca gcagctgcct gtcctgccct ggctcaatgt | 780 |
| gtctacagat ggtgacaatg tccttctgac actggatgtc tctgaggagc aggactttag | 840 |
| cttcttactg tacctgcgtc cagtcccgga tgctctcaaa tccttgtggt acaaaaacct | 900 |
| gactggacct cagaacatta ctttaaacca cacagacctg gttccctgcc tctgcattca | 960 |
| ggtgtggtcg ctagagccag actctgagag ggtcgaattc tgccccttcc gggaagatcc | 1020 |
| cggtgcacac aggaacctct ggcacatagc caggctgcgg gtactgtccc caggggtatg | 1080 |
| gcagctagat gcgccttgct gtcctgccgg gcaaggtaaca ctgtgctggc aggcaccaga | 1140 |
| ccagagtccc tgccagccac ttgtgccacc agtgccccag aagaacgcca ctgtgaatga | 1200 |
| gccacaagat ttccagttgg tggcaggcca ccccaacctc tgtgtccagg tgagcacctg | 1260 |
| ggagaaggtt cagctgcaag cgtgcttgtg ggctgactcc ttggggccct tcaaggatga | 1320 |
| tatgctgtta gtggagatga aaaccggcct caacaacaca tcagtctgtg ccttggaacc | 1380 |
| cagtggctgt acaccactgc ccagcatggc ctccacgaga gctgctcgcc tgggagagga | 1440 |
| gttgctgcaa gacttccgat cacaccagtg tatgcagctg tggaacgatg acaacatggg | 1500 |
| atcgctatgg gcctgcccca tggacaagta catccacagg cgctgggtcc tagtatggct | 1560 |
| ggcctgccta ctcttggctg cggcgctttt cttcttcctc cttctaaaaa aggaccgcag | 1620 |
| gaaagcggcc cgtggctccc gcacggcctt gctcctccac tccgccgacg agcgggcta | 1680 |
| cgagcgtctg tgggagcac tggcgtccgc gttgagccaa atgccactgc gcgtggccgt | 1740 |
| ggacctgtgg agccgccgcg agctgagcgc gcacggagcc ctagcctggt tccaccacca | 1800 |
| gcgacgccgt atcctgcagg agggtggcgt ggtaatcctt ctcttctcgc ccgcggccgt | 1860 |
| ggcgcagtgt cagcagtggc tgcagctcca gacagtggag cccggccgc atgacgccct | 1920 |

```
cgccgcctgg ctcagctgcg tgctacccga tttcctgcaa ggccgggcga ccggccgcta    1980
cgtcggggtc tacttcgacg ggctgctgca cccagactct gtgccctccc cgttccgcgt    2040
cgccccgctc ttctccctgc cctcgcagct gccggctttc ctggatgcac tgcagggagg    2100
ctgctccact tccgcggggc gacccgcgga ccgggtggaa cgagtgaccc aggcgctgcg    2160
gtccgccctg gacagctgta cttctagctc ggaagcccca ggctgctgcg aggaatggga    2220
cctgggaccc tgcactacac tagaataaaa gccgatacag tattcctaa                2269
```

<210> SEQ ID NO 26
<211> LENGTH: 683
<212> TYPE: PRT
<213> ORGANISM: Mus musculus

<400> SEQUENCE: 26

```
Met Pro Val Ser Trp Phe Leu Leu Ser Leu Ala Leu Gly Arg Asn Pro
 1               5                  10                  15

Val Val Val Ser Leu Glu Arg Leu Met Glu Pro Gln Asp Thr Ala Arg
                20                  25                  30

Cys Ser Leu Gly Leu Ser Cys His Leu Trp Asp Gly Asp Val Leu Cys
            35                  40                  45

Leu Pro Gly Ser Leu Gln Ser Ala Pro Gly Pro Val Leu Val Pro Thr
        50                  55                  60

Arg Leu Gln Thr Glu Leu Val Leu Arg Cys Pro Gln Lys Thr Asp Cys
65                  70                  75                  80

Ala Leu Cys Val Arg Val Val Val His Leu Ala Val His Gly His Trp
                85                  90                  95

Ala Glu Pro Glu Glu Ala Gly Lys Ser Asp Ser Glu Leu Gln Glu Ser
            100                 105                 110

Arg Asn Ala Ser Leu Gln Ala Gln Val Val Leu Ser Phe Gln Ala Tyr
        115                 120                 125

Pro Ile Ala Arg Cys Ala Leu Leu Glu Val Gln Val Pro Ala Asp Leu
    130                 135                 140

Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Val Leu Pro Trp
            180                 185                 190

Leu Asn Val Ser Thr Asp Gly Asp Asn Val Leu Leu Thr Leu Asp Val
        195                 200                 205

Ser Glu Glu Gln Asp Phe Ser Phe Leu Leu Tyr Leu Arg Pro Val Pro
    210                 215                 220

Asp Ala Leu Lys Ser Leu Trp Tyr Lys Asn Leu Thr Gly Pro Gln Asn
225                 230                 235                 240

Ile Thr Leu Asn His Thr Asp Leu Val Pro Cys Leu Cys Ile Gln Val
                245                 250                 255

Trp Ser Leu Glu Pro Asp Ser Glu Arg Val Glu Phe Cys Pro Phe Arg
            260                 265                 270

Glu Asp Pro Gly Ala His Arg Asn Leu Trp His Ile Ala Arg Leu Arg
        275                 280                 285

Val Leu Ser Pro Gly Val Trp Gln Leu Asp Ala Pro Cys Cys Leu Pro
    290                 295                 300

Gly Lys Val Thr Leu Cys Trp Gln Ala Pro Asp Gln Ser Pro Cys Gln
305                 310                 315                 320
```

```
Pro Leu Val Pro Pro Val Pro Gln Lys Asn Ala Thr Val Asn Glu Pro
                325                 330                 335

Gln Asp Phe Gln Leu Val Ala Gly His Pro Asn Leu Cys Val Gln Val
            340                 345                 350

Ser Thr Trp Glu Lys Val Gln Leu Gln Ala Cys Leu Trp Ala Asp Ser
        355                 360                 365

Leu Gly Pro Phe Lys Asp Asp Met Leu Leu Val Glu Met Lys Thr Gly
    370                 375                 380

Leu Asn Asn Thr Ser Val Cys Ala Leu Glu Pro Ser Gly Cys Thr Pro
385                 390                 395                 400

Leu Pro Ser Met Ala Ser Thr Arg Ala Ala Arg Leu Gly Glu Glu Leu
            405                 410                 415

Leu Gln Asp Phe Arg Ser His Gln Cys Met Gln Leu Trp Asn Asp Asp
        420                 425                 430

Asn Met Gly Ser Leu Trp Ala Cys Pro Met Asp Lys Tyr Ile His Arg
    435                 440                 445

Arg Trp Val Leu Val Trp Leu Ala Cys Leu Leu Leu Ala Ala Ala Leu
450                 455                 460

Phe Phe Phe Leu Leu Leu Lys Lys Asp Arg Arg Lys Ala Ala Arg Gly
465                 470                 475                 480

Ser Arg Thr Ala Leu Leu His Ser Ala Asp Gly Ala Gly Tyr Glu
            485                 490                 495

Arg Leu Val Gly Ala Leu Ala Ser Ala Leu Ser Gln Met Pro Leu Arg
        500                 505                 510

Val Ala Val Asp Leu Trp Ser Arg Arg Glu Leu Ser Ala His Gly Ala
    515                 520                 525

Leu Ala Trp Phe His His Gln Arg Arg Ile Leu Gln Glu Gly Gly
    530                 535                 540

Val Val Ile Leu Leu Phe Ser Pro Ala Ala Val Ala Gln Cys Gln Gln
545                 550                 555                 560

Trp Leu Gln Leu Gln Thr Val Glu Pro Gly Pro His Asp Ala Leu Ala
            565                 570                 575

Ala Trp Leu Ser Cys Val Leu Pro Asp Phe Leu Gln Gly Arg Ala Thr
        580                 585                 590

Gly Arg Tyr Val Gly Val Tyr Phe Asp Gly Leu Leu His Pro Asp Ser
    595                 600                 605

Val Pro Ser Pro Phe Arg Val Ala Pro Leu Phe Ser Leu Pro Ser Gln
    610                 615                 620

Leu Pro Ala Phe Leu Asp Ala Leu Gln Gly Gly Cys Ser Thr Ser Ala
625                 630                 635                 640

Gly Arg Pro Ala Asp Arg Val Glu Arg Val Thr Gln Ala Leu Arg Ser
            645                 650                 655

Ala Leu Asp Ser Cys Thr Ser Ser Glu Ala Pro Gly Cys Cys Glu
        660                 665                 670

Glu Trp Asp Leu Gly Pro Cys Thr Thr Leu Glu
    675                 680

<210> SEQ ID NO 27
<211> LENGTH: 449
<212> TYPE: PRT
<213> ORGANISM: Mus musculus

<400> SEQUENCE: 27

Met Pro Val Ser Trp Phe Leu Leu Ser Leu Ala Leu Gly Arg Asn Pro
1               5                   10                  15
```

```
Val Val Val Ser Leu Glu Arg Leu Met Glu Pro Gln Asp Thr Ala Arg
            20                  25                  30

Cys Ser Leu Gly Leu Ser Cys His Leu Trp Asp Gly Asp Val Leu Cys
            35                  40                  45

Leu Pro Gly Ser Leu Gln Ser Ala Pro Gly Pro Val Leu Val Pro Thr
 50                      55                      60

Arg Leu Gln Thr Glu Leu Val Leu Arg Cys Pro Gln Lys Thr Asp Cys
 65              70                  75                      80

Ala Leu Cys Val Arg Val Val His Leu Ala Val His Gly His Trp
                85                  90                  95

Ala Glu Pro Glu Glu Ala Gly Lys Ser Asp Ser Glu Leu Gln Glu Ser
            100                 105                 110

Arg Asn Ala Ser Leu Gln Ala Gln Val Val Leu Ser Phe Gln Ala Tyr
            115                 120                 125

Pro Ile Ala Arg Cys Ala Leu Leu Glu Val Gln Val Pro Ala Asp Leu
 130                     135                 140

Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Val Leu Pro Trp
            180                 185                 190

Leu Asn Val Ser Thr Asp Gly Asp Asn Val Leu Thr Leu Asp Val
            195                 200                 205

Ser Glu Glu Gln Asp Phe Ser Phe Leu Leu Tyr Leu Arg Pro Val Pro
            210                 215                 220

Asp Ala Leu Lys Ser Leu Trp Tyr Lys Asn Leu Thr Gly Pro Gln Asn
225                 230                 235                 240

Ile Thr Leu Asn His Thr Asp Leu Val Pro Cys Leu Cys Ile Gln Val
                245                 250                 255

Trp Ser Leu Glu Pro Asp Ser Glu Arg Val Glu Phe Cys Pro Phe Arg
            260                 265                 270

Glu Asp Pro Gly Ala His Arg Asn Leu Trp His Ile Ala Arg Leu Arg
            275                 280                 285

Val Leu Ser Pro Gly Val Trp Gln Leu Asp Ala Pro Cys Cys Leu Pro
            290                 295                 300

Gly Lys Val Thr Leu Cys Trp Gln Ala Pro Asp Gln Ser Pro Cys Gln
305                 310                 315                 320

Pro Leu Val Pro Pro Val Pro Gln Lys Asn Ala Thr Val Asn Glu Pro
                325                 330                 335

Gln Asp Phe Gln Leu Val Ala Gly His Pro Asn Leu Cys Val Gln Val
            340                 345                 350

Ser Thr Trp Glu Lys Val Gln Leu Gln Ala Cys Leu Trp Ala Asp Ser
            355                 360                 365

Leu Gly Pro Phe Lys Asp Asp Met Leu Leu Val Glu Met Lys Thr Gly
 370                 375                 380

Leu Asn Asn Thr Ser Val Cys Ala Leu Glu Pro Ser Gly Cys Thr Pro
385                 390                 395                 400

Leu Pro Ser Met Ala Ser Thr Arg Ala Ala Arg Leu Gly Glu Glu Leu
                405                 410                 415

Leu Gln Asp Phe Arg Ser His Gln Cys Met Gln Leu Trp Asn Asp Asp
            420                 425                 430

Asn Met Gly Ser Leu Trp Ala Cys Pro Met Asp Lys Tyr Ile His Arg
```

435             440             445
Arg

<210> SEQ ID NO 28
<211> LENGTH: 222
<212> TYPE: PRT
<213> ORGANISM: Mus musculus

<400> SEQUENCE: 28

Lys Ser Leu Trp Tyr Lys Asn Leu Thr Gly Pro Gln Asn Ile Thr Leu
1               5                   10                  15

Asn His Thr Asp Leu Val Pro Cys Leu Cys Ile Gln Val Trp Ser Leu
            20                  25                  30

Glu Pro Asp Ser Glu Arg Val Glu Phe Cys Pro Phe Arg Glu Asp Pro
        35                  40                  45

Gly Ala His Arg Asn Leu Trp His Ile Ala Arg Leu Arg Val Leu Ser
    50                  55                  60

Pro Gly Val Trp Gln Leu Asp Ala Pro Cys Cys Leu Pro Gly Lys Val
65                  70                  75                  80

Thr Leu Cys Trp Gln Ala Pro Asp Gln Ser Pro Cys Gln Pro Leu Val
                85                  90                  95

Pro Pro Val Pro Gln Lys Asn Ala Thr Val Asn Glu Pro Gln Asp Phe
            100                 105                 110

Gln Leu Val Ala Gly His Pro Asn Leu Cys Val Gln Val Ser Thr Trp
        115                 120                 125

Glu Lys Val Gln Leu Gln Ala Cys Leu Trp Ala Asp Ser Leu Gly Pro
    130                 135                 140

Phe Lys Asp Asp Met Leu Leu Val Glu Met Lys Thr Gly Leu Asn Asn
145                 150                 155                 160

Thr Ser Val Cys Ala Leu Glu Pro Ser Gly Cys Thr Pro Leu Pro Ser
                165                 170                 175

Met Ala Ser Thr Arg Ala Ala Arg Leu Gly Glu Glu Leu Leu Gln Asp
            180                 185                 190

Phe Arg Ser His Gln Cys Met Gln Leu Trp Asn Asp Asp Asn Met Gly
        195                 200                 205

Ser Leu Trp Ala Cys Pro Met Asp Lys Tyr Ile His Arg Arg
    210                 215                 220

<210> SEQ ID NO 29
<211> LENGTH: 2287
<212> TYPE: DNA
<213> ORGANISM: Mus musculus

<400> SEQUENCE: 29
aaatcgaaag cactccagct gaaactgggc ctggagtcca ggctcactgg agtggggaag      60
catggctgga gaggaattct agcccttgct ctctcccagg acacggggc tgattgtcag     120 caggggcgag gggtctgccc cccttgggg gggcaggacg gggcctcagg cctgggtgct     180
gtccggcacc tggaagatgc ctgtgtcctg gttcctgctg tccttggcac tgggccgaaa     240
ccctgtggtc gtctctctgg agagactgat ggagcctcag acactgcac gctgctctct     300 aggcctctcc tgccacctct gggatggtga cgtgctctgc ctgcctggaa gcctccagtc     360
tgccccaggc cctgtgctag tgcctacccg cctgcagacg gagctggtgc tgaggtgtcc     420
acagaagaca gattgcgccc tctgtgtccg tgtggtggtc cacttggccg tgcatgggca     480
ctgggcagag cctgaagaag ctggaaagtc tgattcagaa ctccaggagt ctaggaacgc     540

```
ctctctccag gcccaggtgg tgctctcctt ccaggcctac cccatcgccc gctgtgccct    600
gctggaggtc caggtgcccg ctgacctggt gcagcctggt cagtccgtgg gttctgcggt    660
atttgactgt ttcgaggcta gtcttggggc tgaggtacag atctggtcct acacgaagcc    720
caggtaccag aaagagctca acctcacaca gcagctgcct gactgcaggg gtcttgaagt    780
ccgggacagc atccagagct gctgggatgg tgacaatgtc cttctgacac tggatgtctc    840
tgaggagcag gactttagct tcttactgta cctgcgtcca gtcccggatg ctctcaaatc    900
cttgtggtac aaaaacctga ctggacctca gaacattact ttaaaccaca cagacctggt    960
tccctgcctc tgcattcagg tgtggtcgct agagccagac tctgagaggg tcgaattctg   1020
ccccttccgg gaagatcccg gtgcacacag gaacctctgg cacatagcca ggctgcgggt   1080
actgtcccca ggggtatggc agctagatgc gccttgctgt ctgccgggca aggtaacact   1140
gtgctggcag gcaccagacc agagtccctg ccagccactt gtgccaccag tgccccagaa   1200
gaacgccact gtgaatgagc acaagatttc cagttggtg gcaggccacc ccaacctctg    1260
tgtccaggtg agcacctggg agaaggttca gctgcaagcg tgcttgtggg ctgactcctt   1320
ggggcccttc aaggatgata tgctgttagt ggagatgaaa accggcctca caacacatc    1380
agtctgtgcc ttggaaccca gtggctgtac accactgccc agcatggcct ccacgagagc   1440
tgctcgcctg ggagaggagt tgctgcaaga cttccgatca caccagtgta tgcagctgtg   1500
gaacgatgac aacatgggat cgctatgggc ctgccccatg acaagtaca tccacaggcg    1560
ctgggtccta gtatgctgg cctgcctact cttggctgcg cgcttttct tcttcctcct    1620
tctaaaaaag gaccgcagga aagcggcccg tggctcccgc acggccttgc tcctccactc   1680
cgccgacgga gcgggctacg agcgtctggt gggagcactg gcgtccgcgt tgagccagat   1740
gccactgcgc gtggccgtgg acctgtggag ccgccgcgag ctgagcgcgc acggagccct   1800
agcctggttc caccaccagc gacgccgtat cctgcaggag ggtggcgtgg taatccttct   1860
cttctcgccc gcgggccgtg cgcagtgtca gcagtggctg cagctccaga cagtggagcc   1920
cgggccgcat gacgccctcg ccgcctggct cagctgcgtg ctacccgatt tcctgcaagg   1980
ccgggcgacc ggccgctacg tcggggtcta cttcgacggg ctgctgcacc agactctgt   2040
gccctccccg ttccgcgtcg ccccgctctt ctccctgccc tcgcagctgc cggcttttcct   2100
ggatgcactg cagggaggct gctccacttc cgcggggcga cccgcggacc gggtggaacg   2160
agtgacccag gcgctgcggt ccgccctgga cagctgtact tctagctcgg aagccccagg   2220
ctgctgcgag gaatgggacc tgggaccctg cactacacta gaataaaagc cgatacagta   2280
ttcctaa                                                              2287
```

<210> SEQ ID NO 30
<211> LENGTH: 689
<212> TYPE: PRT
<213> ORGANISM: Mus musculus

<400> SEQUENCE: 30

```
Met Pro Val Ser Trp Phe Leu Leu Ser Leu Ala Leu Gly Arg Asn Pro
 1               5                  10                  15

Val Val Val Ser Leu Glu Arg Leu Met Glu Pro Gln Asp Thr Ala Arg
            20                  25                  30

Cys Ser Leu Gly Leu Ser Cys His Leu Trp Asp Gly Asp Val Leu Cys
        35                  40                  45

Leu Pro Gly Ser Leu Gln Ser Ala Pro Gly Pro Val Leu Val Pro Thr
    50                  55                  60
```

```
Arg Leu Gln Thr Glu Leu Val Leu Arg Cys Pro Gln Lys Thr Asp Cys
 65                  70                  75                  80

Ala Leu Cys Val Arg Val Val His Leu Ala Val His Gly His Trp
                 85                  90                  95

Ala Glu Pro Glu Glu Ala Gly Lys Ser Asp Ser Glu Leu Gln Glu Ser
            100                 105                 110

Arg Asn Ala Ser Leu Gln Ala Gln Val Val Leu Ser Phe Gln Ala Tyr
        115                 120                 125

Pro Ile Ala Arg Cys Ala Leu Leu Glu Val Gln Val Pro Ala Asp Leu
    130                 135                 140

Val Gln Pro Gly Gln Ser Val Gly Ser Ala Val Phe Asp Cys Phe Glu
145                 150                 155                 160

Ala Ser Leu Gly Ala Glu Val Gln Ile Trp Ser Tyr Thr Lys Pro Arg
                165                 170                 175

Tyr Gln Lys Glu Leu Asn Leu Thr Gln Gln Leu Pro Asp Cys Arg Gly
            180                 185                 190

Leu Glu Val Arg Asp Ser Ile Gln Ser Cys Trp Asp Gly Asp Asn Val
        195                 200                 205

Leu Leu Thr Leu Asp Val Ser Glu Glu Gln Asp Phe Ser Phe Leu Leu
210                 215                 220

Tyr Leu Arg Pro Val Pro Asp Ala Leu Lys Ser Leu Trp Tyr Lys Asn
225                 230                 235                 240

Leu Thr Gly Pro Gln Asn Ile Thr Leu Asn His Thr Asp Leu Val Pro
                245                 250                 255

Cys Leu Cys Ile Gln Val Trp Ser Leu Glu Pro Asp Ser Glu Arg Val
            260                 265                 270

Glu Phe Cys Pro Phe Arg Glu Asp Pro Gly Ala His Arg Asn Leu Trp
        275                 280                 285

His Ile Ala Arg Leu Arg Val Leu Ser Pro Gly Val Trp Gln Leu Asp
    290                 295                 300

Ala Pro Cys Cys Leu Pro Gly Lys Val Thr Leu Cys Trp Gln Ala Pro
305                 310                 315                 320

Asp Gln Ser Pro Cys Gln Pro Leu Val Pro Val Pro Gln Lys Asn
                325                 330                 335

Ala Thr Val Asn Glu Pro Gln Asp Phe Gln Leu Val Ala Gly His Pro
                340                 345                 350

Asn Leu Cys Val Gln Val Ser Thr Trp Glu Lys Val Gln Leu Gln Ala
        355                 360                 365

Cys Leu Trp Ala Asp Ser Leu Gly Pro Phe Lys Asp Asp Met Leu Leu
    370                 375                 380

Val Glu Met Lys Thr Gly Leu Asn Asn Thr Ser Val Cys Ala Leu Glu
385                 390                 395                 400

Pro Ser Gly Cys Thr Pro Leu Pro Ser Met Ala Ser Thr Arg Ala Ala
                405                 410                 415

Arg Leu Gly Glu Glu Leu Leu Gln Asp Phe Arg Ser His Gln Cys Met
            420                 425                 430

Gln Leu Trp Asn Asp Asp Asn Met Gly Ser Leu Trp Ala Cys Pro Met
        435                 440                 445

Asp Lys Tyr Ile His Arg Arg Trp Val Leu Val Trp Leu Ala Cys Leu
    450                 455                 460

Leu Leu Ala Ala Ala Leu Phe Phe Phe Leu Leu Lys Lys Asp Arg
465                 470                 475                 480

Arg Lys Ala Ala Arg Gly Ser Arg Thr Ala Leu Leu Leu His Ser Ala
                485                 490                 495
```

```
Asp Gly Ala Gly Tyr Glu Arg Leu Val Gly Ala Leu Ala Ser Ala Leu
            500                 505                 510

Ser Gln Met Pro Leu Arg Val Ala Val Asp Leu Trp Ser Arg Arg Glu
            515                 520                 525

Leu Ser Ala His Gly Ala Leu Ala Trp Phe His Gln Arg Arg Arg
        530                 535                 540

Ile Leu Gln Glu Gly Gly Val Val Ile Leu Leu Phe Ser Pro Ala Ala
545                 550                 555                 560

Val Ala Gln Cys Gln Gln Trp Leu Gln Leu Gln Thr Val Glu Pro Gly
                565                 570                 575

Pro His Asp Ala Leu Ala Ala Trp Leu Ser Cys Val Leu Pro Asp Phe
            580                 585                 590

Leu Gln Gly Arg Ala Thr Gly Arg Tyr Val Gly Val Tyr Phe Asp Gly
            595                 600                 605

Leu Leu His Pro Asp Ser Val Pro Ser Pro Phe Arg Val Ala Pro Leu
    610                 615                 620

Phe Ser Leu Pro Ser Gln Leu Pro Ala Phe Leu Asp Ala Leu Gln Gly
625                 630                 635                 640

Gly Cys Ser Thr Ser Ala Gly Arg Pro Ala Asp Arg Val Glu Arg Val
                645                 650                 655

Thr Gln Ala Leu Arg Ser Ala Leu Asp Ser Cys Thr Ser Ser Ser Glu
            660                 665                 670

Ala Pro Gly Cys Cys Glu Glu Trp Asp Leu Gly Pro Cys Thr Thr Leu
        675                 680                 685

Glu

<210> SEQ ID NO 31
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 31
tcccgtcccc cgccccaggt c                                          21

<210> SEQ ID NO 32
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 32
ctctccatcc ttatctttca tcaac                                      25

<210> SEQ ID NO 33
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 33
ctctctgctg gctaaacaaa acac                                       24

<210> SEQ ID NO 34
<211> LENGTH: 26
<212> TYPE: DNA
<213> ORGANISM: Artificial Sequence
```

```
<220> FEATURE:
<223> OTHER INFORMATION: oligonucleotide primer

<400> SEQUENCE: 34
ctcatattgc tcaactgtgt gaaaag                                        26

<210> SEQ ID NO 35
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 35
tagaagccac ctgaacacaa atctg                                         25

<210> SEQ ID NO 36
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 36
atcttgcgtt gtatgttgaa aatcaatt                                      28

<210> SEQ ID NO 37
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 37
ttctccacca ggtaaacaag tctac                                         25

<210> SEQ ID NO 38
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 38
ctctccaggc ccaagtcgtg ctct                                          24

<210> SEQ ID NO 39
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 39
ttgtcctggg ggcctcgtgt ctcc                                          24

<210> SEQ ID NO 40
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 40
acgaagccca ggtaccagaa agag                                          24
```

<210> SEQ ID NO 41
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 41
aaaagcgccg cagccaagag tagg                                          24

<210> SEQ ID NO 42
<211> LENGTH: 1293
<212> TYPE: DNA
<213> ORGANISM: Homo sapiens

<400> SEQUENCE: 42
ctggagaggc ttgtggggcc tcaggacgct acccactgct ctccgggcct ctcctgccgc    60
ctctgggaca gtgacatact ctgcctgcct ggggacatcg tgcctgctcc gggccccgtg   120
ctggcgccta cgcacctgca gacagagctg gtgctgaggt gccagaagga gaccgactgt   180
gacctctgtc tgcgtgtggc tgtccacttg gccgtgcatg ggcactggga agagcctgaa   240
gatgaggaaa agtttggagg agcagctgac tcaggggtgg aggagcctag gaatgcctct   300
ctccaggccc aagtcgtgct ctccttccag gcctacccta ctgcccgctg cgtcctgctg   360
gaggtgcaag tgcctgctgc ccttgtgcag tttggtcagt ctgtgggctc tgtggtatat   420
gactgcttcg aggctgccct agggagtgag gtacgaatct ggtcctatac tcagcccagg   480
tacgagaagg aactcaacca cacacagcag ctgcctgccc tgccctggct caacgtgtca   540
gcagatggtg acaacgtgca tctggttctg aatgtctctg aggagcagca cttcggcctc   600
tccctgtact ggaatcaggt ccaggggccc ccaaaacccc ggtggcacaa aaacctgact   660
ggaccgcaga tcattacctt gaaccacaca gacctggttc cctgcctctg tattcaggtg   720
tggcctctgg aacctgactc cgttaggacg aacatctgcc ccttcaggga ggaccccgc    780 gcacaccaga acctctggca agccgcccga ctgcgactgc tgaccctgca gagctggctg   840
ctggacgcac cgtgctcgct gcccgcagaa gcggcactgt gctggcgggc tccgggtggg   900 gaccctgcc agccactggt cccaccgctt cctgggaga acgtcactgt ggacaaggtt    960
ctcgagttcc cattgctgaa aggccaccct aacctctgtg ttcaggtgaa cagctcggag   1020
aagctgcagc tgcaggagtg cttgtgggct gactccctgg ggcctctcaa agacgatgtg   1080
ctactgttgg agacacgagg cccccaggac aacagatccc tctgtgcctt ggaacccagt   1140
ggctgtactt cactacccag caaagcctcc acgagggcag ctcgccttgg agagtactta   1200
ctacaagacc tgcagtcagg ccagtgtctg cagctatggg acgatgactt gggagcgcta   1260
tgggcctgcc ccatggacaa atacatccac aag                                1293

<210> SEQ ID NO 43
<211> LENGTH: 431
<212> TYPE: PRT
<213> ORGANISM: Homo sapiens

<400> SEQUENCE: 43

Leu Glu Arg Leu Val Gly Pro Gln Asp Ala Thr His Cys Ser Pro Gly
 1               5                  10                  15

Leu Ser Cys Arg Leu Trp Asp Ser Asp Ile Leu Cys Leu Pro Gly Asp
                20                  25                  30

Ile Val Pro Ala Pro Gly Pro Val Leu Ala Pro Thr His Leu Gln Thr
            35                  40                  45

-continued

```
Glu Leu Val Leu Arg Cys Gln Lys Glu Thr Asp Cys Asp Leu Cys Leu
 50                  55                  60

Arg Val Ala Val His Leu Ala Val His Gly His Trp Glu Glu Pro Glu
 65                  70                  75                  80

Asp Glu Glu Lys Phe Gly Gly Ala Ala Asp Ser Gly Val Glu Glu Pro
                 85                  90                  95

Arg Asn Ala Ser Leu Gln Ala Gln Val Val Leu Ser Phe Gln Ala Tyr
            100                 105                 110

Pro Thr Ala Arg Cys Val Leu Leu Glu Val Gln Val Pro Ala Ala Leu
        115                 120                 125

Val Gln Phe Gly Gln Ser Val Gly Ser Val Val Tyr Asp Cys Phe Glu
130                 135                 140

Ala Ala Leu Gly Ser Glu Val Arg Ile Trp Ser Tyr Thr Gln Pro Arg
145                 150                 155                 160

Tyr Glu Lys Glu Leu Asn His Thr Gln Gln Leu Pro Ala Leu Pro Trp
                165                 170                 175

Leu Asn Val Ser Ala Asp Gly Asp Asn Val His Leu Val Leu Asn Val
            180                 185                 190

Ser Glu Glu Gln His Phe Gly Leu Ser Leu Tyr Trp Asn Gln Val Gln
        195                 200                 205

Gly Pro Pro Lys Pro Arg Trp His Lys Asn Leu Thr Gly Pro Gln Ile
210                 215                 220

Ile Thr Leu Asn His Thr Asp Leu Val Pro Cys Leu Cys Ile Gln Val
225                 230                 235                 240

Trp Pro Leu Glu Pro Asp Ser Val Arg Thr Asn Ile Cys Pro Phe Arg
                245                 250                 255

Glu Asp Pro Arg Ala His Gln Asn Leu Trp Gln Ala Ala Arg Leu Arg
            260                 265                 270

Leu Leu Thr Leu Gln Ser Trp Leu Leu Asp Ala Pro Cys Ser Leu Pro
        275                 280                 285

Ala Glu Ala Ala Leu Cys Trp Arg Ala Pro Gly Gly Asp Pro Cys Gln
290                 295                 300

Pro Leu Val Pro Pro Leu Ser Trp Glu Asn Val Thr Val Asp Lys Val
305                 310                 315                 320

Leu Glu Phe Pro Leu Leu Lys Gly His Pro Asn Leu Cys Val Gln Val
                325                 330                 335

Asn Ser Ser Glu Lys Leu Gln Leu Gln Glu Cys Leu Trp Ala Asp Ser
            340                 345                 350

Leu Gly Pro Leu Lys Asp Asp Val Leu Leu Leu Glu Thr Arg Gly Pro
        355                 360                 365

Gln Asp Asn Arg Ser Leu Cys Ala Leu Glu Pro Ser Gly Cys Thr Ser
370                 375                 380

Leu Pro Ser Lys Ala Ser Thr Arg Ala Ala Arg Leu Gly Glu Tyr Leu
385                 390                 395                 400

Leu Gln Asp Leu Gln Ser Gly Gln Cys Leu Gln Leu Trp Asp Asp Asp
                405                 410                 415

Leu Gly Ala Leu Trp Ala Cys Pro Met Asp Lys Tyr Ile His Lys
            420                 425                 430
```

<210> SEQ ID NO 44
<211> LENGTH: 699
<212> TYPE: DNA
<213> ORGANISM: Homo sapiens

<400> SEQUENCE: 44

-continued

```
gagcccagag ggcccacaat caagccctgt cctccatgca aatgcccagc acctaacctc      60
ttgggtggac catccgtctt catcttccct ccaaagatca aggatgtact catgatctcc     120
ctgagcccca tagtcacatg tgtggtggtg gatgtgagcg aggatgaccc agatgtccag     180
atcagctggt ttgtgaacaa cgtggaagta cacacagctc agacacaaac ccatagagag     240
gattacaaca gtactctccg ggtggtcagt gccctcccca tccagcacca ggactggatg     300
agtggcaagg agttcaaatg caaggtcaac aacaaagacc tcccagcgcc catcgagaga     360
accatctcaa aacccaaagg gtcagtaaga gctccacagg tatatgtctt gcctccacca     420
gaagaagaga tgactaagaa acaggtcact ctgacctgca tggtcacaga cttcatgcct     480
gaagacattt acgtggagtg gaccaacaac gggaaaacag agctaaacta caagaacact     540
gaaccagtcc tggactctga tggttcttac ttcatgtaca gcaagctgag agtgaaaaag     600
aagaactggg tggaaagaaa tagctactcc tgttcagtgg tccacgaggg tctgcacaat     660
caccacacga ctaagagctt ctcccggact ccgggtaaa                            699
```

<210> SEQ ID NO 45
<211> LENGTH: 233
<212> TYPE: PRT
<213> ORGANISM: Homo sapiens

<400> SEQUENCE: 45

```
Glu Pro Arg Gly Pro Thr Ile Lys Pro Cys Pro Pro Cys Lys Cys Pro
  1               5                  10                  15

Ala Pro Asn Leu Leu Gly Gly Pro Ser Val Phe Ile Phe Pro Pro Lys
             20                  25                  30

Ile Lys Asp Val Leu Met Ile Ser Leu Ser Pro Ile Val Thr Cys Val
         35                  40                  45

Val Val Asp Val Ser Glu Asp Asp Pro Asp Val Gln Ile Ser Trp Phe
     50                  55                  60

Val Asn Asn Val Glu Val His Thr Ala Gln Thr Gln Thr His Arg Glu
 65                  70                  75                  80

Asp Tyr Asn Ser Thr Leu Arg Val Val Ser Ala Leu Pro Ile Gln His
                 85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230
```

<210> SEQ ID NO 46
<211> LENGTH: 69

```
<212> TYPE: DNA
<213> ORGANISM: Artificial Sequence
<220> FEATURE:
<223> OTHER INFORMATION: oligonucleotide primer

<400> SEQUENCE: 46
gtttcgctca gccaggaaat ccatgccgag ttgagacgct tccgtagact ggagaggctt    60
gtggggcct                                                             69

<210> SEQ ID NO 47
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 47
tgtgggccct ctgggctcct tgtggatgta tttgtc                              36

<210> SEQ ID NO 48
<211> LENGTH: 36
<212> TYPE: DNA
<213> ORGANISM: Artificial Sequence
<220> FEATURE:
<223> OTHER INFORMATION: oligonucleotide primer

<400> SEQUENCE: 48
gacaaataca tccacaagga gcccagaggg cccaca                              36

<210> SEQ ID NO 49
<211> LENGTH: 55
<212> TYPE: DNA
<213> ORGANISM: Artificial Sequence
<220> FEATURE:
<223> OTHER INFORMATION: oligonucleotide primer

<400> SEQUENCE: 49
caaccccaga gctgttttaa ggcgcgcctc tagattattt acccggagtc cggga         55

<210> SEQ ID NO 50
<211> LENGTH: 76
<212> TYPE: DNA
<213> ORGANISM: Artificial Sequence
<220> FEATURE:
<223> OTHER INFORMATION: oligonucleotide primer

<400> SEQUENCE: 50
caaccccaga gctgttttaa ggcgcgcctc tagattattc catgggcatg tattcttcct    60
tgtggatgta tttgtc                                                    76

<210> SEQ ID NO 51
<211> LENGTH: 10
<212> TYPE: PRT
<213> ORGANISM: Artificial Sequence
<220> FEATURE:
<223> OTHER INFORMATION: C-terminal his tag

<400> SEQUENCE: 51

Gly Ser Gly Gly His His His His His His
 1               5                  10

<210> SEQ ID NO 52
<211> LENGTH: 10
<212> TYPE: PRT
<213> ORGANISM: Artificial Sequence
<220> FEATURE:
```

<223> OTHER INFORMATION: C-terminal FLAG tag

<400> SEQUENCE: 52

Gly Ser Asp Tyr Lys Asp Asp Asp Asp Lys
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Glu-Glu tag

<400> SEQUENCE: 53

Glu Glu Tyr Met Pro Met Glu
1               5

<210> SEQ ID NO 54
<211> LENGTH: 85
<212> TYPE: DNA
<213> ORGANISM: Artificial Sequence
<220> FEATURE:
<223> OTHER INFORMATION: oligonucleotide primer

<400> SEQUENCE: 54
caaccccaga gctgttttaa ggcgcgcctc tagattagtg atggtgatgg tgatgtccac    60
cagatccctt gtggatgtat ttgtc                                         85

<210> SEQ ID NO 55
<211> LENGTH: 85
<212> TYPE: DNA
<213> ORGANISM: Artificial Sequence
<220> FEATURE:
<223> OTHER INFORMATION: oligonucleotide primer

<400> SEQUENCE: 55
caaccccaga gctgttttaa ggcgcgcctc tagattactt atcatcatca tccttataat    60
cggatccctt gtggatgtat ttgtc                                         85

<210> SEQ ID NO 56
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 56
acgaagccca ggtaccagaa agag                                          24

<210> SEQ ID NO 57
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 57
aaaagcgccg cagccaagag tagg                                          24

<210> SEQ ID NO 58
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 58
cgtaagcggt ggcggttttc                                              20

<210> SEQ ID NO 59
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 59
tgggcagggc acagtcacag                                              20

<210> SEQ ID NO 60
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 60
acttgccatt ctgagggagg tagc                                         24

<210> SEQ ID NO 61
<211> LENGTH: 24
<212> TYPE: DNA
<213> ORGANISM: Artificial Sequence
<220> FEATURE:
<223> OTHER INFORMATION: oligonucleotide primer

<400> SEQUENCE: 61
cacaggtgca gccaactttt agga                                         24

<210> SEQ ID NO 62
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 62
gtgggccgct ctaggcacca                                              20

<210> SEQ ID NO 63
<211> LENGTH: 25
<212> TYPE: DNA
<213> ORGANISM: Artificial Sequence
<220> FEATURE:
<223> OTHER INFORMATION: oligonucleotide primer

<400> SEQUENCE: 63
cggttggcct tagggttcag ggggg                                        25

<210> SEQ ID NO 64
<211> LENGTH: 2127
<212> TYPE: DNA
<213> ORGANISM: Homo sapiens

<400> SEQUENCE: 64
atggatgcaa tgaagagagg gctctgctgt gtgctgctgc tgtgtggcgc cgtcttcgtt    60
tcgctcagcc aggaaatcca tgccgagttg agacgcttcc gtagactgga gaggcttgtg   120
gggcctcagg acgctaccca ctgctctccg ggctctcctt gccgcctctg ggacagtgac   180
atactctgcc tgcctgggga catcgtgcct gctccgggcc ccgtgctggc gcctacgcac   240

```
ctgcagacag agctggtgct gaggtgccag aaggagaccg actgtgacct ctgtctgcgt    300
gtggctgtcc acttggccgt gcatgggcac tgggaagagc ctgaagatga ggaaaagttt    360
ggaggagcag ctgactcagg ggtggaggag cctaggaatg cctctctcca ggcccaagtc    420
gtgctctcct tccaggccta ccctactgcc cgctgcgtcc tgctggaggt gcaagtgcct    480
gctgcccttg tgcagtttgg tcagtctgtg ggctctgtgg tatatgactg cttcgaggct    540
gccctaggga gtgaggtacg aatctggtcc tatactcagc ccaggtacga aaggaactc    600
aaccacacac agcagctgcc tgccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tgactggacc gcagatcatt    780
accttgaacc acacagacct ggttccctgc ctctgtattc aggtgtggcc tctgaacct    840
gactccgtta ggacgaacat ctgccccttc agggaggacc ccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca   1020
ctggtcccac cgctttcctg ggagaacgtc actgtggaca aggttctcga gttcccattg   1080
ctgaaaggcc accctaacct ctgtgttcag gtgaacagct cggagaagct gcagctgcag   1140
gagtgcttgt gggctgactc cctggggcct ctcaaagacg atgtgctact gttggagaca   1200
cgaggccccc aggacaacag atccctctgt gccttggaac ccagtggctg tacttcacta   1260
cccagcaaag cctccacgag ggcagctcgc cttggagagt acttactaca agacctgcag   1320
tcaggccagt gtctgcagct atgggacgat gacttgggag cgctatgggc ctgccccatg   1380
gacaaataca tccacaaggg aggaagtggc ggaggaacag gaagtttggt ccctcgtgga   1440
agcgacaaaa ctcacacatg cccaccgtgc ccagcacctg aactcctggg gggaccgtca   1500
gtcttcctct tccccccaaa acccaaggac accctcatga tctcccggac ccctgaggtc   1560
acatgcgtgg tggtggacgt gagccacgaa gaccctgagg tcaagttcaa ctggtacgtg   1620
gacggcgtgg aggtgcataa tgccaagaca aagccgcggg aggagcagta caacagcacg   1680
taccgtgtgg tcagcgtcct caccgtcctg caccaggact ggctgaatgg caaggagtac   1740
aagtgcaagg tctccaacaa agccctccca gcccccatcg agaaaaccat ctccaaagcc   1800
aaagggcagc cccgagaacc acaggtgtac accctgcccc catcccggga tgagctgacc   1860
aagaaccagg tcagcctgac ctgcctggtc aaaggcttct atcccagcga catcgccgtg   1920
gagtgggaga gcaatgggca gccggagaac aactacaaga ccacgcctcc cgtgctggac   1980
tccgacggct ccttcttcct ctacagcaag ctcaccgtgg acaagagcag gtggcagcag   2040
gggaacgtct tctcatgctc cgtgatgcat gaggctctgc acaaccacta cacgcagaag   2100
agcctctccc tgtctccggg taaataa                                       2127
```

<210> SEQ ID NO 65
<211> LENGTH: 708
<212> TYPE: PRT
<213> ORGANISM: Homo sapiens

<400> SEQUENCE: 65

```
Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
                20                  25                  30

Phe Arg Arg Leu Glu Arg Leu Val Gly Pro Gln Asp Ala Thr His Cys
            35                  40                  45
```

```
Ser Pro Gly Leu Ser Cys Arg Leu Trp Asp Ser Asp Ile Leu Cys Leu
    50                  55                  60

Pro Gly Asp Ile Val Pro Ala Pro Gly Pro Val Leu Ala Pro Thr His
65                  70                  75                  80

Leu Gln Thr Glu Leu Val Leu Arg Cys Gln Lys Glu Thr Asp Cys Asp
                85                  90                  95

Leu Cys Leu Arg Val Ala Val His Leu Ala Val His Gly His Trp Glu
            100                 105                 110

Glu Pro Glu Asp Glu Glu Lys Phe Gly Gly Ala Ala Asp Ser Gly Val
        115                 120                 125

Glu Glu Pro Arg Asn Ala Ser Leu Gln Ala Gln Val Val Leu Ser Phe
    130                 135                 140

Gln Ala Tyr Pro Thr Ala Arg Cys Val Leu Leu Glu Val Gln Val Pro
145                 150                 155                 160

Ala Ala Leu Val Gln Phe Gly Gln Ser Val Gly Ser Val Val Tyr Asp
                165                 170                 175

Cys Phe Glu Ala Ala Leu Gly Ser Glu Val Arg Ile Trp Ser Tyr Thr
            180                 185                 190

Gln Pro Arg Tyr Glu Lys Glu Leu Asn His Thr Gln Gln Leu Pro Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
        435                 440                 445

Asp Asp Asp Leu Gly Ala Leu Trp Ala Cys Pro Met Asp Lys Tyr Ile
    450                 455                 460

His Lys Gly Gly Ser Gly Gly Gly Thr Gly Ser Leu Val Pro Arg Gly
```

```
              465                 470                 475                 480
Ser Asp Lys Thr His Thr Cys Pro Pro Cys Pro Ala Pro Glu Leu Leu
                    485                 490                 495

Gly Gly Pro Ser Val Phe Leu Phe Pro Pro Lys Pro Lys Asp Thr Leu
                500                 505                 510

Met Ile Ser Arg Thr Pro Glu Val Thr Cys Val Val Val Asp Val Ser
            515                 520                 525

His Glu Asp Pro Glu Val Lys Phe Asn Trp Tyr Val Asp Gly Val Glu
        530                 535                 540

Val His Asn Ala Lys Thr Lys Pro Arg Glu Glu Gln Tyr Asn Ser Thr
545                 550                 555                 560

Tyr Arg Val Val Ser Val Leu Thr Val Leu His Gln Asp Trp Leu Asn
                565                 570                 575

Gly Lys Glu Tyr Lys Cys Lys Val Ser Asn Lys Ala Leu Pro Ala Pro
            580                 585                 590

Ile Glu Lys Thr Ile Ser Lys Ala Lys Gly Gln Pro Arg Glu Pro Gln
        595                 600                 605

Val Tyr Thr Leu Pro Pro Ser Arg Asp Glu Leu Thr Lys Asn Gln Val
    610                 615                 620

Ser Leu Thr Cys Leu Val Lys Gly Phe Tyr Pro Ser Asp Ile Ala Val
625                 630                 635                 640

Glu Trp Glu Ser Asn Gly Gln Pro Glu Asn Asn Tyr Lys Thr Thr Pro
                645                 650                 655

Pro Val Leu Asp Ser Asp Gly Ser Phe Phe Leu Tyr Ser Lys Leu Thr
            660                 665                 670

Val Asp Lys Ser Arg Trp Gln Gln Gly Asn Val Phe Ser Cys Ser Val
        675                 680                 685

Met His Glu Ala Leu His Asn His Tyr Thr Gln Lys Ser Leu Ser Leu
    690                 695                 700

Ser Pro Gly Lys
705

<210> SEQ ID NO 66
<211> LENGTH: 1416
<212> TYPE: DNA
<213> ORGANISM: Artificial Sequence
<220> FEATURE:
<223> OTHER INFORMATION: synthetic insert

<400> SEQUENCE: 66
agccaggaaa tccatgccga gttgagacgc ttccgtagac tggagaggct tgtggggcct     60
caggacgcta cccactgctc tccgggcctc tcctgccgcc tctgggacag tgacatactc    120
tgcctgcctg ggacatcgt gcctgctccg ggccccgtgc tggcgcctac gcacctgcag    180
acagagctgg tgctgaggtg ccagaaggag accgactgtg acctctgtct gcgtgtggct    240
gtccacttgg ccgtgcatgg gcactgggaa gagcctgaag atgaggaaaa gtttggagga    300
gcagctgact caggggtgga ggagcctagg aatgcctctc tccaggccca agtcgtgctc    360
tccttccagg cctaccctac tgcccgctgc gtcctgctgg aggtgcaagt gcctgctgcc    420
cttgtgcagt ttggtcagtc tgtgggctct gtggtatatg actgcttcga ggctgcccta    480
gggagtgagg tacgaatctg gtcctatact cagcccaggt acgaagga actcaaccac    540 acacagcagc tgcctgccct gccctggctc aacgtgtcag cagatggtga caacgtgcat    600
ctggttctga atgtctctga ggagcagcac ttcggcctct ccctgtactg gaatcaggtc    660
cagggccccc caaaacccg gtggcacaaa aacctgactg gaccgcagat cattaccttg    720
```

```
aaccacacag acctggttcc ctgcctctgt attcaggtgt ggcctctgga acctgactcc    780
gttaggacga acatctgccc cttcagggag accccccgcg cacaccagaa cctctggcaa    840
gccgcccgac tgcgactgct gaccctgcag agctggctgc tggacgcacc gtgctcgctg    900
cccgcagaag cggcactgtg ctggcgggct ccgggtgggg acccctgcca gccactggtc    960
ccaccgcttt cctgggagaa cgtcactgtg acaaggttc tcgagttccc attgctgaaa    1020
ggccacccta acctctgtgt tcaggtgaac agctcggaga agctgcagct gcaggagtgc    1080
ttgtgggctg actccctggg gcctctcaaa gacgatgtgc tactgttgga gacacgaggc    1140
ccccaggaca acagatccct ctgtgccttg aacccagtg gctgtacttc actacccagc    1200
aaagcctcca cgagggcagc tcgccttgga gagtacttac acaagacct gcagtcaggc    1260 cagtgtctgc agctatggga cgatgacttg ggagcgctat gggcctgccc catggacaaa    1320
tacatccaca agggaggaag tggcggagga acaggaagtt tggtccctcg tggaagcgac    1380
aaaactcaca catgcccacc gtgcccagca cctgaa                              1416

<210> SEQ ID NO 67
<211> LENGTH: 2154
<212> TYPE: DNA
<213> ORGANISM: homo sapians

<400> SEQUENCE: 67
atggatgcaa tgaagagagg ctctgctgt gtgctgctgc tgtgtggcgc cgtcttcgtt     60
tcgctcagcc aggaaatcca tgccgagttg agacgcttcc gtagactgga gaggcttgtg    120
gggcctcagg acgctaccca ctgctctccg ggcctctcct gccgcctctg ggacagtgac    180
atactctgcc tgcctgggga catcgtgcct gctccgggcc ccgtgctggc gcctacgcac    240
ctgcagacag agctggtgct gaggtgccag aaggagaccg actgtgacct ctgtctgcgt    300
gtggctgtcc acttggccgt gcatgggcac tgggaagagc ctgaagatga ggaaaagttt    360
ggaggagcag ctgactcagg ggtggaggag cctaggaatg cctctctcca ggcccaagtc    420
gtgctctcct tccaggccta ccctactgcc cgctgcgtcc tgctggaggt gcaagtgcct    480
gctgcccttg tgcagtttgg tcagtctgtg ggctctgtgg tatatgactg cttcgaggct    540
gccctaggga gtgaggtacg aatctggtcc tatactcagc ccaggtacga gaaggaactc    600
aaccacacac agcagctgcc tgccctgccc tggctcaacg tgtcagcaga tggtgacaac    660
gtgcatctgg ttctgaatgt ctctgaggag cagcacttcg gcctctccct gtactggaat    720
caggtccagg gcccccaaa accccggtgg cacaaaaacc tgactggacc gcagatcatt    780
accttgaacc acacagacct ggttcccctgc ctctgtattc aggtgtggcc tctgaacct    840 gactccgtta ggacgaacat ctgcccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca    1020
ctggtcccac cgctttcctg ggagaacgtc actgtggaca aggttctcga gttcccattg    1080
ctgaaaggcc accctaacct ctgtgttcag gtgaacagct cggagaagct gcagctgcag    1140
gagtgcttgt gggctgactc cctggggcct ctcaaagacg atgtgctact gttggagaca    1200
cgaggccccc aggacaacag atccctctgt gccttgaac ccagtggctg tacttcacta    1260
cccagcaaag cctccacgag ggcagctcgc cttggagagt acttactaca agacctgcag    1320
tcaggccagt gtctgcagct atgggacgat gacttgggag cgctatgggc ctgccccatg    1380
gacaaataca tccacaaggg aggtgggggc tccggcgggg gtggaagcgg tggaggcggg    1440
```

```
tcgggggcg gaggtagtga gcccaaatct tcagacaaaa ctcacacatg cccaccgtgc    1500
ccagcacctg aactcctggg gggaccgtca gtcttcctct tccccccaaa acccaaggac    1560
accctcatga tctcccggac ccctgaggtc acatgcgtgg tggtggacgt gagccacgaa    1620
gaccctgagg tcaagttcaa ctggtacgtg gacggcgtgg aggtgcataa tgccaagaca    1680
aagccgcggg aggagcagta caacagcacg taccgtgtgg tcagcgtcct caccgtcctg    1740
caccaggact ggctgaatgg caaggagtac aagtgcaagg tctccaacaa agccctccca    1800
gcccccatcg agaaaaccat ctccaaagcc aaagggcagc cccgagaacc acaggtgtac    1860
accctgcccc catcccggga tgagctgacc aagaaccagg tcagcctgac ctgcctggtc    1920
aaaggcttct atcccagcga catcgccgtg gagtgggaga gcaatgggca gccggagaac    1980
aactacaaga ccacgcctcc cgtgctggac tccgacggct ccttcttcct ctacagcaag    2040
ctcaccgtgg acaagagcag gtggcagcag gggaacgtct tctcatgctc cgtgatgcat    2100
gaggctctgc acaaccacta cacgcagaag agcctctccc tgtctccggg taaa           2154
```

<210> SEQ ID NO 68
<211> LENGTH: 718
<212> TYPE: PRT
<213> ORGANISM: homosapians

<400> SEQUENCE: 68

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
                20                  25                  30

Phe Arg Arg Leu Glu Arg Leu Val Gly Pro Gln Asp Ala Thr His Cys
         35                  40                  45

Ser Pro Gly Leu Ser Cys Arg Leu Trp Asp Ser Asp Ile Leu Cys Leu
     50                  55                  60

Pro Gly Asp Ile Val Pro Ala Pro Gly Pro Val Leu Ala Pro Thr His
 65                  70                  75                  80

Leu Gln Thr Glu Leu Val Leu Arg Cys Gln Lys Glu Thr Asp Cys Asp
                 85                  90                  95

Leu Cys Leu Arg Val Ala Val His Leu Ala Val His Gly His Trp Glu
            100                 105                 110

Glu Pro Glu Asp Glu Glu Lys Phe Gly Gly Ala Ala Asp Ser Gly Val
        115                 120                 125

Glu Glu Pro Arg Asn Ala Ser Leu Gln Ala Gln Val Val Leu Ser Phe
    130                 135                 140

Gln Ala Tyr Pro Thr Ala Arg Cys Val Leu Glu Val Gln Val Pro
145                 150                 155                 160

Ala Ala Leu Val Gln Phe Gly Gln Ser Val Gly Ser Val Val Tyr Asp
                165                 170                 175

Cys Phe Glu Ala Ala Leu Gly Ser Glu Val Arg Ile Trp Ser Tyr Thr
            180                 185                 190

Gln Pro Arg Tyr Glu Lys Glu Leu Asn His Thr Gln Gln Leu Pro Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255
```

```
Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
            275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Leu Ser Trp Glu Asn Val Thr Val
            340                 345                 350

Asp Lys Val Leu Glu Phe Pro Leu Leu Lys Gly His Pro Asn Leu Cys
            355                 360                 365

Val Gln Val Asn Ser Ser Glu Lys Leu Gln Leu Gln Glu Cys Leu Trp
    370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
                435                 440                 445

Asp Asp Asp Leu Gly Ala Leu Trp Ala Cys Pro Met Asp Lys Tyr Ile
    450                 455                 460

His Lys Gly Gly Gly Ser Gly Gly Gly Ser Gly Gly Gly
465                 470                 475                 480

Ser Gly Gly Gly Ser Glu Pro Lys Ser Ser Asp Lys Thr His Thr
                485                 490                 495

Cys Pro Pro Cys Pro Ala Pro Glu Leu Leu Gly Gly Pro Ser Val Phe
            500                 505                 510

Leu Phe Pro Pro Lys Pro Lys Asp Thr Leu Met Ile Ser Arg Thr Pro
    515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
            610                 615                 620

Ser Arg Asp Glu Leu Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
```

```
                675                 680                 685
Gln Gln Gly Asn Val Phe Ser Cys Ser Val Met His Glu Ala Leu His
            690                 695                 700

Asn His Tyr Thr Gln Lys Ser Leu Ser Leu Ser Pro Gly Lys
705                 710                 715

<210> SEQ ID NO 69
<211> LENGTH: 2052
<212> TYPE: DNA
<213> ORGANISM: homo sapians

<400> SEQUENCE: 69
atgcctgtgc cctggttctt gctgtccttg gcactgggcc gaagcccagt ggtcctttct      60
ctggagaggc ttgtggggcc tcaggacgct acccactgct ctccgggcct ctcctgccgc     120
ctctgggaca gtgacatact ctgcctgcct ggggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg gccgtgcatg ggcactggga gagcctgaa     300 gatgaggaaa agtttggagg agcagctgac tcaggggtgg aggagcctag gaatgcctct     360
ctccaggccc aagtcgtgct ctccttccag gcctaccctc tgcccgctg cgtcctgctg     420 gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgccc tgcctggct caacgtgtca     600 gcagatggtg acaacgtgca tctggttctg aatgtctctg aggagcagca cttcggcctc     660
tccctgtact ggaatcaggt ccagggcccc caaaacccc ggtggcacaa aaacctgact     720
ggaccgcaga tcattacctt gaaccacaca gacctggttc cctgcctctg tattcaggtg     780
tggcctctgg aacctgactc cgttaggacg aacatctgcc ccttcaggga ggaccccgc     840 gcacaccaga acctctggca agccgcccga ctgcgactgc tgaccctgca gagctggctg     900
ctggacgcac cgtgctcgct gcccgcagaa gcggcactgt gctggcgggc tccgggtggg     960 gaccccctgcc agccactggt cccaccgctt tcctgggaga acgtcactgt ggacaaggtt    1020
ctcgagttcc cattgctgaa aggccaccct aacctctgtg ttcaggtgaa cagctcggag    1080
aagctgcagc tgcaggagtg cttgtgggct gactccctgg ggcctctcaa agacgatgtg    1140
ctactgttgg agacacgagg ccccaggac aacagatccc tctgtgcctt ggaacccagt    1200
ggctgtactt cactacccag caaagcctcc acgagggcag ctcgccttgg agagtactta    1260
ctacaagacc tgcagtcagg ccagtgtctg cagctatggg acgatgactt gggagcgcta    1320
tgggcctgcc ccatggacaa atacatccac aaggagccca atcttcaga caaaactcac    1380 acatgcccac cgtgcccagc acctgaagcc gagggggcac cgtcagtctt cctcttcccc    1440
ccaaaaccca aggacaccct catgatctcc cggacccctg aggtcacatg cgtggtggtg    1500
gacgtgagcc acgaagaccc tgaggtcaag ttcaactggt acgtggacgg cgtggaggtg    1560
cataatgcca agacaaagcc gcgggaggag cagtacaaca gcacgtaccg tgtggtcagc    1620
gtcctcaccg tcctgcacca ggactggctg aatggcaagg agtacaagtg caaggtctcc    1680
aacaaagccc tcccatcctc catcgagaaa accatctcca agccaaagg gcagccccga    1740 gaaccacagg tgtacaccct gcccccatcc cgggatgagc tgaccaagaa ccaggtcagc    1800
ctgacctgcc tggtcaaagg cttctatccc agcgacatcg ccgtggagtg ggagagcaat    1860
gggcagccgg agaacaacta caagaccacg cctcccgtgc tggactccga cggctccttc    1920
```

```
ttcctctaca gcaagctcac cgtggacaag agcaggtggc agcaggggaa cgtcttctca    1980
tgctccgtga tgcatgaggc tctgcacaac cactacacgc agaagagcct ctccctgtct    2040
ccgggtaaat aa                                                        2052
```

<210> SEQ ID NO 70
<211> LENGTH: 683
<212> TYPE: PRT
<213> ORGANISM: homo sapians

<400> SEQUENCE: 70

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Ala Leu Pro Trp Leu Asn Val Ser Ala Asp Gly Asp Asn Val His Leu
        195                 200                 205

Val Leu Asn Val Ser Glu Glu Gln His Phe Gly Leu Ser Leu Tyr Trp
    210                 215                 220

Asn Gln Val Gln Gly Pro Pro Lys Pro Arg Trp His Lys Asn Leu Thr
225                 230                 235                 240

Gly Pro Gln Ile Ile Thr Leu Asn His Thr Asp Leu Val Pro Cys Leu
                245                 250                 255

Cys Ile Gln Val Trp Pro Leu Glu Pro Asp Ser Val Arg Thr Asn Ile
            260                 265                 270

Cys Pro Phe Arg Glu Asp Pro Arg Ala His Gln Asn Leu Trp Gln Ala
        275                 280                 285

Ala Arg Leu Arg Leu Leu Thr Leu Gln Ser Trp Leu Leu Asp Ala Pro
    290                 295                 300

Cys Ser Leu Pro Ala Glu Ala Ala Leu Cys Trp Arg Ala Pro Gly Gly
305                 310                 315                 320

Asp Pro Cys Gln Pro Leu Val Pro Pro Leu Ser Trp Glu Asn Val Thr
                325                 330                 335

Val Asp Lys Val Leu Glu Phe Pro Leu Leu Lys Gly His Pro Asn Leu
            340                 345                 350
```

```
Cys Val Gln Val Asn Ser Ser Glu Lys Leu Gln Leu Gln Glu Cys Leu
            355                 360                 365
Trp Ala Asp Ser Leu Gly Pro Leu Lys Asp Asp Val Leu Leu Leu Glu
    370                 375                 380
Thr Arg Gly Pro Gln Asp Asn Arg Ser Leu Cys Ala Leu Glu Pro Ser
385                 390                 395                 400
Gly Cys Thr Ser Leu Pro Ser Lys Ala Ser Thr Arg Ala Ala Arg Leu
                405                 410                 415
Gly Glu Tyr Leu Leu Gln Asp Leu Gln Ser Gly Gln Cys Leu Gln Leu
            420                 425                 430
Trp Asp Asp Leu Gly Ala Leu Trp Ala Cys Pro Met Asp Lys Tyr
    435                 440                 445
Ile His Lys Glu Pro Lys Ser Ser Asp Lys Thr His Thr Cys Pro Pro
    450                 455                 460
Cys Pro Ala Pro Glu Ala Gly Ala Pro Ser Val Phe Leu Phe Pro
465                 470                 475                 480
Pro Lys Pro Lys Asp Thr Leu Met Ile Ser Arg Thr Pro Glu Val Thr
                485                 490                 495
Cys Val Val Val Asp Val Ser His Glu Asp Pro Glu Val Lys Phe Asn
            500                 505                 510
Trp Tyr Val Asp Gly Val Glu Val His Asn Ala Lys Thr Lys Pro Arg
    515                 520                 525
Glu Glu Gln Tyr Asn Ser Thr Tyr Arg Val Val Ser Val Leu Thr Val
530                 535                 540
Leu His Gln Asp Trp Leu Asn Gly Lys Glu Tyr Lys Cys Lys Val Ser
545                 550                 555                 560
Asn Lys Ala Leu Pro Ser Ser Ile Glu Lys Thr Ile Ser Lys Ala Lys
                565                 570                 575
Gly Gln Pro Arg Glu Pro Gln Val Tyr Thr Leu Pro Pro Ser Arg Asp
            580                 585                 590
Glu Leu Thr Lys Asn Gln Val Ser Leu Thr Cys Leu Val Lys Gly Phe
    595                 600                 605
Tyr Pro Ser Asp Ile Ala Val Glu Trp Glu Ser Asn Gly Gln Pro Glu
610                 615                 620
Asn Asn Tyr Lys Thr Thr Pro Pro Val Leu Asp Ser Asp Gly Ser Phe
625                 630                 635                 640
Phe Leu Tyr Ser Lys Leu Thr Val Asp Lys Ser Arg Trp Gln Gln Gly
                645                 650                 655
Asn Val Phe Ser Cys Ser Val Met His Glu Ala Leu His Asn His Tyr
            660                 665                 670
Thr Gln Lys Ser Leu Ser Leu Ser Pro Gly Lys
    675                 680

<210> SEQ ID NO 71
<211> LENGTH: 2130
<212> TYPE: DNA
<213> ORGANISM: Artificial Sequence
<220> FEATURE:
<223> OTHER INFORMATION: Murine signal peptide and exons 1-6 of murine
      IL-17RA, exons 8-16 of human IL-17RC, linker and
      Fc10

<400> SEQUENCE: 71
atggcgattc ggcgctgctg gccacgggtc gtccccgggc ccgcgctggg atggctgctt      60
ctgctgctga acgttctggc cccgggccgc gcctccccgc cctcctcga cttcccggct     120 ccggtctgcg cgcaggaggg gctgagctgc agagtcaaga atagtacttg tctggatgac     180
```

```
agctggatcc accccaaaaa cctgaccccg tcttccccaa aaaacatcta tatcaatctt      240
agtgtttcct ctacccagca cggagaatta gtccctgtgt tgcatgttga gtggaccctg      300
cagacagatg ccagcatcct gtacctcgag ggtgcagagc tgtccgtcct gcagctgaac      360
accaatgagc ggctgtgtgt caagttccag tttctgtcca tgctgcagca tcaccgtaag      420
cggtggcggt tttccttcag ccactttgtg gtagatcctg gccaggagta tgaagtgact      480
gttcaccacc tgccgaagcc catccctgat ggggacccaa accacaaatc caagatcatc      540
tttgtgcctg actgtgagga cagcaagatg aagatgacta cctcatgcgt gagctcagcc      600
ctgccctggc tcaacgtgtc agcagatggt gacaacgtgc atctggttct gaatgtctct      660
gaggagcagc acttcggcct ctccctgtac tggaatcagg tccagggccc cccaaaaccc      720
cggtggcaca aaaacctgac tggaccgcag atcattacct tgaaccacac agacctggtt      780
ccctgcctct gtattcaggt gtggcctctg aacctgact ccgttaggac gaacatctgc      840
cccttcaggg aggaccccccg cgcacaccag aacctctggc aagccgcccg actgcgactg      900
ctgaccctgc agagctggct gctggacgca ccgtgctcgc tgcccgcaga agcggcactg      960
tgctggcggg ctccgggtgg ggaccccctgc cagccactgg tcccaccgct ttcctgggag     1020
aacgtcactg tggacaaggt tctcgagttc ccattgctga aaggccaccc taacctctgt     1080
gttcaggtga acagctcgga gaagctgcag ctgcaggagt gcttgtgggc tgactccctg     1140
gggcctctca agacgatgt gctactgttg gagacacgag gcccccagga caacagatcc     1200
ctctgtgcct tggaacccag tggctgtact tcactaccca gcaaagcctc cacgagggca     1260
gctcgccttg gagagtactt actacaagac ctgcagtcag gccagtgtct gcagctatgg     1320
gacgatgact tgggagcgct atgggcctgc ccatggaca aatacatcca aagggaggt     1380 gggggctccg gcggggtgg aagcggtgga ggcgggtcgg gggcggagg tagtgagccc     1440 aaatcttcag acaaaactca cacatgccca ccgtgcccag cacctgaact cctgggggga     1500
ccgtcagtct tcctcttccc cccaaaaccc aaggacaccc tcatgatctc ccggacccct     1560
gaggtcacat gcgtggtggt ggacgtgagc cacgaagacc ctgaggtcaa gttcaactgg     1620
tacgtggacg gcgtggaggt gcataatgcc aagacaaagc cgcgggagga gcagtacaac     1680
agcacgtacc gtgtggtcag cgtcctcacc gtcctgcacc aggactggct gaatggcaag     1740
gagtacaagt gcaaggtctc caacaaagcc ctcccagccc ccatcgagaa aaccatctcc     1800
aaagccaaag gcagccccg agaaccacag gtgtacaccc tgcccccatc ccgggatgag     1860
ctgaccaaga accaggtcag cctgacctgc ctggtcaaag gcttctatcc cagcgacatc     1920
gccgtggagt gggagagcaa tgggcagccg gagaacaact acaagaccac gcctcccgtg     1980
ctggactccg acggctcctt cttcctctac agcaagctca ccgtggacaa gagcaggtgg     2040
cagcagggga acgtcttctc atgctccgtg atgcatgagg ctctgcacaa ccactacacg     2100
cagaagagcc tctccctgtc tccgggtaaa                                      2130
```

<210> SEQ ID NO 72
<211> LENGTH: 710
<212> TYPE: PRT
<213> ORGANISM: Artificial Sequence
<220> FEATURE:
<223> OTHER INFORMATION: Murine signal peptide and exons 1-6 of murine
      IL-17RA, exons 8-16 of human IL-17RC, linker and
      Fc10

<400> SEQUENCE: 72

Met Ala Ile Arg Arg Cys Trp Pro Arg Val Val Pro Gly Pro Ala Leu

-continued

```
                1               5                  10                 15
        Gly Trp Leu Leu Leu Leu Asn Val Leu Ala Pro Gly Arg Ala Ser
                        20                 25                 30
        Pro Arg Leu Leu Asp Phe Pro Ala Pro Val Cys Ala Gln Glu Gly Leu
                        35                 40                 45
        Ser Cys Arg Val Lys Asn Ser Thr Cys Leu Asp Asp Ser Trp Ile His
                50                 55                 60
        Pro Lys Asn Leu Thr Pro Ser Ser Pro Lys Asn Ile Tyr Ile Asn Leu
        65                 70                 75                 80
        Ser Val Ser Ser Thr Gln His Gly Glu Leu Val Pro Val Leu His Val
                        85                 90                 95
        Glu Trp Thr Leu Gln Thr Asp Ala Ser Ile Leu Tyr Leu Glu Gly Ala
                        100                105                110
        Glu Leu Ser Val Leu Gln Leu Asn Thr Asn Glu Arg Leu Cys Val Lys
                        115                120                125
        Phe Gln Phe Leu Ser Met Leu Gln His His Arg Lys Arg Trp Arg Phe
                        130                135                140
        Ser Phe Ser His Phe Val Val Asp Pro Gly Gln Glu Tyr Glu Val Thr
        145                150                155                160
        Val His His Leu Pro Lys Pro Ile Pro Asp Gly Asp Pro Asn His Lys
                        165                170                175
        Ser Lys Ile Ile Phe Val Pro Asp Cys Glu Asp Ser Lys Met Lys Met
                        180                185                190
        Thr Thr Ser Cys Val Ser Ser Ala Leu Pro Trp Leu Asn Val Ser Ala
                        195                200                205
        Asp Gly Asp Asn Val His Leu Val Leu Asn Val Ser Glu Glu Gln His
                        210                215                220
        Phe Gly Leu Ser Leu Tyr Trp Asn Gln Val Gln Gly Pro Pro Lys Pro
        225                230                235                240
        Arg Trp His Lys Asn Leu Thr Gly Pro Gln Ile Ile Thr Leu Asn His
                        245                250                255
        Thr Asp Leu Val Pro Cys Leu Cys Ile Gln Val Trp Pro Leu Glu Pro
                        260                265                270
        Asp Ser Val Arg Thr Asn Ile Cys Pro Phe Arg Glu Asp Pro Arg Ala
                        275                280                285
        His Gln Asn Leu Trp Gln Ala Ala Arg Leu Arg Leu Leu Thr Leu Gln
                        290                295                300
        Ser Trp Leu Leu Asp Ala Pro Cys Ser Leu Pro Ala Glu Ala Ala Leu
        305                310                315                320
        Cys Trp Arg Ala Pro Gly Gly Asp Pro Cys Gln Pro Leu Val Pro Pro
                        325                330                335
        Leu Ser Trp Glu Asn Val Thr Val Asp Lys Val Leu Glu Phe Pro Leu
                        340                345                350
        Leu Lys Gly His Pro Asn Leu Cys Val Gln Val Asn Ser Ser Glu Lys
                        355                360                365
        Leu Gln Leu Gln Glu Cys Leu Trp Ala Asp Ser Leu Gly Pro Leu Lys
                        370                375                380
        Asp Asp Val Leu Leu Leu Glu Thr Arg Gly Pro Gln Asp Asn Arg Ser
        385                390                395                400
        Leu Cys Ala Leu Glu Pro Ser Gly Cys Thr Ser Leu Pro Ser Lys Ala
                        405                410                415
        Ser Thr Arg Ala Ala Arg Leu Gly Glu Tyr Leu Leu Gln Asp Leu Gln
                        420                425                430
```

```
Ser Gly Gln Cys Leu Gln Leu Trp Asp Asp Leu Gly Ala Leu Trp
        435                 440                 445
Ala Cys Pro Met Asp Lys Tyr Ile His Lys Gly Gly Gly Ser Gly
    450                 455                 460
Gly Gly Gly Ser Gly Gly Gly Ser Gly Gly Gly Ser Glu Pro
465                 470                 475                 480
Lys Ser Ser Asp Lys Thr His Thr Cys Pro Pro Cys Pro Ala Pro Glu
                485                 490                 495
Leu Leu Gly Gly Pro Ser Val Phe Leu Phe Pro Pro Lys Pro Lys Asp
            500                 505                 510
Thr Leu Met Ile Ser Arg Thr Pro Glu Val Thr Cys Val Val Val Asp
        515                 520                 525
Val Ser His Glu Asp Pro Glu Val Lys Phe Asn Trp Tyr Val Asp Gly
    530                 535                 540
Val Glu Val His Asn Ala Lys Thr Lys Pro Arg Glu Glu Gln Tyr Asn
545                 550                 555                 560
Ser Thr Tyr Arg Val Val Ser Val Leu Thr Val Leu His Gln Asp Trp
                565                 570                 575
Leu Asn Gly Lys Glu Tyr Lys Cys Lys Val Ser Asn Lys Ala Leu Pro
            580                 585                 590
Ala Pro Ile Glu Lys Thr Ile Ser Lys Ala Lys Gly Gln Pro Arg Glu
        595                 600                 605
Pro Gln Val Tyr Thr Leu Pro Pro Ser Arg Asp Glu Leu Thr Lys Asn
    610                 615                 620
Gln Val Ser Leu Thr Cys Leu Val Lys Gly Phe Tyr Pro Ser Asp Ile
625                 630                 635                 640
Ala Val Glu Trp Glu Ser Asn Gly Gln Pro Glu Asn Asn Tyr Lys Thr
                645                 650                 655
Thr Pro Pro Val Leu Asp Ser Asp Gly Ser Phe Phe Leu Tyr Ser Lys
            660                 665                 670
Leu Thr Val Asp Lys Ser Arg Trp Gln Gln Gly Asn Val Phe Ser Cys
        675                 680                 685
Ser Val Met His Glu Ala Leu His Asn His Tyr Thr Gln Lys Ser Leu
    690                 695                 700
Ser Leu Ser Pro Gly Lys
705                 710

<210> SEQ ID NO 73
<211> LENGTH: 1638
<212> TYPE: DNA
<213> ORGANISM: Artificial Sequence
<220> FEATURE:
<223> OTHER INFORMATION: otPA (optimized tissue Plasminogen Activator)
      signal peptide and exons 8-16 of human IL-17RC,
      linker and Fc10

<400> SEQUENCE: 73
atggatgcaa tgaagagagg ctctgctgt gtgctgctgc tgtgtggcgc cgtcttcgtt      60
tcgctcagcc aggaaatcca tgccgagttg agacgcttcc gtagagccct gccctggctc     120
aacgtgtcag cagatggtga caacgtgcat ctggttctga atgtctctga ggagcagcac     180
ttcggcctct ccctgtactg gaatcaggtc cagggccccc caaaacccg gtggacaaa       240 aacctgactg gaccgcagat cattaccttg aaccacacag acctggttcc ctgcctctgt     300
attcaggtgt ggcctctgga acctgactcc gttaggacga catctgccc cttcagggag     360 gaccccgcg cacaccagaa cctctggcaa gccgcccgac tgcgactgct gaccctgcag     420
```

```
agctggctgc tggacgcacc gtgctcgctg cccgcagaag cggcactgtg ctggcgggct      480
ccgggtgggg acccctgcca gccactggtc ccaccgcttt cctgggagaa cgtcactgtg      540
gacaaggttc tcgagttccc attgctgaaa ggccacccta acctctgtgt tcaggtgaac      600
agctcggaga agctgcagct gcaggagtgc ttgtgggctg actccctggg gcctctcaaa      660
gacgatgtgc tactgttgga gacacgaggc ccccaggaca cagatccct ctgtgccttg       720 gaacccagtg ctgtacttc actacccagc aaagcctcca cgagggcagc tcgccttgga      780
gagtacttac tacaagacct gcagtcaggc cagtgtctgc agctatggga cgatgacttg      840
ggagcgctat gggcctgccc catggacaaa tacatccaca agggaggtgg gggctccggc      900
gggggtggaa gcggtggagg cgggtcgggg gcggaggta gtgagcccaa atcttcagac       960
aaaactcaca catgcccacc gtgcccagca cctgaactcc tggggggacc gtcagtcttc     1020
ctcttccccc caaaacccaa ggacaccctc atgatctccc ggacccctga ggtcacatgc     1080
gtggtggtgg acgtgagcca cgaagaccct gaggtcaagt tcaactggta cgtggacggc     1140
gtggaggtgc ataatgccaa gacaaagccg cgggaggagc agtacaacag cacgtaccgt     1200
gtggtcagcg tcctcaccgt cctgcaccag gactggctga atggcaagga gtacaagtgc     1260
aaggtctcca acaaagccct cccagccccc atcgagaaaa ccatctccaa agccaaaggg     1320
cagccccgag aaccacaggt gtacaccctg cccccatccc gggatgagct gaccaagaac     1380
caggtcagcc tgacctgcct ggtcaaaggc ttctatccca gcgacatcgc cgtggagtgg     1440
gagagcaatg ggcagccgga gaacaactac aagaccacgc ctcccgtgct ggactccgac     1500
ggctccttct tcctctacag caagctcacc gtggacaaga gcaggtggca gcaggggaac     1560
gtcttctcat gctccgtgat gcatgaggct ctgcacaacc actacacgca gaagagcctc     1620
tccctgtctc cgggtaaa                                                   1638
```

<210> SEQ ID NO 74
<211> LENGTH: 546
<212> TYPE: PRT
<213> ORGANISM: Artificial Sequence
<220> FEATURE:
<223> OTHER INFORMATION: otPA (optimized tissue Plasminogen Activator)
      signal peptide and exons 8-16 of human IL-17RC,
      linker and Fc10

<400> SEQUENCE: 74

Met Asp Ala Met Lys Arg Gly Leu Cys Cys Val Leu Leu Cys Gly
1               5                   10                  15

Ala Val Phe Val Ser Leu Ser Gln Glu Ile His Ala Glu Leu Arg Arg
                20                  25                  30

Phe Arg Arg Ala Leu Pro Trp Leu Asn Val Ser Ala Asp Gly Asp Asn
            35                  40                  45

Val His Leu Val Leu Asn Val Ser Glu Glu Gln His Phe Gly Leu Ser
        50                  55                  60

Leu Tyr Trp Asn Gln Val Gln Gly Pro Pro Lys Pro Arg Trp His Lys
65                  70                  75                  80

Asn Leu Thr Gly Pro Gln Ile Ile Thr Leu Asn His Thr Asp Leu Val
                85                  90                  95

Pro Cys Leu Cys Ile Gln Val Trp Pro Leu Glu Pro Asp Ser Val Arg
            100                 105                 110

Thr Asn Ile Cys Pro Phe Arg Glu Asp Pro Arg Ala His Gln Asn Leu
        115                 120                 125

Trp Gln Ala Ala Arg Leu Arg Leu Leu Thr Leu Gln Ser Trp Leu Leu
    130                 135                 140

```
Asp Ala Pro Cys Ser Leu Pro Ala Glu Ala Leu Cys Trp Arg Ala
145                 150                 155                 160

Pro Gly Gly Asp Pro Cys Gln Pro Leu Val Pro Leu Ser Trp Glu
            165                 170                 175

Asn Val Thr Val Asp Lys Val Leu Glu Phe Pro Leu Leu Lys Gly His
            180                 185                 190

Pro Asn Leu Cys Val Gln Val Asn Ser Ser Glu Lys Leu Gln Leu Gln
            195                 200                 205

Glu Cys Leu Trp Ala Asp Ser Leu Gly Pro Leu Lys Asp Asp Val Leu
210                 215                 220

Leu Leu Glu Thr Arg Gly Pro Gln Asp Asn Arg Ser Leu Cys Ala Leu
225                 230                 235                 240

Glu Pro Ser Gly Cys Thr Ser Leu Pro Ser Lys Ala Ser Thr Arg Ala
            245                 250                 255

Ala Arg Leu Gly Glu Tyr Leu Leu Gln Asp Leu Gln Ser Gly Gln Cys
            260                 265                 270

Leu Gln Leu Trp Asp Asp Asp Leu Gly Ala Leu Trp Ala Cys Pro Met
        275                 280                 285

Asp Lys Tyr Ile His Lys Gly Gly Gly Ser Gly Gly Gly Ser
        290                 295                 300

Gly Gly Gly Gly Ser Gly Gly Gly Ser Glu Pro Lys Ser Ser Asp
305                 310                 315                 320

Lys Thr His Thr Cys Pro Pro Cys Pro Ala Pro Glu Leu Leu Gly Gly
                325                 330                 335

Pro Ser Val Phe Leu Phe Pro Pro Lys Pro Lys Asp Thr Leu Met Ile
            340                 345                 350

Ser Arg Thr Pro Glu Val Thr Cys Val Val Val Asp Val Ser His Glu
            355                 360                 365

Asp Pro Glu Val Lys Phe Asn Trp Tyr Val Asp Gly Val Glu Val His
        370                 375                 380

Asn Ala Lys Thr Lys Pro Arg Glu Glu Gln Tyr Asn Ser Thr Tyr Arg
385                 390                 395                 400

Val Val Ser Val Leu Thr Val Leu His Gln Asp Trp Leu Asn Gly Lys
                405                 410                 415

Glu Tyr Lys Cys Lys Val Ser Asn Lys Ala Leu Pro Ala Pro Ile Glu
            420                 425                 430

Lys Thr Ile Ser Lys Ala Lys Gly Gln Pro Arg Glu Pro Gln Val Tyr
        435                 440                 445

Thr Leu Pro Pro Ser Arg Asp Glu Leu Thr Lys Asn Gln Val Ser Leu
    450                 455                 460

Thr Cys Leu Val Lys Gly Phe Tyr Pro Ser Asp Ile Ala Val Glu Trp
465                 470                 475                 480

Glu Ser Asn Gly Gln Pro Glu Asn Asn Tyr Lys Thr Thr Pro Pro Val
            485                 490                 495

Leu Asp Ser Asp Gly Ser Phe Phe Leu Tyr Ser Lys Leu Thr Val Asp
            500                 505                 510

Lys Ser Arg Trp Gln Gln Gly Asn Val Phe Ser Cys Ser Val Met His
        515                 520                 525

Glu Ala Leu His Asn His Tyr Thr Gln Lys Ser Leu Ser Leu Ser Pro
530                 535                 540

Gly Lys
545
```

-continued

<210> SEQ ID NO 75
<211> LENGTH: 622
<212> TYPE: DNA
<213> ORGANISM: homo sapians

<400> SEQUENCE: 75

```
atgcctgtgc cctggttctt gctgtccttg cactgggcc gaagcccagt ggtcctttct      60
ctggagaggc ttgtggggcc tcaggacgct acccactgct ctccgggcct cctgccgc     120 ctctgggaca gtgacatact ctgcctgcct ggggacatcg tgcctgctcc gggcccgtg     180 ctggcgccta cgcacctgca gacagagctg gtgctgaggt gccagaagga gaccgactgt     240
gacctctgtc tgcgtgtggc tgtccacttg gccgtgcatg ggcactggga gagagcctgaa     300 gatgaggaaa gtttggagg agcagctgac tcaggggtgg aggagcctag gaatgcctct     360
ctccaggccc aagtcgtgct ctccttccag gcctaccta ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact gcagggggct cgaagtctgg     600
aacagcatcc cgagctgctg gg                                            622
```

<210> SEQ ID NO 76
<211> LENGTH: 207
<212> TYPE: PRT
<213> ORGANISM: homo sapians

<400> SEQUENCE: 76

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp
        195                 200                 205

<210> SEQ ID NO 77
<211> LENGTH: 1318
<212> TYPE: DNA

<213> ORGANISM: Artificial Sequence
<220> FEATURE:
<223> OTHER INFORMATION: IL-17RC signal peptide and exons 1-7 of human IL-17RC, and Fc5

<400> SEQUENCE: 77

```
atgcctgtgc cctggttctt gctgtccttg gcactgggcc gaagcccagt ggtcctttct     60
ctggagaggc ttgtggggcc tcaggacgct acccactgct ctccgggcct ctcctgccgc    120
ctctgggaca gtgacatact ctgcctgcct ggggacatcg tgcctgctcc gggccccgtg    180
ctggcgccta cgcacctgca gacagagctg gtgctgaggt gccagaagga gaccgactgt    240
gacctctgtc tgcgtgtggc tgtccacttg gccgtgcatg gcactgggga agagcctgaa    300
gatgaggaaa agtttggagg agcagctgac tcaggggtgg aggagcctag gaatgcctct    360
ctccaggccc aagtcgtgct ctccttccag gcctacccta ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact caggggggct cgaagtctgg    600
aacagcatcc cgagctgctg gggagcccaa atcttcagac aaaactcaca catgcccacc    660
gtgcccagca cctgaagccg agggggcacc gtcagtcttc ctcttccccc caaaacccaa    720
ggacaccctc atgatctccc ggacccctga ggtcacatgc gtggtggtgg acgtgagcca    780
cgaagaccct gaggtcaagt tcaactggta cgtggacggc gtggaggtgc ataatgccaa    840
gacaaagccg cgggaggagc agtacaacag cacgtaccgt gtggtcagcg tcctcaccgt    900
cctgcaccag gactggctga atggcaagga gtacaagtgc aaggtctcca acaaagccct    960
cccatcctcc atcgagaaaa ccatctccaa agccaaaggg cagccccgag aaccacaggt   1020
gtacaccctg cccccatccc gggatgagct gaccaagaac caggtcagcc tgacctgcct   1080
ggtcaaaggc ttctatccca gcgacatcgc cgtggagtgg gagagcaatg ggcagccgga   1140
gaacaactac aagaccacgc ctcccgtgct ggactccgac ggctccttct tcctctacag   1200
caagctcacc gtggacaaga gcaggtggca gcagggaac gtcttctcat gctccgtgat   1260
gcatgaggct ctgcacaacc actacacgca gaagagcctc tccctgtctc cgggtaaa    1318
```

<210> SEQ ID NO 78
<211> LENGTH: 439
<212> TYPE: PRT
<213> ORGANISM: Artificial Sequence
<220> FEATURE:
<223> OTHER INFORMATION: IL-17RC signal peptide and exons 1-7 of human IL-17RC, and Fc5

<400> SEQUENCE: 78

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
                 20                  25                  30

Cys Ser Pro Gly Leu Ser Cys Arg Leu Trp Asp Ser Asp Ile Leu Cys
             35                  40                  45

Leu Pro Gly Asp Ile Val Pro Ala Pro Gly Pro Val Leu Ala Pro Thr
         50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95
```

```
Glu Glu Pro Glu Asp Glu Lys Phe Gly Ala Ala Asp Ser Gly
            100                 105                 110

Val Glu Glu Pro Arg Asn Ala Ser Leu Gln Ala Gln Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
            165                 170                 175

Thr Gln Pro Arg Tyr Glu Lys Glu Leu Asn His Thr Gln Gln Leu Pro
        180                 185                 190

Asp Cys Arg Gly Leu Glu Val Trp Asn Ser Ile Pro Ser Cys Trp Glu
    195                 200                 205

Pro Lys Ser Ser Asp Lys Thr His Thr Cys Pro Pro Cys Pro Ala Pro
        210                 215                 220

Glu Ala Glu Gly Ala Pro Ser Val Phe Leu Phe Pro Pro Lys Pro Lys
225                 230                 235                 240

Asp Thr Leu Met Ile Ser Arg Thr Pro Glu Val Thr Cys Val Val Val
            245                 250                 255

Asp Val Ser His Glu Asp Pro Glu Val Lys Phe Asn Trp Tyr Val Asp
        260                 265                 270

Gly Val Glu Val His Asn Ala Lys Thr Lys Pro Arg Glu Glu Gln Tyr
    275                 280                 285

Asn Ser Thr Tyr Arg Val Val Ser Val Leu Thr Val Leu His Gln Asp
        290                 295                 300

Trp Leu Asn Gly Lys Glu Tyr Lys Cys Lys Val Ser Asn Lys Ala Leu
305                 310                 315                 320

Pro Ser Ser Ile Glu Lys Thr Ile Ser Lys Ala Lys Gly Gln Pro Arg
            325                 330                 335

Glu Pro Gln Val Tyr Thr Leu Pro Pro Ser Arg Asp Glu Leu Thr Lys
        340                 345                 350

Asn Gln Val Ser Leu Thr Cys Leu Val Lys Gly Phe Tyr Pro Ser Asp
    355                 360                 365

Ile Ala Val Glu Trp Glu Ser Asn Gly Gln Pro Glu Asn Asn Tyr Lys
    370                 375                 380

Thr Thr Pro Pro Val Leu Asp Ser Asp Gly Ser Phe Phe Leu Tyr Ser
385                 390                 395                 400

Lys Leu Thr Val Asp Lys Ser Arg Trp Gln Gln Gly Asn Val Phe Ser
            405                 410                 415

Cys Ser Val Met His Glu Ala Leu His Asn His Tyr Thr Gln Lys Ser
        420                 425                 430

Leu Ser Leu Ser Pro Gly Lys
        435

<210> SEQ ID NO 79
<211> LENGTH: 762
<212> TYPE: DNA
<213> ORGANISM: homo sapians

<400> SEQUENCE: 79
atgcctgtgc cctggttctt gctgtccttg gcactgggcc gaagcccagt ggtcctttct        60
ctggagaggc ttgtgggcc tcaggacgct acccactgct ctccgggcct tcctgccgc         120 ctctgggaca gtgacatact ctgcctgcct ggggacatcg tgcctgctcc gggccccgtg       180
```

```
ctggcgccta cgcacctgca gacagagctg gtgctgaggt gccagaagga gaccgactgt    240
gacctctgtc tgcgtgtggc tgtccacttg gccgtgcatg ggcactggga agagcctgaa    300
gatgaggaaa agtttggagg agcagctgac tcaggggtgg aggagcctag gaatgcctct    360
ctccaggccc aagtcgtgct ctccttccag gcctacccta ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcaggggggct cgaagtctgg    600 aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tg                       762
```

<210> SEQ ID NO 80
<211> LENGTH: 254
<212> TYPE: PRT
<213> ORGANISM: homo sapians

<400> SEQUENCE: 80

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu
                245                 250
```

<210> SEQ ID NO 81
<211> LENGTH: 1458
<212> TYPE: DNA

<213> ORGANISM: Artificial Sequence
<220> FEATURE:
<223> OTHER INFORMATION: IL-17RC signal peptide and exons 1-8 of human IL-17RC, and Fc5

<400> SEQUENCE: 81

```
atgcctgtgc cctggttctt gctgtccttg cactgggcc gaagcccagt ggtcctttct      60
ctggagaggc ttgtggggcc tcaggacgct acccactgct ctccgggcct ctcctgccgc    120
ctctgggaca gtgacatact ctgcctgcct ggggacatcg tgcctgctcc gggccccgtg    180
ctggcgccta cgcacctgca gacagagctg gtgctgaggt gccagaagga gaccgactgt    240
gacctctgtc tgcgtgtggc tgtccacttg gccgtgcatg ggcactggga agagcctgaa    300
gatgaggaaa agtttggagg agcagctgac tcaggggtgg aggagcctag gaatgcctct    360
ctccaggccc aagtcgtgct ctccttccag gcctaccta tgcccgctg cgtcctgctg      420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcaggggct cgaagtctgg    600
aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tggagcccaa atcttcagac    780
aaaactcaca catgcccacc gtgcccagca cctgaagccg agggggcacc gtcagtcttc    840
ctcttccccc caaaacccaa ggacaccctc atgatctccc ggacccctga ggtcacatgc    900
gtggtggtgg acgtgagcca cgaagaccct gaggtcaagt tcaactggta cgtggacggc    960
gtggaggtgc ataatgccaa gacaaagccg cgggaggagc agtacaacag cacgtaccgt    1020
gtggtcagcg tcctcaccgt cctgcaccag gactggctga atggcaagga gtacaagtgc    1080
aaggtctcca acaaagccct cccatcctcc atcgagaaaa ccatctccaa agccaagggg    1140
cagccccgag aaccacaggt gtacaccctg cccccatccc gggatgagct gaccaagaac    1200
caggtcagcc tgacctgcct ggtcaaaggc ttctatccca gcgacatcgc cgtggagtgg    1260
gagagcaatg ggcagccgga gaacaactac aagaccacgc ctcccgtgct ggactccgac    1320
ggctccttct cctctacag caagctcacc gtggacaaga gcaggtggca gcaggggaac    1380
gtcttctcat gctccgtgat gcatgaggct ctgcacaacc actacacgca gaagagcctc    1440
tccctgtctc cgggtaaa                                                  1458
```

<210> SEQ ID NO 82
<211> LENGTH: 486
<212> TYPE: PRT
<213> ORGANISM: Artificial Sequence
<220> FEATURE:
<223> OTHER INFORMATION: IL-17RC signal peptide and exons 1-8 of human IL-17RC, and Fc5

<400> SEQUENCE: 82

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60
```

```
His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Ala Ala Asp Ser Gly
            100                 105                 110

Val Glu Glu Pro Arg Asn Ala Ser Leu Gln Ala Gln Val Val Leu Ser
            115                 120                 125

Phe Gln Ala Tyr Pro Thr Ala Arg Cys Val Leu Leu Glu Val Gln Val
        130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Glu Pro
                245                 250                 255

Lys Ser Ser Asp Lys Thr His Thr Cys Pro Cys Pro Ala Pro Glu
            260                 265                 270

Ala Glu Gly Ala Pro Ser Val Phe Leu Phe Pro Pro Lys Pro Lys Asp
        275                 280                 285

Thr Leu Met Ile Ser Arg Thr Pro Glu Val Thr Cys Val Val Val Asp
290                 295                 300

Val Ser His Glu Asp Pro Glu Val Lys Phe Asn Trp Tyr Val Asp Gly
305                 310                 315                 320

Val Glu Val His Asn Ala Lys Thr Lys Pro Arg Glu Glu Gln Tyr Asn
                325                 330                 335

Ser Thr Tyr Arg Val Val Ser Val Leu Thr Val Leu His Gln Asp Trp
            340                 345                 350

Leu Asn Gly Lys Glu Tyr Lys Cys Lys Val Ser Asn Lys Ala Leu Pro
        355                 360                 365

Ser Ser Ile Glu Lys Thr Ile Ser Lys Ala Lys Gly Gln Pro Arg Glu
370                 375                 380

Pro Gln Val Tyr Thr Leu Pro Pro Ser Arg Asp Glu Leu Thr Lys Asn
385                 390                 395                 400

Gln Val Ser Leu Thr Cys Leu Val Lys Gly Phe Tyr Pro Ser Asp Ile
                405                 410                 415

Ala Val Glu Trp Glu Ser Asn Gly Gln Pro Glu Asn Asn Tyr Lys Thr
            420                 425                 430

Thr Pro Pro Val Leu Asp Ser Asp Gly Ser Phe Phe Leu Tyr Ser Lys
        435                 440                 445

Leu Thr Val Asp Lys Ser Arg Trp Gln Gln Gly Asn Val Phe Ser Cys
450                 455                 460

Ser Val Met His Glu Ala Leu His Asn His Tyr Thr Gln Lys Ser Leu
465                 470                 475                 480

Ser Leu Ser Pro Gly Lys
                485
```

<210> SEQ ID NO 83
<211> LENGTH: 822
<212> TYPE: DNA
<213> ORGANISM: homo sapians

<400> SEQUENCE: 83

```
atgcctgtgc ctggttctt gctgtccttg gcactgggcc gaagcccagt ggtcctttct      60
ctggagaggc ttgtggggcc tcaggacgct acccactgct ctccgggcct ctcctgccgc    120
ctctgggaca gtgacatact ctgcctgcct ggggacatcg tgcctgctcc gggccccgtg    180
ctggcgccta cgcacctgca gacagagctg gtgctgaggg ccagaaggga gaccgactgt    240
gacctctgtc tgcgtgtggc tgtccacttg gccgtgcatg gcactggga agagcctgaa      300
gatgaggaaa agtttggagg agcagctgac tcaggggtgg aggagcctag gaatgcctct    360
ctccaggccc aagtcgtgct ctccttccag gcctaccta ctgcccgctg cgtcctgctg      420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcagggggct cgaagtctgg    600
aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tgactggacc gcagatcatt    780
accttgaacc acacagacct ggttccctgc ctctgtattc ag                       822
```

<210> SEQ ID NO 84
<211> LENGTH: 274
<212> TYPE: PRT
<213> ORGANISM: homo sapians

<400> SEQUENCE: 84

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190
```

```
Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln
```

<210> SEQ ID NO 85
<211> LENGTH: 1518
<212> TYPE: DNA
<213> ORGANISM: Artificial Sequence
<220> FEATURE:
<223> OTHER INFORMATION: IL-17RC signal peptide and exons 1-9 of human
      IL-17RC, and Fc5

<400> SEQUENCE: 85

```
atgcctgtgc cctggttctt gctgtccttg cactgggcc gaagcccagt ggtcctttct      60
ctggagagc ttgtggggcc tcaggacgct acccactgct ctccgggcct ctcctgccgc     120
ctctgggaca gtgacatact ctgcctgcct gggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg ccgtgcatg ggcactggga agagcctgaa     300
gatgaggaaa agtttggagg agcagctgac tcaggggtgg aggagcctag gaatgcctct     360
ctccaggccc aagtcgtgct ctccttccag gcctaccta ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact gcaggggct cgaagtctgg     600
aacagcatcc gagctgctg ggccctgccc tggctcaacg tgtcagcaga tggtgacaac     660
gtgcatctgg ttctgaatgt ctctgaggag cagcacttcg gcctctccct gtactggaat     720
caggtccagg gccccccaaa accccggtgg cacaaaaacc tgactggacc gcagatcatt     780
accttgaacc acacagacct ggttccctgc ctctgtattc aggagcccaa atcttcagac     840
aaaactcaca catgcccacc gtgcccagca cctgaagccg agggggcacc gtcagtcttc     900
ctcttccccc caaaacccaa ggacaccctc atgatctccc ggacccctga ggtcacatgc     960
gtggtggtgg acgtgagcca cgaagaccct gaggtcaagt tcaactggta cgtggacggc    1020
gtggaggtgc ataatgccaa gacaaagccg cgggaggagc agtacaacag cacgtaccgt    1080
gtggtcagcg tcctcaccgt cctgcaccag gactggctga atggcaagga gtacaagtgc    1140
aaggtctcca acaaagccct cccatcctcc atcgagaaaa ccatctccaa agccaagggg    1200
cagccccgag aaccacaggt gtacaccctg cccccatccc gggatgagct gaccaagaac    1260
caggtcagcc tgacctgcct ggtcaaaggc ttctatccca gcgacatcgc cgtggagtgg    1320
gagagcaatg ggcagccgga gaacaactac aagaccacgc tcccgtgct ggactccgac    1380
ggctccttct tcctctacag caagctcacc gtggacaaga gcaggtggca gcaggggaac    1440
gtcttctcat gctccgtgat gcatgaggct ctgcacaacc actacacgca gaagagcctc    1500
tccctgtctc cgggtaaa                                                  1518
```

<210> SEQ ID NO 86
<211> LENGTH: 506
<212> TYPE: PRT
<213> ORGANISM: Artificial Sequence
<220> FEATURE:
<223> OTHER INFORMATION: IL-17RC signal peptide and exons 1-9 of human
      IL-17RC, and Fc5

<400> SEQUENCE: 86

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Glu Pro Lys Ser Ser Asp Lys Thr His Thr Cys Pro Pro Cys
        275                 280                 285

Pro Ala Pro Glu Ala Glu Gly Ala Pro Ser Val Phe Leu Phe Pro Pro
    290                 295                 300

Lys Pro Lys Asp Thr Leu Met Ile Ser Arg Thr Pro Glu Val Thr Cys
305                 310                 315                 320

Val Val Val Asp Val Ser His Glu Asp Pro Glu Val Lys Phe Asn Trp
                325                 330                 335

Tyr Val Asp Gly Val Glu Val His Asn Ala Lys Thr Lys Pro Arg Glu
            340                 345                 350

Glu Gln Tyr Asn Ser Thr Tyr Arg Val Val Ser Val Leu Thr Val Leu
        355                 360                 365

His Gln Asp Trp Leu Asn Gly Lys Glu Tyr Lys Cys Lys Val Ser Asn
        370                 375                 380

Lys Ala Leu Pro Ser Ser Ile Glu Lys Thr Ile Ser Lys Ala Lys Gly
385                 390                 395                 400

Gln Pro Arg Glu Pro Gln Val Tyr Thr Leu Pro Pro Ser Arg Asp Glu
                405                 410                 415

Leu Thr Lys Asn Gln Val Ser Leu Thr Cys Leu Val Lys Gly Phe Tyr
            420                 425                 430

Pro Ser Asp Ile Ala Val Glu Trp Glu Ser Asn Gly Gln Pro Glu Asn
        435                 440                 445

Asn Tyr Lys Thr Thr Pro Pro Val Leu Asp Ser Asp Gly Ser Phe Phe
    450                 455                 460

Leu Tyr Ser Lys Leu Thr Val Asp Lys Ser Arg Trp Gln Gln Gly Asn
465                 470                 475                 480

Val Phe Ser Cys Ser Val Met His Glu Ala Leu His Asn His Tyr Thr
                485                 490                 495

Gln Lys Ser Leu Ser Leu Ser Pro Gly Lys
            500                 505

<210> SEQ ID NO 87
<211> LENGTH: 873
<212> TYPE: DNA
<213> ORGANISM: homo sapians

<400> SEQUENCE: 87
atgcctgtgc cctggttctt gctgtccttg gcactgggcc gaagcccagt ggtcctttct        60
ctggagaggc ttgtggggcc tcaggacgct acccactgct ctccgggcct tcctgccgc       120 ctctgggaca gtgacatact ctgcctgcct ggggacatcg tgcctgctcc gggcccgtg       180 ctggcgccta cgcacctgca gacagagctg gtgctgaggt gccagaagga gaccgactgt      240
gacctctgtc tgcgtgtggc tgtccacttg gccgtgcatg gcactgggga agagcctgaa      300
gatgaggaaa gtttggagg agcagctgac tcaggggtgg aggagcctag gaatgcctct       360
ctccaggccc aagtcgtgct ctccttccag gcctaccta ctgcccgctg cgtcctgctg       420
gaggtgcaag tgcctgctgc ccttgtgcag tttggtcagt ctgtgggctc tgtggtatat      480
gactgcttcg aggctgccct agggagtgag gtacgaatct ggtcctatac tcagcccagg      540
tacgagaagg aactcaacca cacacagcag ctgcctgact gcagggggct cgaagtctgg      600
aacagcatcc cgagctgctg ggccctgccc tggctcaacg tgtcagcaga tggtgacaac      660
gtgcatctgg ttctgaatgt ctctgaggag cagcacttcg gcctctccct gtactggaat      720
caggtccagg gcccccaaa accccggtgg cacaaaaacc tgactggacc gcagatcatt       780
accttgaacc acacagacct ggttccctgc ctctgtattc aggtgtggcc tctggaacct      840
gactccgtta ggacgaacat ctgccccttc agg                                   873

<210> SEQ ID NO 88
<211> LENGTH: 291
<212> TYPE: PRT
<213> ORGANISM: homo sapians

<400> SEQUENCE: 88

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

```
Cys Ser Pro Gly Leu Ser Cys Arg Leu Trp Asp Ser Asp Ile Leu Cys
         35                  40                  45
Leu Pro Gly Asp Ile Val Pro Ala Pro Gly Pro Val Leu Ala Pro Thr
 50                  55                  60
His Leu Gln Thr Glu Leu Val Leu Arg Cys Gln Lys Glu Thr Asp Cys
 65                  70                  75                  80
Asp Leu Cys Leu Arg Val Ala Val His Leu Ala Val His Gly His Trp
                 85                  90                  95
Glu Glu Pro Glu Asp Glu Glu Lys Phe Gly Gly Ala Ala Asp Ser Gly
            100                 105                 110
Val Glu Glu Pro Arg Asn Ala Ser Leu Gln Ala Gln Val Val Leu Ser
        115                 120                 125
Phe Gln Ala Tyr Pro Thr Ala Arg Cys Val Leu Leu Glu Val Gln Val
130                 135                 140
Pro Ala Ala Leu Val Gln Phe Gly Gln Ser Val Gly Ser Val Val Tyr
145                 150                 155                 160
Asp Cys Phe Glu Ala Ala Leu Gly Ser Glu Val Arg Ile Trp Ser Tyr
                165                 170                 175
Thr Gln Pro Arg Tyr Glu Lys Glu Leu Asn His Thr Gln Gln Leu Pro
            180                 185                 190
Asp Cys Arg Gly Leu Glu Val Trp Asn Ser Ile Pro Ser Cys Trp Ala
        195                 200                 205
Leu Pro Trp Leu Asn Val Ser Ala Asp Gly Asp Asn Val His Leu Val
210                 215                 220
Leu Asn Val Ser Glu Glu Gln His Phe Gly Leu Ser Leu Tyr Trp Asn
225                 230                 235                 240
Gln Val Gln Gly Pro Pro Lys Pro Arg Trp His Lys Asn Leu Thr Gly
                245                 250                 255
Pro Gln Ile Ile Thr Leu Asn His Thr Asp Leu Val Pro Cys Leu Cys
            260                 265                 270
Ile Gln Val Trp Pro Leu Glu Pro Asp Ser Val Arg Thr Asn Ile Cys
        275                 280                 285
Pro Phe Arg
    290

<210> SEQ ID NO 89
<211> LENGTH: 1569
<212> TYPE: DNA
<213> ORGANISM: Artificial Sequence
<220> FEATURE:
<223> OTHER INFORMATION: IL-17RC signal peptide and exons 1-10 of human
      IL-17RC, and Fc5

<400> SEQUENCE: 89
atgcctgtgc cctggttctt gctgtccttg cactgggcc gaagcccagt ggtcctttct    60
ctggagaggc ttgtggggcc tcaggacgct acccactgct ctccgggcct tcctgccgc   120 ctctgggaca gtgacatact ctgcctgcct ggggacatcg tgcctgctcc gggccccgtg   180
ctggcgccta cgcacctgca gacagagctg gtgctgaggt gccagaagga gaccgactgt   240
gacctctgtc tgcgtgtggc tgtccacttg gccgtgcatg gcactgggga agagcctgaa   300
gatgaggaaa agtttggagg agcagctgac tcaggggtgg aggagcctag gaatgcctct   360
ctccaggccc aagtcgtgct ctccttccag gcctacccta ctgcccgctg cgtcctgctg   420
gaggtgcaag tgcctgctgc ccttgtgcag tttggtcagt ctgtgggctc tgtggtatat   480
gactgcttcg aggctgccct agggagtgag gtacgaatct ggtcctatac tcagcccagg   540
```

```
tacgagaagg aactcaacca cacacagcag ctgcctgact gcaggggggct cgaagtctgg    600
aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa acccggtgg cacaaaaacc tgactggacc gcagatcatt    780
accttgaacc acacagacct ggttccctgc ctctgtattc aggtgtggcc tctggaacct    840
gactccgtta ggacgaacat ctgccccttc agggagccca atcttcaga caaaactcac    900
acatgcccac cgtgcccagc acctgaagcc gagggggcac cgtcagtctt cctcttcccc    960
ccaaaaccca aggacaccct catgatctcc cggacccctg aggtcacatg cgtggtggtg   1020
gacgtgagcc acgaagaccc tgaggtcaag ttcaactggt acgtggacgg cgtggaggtg   1080
cataatgcca agacaaagcc gcgggaggag cagtacaaca gcacgtaccg tgtggtcagc   1140
gtcctcaccg tcctgcacca ggactggctg aatggcaagg agtacaagtg caaggtctcc   1200
aacaaagccc tcccatcctc catcgagaaa accatctcca aagccaaagg gcagccccga   1260
gaaccacagg tgtacaccct gcccccatcc cgggatgagc tgaccaagaa ccaggtcagc   1320
ctgacctgcc tggtcaaagg cttctatccc agcgacatcg ccgtggagtg ggagagcaat   1380
gggcagccgg agaacaacta caagaccacg cctcccgtgc tggactccga cggctccttc   1440
ttcctctaca gcaagctcac cgtggacaag agcaggtggc agcaggggaa cgtcttctca   1500
tgctccgtga tgcatgaggc tctgcacaac cactacacgc agaagagcct ctccctgtct   1560
ccgggtaaa                                                           1569
```

<210> SEQ ID NO 90
<211> LENGTH: 523
<212> TYPE: PRT
<213> ORGANISM: Artificial Sequence
<220> FEATURE:
<223> OTHER INFORMATION: IL-17RC signal peptide and exons 1-10 of human
      IL-17RC, and Fc5

<400> SEQUENCE: 90

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175
```

```
Thr Gln Pro Arg Tyr Glu Lys Glu Leu Asn His Thr Gln Gln Leu Pro
            180                 185                 190
Asp Cys Arg Gly Leu Glu Val Trp Asn Ser Ile Pro Ser Cys Trp Ala
            195                 200                 205
Leu Pro Trp Leu Asn Val Ser Ala Asp Gly Asp Asn Val His Leu Val
    210                 215                 220
Leu Asn Val Ser Glu Glu Gln His Phe Gly Leu Ser Leu Tyr Trp Asn
225                 230                 235                 240
Gln Val Gln Gly Pro Pro Lys Pro Arg Trp His Lys Asn Leu Thr Gly
                245                 250                 255
Pro Gln Ile Ile Thr Leu Asn His Thr Asp Leu Val Pro Cys Leu Cys
            260                 265                 270
Ile Gln Val Trp Pro Leu Glu Pro Asp Ser Val Arg Thr Asn Ile Cys
            275                 280                 285
Pro Phe Arg Glu Pro Lys Ser Ser Asp Lys Thr His Thr Cys Pro Pro
            290                 295                 300
Cys Pro Ala Pro Glu Ala Glu Gly Ala Pro Ser Val Phe Leu Phe Pro
305                 310                 315                 320
Pro Lys Pro Lys Asp Thr Leu Met Ile Ser Arg Thr Pro Glu Val Thr
                325                 330                 335
Cys Val Val Val Asp Val Ser His Glu Asp Pro Glu Val Lys Phe Asn
            340                 345                 350
Trp Tyr Val Asp Gly Val Glu Val His Asn Ala Lys Thr Lys Pro Arg
            355                 360                 365
Glu Glu Gln Tyr Asn Ser Thr Tyr Arg Val Val Ser Val Leu Thr Val
            370                 375                 380
Leu His Gln Asp Trp Leu Asn Gly Lys Glu Tyr Lys Cys Lys Val Ser
385                 390                 395                 400
Asn Lys Ala Leu Pro Ser Ser Ile Glu Lys Thr Ile Ser Lys Ala Lys
                405                 410                 415
Gly Gln Pro Arg Glu Pro Gln Val Tyr Thr Leu Pro Pro Ser Arg Asp
            420                 425                 430
Glu Leu Thr Lys Asn Gln Val Ser Leu Thr Cys Leu Val Lys Gly Phe
            435                 440                 445
Tyr Pro Ser Asp Ile Ala Val Glu Trp Glu Ser Asn Gly Gln Pro Glu
    450                 455                 460
Asn Asn Tyr Lys Thr Thr Pro Pro Val Leu Asp Ser Asp Gly Ser Phe
465                 470                 475                 480
Phe Leu Tyr Ser Lys Leu Thr Val Asp Lys Ser Arg Trp Gln Gln Gly
                485                 490                 495
Asn Val Phe Ser Cys Ser Val Met His Glu Ala Leu His Asn His Tyr
            500                 505                 510
Thr Gln Lys Ser Leu Ser Leu Ser Pro Gly Lys
            515                 520
```

<210> SEQ ID NO 91
<211> LENGTH: 1059
<212> TYPE: DNA
<213> ORGANISM: homo sapians

<400> SEQUENCE: 91

```
atgcctgtgc cctggttctt gctgtccttg gcactgggcc gaagcccagt ggtcctttct     60
ctggagaggc ttgtgggggcc tcaggacgct acccactgct ctccgggcct tcctgccgc    120 ctctgggaca gtgacatact ctgcctgcct ggggacatcg tgcctgctcc gggccccgtg   180
```

```
ctggcgccta cgcacctgca gacagagctg gtgctgaggt gccagaagga gaccgactgt    240
gacctctgtc tgcgtgtggc tgtccacttg gccgtgcatg ggcactggga agagcctgaa    300
gatgaggaaa agtttggagg agcagctgac tcaggggtgg aggagcctag gaatgcctct    360
ctccaggccc aagtcgtgct ctccttccag gcctacccta ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcagggggct cgaagtctgg    600
aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tgactggacc gcagatcatt    780
accttgaacc acacagacct ggttccctgc ctctgtattc aggtgtggcc tctggaacct    840
gactccgtta ggacgaacat ctgccccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca   1020
ctggtcccac cgctttcctg ggagaacgtc actgtggac                          1059
```

<210> SEQ ID NO 92
<211> LENGTH: 353
<212> TYPE: PRT
<213> ORGANISM: homo sapians

<400> SEQUENCE: 92

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220
```

```
Leu Asn Val Ser Glu Glu Gln His Phe Gly Leu Ser Leu Tyr Trp Asn
225                 230                 235                 240

Gln Val Gln Gly Pro Lys Pro Arg Trp His Lys Asn Leu Thr Gly
            245                 250                 255

Pro Gln Ile Ile Thr Leu Asn His Thr Asp Leu Val Pro Cys Leu Cys
        260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
        290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp

<210> SEQ ID NO 93
<211> LENGTH: 1755
<212> TYPE: DNA
<213> ORGANISM: Artificial Sequence
<220> FEATURE:
<223> OTHER INFORMATION: IL-17RC signal peptide and exons 1-11 of human
      IL-17RC, and Fc5

<400> SEQUENCE: 93
atgcctgtgc cctggttctt gctgtccttg gcactgggcc gaagcccagt ggtcctttct      60 ctggagagc ttgtggggcc tcaggacgct acccactgct ctccgggcct ctcctgccgc      120
ctctgggaca gtgacatact ctgcctgcct ggggacatcg tgcctgctcc gggccccgtg      180
ctggcgccta cgcacctgca gacagagctg gtgctgaggt gccagaagga gaccgactgt      240
gacctctgtc tgcgtgtggc tgtccacttg gccgtgcatg gcactgggga gagcctgaa      300 gatgaggaaa agtttggagg agcagctgac tcaggggtgg aggagcctag gaatgcctct      360
ctccaggccc aagtcgtgct ctccttccag gcctacccta ctgcccgctg cgtcctgctg      420
gaggtgcaag tgcctgctgc ccttgtgcag tttggtcagt ctgtgggctc tgtggtatat      480
gactgcttcg aggctgccct agggagtgag gtacgaatct ggtcctatac tcagcccagg      540
tacgagaagg aactcaacca cacacagcag ctgcctgact gcaggggct cgaagtctgg      600 aacagcatcc cgagctgctg gggcctgccc tggctcaacg tgtcagcaga tggtgacaac      660
gtgcatctgg ttctgaatgt ctctgaggag cagcacttcg gcctctccct gtactggaat      720
caggtccagg gccccccaaa accccggtgg cacaaaaacc tgactggacc gcagatcatt      780
accttgaacc acacagacct ggttccctgc ctctgtatto aggtgtggcc tctggaacct      840
gactccgtta ggacgaacat ctgccccttc agggaggacc ccgcgcaca ccagaacctc      900 tggcaagccg cccgactgcg actgctgacc ctgcagagct ggctgctgga cgcaccgtgc      960
tcgctgcccg cagaagcggc actgtgctgg cgggctccgg gtgggaccc ctgccagcca     1020 ctggtcccac cgctttcctg ggagaacgtc actgtggacg agcccaaatc ttcagacaaa     1080
actcacacat gcccaccgtg cccagcacct gaagccgagg ggcaccgtc agtcttcctc     1140 ttcccccaa acccaagga caccctcatg atctccccgga ccctgaggt cacatgcgtg      1200 gtggtggacg tgagccacga agaccctgag gtcaagttca actggtacgt ggacggcgtg     1260
gaggtgcata atgccaagac aaagccgcgg gaggagcagt acaacagcac gtaccgtgtg     1320
```

```
gtcagcgtcc tcaccgtcct gcaccaggac tggctgaatg gcaaggagta caagtgcaag    1380
gtctccaaca aagccctccc atcctccatc gagaaaacca tctccaaagc caagggcag    1440 ccccgagaac acaggtgta caccctgccc ccatcccggg atgagctgac caagaaccag    1500
gtcagcctga cctgcctggt caaaggcttc tatcccagcg acatcgccgt ggagtgggag    1560
agcaatgggc agccggagaa caactacaag accacgcctc ccgtgctgga ctccgacggc    1620
tccttcttcc tctacagcaa gctcaccgtg gacaagagca ggtggcagca ggggaacgtc    1680
ttctcatgct ccgtgatgca tgaggctctg cacaaccact acacgcagaa gagcctctcc    1740
ctgtctccgg gtaaa                                                     1755
```

<210> SEQ ID NO 94
<211> LENGTH: 585
<212> TYPE: PRT
<213> ORGANISM: Artificial Sequence
<220> FEATURE:
<223> OTHER INFORMATION: IL-17RC signal peptide and exons 1-11 of human
      IL-17RC, and Fc5

<400> SEQUENCE: 94

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
```

```
                275                 280                 285
Pro Phe Arg Glu Asp Pro Arg Ala His Gln Asn Leu Trp Gln Ala Ala
290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
                340                 345                 350

Asp Glu Pro Lys Ser Ser Asp Lys Thr His Thr Cys Pro Pro Cys Pro
                355                 360                 365

Ala Pro Glu Ala Glu Gly Ala Pro Ser Val Phe Leu Phe Pro Pro Lys
                370                 375                 380

Pro Lys Asp Thr Leu Met Ile Ser Arg Thr Pro Glu Val Thr Cys Val
385                 390                 395                 400

Val Val Asp Val Ser His Glu Asp Pro Glu Val Lys Phe Asn Trp Tyr
                405                 410                 415

Val Asp Gly Val Glu Val His Asn Ala Lys Thr Lys Pro Arg Glu Glu
                420                 425                 430

Gln Tyr Asn Ser Thr Tyr Arg Val Val Ser Val Leu Thr Val Leu His
                435                 440                 445

Gln Asp Trp Leu Asn Gly Lys Glu Tyr Lys Cys Lys Val Ser Asn Lys
450                 455                 460

Ala Leu Pro Ser Ser Ile Glu Lys Thr Ile Ser Lys Ala Lys Gly Gln
465                 470                 475                 480

Pro Arg Glu Pro Gln Val Tyr Thr Leu Pro Pro Ser Arg Asp Glu Leu
                485                 490                 495

Thr Lys Asn Gln Val Ser Leu Thr Cys Leu Val Lys Gly Phe Tyr Pro
                500                 505                 510

Ser Asp Ile Ala Val Glu Trp Glu Ser Asn Gly Gln Pro Glu Asn Asn
                515                 520                 525

Tyr Lys Thr Thr Pro Pro Val Leu Asp Ser Asp Gly Ser Phe Phe Leu
                530                 535                 540

Tyr Ser Lys Leu Thr Val Asp Lys Ser Arg Trp Gln Gln Gly Asn Val
545                 550                 555                 560

Phe Ser Cys Ser Val Met His Glu Ala Leu His Asn His Tyr Thr Gln
                565                 570                 575

Lys Ser Leu Ser Leu Ser Pro Gly Lys
                580                 585

<210> SEQ ID NO 95
<211> LENGTH: 303
<212> TYPE: DNA
<213> ORGANISM: homo sapiens

<400> SEQUENCE: 95
atgcctgtgc cctggttctt gctgtccttg cactgggcc gaagcccagt ggtcctttct      60
gactccctgg ggcctctcaa agacgatgtg ctactgttgg agacacgagg cccccaggac    120
aacagatccc tctgtgcctt ggaacccagt ggctgtactt cactacccag caaagcctcc    180
acgagggcag ctcgccttgg agagtactta ctacaagacc tgcagtcagg ccagtgtctg    240
cagctatggg acgatgactt gggagcgcta tgggcctgcc ccatggacaa atacatccac    300
aag                                                                  303
```

<210> SEQ ID NO 96
<211> LENGTH: 101
<212> TYPE: PRT
<213> ORGANISM: homo sapians

<400> SEQUENCE: 96

Met Pro Val Pro Trp Phe Leu Leu Ser Leu Ala Leu Gly Arg Ser Pro
1               5                   10                  15

Val Val Leu Ser Asp Ser Leu Gly Pro Leu Lys Asp Asp Val Leu Leu
            20                  25                  30

Leu Glu Thr Arg Gly Pro Gln Asp Asn Arg Ser Leu Cys Ala Leu Glu
        35                  40                  45

Pro Ser Gly Cys Thr Ser Leu Pro Ser Lys Ala Ser Thr Arg Ala Ala
    50                  55                  60

Arg Leu Gly Glu Tyr Leu Leu Gln Asp Leu Gln Ser Gly Gln Cys Leu
65                  70                  75                  80

Gln Leu Trp Asp Asp Asp Leu Gly Ala Leu Trp Ala Cys Pro Met Asp
                85                  90                  95

Lys Tyr Ile His Lys
            100

<210> SEQ ID NO 97
<211> LENGTH: 999
<212> TYPE: DNA
<213> ORGANISM: Artificial Sequence
<220> FEATURE:
<223> OTHER INFORMATION: IL-17RC signal peptide and exons 14-16 of human
      IL-17RC, and Fc5

<400> SEQUENCE: 97
atgcctgtgc cctggttctt gctgtccttg gcactgggcc gaagcccagt ggtcctttct      60
gactccctgg ggcctctcaa agacgatgtg ctactgttgg agacacgagg cccccaggac     120
aacagatccc tctgtgcctt ggaacccagt ggctgtactt cactacccag caaagcctcc     180
acgagggcag ctcgccttgg agagtactta ctacaagacc tgcagtcagg ccagtgtctg     240
cagctatggg acgatgactt gggagcgcta tgggcctgcc ccatggacaa atacatccac     300
aaggagccca atcttcaga caaaactcac acatgcccac cgtgcccagc acctgaagcc      360
gagggggcac cgtcagtctt cctcttcccc ccaaaaccca aggacaccct catgatctcc     420
cggacccctg aggtcacatg cgtggtggtg gacgtgagcc acgaagaccc tgaggtcaag     480
ttcaactggt acgtggacgg cgtggaggtg cataatgcca agacaaagcc gcggaggag      540 cagtacaaca gcacgtaccg tgtggtcagc gtcctcaccg tcctgcacca ggactggctg     600
aatggcaagg agtacaagtg caaggtctcc aacaaagccc tcccatcctc catcgagaaa     660
accatctcca aagccaaagg gcagccccga gaaccacagg tgtacaccct gcccccatcc     720
cgggatgagc tgaccaagaa ccaggtcagc ctgacctgcc tggtcaaagg cttctatccc     780
agcgacatcg ccgtggagtg ggagagcaat gggcagccgg agaacaacta caagaccacg     840
cctcccgtgc tggactccga cggctccttc ttcctctaca gcaagctcac cgtggacaag     900
agcaggtggc agcaggggaa cgtcttctca tgctccgtga tgcatgaggc tctgcacaac     960
cactacacgc agaagagcct ctccctgtct ccgggtaaa                            999

<210> SEQ ID NO 98
<211> LENGTH: 333
<212> TYPE: PRT
<213> ORGANISM: Artificial Sequence
<220> FEATURE:
<223> OTHER INFORMATION: IL-17RC signal peptide and exons 14-16 of human IL-17RC, and Fc5

<400> SEQUENCE: 98

Met Pro Val Pro Trp Phe Leu Leu Ser Leu Ala Leu Gly Arg Ser Pro
1               5                   10                  15

Val Val Leu Ser Asp Ser Leu Gly Pro Leu Lys Asp Val Leu Leu
            20                  25                  30

Leu Glu Thr Arg Gly Pro Gln Asp Asn Arg Ser Leu Cys Ala Leu Glu
            35                  40                  45

Pro Ser Gly Cys Thr Ser Leu Pro Ser Lys Ala Ser Thr Arg Ala Ala
        50                  55                  60

Arg Leu Gly Glu Tyr Leu Leu Gln Asp Leu Gln Ser Gly Gln Cys Leu
65                  70                  75                  80

Gln Leu Trp Asp Asp Leu Gly Ala Leu Trp Ala Cys Pro Met Asp
                85                  90                  95

Lys Tyr Ile His Lys Glu Pro Lys Ser Ser Asp Lys Thr His Thr Cys
                100                 105                 110

Pro Pro Cys Pro Ala Pro Glu Ala Glu Gly Ala Pro Ser Val Phe Leu
            115                 120                 125

Phe Pro Pro Lys Pro Lys Asp Thr Leu Met Ile Ser Arg Thr Pro Glu
130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ser Ser Ile Glu Lys Thr Ile Ser Lys
210                 215                 220

Ala Lys Gly Gln Pro Arg Glu Pro Gln Val Tyr Thr Leu Pro Pro Ser
225                 230                 235                 240

Arg Asp Glu Leu Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330

<210> SEQ ID NO 99
<211> LENGTH: 585
<212> TYPE: DNA
<213> ORGANISM: homo sapians

<400> SEQUENCE: 99
atgcctgtgc cctggttctt gctgtccttg gcactgggcc gaagcccagt ggtcctttct      60
gaggaccccc gcgcacacca gaacctctgg caagccgccc gactgcgact gctgaccctg     120
cagagctggc tgctggacgc accgtgctcg ctgcccgcag aagcggcact gtgctggcgg     180

```
gctccgggtg gggacccctg ccagccactg gtcccaccgc tttcctggga gaacgtcact      240
gtggacaagg ttctcgagtt cccattgctg aaaggccacc ctaacctctg tgttcaggtg      300
aacagctcgg agaagctgca gctgcaggag tgcttgtggg ctgactccct ggggcctctc      360
aaagacgatg tgctactgtt ggagacacga ggcccccagg acaacagatc cctctgtgcc      420
ttggaaccca gtggctgtac ttcactaccc agcaaagcct ccacgagggc agctcgcctt      480
ggagagtact tactacaaga cctgcagtca ggccagtgtc tgcagctatg ggacgatgac      540
ttgggagcgc tatgggcctg ccccatggac aaatacatcc acaag                     585

<210> SEQ ID NO 100
<211> LENGTH: 195
<212> TYPE: PRT
<213> ORGANISM: homo sapians

<400> SEQUENCE: 100

Met Pro Val Pro Trp Phe Leu Leu Ser Leu Ala Leu Gly Arg Ser Pro
  1               5                  10                  15
Val Val Leu Ser Glu Asp Pro Arg Ala His Gln Asn Leu Trp Gln Ala
                 20                  25                  30
Ala Arg Leu Arg Leu Leu Thr Leu Gln Ser Trp Leu Leu Asp Ala Pro
             35                  40                  45
Cys Ser Leu Pro Ala Glu Ala Ala Leu Cys Trp Arg Ala Pro Gly Gly
         50                  55                  60
Asp Pro Cys Gln Pro Leu Val Pro Pro Leu Ser Trp Glu Asn Val Thr
 65                  70                  75                  80
Val Asp Lys Val Leu Glu Phe Pro Leu Leu Lys Gly His Pro Asn Leu
                 85                  90                  95
Cys Val Gln Val Asn Ser Ser Glu Lys Leu Gln Leu Gln Glu Cys Leu
                100                 105                 110
Trp Ala Asp Ser Leu Gly Pro Leu Lys Asp Asp Val Leu Leu Leu Glu
            115                 120                 125
Thr Arg Gly Pro Gln Asp Asn Arg Ser Leu Cys Ala Leu Glu Pro Ser
        130                 135                 140
Gly Cys Thr Ser Leu Pro Ser Lys Ala Ser Thr Arg Ala Ala Arg Leu
145                 150                 155                 160
Gly Glu Tyr Leu Leu Gln Asp Leu Gln Ser Gly Gln Cys Leu Gln Leu
                165                 170                 175
Trp Asp Asp Asp Leu Gly Ala Leu Trp Ala Cys Pro Met Asp Lys Tyr
            180                 185                 190
Ile His Lys
        195

<210> SEQ ID NO 101
<211> LENGTH: 1281
<212> TYPE: DNA
<213> ORGANISM: Artificial Sequence
<220> FEATURE:
<223> OTHER INFORMATION: IL-17RC signal peptide and exons 11-16 of human
      IL-17RC, and Fc5

<400> SEQUENCE: 101
atgcctgtgc cctggttctt gctgtccttg gcactgggcc gaagcccagt ggtccttttct      60 gaggaccccc gcgcacacca gaacctctgg caagccgccc gactgcgact gctgaccctg      120
cagagctggt tgctggacgc accgtgctcg ctgcccgcag aagcggcact gtgctggcgg      180
gctccgggtg gggacccctg ccagccactg gtcccaccgc tttcctggga gaacgtcact      240
```

```
gtggacaagg ttctcgagtt cccattgctg aaaggccacc ctaacctctg tgttcaggtg      300
aacagctcgg agaagctgca gctgcaggag tgcttgtggg ctgactccct ggggcctctc      360
aaagacgatg tgctactgtt ggagacacga ggcccccagg acaacagatc cctctgtgcc      420
ttggaaccca gtggctgtac ttcactaccc agcaaagcct ccacgagggc agctcgcctt      480
ggagagtact tactacaaga cctgcagtca ggccagtgtc tgcagctatg ggacgatgac      540 tgggagcgc tatgggcctg ccccatggac aaatacatcc acaaggagcc caaatcttca      600
gacaaaactc acacatgccc accgtgccca gcacctgaag ccgaggggc accgtcagtc      660 ttcctcttcc ccccaaaacc caaggacacc ctcatgatct cccggacccc tgaggtcaca      720
tgcgtggtgg tggacgtgag ccacgaagac cctgaggtca agttcaactg gtacgtggac      780
ggcgtggagg tgcataatgc caagacaaag ccgcgggagg agcagtacaa cagcacgtac      840
cgtgtggtca gcgtcctcac cgtcctgcac caggactggc tgaatggcaa ggagtacaag      900
tgcaaggtct ccaacaaagc cctcccatcc tccatcgaga aaaccatctc caaagccaaa      960
gggcagcccc gagaaccaca ggtgtacacc ctgcccccat cccgggatga gctgaccaag     1020
aaccaggtca gcctgacctg cctggtcaaa ggcttctatc ccagcgacat cgccgtggag     1080
tgggagagca atgggcagcc ggagaacaac tacaagacca cgcctcccgt gctggactcc     1140
gacggctcct tcttcctcta cagcaagctc accgtggaca gagcaggtg gcagcagggg     1200 aacgtcttct catgctccgt gatgcatgag gctctgcaca accactacac gcagaagagc     1260 ctctcccctgt ctccgggtaa a                                              1281

<210> SEQ ID NO 102
<211> LENGTH: 427
<212> TYPE: PRT
<213> ORGANISM: Artificial Sequence
<220> FEATURE:
<223> OTHER INFORMATION: IL-17RC signal peptide and exons 11-16 of human
      IL-17RC, and Fc5

<400> SEQUENCE: 102

Met Pro Val Pro Trp Phe Leu Leu Ser Leu Ala Leu Gly Arg Ser Pro
  1               5                  10                  15

Val Val Leu Ser Glu Asp Pro Arg Ala His Gln Asn Leu Trp Gln Ala
                 20                  25                  30

Ala Arg Leu Arg Leu Leu Thr Leu Gln Ser Trp Leu Leu Asp Ala Pro
             35                  40                  45

Cys Ser Leu Pro Ala Glu Ala Ala Leu Cys Trp Arg Ala Pro Gly Gly
         50                  55                  60

Asp Pro Cys Gln Pro Leu Val Pro Pro Leu Ser Trp Glu Asn Val Thr
 65                  70                  75                  80

Val Asp Lys Val Leu Glu Phe Pro Leu Leu Lys Gly His Pro Asn Leu
                 85                  90                  95

Cys Val Gln Val Asn Ser Ser Glu Lys Leu Gln Leu Gln Glu Cys Leu
                100                 105                 110

Trp Ala Asp Ser Leu Gly Pro Leu Lys Asp Asp Val Leu Leu Leu Glu
            115                 120                 125

Thr Arg Gly Pro Gln Asp Asn Arg Ser Leu Cys Ala Leu Glu Pro Ser
        130                 135                 140

Gly Cys Thr Ser Leu Pro Ser Lys Ala Ser Thr Arg Ala Ala Arg Leu
145                 150                 155                 160

Gly Glu Tyr Leu Leu Gln Asp Leu Gln Ser Gly Gln Cys Leu Gln Leu
                165                 170                 175
```

| | | | | | | | | | | | |
|---|---|---|---|---|---|---|---|---|---|---|---|
|Trp|Asp|Asp|Leu|Gly|Ala|Leu|Trp|Ala|Cys|Pro|Met|Asp|Lys|Tyr|
| |   |180|   |   |   |185|   |   |   |190|   |

Trp Asp Asp Leu Gly Ala Leu Trp Ala Cys Pro Met Asp Lys Tyr
            180                 185                 190

Ile His Lys Glu Pro Lys Ser Ser Asp Lys Thr His Thr Cys Pro Pro
            195                 200                 205

Cys Pro Ala Pro Glu Ala Glu Gly Ala Pro Ser Val Phe Leu Phe Pro
            210                 215                 220

Pro Lys Pro Lys Asp Thr Leu Met Ile Ser Arg Thr Pro Glu Val Thr
225                 230                 235                 240

Cys Val Val Val Asp Val Ser His Glu Asp Pro Glu Val Lys Phe Asn
                245                 250                 255

Trp Tyr Val Asp Gly Val Glu Val His Asn Ala Lys Thr Lys Pro Arg
                260                 265                 270

Glu Glu Gln Tyr Asn Ser Thr Tyr Arg Val Val Ser Val Leu Thr Val
            275                 280                 285

Leu His Gln Asp Trp Leu Asn Gly Lys Glu Tyr Lys Cys Lys Val Ser
            290                 295                 300

Asn Lys Ala Leu Pro Ser Ser Ile Glu Lys Thr Ile Ser Lys Ala Lys
305                 310                 315                 320

Gly Gln Pro Arg Glu Pro Gln Val Tyr Thr Leu Pro Pro Ser Arg Asp
                325                 330                 335

Glu Leu Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
            355                 360                 365

Asn Asn Tyr Lys Thr Thr Pro Pro Val Leu Asp Ser Asp Gly Ser Phe
370                 375                 380

Phe Leu Tyr Ser Lys Leu Thr Val Asp Lys Ser Arg Trp Gln Gln Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Pro Gly Lys
            420                 425

<210> SEQ ID NO 103
<211> LENGTH: 882
<212> TYPE: DNA
<213> ORGANISM: homo sapiens

<400> SEQUENCE: 103
atgcctgtgc cctggttctt gctgtccttg gcactgggcc aagcccagt ggtcctttct      60 gactgcaggg ggctcgaagt ctggaacagc atcccgagct gctgggccct gccctggctc     120
aacgtgtcag cagatggtga caacgtgcat ctggttctga atgtctctga ggagcagcac     180
ttcggcctct ccctgtactg gaatcaggtc cagggccccc caaaacccg gtggcacaaa     240 aacctgactg gaccgcagat cattaccttg aaccacacag acctggttcc ctgcctctgt     300
attcaggtgt ggcctctgga acctgactcc gttaggacga catctgccc cttcagggag     360 gaccccgcg cacaccagaa cctctggcaa gccgcccgac tgcgactgct gaccctgcag     420
agctggctgc tggacgcacc gtgctcgctg cccgcagaag cggcactgtg ctggcgggct     480
ccgggtgggg acccctgcca gccactggtc caccgctttt cctggagaa cgtcactgtg     540 gacaaggttc tcgagttccc attgctgaaa ggccacccta acctctgtgt tcaggtgaac     600
agctcggaga agctgcagct gcaggagtgc ttgtgggctg actccctggg gcctctcaaa     660
gacgatgtgc tactgttgga gacacgaggc ccccaggaca acagatccct ctgtgccttg     720

```
gaacccagtg gctgtacttc actacccagc aaagcctcca cgagggcagc tcgccttgga    780
gagtacttac tacaagacct gcagtcaggc cagtgtctgc agctatggga cgatgacttg    840
ggagcgctat gggcctgccc catggacaaa tacatccaca ag                      882
```

<210> SEQ ID NO 104
<211> LENGTH: 294
<212> TYPE: PRT
<213> ORGANISM: homo sapiens

<400> SEQUENCE: 104

```
Met Pro Val Pro Trp Phe Leu Leu Ser Leu Ala Leu Gly Arg Ser Pro
  1               5                  10                  15

Val Val Leu Ser Asp Cys Arg Gly Leu Glu Val Trp Asn Ser Ile Pro
             20                  25                  30

Ser Cys Trp Ala Leu Pro Trp Leu Asn Val Ser Ala Asp Gly Asp Asn
         35                  40                  45

Val His Leu Val Leu Asn Val Ser Glu Glu Gln His Phe Gly Leu Ser
     50                  55                  60

Leu Tyr Trp Asn Gln Val Gln Gly Pro Pro Lys Pro Arg Trp His Lys
 65                  70                  75                  80

Asn Leu Thr Gly Pro Gln Ile Ile Thr Leu Asn His Thr Asp Leu Val
                 85                  90                  95

Pro Cys Leu Cys Ile Gln Val Trp Pro Leu Glu Pro Asp Ser Val Arg
            100                 105                 110

Thr Asn Ile Cys Pro Phe Arg Glu Asp Pro Arg Ala His Gln Asn Leu
        115                 120                 125

Trp Gln Ala Ala Arg Leu Arg Leu Leu Thr Leu Gln Ser Trp Leu Leu
    130                 135                 140

Asp Ala Pro Cys Ser Leu Pro Ala Glu Ala Ala Leu Cys Trp Arg Ala
145                 150                 155                 160

Pro Gly Gly Asp Pro Cys Gln Pro Leu Val Pro Pro Leu Ser Trp Glu
                165                 170                 175

Asn Val Thr Val Asp Lys Val Leu Glu Phe Pro Leu Leu Lys Gly His
            180                 185                 190

Pro Asn Leu Cys Val Gln Val Asn Ser Ser Glu Lys Leu Gln Leu Gln
        195                 200                 205

Glu Cys Leu Trp Ala Asp Ser Leu Gly Pro Leu Lys Asp Asp Val Leu
    210                 215                 220

Leu Leu Glu Thr Arg Gly Pro Gln Asp Asn Arg Ser Leu Cys Ala Leu
225                 230                 235                 240

Glu Pro Ser Gly Cys Thr Ser Leu Pro Ser Lys Ala Ser Thr Arg Ala
                245                 250                 255

Ala Arg Leu Gly Glu Tyr Leu Leu Gln Asp Leu Gln Ser Gly Gln Cys
            260                 265                 270

Leu Gln Leu Trp Asp Asp Asp Leu Gly Ala Leu Trp Ala Cys Pro Met
        275                 280                 285

Asp Lys Tyr Ile His Lys
        290
```

<210> SEQ ID NO 105
<211> LENGTH: 1578
<212> TYPE: DNA
<213> ORGANISM: Artificial Sequence
<220> FEATURE:
<223> OTHER INFORMATION: IL-17RC signal peptide and exons 7-16 of human
      IL-17RC, and Fc5

<400> SEQUENCE: 105

```
atgcctgtgc cctggttctt gctgtccttg cactgggcc aagcccagt ggtcctttct      60
gactgcaggg ggctcgaagt ctggaacagc atcccgagct gctgggccct gccctggctc    120
aacgtgtcag cagatggtga caacgtgcat ctggttctga atgtctctga ggagcagcac    180
ttcggcctct ccctgtactg gaatcaggtc cagggccccc caaaacccg gtggcacaaa     240
aacctgactg gaccgcagat cattaccttg aaccacacag acctggttcc ctgcctctgt    300
attcaggtgt ggcctctgga acctgactcc gttaggacga acatctgccc cttcagggag    360
gacccccgcg cacaccagaa cctctggcaa gccgcccgac tgcgactgct gaccctgcag    420
agctggctgc tggacgcacc gtgctcgctg cccgcagaag cggcactgtg ctggcgggct    480
ccgggtgggg accctgccca gccactggtc ccaccgcttt cctgggagaa cgtcactgtg    540
gacaaggttc tcgagttccc attgctgaaa ggccacccta acctctgtgt tcaggtgaac    600
agctcggaga agctgcagct gcaggagtgc ttgtgggctg actccctggg gcctctcaaa    660
gacgatgtgc tactgttgga cacgaggc ccccaggaca cagatccct ctgtgccttg       720
gaacccagtg gctgtacttc actacccagc aaagcctcca cgagggcagc tcgccttgga    780
gagtacttac tacaagacct gcagtcaggc cagtgtctgc agctatggga cgatgacttg    840
ggagcgctat gggcctgccc catggacaaa tacatccaca aggagcccaa atcttcagac    900
aaaactcaca catgcccacc gtgcccagca cctgaagccg agggggcacc gtcagtcttc    960
ctcttccccc caaaacccaa ggacaccctc atgatctccc ggacccctga ggtcacatgc   1020
gtggtggtgg acgtgagcca cgaagaccct gaggtcaagt tcaactggta cgtggacggc   1080
gtggaggtgc ataatgccaa gacaaagccg cgggaggagc agtacaacag cacgtaccgt   1140
gtggtcagcg tcctcaccgt cctgcaccag gactggctga atggcaagga gtacaagtgc   1200
aaggtctccca caaagccct cccatcctcc atcgagaaaa ccatctccaa agccaaaggg   1260
cagccccgag aaccacaggt gtacaccctg cccccatccc gggatgagct gaccaagaac   1320
caggtcagcc tgacctgcct ggtcaaaggc ttctatccca gcgacatcgc cgtggagtgg   1380
gagagcaatg ggcagccgga gaacaactac aagaccacgc ctcccgtgct ggactccgac   1440
ggctccttct cctctacag caagctcacc gtggacaaga gcaggtggca gcaggggaac    1500
gtcttctcat gctccgtgat gcatgaggct ctgcacaacc actacacgca gaagagcctc   1560
tccctgtctc cgggtaaa                                                 1578
```

<210> SEQ ID NO 106
<211> LENGTH: 526
<212> TYPE: PRT
<213> ORGANISM: Artificial Sequence
<220> FEATURE:
<223> OTHER INFORMATION: IL-17RC signal peptide and exons 7-16 of human
      IL-17RC, and Fc5

<400> SEQUENCE: 106

```
Met Pro Val Pro Trp Phe Leu Leu Ser Leu Ala Leu Gly Arg Ser Pro
 1               5                  10                  15

Val Val Leu Ser Asp Cys Arg Gly Leu Glu Val Trp Asn Ser Ile Pro
            20                  25                  30

Ser Cys Trp Ala Leu Pro Trp Leu Asn Val Ser Ala Asp Gly Asp Asn
        35                  40                  45

Val His Leu Val Leu Asn Val Ser Glu Glu Gln His Phe Gly Leu Ser
    50                  55                  60
```

```
Leu Tyr Trp Asn Gln Val Gln Gly Pro Pro Lys Pro Arg Trp His Lys
 65                  70                  75                  80

Asn Leu Thr Gly Pro Gln Ile Ile Thr Leu Asn His Thr Asp Leu Val
                 85                  90                  95

Pro Cys Leu Cys Ile Gln Val Trp Pro Leu Glu Pro Asp Ser Val Arg
            100                 105                 110

Thr Asn Ile Cys Pro Phe Arg Glu Asp Pro Arg Ala His Gln Asn Leu
        115                 120                 125

Trp Gln Ala Ala Arg Leu Arg Leu Leu Thr Leu Gln Ser Trp Leu Leu
130                 135                 140

Asp Ala Pro Cys Ser Leu Pro Ala Glu Ala Leu Cys Trp Arg Ala
145                 150                 155                 160

Pro Gly Gly Asp Pro Cys Gln Pro Leu Val Pro Pro Leu Ser Trp Glu
                165                 170                 175

Asn Val Thr Val Asp Lys Val Leu Glu Phe Pro Leu Leu Lys Gly His
            180                 185                 190

Pro Asn Leu Cys Val Gln Val Asn Ser Ser Glu Lys Leu Gln Leu Gln
        195                 200                 205

Glu Cys Leu Trp Ala Asp Ser Leu Gly Pro Leu Lys Asp Asp Val Leu
    210                 215                 220

Leu Leu Glu Thr Arg Gly Pro Gln Asp Asn Arg Ser Leu Cys Ala Leu
225                 230                 235                 240

Glu Pro Ser Gly Cys Thr Ser Leu Pro Ser Lys Ala Ser Thr Arg Ala
                245                 250                 255

Ala Arg Leu Gly Glu Tyr Leu Leu Gln Asp Leu Gln Ser Gly Gln Cys
            260                 265                 270

Leu Gln Leu Trp Asp Asp Asp Leu Gly Ala Leu Trp Ala Cys Pro Met
        275                 280                 285

Asp Lys Tyr Ile His Lys Glu Pro Lys Ser Ser Asp Lys Thr His Thr
    290                 295                 300

Cys Pro Pro Cys Pro Ala Pro Glu Ala Glu Gly Ala Pro Ser Val Phe
305                 310                 315                 320

Leu Phe Pro Pro Lys Pro Lys Asp Thr Leu Met Ile Ser Arg Thr Pro
                325                 330                 335

Glu Val Thr Cys Val Val Val Asp Val Ser His Glu Asp Pro Glu Val
            340                 345                 350

Lys Phe Asn Trp Tyr Val Asp Gly Val Glu Val His Asn Ala Lys Thr
        355                 360                 365

Lys Pro Arg Glu Glu Gln Tyr Asn Ser Thr Tyr Arg Val Val Ser Val
    370                 375                 380

Leu Thr Val Leu His Gln Asp Trp Leu Asn Gly Lys Glu Tyr Lys Cys
385                 390                 395                 400

Lys Val Ser Asn Lys Ala Leu Pro Ser Ser Ile Glu Lys Thr Ile Ser
                405                 410                 415

Lys Ala Lys Gly Gln Pro Arg Glu Pro Gln Val Tyr Thr Leu Pro Pro
            420                 425                 430

Ser Arg Asp Glu Leu Thr Lys Asn Gln Val Ser Leu Thr Cys Leu Val
        435                 440                 445

Lys Gly Phe Tyr Pro Ser Asp Ile Ala Val Glu Trp Glu Ser Asn Gly
    450                 455                 460

Gln Pro Glu Asn Asn Tyr Lys Thr Thr Pro Pro Val Leu Asp Ser Asp
465                 470                 475                 480

Gly Ser Phe Phe Leu Tyr Ser Lys Leu Thr Val Asp Lys Ser Arg Trp
                485                 490                 495
```

Gln Gln Gly Asn Val Phe Ser Cys Ser Val Met His Glu Ala Leu His
              500                 505                 510

Asn His Tyr Thr Gln Lys Ser Leu Ser Leu Ser Pro Gly Lys
              515                 520                 525

<210> SEQ ID NO 107
<211> LENGTH: 864
<212> TYPE: DNA
<213> ORGANISM: homo sapians

<400> SEQUENCE: 107
atgcctgtgc cctggttctt gctgtccttg gcactgggcc gaagcccagt ggtcctttct      60
ctggagaggc ttgtggggcc tcaggacgct acccactgct ctccgggcct ctcctgccgc     120
ctctgggaca gtgacatact ctgcctgcct ggggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg gccgtgcatg gcactgggga agagcctgaa     300
gatgaggaaa agtttggagg agcagctgac tcaggggtgg aggagcctag aatgcctct      360 ctccaggccc aagtcgtgct ctccttccag gcctaccct a ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact gcaggggggct cgaagtctgg     600 aacagcatcc cgagctgctg ggactccctg gggcctctca agacgatgt gctactgttg     660 gagacacgag gcccccagga caacagatcc ctctgtgcct tggaacccag tggctgtact     720
tcactaccca gcaaagcctc cacgagggca gctcgccttg gagagtactt actacaagac     780
ctgcagtcag gccagtgtct gcagctatgg gacgatgact gggagcgct atgggcctgc      840 cccatggaca aatacatcca caag                                            864

<210> SEQ ID NO 108
<211> LENGTH: 288
<212> TYPE: PRT
<213> ORGANISM: homo sapians

<400> SEQUENCE: 108

Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Leu Gly Ser Glu Val Arg Ile Trp Ser Tyr
            165                 170                 175

Thr Gln Pro Arg Tyr Glu Lys Glu Leu Asn His Thr Gln Leu Pro
        180                 185                 190

Asp Cys Arg Gly Leu Glu Val Trp Asn Ser Ile Pro Ser Cys Trp Asp
    195                 200                 205

Ser Leu Gly Pro Leu Lys Asp Asp Val Leu Leu Glu Thr Arg Gly
    210                 215                 220

Pro Gln Asp Asn Arg Ser Leu Cys Ala Leu Glu Pro Ser Gly Cys Thr
225                 230                 235                 240

Ser Leu Pro Ser Lys Ala Ser Thr Arg Ala Ala Arg Leu Gly Glu Tyr
            245                 250                 255

Leu Leu Gln Asp Leu Gln Ser Gly Gln Cys Leu Gln Leu Trp Asp Asp
        260                 265                 270

Asp Leu Gly Ala Leu Trp Ala Cys Pro Met Asp Lys Tyr Ile His Lys
    275                 280                 285

<210> SEQ ID NO 109
<211> LENGTH: 1560
<212> TYPE: DNA
<213> ORGANISM: Artificial Sequence
<220> FEATURE:
<223> OTHER INFORMATION: IL-17RC signal peptide and exons 1-7 and 14-16
      of human IL-17RC, and Fc5

<400> SEQUENCE: 109

```
atgcctgtgc cctggttctt gctgtccttg cactgggcc gaagcccagt ggtcctttct      60
ctggagaggc ttgtggggcc tcaggacgct acccactgct ctccgggcct ctcctgccgc     120
ctctgggaca gtgacatact ctgcctgcct ggggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg gccgtgcatg ggactgggaa agagcctgaa     300
gatgaggaaa gtttggagg agcagctgac tcaggggtgg aggagcctag gaatgcctct      360
ctccaggccc aagtcgtgct ctccttccag gcctacccta ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact gcaggggggct cgaagtctgg     600
aacagcatcc cgagctgctg ggactccctg ggcctctca aagacgatgt gctactgttg      660
gagacacgag gccccagga caacagatcc ctctgtgcct ggaacccag tggctgtact      720
tcactaccca gcaaagcctc cacgagggca gctcgccttg gagagtactt actacaagac     780
ctgcagtcag gccagtgtct gcagctatgg gacgatgact gggagcgct atgggcctgc     840
cccatggaca atacatcca aggagcccc aaatcttcag acaaaactca cacatgccca     900
ccgtgcccag cacctgaagc cgaggggca ccgtcagtct tcctcttccc cccaaaaccc     960
aaggacaccc tcatgatctc ccggaccct gaggtcacat gcgtggtggt ggacgtgagc     1020
cacgaagacc ctgaggtcaa gttcaactgg tacgtgacg gcgtggaggt gcataatgcc     1080
aagacaaagc cgcgggagga gcagtacaac agcacgtacc gtgtggtcag cgtcctcacc     1140
gtcctgcacc aggactggct gaatggcaag gagtacaagt gcaaggtctc caacaaagcc     1200
ctcccatcct ccatcgagaa aaccatctcc aaagccaaag ggcagccccg agaaccacag     1260
```

-continued

```
gtgtacaccc tgcccccatc ccgggatgag ctgaccaaga accaggtcag cctgacctgc   1320
ctggtcaaag gcttctatcc cagcgacatc gccgtggagt gggagagcaa tgggcagccg   1380
gagaacaact acaagaccac gcctcccgtg ctggactccg acggctcctt cttcctctac   1440
agcaagctca ccgtggacaa gagcaggtgg cagcagggga acgtcttctc atgctccgtg   1500
atgcatgagg ctctgcacaa ccactacacg cagaagagcc tctccctgtc tccgggtaaa   1560
```

<210> SEQ ID NO 110
<211> LENGTH: 520
<212> TYPE: PRT
<213> ORGANISM: Artificial Sequence
<220> FEATURE:
<223> OTHER INFORMATION: IL-17RC signal peptide and exons 1-7 and 14-16
      of human IL-17RC, and Fc5

<400> SEQUENCE: 110

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Asp
        195                 200                 205

Ser Leu Gly Pro Leu Lys Asp Asp Val Leu Leu Leu Glu Thr Arg Gly
    210                 215                 220

Pro Gln Asp Asn Arg Ser Leu Cys Ala Leu Glu Pro Ser Gly Cys Thr
225                 230                 235                 240

Ser Leu Pro Ser Lys Ala Ser Thr Arg Ala Ala Arg Leu Gly Glu Tyr
                245                 250                 255

Leu Leu Gln Asp Leu Gln Ser Gly Gln Cys Leu Gln Leu Trp Asp Asp
            260                 265                 270

Asp Leu Gly Ala Leu Trp Ala Cys Pro Met Asp Lys Tyr Ile His Lys
        275                 280                 285

Glu Pro Lys Ser Ser Asp Lys Thr His Thr Cys Pro Pro Cys Pro Ala
    290                 295                 300

Pro Glu Ala Glu Gly Ala Pro Ser Val Phe Leu Phe Pro Pro Lys Pro
305                 310                 315                 320
```

```
Lys Asp Thr Leu Met Ile Ser Arg Thr Pro Glu Val Thr Cys Val Val
                325                 330                 335
Val Asp Val Ser His Glu Asp Pro Glu Val Lys Phe Asn Trp Tyr Val
                340                 345                 350
Asp Gly Val Glu Val His Asn Ala Lys Thr Lys Pro Arg Glu Glu Gln
                355                 360                 365
Tyr Asn Ser Thr Tyr Arg Val Val Ser Val Leu Thr Val Leu His Gln
    370                 375                 380
Asp Trp Leu Asn Gly Lys Glu Tyr Lys Cys Lys Val Ser Asn Lys Ala
385                 390                 395                 400
Leu Pro Ser Ser Ile Glu Lys Thr Ile Ser Lys Ala Lys Gly Gln Pro
                405                 410                 415
Arg Glu Pro Gln Val Tyr Thr Leu Pro Pro Ser Arg Asp Glu Leu Thr
                420                 425                 430
Lys Asn Gln Val Ser Leu Thr Cys Leu Val Lys Gly Phe Tyr Pro Ser
                435                 440                 445
Asp Ile Ala Val Glu Trp Glu Ser Asn Gly Gln Pro Glu Asn Asn Tyr
    450                 455                 460
Lys Thr Thr Pro Pro Val Leu Asp Ser Asp Gly Ser Phe Phe Leu Tyr
465                 470                 475                 480
Ser Lys Leu Thr Val Asp Lys Ser Arg Trp Gln Gln Gly Asn Val Phe
                485                 490                 495
Ser Cys Ser Val Met His Glu Ala Leu His Asn His Tyr Thr Gln Lys
                500                 505                 510
Ser Leu Ser Leu Ser Pro Gly Lys
    515                 520

<210> SEQ ID NO 111
<211> LENGTH: 1146
<212> TYPE: DNA
<213> ORGANISM: homo sapians

<400> SEQUENCE: 111
atgcctgtgc cctggttctt gctgtccttg gcactgggcc gaagcccagt ggtccttcct    60
ctggagaggc ttgtggggcc tcaggacgct acccactgct ctccgggcct ctcctgccgc   120
ctctgggaca gtgacatact ctgcctgcct ggggacatcg tgcctgctcc gggccccgtg   180
ctggcgccta cgcacctgca gacagagctg gtgctgaggt gccagaagga gaccgactgt   240
gacctctgtc tgcgtgtggc tgtccacttg gccgtgcatg gcactgggga agagcctgaa   300
gatgaggaaa agtttggagg agcagctgac tcaggggtgg aggagcctag gaatgcctct   360
ctccaggccc aagtcgtgct ctccttccag gcctacccta tgcccgctg cgtcctgctg   420 gaggtgcaag tgcctgctgc ccttgtgcag tttggtcagt ctgtgggctc tgtggtatat   480
gactgcttcg aggctgccct agggagtgag gtacgaatct ggtcctatac tcagcccagg   540
tacgagaagg aactcaacca cacacagcag ctgcctgact gcaggggct cgaagtctgg   600 aacagcatcc cgagctgctg ggaggacccc gcgcacacc agaacctctg caagccgcc   660 cgactgcgac tgctgacccct gcagagctgg ctgctggacg caccgtgctc gctgcccgca   720
gaagcggcac tgtgctggcg ggctcccgggt ggggaccccct gccagccact ggtcccaccg   780
ctttcctggg agaacgtcac tgtggacaag gttctcgagt tcccattgct gaaaggccac   840
cctaacctct gtgttcaggt gaacagctcg gagaagctgc agctgcagga gtgcttgtgg   900
gctgactccc tggggcctct caaagacgat gtgctactgt tggagacacg aggccccag   960
```

-continued

```
gacaacagat ccctctgtgc cttggaaccc agtggctgta cttcactacc cagcaaagcc      1020
tccacgaggg cagctcgcct tggagagtac ttactacaag acctgcagtc aggccagtgt      1080
ctgcagctat gggacgatga cttgggagcg ctatgggcct gccccatgga caaatacatc      1140
cacaag                                                                  1146

<210> SEQ ID NO 112
<211> LENGTH: 382
<212> TYPE: PRT
<213> ORGANISM: homo sapians

<400> SEQUENCE: 112

Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Glu
        195                 200                 205

Asp Pro Arg Ala His Gln Asn Leu Trp Gln Ala Ala Arg Leu Arg Leu
    210                 215                 220

Leu Thr Leu Gln Ser Trp Leu Leu Asp Ala Pro Cys Ser Leu Pro Ala
225                 230                 235                 240

Glu Ala Ala Leu Cys Trp Arg Ala Pro Gly Gly Asp Pro Cys Gln Pro
                245                 250                 255

Leu Val Pro Pro Leu Ser Trp Glu Asn Val Thr Val Asp Lys Val Leu
            260                 265                 270

Glu Phe Pro Leu Leu Lys Gly His Pro Asn Leu Cys Val Gln Val Asn
        275                 280                 285

Ser Ser Glu Lys Leu Gln Leu Gln Glu Cys Leu Trp Ala Asp Ser Leu
    290                 295                 300

Gly Pro Leu Lys Asp Asp Val Leu Leu Glu Thr Arg Gly Pro Gln
305                 310                 315                 320

Asp Asn Arg Ser Leu Cys Ala Leu Glu Pro Ser Gly Cys Thr Ser Leu
                325                 330                 335

Pro Ser Lys Ala Ser Thr Arg Ala Ala Arg Leu Gly Glu Tyr Leu Leu
```

```
              340            345                350
Gln Asp Leu Gln Ser Gly Gln Cys Leu Gln Leu Trp Asp Asp Leu
          355                360                365

Gly Ala Leu Trp Ala Cys Pro Met Asp Lys Tyr Ile His Lys
    370                375                380
```

<210> SEQ ID NO 113
<211> LENGTH: 1842
<212> TYPE: DNA
<213> ORGANISM: Artificial Sequence
<220> FEATURE:
<223> OTHER INFORMATION: IL-17RC signal peptide and exons 1-7 and 11-16 of human IL-17RC, and Fc5

<400> SEQUENCE: 113

| | | | | | |
|---|---|---|---|---|---|
| atgcctgtgc | cctggttctt | gctgtccttg | gcactgggcc | gaagcccagt | ggtcctttct | 60 |
| ctggagaggc | ttgtggggcc | tcaggacgct | acccactgct | ctccgggcct | ctcctgccgc | 120 |
| ctctgggaca | gtgacatact | ctgcctgcct | ggggacatcg | tgcctgctcc | gggccccgtg | 180 |
| ctggcgccta | cgcacctgca | gacagagctg | gtgctgaggt | gccagaagga | gaccgactgt | 240 |
| gacctctgtc | tgcgtgtggc | tgtccacttg | gccgtgcatg | gcactgggga | agagcctgaa | 300 |
| gatgaggaaa | gtttggagg | agcagctgac | tcaggggtgg | aggagcctag | gaatgcctct | 360 |
| ctccaggccc | aagtcgtgct | ctccttccag | gcctacccta | ctgcccgctg | cgtcctgctg | 420 |
| gaggtgcaag | tgcctgctgc | ccttgtgcag | tttggtcagt | ctgtgggctc | tgtggtatat | 480 |
| gactgcttcg | aggctgccct | agggagtgag | gtacgaatct | ggtcctatac | tcagcccagg | 540 |
| tacgagaagg | aactcaacca | cacacagcag | ctgcctgact | gcaggggggct | cgaagtctgg | 600 |
| aacagcatcc | cgagctgctg | ggaggacccc | cgcgcacacc | agaacctctg | caagccgcc | 660 |
| cgactgcgac | tgctgaccct | gcagagctgg | ctgctggacg | caccgtgctc | gctgcccgca | 720 |
| gaagcggcac | tgtgctggcg | ggctccgggt | ggggacccct | gccagccact | ggtcccaccg | 780 |
| cttcctgggg | agaacgtcac | tgtggacaag | gttctcgagt | cccattgct | gaaaggccac | 840 |
| cctaacctct | gtgttcaggt | gaacagctcg | gagaagctgc | agctgcagga | gtgcttgtgg | 900 |
| gctgactccc | tggggcctct | caaagacgat | gtgctactgt | tggagacacg | aggcccccag | 960 |
| gacaacagat | ccctctgtgc | cttggaaccc | agtggctgta | cttcactacc | cagcaaagcc | 1020 |
| tccacgaggg | cagctcgcct | tggagagtac | ttactacaag | acctgcagtc | aggccagtgt | 1080 |
| ctgcagctat | gggacgatga | cttgggagcg | ctatgggcct | gccccatgga | caaatacatc | 1140 |
| cacaaggagc | ccaaatcttc | agacaaaact | cacacatgcc | caccgtgccc | agcacctgaa | 1200 |
| gccgaggggg | gaccgtcagt | cttcctcttc | cccccaaaac | ccaaggacac | cctcatgatc | 1260 |
| tcccggaccc | ctgaggtcac | atgcgtggtg | gtggacgtga | gccacgaaga | ccctgaggtc | 1320 |
| aagttcaact | ggtacgtgga | cggcgtggag | gtgcataatg | ccaagacaaa | gccgcgggag | 1380 |
| gagcagtaca | acagcacgta | ccgtgtggtc | agcgtcctca | ccgtcctgca | ccaggactgg | 1440 |
| ctgaatggca | aggagtacaa | gtgcaaggtc | tccaacaaag | ccctcccatc | ctccatcgag | 1500 |
| aaaaccatct | ccaaagccaa | agggcagccc | cgagaaccac | aggtgtacac | cctgccccca | 1560 |
| tcccgggatg | agctgaccaa | gaaccaggtc | agcctgacct | gcctggtcaa | aggcttctat | 1620 |
| cccagcgaca | tcgccgtgga | gtgggagagc | aatgggcagc | cggagaacaa | ctacaagacc | 1680 |
| acgcctcccg | tgctggactc | cgacggctcc | ttcttcctct | acagcaagct | caccgtggac | 1740 |
| aagagcaggt | ggcagcaggg | gaacgtcttc | tcatgctccg | tgatgcatga | ggctctgcac | 1800 |
| aaccactaca | cgcagaagag | cctctccctg | tctccgggta | aa | | 1842 |

<210> SEQ ID NO 114
<211> LENGTH: 614
<212> TYPE: PRT
<213> ORGANISM: Artificial Sequence
<220> FEATURE:
<223> OTHER INFORMATION: IL-17RC signal peptide and exons 1-7 and 11-16 of human IL-17RC, and Fc5

<400> SEQUENCE: 114

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Glu
        195                 200                 205

Asp Pro Arg Ala His Gln Asn Leu Trp Gln Ala Ala Arg Leu Arg Leu
    210                 215                 220

Leu Thr Leu Gln Ser Trp Leu Leu Asp Ala Pro Cys Ser Leu Pro Ala
225                 230                 235                 240

Glu Ala Ala Leu Cys Trp Arg Ala Pro Gly Gly Asp Pro Cys Gln Pro
                245                 250                 255

Leu Val Pro Pro Leu Ser Trp Glu Asn Val Thr Val Asp Lys Val Leu
            260                 265                 270

Glu Phe Pro Leu Leu Lys Gly His Pro Asn Leu Cys Val Gln Val Asn
        275                 280                 285

Ser Ser Glu Lys Leu Gln Leu Gln Glu Cys Leu Trp Ala Asp Ser Leu
    290                 295                 300

Gly Pro Leu Lys Asp Asp Val Leu Leu Leu Glu Thr Arg Gly Pro Gln
305                 310                 315                 320

Asp Asn Arg Ser Leu Cys Ala Leu Glu Pro Ser Gly Cys Thr Ser Leu
                325                 330                 335

Pro Ser Lys Ala Ser Thr Arg Ala Ala Arg Leu Gly Glu Tyr Leu Leu
            340                 345                 350

Gln Asp Leu Gln Ser Gly Gln Cys Leu Gln Leu Trp Asp Asp Asp Leu
        355                 360                 365
```

Gly Ala Leu Trp Ala Cys Pro Met Asp Lys Tyr Ile His Lys Glu Pro
    370                 375                 380

Lys Ser Ser Asp Lys Thr His Thr Cys Pro Pro Cys Pro Ala Pro Glu
385                 390                 395                 400

Ala Glu Gly Ala Pro Ser Val Phe Leu Phe Pro Pro Lys Pro Lys Asp
                405                 410                 415

Thr Leu Met Ile Ser Arg Thr Pro Glu Val Thr Cys Val Val Val Asp
            420                 425                 430

Val Ser His Glu Asp Pro Glu Val Lys Phe Asn Trp Tyr Val Asp Gly
        435                 440                 445

Val Glu Val His Asn Ala Lys Thr Lys Pro Arg Glu Glu Gln Tyr Asn
    450                 455                 460

Ser Thr Tyr Arg Val Val Ser Val Leu Thr Val Leu His Gln Asp Trp
465                 470                 475                 480

Leu Asn Gly Lys Glu Tyr Lys Cys Lys Val Ser Asn Lys Ala Leu Pro
                485                 490                 495

Ser Ser Ile Glu Lys Thr Ile Ser Lys Ala Lys Gly Gln Pro Arg Glu
            500                 505                 510

Pro Gln Val Tyr Thr Leu Pro Pro Ser Arg Asp Glu Leu Thr Lys Asn
        515                 520                 525

Gln Val Ser Leu Thr Cys Leu Val Lys Gly Phe Tyr Pro Ser Asp Ile
    530                 535                 540

Ala Val Glu Trp Glu Ser Asn Gly Gln Pro Glu Asn Asn Tyr Lys Thr
545                 550                 555                 560

Thr Pro Pro Val Leu Asp Ser Asp Gly Ser Phe Phe Leu Tyr Ser Lys
                565                 570                 575

Leu Thr Val Asp Lys Ser Arg Trp Gln Gln Gly Asn Val Phe Ser Cys
            580                 585                 590

Ser Val Met His Glu Ala Leu His Asn His Tyr Thr Gln Lys Ser Leu
        595                 600                 605

Ser Leu Ser Pro Gly Lys
    610

<210> SEQ ID NO 115
<211> LENGTH: 1524
<212> TYPE: DNA
<213> ORGANISM: Artificial Sequence
<220> FEATURE:
<223> OTHER INFORMATION: IL-17RC signal peptide and exons 1-13 of human
      IL-17RC, and exons 7-9 of human IL-17RA

<400> SEQUENCE: 115
atgcctgtgc cctggttctt gctgtccttg gcactgggcc gaagcccagt ggtcctttct      60
ctggagaggc ttgtggggcc tcaggacgct acccactgct ctccgggcct tcctgccgc     120 ctctgggaca gtgacatact ctgcctgcct ggggacatcg tgcctgctcc gggccccgtg    180
ctggcgccta cgcacctgca gacagagctg gtgctgaggt gccagaagga gaccgactgt    240
gacctctgtc tgcgtgtggc tgtccacttg gccgtgcatg gcactgggga gagcctgaa    300 gatgaggaaa agtttggagg agcagctgac tcaggggtgg aggagcctag gaatgcctct    360
ctccaggccc aagtcgtgct ctccttccag gcctacccta tgcccgctg cgtcctgctg    420 gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcaggggct cgaagtctgg    600

```
aacagcatcc cgagctgctg ggccctgccc tggctcaacg tgtcagcaga tggtgacaac      660
gtgcatctgg ttctgaatgt ctctgaggag cagcacttcg gcctctccct gtactggaat      720
caggtccagg gccccccaaa accccggtgg cacaaaaacc tgactggacc gcagatcatt      780
accttgaacc acacagacct ggttccctgc ctctgtattc aggtgtggcc tctggaacct      840
gactccgtta ggacgaacat ctgccccttc agggaggacc cccgcgcaca ccagaacctc      900
tggcaagccg cccgactgcg actgctgacc ctgcagagct ggctgctgga cgcaccgtgc      960
tcgctgcccg cagaagcggc actgtgctgg cgggctccgg gtggggaccc ctgccagcca     1020
ctggtcccac cgctttcctg ggagaacgtc actgtggaca aggttctcga gttcccattg     1080
ctgaaaggcc accctaacct ctgtgttcag gtgaacagct cggagaagct gcagctgcag     1140
gagtgcttgt gggctggcag cctttgggat cccaacatca ctgtggagac cttgacaca     1200
cagcatctgc gagtggactt caccctgtgg aatgaatcca ccccctacca ggtcctgctg     1260
gaaagtttct ccgactcaga gaaccacagc tgctttgatg tcgttaaaca aatatttgcg     1320
cccaggcaag aagaattcca tcagcgagct aatgtcacat tcactctaag caagtttcac     1380
tggtgctgcc atcaccacgt gcaggtccag cccttcttca gcagctgcct aaatgactgt     1440
ttgagacacg ctgtgactgt gccctgccca gtaatctcaa ataccacagt tcccaagcca     1500
gttgcagact acattcccct gtgg                                            1524

<210> SEQ ID NO 116
<211> LENGTH: 508
<212> TYPE: PRT
<213> ORGANISM: Artificial Sequence
<220> FEATURE:
<223> OTHER INFORMATION: IL-17RC signal peptide and exons 1-13 of human
      IL-17RC, and exons 7-9 of human IL-17RA

<400> SEQUENCE: 116

Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Cys Arg Gly Leu Glu Val Trp Asn Ser Ile Pro Ser Cys Trp Ala
```

```
                    195                 200                 205
Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
225                 230                 235                 240

Gln Val Gln Gly Pro Lys Pro Arg Trp His Lys Asn Leu Thr Gly
                245                 250                 255

Pro Gln Ile Ile Thr Leu Asn His Thr Asp Leu Val Pro Cys Leu Cys
                260                 265                 270

Ile Gln Val Trp Pro Leu Glu Pro Asp Ser Val Arg Thr Asn Ile Cys
            275                 280                 285

Pro Phe Arg Glu Asp Pro Arg Ala His Gln Asn Leu Trp Gln Ala Ala
    290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
                340                 345                 350

Asp Lys Val Leu Glu Phe Pro Leu Leu Lys Gly His Pro Asn Leu Cys
            355                 360                 365

Val Gln Val Asn Ser Ser Glu Lys Leu Gln Leu Gln Glu Cys Leu Trp
    370                 375                 380

Ala Gly Ser Leu Trp Asp Pro Asn Ile Thr Val Glu Thr Leu Asp Thr
385                 390                 395                 400

Gln His Leu Arg Val Asp Phe Thr Leu Trp Asn Glu Ser Thr Pro Tyr
                405                 410                 415

Gln Val Leu Leu Glu Ser Phe Ser Asp Ser Glu Asn His Ser Cys Phe
                420                 425                 430

Asp Val Val Lys Gln Ile Phe Ala Pro Arg Gln Glu Glu Phe His Gln
            435                 440                 445

Arg Ala Asn Val Thr Phe Thr Leu Ser Lys Phe His Trp Cys Cys His
    450                 455                 460

His His Val Gln Val Gln Pro Phe Phe Ser Ser Cys Leu Asn Asp Cys
465                 470                 475                 480

Leu Arg His Ala Val Thr Val Pro Cys Pro Val Ile Ser Asn Thr Thr
                485                 490                 495

Val Pro Lys Pro Val Ala Asp Tyr Ile Pro Leu Trp
            500                 505
```

<210> SEQ ID NO 117
<211> LENGTH: 2220
<212> TYPE: DNA
<213> ORGANISM: Artificial Sequence
<220> FEATURE:
<223> OTHER INFORMATION: IL-17RC signal peptide and exons 1-13 of human
      IL-17RC, and exons 7-9 of human IL-17RA, and Fc5

<400> SEQUENCE: 117

```
atgcctgtgc cctggttctt gctgtccttg gcactgggcc gaagcccagt ggtcctttct      60
ctggagaggc ttgtgggcc tcaggacgct acccactgct ctccgggcct ctcctgccgc      120
ctctgggaca gtgacatact ctgcctgcct ggggacatcg tgcctgctcc gggccccgtg      180
ctggcgccta cgcacctgca gacagagctg gtgctgaggt gccagaagga gaccgactgt      240
gacctctgtc tgcgtgtggc tgtccacttg gccgtgcatg gcactgggga agagcctgaa      300
```

```
gatgaggaaa agtttggagg agcagctgac tcaggggtgg aggagcctag gaatgcctct    360
ctccaggccc aagtcgtgct ctccttccag gcctaccota ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcaggggct cgaagtctgg      600
aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg gccccccaaa accccggtgg cacaaaaacc tgactggacc gcagatcatt    780
accttgaacc acacagacct ggttccctgc ctctgtattc aggtgtggcc tctggaacct    840
gactccgtta ggacgaacat ctgccccttc agggaggacc ccgcgcaca ccagaacctc      900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca    1020
ctggtcccac cgctttcctg ggagaacgtc actgtggaca aggttctcga gttcccattg    1080
ctgaaaggcc accctaacct ctgtgttcag gtgaacagct cggagaagct gcagctgcag    1140
gagtgcttgt gggctggcag cctttgggat cccaacatca ctgtggagac cttggacaca    1200
cagcatctgc gagtggactt caccctgtgg aatgaatcca ccccctacca ggtcctgctg    1260
gaaagtttct ccgactcaga gaaccacagc tgctttgatg tcgttaaaca aatatttgcg    1320
cccaggcaag aagaattcca tcagcgagct aatgtcacat tcactctaag caagtttcac    1380
tggtgctgcc atcaccacgt gcaggtccag ccttcttca gcagctgcct aaatgactgt     1440
ttgagacacg ctgtgactgt gccctgccca gtaatctcaa ataccacagt tcccaagcca    1500
gttgcagact acattcccct gtgggagccc aaatcttcag acaaaactca cacatgccca    1560
ccgtgcccag cacctgaagc cgaggggca ccgtcagtct tcctcttccc cccaaaaccc     1620
aaggacaccc tcatgatctc ccggacccct gaggtcacat gcgtggtggt ggacgtgagc    1680
cacgaagacc ctgaggtcaa gttcaactgg tacgtggacg gcgtggaggt gcataatgcc    1740
aagacaaagc cgcgggagga gcagtacaac agcacgtacc gtgtggtcag cgtcctcacc    1800
gtcctgcacc aggactggct gaatggcaag gagtacaagt gcaaggtctc caacaaagcc    1860
ctcccatcct ccatcgagaa aaccatctcc aaagccaaag gcagccccg agaaccacag     1920
gtgtacaccc tgccccccatc ccgggatgag ctgaccaaga accaggtcag cctgacctgc    1980
ctggtcaaag gcttctatcc cagcgacatc gccgtggagt gggagagcaa tgggcagccg    2040
gagaacaact acaagaccac gcctcccgtg ctggactccg acggctcctt cttcctctac    2100
agcaagctca ccgtggacaa gagcaggtgg cagcagggga acgtcttctc atgctccgtg    2160
atgcatgagg ctctgcacaa ccactacacg cagaagagcc tctccctgtc tccgggtaaa    2220
```

<210> SEQ ID NO 118
<211> LENGTH: 740
<212> TYPE: PRT
<213> ORGANISM: Artificial Sequence
<220> FEATURE:
<223> OTHER INFORMATION: IL-17RC signal peptide and exons 1-13 of human
      IL-17RC, and exons 7-9 of human IL-17RA, and Fc5

<400> SEQUENCE: 118

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

```
Cys Ser Pro Gly Leu Ser Cys Arg Leu Trp Asp Ser Asp Ile Leu Cys
            35                  40                  45
Leu Pro Gly Asp Ile Val Pro Ala Pro Gly Pro Val Leu Ala Pro Thr
 50                  55                  60
His Leu Gln Thr Glu Leu Val Leu Arg Cys Gln Lys Glu Thr Asp Cys
 65                  70                  75                  80
Asp Leu Cys Leu Arg Val Ala Val His Leu Ala Val His Gly His Trp
                 85                  90                  95
Glu Glu Pro Glu Asp Glu Glu Lys Phe Gly Ala Ala Asp Ser Gly
                100                 105                 110
Val Glu Glu Pro Arg Asn Ala Ser Leu Gln Ala Gln Val Val Leu Ser
                115                 120                 125
Phe Gln Ala Tyr Pro Thr Ala Arg Cys Val Leu Leu Glu Val Gln Val
130                 135                 140
Pro Ala Ala Leu Val Gln Phe Gly Gln Ser Val Gly Ser Val Val Tyr
145                 150                 155                 160
Asp Cys Phe Glu Ala Ala Leu Gly Ser Glu Val Arg Ile Trp Ser Tyr
                165                 170                 175
Thr Gln Pro Arg Tyr Glu Lys Glu Leu Asn His Thr Gln Gln Leu Pro
                180                 185                 190
Asp Cys Arg Gly Leu Glu Val Trp Asn Ser Ile Pro Ser Cys Trp Ala
                195                 200                 205
Leu Pro Trp Leu Asn Val Ser Ala Asp Gly Asp Asn Val His Leu Val
                210                 215                 220
Leu Asn Val Ser Glu Glu Gln His Phe Gly Leu Ser Leu Tyr Trp Asn
225                 230                 235                 240
Gln Val Gln Gly Pro Pro Lys Pro Arg Trp His Lys Asn Leu Thr Gly
                245                 250                 255
Pro Gln Ile Ile Thr Leu Asn His Thr Asp Leu Val Pro Cys Leu Cys
                260                 265                 270
Ile Gln Val Trp Pro Leu Glu Pro Asp Ser Val Arg Thr Asn Ile Cys
                275                 280                 285
Pro Phe Arg Glu Asp Pro Arg Ala His Gln Asn Leu Trp Gln Ala Ala
                290                 295                 300
Arg Leu Arg Leu Leu Thr Leu Gln Ser Trp Leu Leu Asp Ala Pro Cys
305                 310                 315                 320
Ser Leu Pro Ala Glu Ala Ala Leu Cys Trp Arg Ala Pro Gly Gly Asp
                325                 330                 335
Pro Cys Gln Pro Leu Val Pro Pro Leu Ser Trp Glu Asn Val Thr Val
                340                 345                 350
Asp Lys Val Leu Glu Phe Pro Leu Leu Lys Gly His Pro Asn Leu Cys
                355                 360                 365
Val Gln Val Asn Ser Ser Glu Lys Leu Gln Leu Gln Glu Cys Leu Trp
                370                 375                 380
Ala Gly Ser Leu Trp Asp Pro Asn Ile Thr Val Glu Thr Leu Asp Thr
385                 390                 395                 400
Gln His Leu Arg Val Asp Phe Thr Leu Trp Asn Glu Ser Thr Pro Tyr
                405                 410                 415
Gln Val Leu Leu Glu Ser Phe Ser Asp Ser Glu Asn His Ser Cys Phe
                420                 425                 430
Asp Val Val Lys Gln Ile Phe Ala Pro Arg Gln Glu Glu Phe His Gln
                435                 440                 445
Arg Ala Asn Val Thr Phe Thr Leu Ser Lys Phe His Trp Cys Cys His
```

-continued

```
                450             455             460
His His Val Gln Val Gln Pro Phe Phe Ser Ser Cys Leu Asn Asp Cys
465                 470                 475                 480

Leu Arg His Ala Val Thr Val Pro Cys Pro Val Ile Ser Asn Thr Thr
                485                 490                 495

Val Pro Lys Pro Val Ala Asp Tyr Ile Pro Leu Trp Glu Pro Lys Ser
            500                 505                 510

Ser Asp Lys Thr His Thr Cys Pro Pro Cys Pro Ala Pro Glu Ala Glu
            515                 520                 525

Gly Ala Pro Ser Val Phe Leu Phe Pro Pro Lys Pro Lys Asp Thr Leu
        530                 535                 540

Met Ile Ser Arg Thr Pro Glu Val Thr Cys Val Val Val Asp Val Ser
545                 550                 555                 560

His Glu Asp Pro Glu Val Lys Phe Asn Trp Tyr Val Asp Gly Val Glu
                565                 570                 575

Val His Asn Ala Lys Thr Lys Pro Arg Glu Glu Gln Tyr Asn Ser Thr
            580                 585                 590

Tyr Arg Val Val Ser Val Leu Thr Val Leu His Gln Asp Trp Leu Asn
        595                 600                 605

Gly Lys Glu Tyr Lys Cys Lys Val Ser Asn Lys Ala Leu Pro Ser Ser
610                 615                 620

Ile Glu Lys Thr Ile Ser Lys Ala Lys Gly Gln Pro Arg Glu Pro Gln
625                 630                 635                 640

Val Tyr Thr Leu Pro Pro Ser Arg Asp Glu Leu Thr Lys Asn Gln Val
                645                 650                 655

Ser Leu Thr Cys Leu Val Lys Gly Phe Tyr Pro Ser Asp Ile Ala Val
            660                 665                 670

Glu Trp Glu Ser Asn Gly Gln Pro Glu Asn Asn Tyr Lys Thr Thr Pro
        675                 680                 685

Pro Val Leu Asp Ser Asp Gly Ser Phe Phe Leu Tyr Ser Lys Leu Thr
        690                 695                 700

Val Asp Lys Ser Arg Trp Gln Gln Gly Asn Val Phe Ser Cys Ser Val
705                 710                 715                 720

Met His Glu Ala Leu His Asn His Tyr Thr Gln Lys Ser Leu Ser Leu
                725                 730                 735

Ser Pro Gly Lys
            740
```

<210> SEQ ID NO 119
<211> LENGTH: 1500
<212> TYPE: DNA
<213> ORGANISM: Artificial Sequence
<220> FEATURE:
<223> OTHER INFORMATION: Murine IL-17RA signal peptide and exons 1-6 of murine IL-17RA, exons 8-13 of human IL-17RC, and exons 7-9 of murine Il-17RA

<400> SEQUENCE: 119

```
atggcgattc ggcgctgctg gccacgggtc gtccccgggc cgcgctgggg atggctgctt    60
ctgctgctga acgttctggc cccgggccgc gcctccccgc gcctcctcga cttcccggct   120
ccggtctgcg cgcaggaggg gctgagctgc agagtcaaga atagtacttg tctggatgac   180
agctggatcc accccaaaaa cctgaccccg tcttcccaa aaaacatcta tatcaatctt   240
agtgtttcct ctacccagca cggagaatta gtcctgtgt tgcatgttga gtggaccctg   300
cagacagatg ccagcatcct gtacctcgag ggtgcagagc tgtccgtcct gcagctgaac   360
```

```
accaatgagc ggctgtgtgt caagttccag tttctgtcca tgctgcagca tcaccgtaag    420
cggtggcggt tttccttcag ccactttgtg gtagatcctg gccaggagta tgaagtgact    480
gttcaccacc tgccgaagcc catccctgat ggggacccaa accacaaatc caagatcatc    540
tttgtgcctg actgtgagga cagcaagatg aagatgacta cctcatgcgt gagctcagcc    600
ctgccctggc tcaacgtgtc agcagatggt gacaacgtgc atctggttct gaatgtctct    660
gaggagcagc acttcggcct ctccctgtac tggaatcagg tccagggccc cccaaaaccc    720
cggtggcaca aaaacctgac tggaccgcag atcattacct gaaccacac agacctggtt    780
ccctgcctct gtattcaggt gtggcctctg aacctgact ccgttaggac gaacatctgc     840
cccttcaggg aggaccccg cgcacaccag aacctctggc aagccgcccg actgcgactg     900
ctgaccctgc agagctggct gctggacgca ccgtgctcgc tgcccgcaga agcggcactg    960
tgctggcggg ctccgggtgg ggaccctgc cagccactgg tcccaccgct ttcctgggag    1020
aacgtcactg tggacaaggt tctcgagttc ccattgctga aggccaccc taacctctgt    1080
gttcaggtga acagctcgga gaagctgcag ctgcaggagt gcttgtgggc tggcagcctt    1140
tgggatccca acatcactgt ggagaccttg gacacacagc atctgcgagt ggacttcacc    1200
ctgtggaatg aatccacccc ctaccaggtc ctgctggaaa gtttctccga ctcagagaac    1260
cacagctgct tgatgtcgt taaacaaata tttgcgccca ggcaagaaga attccatcag    1320
cgagctaatg tcacattcac tctaagcaag tttcactggt gctgccatca ccacgtgcag    1380
gtccagccct tcttcagcag ctgcctaaat gactgtttga cacgctgt gactgtgccc     1440
tgcccagtaa tctcaaatac cacagttccc aagccagttg cagactacat tcccctgtgg    1500
```

<210> SEQ ID NO 120
<211> LENGTH: 500
<212> TYPE: PRT
<213> ORGANISM: Artificial Sequence
<220> FEATURE:
<223> OTHER INFORMATION: Murine IL-17RA signal peptide and exons 1-6 of
      murine IL-17RA, exons 8-13 of human IL-17RC, and
      exons 7-9 of murine Il-17RA

<400> SEQUENCE: 120

Met Ala Ile Arg Arg Cys Trp Pro Arg Val Val Pro Gly Pro Ala Leu
1               5                   10                  15

Gly Trp Leu Leu Leu Leu Asn Val Leu Ala Pro Gly Arg Ala Ser
                20                  25                  30

Pro Arg Leu Leu Asp Phe Pro Ala Pro Val Cys Ala Gln Glu Gly Leu
            35                  40                  45

Ser Cys Arg Val Lys Asn Ser Thr Cys Leu Asp Asp Ser Trp Ile His
        50                  55                  60

Pro Lys Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

```
Val His His Leu Pro Lys Pro Ile Pro Asp Gly Asp Pro Asn His Lys
            165                 170                 175

Ser Lys Ile Ile Phe Val Pro Asp Cys Glu Asp Ser Lys Met Lys Met
            180                 185                 190

Thr Thr Ser Cys Val Ser Ser Ala Leu Pro Trp Leu Asn Val Ser Ala
            195                 200                 205

Asp Gly Asp Asn Val His Leu Val Leu Asn Val Ser Glu Glu Gln His
            210                 215                 220

Phe Gly Leu Ser Leu Tyr Trp Asn Gln Val Gln Gly Pro Pro Lys Pro
225                 230                 235                 240

Arg Trp His Lys Asn Leu Thr Gly Pro Gln Ile Ile Thr Leu Asn His
            245                 250                 255

Thr Asp Leu Val Pro Cys Leu Cys Ile Gln Val Trp Pro Leu Glu Pro
            260                 265                 270

Asp Ser Val Arg Thr Asn Ile Cys Pro Phe Arg Glu Asp Pro Arg Ala
            275                 280                 285

His Gln Asn Leu Trp Gln Ala Ala Arg Leu Arg Leu Leu Thr Leu Gln
            290                 295                 300

Ser Trp Leu Leu Asp Ala Pro Cys Ser Leu Pro Ala Glu Ala Ala Leu
305                 310                 315                 320

Cys Trp Arg Ala Pro Gly Gly Asp Pro Cys Gln Pro Leu Val Pro Pro
            325                 330                 335

Leu Ser Trp Glu Asn Val Thr Val Asp Lys Val Leu Glu Phe Pro Leu
            340                 345                 350

Leu Lys Gly His Pro Asn Leu Cys Val Gln Val Asn Ser Ser Glu Lys
            355                 360                 365

Leu Gln Leu Gln Glu Cys Leu Trp Ala Gly Ser Leu Trp Asp Pro Asn
            370                 375                 380

Ile Thr Val Glu Thr Leu Asp Thr Gln His Leu Arg Val Asp Phe Thr
385                 390                 395                 400

Leu Trp Asn Glu Ser Thr Pro Tyr Gln Val Leu Leu Glu Ser Phe Ser
            405                 410                 415

Asp Ser Glu Asn His Ser Cys Phe Asp Val Val Lys Gln Ile Phe Ala
            420                 425                 430

Pro Arg Gln Glu Glu Phe His Gln Arg Ala Asn Val Thr Phe Thr Leu
            435                 440                 445

Ser Lys Phe His Trp Cys Cys His His Val Gln Val Gln Pro Phe Phe
            450                 455                 460

Phe Ser Ser Cys Leu Asn Asp Cys Leu Arg His Ala Val Thr Val Pro
465                 470                 475                 480

Cys Pro Val Ile Ser Asn Thr Thr Val Pro Lys Pro Val Ala Asp Tyr
            485                 490                 495

Ile Pro Leu Trp
            500

<210> SEQ ID NO 121
<211> LENGTH: 2196
<212> TYPE: DNA
<213> ORGANISM: Artificial Sequence
<220> FEATURE:
<223> OTHER INFORMATION: Murine IL-17RA signal peptide and exons 1-6 of
      murine  IL-17RA, exons 8-13 of human IL-17RC, and
      exons 7-9 of murine Il-17RA and Fc5

<400> SEQUENCE: 121
atggcgattc ggcgctgctg gccacgggtc gtcccgggc ccgcgctggg atggctgctt      60
```

```
ctgctgctga acgttctggc cccgggccgc gcctccccgc gcctcctcga cttcccggct    120
ccggtctgcg cgcaggaggg gctgagctgc agagtcaaga atagtacttg tctggatgac    180
agctggatcc accccaaaaa cctgaccccg tcttccccaa aaacatctca tatcaatctt    240
agtgtttcct ctaccagca cggagaatta gtccctgtgt tgcatgttga gtggaccctg    300
cagacagatg ccagcatcct gtacctcgag ggtgcagagc tgtccgtcct gcagctgaac    360
accaatgagc ggctgtgtgt caagttccag tttctgtcca tgctgcagca tcaccgtaag    420
cggtggcggt tttccttcag ccactttgtg gtagatcctg gccaggagta tgaagtgact    480
gttcaccacc tgccgaagcc catccctgat ggggacccaa accacaaatc caagatcatc    540
tttgtgcctg actgtgagga cagcaagatg aagatgacta cctcatgcgt gagctcagcc    600
ctgccctggc tcaacgtgtc agcagatggt gacaacgtgc atctggttct gaatgtctct    660
gaggagcagc acttcggcct ctccctgtac tggaatcagg tccagggccc cccaaaaccc    720
cggtggcaca aaaacctgac tggaccgcag atcattacct tgaaccacac agacctggtt    780
ccctgcctct gtattcaggt gtggcctctg gaacctgact ccgttaggac gaacatctgc    840
cccttcaggg aggaccccg cgcacaccag aacctctggc aagccgcccg actgcgactg    900
ctgaccctgc agagctggct gctggacgca ccgtgctcgc tgcccgcaga gcggcactg    960
tgctggcggg ctccgggtgg ggaccccctgc cagccactgg tcccaccgct ttcctgggag   1020
aacgtcactg tggacaaggt tctcgagttc ccattgctga aaggccaccc taacctctgt   1080
gttcaggtga acagctcgga gaagctgcag ctgcaggagt gcttgtgggc tggcagcctt   1140
tgggatccca acatcactgt ggagaccttg gacacacagc atctgcgagt ggacttcacc   1200
ctgtggaatg aatccacccc ctaccaggtc ctgctggaaa gtttctccga ctcagagaac   1260
cacagctgct ttgatgtcgt taaacaaata tttgcgccca ggcaagaaga attccatcag   1320
cgagctaatg tcacattcac tctaagcaag tttcactggt gctgccatca ccacgtgcag   1380
gtccagccct tcttcagcag ctgcctaaat gactgtttga cacgctgt gactgtgccc    1440
tgcccagtaa tctcaaatac cacagttccc aagccagttg cagactacat tcccctgtgg   1500
gagcccaaat cttcagacaa aactcacaca tgccccaccgt gcccagcacc tgaagccgag   1560
ggggcaccgt cagtcttcct cttccccca aaacccaagg acaccctcat gatctcccgg   1620
acccctgagg tcacatgcgt ggtggtggac gtgagccacg aagaccctga ggtcaagttc   1680
aactggtacg tggacggcgt ggaggtgcat aatgccaaga caaagccgcg ggaggagcag   1740
tacaacagca cgtaccgtgt ggtcagcgtc ctcaccgtcc tgcaccagga ctggctgaat   1800
ggcaaggagt acaagtgcaa ggtctccaac aaagccctcc catcctccat cgagaaaacc   1860
atctccaaag ccaaagggca gccccgagaa ccacaggtgt acaccctgcc cccatcccgg   1920
gatgagctga ccaagaacca ggtcagcctg acctgcctgg tcaaaggctt ctatcccagc   1980
gacatcgccg tggagtggga gagcaatggg cagccggaga caactacaa gaccacgcct    2040
cccgtgctgg actccgacgg ctccttcttc ctctacagca agctcaccgt ggacaagagc   2100
aggtggcagc aggggaacgt cttctcatgc tccgtgatgc atgaggctct gcacaaccac   2160
tacacgcaga agagcctctc cctgtctccg ggtaaa                             2196
```

<210> SEQ ID NO 122
<211> LENGTH: 2196
<212> TYPE: PRT
<213> ORGANISM: Artificial Sequence
<220> FEATURE:
<223> OTHER INFORMATION: Murine IL-17RA signal peptide and exons 1-6 of
      murine IL-17RA, exons 8-13 of human IL-17RC, and -continued exons 7-9 of murine Il-17RA and Fc5

<400> SEQUENCE: 122

```
Ala Thr Gly Gly Cys Gly Ala Thr Thr Cys Gly Cys Gly Cys Thr
 1               5                  10                  15
Gly Cys Thr Gly Gly Cys Cys Ala Cys Gly Gly Gly Thr Cys Gly Thr
                20                  25                  30
Cys Cys Cys Cys Gly Gly Gly Cys Cys Gly Cys Gly Cys Thr Gly
                35                  40                  45
Gly Gly Ala Thr Gly Gly Cys Thr Gly Cys Thr Thr Cys Thr Gly Cys
             50                  55                  60
Thr Gly Cys Thr Gly Ala Ala Cys Gly Thr Thr Cys Thr Gly Gly Cys
 65                  70                  75                  80
Cys Cys Cys Gly Gly Gly Cys Cys Gly Cys Gly Cys Thr Cys Cys
                85                  90                  95
Cys Cys Gly Cys Gly Cys Cys Thr Cys Cys Thr Cys Gly Ala Cys Thr
               100                 105                 110
Thr Cys Cys Cys Gly Gly Cys Thr Cys Cys Gly Gly Thr Cys Thr Gly
               115                 120                 125
Cys Gly Cys Gly Cys Ala Gly Gly Ala Gly Gly Gly Cys Thr Gly
               130                 135                 140
Ala Gly Cys Thr Gly Cys Ala Gly Ala Gly Thr Cys Ala Ala Gly Ala
145                 150                 155                 160
Ala Thr Ala Gly Thr Ala Cys Thr Thr Gly Thr Cys Thr Gly Gly Ala
                165                 170                 175
Thr Gly Ala Cys Ala Gly Cys Thr Gly Gly Ala Thr Cys Cys Ala Cys
                180                 185                 190
Cys Cys Cys Ala Ala Ala Ala Cys Cys Thr Gly Ala Cys Cys Cys
                195                 200                 205
Cys Gly Thr Cys Thr Thr Cys Cys Cys Ala Ala Ala Ala Ala
                210                 215                 220
Cys Ala Thr Cys Thr Ala Thr Ala Thr Cys Ala Ala Thr Cys Thr Thr
225                 230                 235                 240
Ala Gly Thr Gly Thr Thr Thr Cys Cys Thr Cys Thr Ala Cys Cys Cys
                245                 250                 255
Ala Gly Cys Ala Cys Gly Gly Ala Gly Ala Ala Thr Thr Ala Gly Thr
                260                 265                 270
Cys Cys Cys Thr Gly Thr Gly Thr Thr Gly Cys Ala Thr Gly Thr Thr
                275                 280                 285
Gly Ala Gly Thr Gly Gly Ala Cys Cys Cys Thr Gly Cys Ala Gly Ala
                290                 295                 300
Cys Ala Gly Ala Thr Gly Cys Cys Ala Gly Cys Ala Thr Cys Cys Thr
305                 310                 315                 320
Gly Thr Ala Cys Cys Thr Cys Gly Ala Gly Gly Thr Gly Cys Ala
                325                 330                 335
Gly Ala Gly Cys Thr Gly Thr Cys Cys Gly Thr Cys Cys Thr Gly Cys
                340                 345                 350
Ala Gly Cys Thr Gly Ala Ala Cys Ala Cys Ala Ala Thr Gly Ala
                355                 360                 365
Gly Cys Gly Gly Cys Thr Gly Thr Gly Thr Cys Ala Ala Gly
                370                 375                 380
Thr Thr Cys Cys Ala Gly Thr Thr Thr Cys Gly Thr Cys Cys Ala
385                 390                 395                 400
Thr Gly Cys Thr Gly Cys Ala Gly Cys Ala Thr Cys Ala Cys Cys Gly
```

```
                405             410             415
Thr Ala Ala Gly Cys Gly Gly Thr Gly Cys Gly Thr Thr Thr
            420             425             430
Thr Cys Cys Thr Thr Cys Ala Gly Cys Cys Ala Cys Thr Thr Thr Gly
            435             440             445
Thr Gly Gly Thr Ala Gly Ala Thr Cys Thr Gly Gly Cys Cys Ala
        450             455             460
Gly Gly Ala Gly Thr Ala Thr Gly Ala Ala Gly Thr Gly Ala Cys Thr
465             470             475             480
Gly Thr Thr Cys Ala Cys Cys Ala Cys Thr Gly Cys Cys Gly Ala
            485             490             495
Ala Gly Cys Cys Cys Ala Thr Cys Cys Thr Gly Ala Thr Gly Gly
            500             505             510
Gly Gly Ala Cys Cys Cys Ala Ala Cys Cys Ala Cys Ala Ala Ala
        515             520             525
Thr Cys Cys Ala Ala Gly Ala Thr Cys Ala Thr Cys Thr Thr Gly
    530             535             540
Thr Gly Cys Cys Thr Gly Ala Cys Thr Gly Thr Gly Ala Gly Gly Ala
545             550             555             560
Cys Ala Gly Cys Ala Ala Gly Ala Thr Gly Ala Ala Gly Ala Thr Gly
            565             570             575
Ala Cys Thr Ala Cys Cys Thr Cys Ala Thr Gly Cys Gly Gly Ala
            580             585             590
Gly Cys Thr Cys Ala Gly Cys Cys Thr Gly Cys Cys Cys Thr Gly
            595             600             605
Gly Cys Thr Cys Ala Ala Cys Gly Thr Gly Thr Cys Ala Gly Cys Ala
        610             615             620
Gly Ala Thr Gly Gly Thr Gly Ala Cys Ala Ala Cys Gly Thr Gly Cys
625             630             635             640
Ala Thr Cys Thr Gly Gly Thr Cys Thr Gly Ala Ala Thr Gly Thr
            645             650             655
Cys Thr Cys Thr Gly Ala Gly Gly Ala Gly Cys Ala Gly Cys Ala Cys
            660             665             670
Thr Thr Cys Gly Gly Cys Cys Thr Cys Thr Cys Cys Thr Gly Thr
            675             680             685
Ala Cys Thr Gly Gly Ala Ala Thr Cys Ala Gly Gly Thr Cys Cys Ala
        690             695             700
Gly Gly Gly Cys Cys Cys Cys Cys Ala Ala Ala Cys Cys Cys
705             710             715             720
Cys Gly Gly Thr Gly Gly Cys Ala Cys Ala Ala Ala Ala Cys Cys
            725             730             735
Thr Gly Ala Cys Thr Gly Gly Ala Cys Cys Gly Cys Ala Gly Ala Thr
        740             745             750
Cys Ala Thr Thr Ala Cys Cys Thr Thr Gly Ala Ala Cys Cys Ala Cys
    755             760             765
Ala Cys Ala Gly Ala Cys Cys Thr Gly Gly Thr Thr Cys Cys Cys Thr
770             775             780
Gly Cys Cys Thr Cys Thr Gly Thr Ala Thr Thr Cys Ala Gly Gly Thr
785             790             795             800
Gly Thr Gly Gly Cys Cys Thr Cys Thr Gly Gly Ala Ala Cys Cys Thr
            805             810             815
Gly Ala Cys Thr Cys Cys Gly Thr Thr Ala Gly Gly Ala Cys Gly Ala
            820             825             830
```

```
Ala Cys Ala Thr Cys Thr Gly Cys Cys Cys Thr Thr Cys Ala Gly
        835                 840                 845
Gly Gly Ala Gly Gly Ala Cys Cys Cys Cys Gly Cys Gly Cys Ala
        850                 855                 860
Cys Ala Cys Cys Ala Gly Ala Ala Cys Thr Cys Thr Gly Gly Cys
865                 870                 875                 880
Ala Ala Gly Cys Cys Gly Cys Cys Cys Gly Ala Cys Thr Gly Cys
                885                 890                 895
Ala Cys Thr Gly Cys Thr Gly Ala Cys Cys Thr Gly Cys Ala Gly
            900                 905                 910
Ala Gly Cys Thr Gly Gly Cys Thr Gly Cys Thr Gly Gly Ala Cys Gly
        915                 920                 925
Cys Ala Cys Cys Gly Thr Gly Cys Thr Cys Gly Cys Thr Gly Cys Cys
    930                 935                 940
Cys Gly Cys Ala Gly Ala Ala Gly Cys Gly Gly Cys Ala Cys Thr Gly
945                 950                 955                 960
Thr Gly Cys Thr Gly Gly Cys Gly Gly Gly Cys Thr Cys Cys Gly Gly
                965                 970                 975
Gly Thr Gly Gly Gly Gly Ala Cys Cys Cys Thr Gly Cys Cys Ala
        980                 985                 990
Gly Cys Cys Ala Cys Thr Gly Gly Thr Cys Cys Ala Cys Cys Gly
    995                 1000                1005
Cys Thr Thr Thr Cys Cys Thr Gly Gly Gly Ala Gly Ala Ala Cys Gly
    1010                1015                1020
Thr Cys Ala Cys Thr Gly Thr Gly Gly Ala Cys Ala Ala Gly Gly Thr
1025                1030                1035                1040
Thr Cys Thr Cys Gly Ala Gly Thr Thr Cys Cys Cys Ala Thr Thr Gly
                1045                1050                1055
Cys Thr Gly Ala Ala Ala Gly Gly Cys Cys Ala Cys Cys Thr Ala
        1060                1065                1070
Ala Cys Cys Thr Cys Thr Gly Thr Gly Thr Thr Cys Ala Gly Gly Thr
    1075                1080                1085
Gly Ala Ala Cys Ala Gly Cys Thr Cys Gly Gly Ala Gly Ala Ala Gly
    1090                1095                1100
Cys Thr Gly Cys Ala Gly Cys Thr Gly Cys Ala Gly Gly Ala Gly Thr
1105                1110                1115                1120
Gly Cys Thr Thr Gly Thr Gly Gly Cys Thr Gly Cys Gly Ala Gly
                1125                1130                1135
Cys Cys Thr Thr Thr Gly Gly Gly Ala Thr Cys Cys Ala Ala Cys
        1140                1145                1150
Ala Thr Cys Ala Cys Thr Gly Thr Gly Gly Ala Gly Ala Cys Cys Thr
    1155                1160                1165
Thr Gly Gly Ala Cys Ala Cys Ala Cys Ala Gly Cys Ala Thr Cys Thr
1170                1175                1180
Gly Cys Gly Ala Gly Thr Gly Gly Ala Cys Thr Thr Cys Ala Cys Cys
1185                1190                1195                1200
Cys Thr Gly Thr Gly Gly Ala Ala Thr Gly Ala Ala Thr Cys Cys Ala
                1205                1210                1215
Cys Cys Cys Cys Cys Thr Ala Cys Cys Ala Gly Gly Thr Cys Cys Thr
    1220                1225                1230
Gly Cys Thr Gly Gly Ala Ala Ala Gly Thr Thr Thr Cys Thr Cys Cys
    1235                1240                1245
Gly Ala Cys Thr Cys Ala Gly Ala Gly Ala Ala Cys Cys Ala Cys Ala
    1250                1255                1260
```

-continued

```
Gly Cys Thr Gly Cys Thr Thr Thr Gly Ala Thr Gly Thr Cys Gly Thr
1265                1270                1275                1280

Thr Ala Ala Ala Cys Ala Ala Ala Thr Ala Thr Thr Thr Gly Cys Gly
                1285                1290                1295

Cys Cys Cys Ala Gly Gly Cys Ala Ala Gly Ala Ala Gly Ala Ala Thr
            1300                1305                1310

Thr Cys Cys Ala Thr Cys Ala Gly Cys Gly Ala Gly Cys Thr Ala Ala
        1315                1320                1325

Thr Gly Thr Cys Ala Cys Ala Thr Thr Cys Ala Cys Thr Cys Thr Ala
    1330                1335                1340

Ala Gly Cys Ala Ala Gly Thr Thr Thr Cys Ala Cys Thr Gly Gly Thr
1345                1350                1355                1360

Gly Cys Thr Gly Cys Cys Ala Thr Cys Ala Cys Cys Ala Cys Gly Thr
                1365                1370                1375

Gly Cys Ala Gly Gly Thr Cys Cys Ala Gly Cys Cys Cys Thr Thr Cys
            1380                1385                1390

Thr Thr Cys Ala Gly Cys Ala Gly Cys Thr Gly Cys Cys Thr Ala Ala
        1395                1400                1405

Ala Thr Gly Ala Cys Thr Gly Thr Thr Thr Gly Ala Gly Ala Cys Ala
    1410                1415                1420

Cys Gly Cys Thr Gly Thr Gly Ala Cys Thr Gly Thr Gly Cys Cys Cys
1425                1430                1435                1440

Thr Gly Cys Cys Cys Ala Gly Thr Ala Ala Thr Cys Thr Cys Ala Ala
                1445                1450                1455

Ala Thr Ala Cys Cys Ala Cys Ala Gly Thr Thr Cys Cys Cys Ala Ala
            1460                1465                1470

Gly Cys Cys Ala Gly Thr Thr Gly Cys Ala Gly Ala Cys Thr Ala Cys
        1475                1480                1485

Ala Thr Thr Cys Cys Cys Cys Thr Gly Thr Gly Gly Ala Gly Cys
    1490                1495                1500

Cys Cys Ala Ala Ala Thr Cys Thr Thr Cys Ala Gly Ala Cys Ala Ala
1505                1510                1515                1520

Ala Ala Cys Thr Cys Ala Cys Ala Cys Ala Thr Gly Cys Cys Cys Ala
                1525                1530                1535

Cys Cys Gly Thr Gly Cys Cys Cys Ala Gly Cys Ala Cys Cys Thr Gly
            1540                1545                1550

Ala Ala Gly Cys Cys Gly Ala Gly Gly Gly Gly Gly Cys Ala Cys Cys
        1555                1560                1565

Gly Thr Cys Ala Gly Thr Cys Thr Thr Cys Cys Thr Cys Thr Thr Cys
    1570                1575                1580

Cys Cys Cys Cys Cys Ala Ala Ala Ala Cys Cys Cys Ala Ala Gly Gly
1585                1590                1595                1600

Ala Cys Ala Cys Cys Cys Thr Cys Ala Thr Gly Ala Thr Cys Thr Cys
                1605                1610                1615

Cys Cys Gly Gly Ala Cys Cys Cys Cys Thr Gly Ala Gly Gly Thr Cys
            1620                1625                1630

Ala Cys Ala Thr Gly Cys Gly Thr Gly Gly Thr Gly Gly Thr Gly Gly
        1635                1640                1645

Ala Cys Gly Thr Gly Ala Gly Cys Cys Ala Cys Gly Ala Ala Gly Ala
    1650                1655                1660

Cys Cys Cys Thr Gly Ala Gly Gly Thr Cys Ala Ala Gly Thr Thr Cys
1665                1670                1675                1680

Ala Ala Cys Thr Gly Gly Thr Ala Cys Gly Thr Gly Gly Ala Cys Gly
```

-continued

```
                1685                1690                1695
Gly Cys Gly Thr Gly Ala Gly Gly Thr Gly Cys Ala Thr Ala Ala
            1700                1705                1710
Thr Gly Cys Cys Ala Ala Gly Ala Cys Ala Ala Ala Gly Cys Cys Gly
    1715                1720                1725
Cys Gly Gly Gly Ala Gly Gly Ala Gly Cys Ala Gly Thr Ala Cys Ala
    1730                1735                1740
Ala Cys Ala Gly Cys Ala Cys Gly Thr Ala Cys Cys Gly Thr Gly Thr
1745                1750                1755                1760
Gly Gly Thr Cys Ala Gly Cys Gly Thr Cys Cys Thr Cys Ala Cys Cys
            1765                1770                1775
Gly Thr Cys Cys Thr Gly Cys Ala Cys Ala Gly Gly Ala Cys Thr
            1780                1785                1790
Gly Gly Cys Thr Gly Ala Ala Thr Gly Gly Cys Ala Ala Gly Gly Ala
            1795                1800                1805
Gly Thr Ala Cys Ala Ala Gly Thr Gly Cys Ala Ala Gly Gly Thr Cys
            1810                1815                1820
Thr Cys Cys Ala Ala Cys Ala Ala Ala Gly Cys Cys Cys Thr Cys Cys
1825                1830                1835                1840
Cys Ala Thr Cys Cys Thr Cys Ala Thr Cys Gly Ala Gly Ala Ala
            1845                1850                1855
Ala Ala Cys Cys Ala Thr Cys Thr Cys Ala Ala Ala Gly Cys Cys
            1860                1865                1870
Ala Ala Ala Gly Gly Gly Cys Ala Gly Cys Cys Cys Cys Gly Ala Gly
            1875                1880                1885
Ala Ala Cys Cys Ala Cys Ala Gly Gly Thr Gly Thr Ala Cys Ala Cys
            1890                1895                1900
Cys Cys Thr Gly Cys Cys Cys Cys Cys Ala Thr Cys Cys Gly Gly Gly
1905                1910                1915                1920
Gly Ala Thr Gly Ala Gly Cys Thr Gly Ala Cys Cys Ala Ala Gly Ala
            1925                1930                1935
Ala Cys Cys Ala Gly Gly Thr Cys Ala Gly Cys Cys Thr Gly Ala Cys
            1940                1945                1950
Cys Thr Gly Cys Cys Thr Gly Gly Thr Cys Ala Ala Ala Gly Gly Cys
            1955                1960                1965
Thr Thr Cys Thr Ala Thr Cys Cys Cys Ala Gly Cys Gly Ala Cys Ala
            1970                1975                1980
Thr Cys Gly Cys Cys Gly Thr Gly Gly Ala Gly Thr Gly Gly Gly Ala
1985                1990                1995                2000
Gly Ala Gly Cys Ala Ala Thr Gly Gly Gly Cys Ala Gly Cys Cys Gly
            2005                2010                2015
Gly Ala Gly Ala Ala Cys Ala Ala Cys Thr Ala Cys Ala Ala Gly Ala
            2020                2025                2030
Cys Cys Ala Cys Gly Cys Cys Thr Cys Cys Gly Thr Gly Cys Thr
            2035                2040                2045
Gly Gly Ala Cys Thr Cys Cys Gly Ala Cys Gly Gly Cys Thr Cys Cys
            2050                2055                2060
Thr Thr Cys Thr Thr Cys Cys Thr Cys Thr Ala Cys Ala Gly Cys Ala
2065                2070                2075                2080
Ala Gly Cys Thr Cys Ala Cys Cys Gly Thr Gly Gly Ala Cys Ala Ala
            2085                2090                2095
Gly Ala Gly Cys Ala Gly Gly Thr Gly Gly Cys Ala Gly Cys Ala Gly
            2100                2105                2110
```

Gly Gly Gly Ala Ala Cys Gly Thr Cys Thr Thr Cys Thr Cys Ala Thr
                2115                2120                2125

Gly Cys Thr Cys Cys Gly Thr Gly Ala Thr Gly Cys Ala Thr Gly Ala
        2130                2135                2140

Gly Gly Cys Thr Cys Thr Gly Cys Ala Cys Ala Ala Cys Cys Ala Cys
2145                2150                2155                2160

Thr Ala Cys Ala Cys Gly Cys Ala Gly Ala Ala Gly Ala Gly Cys Cys
            2165                2170                2175

Thr Cys Thr Cys Cys Cys Thr Gly Thr Cys Thr Cys Cys Gly Gly Gly
        2180                2185                2190

Thr Ala Ala Ala
        2195

<210> SEQ ID NO 123
<211> LENGTH: 1272
<212> TYPE: DNA
<213> ORGANISM: Artificial Sequence
<220> FEATURE:
<223> OTHER INFORMATION: IL-17RC signal peptide and exons 1-6 of human
      IL-17RC, and Fc5

<400> SEQUENCE: 123

| | | |
|---|---|---|
| atgcctgtgc cctggttctt gctgtccttg gcactgggcc gaagcccagt ggtcctttct | 60 |
| ctggagaggc ttgtggggcc tcaggacgct acccactgct ctccgggcct cctgccgc | 120 |
| ctctgggaca gtgacatact ctgcctgcct ggggacatcg tgcctgctcc gggccccgtg | 180 |
| ctggcgccta cgcacctgca gacagagctg gtgctgaggt gccagaagga gaccgactgt | 240 |
| gacctctgtc tgcgtgtggc tgtccacttg gccgtgcatg ggcactggga gagcctgaa | 300 |
| gatgaggaaa gtttggagg agcagctgac tcagggtgg aggagcctag gaatgcctct | 360 |
| ctccaggccc aagtcgtgct ctccttccag gcctaccccta ctgcccgctg cgtcctgctg | 420 |
| gaggtgcaag tgcctgctgc ccttgtgcag tttggtcagt ctgtgggctc tgtggtatat | 480 |
| gactgcttcg aggctgccct agggagtgag gtacgaatct ggtcctatac tcagcccagg | 540 |
| tacgagaagg aactcaacca cacacagcag ctgcctgagc ccaaatcttc agacaaaact | 600 |
| cacacatgcc caccgtgccc agcacctgaa gccgaggggg caccgtcagt cttcctcttc | 660 |
| cccccaaaac ccaaggacac cctcatgatc tcccggaccc ctgaggtcac atgcgtggtg | 720 |
| gtggacgtga gccacgaaga ccctgaggtc aagttcaact ggtacgtgga cggcgtggag | 780 |
| gtgcataatg ccaagacaaa gccgcgggag gagcagtaca acagcacgta ccgtgtggtc | 840 |
| agcgtcctca ccgtcctgca ccaggactgg ctgaatggca aggagtacaa gtgcaaggtc | 900 |
| tccaacaaag ccctcccatc ctccatcgag aaaaccatct ccaaagccaa agggcagccc | 960 |
| cgagaaccac aggtgtacac cctgccccca tcccgggatg agctgaccaa gaaccaggtc | 1020 |
| agcctgacct gcctggtcaa aggcttctat cccagcgaca tcgccgtgga gtgggagagc | 1080 |
| aatgggcagc cggagaacaa ctacaagacc acgcctcccg tgctggactc cgacggctcc | 1140 |
| ttcttcctct acagcaagct caccgtggac aagagcaggt ggcagcaggg gaacgtcttc | 1200 |
| tcatgctccg tgatgcatga ggctctgcac aaccactaca cgcagaagag cctctccctg | 1260 |
| tctccgggta aa | 1272 |

<210> SEQ ID NO 124
<211> LENGTH: 424
<212> TYPE: PRT
<213> ORGANISM: Artificial Sequence
<220> FEATURE:
<223> OTHER INFORMATION: IL-17RC signal peptide and exons 1-6 of human -continued IL-17RC, and Fc5

<400> SEQUENCE: 124

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Glu Pro Lys Ser Ser Asp Lys Thr His Thr Cys Pro Pro Cys Pro Ala
        195                 200                 205

Pro Glu Ala Glu Gly Ala Pro Ser Val Phe Leu Phe Pro Pro Lys Pro
    210                 215                 220

Lys Asp Thr Leu Met Ile Ser Arg Thr Pro Glu Val Thr Cys Val Val
225                 230                 235                 240

Val Asp Val Ser His Glu Asp Pro Glu Val Lys Phe Asn Trp Tyr Val
                245                 250                 255

Asp Gly Val Glu Val His Asn Ala Lys Thr Lys Pro Arg Glu Glu Gln
            260                 265                 270

Tyr Asn Ser Thr Tyr Arg Val Val Ser Val Leu Thr Val Leu His Gln
        275                 280                 285

Asp Trp Leu Asn Gly Lys Glu Tyr Lys Cys Lys Val Ser Asn Lys Ala
    290                 295                 300

Leu Pro Ser Ser Ile Glu Lys Thr Ile Ser Lys Ala Lys Gly Gln Pro
305                 310                 315                 320

Arg Glu Pro Gln Val Tyr Thr Leu Pro Pro Ser Arg Asp Glu Leu Thr
                325                 330                 335

Lys Asn Gln Val Ser Leu Thr Cys Leu Val Lys Gly Phe Tyr Pro Ser
            340                 345                 350

Asp Ile Ala Val Glu Trp Glu Ser Asn Gly Gln Pro Glu Asn Asn Tyr
        355                 360                 365

Lys Thr Thr Pro Pro Val Leu Asp Ser Asp Gly Ser Phe Phe Leu Tyr
    370                 375                 380

Ser Lys Leu Thr Val Asp Lys Ser Arg Trp Gln Gln Gly Asn Val Phe
385                 390                 395                 400

Ser Cys Ser Val Met His Glu Ala Leu His Asn His Tyr Thr Gln Lys
```

405                 410                 415
Ser Leu Ser Leu Ser Pro Gly Lys
        420

<210> SEQ ID NO 125
<211> LENGTH: 1794
<212> TYPE: DNA
<213> ORGANISM: Artificial Sequence
<220> FEATURE:
<223> OTHER INFORMATION: IL-17RC signal peptide and exons 1-6 and 11-16
      of human IL-17RC, and Fc5

<400> SEQUENCE: 125

```
atgcctgtgc cctggttctt gctgtccttg gcactgggcc gaagcccagt ggtcctttct       60
ctggagaggc ttgtggggcc tcaggacgct acccactgct ctccgggcct tcctgccgc      120
ctctgggaca gtgacatact ctgcctgcct ggggacatcg tgcctgctcc gggccccgtg      180
ctggcgccta cgcacctgca gacagagctg gtgctgaggt gccagaagga gaccgactgt      240
gacctctgtc tgcgtgtggc tgtccacttg gccgtgcatg ggcactggga gagcctgaa      300
gatgaggaaa gtttggagg agcagctgac tcaggggtgg aggagcctag gaatgcctct      360
ctccaggccc aagtcgtgct ctccttccag gcctaccccta ctgcccgctg cgtcctgctg      420
gaggtgcaag tgcctgctgc ccttgtgcag tttggtcagt ctgtgggctc tgtggtatat      480
gactgcttcg aggctgccct agggagtgag gtacgaatct ggtcctatac tcagcccagg      540
tacgagaagg aactcaacca cacacagcag ctgcctgacc cccgcgcaca ccagaacctc      600
tggcaagccg cccgactgcg actgctgacc ctgcagagct ggctgctgga cgcaccgtgc      660
tcgctgcccg cagaagcggc actgtgctgg cgggctccgg tggggaccc ctgccagcca      720
ctggtcccac cgcttttcctg ggagaacgtc actgtggaca aggttctcga gttcccattg      780
ctgaaaggcc accctaacct ctgtgttcag gtgaacagct cggagaagct gcagctgcag      840
gagtgcttgt gggctgactc cctggggcct ctcaaagacg atgtgctact gttggagaca      900
cgaggccccc aggacaacag atccctctgt gccttggaac ccagtggctg tacttcacta      960
cccagcaaag cctccacgag ggcagctcgc cttggagagt acttactaca agacctgcag     1020
tcaggccagt gtctgcagct atgggacgat gacttgggag cgctatgggc ctgccccatg     1080
gacaaataca tccacaagga gcccaaatct tcagacaaaa ctcacacatg cccaccgtgc     1140
ccagcacctg aagccgaggg ggcaccgtca gtcttcctct tccccccaaa acccaaggac     1200
accctcatga tctcccggac ccctgaggtc acatgcgtgg tggtgacgt gagccacgaa     1260
gaccctgagg tcaagttcaa ctggtacgtg gacggcgtgg aggtgcataa tgccaagaca     1320
aagccgcggg aggagcagta caacagcacg taccgtgtgg tcagcgtcct caccgtcctg     1380
caccaggact ggctgaatgg caaggagtac aagtgcaagg tctccaacaa agccctccca     1440
tcctccatcg agaaaaccat ctccaaagcc aaagggcagc cccgagaacc acaggtgtac     1500
accctgcccc catcccggga tgagctgacc aagaaccagg tcagcctgac ctgcctggtc     1560
aaaggcttct atcccagcga catcgccgtg gagtgggaga gcaatgggca gccggagaac     1620
aactacaaga ccacgcctcc cgtgctggac tccgacggct ccttcttcct ctacagcaag     1680
ctcaccgtgg acaagagcag gtggcagcag gggaacgtct tctcatgctc cgtgatgcat     1740
gaggctctgc acaaccacta cacgcagaag agcctctccc tgtctccggg taaa           1794
```

<210> SEQ ID NO 126
<211> LENGTH: 598
<212> TYPE: PRT

<213> ORGANISM: Artificial Sequence
<220> FEATURE:
<223> OTHER INFORMATION: IL-17RC signal peptide and exons 1-6 and 11-16 of human IL-17RC, and Fc5

<400> SEQUENCE: 126

```
Met Pro Val Pro Trp Phe Leu Leu Ser Leu Ala Leu Gly Arg Ser Pro
 1               5                  10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
 50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Pro Arg Ala His Gln Asn Leu Trp Gln Ala Ala Arg Leu Arg Leu
        195                 200                 205

Leu Thr Leu Gln Ser Trp Leu Leu Asp Ala Pro Cys Ser Leu Pro Ala
210                 215                 220

Glu Ala Ala Leu Cys Trp Arg Ala Pro Gly Gly Asp Pro Cys Gln Pro
225                 230                 235                 240

Leu Val Pro Pro Leu Ser Trp Glu Asn Val Thr Val Asp Lys Val Leu
                245                 250                 255

Glu Phe Pro Leu Leu Lys Gly His Pro Asn Leu Cys Val Gln Val Asn
            260                 265                 270

Ser Ser Glu Lys Leu Gln Leu Gln Glu Cys Leu Trp Ala Asp Ser Leu
        275                 280                 285

Gly Pro Leu Lys Asp Asp Val Leu Leu Leu Glu Thr Arg Gly Pro Gln
290                 295                 300

Asp Asn Arg Ser Leu Cys Ala Leu Glu Pro Ser Gly Cys Thr Ser Leu
305                 310                 315                 320

Pro Ser Lys Ala Ser Thr Arg Ala Ala Arg Leu Gly Glu Tyr Leu Leu
                325                 330                 335

Gln Asp Leu Gln Ser Gly Gln Cys Leu Gln Leu Trp Asp Asp Asp Leu
            340                 345                 350

Gly Ala Leu Trp Ala Cys Pro Met Asp Lys Tyr Ile His Lys Glu Pro
        355                 360                 365

Lys Ser Ser Asp Lys Thr His Thr Cys Pro Pro Cys Pro Ala Pro Glu
370                 375                 380

Ala Glu Gly Ala Pro Ser Val Phe Leu Phe Pro Pro Lys Pro Lys Asp
```

```
                385                 390                 395                 400
Thr Leu Met Ile Ser Arg Thr Pro Glu Val Thr Cys Val Val Val Asp
                    405                 410                 415

Val Ser His Glu Asp Pro Glu Val Lys Phe Asn Trp Tyr Val Asp Gly
                420                 425                 430

Val Glu Val His Asn Ala Lys Thr Lys Pro Arg Glu Glu Gln Tyr Asn
            435                 440                 445

Ser Thr Tyr Arg Val Val Ser Val Leu Thr Val Leu His Gln Asp Trp
        450                 455                 460

Leu Asn Gly Lys Glu Tyr Lys Cys Lys Val Ser Asn Lys Ala Leu Pro
465                 470                 475                 480

Ser Ser Ile Glu Lys Thr Ile Ser Lys Ala Lys Gly Gln Pro Arg Glu
                485                 490                 495

Pro Gln Val Tyr Thr Leu Pro Pro Ser Arg Asp Glu Leu Thr Lys Asn
                500                 505                 510

Gln Val Ser Leu Thr Cys Leu Val Lys Gly Phe Tyr Pro Ser Asp Ile
            515                 520                 525

Ala Val Glu Trp Glu Ser Asn Gly Gln Pro Glu Asn Asn Tyr Lys Thr
        530                 535                 540

Thr Pro Pro Val Leu Asp Ser Asp Gly Ser Phe Phe Leu Tyr Ser Lys
545                 550                 555                 560

Leu Thr Val Asp Lys Ser Arg Trp Gln Gln Gly Asn Val Phe Ser Cys
                565                 570                 575

Ser Val Met His Glu Ala Leu His Asn His Tyr Thr Gln Lys Ser Leu
                580                 585                 590

Ser Leu Ser Pro Gly Lys
        595

<210> SEQ ID NO 127
<211> LENGTH: 1515
<212> TYPE: DNA
<213> ORGANISM: Artificial Sequence
<220> FEATURE:
<223> OTHER INFORMATION: IL-17RC signal peptide and exons 1-6 and 14-16
      of human IL-17RC, and Fc5

<400> SEQUENCE: 127
atgcctgtgc cctggttctt gctgtccttg gcactgggcc aagcccagt ggtcctttct      60 ctggagaggc ttgtggggcc tcaggacgct acccactgct ctccgggcct tcctgccgc     120 ctctgggaca gtgacatact ctgcctgcct gggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg gccgtgcatg gcactgggga agagcctgaa     300
gatgaggaaa agtttggagg agcagctgac tcaggggtgg aggagcctag gaatgcctct     360
ctccaggccc aagtcgtgct ctccttccag gcctacccta ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact ccctggggcc tctcaaagac     600
gatgtgctac tgttggagac acgaggcccc caggacaaca gatccctctg tgccttggaa     660
cccagtggct gtacttcact acccagcaaa gcctccacga gggcagctcg ccttggagag     720
tacttactac aagacctgca gtcaggccag tgtctgcagc tatgggacga tgacttggga     780
gcgctatggg cctgccccat ggacaaatac atccacaagg agcccaaatc ttcagacaaa     840
```

```
actcacacat gcccaccgtg cccagcacct gaagccgagg gggcaccgtc agtcttcctc      900
ttccccccaa acccaagga caccctcatg atctcccgga cccctgaggt cacatgcgtg      960
gtggtggacg tgagccacga agaccctgag gtcaagttca actggtacgt ggacggcgtg     1020
gaggtgcata atgccaagac aaagccgcgg gaggagcagt acaacagcac gtaccgtgtg     1080
gtcagcgtcc tcaccgtcct gcaccaggac tggctgaatg gcaaggagta caagtgcaag     1140
gtctccaaca agcccctccc atcctccatc gagaaaacca tctccaaagc caagggcag     1200 ccccgagaac cacaggtgta caccctgccc ccatcccggg atgagctgac caagaaccag     1260
gtcagcctga cctgcctggt caaaggcttc tatcccagcg acatcgccgt ggagtgggag     1320
agcaatgggc agccggagaa caactacaag accacgcctc ccgtgctgga ctccgacggc     1380
tccttcttcc tctacagcaa gctcaccgtg gacaagagca ggtggcagca ggggaacgtc     1440
ttctcatgct ccgtgatgca tgaggctctg cacaaccact acacgcagaa gagcctctcc     1500
ctgtctccgg gtaaa                                                     1515

<210> SEQ ID NO 128
<211> LENGTH: 505
<212> TYPE: PRT
<213> ORGANISM: Artificial Sequence
<220> FEATURE:
<223> OTHER INFORMATION: IL-17RC signal peptide and exons 1-6 and 14-16
      of human IL-17RC, and Fc5

<400> SEQUENCE: 128

Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
                 20                  25                  30

Cys Ser Pro Gly Leu Ser Cys Arg Leu Trp Asp Ser Asp Ile Leu Cys
             35                  40                  45

Leu Pro Gly Asp Ile Val Pro Ala Pro Gly Pro Val Leu Ala Pro Thr
         50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Ser Leu Gly Pro Leu Lys Asp Asp Val Leu Leu Leu Glu Thr Arg
        195                 200                 205

Gly Pro Gln Asp Asn Arg Ser Leu Cys Ala Leu Glu Pro Ser Gly Cys
    210                 215                 220

Thr Ser Leu Pro Ser Lys Ala Ser Thr Arg Ala Ala Arg Leu Gly Glu
225                 230                 235                 240
```

```
Tyr Leu Leu Gln Asp Leu Gln Ser Gly Gln Cys Leu Gln Leu Trp Asp
                245                 250                 255
Asp Asp Leu Gly Ala Leu Trp Ala Cys Pro Met Asp Lys Tyr Ile His
            260                 265                 270
Lys Glu Pro Lys Ser Ser Asp Lys Thr His Thr Cys Pro Pro Cys Pro
        275                 280                 285
Ala Pro Glu Ala Glu Gly Ala Pro Ser Val Phe Leu Phe Pro Pro Lys
    290                 295                 300
Pro Lys Asp Thr Leu Met Ile Ser Arg Thr Pro Glu Val Thr Cys Val
305                 310                 315                 320
Val Val Asp Val Ser His Glu Asp Pro Glu Val Lys Phe Asn Trp Tyr
                325                 330                 335
Val Asp Gly Val Glu Val His Asn Ala Lys Thr Lys Pro Arg Glu Glu
            340                 345                 350
Gln Tyr Asn Ser Thr Tyr Arg Val Val Ser Val Leu Thr Val Leu His
        355                 360                 365
Gln Asp Trp Leu Asn Gly Lys Glu Tyr Lys Cys Lys Val Ser Asn Lys
    370                 375                 380
Ala Leu Pro Ser Ser Ile Glu Lys Thr Ile Ser Lys Ala Lys Gly Gln
385                 390                 395                 400
Pro Arg Glu Pro Gln Val Tyr Thr Leu Pro Pro Ser Arg Asp Glu Leu
                405                 410                 415
Thr Lys Asn Gln Val Ser Leu Thr Cys Leu Val Lys Gly Phe Tyr Pro
            420                 425                 430
Ser Asp Ile Ala Val Glu Trp Glu Ser Asn Gly Gln Pro Glu Asn Asn
        435                 440                 445
Tyr Lys Thr Thr Pro Pro Val Leu Asp Ser Asp Gly Ser Phe Phe Leu
    450                 455                 460
Tyr Ser Lys Leu Thr Val Asp Lys Ser Arg Trp Gln Gln Gly Asn Val
465                 470                 475                 480
Phe Ser Cys Ser Val Met His Glu Ala Leu His Asn His Tyr Thr Gln
                485                 490                 495
Lys Ser Leu Ser Leu Ser Pro Gly Lys
            500                 505
```

<210> SEQ ID NO 129
<211> LENGTH: 1335
<212> TYPE: DNA
<213> ORGANISM: Artificial Sequence
<220> FEATURE:
<223> OTHER INFORMATION: Optimized tissue Plasminogen Activator (otPA)
    pre-pro signal sequence and exons 8-13 of human
    IL-17RC, and Fc5

<400> SEQUENCE: 129

```
atggatgcaa tgaagagagg gctctgctgt gtgctgctgc tgtgtggcgc cgtcttcgtt      60
tcgctcagcc aggaaatcca tgccgagttg agacgcttcc gtagagccct gcctggctc     120
aacgtgtcag cagatggtga caacgtgcat ctggttctga atgtctctga ggagcagcac    180
ttcggcctct ccctgtactg gaatcaggtc cagggccccc caaaacccg gtggcacaaa     240
aacctgactg gaccgcagat cattaccttg aaccacacag acctggttcc ctgcctctgt    300
attcaggtgt ggcctctgga acctgactcc gttaggacga catctgccc cttcagggag     360
gaccccccgcg cacaccagaa cctctggcaa gccgcccgac tgcgactgct gaccctgcag    420
agctggctgc tggacgcacc gtgctcgctg cccgcagaag cggcactgtg ctggcgggct    480
ccgggtgggg acccctgcca gccactggtc ccaccgcttt cctgggagaa cgtcactgtg    540
```

```
gacaaggttc tcgagttccc attgctgaaa ggccacccta acctctgtgt tcaggtgaac      600
agctcggaga agctgcagct gcaggagtgc ttgtgggctg agcccaaatc ttcagacaaa      660
actcacacat gcccaccgtg cccagcacct gaagccgagg gggcaccgtc agtcttcctc      720
ttccccccaa aacccaagga caccctcatg atctcccgga ccccctgaggt cacatgcgtg    780 gtggtggacg tgagccacga agaccctgag gtcaagttca actggtacgt ggacggcgtg     840
gaggtgcata atgccaagac aaagccgcgg gaggagcagt acaacagcac gtaccgtgtg     900
gtcagcgtcc tcaccgtcct gcaccaggac tggctgaatg gcaaggagta caagtgcaag     960
gtctccaaca aagccctccc atcctccatc gagaaaacca tctccaaagc caaagggcag     1020
ccccgagaac cacaggtgta caccctgccc ccatcccggg atgagctgac caagaaccag    1080
gtcagcctga cctgcctggt caaaggcttc tatcccagcg acatcgccgt ggagtgggag    1140
agcaatgggc agccggagaa caactacaag accacgcctc ccgtgctgga ctccgacggc    1200
tccttcttcc tctacagcaa gctcaccgtg gacaagagca ggtggcagca ggggaacgtc    1260
ttctcatgct ccgtgatgca tgaggctctg cacaaccact acacgcagaa gagcctctcc    1320
ctgtctccgg gtaaa                                                       1335

<210> SEQ ID NO 130
<211> LENGTH: 445
<212> TYPE: PRT
<213> ORGANISM: Artificial Sequence
<220> FEATURE:
<223> OTHER INFORMATION: Optimized tissue Plasminogen Activator (otPA)
      pre-pro signal sequence and exons 8-13 of human
      IL-17RC, and Fc5

<400> SEQUENCE: 130

Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Leu Pro Trp Leu Asn Val Ser Ala Asp Gly Asp Asn
        35                  40                  45

Val His Leu Val Leu Asn Val Ser Glu Glu Gln His Phe Gly Leu Ser
    50                  55                  60

Leu Tyr Trp Asn Gln Val Gln Gly Pro Pro Lys Pro Arg Trp His Lys
65                  70                  75                  80

Asn Leu Thr Gly Pro Gln Ile Ile Thr Leu Asn His Thr Asp Leu Val
                85                  90                  95

Pro Cys Leu Cys Ile Gln Val Trp Pro Leu Glu Pro Asp Ser Val Arg
            100                 105                 110

Thr Asn Ile Cys Pro Phe Arg Glu Asp Pro Arg Ala His Gln Asn Leu
        115                 120                 125

Trp Gln Ala Ala Arg Leu Arg Leu Leu Thr Leu Gln Ser Trp Leu Leu
    130                 135                 140

Asp Ala Pro Cys Ser Leu Pro Ala Glu Ala Ala Leu Cys Trp Arg Ala
145                 150                 155                 160

Pro Gly Gly Asp Pro Cys Gln Pro Leu Val Pro Pro Leu Ser Trp Glu
                165                 170                 175

Asn Val Thr Val Asp Lys Val Leu Glu Phe Pro Leu Leu Lys Gly His
            180                 185                 190

Pro Asn Leu Cys Val Gln Val Asn Ser Ser Glu Lys Leu Gln Leu Gln
        195                 200                 205
```

| | | | | | | | | | | | |
|---|---|---|---|---|---|---|---|---|---|---|---|
|Glu|Cys|Leu|Trp|Ala|Glu|Pro|Lys|Ser|Ser|Asp|Lys|Thr|His|Thr|Cys|
| |210| | | |215| | | |220| | | | | | |

Glu Cys Leu Trp Ala Glu Pro Lys Ser Ser Asp Lys Thr His Thr Cys
    210                 215                 220

Pro Pro Cys Pro Ala Pro Glu Ala Glu Gly Ala Pro Ser Val Phe Leu
225             230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 131
<211> LENGTH: 1299
<212> TYPE: DNA
<213> ORGANISM: Artificial Sequence
<220> FEATURE:
<223> OTHER INFORMATION: Optimized tissue Plasminogen Activator (otPA)
      pre-pro signal sequence and exons 8-10 and 14-16
      of human IL-17RC, and Fc5

<400> SEQUENCE: 131

```
atggatgcaa tgaagagagg ctctgctgt gtgctgctgc tgtgtggcgc cgtcttcgtt      60
tcgctcagcc aggaaatcca tgccgagttg agacgcttcc gtagagccct gccctggctc    120
aacgtgtcag cagatggtga caacgtgcat ctggttctga atgtctctga ggagcagcac    180
ttcggcctct ccctgtactg gaatcaggtc cagggccccc caaaacccg gtggcacaaa    240 aacctgactg gaccgcagat cattaccttg aaccacacag acctggttcc ctgcctctgt    300
attcaggtgt ggcctctgga acctgactcc gttaggacga catctgccc cttcagggag    360 gactccctgg ggcctctcaa agacgatgtg ctactgttgg agacacgagg cccccaggac    420
aacagatccc tctgtgcctt ggaacccagt ggctgtactt cactaccag caaagcctcc    480 acgagggcag ctcgccttgg agagtactta ctacaagacc tgcagtcagg ccagtgtctg    540
cagctatggg acgatgactt gggagcgcta tgggcctgcc ccatggacaa atacatccac    600
aaggagccca atcttcaga caaaactcac acatgcccac cgtgcccagc acctgaagcc    660
gagggggcac cgtcagtctt cctcttcccc ccaaaaccca aggacaccct catgatctcc    720
```

```
cggaccnctg aggtcacatg cgtggtggtg gacgtgagcc acgaagaccc tgaggtcaag    780
ttcaactggt acgtggacgg cgtggaggtg cataatgcca agacaaagcc gcgggaggag    840
cagtacaaca gcacgtaccg tgtggtcagc gtcctcaccg tcctgcacca ggactggctg    900
aatggcaagg agtacaagtg caaggtctcc aacaaagccc tcccatcctc catcgagaaa    960
accatctcca aagccaaagg gcagccccga gaaccacagg tgtacaccct gcccccatcc   1020
cgggatgagc tgaccaagaa ccaggtcagc ctgacctgcc tggtcaaagg cttctatccc   1080
agcgacatcg ccgtggagtg ggagagcaat gggcagccgg agaacaacta caagaccacg   1140
cctcccgtgc tggactccga cggctccttc ttcctctaca gcaagctcac cgtggacaag   1200
agcaggtggc agcaggggaa cgtcttctca tgctccgtga tgcatgaggc tctgcacaac   1260
cactacacgc agaagagcct ctccctgtct ccgggtaaa                          1299
```

<210> SEQ ID NO 132
<211> LENGTH: 433
<212> TYPE: PRT
<213> ORGANISM: Artificial Sequence
<220> FEATURE:
<223> OTHER INFORMATION: Optimized tissue Plasminogen Activator (otPA)
      pre-pro signal sequence and exons 8-10 and 14-16
      of human IL-17RC, and Fc5

<400> SEQUENCE: 132

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Ala Leu Pro Trp Leu Asn Val Ser Ala Asp Gly Asp Asn
        35                  40                  45

Val His Leu Val Leu Asn Val Ser Glu Glu Gln His Phe Gly Leu Ser
    50                  55                  60

Leu Tyr Trp Asn Gln Val Gln Gly Pro Pro Lys Pro Arg Trp His Lys
65                  70                  75                  80

Asn Leu Thr Gly Pro Gln Ile Ile Thr Leu Asn His Thr Asp Leu Val
                85                  90                  95

Pro Cys Leu Cys Ile Gln Val Trp Pro Leu Glu Pro Asp Ser Val Arg
            100                 105                 110

Thr Asn Ile Cys Pro Phe Arg Glu Asp Ser Leu Gly Pro Leu Lys Asp
        115                 120                 125

Asp Val Leu Leu Leu Glu Thr Arg Gly Pro Gln Asp Asn Arg Ser Leu
    130                 135                 140

Cys Ala Leu Glu Pro Ser Gly Cys Thr Ser Leu Pro Ser Lys Ala Ser
145                 150                 155                 160

Thr Arg Ala Ala Arg Leu Gly Glu Tyr Leu Leu Gln Asp Leu Gln Ser
                165                 170                 175

Gly Gln Cys Leu Gln Leu Trp Asp Asp Asp Leu Gly Ala Leu Trp Ala
            180                 185                 190

Cys Pro Met Asp Lys Tyr Ile His Lys Glu Pro Lys Ser Ser Asp Lys
        195                 200                 205

Thr His Thr Cys Pro Pro Cys Pro Ala Pro Glu Ala Glu Gly Ala Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255
```

```
Pro Glu Val Lys Phe Asn Trp Tyr Val Asp Gly Val Glu Val His Asn
        260                 265                 270
Ala Lys Thr Lys Pro Arg Glu Glu Gln Tyr Asn Ser Thr Tyr Arg Val
        275                 280                 285
Val Ser Val Leu Thr Val Leu His Gln Asp Trp Leu Asn Gly Lys Glu
        290                 295                 300
Tyr Lys Cys Lys Val Ser Asn Lys Ala Leu Pro Ser Ser Ile Glu Lys
305                 310                 315                 320
Thr Ile Ser Lys Ala Lys Gly Gln Pro Arg Glu Pro Gln Val Tyr Thr
                325                 330                 335
Leu Pro Pro Ser Arg Asp Glu Leu Thr Lys Asn Gln Val Ser Leu Thr
        340                 345                 350
Cys Leu Val Lys Gly Phe Tyr Pro Ser Asp Ile Ala Val Glu Trp Glu
        355                 360                 365
Ser Asn Gly Gln Pro Glu Asn Asn Tyr Lys Thr Thr Pro Pro Val Leu
        370                 375                 380
Asp Ser Asp Gly Ser Phe Phe Leu Tyr Ser Lys Leu Thr Val Asp Lys
385                 390                 395                 400
Ser Arg Trp Gln Gln Gly Asn Val Phe Ser Cys Ser Val Met His Glu
                405                 410                 415
Ala Leu His Asn His Tyr Thr Gln Lys Ser Leu Ser Leu Ser Pro Gly
                420                 425                 430
Lys
```

<210> SEQ ID NO 133
<211> LENGTH: 1056
<212> TYPE: DNA
<213> ORGANISM: Artificial Sequence
<220> FEATURE:
<223> OTHER INFORMATION: Optimized tissue Plasminogen Activator (otPA)
      pre-pro signal sequence and exons 8-10 of human
      IL-17RC, and Fc5

<400> SEQUENCE: 133

```
atggatgcaa tgaagagagg gctctgctgt gtgctgctgc tgtgtggcgc cgtcttcgtt     60
tcgctcagcc aggaaatcca tgccgagttg agacgcttcc gtagagccct gccctggctc    120
aacgtgtcag cagatggtga caacgtgcat ctggttctga atgtctctga ggagcagcac    180
ttcggcctct ccctgtactg gaatcaggtc cagggccccc caaaaccccg gtggcacaaa    240
aacctgactg gaccgcagat cattaccttg aaccacacag acctggttcc ctgcctctgt    300
attcaggtgt ggcctctgga acctgactcc gttaggacga catctgcccc ttcagggag    360
gagcccaaat cttcagacaa aactcacaca tgcccaccgt gcccagcacc tgaagccgag    420
ggggcaccgt cagtcttcct cttccccca aacccaagg acaccctcat gatctcccgg    480
acccctgagg tcacatgcgt ggtggtggac gtgagccacg aagaccctga ggtcaagttc    540
aactggtacg tggacggcgt ggaggtgcat aatgccaaga caaagccgcg ggaggagcag    600
tacaacagca cgtaccgtgt ggtcagcgtc ctcaccgtcc tgcaccagga ctggctgaat    660
ggcaaggagt acaagtgcaa ggtctccaac aaagccctcc catcctccat cgagaaaacc    720
atctccaaag ccaaagggca gccccgagaa ccacaggtgt acaccctgcc cccatcccgg    780
gatgagctga ccaagaacca ggtcagcctg acctgcctgg tcaaaggctt ctatcccagc    840
gacatcgccg tggagtggga gagcaatggg cagccggaga caactacaa gaccacgcct    900
cccgtgctgg actccgacgg ctccttcttc ctctacagca agctcaccgt ggacaagagc    960
```

```
aggtggcagc aggggaacgt cttctcatgc tccgtgatgc atgaggctct gcacaaccac  1020
tacacgcaga agagcctctc cctgtctccg ggtaaa                             1056
```

<210> SEQ ID NO 134
<211> LENGTH: 352
<212> TYPE: PRT
<213> ORGANISM: Artificial Sequence
<220> FEATURE:
<223> OTHER INFORMATION: Optimized tissue Plasminogen Activator (otPA)
      pre-pro signal sequence and exons 8-10 of human
      IL-17RC, and Fc5

<400> SEQUENCE: 134

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Ala Leu Pro Trp Leu Asn Val Ser Ala Asp Gly Asp Asn
        35                  40                  45

Val His Leu Val Leu Asn Val Ser Glu Glu Gln His Phe Gly Leu Ser
    50                  55                  60

Leu Tyr Trp Asn Gln Val Gln Gly Pro Pro Lys Pro Arg Trp His Lys
65                  70                  75                  80

Asn Leu Thr Gly Pro Gln Ile Ile Thr Leu Asn His Thr Asp Leu Val
                85                  90                  95

Pro Cys Leu Cys Ile Gln Val Trp Pro Leu Glu Pro Asp Ser Val Arg
            100                 105                 110

Thr Asn Ile Cys Pro Phe Arg Glu Glu Pro Lys Ser Ser Asp Lys Thr
        115                 120                 125

His Thr Cys Pro Pro Cys Pro Ala Pro Glu Ala Glu Gly Ala Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Lys Phe Asn Trp Tyr Val Asp Gly Val Glu Val His Asn Ala
            180                 185                 190

Lys Thr Lys Pro Arg Glu Glu Gln Tyr Asn Ser Thr Tyr Arg Val Val
        195                 200                 205

Ser Val Leu Thr Val Leu His Gln Asp Trp Leu Asn Gly Lys Glu Tyr
    210                 215                 220

Lys Cys Lys Val Ser Asn Lys Ala Leu Pro Ser Ser Ile Glu Lys Thr
225                 230                 235                 240

Ile Ser Lys Ala Lys Gly Gln Pro Arg Glu Pro Gln Val Tyr Thr Leu
                245                 250                 255

Pro Pro Ser Arg Asp Glu Leu Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Val Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
```

<210> SEQ ID NO 135
<211> LENGTH: 1080
<212> TYPE: DNA
<213> ORGANISM: Artificial Sequence
<220> FEATURE:
<223> OTHER INFORMATION: Optimized tissue Plasminogen Activator (otPA) pre-pro signal sequence and exons 11-13 of human IL-17RC, and Fc5

<400> SEQUENCE: 135

```
atggatgcaa tgaagagagg gctctgctgt gtgctgctgc tgtgtggcgc cgtcttcgtt    60
tcgctcagcc aggaaatcca tgccgagttg agacgcttcc gtagagaccc ccgcgcacac   120
cagaacctct ggcaagccgc ccgactgcga ctgctgaccc tgcagagctg gctgctggac   180
gcaccgtgct cgctgcccgc agaagcggca ctgtgctggc gggctccggg tggggacccc   240
tgccagccac tggtcccacc gctttcctgg gagaacgtca ctgtggacaa ggttctcgag   300
ttcccattgc tgaaaggcca ccctaacctc tgtgttcagg tgaacagctc ggagaagctg   360
cagctgcagg agtgcttgtg ggctgagccc aaatcttcag acaaaactca cacatgccca   420
ccgtgcccag cacctgaagc cgaggggggca ccgtcagtct tcctcttccc cccaaaaccc   480
aaggacaccc tcatgatctc ccggacccct gaggtcacat gcgtggtggt ggacgtgagc   540
cacgaagacc ctgaggtcaa gttcaactgg tacgtggacg gcgtggaggt gcataatgcc   600
aagacaaagc cgcgggagga gcagtacaac agcacgtacc gtgtggtcag cgtcctcacc   660
gtcctgcacc aggactggct gaatggcaag gagtacaagt gcaaggtctc caacaaagcc   720
ctcccatcct ccatcgagaa aaccatctcc aaagccaaag gcagccccg agaaccacag   780
gtgtacaccc tgcccccatc ccgggatgag ctgaccaaga accaggtcag cctgacctgc   840
ctggtcaaag gcttctatcc agcgacatc gccgtggagt gggagagcaa tgggcagccg   900
gagaacaact acaagaccac gcctcccgtg ctggactccg acggctcctt cttcctctac   960
agcaagctca ccgtggacaa gagcaggtgg cagcagggga acgtcttctc atgctccgtg  1020
atgcatgagg ctctgcacaa ccactacacg cagaagagcc tctccctgtc tccgggtaaa  1080
```

<210> SEQ ID NO 136
<211> LENGTH: 360
<212> TYPE: PRT
<213> ORGANISM: Artificial Sequence
<220> FEATURE:
<223> OTHER INFORMATION: Optimized tissue Plasminogen Activator (otPA) pre-pro signal sequence and exons 11-13 of human IL-17RC, and Fc5

<400> SEQUENCE: 136

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Asp Pro Arg Ala His Gln Asn Leu Trp Gln Ala Ala Arg
        35                  40                  45

Leu Arg Leu Leu Thr Leu Gln Ser Trp Leu Leu Asp Ala Pro Cys Ser
    50                  55                  60

Leu Pro Ala Glu Ala Ala Leu Cys Trp Arg Ala Pro Gly Gly Asp Pro
65                  70                  75                  80

Cys Gln Pro Leu Val Pro Pro Leu Ser Trp Glu Asn Val Thr Val Asp
                85                  90                  95
```

```
Lys Val Leu Glu Phe Pro Leu Lys Gly His Pro Asn Leu Cys Val
            100                 105                 110
Gln Val Asn Ser Ser Glu Lys Leu Gln Leu Gln Glu Cys Leu Trp Ala
        115                 120                 125
Glu Pro Lys Ser Ser Asp Lys Thr His Thr Cys Pro Pro Cys Pro Ala
130                 135                 140
Pro Glu Ala Glu Gly Ala Pro Ser Val Phe Leu Phe Pro Pro Lys Pro
145                 150                 155                 160
Lys Asp Thr Leu Met Ile Ser Arg Thr Pro Glu Val Thr Cys Val Val
                165                 170                 175
Val Asp Val Ser His Glu Asp Pro Glu Val Lys Phe Asn Trp Tyr Val
            180                 185                 190
Asp Gly Val Glu Val His Asn Ala Lys Thr Lys Pro Arg Glu Glu Gln
        195                 200                 205
Tyr Asn Ser Thr Tyr Arg Val Val Ser Val Leu Thr Val Leu His Gln
210                 215                 220
Asp Trp Leu Asn Gly Lys Glu Tyr Lys Cys Lys Val Ser Asn Lys Ala
225                 230                 235                 240
Leu Pro Ser Ser Ile Glu Lys Thr Ile Ser Lys Ala Lys Gly Gln Pro
                245                 250                 255
Arg Glu Pro Gln Val Tyr Thr Leu Pro Pro Ser Arg Asp Glu Leu Thr
            260                 265                 270
Lys Asn Gln Val Ser Leu Thr Cys Leu Val Lys Gly Phe Tyr Pro Ser
        275                 280                 285
Asp Ile Ala Val Glu Trp Glu Ser Asn Gly Gln Pro Glu Asn Asn Tyr
290                 295                 300
Lys Thr Thr Pro Pro Val Leu Asp Ser Asp Gly Ser Phe Phe Leu Tyr
305                 310                 315                 320
Ser Lys Leu Thr Val Asp Lys Ser Arg Trp Gln Gln Gly Asn Val Phe
                325                 330                 335
Ser Cys Ser Val Met His Glu Ala Leu His Asn His Tyr Thr Gln Lys
            340                 345                 350
Ser Leu Ser Leu Ser Pro Gly Lys
        355                 360

<210> SEQ ID NO 137
<211> LENGTH: 1164
<212> TYPE: DNA
<213> ORGANISM: Artificial Sequence
<220> FEATURE:
<223> OTHER INFORMATION: Optimized tissue Plasminogen Activator (otPA)
      pre-pro signal sequence and exons 7-10 of human
      IL-17RC, and Fc5

<400> SEQUENCE: 137
atggatgcaa tgaagagagg gctctgctgt gtgctgctgc tgtgtggcgc cgtcttcgtt      60
tcgctcagcc aggaaatcca tgccgagttg agacgcttcc gtagaggcag cctgtgggac     120
cccaacatca ccgtggagac cctggaggcc accagctgc gtgtgagctt caccctgtgg      180
aacgaatcta cccattacca gatcctgctg accagttttc gcacatgga gaaccacagt      240 tgctttgagc acatgcacca catacctgcg cccagaccag aagagttcca ccagcgatcc     300
aacgtcacac tcactctacg caaccttaaa gggtgctgtc gccaccaagt gcagatccag     360 ccttcttca gcagctgcct caatgactgc ctcagacact ccgcgactgt ttcctgccca      420
gaaatgccag acactccaga accaattccg gactacatgc cctgtgggaa gcccaaatct     480
tcagacaaaa ctcacacatg cccaccgtgc ccagcacctg aagccgaggg ggcaccgtca     540
```

```
gtcttcctct tcccccccaaa acccaaggac accctcatga tctcccggac ccctgaggtc    600
acatgcgtgg tggtggacgt gagccacgaa gaccctgagg tcaagttcaa ctggtacgtg    660
gacggcgtgg aggtgcataa tgccaagaca aagccgcggg aggagcagta caacagcacg    720
taccgtgtgg tcagcgtcct caccgtcctg caccaggact ggctgaatgg caaggagtac    780
aagtgcaagg tctccaacaa agccctccca tcctccatcg agaaaaccat ctccaaagcc    840
aaagggcagc ccgagaacc acaggtgtac accctgcccc catcccggga tgagctgacc    900
aagaaccagg tcagcctgac ctgcctggtc aaaggcttct atcccagcga catcgccgtg    960
gagtgggaga gcaatgggca gccggagaac aactacaaga ccacgcctcc cgtgctggac   1020
tccgacggct ccttcttcct ctacagcaag ctcaccgtgg acaagagcag gtggcagcag   1080
gggaacgtct tctcatgctc cgtgatgcat gaggctctgc acaaccacta cacgcagaag   1140
agcctctccc tgtctccggg taaa                                           1164
```

<210> SEQ ID NO 138
<211> LENGTH: 388
<212> TYPE: PRT
<213> ORGANISM: Artificial Sequence
<220> FEATURE:
<223> OTHER INFORMATION: Optimized tissue Plasminogen Activator (otPA)
      pre-pro signal sequence and exons 7-10 of human
      IL-17RC, and Fc5

<400> SEQUENCE: 138

```
Met Asp Ala Met Lys Arg Gly Leu Cys Cys Val Leu Leu Leu Cys Gly
  1               5                  10                  15

Ala Val Phe Val Ser Leu Ser Gln Glu Ile His Ala Glu Leu Arg Arg
             20                  25                  30

Phe Arg Arg Gly Ser Leu Trp Asp Pro Asn Ile Thr Val Glu Thr Leu
         35                  40                  45

Glu Ala His Gln Leu Arg Val Ser Phe Thr Leu Trp Asn Glu Ser Thr
     50                  55                  60

His Tyr Gln Ile Leu Leu Thr Ser Phe Pro His Met Glu Asn His Ser
 65                  70                  75                  80

Cys Phe Glu His Met His His Ile Pro Ala Pro Arg Pro Glu Glu Phe
                 85                  90                  95

His Gln Arg Ser Asn Val Thr Leu Thr Leu Arg Asn Leu Lys Gly Cys
            100                 105                 110

Cys Arg His Gln Val Gln Ile Gln Pro Phe Phe Ser Ser Cys Leu Asn
        115                 120                 125

Asp Cys Leu Arg His Ser Ala Thr Val Ser Cys Pro Glu Met Pro Asp
    130                 135                 140

Thr Pro Glu Pro Ile Pro Asp Tyr Met Pro Leu Trp Glu Pro Lys Ser
145                 150                 155                 160

Ser Asp Lys Thr His Thr Cys Pro Pro Cys Pro Ala Pro Glu Ala Glu
                165                 170                 175

Gly Ala Pro Ser Val Phe Leu Phe Pro Pro Lys Pro Lys Asp Thr Leu
            180                 185                 190

Met Ile Ser Arg Thr Pro Glu Val Thr Cys Val Val Val Asp Val Ser
        195                 200                 205

His Glu Asp Pro Glu Val Lys Phe Asn Trp Tyr Val Asp Gly Val Glu
    210                 215                 220

Val His Asn Ala Lys Thr Lys Pro Arg Glu Glu Gln Tyr Asn Ser Thr
225                 230                 235                 240
```

```
Tyr Arg Val Val Ser Val Leu Thr Val Leu His Gln Asp Trp Leu Asn
                245                 250                 255
Gly Lys Glu Tyr Lys Cys Lys Val Ser Asn Lys Ala Leu Pro Ser Ser
            260                 265                 270
Ile Glu Lys Thr Ile Ser Lys Ala Lys Gly Gln Pro Arg Glu Pro Gln
        275                 280                 285
Val Tyr Thr Leu Pro Pro Ser Arg Asp Glu Leu Thr Lys Asn Gln Val
    290                 295                 300
Ser Leu Thr Cys Leu Val Lys Gly Phe Tyr Pro Ser Asp Ile Ala Val
305                 310                 315                 320
Glu Trp Glu Ser Asn Gly Gln Pro Glu Asn Asn Tyr Lys Thr Thr Pro
                325                 330                 335
Pro Val Leu Asp Ser Asp Gly Ser Phe Phe Leu Tyr Ser Lys Leu Thr
            340                 345                 350
Val Asp Lys Ser Arg Trp Gln Gln Gly Asn Val Phe Ser Cys Ser Val
        355                 360                 365
Met His Glu Ala Leu His Asn His Tyr Thr Gln Lys Ser Leu Ser Leu
    370                 375                 380
Ser Pro Gly Lys
385

<210> SEQ ID NO 139
<211> LENGTH: 2433
<212> TYPE: DNA
<213> ORGANISM: Artificial Sequence
<220> FEATURE:
<223> OTHER INFORMATION: IL-17RA signal sequence and exons 1-10 of
      IL-17RA and exons 8-16 of human IL-17RC, and Fc5

<400> SEQUENCE: 139
atgggggccg cacgcagccc gccgtccgct gtcccggggc ccctgctggg gctgctcctg     60
ctgctcctgg gcgtgctggc cccgggtggc gcctccctgc gactcctgga ccaccgggcg    120
ctggtctgct cccagccggg gctaaactgc acggtcaaga atagtacctg cctggatgac    180 agctggatte accctcgaaa cctgaccccc tcctccccaa aggacctgca gatccagctg    240
cactttgccc acacccaaca aggagacctg ttccccgtgg ctcacatcga atggacactg    300
cagacagacg ccagcatcct gtacctcgag ggtgcagagt tatctgtcct gcagctgaac    360
accaatgaac gttttgtgcgt caggttttgag tttctgtcca aactgaggca tcaccacagg    420
cggtggcgtt ttaccttcag ccactttgtg gttgaccctg accaggaata tgaggtgacc    480
gttcaccacc tgcccaagcc catccctgat ggggacccaa accaccagtc caagaatttc    540
cttgtgcctg actgtgagca cgccaggatg aaggtaacca cgccatgcat gagctcaggc    600
agcctgtggg accccaacat caccgtggag accctggagg cccaccagct gcgtgtgagc    660
ttcaccctgt ggaacgaatc tacccattac cagatcctgc tgaccagttt tccgcacatg    720
gagaaccaca gttgctttga gcacatgcac acatacctg cgcccagacc agaagagttc    780
caccagcgat ccaacgtcac actcactcta cgcaaccta aagggtgctg tcgccaccaa    840
gtgcagatcc agccctttctt cagcagctgc ctcaatgact gcctcagaca ctccgcgact    900
gtttcctgcc cagaaatgcc agacactcca gaaccaattc cggactacat gcccctgtgg    960 gccctgcct ggctcaacgt gtcagcagat ggtgacaacg tgcatctggt tctgaatgtc   1020
tctgaggagc agcacttcgg cctctcctg tactggaatc aggtccaggg cccccccaaa   1080
ccccggtggc acaaaaacct gactggaccg cagatcatta ccttgaacca cagacctg   1140 gttccctgcc tctgtattca ggtgtggcct ctggaacctg actccgttag gacgaacatc   1200
```

```
tgccccttca gggaggaccc ccgcgcacac cagaacctct ggcaagccgc ccgactgcga   1260
ctgctgaccc tgcagagctg gctgctggac gcaccgtgct cgctgcccgc agaagcggca   1320
ctgtgctggc gggctccggg tggggacccc tgccagccac tggtcccacc gctttcctgg   1380
gagaacgtca ctgtggacaa ggttctcgag ttcccattgc tgaaaggcca ccctaacctc   1440
tgtgttcagg tgaacagctc ggagaagctg cagctgcagg agtgcttgtg ggctgactcc   1500
ctggggcctc tcaaagacga tgtgctactg ttggagacac gaggccccca ggacaacaga   1560
tccctctgtg ccttggaacc cagtggctgt acttcactac ccagcaaagc ctccacgagg   1620
gcagctcgcc ttggagagta cttactacaa gacctgcagt caggccagtg tctgcagcta   1680
tgggacgatg acttgggagc ctatgggcc tgccccatgg acaaatacat ccacaaggag   1740
cccaaatctt cagacaaaac tcacacatgc ccaccgtgcc cagcacctga gccgagggg   1800 gcaccgtcag tcttcctctt ccccccaaaa cccaaggaca ccctcatgat ctcccggacc   1860
cctgaggtca catgcgtggt ggtggacgtg agccacgaag accctgaggt caagttcaac   1920
tggtacgtgg acggcgtgga ggtgcataat gccaagacaa agccgcggga ggagcagtac   1980
aacagcacgt accgtgtggt cagcgtcctc accgtcctgc accaggactg gctgaatggc   2040
aaggagtaca agtgcaaggt ctccaacaaa gccctcccat cctccatcga gaaaaccatc   2100
tccaaagcca aagggcagcc ccgagaacca caggtgtaca ccctgccccc atcccgggat   2160
gagctgacca agaaccaggt cagcctgacc tgcctggtca aaggcttcta tcccagcgac   2220
atcgccgtgg agtgggagag caatgggcag ccggagaaca actacaagac cacgcctccc   2280
gtgctggact ccgacggctc cttcttcctc tacagcaagc tcaccgtgga caagagcagg   2340
tggcagcagg ggaacgtctt ctcatgctcc gtgatgcatg aggctctgca caaccactac   2400
acgcagaaga gcctctccct gtctccgggt aaa                                 2433

<210> SEQ ID NO 140
<211> LENGTH: 811
<212> TYPE: PRT
<213> ORGANISM: Artificial Sequence
<220> FEATURE:
<223> OTHER INFORMATION: IL-17RA signal sequence and exons 1-10 of
      IL-17RA and exons 8-16 of human IL-17RC, and Fc5

<400> SEQUENCE: 140

Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140
```

```
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
            180                 185                 190
Thr Thr Pro Cys Met Ser Ser Gly Ser Leu Trp Asp Pro Asn Ile Thr
        195                 200                 205
Val Glu Thr Leu Glu Ala His Gln Leu Arg Val Ser Phe Thr Leu Trp
    210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
                245                 250                 255
Pro Glu Glu Phe His Gln Arg Ser Asn Val Thr Leu Thr Leu Arg Asn
            260                 265                 270
Leu Lys Gly Cys Cys Arg His Gln Val Gln Ile Gln Pro Phe Phe Ser
        275                 280                 285
Ser Cys Leu Asn Asp Cys Leu Arg His Ser Ala Thr Val Ser Cys Pro
    290                 295                 300
Glu Met Pro Asp Thr Pro Glu Pro Ile Pro Asp Tyr Met Pro Leu Trp
305                 310                 315                 320
Ala Leu Pro Trp Leu Asn Val Ser Ala Asp Gly Asp Asn Val His Leu
                325                 330                 335
Val Leu Asn Val Ser Glu Glu Gln His Phe Gly Leu Ser Leu Tyr Trp
            340                 345                 350
Asn Gln Val Gln Gly Pro Pro Lys Pro Arg Trp His Lys Asn Leu Thr
        355                 360                 365
Gly Pro Gln Ile Ile Thr Leu Asn His Thr Asp Leu Val Pro Cys Leu
    370                 375                 380
Cys Ile Gln Val Trp Pro Leu Glu Pro Asp Ser Val Arg Thr Asn Ile
385                 390                 395                 400
Cys Pro Phe Arg Glu Asp Pro Arg Ala His Gln Asn Leu Trp Gln Ala
                405                 410                 415
Ala Arg Leu Arg Leu Leu Thr Leu Gln Ser Trp Leu Leu Asp Ala Pro
            420                 425                 430
Cys Ser Leu Pro Ala Glu Ala Ala Leu Cys Trp Arg Ala Pro Gly Gly
        435                 440                 445
Asp Pro Cys Gln Pro Leu Val Pro Pro Leu Ser Trp Glu Asn Val Thr
    450                 455                 460
Val Asp Lys Val Leu Glu Phe Pro Leu Leu Lys Gly His Pro Asn Leu
465                 470                 475                 480
Cys Val Gln Val Asn Ser Ser Glu Lys Leu Gln Leu Gln Glu Cys Leu
                485                 490                 495
Trp Ala Asp Ser Leu Gly Pro Leu Lys Asp Asp Val Leu Leu Leu Glu
            500                 505                 510
Thr Arg Gly Pro Gln Asp Asn Arg Ser Leu Cys Ala Leu Glu Pro Ser
        515                 520                 525
Gly Cys Thr Ser Leu Pro Ser Lys Ala Ser Thr Arg Ala Ala Arg Leu
    530                 535                 540
Gly Glu Tyr Leu Leu Gln Asp Leu Gln Ser Gly Gln Cys Leu Gln Leu
545                 550                 555                 560
Trp Asp Asp Asp Leu Gly Ala Leu Trp Ala Cys Pro Met Asp Lys Tyr
```

Ile His Lys Glu Pro Lys Ser Ser Asp Lys Thr His Thr Cys Pro Pro
565                     570                     575
                580                     585                     590

Cys Pro Ala Pro Glu Ala Glu Gly Ala Pro Ser Val Phe Leu Phe Pro
            595                     600                     605

Pro Lys Pro Lys Asp Thr Leu Met Ile Ser Arg Thr Pro Glu Val Thr
610                     615                     620

Cys Val Val Val Asp Val Ser His Glu Asp Pro Glu Val Lys Phe Asn
625                     630                     635                     640

Trp Tyr Val Asp Gly Val Glu Val His Asn Ala Lys Thr Lys Pro Arg
                645                     650                     655

Glu Glu Gln Tyr Asn Ser Thr Tyr Arg Val Val Ser Val Leu Thr Val
                660                     665                     670

Leu His Gln Asp Trp Leu Asn Gly Lys Glu Tyr Lys Cys Lys Val Ser
                675                     680                     685

Asn Lys Ala Leu Pro Ser Ser Ile Glu Lys Thr Ile Ser Lys Ala Lys
690                     695                     700

Gly Gln Pro Arg Glu Pro Gln Val Tyr Thr Leu Pro Pro Ser Arg Asp
705                     710                     715                     720

Glu Leu Thr Lys Asn Gln Val Ser Leu Thr Cys Leu Val Lys Gly Phe
                725                     730                     735

Tyr Pro Ser Asp Ile Ala Val Glu Trp Glu Ser Asn Gly Gln Pro Glu
                740                     745                     750

Asn Asn Tyr Lys Thr Thr Pro Pro Val Leu Asp Ser Asp Gly Ser Phe
                755                     760                     765

Phe Leu Tyr Ser Lys Leu Thr Val Asp Lys Ser Arg Trp Gln Gln Gly
                770                     775                     780

Asn Val Phe Ser Cys Ser Val Met His Glu Ala Leu His Asn His Tyr
785                     790                     795                     800

Thr Gln Lys Ser Leu Ser Leu Ser Pro Gly Lys
                805                     810

<210> SEQ ID NO 141
<211> LENGTH: 2190
<212> TYPE: DNA
<213> ORGANISM: Artificial Sequence
<220> FEATURE:
<223> OTHER INFORMATION: IL-17RA signal sequence and exons 1-6 of
      IL-17RA and exons 8-13 of human IL-17RC and exons 7-10 of
      IL-17RA, and Fc5

<400> SEQUENCE: 141
atgggggccg cacgcagccc gccgtccgct gtcccggggc ccctgctggg gctgctcctg      60
ctgctcctgg gcgtgctggc cccgggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttccccgtgg ctcacatcga atggacactg     300
cagacagacg ccagcatcct gtacctcgag ggtgcagagt tatctgtcct gcagctgaac     360
accaatgaac gtttgtgcgt caggtttgag tttctgtcca aactgaggca tcaccacagg     420
cggtggcgtt taccttcag ccactttgtg gttgaccctg accaggaata tgaggtgacc     480
gttcaccacc tgcccaagcc catccctgat ggggacccaa accaccagtc aagaatttc      540 cttgtgcctg actgtgagca cgccaggatg aaggtaacca cgccatgcat gagctcagcc     600
ctgccctggc tcaacgtgtc agcagatggt gacaacgtgc atctggttct gaatgtctct     660

```
gaggagcagc acttcggcct ctccctgtac tggaatcagg tccagggccc cccaaaaccc    720
cggtggcaca aaaacctgac tggaccgcag atcattacct gaaccacac agacctggtt     780
ccctgcctct gtattcaggt gtggcctctg aacctgact ccgttaggac gaacatctgc     840
cccttcaggg aggaccccg cgcacaccag aacctctggc aagccgcccg actgcgactg     900
ctgaccctgc agagctggct gctggacgca ccgtgctcgc tgcccgcaga agcggcactg     960
tgctggcggg ctccgggtgg ggaccccctgc cagccactgg tcccaccgct ttcctgggag   1020
aacgtcactg tggacaaggt tctcgagttc ccattgctga aggccaccc taacctctgt    1080
gttcaggtga acagctcgga aagctgcag ctgcaggagt gcttgtgggc tggcagcctg    1140
tgggacccca acatcaccgt ggagaccctg gaggcccacc agctgcgtgt gagcttcacc   1200
ctgtggaacg aatctaccca ttaccagatc ctgctgacca gttttccgca catggagaac   1260
cacagttgct ttgagcacat gcaccacata cctgcgccca accagaaga gttccaccag    1320
cgatccaacg tcacactcac tctacgcaac cttaaagggt gctgtcgcca ccaagtgcag   1380
atccagccct tcttcagcag ctgcctcaat gactgcctca gacactccgc gactgtttcc   1440
tgcccagaaa tgccagacac tccagaacca attccggact acatgcccct gtgggagccc   1500
aaatcttcag acaaaactca cacatgccca ccgtgcccag cacctgaagc cgaggggca    1560
ccgtcagtct tcctcttccc cccaaaaccc aaggacaccc tcatgatctc ccggacccct   1620
gaggtcacat gcgtggtggt ggacgtgagc cacgaagacc ctgaggtcaa gttcaactgg   1680
tacgtggacg gcgtggaggt gcataatgcc aagacaaagc cgcgggagga gcagtacaac   1740
agcacgtacc gtgtggtcag cgtcctcacc gtcctgcacc aggactggct gaatggcaag   1800
gagtacaagt gcaaggtctc caacaaagcc ctcccatcct ccatcgagaa aaccatctcc   1860
aaagccaaag ggcagccccg agaaccacag gtgtacaccc tgcccccatc ccgggatgag   1920
ctgaccaaga accaggtcag cctgacctgc ctggtcaaag cttctatcc agcgacatc    1980
gccgtggagt gggagagcaa tgggcagccg gagaacaact acaagaccac gcctcccgtg   2040
ctggactccg acggctcctt cttcctctac agcaagctca ccgtggacaa gagcaggtgg   2100
cagcagggga acgtcttctc atgctccgtg atgcatgagg ctctgcacaa ccactacacg   2160
cagaagagcc tctccctgtc tccgggtaaa                                   2190
```

<210> SEQ ID NO 142
<211> LENGTH: 730
<212> TYPE: PRT
<213> ORGANISM: Artificial Sequence
<220> FEATURE:
<223> OTHER INFORMATION: IL-17RA signal sequence and exons 1-6 of
      IL-17RA and exons 8-13 of human IL-17RC and exons 7-10 of
      IL-17RA, and Fc5

<400> SEQUENCE: 142

```
Met Gly Ala Ala Arg Ser Pro Pro Ser Ala Val Pro Gly Pro Leu Leu
  1               5                  10                  15

Gly Leu Leu Leu Leu Leu Leu Gly Val Leu Ala Pro Gly Gly Ala Ser
             20                  25                  30

Leu Arg Leu Leu Asp His Arg Ala Leu Val Cys Ser Gln Pro Gly Leu
         35                  40                  45

Asn Cys Thr Val Lys Asn Ser Thr Cys Leu Asp Asp Ser Trp Ile His
     50                  55                  60

Pro Arg Asn Leu Thr Pro Ser Ser Pro Lys Asp Leu Gln Ile Gln Leu
 65                  70                  75                  80
```

```
His Phe Ala His Thr Gln Gln Gly Asp Leu Phe Pro Val Ala His Ile
                85                  90                  95
Glu Trp Thr Leu Gln Thr Asp Ala Ser Ile Leu Tyr Leu Glu Gly Ala
            100                 105                 110
Glu Leu Ser Val Leu Gln Leu Asn Thr Asn Glu Arg Leu Cys Val Arg
        115                 120                 125
Phe Glu Phe Leu Ser Lys Leu Arg His His Arg Arg Trp Arg Phe
    130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
            180                 185                 190
Thr Thr Pro Cys Met Ser Ser Ala Leu Pro Trp Leu Asn Val Ser Ala
        195                 200                 205
Asp Gly Asp Asn Val His Leu Val Leu Asn Val Ser Glu Glu Gln His
    210                 215                 220
Phe Gly Leu Ser Leu Tyr Trp Asn Gln Val Gln Gly Pro Pro Lys Pro
225                 230                 235                 240
Arg Trp His Lys Asn Leu Thr Gly Pro Gln Ile Ile Thr Leu Asn His
                245                 250                 255
Thr Asp Leu Val Pro Cys Leu Cys Ile Gln Val Trp Pro Leu Glu Pro
            260                 265                 270
Asp Ser Val Arg Thr Asn Ile Cys Pro Phe Arg Glu Asp Pro Arg Ala
        275                 280                 285
His Gln Asn Leu Trp Gln Ala Ala Arg Leu Arg Leu Leu Thr Leu Gln
    290                 295                 300
Ser Trp Leu Leu Asp Ala Pro Cys Ser Leu Pro Ala Glu Ala Ala Leu
305                 310                 315                 320
Cys Trp Arg Ala Pro Gly Gly Asp Pro Cys Gln Pro Leu Val Pro Pro
                325                 330                 335
Leu Ser Trp Glu Asn Val Thr Val Asp Lys Val Leu Glu Phe Pro Leu
            340                 345                 350
Leu Lys Gly His Pro Asn Leu Cys Val Gln Val Asn Ser Ser Glu Lys
        355                 360                 365
Leu Gln Leu Gln Glu Cys Leu Trp Ala Gly Ser Leu Trp Asp Pro Asn
    370                 375                 380
Ile Thr Val Glu Thr Leu Glu Ala His Gln Leu Arg Val Ser Phe Thr
385                 390                 395                 400
Leu Trp Asn Glu Ser Thr His Tyr Gln Ile Leu Leu Thr Ser Phe Pro
                405                 410                 415
His Met Glu Asn His Ser Cys Phe Glu His Met His His Ile Pro Ala
            420                 425                 430
Pro Arg Pro Glu Glu Phe His Gln Arg Ser Asn Val Thr Leu Thr Leu
        435                 440                 445
Arg Asn Leu Lys Gly Cys Cys Arg His Gln Val Gln Ile Gln Pro Phe
    450                 455                 460
Phe Ser Ser Cys Leu Asn Asp Cys Leu Arg His Ser Ala Thr Val Ser
465                 470                 475                 480
Cys Pro Glu Met Pro Asp Thr Pro Glu Pro Ile Pro Asp Tyr Met Pro
                485                 490                 495
Leu Trp Glu Pro Lys Ser Ser Asp Lys Thr His Thr Cys Pro Pro Cys
            500                 505                 510
```

Pro Ala Pro Glu Ala Glu Gly Ala Pro Ser Val Phe Leu Phe Pro Pro
        515                 520                 525

Lys Pro Lys Asp Thr Leu Met Ile Ser Arg Thr Pro Glu Val Thr Cys
    530                 535                 540

Val Val Val Asp Val Ser His Glu Asp Pro Glu Val Lys Phe Asn Trp
545                 550                 555                 560

Tyr Val Asp Gly Val Glu Val His Asn Ala Lys Thr Lys Pro Arg Glu
                565                 570                 575

Glu Gln Tyr Asn Ser Thr Tyr Arg Val Val Ser Val Leu Thr Val Leu
            580                 585                 590

His Gln Asp Trp Leu Asn Gly Lys Glu Tyr Lys Cys Lys Val Ser Asn
        595                 600                 605

Lys Ala Leu Pro Ser Ser Ile Glu Lys Thr Ile Ser Lys Ala Lys Gly
    610                 615                 620

Gln Pro Arg Glu Pro Gln Val Tyr Thr Leu Pro Pro Ser Arg Asp Glu
625                 630                 635                 640

Leu Thr Lys Asn Gln Val Ser Leu Thr Cys Leu Val Lys Gly Phe Tyr
                645                 650                 655

Pro Ser Asp Ile Ala Val Glu Trp Glu Ser Asn Gly Gln Pro Glu Asn
            660                 665                 670

Asn Tyr Lys Thr Thr Pro Pro Val Leu Asp Ser Asp Gly Ser Phe Phe
        675                 680                 685

Leu Tyr Ser Lys Leu Thr Val Asp Lys Ser Arg Trp Gln Gln Gly Asn
    690                 695                 700

Val Phe Ser Cys Ser Val Met His Glu Ala Leu His Asn His Tyr Thr
705                 710                 715                 720

Gln Lys Ser Leu Ser Leu Ser Pro Gly Lys
                725                 730

<210> SEQ ID NO 143
<211> LENGTH: 2124
<212> TYPE: DNA
<213> ORGANISM: Artificial Sequence
<220> FEATURE:
<223> OTHER INFORMATION: IL-17RA signal sequence and exons 1-3 of
      IL-17RA and exons 4-16 of human IL-17RC  and Fc5

<400> SEQUENCE: 143

```
atgggggccg cacgcagccc gccgtccgct gtcccggggc ccctgctggg gctgctcctg      60
ctgctcctgg gcgtgctggc cccgggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttccccgtgg ctcacatcga atggacactg     300
cagacagacg ggcactggga agagcctgaa gatgaggaaa agtttggagg agcagctgac     360
tcaggggtgg aggagcctag gaatgcctct ctccaggccc aagtcgtgct ctccttccag     420
gcctaccccta ctgcccgctg cgtcctgctg gaggtgcaag tgcctgctgc ccttgtgcag     480
tttggtcagt ctgtgggctc tgtggtatat gactgcttcg aggctgccct agggagtgag     540
gtacgaatct ggtcctatac tcagcccagg tacgagaagg aactcaacca cacacagcag     600
ctgcctgact gcagggggct cgaagtctgg aattccatcc gagctgctg ggccctgccc     660
tggctcaacg tgtcagcaga tggtgacaac gtgcatctgg ttctgaatgt ctctgaggag     720
cagcacttcg gcctctccct gtactggaat caggtccagg gcccccaaa accccggtgg    780
```

```
cacaaaaacc tgactggacc gcagatcatt accttgaacc acacagacct ggttccctgc    840
ctctgtattc aggtgtggcc tctggaacct gactccgtta ggacgaacat ctgccccttc    900
agggaggacc cccgcgcaca ccagaacctc tggcaagccg cccgactgcg actgctgacc    960
ctgcagagct ggctgctgga cgcaccgtgc tcgctgcccg cagaagcggc actgtgctgg   1020
cgggctccgg gtgggaccc tgccagcca ctggtcccac cgctttcctg ggagaacgtc   1080
actgtggaca aggttctcga gttcccattg ctgaaaggcc accctaacct ctgtgttcag   1140
gtgaacagct cggagaagct gcagctgcag gagtgcttgt gggctgactc cctggggcct   1200
ctcaaagacg atgtgctact gttggagaca cgaggccccc aggacaacag atccctctgt   1260
gccttggaac ccagtggctg tacttcacta cccagcaaag cctccacgag ggcagctcgc   1320
cttggagagt acttactaca agacctgcag tcaggccagt gtctgcagct atgggacgat   1380
gacttgggag cgctatgggc ctgccccatg gacaaataca tccacaagga gcccaaatct   1440
tcagacaaaa ctcacacatg cccaccgtgc ccagcacctg aagccgaggg ggcaccgtca   1500
gtcttcctct tccccccaaa acccaaggac accctcatga tctcccggac ccctgaggtc   1560
acatgcgtgg tggtggacgt gagccacgaa gaccctgagg tcaagttcaa ctggtacgtg   1620
gacggcgtgg aggtgcataa tgccaagaca aagccgcggg aggagcagta caacagcacg   1680
taccgtgtgg tcagcgtcct caccgtcctg caccaggact ggctgaatgg caaggagtac   1740
aagtgcaagg tctccaacaa agccctccca tcctccatcg agaaaaccat ctccaaagcc   1800
aaagggcagc cccgagaacc acaggtgtac accctgcccc catcccggga tgagctgacc   1860
aagaaccagg tcagcctgac ctgcctggtc aaaggcttct atcccagcga catcgccgtg   1920
gagtgggaga gcaatgggca gccggagaac aactacaaga ccacgcctcc cgtgctggac   1980
tccgacggct ccttcttcct ctacagcaag ctcaccgtgg acaagagcag gtggcagcag   2040
gggaacgtct tctcatgctc cgtgatgcat gaggctctgc acaaccacta cacgcagaag   2100
agcctctccc tgtctccggg taaa                                          2124
```

<210> SEQ ID NO 144
<211> LENGTH: 708
<212> TYPE: PRT
<213> ORGANISM: Artificial Sequence
<220> FEATURE:
<223> OTHER INFORMATION: IL-17RA signal sequence and exons 1-3 of
      IL-17RA and exons 4-16 of human IL-17RC and Fc5

<400> SEQUENCE: 144

Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Gly His Trp Glu Pro Glu Asp Glu
            100                 105                 110

Glu Lys Phe Gly Gly Ala Ala Asp Ser Gly Val Glu Glu Pro Arg Asn
        115                 120                 125

-continued

```
Ala Ser Leu Gln Ala Gln Val Leu Ser Phe Gln Ala Tyr Pro Thr
    130                 135                 140
Ala Arg Cys Val Leu Leu Glu Val Gln Val Pro Ala Ala Leu Val Gln
145                 150                 155                 160
Phe Gly Gln Ser Val Gly Ser Val Val Tyr Asp Cys Phe Glu Ala Ala
                165                 170                 175
Leu Gly Ser Glu Val Arg Ile Trp Ser Tyr Thr Gln Pro Arg Tyr Glu
            180                 185                 190
Lys Glu Leu Asn His Thr Gln Gln Leu Pro Asp Cys Arg Gly Leu Glu
        195                 200                 205
Val Trp Asn Ser Ile Pro Ser Cys Trp Ala Leu Pro Trp Leu Asn Val
    210                 215                 220
Ser Ala Asp Gly Asp Asn Val His Leu Val Leu Asn Val Ser Glu Glu
225                 230                 235                 240
Gln His Phe Gly Leu Ser Leu Tyr Trp Asn Gln Val Gln Gly Pro Pro
                245                 250                 255
Lys Pro Arg Trp His Lys Asn Leu Thr Gly Pro Gln Ile Ile Thr Leu
            260                 265                 270
Asn His Thr Asp Leu Val Pro Cys Leu Cys Ile Gln Val Trp Pro Leu
        275                 280                 285
Glu Pro Asp Ser Val Arg Thr Asn Ile Cys Pro Phe Arg Glu Asp Pro
    290                 295                 300
Arg Ala His Gln Asn Leu Trp Gln Ala Ala Arg Leu Arg Leu Leu Thr
305                 310                 315                 320
Leu Gln Ser Trp Leu Leu Asp Ala Pro Cys Ser Leu Pro Ala Glu Ala
                325                 330                 335
Ala Leu Cys Trp Arg Ala Pro Gly Gly Asp Pro Cys Gln Pro Leu Val
            340                 345                 350
Pro Pro Leu Ser Trp Glu Asn Val Thr Val Asp Lys Val Leu Glu Phe
        355                 360                 365
Pro Leu Leu Lys Gly His Pro Asn Leu Cys Val Gln Val Asn Ser Ser
    370                 375                 380
Glu Lys Leu Gln Leu Gln Glu Cys Leu Trp Ala Asp Ser Leu Gly Pro
385                 390                 395                 400
Leu Lys Asp Asp Val Leu Leu Leu Glu Thr Arg Gly Pro Gln Asp Asn
                405                 410                 415
Arg Ser Leu Cys Ala Leu Glu Pro Ser Gly Cys Thr Ser Leu Pro Ser
            420                 425                 430
Lys Ala Ser Thr Arg Ala Ala Arg Leu Gly Glu Tyr Leu Leu Gln Asp
        435                 440                 445
Leu Gln Ser Gly Gln Cys Leu Gln Leu Trp Asp Asp Leu Gly Ala
    450                 455                 460
Leu Trp Ala Cys Pro Met Asp Lys Tyr Ile His Lys Glu Pro Lys Ser
465                 470                 475                 480
Ser Asp Lys Thr His Thr Cys Pro Cys Pro Ala Pro Glu Ala Glu
                485                 490                 495
Gly Ala Pro Ser Val Phe Leu Phe Pro Pro Lys Pro Lys Asp Thr Leu
            500                 505                 510
Met Ile Ser Arg Thr Pro Glu Val Thr Cys Val Val Val Asp Val Ser
        515                 520                 525
His Glu Asp Pro Glu Val Lys Phe Asn Trp Tyr Val Asp Gly Val Glu
    530                 535                 540
Val His Asn Ala Lys Thr Lys Pro Arg Glu Glu Gln Tyr Asn Ser Thr
```

-continued

```
                545              550              555              560
Tyr Arg Val Val Ser Val Leu Thr Val Leu His Gln Asp Trp Leu Asn
                    565              570              575
Gly Lys Glu Tyr Lys Cys Lys Val Ser Asn Lys Ala Leu Pro Ser Ser
                580              585              590
Ile Glu Lys Thr Ile Ser Lys Ala Lys Gly Gln Pro Arg Glu Pro Gln
            595              600              605
Val Tyr Thr Leu Pro Pro Ser Arg Asp Glu Leu Thr Lys Asn Gln Val
        610              615              620
Ser Leu Thr Cys Leu Val Lys Gly Phe Tyr Pro Ser Asp Ile Ala Val
625              630              635              640
Glu Trp Glu Ser Asn Gly Gln Pro Glu Asn Asn Tyr Lys Thr Thr Pro
                    645              650              655
Pro Val Leu Asp Ser Asp Gly Ser Phe Phe Leu Tyr Ser Lys Leu Thr
                660              665              670
Val Asp Lys Ser Arg Trp Gln Gln Gly Asn Val Phe Ser Cys Ser Val
            675              680              685
Met His Glu Ala Leu His Asn His Tyr Thr Gln Lys Ser Leu Ser Leu
        690              695              700
Ser Pro Gly Lys
705

<210> SEQ ID NO 145
<211> LENGTH: 2127
<212> TYPE: DNA
<213> ORGANISM: Artificial Sequence
<220> FEATURE:
<223> OTHER INFORMATION: IL-17RA signal sequence and exon 1 of IL-17RA
      and exons 2-16 of human IL-17RC and Fc5

<400> SEQUENCE: 145
atgggggccg cacgcagccc gccgtccgct gtcccggggc cctgctgggg gctgctcctg      60
ctgctcctgg gcgtgctggc cccggtggc gcctccctgc gactcctgga ccaccgggcg      120
ctggtctgct cccagccggg cctctcctgc cgcctctggg acagtgacat actctgcctg     180
cctggggaca tcgtgcctgc tccgggcccc gtgctggcgc tacgcacct gcagacagag      240 ctggtgctga ggtgccagaa ggagaccgac tgtgacctct gtctgcgtgt ggctgtccac     300
ttggccgtgc atgggcactg gaagagcct gaagatgagg aaaagtttgg aggagcagct     360
gactcagggg tggaggagcc taggaatgcc tctctccagg cccaagtcgt gctctccttc     420
caggcctacc ctactgcccg ctgcgtcctg ctggaggtgc aagtgcctgc tgcccttgtg     480
cagtttggtc agtctgtggg ctctgtggta tatgactgct cgaggctgc cctagggagt      540 gaggtacgaa tctggtccta tactcagccc aggtacgaga aggaactcaa ccacacacag     600
cagctgcctg actgcagggg gctcgaagtc tggaattcca tcccgagctg ctgggccctg     660
ccctggctca acgtgtcagc agatggtgac aacgtgcatc tggttctgaa tgtctctgag     720
gagcagcact tcggcctctc cctgtactgg aatcaggtcc agggcccccc aaaaccccgg     780
tggcacaaaa acctgactgg accgcagatc attaccttga accacacaga cctggttccc     840
tgcctctgta ttcaggtgtg gcctctggaa cctgactccg ttaggacgaa catctgcccc     900
ttcagggagg accccgcgc acaccagaac ctctggcaag ccgcccgact gcgactgctg     960
accctgcaga gctggctgct ggacgcaccg tgctcgctgc ccgcagaagc ggcactgtgc     1020
tggcgggctc cgggtgggga cccctgccag ccactggtcc caccgctttc ctgggagaac     1080
gtcactgtgg acaaggttct cgagttccca ttgctgaaag gccaccctaa cctctgtgtt     1140
```

```
caggtgaaca gctcggagaa gctgcagctg caggagtgct tgtgggctga ctccctgggg    1200
cctctcaaag acgatgtgct actgttggag acacgaggcc cccaggacaa cagatccctc    1260
tgtgccttgg aacccagtgg ctgtacttca ctacccagca aagcctccac gagggcagct    1320
cgccttggag agtacttact acaagacctg cagtcaggcc agtgtctgca gctatgggac    1380
gatgacttgg gagcgctatg ggcctgcccc atggacaaat acatccacaa ggagcccaaa    1440
tcttcagaca aaactcacac atgcccaccg tgcccagcac ctgaagccga gggggcaccg    1500
tcagtcttcc tcttcccccc aaaacccaag gacaccctca tgatctcccg gacccctgag    1560
gtcacatgcg tggtggtgga cgtgagccac gaagaccctg aggtcaagtt caactggtac    1620
gtggacggcg tggaggtgca taatgccaag acaaagccgc gggaggagca gtacaacagc    1680
acgtaccgtg tggtcagcgt cctcaccgtc ctgcaccagg actggctgaa tggcaaggag    1740
tacaagtgca aggtctccaa caaagccctc ccatcctcca tcgagaaaac catctccaaa    1800
gccaaagggc agccccgaga accacaggtg tacaccctgc ccccatcccg ggatgagctg    1860
accaagaacc aggtcagcct gacctgcctg gtcaaaggct tctatccag cgacatcgcc     1920 gtggagtggg agagcaatgg gcagccggag aacaactaca agaccacgcc tcccgtgctg    1980
gactccgacg gctccttctt cctctacagc aagctcaccg tggacaagag caggtggcag    2040
caggggaacg tcttctcatg ctccgtgatg catgaggctc tgcacaacca ctacacgcag    2100
aagagcctct ccctgtctcc gggtaaa                                        2127
```

<210> SEQ ID NO 146
<211> LENGTH: 709
<212> TYPE: PRT
<213> ORGANISM: Artificial Sequence
<220> FEATURE:
<223> OTHER INFORMATION: IL-17RA signal sequence and exon 1 of IL-17RA
      and exons 2-16 of human IL-17RC and Fc5

<400> SEQUENCE: 146

```
Met Gly Ala Ala Arg Ser Pro Pro Ser Ala Val Pro Gly Pro Leu Leu
 1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Ser Cys Arg Leu Trp Asp Ser Asp Ile Leu Cys Leu Pro Gly Asp Ile
    50                  55                  60

Val Pro Ala Pro Gly Pro Val Leu Ala Pro Thr His Leu Gln Thr Glu
65                  70                  75                  80

Leu Val Leu Arg Cys Gln Lys Glu Thr Asp Cys Asp Leu Cys Leu Arg
                85                  90                  95

Val Ala Val His Leu Ala Val His Gly His Trp Glu Glu Pro Glu Asp
            100                 105                 110

Glu Glu Lys Phe Gly Gly Ala Ala Asp Ser Gly Val Glu Glu Pro Arg
        115                 120                 125

Asn Ala Ser Leu Gln Ala Gln Val Val Leu Ser Phe Gln Ala Tyr Pro
    130                 135                 140

Thr Ala Arg Cys Val Leu Leu Glu Val Gln Val Pro Ala Ala Leu Val
145                 150                 155                 160

Gln Phe Gly Gln Ser Val Gly Ser Val Val Tyr Asp Cys Phe Glu Ala
                165                 170                 175

Ala Leu Gly Ser Glu Val Arg Ile Trp Ser Tyr Thr Gln Pro Arg Tyr
```

```
                    180                 185                 190
Glu Lys Glu Leu Asn His Thr Gln Gln Leu Pro Asp Cys Arg Gly Leu
            195                 200                 205
Glu Val Trp Asn Ser Ile Pro Ser Cys Trp Ala Leu Pro Trp Leu Asn
        210                 215                 220
Val Ser Ala Asp Gly Asp Asn Val His Leu Val Leu Asn Val Ser Glu
225                 230                 235                 240
Glu Gln His Phe Gly Leu Ser Leu Tyr Trp Asn Gln Val Gln Gly Pro
                245                 250                 255
Pro Lys Pro Arg Trp His Lys Asn Leu Thr Gly Pro Gln Ile Ile Thr
            260                 265                 270
Leu Asn His Thr Asp Leu Val Pro Cys Leu Cys Ile Gln Val Trp Pro
        275                 280                 285
Leu Glu Pro Asp Ser Val Arg Thr Asn Ile Cys Pro Phe Arg Glu Asp
290                 295                 300
Pro Arg Ala His Gln Asn Leu Trp Gln Ala Ala Arg Leu Arg Leu Leu
305                 310                 315                 320
Thr Leu Gln Ser Trp Leu Leu Asp Ala Pro Cys Ser Leu Pro Ala Glu
                325                 330                 335
Ala Ala Leu Cys Trp Arg Ala Pro Gly Gly Asp Pro Cys Gln Pro Leu
            340                 345                 350
Val Pro Pro Leu Ser Trp Glu Asn Val Thr Val Asp Lys Val Leu Glu
        355                 360                 365
Phe Pro Leu Leu Lys Gly His Pro Asn Leu Cys Val Gln Val Asn Ser
    370                 375                 380
Ser Glu Lys Leu Gln Leu Gln Glu Cys Leu Trp Ala Asp Ser Leu Gly
385                 390                 395                 400
Pro Leu Lys Asp Asp Val Leu Leu Leu Glu Thr Arg Gly Pro Gln Asp
                405                 410                 415
Asn Arg Ser Leu Cys Ala Leu Glu Pro Ser Gly Cys Thr Ser Leu Pro
            420                 425                 430
Ser Lys Ala Ser Thr Arg Ala Ala Arg Leu Gly Glu Tyr Leu Leu Gln
        435                 440                 445
Asp Leu Gln Ser Gly Gln Cys Leu Gln Leu Trp Asp Asp Asp Leu Gly
    450                 455                 460
Ala Leu Trp Ala Cys Pro Met Asp Lys Tyr Ile His Lys Glu Pro Lys
465                 470                 475                 480
Ser Ser Asp Lys Thr His Thr Cys Pro Pro Cys Pro Ala Pro Glu Ala
                485                 490                 495
Glu Gly Ala Pro Ser Val Phe Leu Phe Pro Pro Lys Pro Lys Asp Thr
            500                 505                 510
Leu Met Ile Ser Arg Thr Pro Glu Val Thr Cys Val Val Val Asp Val
        515                 520                 525
Ser His Glu Asp Pro Glu Val Lys Phe Asn Trp Tyr Val Asp Gly Val
    530                 535                 540
Glu Val His Asn Ala Lys Thr Lys Pro Arg Glu Glu Gln Tyr Asn Ser
545                 550                 555                 560
Thr Tyr Arg Val Val Ser Val Leu Thr Val Leu His Gln Asp Trp Leu
                565                 570                 575
Asn Gly Lys Glu Tyr Lys Cys Lys Val Ser Asn Lys Ala Leu Pro Ser
            580                 585                 590
Ser Ile Glu Lys Thr Ile Ser Lys Ala Lys Gly Gln Pro Arg Glu Pro
        595                 600                 605
```

```
Gln Val Tyr Thr Leu Pro Pro Ser Arg Asp Glu Leu Thr Lys Asn Gln
        610                 615                 620

Val Ser Leu Thr Cys Leu Val Lys Gly Phe Tyr Pro Ser Asp Ile Ala
625                 630                 635                 640

Val Glu Trp Glu Ser Asn Gly Gln Pro Glu Asn Asn Tyr Lys Thr Thr
                645                 650                 655

Pro Pro Val Leu Asp Ser Asp Gly Ser Phe Phe Leu Tyr Ser Lys Leu
            660                 665                 670

Thr Val Asp Lys Ser Arg Trp Gln Gln Gly Asn Val Phe Ser Cys Ser
            675                 680                 685

Val Met His Glu Ala Leu His Asn His Tyr Thr Gln Lys Ser Leu Ser
        690                 695                 700

Leu Ser Pro Gly Lys
705

<210> SEQ ID NO 147
<211> LENGTH: 2094
<212> TYPE: DNA
<213> ORGANISM: Artificial Sequence
<220> FEATURE:
<223> OTHER INFORMATION: IL-17RC signal sequence and exons 1-16 of
      IL-17RCx4 with Cys194Ser and Cys202Ser
      substitutions and exons 2-16 of human IL-17RC and
      Fc5

<400> SEQUENCE: 147
atgcctgtgc cctggttctt gctgtccttg gcactgggcc gaagcccagt ggtcctttct      60
ctggagaggc ttgtggggcc tcaggacgct acccactgct ctccgggcct ctcctgccgc     120
ctctgggaca gtgacatact ctgcctgcct ggggacatcg tgcctgctcc gggccccgtg     180
ctggcgccta cgcacctgca gacagagctg gtgctgaggt gccagaagga gaccgactgt     240
gacctctgtc tgcgtgtggc tgtccacttg gccgtgcatg gcactgggga agagcctgaa     300
gatgaggaaa agtttggagg agcagctgac tcaggggtgg aggagcctag gaatgcctct     360
ctccaggccc aagtcgtgct ctccttccag gcctaccctg ctgcccgctg cgtcctgctg     420
gaggtgcaag tgcctgctgc ccttgtgcag tttggtcagt ctgtgggctc tgtggtatat     480
gactgcttcg aggctgccct agggagtgag gtacgaatct ggtcctatac tcagcccagg     540
tacgagaagg aactcaacca cacacagcag ctgcctgact ccaggggggct cgaagtctgg     600 aattccatcc cgagctcctg ggccctgccc tggctcaacg tgtcagcaga tggtgacaac     660
gtgcatctgg ttctgaatgt ctctgaggag cagcacttcg cctctccct gtactggaat     720 caggtccagg gcccccaaa accccggtgg cacaaaaacc tgactggacc gcagatcatt     780
accttgaacc acacagacct ggttccctgc ctctgtattc aggtgtggcc tctggaacct     840
gactccgtta ggacgaacat ctgccccttc agggaggacc ccgcgcaca ccagaacctc     900 tggcaagccg cccgactgcg actgctgacc ctgcagagct ggctgctgga cgcaccgtgc     960
tcgctgcccg cagaagcggc actgtgctgg cgggctccgg gtgggaccc ctgccagcca    1020 ctggtcccac cgctttcctg ggagaacgtc actgtggaca aggttctcga gttcccattg    1080
ctgaaaggcc accctaacct ctgtgttcag gtgaacagct cggagaagct gcagctgcag    1140
gagtgcttgt gggctgactc cctggggcct tcaaagacg atgtgctact gttggagaca    1200
cgaggccccc aggacaacag atccctctgt gccttggaaa ccagtggctg tacttcacta    1260
cccagcaaag cctccacgag ggcagctcgc cttggagagt acttactaca agacctgcag    1320
tcaggccagt gtctgcagct atgggacgat gacttgggag cgctatgggc ctgccccatg    1380
```

```
gacaaataca tccacaagga gcccaaatct tcagacaaaa ctcacacatg cccaccgtgc    1440
ccagcacctg aagccgaggg ggcaccgtca gtcttcctct tccccccaaa acccaaggac    1500
accctcatga tctcccggac ccctgaggtc acatgcgtgg tggtggacgt gagccacgaa    1560
gaccctgagg tcaagttcaa ctggtacgtg gacggcgtgg aggtgcataa tgccaagaca    1620
aagccgcggg aggagcagta caacagcacg taccgtgtgg tcagcgtcct caccgtcctg    1680
caccaggact ggctgaatgg caaggagtac aagtgcaagg tctccaacaa agccctccca    1740
tcctccatcg agaaaaccat ctccaaagcc aagggcagc cccgagaacc acaggtgtac    1800
accctgcccc catcccggga tgagctgacc aagaaccagg tcagcctgac ctgcctggtc    1860
aaaggcttct atcccagcga catcgccgtg gagtgggaga gcaatgggca gccggagaac    1920
aactacaaga ccacgcctcc cgtgctggac tccgacggct ccttcttcct ctacagcaag    1980
ctcaccgtgg acaagagcag gtggcagcag gggaacgtct tctcatgctc cgtgatgcat    2040
gaggctctgc acaaccacta cacgcagaag agcctctccc tgtctccggg taaa         2094
```

<210> SEQ ID NO 148
<211> LENGTH: 698
<212> TYPE: PRT
<213> ORGANISM: Artificial Sequence
<220> FEATURE:
<223> OTHER INFORMATION: IL-17RC signal sequence and exons 1-16 of
      IL-17RCx4 with Cys194Ser and Cys202Ser
      substitutions and exons 2-16 of human IL-17RC and
      Fc5

<400> SEQUENCE: 148

```
Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30

Cys Ser Pro Gly Leu Ser Cys Arg Leu Trp Asp Ser Asp Ile Leu Cys
        35                  40                  45

Leu Pro Gly Asp Ile Val Pro Ala Pro Gly Pro Val Leu Ala Pro Thr
    50                  55                  60

His Leu Gln Thr Glu Leu Val Leu Arg Cys Gln Lys Glu Thr Asp Cys
65                  70                  75                  80

Asp Leu Cys Leu Arg Val Ala Val His Leu Ala Val His Gly His Trp
                85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Asp Ser Arg Gly Leu Glu Val Trp Asn Ser Ile Pro Ser Ser Trp Ala
        195                 200                 205

Leu Pro Trp Leu Asn Val Ser Ala Asp Gly Asp Asn Val His Leu Val
    210                 215                 220

Leu Asn Val Ser Glu Glu Gln His Phe Gly Leu Ser Leu Tyr Trp Asn
```

-continued

```
              225                 230                 235                 240
Gln Val Gln Gly Pro Pro Lys Pro Arg Trp His Lys Asn Leu Thr Gly
                245                 250                 255
Pro Gln Ile Ile Thr Leu Asn His Thr Asp Leu Val Pro Cys Leu Cys
                260                 265                 270
Ile Gln Val Trp Pro Leu Glu Pro Asp Ser Val Arg Thr Asn Ile Cys
                275                 280                 285
Pro Phe Arg Glu Asp Pro Arg Ala His Gln Asn Leu Trp Gln Ala Ala
        290                 295                 300
Arg Leu Arg Leu Leu Thr Leu Gln Ser Trp Leu Leu Asp Ala Pro Cys
305                 310                 315                 320
Ser Leu Pro Ala Glu Ala Ala Leu Cys Trp Arg Ala Pro Gly Gly Asp
                325                 330                 335
Pro Cys Gln Pro Leu Val Pro Leu Ser Trp Glu Asn Val Thr Val
                340                 345                 350
Asp Lys Val Leu Glu Phe Pro Leu Leu Lys Gly His Pro Asn Leu Cys
                355                 360                 365
Val Gln Val Asn Ser Ser Glu Lys Leu Gln Leu Gln Glu Cys Leu Trp
        370                 375                 380
Ala Asp Ser Leu Gly Pro Leu Lys Asp Val Leu Leu Leu Glu Thr
385                 390                 395                 400
Arg Gly Pro Gln Asp Asn Arg Ser Leu Cys Ala Leu Glu Pro Ser Gly
                405                 410                 415
Cys Thr Ser Leu Pro Ser Lys Ala Ser Thr Arg Ala Ala Arg Leu Gly
                420                 425                 430
Glu Tyr Leu Leu Gln Asp Leu Gln Ser Gly Gln Cys Leu Gln Leu Trp
        435                 440                 445
Asp Asp Asp Leu Gly Ala Leu Trp Ala Cys Pro Met Asp Lys Tyr Ile
        450                 455                 460
His Lys Glu Pro Lys Ser Ser Asp Lys Thr His Thr Cys Pro Pro Cys
465                 470                 475                 480
Pro Ala Pro Glu Ala Glu Gly Ala Pro Ser Val Phe Leu Phe Pro Pro
                485                 490                 495
Lys Pro Lys Asp Thr Leu Met Ile Ser Arg Thr Pro Glu Val Thr Cys
                500                 505                 510
Val Val Val Asp Val Ser His Glu Asp Pro Glu Val Lys Phe Asn Trp
        515                 520                 525
Tyr Val Asp Gly Val Glu Val His Asn Ala Lys Thr Lys Pro Arg Glu
        530                 535                 540
Glu Gln Tyr Asn Ser Thr Tyr Arg Val Val Ser Val Leu Thr Val Leu
545                 550                 555                 560
His Gln Asp Trp Leu Asn Gly Lys Glu Tyr Lys Cys Lys Val Ser Asn
                565                 570                 575
Lys Ala Leu Pro Ser Ser Ile Glu Lys Thr Ile Ser Lys Ala Lys Gly
                580                 585                 590
Gln Pro Arg Glu Pro Gln Val Tyr Thr Leu Pro Pro Ser Arg Asp Glu
        595                 600                 605
Leu Thr Lys Asn Gln Val Ser Leu Thr Cys Leu Val Lys Gly Phe Tyr
        610                 615                 620
Pro Ser Asp Ile Ala Val Glu Trp Glu Ser Asn Gly Gln Pro Glu Asn
625                 630                 635                 640
Asn Tyr Lys Thr Thr Pro Pro Val Leu Asp Ser Asp Gly Ser Phe Phe
                645                 650                 655
```

```
Leu Tyr Ser Lys Leu Thr Val Asp Lys Ser Arg Trp Gln Gln Gly Asn
            660                 665                 670

Val Phe Ser Cys Ser Val Met His Glu Ala Leu His Asn His Tyr Thr
        675                 680                 685

Gln Lys Ser Leu Ser Leu Ser Pro Gly Lys
        690                 695

<210> SEQ ID NO 149
<211> LENGTH: 2061
<212> TYPE: DNA
<213> ORGANISM: Artificial Sequence
<220> FEATURE:
<223> OTHER INFORMATION: IL-17RC signal sequence and exons 1-6 and 8-16
      of IL-17RC with GlyGlyGlySer linker between exons 6
      and 8, and Fc5

<400> SEQUENCE: 149
atgcctgtgc cctggttctt gctgtccttg gcactgggcc gaagcccagt ggtcctttct     60
ctggagaggc ttgtggggcc tcaggacgct acccactgct ctccgggcct cctgccgcc    120
ctctgggaca gtgacatact ctgcctgcct ggggacatcg tgcctgctcc gggccccgtg    180
ctggcgccta cgcacctgca gacagagctg gtgctgaggt gccagaagga gaccgactgt    240
gacctctgtc tgcgtgtggc tgtccacttg gccgtgcatg gcactgggga gagcctgaa    300
gatgaggaaa agtttggagg agcagctgac tcaggggtgg aggagcctag gaatgcctct    360
ctccaggccc aagtcgtgct ctccttccag gcctacccta ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctggag aggatccgc cctgccctgg    600
ctcaacgtgt cagcagatgg tgacaacgtg catctggttc tgaatgtctc tgaggagcag    660
cacttcggcc tctccctgta ctggaatcag gtccagggcc cccaaaaacc ccggtggcac    720
aaaaacctga ctggaccgca gatcattacc ttgaaccaca cagacctggt tccctgcctc    780
tgtattcagg tgtggcctct ggaacctgac tccgttagga cgaacatctg ccccttcagg    840
gaggaccccc gcgcacacca gaacctctgg caagccgccc gactgcgact gctgaccctg    900
cagagctggc tgctggacgc accgtgctcg ctgcccgcag aagcggcact gtgctggcgg    960
gctccgggtg gggaccccct gccagccactg gtcccaccgc tttcctggga acgtcact   1020
gtggacaagg ttctcgagtt cccattgctg aaaggccacc ctaacctctg tgttcaggtg   1080
aacagctcgg agaagctgca gctgcaggag tgcttgtggg ctgactccct ggggcctctc   1140
aaagacgatg tgctactgtt ggagacacga ggccccagg acaacagatc cctctgtgcc   1200
ttggaaccca gtggctgtac ttcactaccc agcaaagcct ccacgagggc agctcgcctt   1260
ggagagtact tactacaaga cctgcagtca ggccagtgtc tgcagctatg ggacgatgac   1320
ttgggagcgc tatgggcctg ccccatggac aaatacatcc acaaggagcc caaatcttca   1380
gacaaaactc acacatgccc accgtgccca gcacctgaag ccgaggggc accgtcagtc   1440
ttcctcttcc cccaaaaacc caaggacacc ctcatgatct cccggacccc tgaggtcaca   1500
tgcgtggtgg tggacgtgag ccacgaagac cctgaggtca agttcaactg gtacgtggac   1560
ggcgtggagg tgcataatgc caagacaaag ccgcgggagg agcagtacaa cagcacgtac   1620
cgtgtggtca gcgtcctcac cgtcctgcac caggactggc tgaatggcaa ggagtacaag   1680
tgcaaggtct ccaacaaagc cctcccatcc tccatcgaga aaccatctc caaagccaaa   1740
gggcagcccc gagaaccaca ggtgtacacc ctgcccccat cccgggatga gctgaccaag   1800
```

-continued

```
aaccaggtca gcctgacctg cctggtcaaa ggcttctatc ccagcgacat cgccgtggag    1860
tgggagagca atgggcagcc ggagaacaac tacaagacca cgcctcccgt gctggactcc    1920
gacggctcct tcttcctcta cagcaagctc accgtggaca gagcaggtg gcagcagggg     1980 aacgtcttct catgctccgt gatgcatgag gctctgcaca accactacac gcagaagagc    2040
ctctccctgt ctccgggtaa a                                              2061
```

<210> SEQ ID NO 150
<211> LENGTH: 687
<212> TYPE: PRT
<213> ORGANISM: Artificial Sequence
<220> FEATURE:
<223> OTHER INFORMATION: IL-17RC signal sequence and exons 1-6 and 8-16 of IL-17RC with GlyGlyGlySer linker between exons 6 and 8, and Fc5

<400> SEQUENCE: 150

```
Met Pro Val Pro Trp Phe Leu Leu Ser Leu Ala Leu Gly Arg Ser Pro
  1               5                  10                  15

Val Val Leu Ser Leu Glu Arg Leu Val Gly Pro Gln Asp Ala Thr His
             20                  25                  30

Cys Ser Pro Gly Leu Ser Cys Arg Leu Trp Asp Ser Asp Ile Leu Cys
         35                  40                  45

Leu Pro Gly Asp Ile Val Pro Ala Pro Gly Pro Val Leu Ala Pro Thr
     50                  55                  60

His Leu Gln Thr Glu Leu Val Leu Arg Cys Gln Lys Glu Thr Asp Cys
 65                  70                  75                  80

Asp Leu Cys Leu Arg Val Ala Val His Leu Ala Val His Gly His Trp
                 85                  90                  95

Glu Glu Pro Glu Asp Glu Glu Lys Phe Gly Gly Ala Ala Asp Ser Gly
            100                 105                 110

Val Glu Glu Pro Arg Asn Ala Ser Leu Gln Ala Gln Val Val Leu Ser
        115                 120                 125

Phe Gln Ala Tyr Pro Thr Ala Arg Cys Val Leu Leu Glu Val Gln Val
    130                 135                 140

Pro Ala Ala Leu Val Gln Phe Gly Gln Ser Val Gly Ser Val Val Tyr
145                 150                 155                 160

Asp Cys Phe Glu Ala Ala Leu Gly Ser Glu Val Arg Ile Trp Ser Tyr
                165                 170                 175

Thr Gln Pro Arg Tyr Glu Lys Glu Leu Asn His Thr Gln Gln Leu Pro
            180                 185                 190

Gly Gly Gly Ser Ala Leu Pro Trp Leu Asn Val Ser Ala Asp Gly Asp
        195                 200                 205

Asn Val His Leu Val Leu Asn Val Ser Glu Glu Gln His Phe Gly Leu
    210                 215                 220

Ser Leu Tyr Trp Asn Gln Val Gln Gly Pro Pro Lys Pro Arg Trp His
225                 230                 235                 240

Lys Asn Leu Thr Gly Pro Gln Ile Ile Thr Leu Asn His Thr Asp Leu
                245                 250                 255

Val Pro Cys Leu Cys Ile Gln Val Trp Pro Leu Glu Pro Asp Ser Val
            260                 265                 270

Arg Thr Asn Ile Cys Pro Phe Arg Glu Asp Pro Arg Ala His Gln Asn
        275                 280                 285

Leu Trp Gln Ala Ala Arg Leu Arg Leu Leu Thr Leu Gln Ser Trp Leu
    290                 295                 300
```

Leu Asp Ala Pro Cys Ser Leu Pro Ala Glu Ala Leu Cys Trp Arg
305                 310                 315                 320

Ala Pro Gly Gly Asp Pro Cys Gln Pro Leu Val Pro Leu Ser Trp
            325                 330                 335

Glu Asn Val Thr Val Asp Lys Val Leu Glu Phe Pro Leu Leu Lys Gly
                340                 345                 350

His Pro Asn Leu Cys Val Gln Val Asn Ser Ser Glu Lys Leu Gln Leu
            355                 360                 365

Gln Glu Cys Leu Trp Ala Asp Ser Leu Gly Pro Leu Lys Asp Asp Val
370                 375                 380

Leu Leu Leu Glu Thr Arg Gly Pro Gln Asp Asn Arg Ser Leu Cys Ala
385                 390                 395                 400

Leu Glu Pro Ser Gly Cys Thr Ser Leu Pro Ser Lys Ala Ser Thr Arg
                405                 410                 415

Ala Ala Arg Leu Gly Glu Tyr Leu Leu Gln Asp Leu Gln Ser Gly Gln
            420                 425                 430

Cys Leu Gln Leu Trp Asp Asp Asp Leu Gly Ala Leu Trp Ala Cys Pro
435                 440                 445

Met Asp Lys Tyr Ile His Lys Glu Pro Lys Ser Ser Asp Lys Thr His
450                 455                 460

Thr Cys Pro Pro Cys Pro Ala Pro Glu Ala Glu Gly Ala Pro Ser Val
465                 470                 475                 480

Phe Leu Phe Pro Pro Lys Pro Lys Asp Thr Leu Met Ile Ser Arg Thr
                485                 490                 495

Pro Glu Val Thr Cys Val Val Val Asp Val Ser His Glu Asp Pro Glu
            500                 505                 510

Val Lys Phe Asn Trp Tyr Val Asp Gly Val Glu Val His Asn Ala Lys
            515                 520                 525

Thr Lys Pro Arg Glu Glu Gln Tyr Asn Ser Thr Tyr Arg Val Val Ser
530                 535                 540

Val Leu Thr Val Leu His Gln Asp Trp Leu Asn Gly Lys Glu Tyr Lys
545                 550                 555                 560

Cys Lys Val Ser Asn Lys Ala Leu Pro Ser Ser Ile Glu Lys Thr Ile
                565                 570                 575

Ser Lys Ala Lys Gly Gln Pro Arg Glu Pro Gln Val Tyr Thr Leu Pro
            580                 585                 590

Pro Ser Arg Asp Glu Leu Thr Lys Asn Gln Val Ser Leu Thr Cys Leu
            595                 600                 605

Val Lys Gly Phe Tyr Pro Ser Asp Ile Ala Val Glu Trp Glu Ser Asn
610                 615                 620

Gly Gln Pro Glu Asn Asn Tyr Lys Thr Thr Pro Pro Val Leu Asp Ser
625                 630                 635                 640

Asp Gly Ser Phe Phe Leu Tyr Ser Lys Leu Thr Val Asp Lys Ser Arg
                645                 650                 655

Trp Gln Gln Gly Asn Val Phe Ser Cys Ser Val Met His Glu Ala Leu
            660                 665                 670

His Asn His Tyr Thr Gln Lys Ser Leu Ser Leu Ser Pro Gly Lys
            675                 680                 685

<210> SEQ ID NO 151
<211> LENGTH: 2094
<212> TYPE: DNA
<213> ORGANISM: Artificial Sequence
<220> FEATURE:
<223> OTHER INFORMATION: otPA pre-pro signal sequence and exons 1-6 and
      8-16 of IL-17RC with a Leu21Ala substitution, and Fc5

<400> SEQUENCE: 151

| | | | | | |
|---|---|---|---|---|---|
| atggatgcaa | tgaagagagg | gctctgctgt | gtgctgctgc | tgtgtggcgc | cgtcttcgtt | 60 |
| tcgctcagcc | aggaaatcca | tgccgagttg | agacgcttcc | gtagagcaga | gaggcttgtg | 120 |
| gggcctcagg | acgctaccca | ctgctctccg | ggcctctcct | gccgcctctg | ggacagtgac | 180 |
| atactctgcc | tgcctgggga | catcgtgcct | gctccgggcc | ccgtgctggc | gcctacgcac | 240 |
| ctgcagacag | agctggtgct | gaggtgccag | aaggagaccg | actgtgacct | ctgtctgcgt | 300 |
| gtggctgtcc | acttggccgt | gcatgggcac | tgggaagagc | ctgaagatga | ggaaaagttt | 360 |
| ggaggagcag | ctgactcagg | ggtggaggag | cctaggaatg | cctctctcca | ggcccaagtc | 420 |
| gtgctctcct | tccaggccta | ccctactgcc | cgctgcgtcc | tgctggaggt | gcaagtgcct | 480 |
| gctgcccttg | tgcagtttgg | tcagtctgtg | ggctctgtgg | tatatgactg | cttcgaggct | 540 |
| gccctaggga | gtgaggtacg | aatctggtcc | tatactcagc | caggtacga | gaaggaactc | 600 |
| aaccacacac | agcagctgcc | tgccctgccc | tggctcaacg | tgtcagcaga | tggtgacaac | 660 |
| gtgcatctgg | ttctgaatgt | ctctgaggag | cagcacttcg | gcctctccct | gtactggaat | 720 |
| caggtccagg | gcccccaaa | accccgtgg | cacaaaaacc | tgactggacc | gcagatcatt | 780 |
| accttgaacc | acacagacct | ggttccctgc | ctctgtattc | aggtgtggcc | tctgaacct | 840 |
| gactccgtta | ggacgaacat | ctgccccttc | agggaggacc | cccgcgcaca | ccagaacctc | 900 |
| tggcaagccg | cccgactgcg | actgctgacc | ctgcagagct | ggctgctgga | cgcaccgtgc | 960 |
| tcgctgcccg | cagaagcggc | actgtgctgg | cgggctccgg | gtggggaccc | ctgccagcca | 1020 |
| ctggtcccac | cgctttcctg | ggagaacgtc | actgtggaca | aggttctcga | gttcccattg | 1080 |
| ctgaaaggcc | accctaacct | ctgtgttcag | gtgaacagct | cggagaagct | gcagctgcag | 1140 |
| gagtgcttgt | gggctgactc | cctggggcct | ctcaaagacg | atgtgctact | gttggagaca | 1200 |
| cgaggccccc | aggacaacag | atccctctgt | gccttggaac | ccagtggctg | tacttcacta | 1260 |
| cccagcaaag | cctccacgag | ggcagctcgc | cttggagagt | acttactaca | agacctgcag | 1320 |
| tcaggccagt | gtctgcagct | atgggacgat | gacttgggag | cgctatgggc | ctgccccatg | 1380 |
| gacaaataca | tccacaagga | gcccaaatct | tcagacaaaa | ctcacacatg | cccaccgtgc | 1440 |
| ccagcacctg | aagccgaggg | ggcaccgtca | gtcttcctct | tccccccaaa | acccaaggac | 1500 |
| accctcatga | tctcccggac | ccctgaggtc | acatgcgtgg | tggtggacgt | gagccacgaa | 1560 |
| gaccctgagg | tcaagttcaa | ctggtacgtg | gacggcgtgg | aggtgcataa | tgccaagaca | 1620 |
| aagccgcggg | aggagcagta | caacagcacg | taccgtgtgg | tcagcgtcct | caccgtcctg | 1680 |
| caccaggact | ggctgaatgg | caaggagtac | aagtgcaagg | tctccaacaa | agccctccca | 1740 |
| tcctccatcg | agaaaaccat | ctccaaagcc | aaagggcagc | cccgagaacc | acaggtgtac | 1800 |
| accctgcccc | catcccggga | tgagctgacc | aagaaccagg | tcagcctgac | ctgcctggtc | 1860 |
| aaaggcttct | atcccagcga | catcgccgtg | gagtgggaga | gcaatgggca | gccggagaac | 1920 |
| aactacaaga | ccacgcctcc | cgtgctggac | tccgacggct | ccttcttcct | ctacagcaag | 1980 |
| ctcaccgtgg | acaagagcag | gtggcagcag | gggaacgtct | tctcatgctc | cgtgatgcat | 2040 |
| gaggctctgc | acaaccacta | cacgcagaag | agcctctccc | tgtctccggg | taaa | 2094 |

<210> SEQ ID NO 152
<211> LENGTH: 698
<212> TYPE: PRT
<213> ORGANISM: Artificial Sequence
<220> FEATURE:

<223> OTHER INFORMATION: otPA pre-pro signal sequence and exons 1-6 and
      8-16 of IL-17RC with a Leu21Ala substitution, and
      Fc5

<400> SEQUENCE: 152

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
             20                  25                  30

Phe Arg Arg Ala Glu Arg Leu Val Gly Pro Gln Asp Ala Thr His Cys
         35                  40                  45

Ser Pro Gly Leu Ser Cys Arg Leu Trp Asp Ser Asp Ile Leu Cys Leu
 50                  55                  60

Pro Gly Asp Ile Val Pro Ala Pro Gly Pro Val Leu Ala Pro Thr His
 65                  70                  75                  80

Leu Gln Thr Glu Leu Val Leu Arg Cys Gln Lys Glu Thr Asp Cys Asp
                 85                  90                  95

Leu Cys Leu Arg Val Ala Val His Leu Ala Val His Gly His Trp Glu
            100                 105                 110

Glu Pro Glu Asp Glu Glu Lys Phe Gly Gly Ala Ala Asp Ser Gly Val
        115                 120                 125

Glu Glu Pro Arg Asn Ala Ser Leu Gln Ala Gln Val Val Leu Ser Phe
130                 135                 140

Gln Ala Tyr Pro Thr Ala Arg Cys Val Leu Leu Glu Val Gln Val Pro
145                 150                 155                 160

Ala Ala Leu Val Gln Phe Gly Gln Ser Val Gly Ser Val Val Tyr Asp
                165                 170                 175

Cys Phe Glu Ala Ala Leu Gly Ser Glu Val Arg Ile Trp Ser Tyr Thr
            180                 185                 190

Gln Pro Arg Tyr Glu Lys Glu Leu Asn His Thr Gln Gln Leu Pro Ala
        195                 200                 205

Leu Pro Trp Leu Asn Val Ser Ala Asp Gly Asp Asn Val His Leu Val
210                 215                 220

Leu Asn Val Ser Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
        275                 280                 285

Pro Phe Arg Glu Asp Pro Arg Ala His Gln Asn Leu Trp Gln Ala Ala
290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
        355                 360                 365

Val Gln Val Asn Ser Ser Glu Lys Leu Gln Leu Gln Glu Cys Leu Trp
370                 375                 380

Ala Asp Ser Leu Gly Pro Leu Lys Asp Asp Val Leu Leu Leu Glu Thr
385                 390                 395                 400
```

```
Arg Gly Pro Gln Asp Asn Arg Ser Leu Cys Ala Leu Glu Pro Ser Gly
            405                 410                 415

Cys Thr Ser Leu Pro Ser Lys Ala Ser Thr Arg Ala Ala Arg Leu Gly
            420                 425                 430

Glu Tyr Leu Leu Gln Asp Leu Gln Ser Gly Gln Cys Leu Gln Leu Trp
            435                 440                 445

Asp Asp Asp Leu Gly Ala Leu Trp Ala Cys Pro Met Asp Lys Tyr Ile
            450                 455                 460

His Lys Glu Pro Lys Ser Ser Asp Lys Thr His Thr Cys Pro Pro Cys
465                 470                 475                 480

Pro Ala Pro Glu Ala Glu Gly Ala Pro Ser Val Phe Leu Phe Pro Pro
                485                 490                 495

Lys Pro Lys Asp Thr Leu Met Ile Ser Arg Thr Pro Glu Val Thr Cys
            500                 505                 510

Val Val Val Asp Val Ser His Glu Asp Pro Glu Val Lys Phe Asn Trp
            515                 520                 525

Tyr Val Asp Gly Val Glu Val His Asn Ala Lys Thr Lys Pro Arg Glu
            530                 535                 540

Glu Gln Tyr Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
                565                 570                 575

Lys Ala Leu Pro Ser Ser Ile Glu Lys Thr Ile Ser Lys Ala Lys Gly
            580                 585                 590

Gln Pro Arg Glu Pro Gln Val Tyr Thr Leu Pro Pro Ser Arg Asp Glu
            595                 600                 605

Leu Thr Lys Asn Gln Val Ser Leu Thr Cys Leu Val Lys Gly Phe Tyr
            610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
                645                 650                 655

Leu Tyr Ser Lys Leu Thr Val Asp Lys Ser Arg Trp Gln Gln Gly Asn
            660                 665                 670

Val Phe Ser Cys Ser Val Met His Glu Ala Leu His Asn His Tyr Thr
            675                 680                 685

Gln Lys Ser Leu Ser Leu Ser Pro Gly Lys
            690                 695

<210> SEQ ID NO 153
<211> LENGTH: 2097
<212> TYPE: DNA
<213> ORGANISM: Artificial Sequence
<220> FEATURE:
<223> OTHER INFORMATION: Exons 1-6 and 8-16 of IL17RC with Ser215Thr and
      Ser228Thr substitutions

<400> SEQUENCE: 153
atggatgcaa tgaagagagg gctctgctgt gtgctgctgc tgtgtggcgc cgtcttcgtt      60
tcgctcagcc aggaaatcca tgccgagttg agacgcttcc gtagactgga gaggcttgtg     120
gggcctcagg acgctaccca ctgctctccg ggcctctcct gccgcctctg ggacagtgac     180
atactctgcc tgcctgggga catcgtgcct gctccgggcc ccgtgctggc gcctacgcac     240
ctgcagacag agctggtgct gaggtgccag aaggagaccg actgtgacct ctgtctgcgt     300
gtggctgtcc acttggccgt gcatgggcac tgggaagagc ctgaagatga ggaaaagttt     360
```

```
ggaggagcag ctgactcagg ggtggaggag cctaggaatg cctctctcca ggcccaagtc    420
gtgctctcct tccaggccta ccctactgcc cgctgcgtcc tgctggaggt gcaagtgcct    480 gctgccttg tgcagtttgg tcagtctgtg ggctctgtgg tatatgactg cttcgaggct    540
gccctaggga gtgaggtacg aatctggtcc tatactcagc ccaggtacga aaggaactc    600 aaccacacac agcagctgcc tgccctgccc tggctcaacg tgacagcaga tggtgacaac    660
gtgcatctgg ttctgaatgt cacagaggag cagcacttcg gcctctccct gtactggaat    720
caggtccagg gccccccaaa accccggtgg cacaaaaacc tgactggacc gcagatcatt    780
accttgaacc acacagacct ggttccctgc ctctgtattc aggtgtggcc tctggaacct    840
gactccgtta ggacgaacat ctgccccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtgggacccc tgccagcca   1020 ctggtcccac cgctttcctg ggagaacgtc actgtggaca aggttctcga gttcccattg   1080
ctgaaaggcc accctaacct ctgtgttcag gtgaacagct cggagaagct gcagctgcag   1140
gagtgcttgt gggctgactc cctggggcct tcaaagacg atgtgctact gttgagaca   1200 cgaggccccc aggacaacag atccctctgt gccttggaac ccagtggctg tacttcacta   1260
cccagcaaag cctccacgag ggcagctcgc cttgagagt acttactaca agacctgcag   1320
tcaggccagt gtctgcagct atgggacgat gacttgggag cgctatgggc ctgccccatg   1380
gacaaataca tccacaagga gcccaaatct tcagacaaaa ctcacacatg cccaccgtgc   1440
ccagcacctg aagccgaggg ggcaccgtca gtcttcctct tccccccaaa acccaaggac   1500
accctcatga tctcccggac ccctgaggtc acatgcgtgg tggtggacgt gagccacgaa   1560
gaccctgagg tcaagttcaa ctggtacgtg gacggcgtgg aggtgcataa tgccaagaca   1620
aagccgcggg aggagcagta caacagcacg taccgtgtgg tcagcgtcct caccgtcctg   1680
caccaggact ggctgaatgg caaggagtac aagtgcaagg tctccaacaa agccctccca   1740
tcctccatcg agaaaaccat ctccaaagcc aagggcagc cccgagaacc acaggtgtac   1800
accctgcccc catcccggga tgagctgacc aagaaccagg tcagcctgac ctgcctggtc   1860
aaaggcttct atcccagcga catcgccgtg gagtgggaga gcaatgggca gccggagaac   1920
aactacaaga ccacgcctcc cgtgctggac tccgacggct ccttcttcct ctacagcaag   1980
ctcaccgtgg acaagagcag gtggcagcag gggaacgtct tctcatgctc cgtgatgcat   2040
gaggctctgc acaaccacta cacgcagaag agcctctccc tgtctccggg taaatga     2097
```

<210> SEQ ID NO 154
<211> LENGTH: 698
<212> TYPE: PRT
<213> ORGANISM: Artificial Sequence
<220> FEATURE:
<223> OTHER INFORMATION: Exons 1-6 and 8-16 of IL17RC with Ser215Thr and Ser228Thr substitutions and Fc5

<400> SEQUENCE: 154

```
Met Asp Ala Met Lys Arg Gly Leu Cys Cys Val Leu Leu Leu Cys Gly
1               5                   10                  15

Ala Val Phe Val Ser Leu Ser Gln Glu Ile His Ala Glu Leu Arg Arg
            20                  25                  30

Phe Arg Arg Leu Glu Arg Leu Val Gly Pro Gln Asp Ala Thr His Cys
        35                  40                  45

Ser Pro Gly Leu Ser Cys Arg Leu Trp Asp Ser Asp Ile Leu Cys Leu
```

```
                50                    55                    60
Pro Gly Asp Ile Val Pro Ala Pro Gly Pro Val Leu Ala Pro Thr His
65                  70                  75                  80

Leu Gln Thr Glu Leu Val Leu Arg Cys Gln Lys Glu Thr Asp Cys Asp
                    85                  90                  95

Leu Cys Leu Arg Val Ala Val His Leu Ala Val His Gly His Trp Glu
                100                 105                 110

Glu Pro Glu Asp Glu Glu Lys Phe Gly Gly Ala Ala Asp Ser Gly Val
                115                 120                 125

Glu Glu Pro Arg Asn Ala Ser Leu Gln Ala Gln Val Val Leu Ser Phe
130                 135                 140

Gln Ala Tyr Pro Thr Ala Arg Cys Val Leu Glu Val Gln Val Pro
145                 150                 155                 160

Ala Ala Leu Val Gln Phe Gly Gln Ser Val Gly Ser Val Val Tyr Asp
                165                 170                 175

Cys Phe Glu Ala Ala Leu Gly Ser Glu Val Arg Ile Trp Ser Tyr Thr
                180                 185                 190

Gln Pro Arg Tyr Glu Lys Glu Leu Asn His Thr Gln Gln Leu Pro Ala
                195                 200                 205

Leu Pro Trp Leu Asn Val Thr Ala Asp Gly Asp Asn Val His Leu Val
210                 215                 220

Leu Asn Val Thr Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
                260                 265                 270

Ile Gln Val Trp Pro Leu Glu Pro Asp Ser Val Arg Thr Asn Ile Cys
                275                 280                 285

Pro Phe Arg Glu Asp Pro Arg Ala His Gln Asn Leu Trp Gln Ala Ala
                290                 295                 300

Arg Leu Arg Leu Leu Thr Leu Gln Ser Trp Leu Leu Asp Ala Pro Cys
305                 310                 315                 320

Ser Leu Pro Ala Glu Ala Ala Leu Cys Trp Arg Ala Pro Gly Gly Asp
                325                 330                 335

Pro Cys Gln Pro Leu Val Pro Pro Leu Ser Trp Glu Asn Val Thr Val
                340                 345                 350

Asp Lys Val Leu Glu Phe Pro Leu Leu Lys Gly His Pro Asn Leu Cys
                355                 360                 365

Val Gln Val Asn Ser Ser Glu Lys Leu Gln Leu Gln Glu Cys Leu Trp
370                 375                 380

Ala Asp Ser Leu Gly Pro Leu Lys Asp Val Leu Leu Leu Glu Thr
385                 390                 395                 400

Arg Gly Pro Gln Asp Asn Arg Ser Leu Cys Ala Leu Glu Pro Ser Gly
                405                 410                 415

Cys Thr Ser Leu Pro Ser Lys Ala Ser Thr Arg Ala Ala Arg Leu Gly
                420                 425                 430

Glu Tyr Leu Leu Gln Asp Leu Gln Ser Gly Gln Cys Leu Gln Leu Trp
                435                 440                 445

Asp Asp Asp Leu Gly Ala Leu Trp Ala Cys Pro Met Asp Lys Tyr Ile
                450                 455                 460

His Lys Glu Pro Lys Ser Ser Asp Lys Thr His Thr Cys Pro Pro Cys
465                 470                 475                 480
```

```
Pro Ala Pro Glu Ala Glu Gly Ala Pro Ser Val Phe Leu Phe Pro Pro
            485                 490                 495

Lys Pro Lys Asp Thr Leu Met Ile Ser Arg Thr Pro Glu Val Thr Cys
        500                 505                 510

Val Val Val Asp Val Ser His Glu Asp Pro Glu Val Lys Phe Asn Trp
    515                 520                 525

Tyr Val Asp Gly Val Glu Val His Asn Ala Lys Thr Lys Pro Arg Glu
530                 535                 540

Glu Gln Tyr Asn Ser Thr Tyr Arg Val Val Ser Val Leu Thr Val Leu
545                 550                 555                 560

His Gln Asp Trp Leu Asn Gly Lys Glu Tyr Lys Cys Lys Val Ser Asn
                565                 570                 575

Lys Ala Leu Pro Ser Ser Ile Glu Lys Thr Ile Ser Lys Ala Lys Gly
            580                 585                 590

Gln Pro Arg Glu Pro Gln Val Tyr Thr Leu Pro Pro Ser Arg Asp Glu
        595                 600                 605

Leu Thr Lys Asn Gln Val Ser Leu Thr Cys Leu Val Lys Gly Phe Tyr
    610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
                645                 650                 655

Leu Tyr Ser Lys Leu Thr Val Asp Lys Ser Arg Trp Gln Gln Gly Asn
            660                 665                 670

Val Phe Ser Cys Ser Val Met His Glu Ala Leu His Asn His Tyr Thr
        675                 680                 685

Gln Lys Ser Leu Ser Leu Ser Pro Gly Lys
    690                 695

<210> SEQ ID NO 155
<211> LENGTH: 2094
<212> TYPE: DNA
<213> ORGANISM: Artificial Sequence
<220> FEATURE:
<223> OTHER INFORMATION: Exons 1-6 and 8-16 of IL17RC with Ser to Thr
      substitutions and at residues 120, 215, 228, 374,
      and 408 and Fc5

<400> SEQUENCE: 155
atggatgcaa tgaagagagg gctctgctgt gtgctgctgc tgtgtggcgc cgtcttcgtt      60
tcgctcagcc aggaaatcca tgccgagttg agacgcttcc gtagactgga gaggcttgtg     120
gggcctcagg acgctaccca ctgctctccg ggcctctcct gccgcctctg ggacagtgac     180
atactctgcc tgcctgggga catcgtgcct gctccgggcc ccgtgctggc gcctacgcac     240
ctgcagacag agctggtgct gaggtgccag aaggagaccg actgtgacct ctgtctgcgt     300
gtggctgtcc acttggccgt gcatgggcac tgggaagagc tgaagatgga gaaaagtttt     360
ggaggagcag ctgactcagg ggtggaggag cctaggaatg ccacactcca ggcccaagtc     420
gtgctctcct tccaggccta ccctactgcc cgctgcgtcc tgctggaggt gcaagtgcct     480
gctgcccttg tgcagtttgg tcagtctgtg ggctctgtgg tatatgactg cttcgaggct     540
gccctaggga gtgaggtacg aatctggtcc tatactcagc caggtacgaa gaggaactc      600 aaccacacac agcagctgcc tgccctgccc tggctcaacg tgacagcaga tggtgacaac     660
gtgcatctgg ttctgaatgt cacagaggag cagcacttcg cctctccct gtactggaat     720 caggtccagg gcccccaaa accccggtgg cacaaaaacc tgactggacc gcagatcatt     780
```

```
accttgaacc acacagacct ggttccctgc ctctgtattc aggtgtggcc tctggaacct    840
gactccgtta ggacgaacat ctgccccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca   1020
ctggtcccac cgctttcctg ggagaacgtc actgtggaca aggttctcga gttcccattg   1080
ctgaaaggcc accctaacct ctgtgttcag gtgaacagca cagagaagct gcagctgcag   1140
gagtgcttgt gggctgactc cctggggcct ctcaaagacg atgtgctact gttggagaca   1200
cgaggccccc aggacaacag aacactctgt gccttggaac ccgtggctg tacttcacta   1260
cccagcaaag cctccacgag ggcagctcgc cttggagagt acttactaca agacctgcag   1320
tcaggccagt gtctgcagct atgggacgat gacttgggag cgctatgggc ctgccccatg   1380
gacaaataca tccacaagga gcccaaatct tcagacaaaa ctcacacatg cccaccgtgc   1440
ccagcacctg aagccgaggg ggcaccgtca gtcttcctct tccccccaaa acccaaggac   1500
accctcatga tctcccggac ccctgaggtc acatgcgtgg tggtggacgt gagccacgaa   1560
gaccctgagg tcaagttcaa ctggtacgtg gacggcgtgg aggtgcataa tgccaagaca   1620
aagccgcggg aggagcagta caacagcacg taccgtgtgg tcagcgtcct caccgtcctg   1680
caccaggact ggctgaatgg caaggagtac aagtgcaagg tctccaacaa agccctccca   1740
tcctccatcg agaaaaccat ctccaaagcc aagggcagc cccgagaacc acaggtgtac   1800
accctgcccc catcccggga tgagctgacc aagaaccagg tcagcctgac ctgcctggtc   1860
aaaggcttct atcccagcga catcgccgtg gagtgggaga gcaatgggca gccggagaac   1920
aactacaaga ccacgcctcc cgtgctggac tccgacggct ccttcttcct ctacagcaag   1980
ctcaccgtgg acaagagcag gtggcagcag gggaacgtct tctcatgctc cgtgatgcat   2040
gaggctctgc acaaccacta cacgcagaag agcctctccc tgtctccggg taaa          2094
```

<210> SEQ ID NO 156
<211> LENGTH: 698
<212> TYPE: PRT
<213> ORGANISM: Artificial Sequence
<220> FEATURE:
<223> OTHER INFORMATION: Exons 1-6 and 8-16 of IL17RC with Ser to Thr
    substitutions at residues 120, 215, 228, 374, and
    408 and Fc5

<400> SEQUENCE: 156

```
Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg Leu Glu Arg Leu Val Gly Pro Gln Asp Ala Thr His Cys
        35                  40                  45

Ser Pro Gly Leu Ser Cys Arg Leu Trp Asp Ser Asp Ile Leu Cys Leu
    50                  55                  60

Pro Gly Asp Ile Val Pro Ala Pro Gly Pro Val Leu Ala Pro Thr His
65                  70                  75                  80

Leu Gln Thr Glu Leu Val Leu Arg Cys Gln Lys Glu Thr Asp Cys Asp
                85                  90                  95

Leu Cys Leu Arg Val Ala Val His Leu Ala Val His Gly His Trp Glu
            100                 105                 110

Glu Pro Glu Asp Glu Glu Lys Phe Gly Gly Ala Ala Asp Ser Gly Val
        115                 120                 125
```

-continued

```
Glu Glu Pro Arg Asn Ala Thr Leu Gln Ala Gln Val Val Leu Ser Phe
130                 135                 140

Gln Ala Tyr Pro Thr Ala Arg Cys Val Leu Glu Val Gln Val Pro
145                 150                 155                 160

Ala Ala Leu Val Gln Phe Gly Gln Ser Val Gly Ser Val Val Tyr Asp
            165                 170                 175

Cys Phe Glu Ala Ala Leu Gly Ser Glu Val Arg Ile Trp Ser Tyr Thr
            180                 185                 190

Gln Pro Arg Tyr Glu Lys Glu Leu Asn His Thr Gln Gln Leu Pro Ala
            195                 200                 205

Leu Pro Trp Leu Asn Val Thr Ala Asp Gly Asp Asn Val His Leu Val
210                 215                 220

Leu Asn Val Thr Glu Glu Gln His Phe Gly Leu Ser Leu Tyr Trp Asn
225                 230                 235                 240

Gln Val Gln Gly Pro Pro Lys Pro Arg Trp His Lys Asn Leu Thr Gly
                245                 250                 255

Pro Gln Ile Ile Thr Leu Asn His Thr Asp Leu Val Pro Cys Leu Cys
            260                 265                 270

Ile Gln Val Trp Pro Leu Glu Pro Asp Ser Val Arg Thr Asn Ile Cys
            275                 280                 285

Pro Phe Arg Glu Asp Pro Arg Ala His Gln Asn Leu Trp Gln Ala Ala
            290                 295                 300

Arg Leu Arg Leu Leu Thr Leu Gln Ser Trp Leu Leu Asp Ala Pro Cys
305                 310                 315                 320

Ser Leu Pro Ala Glu Ala Leu Cys Trp Arg Ala Pro Gly Gly Asp
                325                 330                 335

Pro Cys Gln Pro Leu Val Pro Pro Leu Ser Trp Glu Asn Val Thr Val
            340                 345                 350

Asp Lys Val Leu Glu Phe Pro Leu Leu Lys Gly His Pro Asn Leu Cys
            355                 360                 365

Val Gln Val Asn Ser Thr Glu Lys Leu Gln Leu Gln Glu Cys Leu Trp
            370                 375                 380

Ala Asp Ser Leu Gly Pro Leu Lys Asp Asp Val Leu Leu Leu Glu Thr
385                 390                 395                 400

Arg Gly Pro Gln Asp Asn Arg Thr Leu Cys Ala Leu Glu Pro Ser Gly
                405                 410                 415

Cys Thr Ser Leu Pro Ser Lys Ala Ser Thr Arg Ala Ala Arg Leu Gly
                420                 425                 430

Glu Tyr Leu Leu Gln Asp Leu Gln Ser Gly Gln Cys Leu Gln Leu Trp
            435                 440                 445

Asp Asp Asp Leu Gly Ala Leu Trp Ala Cys Pro Met Asp Lys Tyr Ile
450                 455                 460

His Lys Glu Pro Lys Ser Ser Asp Lys Thr His Thr Cys Pro Pro Cys
465                 470                 475                 480

Pro Ala Pro Glu Ala Glu Gly Ala Pro Ser Val Phe Leu Phe Pro Pro
                485                 490                 495

Lys Pro Lys Asp Thr Leu Met Ile Ser Arg Thr Pro Glu Val Thr Cys
            500                 505                 510

Val Val Val Asp Val Ser His Glu Asp Pro Glu Val Lys Phe Asn Trp
            515                 520                 525

Tyr Val Asp Gly Val Glu Val His Asn Ala Lys Thr Lys Pro Arg Glu
            530                 535                 540

Glu Gln Tyr Asn Ser Thr Tyr Arg Val Val Ser Val Leu Thr Val Leu
545                 550                 555                 560
```

```
His Gln Asp Trp Leu Asn Gly Lys Glu Tyr Lys Cys Lys Val Ser Asn
                565                 570                 575

Lys Ala Leu Pro Ser Ser Ile Glu Lys Thr Ile Ser Lys Ala Lys Gly
            580                 585                 590

Gln Pro Arg Glu Pro Gln Val Tyr Thr Leu Pro Pro Ser Arg Asp Glu
        595                 600                 605

Leu Thr Lys Asn Gln Val Ser Leu Thr Cys Leu Val Lys Gly Phe Tyr
    610                 615                 620

Pro Ser Asp Ile Ala Val Glu Trp Glu Ser Asn Gly Gln Pro Glu Asn
625                 630                 635                 640

Asn Tyr Lys Thr Thr Pro Pro Val Leu Asp Ser Asp Gly Ser Phe Phe
            645                 650                 655

Leu Tyr Ser Lys Leu Thr Val Asp Lys Ser Arg Trp Gln Gln Gly Asn
        660                 665                 670

Val Phe Ser Cys Ser Val Met His Glu Ala Leu His Asn His Tyr Thr
    675                 680                 685

Gln Lys Ser Leu Ser Leu Ser Pro Gly Lys
    690                 695

<210> SEQ ID NO 157
<211> LENGTH: 2070
<212> TYPE: DNA
<213> ORGANISM: Artificial Sequence
<220> FEATURE:
<223> OTHER INFORMATION: IL-17RA signal peptide and exons 1-6 of IL-17RA
      and exons 8-16 of IL-17RC and Fc5

<400> SEQUENCE: 157
atgggggccg cacgcagccc gccgtccgct gtcccggggc ccctgctggg gctgctcctg      60
ctgctcctgg gcgtgctggc cccggtggc gcctccctgc gactcctgga ccaccgggcg     120
ctggtctgct cccagccggg gctaaactgc acggtcaaga atagtacctg cctggatgac     180
agctggattc accctcgaaa cctgaccccc tcctccccaa aggacctgca gatccagctg     240
cactttgccc acacccaaca aggagacctg ttccccgtgg ctcacatcga atggacactg     300
cagacagacg ccagcatcct gtacctcgag ggtgcagagt tatctgtcct gcagctgaac     360
accaatgaac gtttgtgcgt caggtttgag tttctgtcca aactgaggca tcaccacagg     420
cggtggcgtt ttaccttcag ccactttgtg gttgaccctg accaggaata tgaggtgacc     480
gttcaccacc tgcccaagcc catccctgat ggggacccaa accaccagtc caagaatttc     540
cttgtgcctg actgtgagca cgccaggatg aaggtaacca cgccatgcat gagctcagcc     600
ctgccctggc tcaacgtgtc agcagatggt gacaacgtgc atctggttct gaatgtctct     660
gaggagcagc acttcggcct ctccctgtac tggaatcagg tccagggccc cccaaaaccc     720
cggtggcaca aaaacctgac tggaccgcag atcattacct tgaaccacac agacctggtt     780
ccctgcctct gtattcaggt gtggcctctg aacctgact ccgttaggac gaacatctgc     840
cccttcaggg aggaccccg cgcacaccag aacctctggc aagccgcccg actgcgactg     900
ctgaccctgc agagctggct gctggacgca ccgtgctcgc tgcccgcaga gcggcactg     960 tgctggcggg ctccgggtgg ggaccctgc cagccactgg tcccaccgct tcctgggag    1020 aacgtcactg tggacaaggt tctcgagttc ccattgctga aggccaccc taacctctgt    1080 gttcaggtga acagctcgga gaagctgcag ctgcaggagt gcttgtgggc tgactccctg    1140
gggcctctca agacgatgt gctactgttg agacacgag ccccaggga caacagatcc    1200 ctctgtgcct tggaacccag tggctgtact tcactaccca gcaaagcctc cacgagggca    1260
```

```
gctcgccttg gagagtactt actacaagac ctgcagtcag ccagtgtct gcagctatgg   1320 gacgatgact tgggagcgct atgggcctgc cccatggaca atacatcca caaggagccc   1380 aaatcttcag acaaaactca cacatgccca ccgtgcccag cacctgaagc cgagggggca   1440
ccgtcagtct tcctcttccc cccaaaaccc aaggacaccc tcatgatctc ccggacccct   1500
gaggtcacat gcgtggtggt ggacgtgagc cacgaagacc ctgaggtcaa gttcaactgg   1560
tacgtggacg gcgtggaggt gcataatgcc aagacaaagc cgcgggagga gcagtacaac   1620
agcacgtacc gtgtggtcag cgtcctcacc gtcctgcacc aggactggct gaatggcaag   1680
gagtacaagt gcaaggtctc caacaaagcc ctcccatcct ccatcgagaa aaccatctcc   1740
aaagccaaag ggcagccccg agaaccacag gtgtacaccc tgcccccatc ccgggatgag   1800
ctgaccaaga accaggtcag cctgacctgc ctggtcaaag gcttctatcc cagcgacatc   1860
gccgtggagt gggagagcaa tgggcagccg gagaacaact acaagaccac gcctcccgtg   1920
ctggactccg acggctcctt cttcctctac agcaagctca ccgtggacaa gagcaggtgg   1980
cagcagggga acgtcttctc atgctccgtg atgcatgagg ctctgcacaa ccactacacg   2040
cagaagagcc tctccctgtc tccgggtaaa                                    2070
```

<210> SEQ ID NO 158
<211> LENGTH: 690
<212> TYPE: PRT
<213> ORGANISM: Artificial Sequence
<220> FEATURE:
<223> OTHER INFORMATION: IL-17RA signal peptide and exons 1-6 of IL-17RA
      and exons 8-16 of IL-17RC and Fc5

<400> SEQUENCE: 158

Met Gly Ala Ala Arg Ser Pro Pro Ser Ala Val Pro Gly Pro Leu Leu
 1               5                  10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Ala Leu Pro Trp Leu Asn Val Ser Ala
        195                 200                 205

Asp Gly Asp Asn Val His Leu Val Leu Asn Val Ser Glu Glu Gln His

-continued

```
            210                 215                 220
Phe Gly Leu Ser Leu Tyr Trp Asn Gln Val Gln Gly Pro Pro Lys Pro
225                 230                 235                 240

Arg Trp His Lys Asn Leu Thr Gly Pro Gln Ile Ile Thr Leu Asn His
                245                 250                 255

Thr Asp Leu Val Pro Cys Leu Cys Ile Gln Val Trp Pro Leu Glu Pro
                260                 265                 270

Asp Ser Val Arg Thr Asn Ile Cys Pro Phe Arg Glu Asp Pro Arg Ala
                275                 280                 285

His Gln Asn Leu Trp Gln Ala Ala Arg Leu Arg Leu Leu Thr Leu Gln
                290                 295                 300

Ser Trp Leu Leu Asp Ala Pro Cys Ser Leu Pro Ala Glu Ala Ala Leu
305                 310                 315                 320

Cys Trp Arg Ala Pro Gly Gly Asp Pro Cys Gln Pro Leu Val Pro Pro
                325                 330                 335

Leu Ser Trp Glu Asn Val Thr Val Asp Lys Val Leu Glu Phe Pro Leu
                340                 345                 350

Leu Lys Gly His Pro Asn Leu Cys Val Gln Val Asn Ser Ser Glu Lys
                355                 360                 365

Leu Gln Leu Gln Glu Cys Leu Trp Ala Asp Ser Leu Gly Pro Leu Lys
                370                 375                 380

Asp Asp Val Leu Leu Leu Glu Thr Arg Gly Pro Gln Asp Asn Arg Ser
385                 390                 395                 400

Leu Cys Ala Leu Glu Pro Ser Gly Cys Thr Ser Leu Pro Ser Lys Ala
                405                 410                 415

Ser Thr Arg Ala Ala Arg Leu Gly Glu Tyr Leu Leu Gln Asp Leu Gln
                420                 425                 430

Ser Gly Gln Cys Leu Gln Leu Trp Asp Asp Asp Leu Gly Ala Leu Trp
                435                 440                 445

Ala Cys Pro Met Asp Lys Tyr Ile His Lys Glu Pro Lys Ser Ser Asp
                450                 455                 460

Lys Thr His Thr Cys Pro Pro Cys Pro Ala Pro Glu Ala Glu Gly Ala
465                 470                 475                 480

Pro Ser Val Phe Leu Phe Pro Pro Lys Pro Lys Asp Thr Leu Met Ile
                485                 490                 495

Ser Arg Thr Pro Glu Val Thr Cys Val Val Val Asp Val Ser His Glu
                500                 505                 510

Asp Pro Glu Val Lys Phe Asn Trp Tyr Val Asp Gly Val Glu Val His
                515                 520                 525

Asn Ala Lys Thr Lys Pro Arg Glu Glu Gln Tyr Asn Ser Thr Tyr Arg
                530                 535                 540

Val Val Ser Val Leu Thr Val Leu His Gln Asp Trp Leu Asn Gly Lys
545                 550                 555                 560

Glu Tyr Lys Cys Lys Val Ser Asn Lys Ala Leu Pro Ser Ser Ile Glu
                565                 570                 575

Lys Thr Ile Ser Lys Ala Lys Gly Gln Pro Arg Glu Pro Gln Val Tyr
                580                 585                 590

Thr Leu Pro Pro Ser Arg Asp Glu Leu Thr Lys Asn Gln Val Ser Leu
                595                 600                 605

Thr Cys Leu Val Lys Gly Phe Tyr Pro Ser Asp Ile Ala Val Glu Trp
                610                 615                 620

Glu Ser Asn Gly Gln Pro Glu Asn Asn Tyr Lys Thr Thr Pro Pro Val
625                 630                 635                 640
```

```
Leu Asp Ser Asp Gly Ser Phe Phe Leu Tyr Ser Lys Leu Thr Val Asp
                645                 650                 655

Lys Ser Arg Trp Gln Gln Gly Asn Val Phe Ser Cys Ser Val Met His
            660                 665                 670

Glu Ala Leu His Asn His Tyr Thr Gln Lys Ser Leu Ser Leu Ser Pro
        675                 680                 685

Gly Lys
    690

<210> SEQ ID NO 159
<211> LENGTH: 252
<212> TYPE: DNA
<213> ORGANISM: Artificial Sequence
<220> FEATURE:
<223> OTHER INFORMATION: Domain 1

<400> SEQUENCE: 159
gccctgccct ggctcaacgt gtcagcagat ggtgacaacg tgcatctggt tctgaatgtc      60
tctgaggagc agcacttcgg cctctccctg tactggaatc aggtccaggg ccccccaaaa     120
ccccggtggc acaaaaacct gactggaccg cagatcatta ccttgaacca cacagacctg     180
gttccctgcc tctgtattca ggtgtggcct ctggaacctg actccgttag gacgaacatc     240
tgccccttca gg                                                         252

<210> SEQ ID NO 160
<211> LENGTH: 84
<212> TYPE: PRT
<213> ORGANISM: Artificial Sequence
<220> FEATURE:
<223> OTHER INFORMATION: Domain 1

<400> SEQUENCE: 160

Ala Leu Pro Trp Leu Asn Val Ser Ala Asp Gly Asp Asn Val His Leu
1               5                   10                  15

Val Leu Asn Val Ser Glu Glu Gln His Phe Gly Leu Ser Leu Tyr Trp
            20                  25                  30

Asn Gln Val Gln Gly Pro Pro Lys Pro Arg Trp His Lys Asn Leu Thr
        35                  40                  45

Gly Pro Gln Ile Ile Thr Leu Asn His Thr Asp Leu Val Pro Cys Leu
    50                  55                  60

Cys Ile Gln Val Trp Pro Leu Glu Pro Asp Ser Val Arg Thr Asn Ile
65                  70                  75                  80

Cys Pro Phe Arg

<210> SEQ ID NO 161
<211> LENGTH: 282
<212> TYPE: DNA
<213> ORGANISM: Artificial Sequence
<220> FEATURE:
<223> OTHER INFORMATION: Domain 2

<400> SEQUENCE: 161
gaggaccccc gcgcacacca gaacctctgg caagccgccc gactgcgact gctgaccctg     60
cagagctggc tgctggacgc accgtgctcg ctgcccgcag aagcggcact gtgctggcgg    120
gctccgggtg ggaccccctg ccagccactg gtcccaccgc tttcctggga gaacgtcact    180
gtggacaagg ttctcgagtt cccattgctg aaaggccacc ctaacctctg tgttcaggtg    240
aacagctcgg agaagctgca gctgcaggag tgcttgtggg ct                       282
```

<210> SEQ ID NO 162
<211> LENGTH: 94
<212> TYPE: PRT
<213> ORGANISM: Artificial Sequence
<220> FEATURE:
<223> OTHER INFORMATION: Domain 2

<400> SEQUENCE: 162

```
Glu Asp Pro Arg Ala His Gln Asn Leu Trp Gln Ala Ala Arg Leu Arg
 1               5                  10                  15
Leu Leu Thr Leu Gln Ser Trp Leu Leu Asp Ala Pro Cys Ser Leu Pro
             20                  25                  30
Ala Glu Ala Ala Leu Cys Trp Arg Ala Pro Gly Gly Asp Pro Cys Gln
         35                  40                  45
Pro Leu Val Pro Pro Leu Ser Trp Glu Asn Val Thr Val Asp Lys Val
     50                  55                  60
Leu Glu Phe Pro Leu Leu Lys Gly His Pro Asn Leu Cys Val Gln Val
 65                  70                  75                  80
Asn Ser Ser Glu Lys Leu Gln Leu Gln Glu Cys Leu Trp Ala
                 85                  90
```

<210> SEQ ID NO 163
<211> LENGTH: 231
<212> TYPE: DNA
<213> ORGANISM: Artificial Sequence
<220> FEATURE:
<223> OTHER INFORMATION: Domain 3

<400> SEQUENCE: 163

```
gactccctgg ggcctctcaa agacgatgtg ctactgttgg agacacgagg cccccaggac    60
aacagatccc tctgtgcctt ggaacccagt ggctgtactt cactacccag caaagcctcc   120
acgagggcag ctcgccttgg agagtactta ctacaagacc tgcagtcagg ccagtgtctg   180
cagctatggg acgatgactt gggagcgcta tgggcctgcc catggacaa a             231
```

<210> SEQ ID NO 164
<211> LENGTH: 77
<212> TYPE: PRT
<213> ORGANISM: Artificial Sequence
<220> FEATURE:
<223> OTHER INFORMATION: Domain 3

<400> SEQUENCE: 164

```
Asp Ser Leu Gly Pro Leu Lys Asp Asp Val Leu Leu Leu Glu Thr Arg
 1               5                  10                  15
Gly Pro Gln Asp Asn Arg Ser Leu Cys Ala Leu Glu Pro Ser Gly Cys
             20                  25                  30
Thr Ser Leu Pro Ser Lys Ala Ser Thr Arg Ala Ala Arg Leu Gly Glu
         35                  40                  45
Tyr Leu Leu Gln Asp Leu Gln Ser Gly Gln Cys Leu Gln Leu Trp Asp
     50                  55                  60
Asp Asp Leu Gly Ala Leu Trp Ala Cys Pro Met Asp Lys
 65                  70                  75
```

<210> SEQ ID NO 165
<211> LENGTH: 2124
<212> TYPE: DNA
<213> ORGANISM: homo sapians

<400> SEQUENCE: 165

```
atgcctgtgc cctggttctt gctgtccttg gcactgggcc gaagcccagt ggtcctttct    60
```

-continued

```
ctggagaggc ttgtggggcc tcaggacgct acccactgct ctccgggcct ctcctgccgc    120
ctctgggaca gtgacatact ctgcctgcct ggggacatcg tgcctgctcc gggccccgtg    180
ctggcgccta cgcacctgca gacagagctg gtgctgaggt gccagaagga gaccgactgt    240
gacctctgtc tgcgtgtggc tgtccacttg gccgtgcatg ggcactggga agagcctgaa    300
gatgaggaaa agtttggagg agcagctgac tcaggggtgg aggagcctag gaatgcctct    360
ctccaggccc aagtcgtgct ctccttccag gcctacccta ctgcccgctg cgtcctgctg    420
gaggtgcaag tgcctgctgc ccttgtgcag tttggtcagt ctgtgggctc tgtggtatat    480
gactgcttcg aggctgccct agggagtgag gtacgaatct ggtcctatac tcagcccagg    540
tacgagaagg aactcaacca cacacagcag ctgcctgact gcaggggggct cgaagtctgg    600 aacagcatcc cgagctgctg ggccctgccc tggctcaacg tgtcagcaga tggtgacaac    660
gtgcatctgg ttctgaatgt ctctgaggag cagcacttcg gcctctccct gtactggaat    720
caggtccagg ccccccaaa accccggtgg cacaaaaacc tgactggacc gcagatcatt    780
accttgaacc acacagacct ggttccctgc ctctgtattc aggtgtggcc tctggaacct    840
gactccgtta ggacgaacat ctgccccttc agggaggacc cccgcgcaca ccagaacctc    900
tggcaagccg cccgactgcg actgctgacc ctgcagagct ggctgctgga cgcaccgtgc    960
tcgctgcccg cagaagcggc actgtgctgg cgggctccgg gtggggaccc ctgccagcca    1020
ctggtcccac cgctttcctg ggagaacgtc actgtggaca aggttctcga gttcccattg    1080
ctgaaaggcc accctaacct ctgtgttcag gtgaacagct cggagaagct gcagctgcag    1140
gagtgcttgt gggctgactc cctggggcct ctcaaagacg atgtgctact gttggagaca    1200
cgaggccccc aggacaacag atccctctgt gccttggaac ccagtggctg tacttcacta    1260
cccagcaaag cctccacgag ggcagctcgc cttggagagt acttactaca agacctgcag    1320
tcaggccagt gtctgcagct atgggacgat gacttgggag cgctatgggc ctgccccatg    1380
gacaaataca tccacaagcg ctgggccctc gtgtggctgg cctgcctact ctttgccgct    1440
gcgctttccc tcatcctcct tctcaaaaag gatcacgcga aagcggccgc caggggccgc    1500
gcggctctgc tcctctactc agccgatgac tcgggtttcg agcgcctggt gggcgccctg    1560
gcgtcggccc tgtgccagct gccgctgcgc gtggccgtag acctgtggag ccgtcgtgaa    1620
ctgagcgcgc aggggcccgt ggcttggttt cacgcgcagc ggcgccagac cctgcaggag    1680
ggcggcgtgg tggtcttgct cttctctccc ggtgcggtgg cgctgtgcag cgagtggcta    1740
caggatgggg tgtccgggcc cggggcgcac ggcccgcacg acgccttccg cgcctcgctc    1800
agctgcgtgc tgcccgactt cttgcagggc cgggcgcccg gcagctacgt gggggcctgc    1860
ttcgacaggc tgctccaccc ggacgccgta cccgcccttt ccgcaccgt gcccgtcttc    1920 acactgccct cccaactgcc agacttcctg ggggccctgc agcagcctcg cgccccgcgt    1980 tccgggcgg tccaagagag agcggagcaa gtgtcccggg cccttcagcc agccctggat    2040
agctacttcc atcccccggg gactcccgcg ccgggacgcg gggtgggacc aggggcggga    2100
cctggggcgg gggacgggac ttaa    2124
```

<210> SEQ ID NO 166
<211> LENGTH: 707
<212> TYPE: PRT
<213> ORGANISM: homo sapians

<400> SEQUENCE: 166

Met Pro Val Pro Trp Phe Leu Leu Ser Leu Ala Leu Gly Arg Ser Pro
1               5                   10                  15

Val Val Leu Ser Leu Glu Arg Leu Val Gly Pro Gln Asp Ala Thr His
            20                  25                  30
Cys Ser Pro Gly Leu Ser Cys Arg Leu Trp Asp Ser Asp Ile Leu Cys
            35                  40                  45
Leu Pro Gly Asp Ile Val Pro Ala Pro Gly Pro Val Leu Ala Pro Thr
50                  55                  60
His Leu Gln Thr Glu Leu Val Leu Arg Cys Gln Lys Glu Thr Asp Cys
65                  70                  75                  80
Asp Leu Cys Leu Arg Val Ala Val His Leu Ala Val His Gly His Trp
            85                  90                  95
Glu Glu Pro Glu Asp Glu Lys Phe Gly Gly Ala Ala Asp Ser Gly
                100                 105                 110
Val Glu Glu Pro Arg Asn Ala Ser Leu Gln Ala Gln Val Val Leu Ser
            115                 120                 125
Phe Gln Ala Tyr Pro Thr Ala Arg Cys Val Leu Leu Glu Val Gln Val
130                 135                 140
Pro Ala Ala Leu Val Gln Phe Gly Gln Ser Val Gly Ser Val Val Tyr
145                 150                 155                 160
Asp Cys Phe Glu Ala Ala Leu Gly Ser Glu Val Arg Ile Trp Ser Tyr
            165                 170                 175
Thr Gln Pro Arg Tyr Glu Lys Glu Leu Asn His Thr Gln Gln Leu Pro
            180                 185                 190
Asp Cys Arg Gly Leu Glu Val Trp Asn Ser Ile Pro Ser Cys Trp Ala
            195                 200                 205
Leu Pro Trp Leu Asn Val Ser Ala Asp Gly Asp Asn Val His Leu Val
210                 215                 220
Leu Asn Val Ser Glu Glu Gln His Phe Gly Leu Ser Leu Tyr Trp Asn
225                 230                 235                 240
Gln Val Gln Gly Pro Pro Lys Pro Arg Trp His Lys Asn Leu Thr Gly
            245                 250                 255
Pro Gln Ile Ile Thr Leu Asn His Thr Asp Leu Val Pro Cys Leu Cys
            260                 265                 270
Ile Gln Val Trp Pro Leu Glu Pro Asp Ser Val Arg Thr Asn Ile Cys
            275                 280                 285
Pro Phe Arg Glu Asp Pro Arg Ala His Gln Asn Leu Trp Gln Ala Ala
            290                 295                 300
Arg Leu Arg Leu Leu Thr Leu Gln Ser Trp Leu Leu Asp Ala Pro Cys
305                 310                 315                 320
Ser Leu Pro Ala Glu Ala Ala Leu Cys Trp Arg Ala Pro Gly Gly Asp
            325                 330                 335
Pro Cys Gln Pro Leu Val Pro Pro Leu Ser Trp Glu Asn Val Thr Val
            340                 345                 350
Asp Lys Val Leu Glu Phe Pro Leu Leu Lys Gly His Pro Asn Leu Cys
            355                 360                 365
Val Gln Val Asn Ser Ser Glu Lys Leu Gln Leu Gln Glu Cys Leu Trp
370                 375                 380
Ala Asp Ser Leu Gly Pro Leu Lys Asp Asp Val Leu Leu Leu Glu Thr
385                 390                 395                 400
Arg Gly Pro Gln Asp Asn Arg Ser Leu Cys Ala Leu Glu Pro Ser Gly
            405                 410                 415
Cys Thr Ser Leu Pro Ser Lys Ala Ser Thr Arg Ala Ala Arg Leu Gly
            420                 425                 430
Glu Tyr Leu Leu Gln Asp Leu Gln Ser Gly Gln Cys Leu Gln Leu Trp

Asp Asp Asp Leu Gly Ala Leu Trp Ala Cys Pro Met Asp Lys Tyr Ile
450                 455                 460

His Lys Arg Trp Ala Leu Val Trp Leu Ala Cys Leu Leu Phe Ala Ala
465                 470                 475                 480

Ala Leu Ser Leu Ile Leu Leu Lys Lys Asp His Ala Lys Ala Ala
            485                 490                 495

Ala Arg Gly Arg Ala Ala Leu Leu Tyr Ser Ala Asp Ser Gly
            500                 505                 510

Phe Glu Arg Leu Val Gly Ala Leu Ala Ser Ala Leu Cys Gln Leu Pro
            515                 520                 525

Leu Arg Val Ala Val Asp Leu Trp Ser Arg Arg Glu Leu Ser Ala Gln
            530                 535                 540

Gly Pro Val Ala Trp Phe His Ala Gln Arg Arg Gln Thr Leu Gln Glu
545                 550                 555                 560

Gly Gly Val Val Val Leu Leu Phe Ser Pro Gly Ala Val Ala Leu Cys
                565                 570                 575

Ser Glu Trp Leu Gln Asp Gly Val Ser Gly Pro Gly Ala His Gly Pro
            580                 585                 590

His Asp Ala Phe Arg Ala Ser Leu Ser Cys Val Leu Pro Asp Phe Leu
            595                 600                 605

Gln Gly Arg Ala Pro Gly Ser Tyr Val Gly Ala Cys Phe Asp Arg Leu
            610                 615                 620

Leu His Pro Asp Ala Val Pro Ala Leu Phe Arg Thr Val Pro Val Phe
625                 630                 635                 640

Thr Leu Pro Ser Gln Leu Pro Asp Phe Leu Gly Ala Leu Gln Gln Pro
                645                 650                 655

Arg Ala Pro Arg Ser Gly Arg Leu Gln Glu Arg Ala Glu Gln Val Ser
            660                 665                 670

Arg Ala Leu Gln Pro Ala Leu Asp Ser Tyr Phe His Pro Pro Gly Thr
            675                 680                 685

Pro Ala Pro Gly Arg Gly Val Gly Pro Gly Ala Gly Pro Gly Ala Gly
690                 695                 700

Asp Gly Thr
705

<210> SEQ ID NO 167
<211> LENGTH: 3120
<212> TYPE: DNA
<213> ORGANISM: homo sapiens

<400> SEQUENCE: 167
ggggccgagc cctccgcgac gccacccggg ccatggggc cgcacgcagc ccgccgtccg      60
ctgtcccggg gccctgctg gggctgctcc tgctgctcct gggcgtgctg gccccgggtg     120
gcgcctccct gcgactcctg gaccaccggg cgctggtctg ctcccagccg ggctaaaact     180
gcacggtcaa gaatagtacc tgcctggatg acagctggat tcaccctcga aacctgaccc     240
cctcctcccc aaaggacctg cagatccagc tgcactttgc ccacacccaa caaggagacc     300
tgttccccgt ggctcacatc gaatggacac tgcagacaga cgccagcatc ctgtacctcg     360
agggtgcaga gttatctgtc ctgcagctga acaccaatga acgtttgtgc gtcaggtttg     420
agtttctgtc caaactgagg catcaccaca ggcggtggcg ttttaccttc agccactttg     480
tggttgaccc tgaccaggaa tatgaggtga ccgttcacca cctgcccaag ccatccctg      540 atggggaccc aaaccaccag tccaagaatt ccttgtgcc tgactgtgag cacgccagga     600

```
tgaaggtaac cacgccatgc atgagctcag gcagcctgtg ggaccccaac atcaccgtgg      660
agaccctgga ggcccaccag ctgcgtgtga gcttcaccct gtggaacgaa tctacccatt      720
accagatcct gctgaccagt tttccgcaca tggagaacca cagttgcttt gagcacatgc      780
accacatacc tgcgcccaga ccagaagagt tccaccagcg atccaacgtc acactcactc      840
tacgcaacct taaagggtgc tgtcgccacc aagtgcagat ccagcccttc ttcagcagct      900
gcctcaatga ctgcctcaga cactccgcga ctgtttcctg cccagaaatg ccagacactc      960
cagaaccaat tccggactac atgcccctgt gggtgtactg gttcatcacg gcatctccca     1020
tcctgctggt gggctccgtc atcctgctca tcgtctgcat gacctggagg ctagctgggc     1080
ctggaagtga aaaatacagt gatgacacca aatacaccga tggcctgcct gcggctgacc     1140 tgatccccc accgctgaag cccaggaagg tctggatcat ctactcagcc gaccacccc      1200 tctacgtgga cgtggtcctg aaattcgccc agttcctgct caccgcctgc ggcacggaag     1260
tggccctgga cctgctggaa gagcaggcca tctcggaggc aggagtcatg acctgggtgg     1320
gccgtcagaa gcaggagatg gtggagagca actctaagat catcgtcctg tgctcccgcg     1380
gcacgcgcgc caagtggcag cgctcctgg gccggggggc cctgtgcgg ctgcgctgcg     1440 accacggaaa gcccgtgggg gacctgttca ctgcagccat gaacatgatc ctcccggact     1500
tcaagaggcc agcctgcttc ggcacctacg tagtctgcta cttcagcgag gtcagctgtg     1560
acggcgacgt ccccgacctg ttcggcgcgg cgccgcggta cccgctcatg gacaggttcg     1620
aggaggtgta cttccgcatc caggacctgg agatgttcca gccgggccgc atgcaccgcg     1680 tagggagct gtcgggggac aactacctgc ggagcccggg cggcaggcag ctccgcgccg     1740
ccctggacag gttccgggac tggcaggtcc gctgtcccga ctggttcgaa tgtgagaacc     1800
tctactcagc agatgaccag gatgccccgt ccctggacga agaggtgttt gaggagccac     1860
tgctgcctcc gggaaccggc atcgtgaagc gggcgcccct ggtgcgcgag cctggctccc     1920
aggcctgcct ggccatagac ccgctggtcg gggaggaagg aggagcagca gtggcaaagc     1980
tggaacctca cctgcagccc cggggtcagc cagcgccgca gccctccac accctggtgc     2040 tcgccgcaga ggagggggcc ctggtggccg cggtggagcc tgggcccctg gctgacggtg     2100
ccgcagtccg gctggcactg gcgggggagg gcgaggcctg cccgctgctg ggcagcccgg     2160
gcgctgggcg aaatagcgtc ctcttcctcc ccgtggaccc cgaggactcg cccccttggca    2220 gcagcacccc catggcgtct cctgacctcc ttccagagga cgtgagggag cacctcgaag     2280
gcttgatgct ctcgctcttc gagcagagtc tgagctgcca ggcccagggg ggctgcagta     2340
gacccgccat ggtcctcaca gacccacaca cgccctacga ggaggagcag cggcagtcag     2400
tgcagtctga ccagggctac atctccagga gctccccgca gcccccgag ggactcacgg      2460 aaatggagga agaggaggaa gaggagcagg acccagggaa gccggccctg ccactctctc     2520
ccgaggacct ggagagcctg aggagcctcc agcggcagct gcttttccgc cagctgcaga     2580
agaactcggg ctgggacacg atggggtcag agtcagaggg gccagtgca tgagggcggc     2640 tccccaggga ccgcccagat cccagctttg agagaggagt gtgtgtgcac gtattcatct     2700
gtgtgtacat gtctgcatgt gtatatgttc gtgtgtgaaa tgtaggcttt aaaatgtaaa     2760
tgtctggatt ttaatcccag gcatccctcc taacttttct ttgtgcagcg gtctggttat     2820
cgtctatccc caggggaatc cacacagccc gctcccagga gctaatggta gagcgtcctt     2880
gaggctccat tattcgttca ttcagcattt attgtgcacc tactatgtgg cgggcatttg     2940
ggataccaag ataaattgca tgcggcatgg ccccagccat gaaggaactt aaccgctagt     3000
```
gccgaggaca cgttaaacga acaggatggg ccgggcacgg tggctcacgc ctgtaatccc    3060
agcacactgg gaggccgagg caggtggatc actctgaggt caggagtttg agccagcctg    3120

<210> SEQ ID NO 168
<211> LENGTH: 78
<212> TYPE: DNA
<213> ORGANISM: Artificial Sequence
<220> FEATURE:
<223> OTHER INFORMATION: human growth hormone signal peptide
<220> FEATURE:
<221> NAME/KEY: CDS
<222> LOCATION: (1)...(78)

<400> SEQUENCE: 168 atg gct aca ggc tcc cgg acg tcc ctg ctc ctg gct ttt ggc ctg ctc        48
Met Ala Thr Gly Ser Arg Thr Ser Leu Leu Leu Ala Phe Gly Leu Leu
 1               5                  10                  15 tgc ctg ccc tgg ctt caa gag ggc agt gcc                                78
Cys Leu Pro Trp Leu Gln Glu Gly Ser Ala
             20                  25

<210> SEQ ID NO 169
<211> LENGTH: 26
<212> TYPE: PRT
<213> ORGANISM: Artificial Sequence
<220> FEATURE:
<223> OTHER INFORMATION: human growth hormone signal peptide

<400> SEQUENCE: 169

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala
             20                  25

<210> SEQ ID NO 170
<211> LENGTH: 57
<212> TYPE: DNA
<213> ORGANISM: Artificial Sequence
<220> FEATURE:
<223> OTHER INFORMATION: Mouse Immunoglobulin Heavy Chain Variable
      Region (VH 26-10) Signal Peptide
<220> FEATURE:
<221> NAME/KEY: CDS
<222> LOCATION: (1)...(57)

<400> SEQUENCE: 170 atg gga tgg agc tgg atc ttt ctc ttt ctt ctg tca gga act gca ggt        48
Met Gly Trp Ser Trp Ile Phe Leu Phe Leu Leu Ser Gly Thr Ala Gly
 1               5                  10                  15 gtc ctc tct                                                            57
Val Leu Ser <210> SEQ ID NO 171
<211> LENGTH: 19
<212> TYPE: PRT
<213> ORGANISM: Artificial Sequence
<220> FEATURE:
<223> OTHER INFORMATION: Mouse Immunoglobulin Heavy Chain Variable
      Region (VH 26-10) Signal Peptide

<400> SEQUENCE: 171

Met Gly Trp Ser Trp Ile Phe Leu Phe Leu Leu Ser Gly Thr Ala Gly
 1               5                  10                  15

Val Leu Ser

-continued

<210> SEQ ID NO 172
<211> LENGTH: 48
<212> TYPE: DNA
<213> ORGANISM: Artificial Sequence
<220> FEATURE:
<223> OTHER INFORMATION: Human CD33 Signal Peptide
<220> FEATURE:
<221> NAME/KEY: CDS
<222> LOCATION: (1)...(48)

<400> SEQUENCE: 172

| atg | ccg | ctg | ctg | cta | ctg | ctg | ccc | ctg | ctg | tgg | gca | ggg | gcc | ctg | gct | 48 |
|---|---|---|---|---|---|---|---|---|---|---|---|---|---|---|---|---|
| Met | Pro | Leu | Leu | Leu | Leu | Leu | Pro | Leu | Leu | Trp | Ala | Gly | Ala | Leu | Ala | |
| 1 | | | | 5 | | | | | 10 | | | | | 15 | | |

<210> SEQ ID NO 173
<211> LENGTH: 16
<212> TYPE: PRT
<213> ORGANISM: Artificial Sequence
<220> FEATURE:
<223> OTHER INFORMATION: Human CD33 Signal Peptide

<400> SEQUENCE: 173

Met Pro Leu Leu Leu Leu Leu Pro Leu Leu Trp Ala Gly Ala Leu Ala
1               5                   10                  15

<210> SEQ ID NO 174
<211> LENGTH: 696
<212> TYPE: DNA
<213> ORGANISM: Artificial Sequence
<220> FEATURE:
<223> OTHER INFORMATION: Fc10 immunoglobulin heavy chain constant
      region
<220> FEATURE:
<221> NAME/KEY: CDS
<222> LOCATION: (1)...(696)

<400> SEQUENCE: 174

| gag | ccc | aaa | tct | tca | gac | aaa | act | cac | aca | tgc | cca | ccg | tgc | cca | gca | 48 |
|---|---|---|---|---|---|---|---|---|---|---|---|---|---|---|---|---|
| Glu | Pro | Lys | Ser | Ser | Asp | Lys | Thr | His | Thr | Cys | Pro | Pro | Cys | Pro | Ala | |
| 1 | | | | 5 | | | | | 10 | | | | | 15 | | |

| cct | gaa | ctc | ctg | ggg | gga | ccg | tca | gtc | ttc | ctc | ttc | ccc | cca | aaa | ccc | 96 |
|---|---|---|---|---|---|---|---|---|---|---|---|---|---|---|---|---|
| Pro | Glu | Leu | Leu | Gly | Gly | Pro | Ser | Val | Phe | Leu | Phe | Pro | Pro | Lys | Pro | |
| | | | 20 | | | | | 25 | | | | | 30 | | | |

| aag | gac | acc | ctc | atg | atc | tcc | cgg | acc | cct | gag | gtc | aca | tgc | gtg | gtg | 144 |
|---|---|---|---|---|---|---|---|---|---|---|---|---|---|---|---|---|
| Lys | Asp | Thr | Leu | Met | Ile | Ser | Arg | Thr | Pro | Glu | Val | Thr | Cys | Val | Val | |
| | | 35 | | | | | 40 | | | | | 45 | | | | |

| gtg | gac | gtg | agc | cac | gaa | gac | cct | gag | gtc | aag | ttc | aac | tgg | tac | gtg | 192 |
|---|---|---|---|---|---|---|---|---|---|---|---|---|---|---|---|---|
| Val | Asp | Val | Ser | His | Glu | Asp | Pro | Glu | Val | Lys | Phe | Asn | Trp | Tyr | Val | |
| | 50 | | | | | 55 | | | | | 60 | | | | | |

| gac | ggc | gtg | gag | gtg | cat | aat | gcc | aag | aca | aag | ccg | cgg | gag | gag | cag | 240 |
|---|---|---|---|---|---|---|---|---|---|---|---|---|---|---|---|---|
| Asp | Gly | Val | Glu | Val | His | Asn | Ala | Lys | Thr | Lys | Pro | Arg | Glu | Glu | Gln | |
| 65 | | | | 70 | | | | | 75 | | | | | 80 | | |

| tac | aac | agc | acg | tac | cgt | gtg | gtc | agc | gtc | ctc | acc | gtc | ctg | cac | cag | 288 |
|---|---|---|---|---|---|---|---|---|---|---|---|---|---|---|---|---|
| Tyr | Asn | Ser | Thr | Tyr | Arg | Val | Val | Ser | Val | Leu | Thr | Val | Leu | His | Gln | |
| | | | 85 | | | | | 90 | | | | | 95 | | | |

| gac | tgg | ctg | aat | ggc | aag | gag | tac | aag | tgc | aag | gtc | tcc | aac | aaa | gcc | 336 |
|---|---|---|---|---|---|---|---|---|---|---|---|---|---|---|---|---|
| Asp | Trp | Leu | Asn | Gly | Lys | Glu | Tyr | Lys | Cys | Lys | Val | Ser | Asn | Lys | Ala | |
| | | | 100 | | | | | 105 | | | | | 110 | | | |

| ctc | cca | gcc | ccc | atc | gag | aaa | acc | atc | tcc | aaa | gcc | aaa | ggg | cag | ccc | 384 |
|---|---|---|---|---|---|---|---|---|---|---|---|---|---|---|---|---|
| Leu | Pro | Ala | Pro | Ile | Glu | Lys | Thr | Ile | Ser | Lys | Ala | Lys | Gly | Gln | Pro | |
| | | 115 | | | | | 120 | | | | | 125 | | | | |

| cga | gaa | cca | cag | gtg | tac | acc | ctg | ccc | cca | tcc | cgg | gat | gag | ctg | acc | 432 |
|---|---|---|---|---|---|---|---|---|---|---|---|---|---|---|---|---|
| Arg | Glu | Pro | Gln | Val | Tyr | Thr | Leu | Pro | Pro | Ser | Arg | Asp | Glu | Leu | Thr | |
| | 130 | | | | | 135 | | | | | 140 | | | | | |

| aag | aac | cag | gtc | agc | ctg | acc | tgc | ctg | gtc | aaa | ggc | ttc | tat | ccc | agc | 480 |
|---|---|---|---|---|---|---|---|---|---|---|---|---|---|---|---|---|

```
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac       528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac       576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc       624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag       672
Ser Cys Ser Val Met His Glu Ala Leu His Asn His Tyr Thr Gln Lys
    210                 215                 220 agc ctc tcc ctg tct ccg ggt aaa                                       696
Ser Leu Ser Leu Ser Pro Gly Lys
225                 230

<210> SEQ ID NO 175
<211> LENGTH: 232
<212> TYPE: PRT
<213> ORGANISM: Artificial Sequence
<220> FEATURE:
<223> OTHER INFORMATION: Fc10 immunoglobulin heavy chain constant region

<400> SEQUENCE: 175

Glu Pro Lys Ser Ser Asp Lys Thr His Thr Cys Pro Pro Cys Pro Ala
  1               5                  10                  15

Pro Glu Leu Leu Gly Gly Pro Ser Val Phe Leu Phe Pro Pro Lys Pro
                20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
        50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 176
```

-continued

```
<211> LENGTH: 60
<212> TYPE: DNA
<213> ORGANISM: Artificial Sequence
<220> FEATURE:
<223> OTHER INFORMATION: linker
<220> FEATURE:
<221> NAME/KEY: CDS
<222> LOCATION: (1)...(60)

<400> SEQUENCE: 176 gga ggt ggg ggc tcc ggc ggg ggt gga agc ggt gga ggc ggg tcg ggg     48
Gly Gly Gly Gly Ser Gly Gly Gly Gly Ser Gly Gly Gly Gly Ser Gly
 1               5                  10                  15 ggc gga ggt agt                                                     60
Gly Gly Gly Ser
            20

<210> SEQ ID NO 177
<211> LENGTH: 20
<212> TYPE: PRT
<213> ORGANISM: Artificial Sequence
<220> FEATURE:
<223> OTHER INFORMATION: linker

<400> SEQUENCE: 177

Gly Gly Gly Gly Ser Gly Gly Gly Gly Ser Gly Gly Gly Gly Ser Gly
 1               5                  10                  15

Gly Gly Gly Ser
            20

<210> SEQ ID NO 178
<211> LENGTH: 35
<212> TYPE: PRT
<213> ORGANISM: Artificial Sequence
<220> FEATURE:
<223> OTHER INFORMATION: pre-pro signal sequence from otPA

<400> SEQUENCE: 178

Met Asp Ala Met Lys Arg Gly Leu Cys Cys Val Leu Leu Leu Cys Gly
 1               5                  10                  15

Ala Val Phe Val Ser Leu Ser Gln Glu Ile His Ala Glu Leu Arg Arg
            20                  25                  30

Phe Arg Arg
        35

<210> SEQ ID NO 179
<211> LENGTH: 696
<212> TYPE: DNA
<213> ORGANISM: Artificial Sequence
<220> FEATURE:
<223> OTHER INFORMATION: Fc5 immunoglobulin heavy chain constant region
<220> FEATURE:
<221> NAME/KEY: CDS
<222> LOCATION: (1)...(696)

<400> SEQUENCE: 179 gag ccc aaa tct tca gac aaa act cac aca tgc cca ccg tgc cca gca     48
Glu Pro Lys Ser Ser Asp Lys Thr His Thr Cys Pro Pro Cys Pro Ala
 1               5                  10                  15 cct gaa gcc gag ggg gca ccg tca gtc ttc ctc ttc ccc cca aaa ccc     96
Pro Glu Ala Glu Gly Ala Pro Ser Val Phe Leu Phe Pro Pro Lys Pro
            20                  25                  30 aag gac acc ctc atg atc tcc cgg acc cct gag gtc aca tgc gtg gtg    144
Lys Asp Thr Leu Met Ile Ser Arg Thr Pro Glu Val Thr Cys Val Val
        35                  40                  45 gtg gac gtg agc cac gaa gac cct gag gtc aag ttc aac tgg tac gtg    192
```

```
Val Asp Val Ser His Glu Asp Pro Glu Val Lys Phe Asn Trp Tyr Val
     50                  55                  60 gac ggc gtg gag gtg cat aat gcc aag aca aag ccg cgg gag gag cag      240
Asp Gly Val Glu Val His Asn Ala Lys Thr Lys Pro Arg Glu Glu Gln
 65                  70                  75                  80 tac aac agc acg tac cgt gtg gtc agc gtc ctc acc gtc ctg cac cag      288
Tyr Asn Ser Thr Tyr Arg Val Val Ser Val Leu Thr Val Leu His Gln
                 85                  90                  95 gac tgg ctg aat ggc aag gag tac aag tgc aag gtc tcc aac aaa gcc      336
Asp Trp Leu Asn Gly Lys Glu Tyr Lys Cys Lys Val Ser Asn Lys Ala
             100                 105                 110 ctc cca tcc tcc atc gag aaa acc atc tcc aaa gcc aaa ggg cag ccc      384
Leu Pro Ser Ser Ile Glu Lys Thr Ile Ser Lys Ala Lys Gly Gln Pro
         115                 120                 125 cga gaa cca cag gtg tac acc ctg ccc cca tcc cgg gat gag ctg acc      432
Arg Glu Pro Gln Val Tyr Thr Leu Pro Pro Ser Arg Asp Glu Leu Thr
     130                 135                 140 aag aac cag gtc agc ctg acc tgc ctg gtc aaa ggc ttc tat ccc agc      480
Lys Asn Gln Val Ser Leu Thr Cys Leu Val Lys Gly Phe Tyr Pro Ser
145                 150                 155                 160 gac atc gcc gtg gag tgg gag agc aat ggg cag ccg gag aac aac tac      528
Asp Ile Ala Val Glu Trp Glu Ser Asn Gly Gln Pro Glu Asn Asn Tyr
                165                 170                 175 aag acc acg cct ccc gtg ctg gac tcc gac ggc tcc ttc ttc ctc tac      576
Lys Thr Thr Pro Pro Val Leu Asp Ser Asp Gly Ser Phe Phe Leu Tyr
            180                 185                 190 agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205 tca tgc tcc gtg atg cat gag gct ctg cac aac cac tac acg cag aag      672
Ser Cys Ser Val Met His Glu Ala Leu His Asn His Tyr Thr Gln Lys
    210                 215                 220 agc ctc tcc ctg tct ccg ggt aaa                                      696
Ser Leu Ser Leu Ser Pro Gly Lys
225                 230

<210> SEQ ID NO 180
<211> LENGTH: 232
<212> TYPE: PRT
<213> ORGANISM: Artificial Sequence
<220> FEATURE:
<223> OTHER INFORMATION: Fc5 immunoglobulin heavy chain constant region

<400> SEQUENCE: 180

Glu Pro Lys Ser Ser Asp Lys Thr His Thr Cys Pro Pro Cys Pro Ala
 1               5                  10                  15

Pro Glu Ala Glu Gly Ala Pro Ser Val Phe Leu Phe Pro Pro Lys Pro
             20                  25                  30

Lys Asp Thr Leu Met Ile Ser Arg Thr Pro Glu Val Thr Cys Val Val
         35                  40                  45

Val Asp Val Ser His Glu Asp Pro Glu Val Lys Phe Asn Trp Tyr Val
     50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
             100                 105                 110

Leu Pro Ser Ser Ile Glu Lys Thr Ile Ser Lys Ala Lys Gly Gln Pro
         115                 120                 125
```

```
Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 181
<211> LENGTH: 31
<212> TYPE: PRT
<213> ORGANISM: Artificial Sequence
<220> FEATURE:
<223> OTHER INFORMATION: Murine Il-17RA signal peptide

<400> SEQUENCE: 181

Met Ala Ile Arg Arg Cys Trp Pro Arg Val Val Pro Gly Pro Ala Leu
1               5                   10                  15

Gly Trp Leu Leu Leu Leu Leu Asn Val Leu Ala Pro Gly Arg Ala
            20                  25                  30

<210> SEQ ID NO 182
<211> LENGTH: 1974
<212> TYPE: DNA
<213> ORGANISM: Artificial Sequence
<220> FEATURE:
<221> NAME/KEY: CDS
<222> LOCATION: (1)...(1974)
<220> FEATURE:
<223> OTHER INFORMATION: Exons 1-6 of IL-17RA with an N-terminal Serine
      deletion, exons 8-16 of IL-17RC and Fc5

<400> SEQUENCE: 182 ctg cga ctc ctg gac cac cgg gcg ctg gtc tgc tcc cag ccg ggg cta     48
Leu Arg Leu Leu Asp His Arg Ala Leu Val Cys Ser Gln Pro Gly Leu
1               5                   10                  15 aac tgc acg gtc aag aat agt acc tgc ctg gat gac agc tgg att cac     96
Asn Cys Thr Val Lys Asn Ser Thr Cys Leu Asp Asp Ser Trp Ile His
            20                  25                  30 cct cga aac ctg acc ccc tcc tcc cca aag gac ctg cag atc cag ctg    144
Pro Arg Asn Leu Thr Pro Ser Ser Pro Lys Asp Leu Gln Ile Gln Leu
        35                  40                  45 cac ttt gcc cac acc caa caa gga gac ctg ttc ccc gtg gct cac atc    192
His Phe Ala His Thr Gln Gln Gly Asp Leu Phe Pro Val Ala His Ile
    50                  55                  60 gaa tgg aca ctg cag aca gac gcc agc atc ctg tac ctc gag ggt gca    240
Glu Trp Thr Leu Gln Thr Asp Ala Ser Ile Leu Tyr Leu Glu Gly Ala
65                  70                  75                  80 gag tta tct gtc ctg cag ctg aac acc aat gaa cgt ttg tgc gtc agg    288
Glu Leu Ser Val Leu Gln Leu Asn Thr Asn Glu Arg Leu Cys Val Arg
                85                  90                  95 ttt gag ttt ctg tcc aaa ctg agg cat cac cac agg cgg tgg cgt ttt    336
Phe Glu Phe Leu Ser Lys Leu Arg His His His Arg Arg Trp Arg Phe
            100                 105                 110
```

| | | |
|---|---|---|
| acc ttc agc cac ttt gtg gtt gac cct gac cag gaa tat gag gtg acc<br>Thr Phe Ser His Phe Val Val Asp Pro Asp Gln Glu Tyr Glu Val Thr<br>115                       120                   125 | 384 | |
| gtt cac cac ctg ccc aag ccc atc cct gat ggg gac cca aac cac cag<br>Val His His Leu Pro Lys Pro Ile Pro Asp Gly Asp Pro Asn His Gln<br>    130                  135                   140 | 432 | |
| tcc aag aat ttc ctt gtg cct gac tgt gag cac gcc agg atg aag gta<br>Ser Lys Asn Phe Leu Val Pro Asp Cys Glu His Ala Arg Met Lys Val<br>145                       150                155                 160 | 480 | |
| acc acg cca tgc atg agc tca gcc ctg ccc tgg ctc aac gtg tca gca<br>Thr Thr Pro Cys Met Ser Ser Ala Leu Pro Trp Leu Asn Val Ser Ala<br>                 165                  170               175 | 528 | |
| gat ggt gac aac gtg cat ctg gtt ctg aat gtc tct gag gag cag cac<br>Asp Gly Asp Asn Val His Leu Val Leu Asn Val Ser Glu Glu Gln His<br>          180                   185                 190 | 576 | |
| ttc ggc ctc tcc ctg tac tgg aat cag gtc cag ggc ccc cca aaa ccc<br>Phe Gly Leu Ser Leu Tyr Trp Asn Gln Val Gln Gly Pro Pro Lys Pro<br>             195                 200               205 | 624 | |
| cgg tgg cac aaa aac ctg act gga ccg cag atc att acc ttg aac cac<br>Arg Trp His Lys Asn Leu Thr Gly Pro Gln Ile Ile Thr Leu Asn His<br> 210                      215                   220 | 672 | |
| aca gac ctg gtt ccc tgc ctc tgt att cag gtg tgg cct ctg gaa cct<br>Thr Asp Leu Val Pro Cys Leu Cys Ile Gln Val Trp Pro Leu Glu Pro<br>225                      230                235               240 | 720 | |
| gac tcc gtt agg acg aac atc tgc ccc ttc agg gag gac ccc cgc gca<br>Asp Ser Val Arg Thr Asn Ile Cys Pro Phe Arg Glu Asp Pro Arg Ala<br>                     245                 250               255 | 768 | |
| cac cag aac ctc tgg caa gcc gcc cga ctg cga ctg ctg acc ctg cag<br>His Gln Asn Leu Trp Gln Ala Ala Arg Leu Arg Leu Leu Thr Leu Gln<br>        260                   265                 270 | 816 | |
| agc tgg ctg ctg gac gca ccg tgc tcg ctg ccc gca gaa gcg gca ctg<br>Ser Trp Leu Leu Asp Ala Pro Cys Ser Leu Pro Ala Glu Ala Ala Leu<br>     275                   280                 285 | 864 | |
| tgc tgg cgg gct ccg ggt ggg gac ccc tgc cag cca ctg gtc cca ccg<br>Cys Trp Arg Ala Pro Gly Gly Asp Pro Cys Gln Pro Leu Val Pro Pro<br> 290                      295                   300 | 912 | |
| ctt tcc tgg gag aac gtc act gtg gac aag gtt ctc gag ttc cca ttg<br>Leu Ser Trp Glu Asn Val Thr Val Asp Lys Val Leu Glu Phe Pro Leu<br>305                      310                315               320 | 960 | |
| ctg aaa ggc cac cct aac ctc tgt gtt cag gtg aac agc tcg gag aag<br>Leu Lys Gly His Pro Asn Leu Cys Val Gln Val Asn Ser Ser Glu Lys<br>                   325                 330               335 | 1008 | |
| ctg cag ctg cag gag tgc ttg tgg gct gac tcc ctg ggg cct ctc aaa<br>Leu Gln Leu Gln Glu Cys Leu Trp Ala Asp Ser Leu Gly Pro Leu Lys<br>        340                   345                 350 | 1056 | |
| gac gat gtg cta ctg ttg gag aca cga ggc ccc cag gac aac aga tcc<br>Asp Asp Val Leu Leu Leu Glu Thr Arg Gly Pro Gln Asp Asn Arg Ser<br>     355                   360                 365 | 1104 | |
| ctc tgt gcc ttg gaa ccc agt ggc tgt act tca cta ccc agc aaa gcc<br>Leu Cys Ala Leu Glu Pro Ser Gly Cys Thr Ser Leu Pro Ser Lys Ala<br> 370                      375                380 | 1152 | |
| tcc acg agg gca gct cgc ctt gga gag tac tta cta caa gac ctg cag<br>Ser Thr Arg Ala Ala Arg Leu Gly Glu Tyr Leu Leu Gln Asp Leu Gln<br>385                      390                395               400 | 1200 | |
| tca ggc cag tgt ctg cag cta tgg gac gat gac ttg gga gcg cta tgg<br>Ser Gly Gln Cys Leu Gln Leu Trp Asp Asp Asp Leu Gly Ala Leu Trp<br>                   405                 410               415 | 1248 | |
| gcc tgc ccc atg gac aaa tac atc cac aag gag ccc aaa tct tca gac<br>Ala Cys Pro Met Asp Lys Tyr Ile His Lys Glu Pro Lys Ser Ser Asp<br>        420                   425                 430 | 1296 | |

```
aaa act cac aca tgc cca ccg tgc cca gca cct gaa gcc gag ggg gca        1344
Lys Thr His Thr Cys Pro Pro Cys Pro Ala Pro Glu Ala Glu Gly Ala
        435                 440                 445 ccg tca gtc ttc ctc ttc ccc cca aaa ccc aag gac acc ctc atg atc        1392
Pro Ser Val Phe Leu Phe Pro Pro Lys Pro Lys Asp Thr Leu Met Ile
    450                 455                 460 tcc cgg acc cct gag gtc aca tgc gtg gtg gtg gac gtg agc cac gaa        1440
Ser Arg Thr Pro Glu Val Thr Cys Val Val Val Asp Val Ser His Glu
465                 470                 475                 480 gac cct gag gtc aag ttc aac tgg tac gtg gac ggc gtg gag gtg cat        1488
Asp Pro Glu Val Lys Phe Asn Trp Tyr Val Asp Gly Val Glu Val His
                485                 490                 495 aat gcc aag aca aag ccg cgg gag gag cag tac aac agc acg tac cgt        1536
Asn Ala Lys Thr Lys Pro Arg Glu Glu Gln Tyr Asn Ser Thr Tyr Arg
            500                 505                 510 gtg gtc agc gtc ctc acc gtc ctg cac cag gac tgg ctg aat ggc aag        1584
Val Val Ser Val Leu Thr Val Leu His Gln Asp Trp Leu Asn Gly Lys
        515                 520                 525 gag tac aag tgc aag gtc tcc aac aaa gcc ctc cca tcc tcc atc gag        1632
Glu Tyr Lys Cys Lys Val Ser Asn Lys Ala Leu Pro Ser Ser Ile Glu
    530                 535                 540 aaa acc atc tcc aaa gcc aaa ggg cag ccc cga gaa cca cag gtg tac        1680
Lys Thr Ile Ser Lys Ala Lys Gly Gln Pro Arg Glu Pro Gln Val Tyr
545                 550                 555                 560 acc ctg ccc cca tcc cgg gat gag ctg acc aag aac cag gtc agc ctg        1728
Thr Leu Pro Pro Ser Arg Asp Glu Leu Thr Lys Asn Gln Val Ser Leu
                565                 570                 575 acc tgc ctg gtc aaa ggc ttc tat ccc agc gac atc gcc gtg gag tgg        1776
Thr Cys Leu Val Lys Gly Phe Tyr Pro Ser Asp Ile Ala Val Glu Trp
            580                 585                 590 gag agc aat ggg cag ccg gag aac aac tac aag acc acg cct ccc gtg        1824
Glu Ser Asn Gly Gln Pro Glu Asn Asn Tyr Lys Thr Thr Pro Pro Val
        595                 600                 605 ctg gac tcc gac ggc tcc ttc ttc ctc tac agc aag ctc acc gtg gac        1872
Leu Asp Ser Asp Gly Ser Phe Phe Leu Tyr Ser Lys Leu Thr Val Asp
    610                 615                 620 aag agc agg tgg cag cag ggg aac gtc ttc tca tgc tcc gtg atg cat        1920
Lys Ser Arg Trp Gln Gln Gly Asn Val Phe Ser Cys Ser Val Met His
625                 630                 635                 640 gag gct ctg cac aac cac tac acg cag aag agc ctc tcc ctg tct ccg        1968
Glu Ala Leu His Asn His Tyr Thr Gln Lys Ser Leu Ser Leu Ser Pro
                645                 650                 655 ggt aaa                                                                1974
Gly Lys <210> SEQ ID NO 183
<211> LENGTH: 658
<212> TYPE: PRT
<213> ORGANISM: Artificial Sequence
<220> FEATURE:
<223> OTHER INFORMATION: Exons 1-6 of IL-17RA with an N-terminal Serine
      deletion, exons 8-16 of IL-17RC and Fc5

<400> SEQUENCE: 183

Leu Arg Leu Leu Asp His Arg Ala Leu Val Cys Ser Gln Pro Gly Leu
1               5                   10                  15

Asn Cys Thr Val Lys Asn Ser Thr Cys Leu Asp Asp Ser Trp Ile His
                20                  25                  30

Pro Arg Asn Leu Thr Pro Ser Ser Pro Lys Asp Leu Gln Ile Gln Leu
            35                  40                  45

His Phe Ala His Thr Gln Gln Gly Asp Leu Phe Pro Val Ala His Ile
```

-continued

```
            50                  55                  60
Glu Trp Thr Leu Gln Thr Asp Ala Ser Ile Leu Tyr Leu Glu Gly Ala
 65                  70                  75                  80

Glu Leu Ser Val Leu Gln Leu Asn Thr Asn Glu Arg Leu Cys Val Arg
                 85                  90                  95

Phe Glu Phe Leu Ser Lys Leu Arg His His Arg Arg Trp Arg Phe
                100                 105                 110

Thr Phe Ser His Phe Val Val Asp Pro Asp Gln Glu Tyr Glu Val Thr
            115                 120                 125

Val His His Leu Pro Lys Pro Ile Pro Asp Gly Asp Pro Asn His Gln
    130                 135                 140

Ser Lys Asn Phe Leu Val Pro Asp Cys Glu His Ala Arg Met Lys Val
145                 150                 155                 160

Thr Thr Pro Cys Met Ser Ser Ala Leu Pro Trp Leu Asn Val Ser Ala
                165                 170                 175

Asp Gly Asp Asn Val His Leu Val Leu Asn Val Ser Glu Glu Gln His
            180                 185                 190

Phe Gly Leu Ser Leu Tyr Trp Asn Gln Val Gln Gly Pro Pro Lys Pro
        195                 200                 205

Arg Trp His Lys Asn Leu Thr Gly Pro Gln Ile Ile Thr Leu Asn His
    210                 215                 220

Thr Asp Leu Val Pro Cys Leu Cys Ile Gln Val Trp Pro Leu Glu Pro
225                 230                 235                 240

Asp Ser Val Arg Thr Asn Ile Cys Pro Phe Arg Glu Asp Pro Arg Ala
                245                 250                 255

His Gln Asn Leu Trp Gln Ala Ala Arg Leu Arg Leu Leu Thr Leu Gln
            260                 265                 270

Ser Trp Leu Leu Asp Ala Pro Cys Ser Leu Pro Ala Glu Ala Ala Leu
        275                 280                 285

Cys Trp Arg Ala Pro Gly Gly Asp Pro Cys Gln Pro Leu Val Pro Pro
    290                 295                 300

Leu Ser Trp Glu Asn Val Thr Val Asp Lys Val Leu Glu Phe Pro Leu
305                 310                 315                 320

Leu Lys Gly His Pro Asn Leu Cys Val Gln Val Asn Ser Ser Glu Lys
                325                 330                 335

Leu Gln Leu Gln Glu Cys Leu Trp Ala Asp Ser Leu Gly Pro Leu Lys
            340                 345                 350

Asp Asp Val Leu Leu Leu Glu Thr Arg Gly Pro Gln Asp Asn Arg Ser
        355                 360                 365

Leu Cys Ala Leu Glu Pro Ser Gly Cys Thr Ser Leu Pro Ser Lys Ala
    370                 375                 380

Ser Thr Arg Ala Ala Arg Leu Gly Glu Tyr Leu Leu Gln Asp Leu Gln
385                 390                 395                 400

Ser Gly Gln Cys Leu Gln Leu Trp Asp Asp Leu Gly Ala Leu Trp
                405                 410                 415

Ala Cys Pro Met Asp Lys Tyr Ile His Lys Glu Pro Lys Ser Ser Asp
            420                 425                 430

Lys Thr His Thr Cys Pro Pro Cys Pro Ala Pro Glu Ala Glu Gly Ala
        435                 440                 445

Pro Ser Val Phe Leu Phe Pro Pro Lys Pro Lys Asp Thr Leu Met Ile
    450                 455                 460

Ser Arg Thr Pro Glu Val Thr Cys Val Val Val Asp Val Ser His Glu
465                 470                 475                 480
```

```
Asp Pro Glu Val Lys Phe Asn Trp Tyr Val Asp Gly Val Glu Val His
            485                 490                 495
Asn Ala Lys Thr Lys Pro Arg Glu Glu Gln Tyr Asn Ser Thr Tyr Arg
            500                 505                 510
Val Val Ser Val Leu Thr Val Leu His Gln Asp Trp Leu Asn Gly Lys
            515                 520                 525
Glu Tyr Lys Cys Lys Val Ser Asn Lys Ala Leu Pro Ser Ser Ile Glu
            530                 535                 540
Lys Thr Ile Ser Lys Ala Lys Gly Gln Pro Arg Glu Pro Gln Val Tyr
545                 550                 555                 560
Thr Leu Pro Pro Ser Arg Asp Glu Leu Thr Lys Asn Gln Val Ser Leu
            565                 570                 575
Thr Cys Leu Val Lys Gly Phe Tyr Pro Ser Asp Ile Ala Val Glu Trp
            580                 585                 590
Glu Ser Asn Gly Gln Pro Glu Asn Asn Tyr Lys Thr Thr Pro Pro Val
            595                 600                 605
Leu Asp Ser Asp Gly Ser Phe Phe Leu Tyr Ser Lys Leu Thr Val Asp
            610                 615                 620
Lys Ser Arg Trp Gln Gln Gly Asn Val Phe Ser Cys Ser Val Met His
625                 630                 635                 640
Glu Ala Leu His Asn His Tyr Thr Gln Lys Ser Leu Ser Leu Ser Pro
            645                 650                 655
Gly Lys

<210> SEQ ID NO 184
<211> LENGTH: 96
<212> TYPE: DNA
<213> ORGANISM: Homo sapiens
<220> FEATURE:
<221> NAME/KEY: CDS
<222> LOCATION: (1)...(96)

<400> SEQUENCE: 184 atg ggg gcc gca cgc agc ccg ccg tcc gct gtc ccg ggg ccc ctg ctg    48
Met Gly Ala Ala Arg Ser Pro Pro Ser Ala Val Pro Gly Pro Leu Leu
1               5                   10                  15 ggg ctg ctc ctg ctg ctc ctg ggc gtg ctg gcc ccg ggt ggc gcc tcc    96
Gly Leu Leu Leu Leu Leu Leu Gly Val Leu Ala Pro Gly Gly Ala Ser
                20                  25                  30

<210> SEQ ID NO 185
<211> LENGTH: 32
<212> TYPE: PRT
<213> ORGANISM: Homo sapiens

<400> SEQUENCE: 185

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

<210> SEQ ID NO 186
<211> LENGTH: 492
<212> TYPE: DNA
<213> ORGANISM: Artificial Sequence
<220> FEATURE:
<223> OTHER INFORMATION: IL17A CH6 coding sequence

<400> SEQUENCE: 186
atgactcctg ggaagacctc attggtgtca ctgctactgc tgctgagcct ggaggccata    60
```

```
gtgaaggcag gaatcacaat cccacgaaat ccaggatgcc caaattctga ggacaagaac    120
ttcccccgga ctgtgatggt caacctgaac atccataacc ggaataccaa taccaatccc    180
aaaaggtcct cagattacta caaccgatcc acctcacctt ggaatctcca ccgcaatgag    240
gaccctgaga gatatccctc tgtgatctgg gaggcaaagt gccgccactt gggctgcatc    300
aacgctgatg ggaacgtgga ctaccacatg aactctgtcc ccatccagca agagatcctg    360
gtcctgcgca gggagcctcc acactgcccc aactccttcc ggctggagaa gatactggtg    420
tccgtgggct gcacctgtgt caccccgatt gtccaccatg tggcctccgg acaccatcac    480
catcatcatt aa                                                        492

<210> SEQ ID NO 187
<211> LENGTH: 163
<212> TYPE: PRT
<213> ORGANISM: Artificial Sequence
<220> FEATURE:
<223> OTHER INFORMATION: IL17A-CH6

<400> SEQUENCE: 187

Met Thr Pro Gly Lys Thr Ser Leu Val Ser Leu Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala Ser Gly His His His
145                 150                 155                 160

His His His

<210> SEQ ID NO 188
<211> LENGTH: 519
<212> TYPE: DNA
<213> ORGANISM: Artificial Sequence
<220> FEATURE:
<223> OTHER INFORMATION: IL17F-CEE coding sequence

<400> SEQUENCE: 188
atgacagtga agaccctgca tggcccagcc atggtcaagt acttgctgct gtcgatattg     60
gggcttgcct ttctgagtga ggcggcagct cggaaaatcc ccaaagtagg acatactttt    120
ttccaaaagc ctgagagttg cccgcctgtg ccaggaggta gtatgaagct tgacattggc    180
atcatcaatg aaaaccagcg cgtttccatg tcacgtaaca tcgagagccg ctccacctcc    240
ccctggaatt acactgtcac ttgggacccc aacggtacc ctcgaagt tgtacaggcc    300 cagtgtagga acttgggctg catcaatgct caaggaaagg aagacatctc catgaattcc    360
```

```
-continued gttcccatcc agcaagagac cctggtcgtc cggaggaagc accaaggctg ctctgtttct    420
ttccagttgg agaaggtgct ggtgactgtt ggctgcacct gcgtcacccc tgtcatccac    480
catgtgcagt ccggagaaga atatatgccc atggaataa                          519

<210> SEQ ID NO 189
<211> LENGTH: 172
<212> TYPE: PRT
<213> ORGANISM: Artificial Sequence
<220> FEATURE:
<223> OTHER INFORMATION: IL17F-CEE

<400> SEQUENCE: 189

Met Thr Val Lys Thr Leu His Gly Pro Ala Met Val Lys Tyr Leu Leu
1               5                   10                  15

Leu Ser Ile Leu Gly Leu Ala Phe Leu Ser Glu Ala Ala Ala Arg Lys
                20                  25                  30

Ile Pro Lys Val Gly His Thr Phe Phe Gln Lys Pro Glu Ser Cys Pro
            35                  40                  45

Pro Val Pro Gly Gly Ser Met Lys Leu Asp Ile Gly Ile Ile Asn Glu
        50                  55                  60

Asn Gln Arg Val Ser Met Ser Arg Asn Ile Glu Ser Arg Ser Thr Ser
65                  70                  75                  80

Pro Trp Asn Tyr Thr Val Thr Trp Asp Pro Asn Arg Tyr Pro Ser Glu
                85                  90                  95

Val Val Gln Ala Gln Cys Arg Asn Leu Gly Cys Ile Asn Ala Gln Gly
            100                 105                 110

Lys Glu Asp Ile Ser Met Asn Ser Val Pro Ile Gln Gln Glu Thr Leu
        115                 120                 125

Val Val Arg Arg Lys His Gln Gly Cys Ser Val Ser Phe Gln Leu Glu
    130                 135                 140

Lys Val Leu Val Thr Val Gly Cys Thr Cys Val Thr Pro Val Ile His
145                 150                 155                 160

His Val Gln Ser Gly Glu Glu Tyr Met Pro Met Glu
                165                 170

<210> SEQ ID NO 190
<211> LENGTH: 7
<212> TYPE: PRT
<213> ORGANISM: Artificial Sequence
<220> FEATURE:
<223> OTHER INFORMATION: EE tag

<400> SEQUENCE: 190

Glu Glu Tyr Met Pro Met Glu
1               5
```

METHODS OF TREATING INFLAMMATION USING SOLUBLE IL-17RA/RC FUSION PROTEINS

CROSS-REFERENCE TO RELATED APPLICATIONS

The present application is a continuation of U.S. patent application Ser. No. 12/828,041, filed Jun. 30, 2011, which is a divisional of U.S. patent application Ser. No. 12/055,597, filed Mar. 26, 2008, now U.S. Pat. No. 7,790,676, which claims the benefit of U.S. Provisional Patent Application Nos. 60/983,822, filed Oct. 30, 2007, and 60/908,554, filed Mar. 28, 2007, each of which is herein incorporated by reference in its entirety.

BACKGROUND OF THE INVENTION

Cytokines are soluble, small proteins that mediate a variety of biological effects, including the regulation of the growth and differentiation of many cell types (see, for example, Arai et al., *Annu. Rev. Biochem.* 59:783 (1990); Mosmann, *Curr. Opin. Immunol.* 3:311 (1991); Paul and Seder, *Cell* 76:241 (1994)). Proteins that constitute the cytokine group include interleukins, interferons, colony stimulating factors, tumor necrosis factors, and other regulatory molecules. For example, human interleukin-17 is a cytokine which stimulates the expression of interleukin-6, intracellular adhesion molecule 1, interleukin-8, granulocyte macrophage colony-stimulating factor, and prostaglandin E2 expression, and plays a role in the preferential maturation of $CD34^+$ hematopoietic precursors into neutrophils (Yao et al., *J. Immunol.* 155:5483 (1995); Fossiez et al., *J. Exp. Med.* 183:2593 (1996)).

Receptors that bind cytokines are typically composed of one or more integral membrane proteins that bind the cytokine with high affinity and transduce this binding event to the cell through the cytoplasmic portions of the certain receptor subunits. Cytokine receptors have been grouped into several classes on the basis of similarities in their extracellular ligand binding domains.

The demonstrated in vivo activities of cytokines and their receptors illustrate the clinical potential of, and need for, other cytokines, cytokine receptors, cytokine agonists, and cytokine antagonists. For example, demonstrated in vivo activities of the pro-inflammatory cytokine family illustrates the enormous clinical potential of, and need for antagonists of pro-inflammatory molecules.

BRIEF DESCRIPTION OF THE DRAWINGS

FIGS. 1A and 1B are graphic representations of the exon structure of human IL-17RCx1 (SEQ ID NO:2). For those amino acid where codon was spliced by exon/intron junction, the junction was moved to include the entire codon.

FIGS. 2A and 2B are graphic representations of the exon structure of human IL-17RCx4 (SEQ ID NO:166).

FIG. 3 is a graphic representation of the exon structure of human IL-17RA (SEQ ID NO:21).

FIGS. 4A and 4B are graphic representations of the exon structure of a preferred soluble polypeptide of the present invention as described herein and in SEQ ID NOs:157 and 158. This soluble polypeptide comprises exons from both human IL-17RA (SEQ ID NO:21) and human IL-17RCx1 (SEQ ID NO:2).

DETAILED DESCRIPTION OF THE INVENTION

Figure 5:
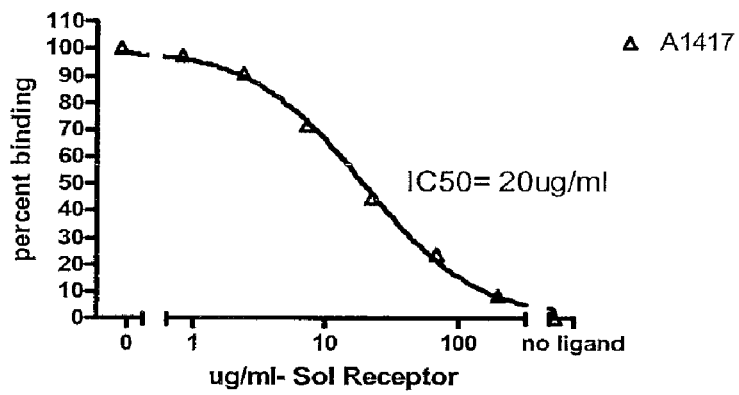
FIG. 5 is a graphical representation of a typical assay result using the protocol outlined in Example 34. The graph was generated using the Prizm software program. The Y values represent the MFI normalized to maximum and minimum (100% and 0%) based on ligand only and no ligand/no soluble receptor control wells, and thus the percent binding of the ligand to the cells. The software calculates the IC50 for each curve.

The present invention addresses these needs by providing antagonists to pro-inflammatory cytokines IL-17A and IL-17F. Specifically, the pro-inflammatory cytokines IL-17A and IL-17F have a high degree of sequence similarity, share many biological properties, and are both produced by activated T cells. They have both been implicated as factors that contribute to the progression of various autoimmune and inflammatory diseases including rheumatoid arthritis and asthma. In fact, reagents that negate IL-17A function significantly ameliorate disease incidence and severity in several mouse models of human disease. IL-17A mediates its effects through interaction with its cognate receptor, the IL-17 receptor (IL-17R), but the receptor for IL-17F had not yet been identified. Previously, we had reported that IL-17RC is a receptor for both IL-17A and IL-17F, and binds both with a similar high affinity. IL-17R on the other hand, binds IL-17A with high affinity, but binds IL-17F with very low affinity. Consistent with this, it has been shown that a soluble form of IL-17R blocks IL-17A binding and signaling in cells expressing either receptor, but does not interfere with binding or function of IL-17F to IL-17RC.

Since IL-17A intervention has been proposed as an effective therapy for several auto-immune diseases, using the antagonists of the present invention, which may block, inhibit, reduce, antagonize or neutralize the activity of IL-17A, IL-17F, or both IL-17A and IL-17F, which include soluble IL-17RC and IL-17RC/IL-17RA receptors, will have advantages over therapies that target only one of these two cytokines. The invention further provides uses therefor in inflammatory disease, as well as related compositions and methods.

A) Overview

Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines, i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)—CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through the TCR, activation of T cells involves additional costimulation induced by cytokines released by the antigen presenting cell or through interactions with membrane bound molecules on the antigen presenting cell and the T cell. The cytokines IL-1 and IL-6 have been shown to provide a costimulatory signal. Also, the interaction between the B7 molecule expressed on the surface of an antigen presenting cell and CD28 and CTLA-4 molecules expressed on the T cell surface effect T cell activation. Activated T cells express an increased number of cellular adhesion molecules, such as ICAM-1, integrins, VLA-4, LFA-1, CD56, etc.

T-cell proliferation in a mixed lymphocyte culture or mixed lymphocyte reaction (MLR) is an established indication of the ability of a compound to stimulate the immune system. In many immune responses, inflammatory cells infiltrate the site of injury or infection. The migrating cells may be neutrophilic, eosinophilic, monocytic or lymphocytic as can be determined by histologic examination of the affected tissues. See *Current Protocols in Immunology*, ed. John E. Coligan, 1994, John Wiley & Sons, Inc.

Immune related diseases could be treated by suppressing the immune response. Using soluble receptors and/or neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Interleukin-17 (IL-17A) has been identified as a cellular ortholog of a protein encoded by the T lymphotropic Herpes virus Saimiri (HSV) (see Rouvier et al., *J. Immunol.*, 150(12): 5445-5456 (1993); Yao et al., *J. Immunol.*, 122(12):5483-5486 (1995) and Yao et al., *Immunity*, 3(6):811-821 (1995)). Subsequent characterization has shown that this protein is a potent cytokine that acts to induce proinflammatory responses in a wide variety of peripheral tissues. IL-17A is a disulfide-linked homodimeric cytokine of about 32 kDa which is synthesized and secreted only by $CD4^+$ activated memory T cells (reviewed in Fossiez et al., *Int. Rev. Immunol.*, 16:541-551 (1998)). Specifically, IL-17 is synthesized as a precursor polypeptide of 155 amino acids with an N-terminal signal sequence of 19-23 residues and is secreted as a disulfide-linked homodimeric glycoprotein. Il-17A is disclosed in WO9518826 (1995), WO9715320 (1997) and WO9704097 (1997), as well as U.S. Pat. No. 6,063,372.

Despite its restricted tissue distribution, IL-17A exhibits pleitropic biological activities on various types of cells. IL-17A has been found to stimulate the production of many cytokines. It induces the secretion of IL-6, IL-8, IL-12, leukemia inhibitory factor (LIF), prostaglandin E2, MCP-1 and G-CSF by adherent cells like fibroblasts, keratinocytes, epithelial and endothelial cells. IL-17A also has the ability to induce ICAM-1 surface expression, proliferation of T cells, and growth and differentiation of $CD34^+$ human progenitors into neutrophils. IL-17A has also been implicated in bone metabolism, and has been suggested to play an important role in pathological conditions characterized by the presence of activated T cells and TNF-α production such as rheumatoid arthritis and loosening of bone implants (Van Bezooijen et al., *J. Bone Miner. Res.* 14:1513-1521 (1999)). Activated T cells of synovial tissue derived from rheumatoid arthritis patients were found to secrete higher amounts of IL-17A than those derived from normal individuals or osteoarthritis patients (Chabaud et al., *Arthritis Rheum.* 42:963-970 (1999)). It was suggested that this proinflammatory cytokine actively contributes to synovial inflammation in rheumatoid arthritis. Apart from its proinflammatory role, IL-17A seems to contribute to the pathology of rheumatoid arthritis by yet another mechanism. For example, IL-17A has been shown to induce the expression of osteoclast differentiation factor (ODF) mRNA in osteoblasts (Kotake et al., *J. Clin. Invest.*, 103: 1345-1352 (1999)). ODF stimulates differentiation of progenitor cells into osteoclasts, the cells involved in bone resorption.

Since the level of IL-17A is significantly increased in synovial fluid of rheumatoid arthritis patients, it appears that IL-17A induced osteoclast formation plays a crucial role in bone resorption in rheumatoid arthritis. IL-17A is also believed to play a key role in certain other autoimmune disorders such as multiple sclerosis (Matusevicius et al., *Mult. Scler.*, 5:101-104 (1999)). IL-17A has further been shown, by intracellular signalling, to stimulate $Ca^{2+}$ influx and a reduction in [cAMP], in human macrophages (Jovanovic et al., *J. Immunol.*, 160:3513 (1998)). Fibroblasts treated with IL-17A induce the activation of NF-κB, (Yao et al., *Immunity*, 3:811 (1995), Jovanovic et al., supra), while macrophages treated with it activate NF-κB and mitogen-activated protein kinases (Shalom-Barek et al., *J. Biol. Chem.*, 273:27467 (1998)).

Additionally, IL-17A also shares sequence similarity with mammalian cytokine-like factor 7 that is involved in bone and cartilage growth. Other proteins with which IL-17A polypeptides share sequence similarity are human embryo-derived interleukin-related factor (EDIRF) and interleukin-20.

Consistent with IL-17A's wide-range of effects, the cell surface receptor for IL-17A has been found to be widely expressed in many tissues and cell types (Yao et al., Cytokine, 9:794 [1997]). While the amino acid sequence of the human IL-17A receptor (IL-17R) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17A itself to other known proteins indicates that IL-17A and its receptor may be part of a novel family of signalling proteins and receptors. It has been demonstrated that IL-17A activity is mediated through binding to its unique cell surface receptor, wherein previous studies have shown that contacting T cells with a soluble form of the IL-17A receptor polypeptide inhibited T cell proliferation and IL-2 production induced by PHA, concanavalin A and anti-TCR monoclonal antibody (Yao et al., J. Immunol., 155: 5483-5486 (1995)). As such, there is significant interest in identifying and characterizing novel polypeptides having homology to the known cytokine receptors, specifically IL-17A receptors.

The expression pattern of IL-17F appears to be similar to that of IL-17A, such that it includes only activated CD4+ T cells and monocytes (Starnes et al. *J. Immunol.* 167:4137-4140 (2001)). IL-17F has been demonstrated to induce G-CSF, IL-6, and IL-8 in fibroblasts (Hymowitz et al, *EMBO J.* 20:5322-5341 (2001)) and TGF-β in endothelial cells (Starnes et al. *J. Immunol.* 167: 4137-4140 (2001)). It has recently been reported that IL-23, a cytokine produced by dendritic cell, can mediate the production of both IL-17A and IL-17F, primarily in memory T cells (Aggarwal et al. *J. Biol. Chem.* 278:1910-1914 (2003)).

Moreover, over expression or upregulation of both IL-17A and IL-17F have been shown in arthritic and asthmatic individuals (reviewed in Moseley et al., *Cytokine Growth Factor Rev* 14:155-174 (2003)). With regards to arthritis, these cytokines act in a manner characteristic to the cartilage and joint destruction that is associated with rheumatoid- and osteo-arthritis. For example, IL-17A and IL-17F have been demonstrated to enhance matrix degradation in articular cartilage explants via release of cartilage proteoglycan glycosaminoglycans and collagen fragments, while inhibiting the synthesis of new proteoglycans and collagens (Cai et al., *Cytokine* 16:10-21 (2001); Attur et al., *Arthritis Rheum* 44:2078-2083 (2001)).

Similar to IL-17A, overexpression of IL-17F in mice has also been shown to increase lung neutrophil recruitment and result in increased expression of Th1-associated cytokines in the lung, including IL-6, IFN-gamma, IP-10 and MIG (Starnes et al., *J. Immunol.* 167:4137-4140 (2001)). IL-17F was also upregulated in T cells from allergen-challenged asthmatics (Kawaguchi et al., *J. Immunol.* 167:4430-4435 (2001)), and found to induce IL-6 and IL-8 production in NHBE. In contrast to IL-17A, IL-17F appears to inhibit angiogenesis in vitro (Starnes et al., *J. Immunol.* 167:4137-4140 (2001)).

IL-17F mRNA was not detected by northern blot in various human tissues but was dramatically induced upon activation of CD4$^+$ T cells and monocytes. (Id.) In mice, Th2 cells and mast cells were found to express IL-17F upon activation. (See Dumont, *Expert Opin. Ther. Patents* 13(3) (2003).) Like IL-17A, the expression of IL-17F was also found to be upregulated by IL-23 in mouse.

The Il-17 cytokine/receptor families appear to represent a unique signaling system within the cytokine network that will offer innovative approaches to the manipulation of immune and inflammatory responses. Accordingly, the present invention is based on the discovery of a new IL-17 family receptor, IL-17RC and its ability to bind both IL-17A and IL-17F.

IL-17RC was initially identified using a bioinformatics approach to search for proteins related to IL-17RA and identified through a cDNA encoding the IL-17 receptor-related protein IL-17RC. In spite of its obvious similarity to the IL-17 receptor (IL-17RA), which binds to the prototypical member of the IL-17 family IL-17A, and the identification of five other members of the IL-17 cytokine family, a specific ligand for IL-17RC had not been previously reported. However, IL-17A and IL-17F were identified as the specific ligands for IL-17RC as described in U.S. patent application Ser. No. 11/150,533, filed on Jun. 10, 2005 and published as US Patent Publication No. 20060002925. Specifically, these ligands were identified using Baby Hamster Kidney cells (BHK) that were stably transfected with constructs encoding either human IL-17RA (hIL-17RA) or IL-17RC (hIL-17RC). Expression of receptors on the surface was confirmed by FACS analysis using either a monoclonal antibody to hIL-17RA or a polyclonal antiserum to hIL-17RC. To assess cytokine binding, biotinylated forms of human IL-17A, C, D, E, and F and fluorochrome-conjugated streptavidin were used to detect cytokine binding to transfected cells by flow cytometry. The results clearly showed that stably transfected BHK cells expressing hIL-17RA clearly bound human IL-17A (hIL-17A) as expected, whereas those transfected with empty expression vector failed to bind any members of the IL-17 family tested. Relatively weak binding of human IL-17F (hIL-17F) to hIL-17RA-transfected cells was also observed, but there was no significant binding of other members of the IL-17 family tested. Other IL-17 family members were examined for binding of to hIL-17RC-transfected cells and it was noted that these cells showed significant binding to hIL-17F. In addition, significant binding of hIL-17A to these cells was seen, but no binding of hIL-17C, D, or E. This data proved that hIL-17RC was the receptor for both hIL-17F and hIL-17A.

Additionally, the level of fluorescence over a range of cytokine concentrations was examined to determine relative affinities of hIL-17A and F for hIL-17RA and hIL-17RC. By comparing mean fluorescence intensities of the individual cytokines on each transfectant, it was noted that hIL-17A bound much better to hIL-17RA than hIL-17F did, but that both cytokines seemed to bind equally well to hIL-17RC-transfected cells. Interestingly, cytokine binding to cells that expressed both receptors seemed to be additive, with no evidence of cooperativity.

Next, the specificity of this binding was investigated by attempting to compete for binding with unlabeled cytokine. Transfected BHK cells were incubated with a fixed concentration of biotinylated cytokine and increasing concentrations of unlabeled cytokine and the amount of bound biotinylated material was quantitated by FACS. It was shown that the binding of both hIL-17A and F to hIL-17RC was specific since increasing concentrations of unlabeled cytokine interfered with binding of the biotinylated material. In fact, unlabeled hIL-17A and F effectively cross-competed for binding of biotinylated forms of both cytokines to hIL-17RC-transfected cells, suggesting that the two cytokines were binding hIL-17RC with similar affinities, and that they were binding to overlapping, if not identical sites. Uunlabeled hIL-17A also effectively competed for binding of both biotinylated hIL-17A and F to hIL-17RA-transfected cells, while unlabeled hIL-17F showed essentially no ability to compete for hIL-17A binding to hIL-17RA. This indicated that although hIL-17F showed specific binding to hIL-17RA, the avidity of this interaction appeared to be significantly lower than the interaction of hIL-17A and hIL-17RA.

Saturation binding studies were done to measure the affinity of hIL-17A and F binding to hIL-17RC and hIL-17RA. BHK cell lines stably expressing hIL-17RA or hIL-17RC were incubated with iodinated hIL-17A or F under saturation binding conditions to determine the affinity constants of each cytokine for each receptor. hIL-17A bound both hIL-17RA and hIL-17RC with comparable affinities (Table 1). Specifically, BHK cells transfected with the indicated receptor were used to establish $K_d$ values for hIL-17 A and hIL-17F as described in Methods. Results shown are mean $K_d$ values derived from triplicate determinations.

TABLE 1

|  | hIL-17A | hIL-17F |
| --- | --- | --- |
| hIL-17RC (x1)[1] | 0.6 nM | 1.0 nM |
| hIL-17RA | 1.9 nM | 1.5 µM |

[1]Denotes the x1 splice variant of hIL-17RC.

In addition, the affinity of hIL-17F for hIL-17RC was very similar to the affinity of hIL-17A for this receptor (see Table 1 above). However, consistent with results obtained using biotinylated cytokines, the affinity of hIL-17F for hIL-17RA was roughly 1000-fold lower relative to other affinities measured (Id.). This indicates that hIL-17A and F bind hIL-17RC with similar affinities, but their affinities for hIL-17RA differ dramatically.

The observation that hIL-17RC bound both hIL-17A and F with high affinity suggests that cells expressing hIL-17RC should be equally capable of responding to hIL-17A and F. On the other hand, since hIL-17RA bound hIL-17A with high affinity, but hIL-17F about 1000-fold less well, the implication is that cells expressing hIL-17RA would, under physiologic conditions, only respond to hIL-17A. Previously, it had been shown that hIL-17RA is expressed ubiquitously, but its expression has been reported to be higher in hematopoietic cells with lower expression in other tissues. Therefore, the expression of hIL-17RC was examined to determine the extent of overlap in the expression patterns. Northern blot analysis showed that hIL-17RC was expressed at high levels in glandular tissues such as adrenal gland, prostate, liver, and thyroid with no detectable expression in hematopoietic tissues.

To further investigate expression of these receptors in hematopoietic cells, the binding of biotinylated hIL-17A and F to peripheral blood mononuclear cells (PBMC) by multi-parameter FACS analysis was also examined. Results indicated that hIL-17A bound to virtually all PBMC subsets examined, whereas hIL-17F failed to show detectable binding to any of these populations. This is consistent with the capacity of hIL-17RA to bind hIL-17A with high affinity, but not hIL-17F, and with the failure to detect hIL-17RC mRNA in PBMC. Collectively, these data indicate that IL-17RC is preferentially expressed in non-hematopoietic tissues, while IL-17RA is preferentially expressed in hematopoietic cells.

The high affinity binding of hIL-17A and F to hIL-17RC-transfected cells suggests that an efficacious therapeutic might be a soluble form of hIL-17RC. Such a molecule would be an effective antagonist of these two cytokines. To test this directly, a soluble form of human hIL-17RC was produced as an Fc-fusion protein and tested its ability to inhibit the binding of both hIL-17A and F. These effects were then compared with results obtained using a soluble form of hIL-17RA. Increasing concentrations of hIL-17RC-Ig or hIL-17RA-Ig were included in binding reactions and FACS analysis was used to assess effects of the soluble receptors on binding of biotinylated cytokines to stably transfected BHK cells. Soluble hIL-17RC inhibited the binding of both hIL-17A and F to a similar extent, whereas an Fc-fusion protein of another member of the IL-17R family, hIL-17RD, had no effect. On the other hand, soluble hIL-17RA effectively blocked binding of hIL-17A, but had essentially no effect on the binding of hIL-17F. Similar results were obtained examining binding of hIL-17A to hematopoietic cells. This binding was effectively blocked using hIL-17RA-Ig and hIL-17RC-Ig, but not hIL-17RD-Ig. These data are consistent with results obtained from affinity measurements and indicate that the soluble receptors are behaving the same as their membrane-anchored forms.

As an additional assessment of the capacity of the human hIL-17RC-Ig to bind to hIL-17A and F, the affinity of the soluble receptor for these cytokines was assessed using Biacore analysis. Soluble hIL-17RC bound to both hIL-17A and F with high affinity (Table 2), providing additional support for the idea of using this reagent as an antagonist for the effects of both hIL-17A and F in vivo. Specifically, soluble receptors were captured onto chips and binding experiments were performed as described below. ND=no detectable binding.

TABLE 2

|  | $k_a$ (on-rate) | $k_d$ (off-rate) | $K_D$ |
| --- | --- | --- | --- |
| hIL-17RC-Ig | | | |
| mIL17A |  | ND |  |
| mIL17F |  | ND |  |
| hIL17A | 1.05E+06 | 4.90E-04 | 0.469 nM |
|  | 1.24E+06 | 4.38E-04 | 0.352 nM |
| hIL17F | 9.91E+05 | 4.31E-04 | 0.435 nM |
|  | 1.11E+06 | 3.84E-04 | 0.346 nM |
| mL-17RA-Ig | | | |
| mIL17A | 9.78E+05 | 6.79E-05 | 0.069 nM |
|  | 1.12E+06 | 7.99E-05 | 0.072 nM |
| mIL17F |  | ND |  |

The number of splice variants in humans is much greater and therefore we performed our initial experiments on only a subset of these molecules. Those chosen for this analysis also differed in their inclusion or exclusion of exon 7, but, unlike the mouse, all splice variants incorporated all of exon 8. The cryptic splice acceptor found in the middle of the mouse exon 8 sequence is not present in human exon 8. However, the other splice variants tested either included or excluded hIL-17RC exon 12. These variants were designated hIL-17RCx1 (identical in exon composition to mouse x1 above), hIL-17RCx4 (identical in exon composition to mouse x4 above), hIL-17RCx2, and hIL-17RCx7. Again, these splice variants were transiently expressed in 293F cells and were tested for their ability to bind biotinylated mouse and human IL-17A and F and the results are summarized in Table 3.

TABLE 3

| | | Exons[1] | | | Cytokine Binding[2] | | | |
|---|---|---|---|---|---|---|---|---|
| | Variant | 7 | 8 | 12 | hIL-17A | hIL-17F | mIL-17A | mIL-17F |
| Human | IL-17RCx4 | + | + | + | + | + | − | + |
| | IL-17RCx1 | − | + | + | + | + | − | − |
| | IL-17RCx2 | − | + | − | − | − | − | − |
| | IL-17RCx7 | + | + | − | − | − | − | − |

[1] Denotes exons completely included in transcript.
[2] (+) indicates a detectable, significant cytokine binding as assessed by a significant increase in fluorescence by FACS. (−) indicates no significant change in fluorescence.

Consistent with the experiments presented earlier, hIL-17RCx1 bound to both hIL-17A and F, but did not bind to either mouse cytokine. hIL-17RCx4 also bound to both human cytokines, and like its mouse counterpart, it bound to mIL-17F, but not mIL-17A. hIL-17RCx2 and x7 failed to bind any of the four cytokines tested, although they were clearly expressed on the surface of transfected cells since a polyclonal antiserum against hIL-17RC stained CD8+ cells (data not shown). These binding results were faithfully recapitulated in stably transfected BHK cells as well. Collectively, these data support conclusions regarding essential portions of the IL-17RC protein required for binding to the human cytokines.

Numerous publications have implicated IL-17A and, to a lesser extent, IL-17F as contributing to disease progression and severity in mouse collagen-induced arthritis (CIA) and human rheumatoid arthritis. The expression of both mIL-17A and F in the joints or draining lymph nodes (DLN) from mice that had been immunized with collagen to induce CIA was examined. Analysis by real-time PCR clearly demonstrated that both cytokines were upregulated in both tissues in diseased mice relative to unimmunized controls, clearly indicating that expression correlated with disease. In addition, the relative expression of mIL-17RA and mIL-17RC was also examined in the same tissues. However, in this case, there was not a reproducible correlation of expression of either receptor with disease. Moreover, what was obvious was the discrepancy in expression comparing DLN to non-hematopoietic tissue (hind foot). Consistent with the previous results looking at expression of the human receptors, mIL-17RA was found to be more highly expressed in hematopoietic tissue, and mIL-17RC to be more highly expressed in non-hematopoietic tissue. This data suggests that expression of mIL-17A and mIL-17F expression correlates with disease, that both of the requisite receptors are present in diseased and normal tissue, and suggests that neutralization of these cytokines may be an effective therapy to prevent disease progression.

Accordingly, the cognate receptor for IL-17A and F has been shown to be IL-17RC. Notably, hIL-17RC binds to hIL-17A and F with similar affinities. Since these two members of the IL-17 family share 55% sequence identity, it is perhaps not surprising that they share receptors. However, hIL-17RA binds hIL-17A with high affinity, but binds hIL-17F with an affinity that is nearly 1000-fold lower, suggesting that under physiologic conditions, hIL-17RA would not bind hIL-17F. The implication is that cells that express hIL-17RC should respond to both hIL-17A and F, whereas cells that only express hIL-17RA will only respond to IL-17A. This difference has the potential to impact how these cytokines affect different tissues. Through expression analysis it was shown that although IL-17RA is expressed ubiquitously, it is more highly expressed in hematopoietic cells, whereas IL-17RC tends to be expressed in non-hematopoietic tissues with no expression in hematopoietic cells. Consistent with this, all subsets of human peripheral blood mononuclear cells bind hIL-17A, but do not bind hIL-17F. Moreover, this suggests that non-hematopoietic tissues should respond to both IL-17A and F, whereas hematopoietic cells should only respond to IL-17A.

This examination of cytokine binding to the different IL-17RC splice variants has revealed two portions of the receptor that are essential for cytokine binding, and there are subtle differences in the binding characteristics of the mouse and human cytokines. Moreover, these characteristics are consistent for the cytokines regardless of the species of the receptor examined. As shown from the data presented in Table 3, exon 12 and all of exon 8 are required for hIL-17A and F to bind to IL-17RC, since these cytokines only bind to the human x1 variants and the human x4 variants. Each of these isoforms includes all of exon 8 and exon 12, although they differ with respect to whether exon 7 is included or not. This implies that exon 7 is dispensable for binding of the human cytokines.

The importance of generating an antagonist to both IL-17A and IL-17F function seems clear from available information that shows a strong correlation between IL-17A and F expression and progression of a number of autoimmune and inflammatory diseases. These two cytokines induce other inflammatory cytokines and chemokines as well as matrix metalloproteases, which contribute to collagen and bone destruction in autoimmune arthritis. This reagent should serve as an effective therapeutic for rheumatoid arthritis and in other inflammatory diseases in which hL-17A and F play a role.

Thus, soluble forms of human IL-17RC were developed to serve as an antagonist to both IL-17A and IL-17F. Therapeutically, these soluble IL-17RC polypeptides were efficacious. However, due to numerous factors, soluble IL-17RC is not easily secreted from the numerous and varying production systems available in the art. Nor is it secreted in adequate quantities needed for manufacturing purposes. Thus, there is a need in the art to develop antagonists to IL-17A and IL-17F that can be expressed and secreted in quantities that can be scaled up for manufacturing.

Accordingly, the present invention answers this need by providing IL-17A and IL-17F antagonists that can be expressed and secreted. Specifically, the present invention is based on the development and discovery of a number non-naturally occurring soluble molecules or soluble polypeptides that bind to, antagonize and/or block the binding of IL-17A and IL-17F to their cognate receptor(s). These soluble polypeptides comprise portions of IL-17RC. These soluble polypeptides can also comprise portions of both IL-17RC and IL-17RA ("IL-17RC/IL-17RA").

One such preferred embodiment is described in FIGS. 4A and 4B, as well as in SEQ ID NOs:157 and 158. This soluble polypeptide comprises exons 1-6 of human IL-17RA (SEQ ID NO:21) and exons 8-16 of human IL-17RCx1 (SEQ ID NO:2). More specifically, this soluble polypeptide is fused if an Fc molecule, such as Fc5 as contained in SEQ ID Nos:157 and 158. However, one skilled in the art would easily recognize that any Fc molecule can be utilized as well as any other molecule that would result in dimerization.

As such, antagonists to IL-17F and IL-17A activity, such as IL-17RC and IL-17RC/IL-17RA soluble receptors of the present invention, are useful in therapeutic treatment of inflammatory diseases, particularly as antagonists to both IL-17F and IL-17A singly or together in the treatment of diseases involving these molecules. Moreover, antagonists to IL-17A and IL-17F activity, such as the soluble receptors of the present invention, are useful in therapeutic treatment of other inflammatory diseases for example as bind, block, inhibit, reduce, antagonize or neutralize IL-17F and IL-17A (either individually or together) in the treatment of psoriasis, atopic and contact dermatitis, IBD, IBS, colitis, endotoxemia, arthritis, rheumatoid arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), multiple sclerosis, systemic sclerosis, nephrotic syndrome, organ allograft rejection, graft vs. host disease (GVHD), kidney, lung, heart, etc. transplant rejection, streptococcal cell wall (SCW)-induced arthritis, osteoarthritis, gingivitis/periodontitis, herpetic stromal keratitis, cancers including prostate, renal, colon, ovarian, cervical, leukemia, angiogenesis, restenosis and Kawasaki disease.

Cytokine receptors subunits are characterized by a multi-domain structure comprising a ligand-binding domain and an effector domain that is typically involved in signal transduction. Multimeric cytokine receptors include monomers, homodimers (e.g., PDGF receptor $\alpha\alpha$ and $\beta\beta$ isoforms, erythropoietin receptor, MPL [thrombopoietin receptor], and G-CSF receptor), heterodimers whose subunits each have ligand-binding and effector domains (e.g., PDGF receptor $\alpha\beta$ isoform), and multimers having component subunits with disparate functions (e.g., IL-2, IL-3, IL-4, IL-5, IL-6, IL-7, and GM-CSF receptors). Some receptor subunits are common to a plurality of receptors. For example, the AIC2B subunit, which cannot bind ligand on its own but includes an intracellular signal transduction domain, is a component of IL-3 and GM-CSF receptors. Many cytokine receptors can be placed into one of four related families on the basis of their structures and functions. Class I hematopoietic receptors, for example, are characterized by the presence of a domain containing conserved cysteine residues and the WSXWS motif. Additional domains, including protein kinase domains; fibronectin type III domains; and immunoglobulin domains, which are characterized by disulfide-bonded loops, are present in certain hematopoietic receptors. Cytokine receptor structure has been reviewed by Urdal, *Ann. Reports Med. Chem.* 26:221-228, 1991 and Cosman, *Cytokine* 5:95-106, 1993. It is generally believed that under selective pressure for organisms to acquire new biological functions, new receptor family members arose from duplication of existing receptor genes leading to the existence of multi-gene families. Family members thus contain vestiges of the ancestral gene, and these characteristic features can be exploited in the isolation and identification of additional family members.

Accordingly, the present invention is directed to Il-17A and IL-17F antagonists that block each respective ligand from binding and/or signaling through its corresponding receptor or receptors.

In preferred embodiments, such antagonists are based on IL-17RC's polypeptide structure as depicted in FIGS. 1-4. The IL-17RC receptor has a large number of splice variants based on the inclusion or exclusion of specific exons. As described below, some of these exons are required for ligand (IL-17A and/or IL-17F) binding.

The present invention is based in part of the discovery of structural similarity ("domains") between IL-17RC and other members of the IL-17 family, such as IL-17RA (SEQ ID NO:21). Specifically, three domains were identified:

1) Domain 1 (SEQ ID NOs: 159 and 160) comprises exons 8-10 of IL-17RC. This corresponds to IL-17RCx1's amino acid residues 193-276 of (SEQ ID NO:2) and IL-17RCx4's amino acid residues 208-291 of (SEQ ID NO:166).

2) Domain 2 (SEQ ID NOs: 161 and 162) comprises exons 11-13 of IL-17RC. This corresponds to IL-17RCx1's amino acid residues 277-370 of (SEQ ID NO:2) and IL-17RCx4's amino acid residues 292-385 of (SEQ ID NO:166).

3) Domain 3 (SEQ ID NOs: 163 and 164) comprises exons 14-16 of IL-17RC. This corresponds to IL-17RCx1's amino acid residues 371-447 of (SEQ ID NO:2) and IL-17RCx4's amino acid residues 386-462 of (SEQ ID NO:166).

Thus, the present invention is directed to soluble IL-17RC polypeptides based on different combinations of the exons depicted in FIG. 1. Specifically, examples of these soluble polypeptides include:

1) Variant 1210 (SEQ ID NOs: 67 and 68) which includes exons 1-6 and 8-16 of human IL-17RCx1, fused to Fc10 (SEQ ID NOs: 174 and 175) via a linker (SEQ ID NOs: 176 and 177). Variant 1210 also has a pre-pro signal peptide from otPA (polypeptide sequence shown in SEQ ID NO: 178). Fc5, or any equivalent known in the art, may also be used in place of Fc10.

2) Variant 1390 (SEQ ID NOs: 69 and 70) which includes exons 1-6 and 8-16 of human IL-17RCx1, fused to Fc10 (SEQ ID NOs: 174 and 175). Variant 1390 also has the native signal sequence. Fc5, or any equivalent known in the art, may also be used in place of Fc10.

3) Variant 1341 (SEQ ID NOs: 71 and 72) which includes exons 1-6 of murine IL-17RA and 8-16 of human IL-17RCx1, fused to Fc10 (SEQ ID NOs: 174 and 175) via a linker (SEQ ID NOs: 176 and 177). Variant 1341 also has a signal peptide from murine IL-17RA (SEQ ID NO:181). Fc5, or any equivalent known in the art, may also be used in place of Fc10.

4) Variant 1342 (SEQ ID NOs: 73 and 74) which includes exons 8-16 of human IL-17RCx1, fused to Fc10 (SEQ ID NOs: 174 and 175) via a linker (SEQ ID NOs: 176 and 177). Variant 1342 also has a pre-pro signal peptide from otPA (polypeptide sequence shown in SEQ ID NO: 178). Fc5, or any equivalent known in the art, may also be used in place of Fc10.

5) Variant 51 (SEQ ID NOs: 77 and 78) which includes exons 1-7 of human IL-17RCx1, fused to Fc5 (SEQ ID NOs: 179 and 180). Variant 51 also has the native signal sequence. Fc10, or any equivalent known in the art, may also be used in place of Fc5.

6) Variant S2 (SEQ ID NOs: 81 and 82) which includes exons 1-8 of human IL-17RCx1, fused to Fc5 (SEQ ID NOs: 179 and 180). Variant S2 also has the native signal sequence. Fc10, or any equivalent known in the art, may also be used in place of Fc5.

7) Variant S3 (SEQ ID NOs: 85 and 86) which includes exons 1-9 of human IL-17RCx1, fused to Fc5 (SEQ ID NOs: 179 and 180). Variant S3 also has the native signal sequence. Fc10, or any equivalent known in the art, may also be used in place of Fc5.

8) Variant S4 (SEQ ID NOs: 89 and 90) which includes exons 1-10 of human IL-17RCx1, fused to Fc5 (SEQ ID NOs: 179 and 180). Variant S4 also has the native signal sequence. Fc10, or any equivalent known in the art, may also be used in place of Fc5.

9) Variant S5 (SEQ ID NOs: 93 and 94) which includes exons 1-11 of human IL-17RCx1, fused to Fc5 (SEQ ID NOs:

179 and 180). Variant S5 also has the native signal sequence. Fc10, or any equivalent known in the art, may also be used in place of Fc5.

10) Variant S6 (SEQ ID NOs: 97 and 98) which includes exons 14-16 of human IL-17RCx1, fused to Fc5 (SEQ ID NOs: 179 and 180). Variant S6 also has the native signal sequence. Fc10, or any equivalent known in the art, may also be used in place of Fc5.

11) Variant S7 (SEQ ID NOs: 101 and 102) which includes exons 11-16 of human IL-17RCx1, fused to Fc5 (SEQ ID NOs: 179 and 180). Variant S7 also has the native signal sequence. Fc10, or any equivalent known in the art, may also be used in place of Fc5.

12) Variant S10 (SEQ ID NOs: 105 and 106) which includes exons 7-16 of human IL-17RCx1, fused to Fc5 (SEQ ID NOs: 179 and 180). Variant S10 also has the native signal sequence. Fc10, or any equivalent known in the art, may also be used in place of Fc5.

13) Variant S11 (SEQ ID NOs: 109 and 110) which includes exons 1-7 and 14-16 of human IL-17RCx1, fused to Fc5 (SEQ ID NOs: 179 and 180). Variant S11 also has the native signal sequence. Fc10, or any equivalent known in the art, may also be used in place of Fc5.

14) Variant S12 (SEQ ID NOs: 113 and 114) which includes exons 1-7 and 11-16 of human IL-17RCx1, fused to Fc5 (SEQ ID NOs: 179 and 180). Variant S12 also has the native signal sequence. Fc10, or any equivalent known in the art, may also be used in place of Fc5.

15) Variant S13 (SEQ ID NOs: 117 and 118) which includes exons 1-13 of human IL-17RCx1 and exons 7-9 of human IL-17RA, fused to Fc5 (SEQ ID NOs: 179 and 180). Variant S13 also has the native signal sequence. Fc10, or any equivalent known in the art, may also be used in place of Fc5.

16) Variant S14 (SEQ ID NOs: 121 and 122) which includes exons 1-6 of murine IL-17RA, exons 8-13 of human IL-17RCx1 and exons 7-9 of murine IL-17RA, fused to Fc5 (SEQ ID NOs: 179 and 180). Variant S13 also has the native signal sequence. Fc10, or any equivalent known in the art, may also be used in place of Fc5.

17) Variant 1407 (SEQ ID NOs: 139 and 140) which includes exons 1-10 of human IL-17RA and 8-16 of human IL-17RCx1, fused to Fc5 (SEQ ID NOs: 179 and 180). Variant 1407 also has the native signal peptide from human IL-17RA. Fc10, or any equivalent known in the art, may also be used in place of Fc5.

18) Variant 1459 (SEQ ID NOs: 151 and 152) which includes exons 1-6 and 8-16 of human IL-17RCx1, fused to Fc5 (SEQ ID NOs: 179 and 180) with a Leu21Ala substitution (as compared with IL-17RCx1). Variant 1459 also has a pre-pro signal peptide from otPA (polypeptide sequence shown in SEQ ID NO: 178). Fc10, or any equivalent known in the art, may also be used in place of Fc5.

19) Variant 1454 (SEQ ID NOs: 157 and 158) which includes exons 1-6 of human IL-17RA and 8-16 of human IL-17RCx1, fused to Fc5 (SEQ ID NOs: 179 and 180). Variant 1454 also has the native signal peptide from human IL-17RA. Fc10, or any equivalent known in the art, may also be used in place of Fc5. The mature form of variant 1454 polypeptide is shown in SEQ ID NO:183, which is encoded by the nucleic acid molecule of SEQ ID NO:182. Other secretory signal sequences may be substituted for the human IL-17RA signal sequence for expression in eukaryotic cells, including, for example, the human IL-17RC signal sequence (e.g., amino acid residues 1-20 of SEQ ID NO:2), otPA pre-pro signal sequence (SEQ ID NO:178), human growth hormone signal sequence (SEQ ID NOs:168 and 169), and human CD33 signal sequence (SEQ ID NOs:172 and 173).

Optionally, the C-terminal amino acid residue (residue 658 (Lys) of SEQ ID NO:183) is cleaved or deleted from variant 1454.

The above-described variants represent only a limited number of the embodiments of the present invention. One skilled in the art could readily, and without undue experimentation, design and test other IL-17RC and/or IL-17RC/IL-17RA variants based on the teachings of the present application and in particular FIGS. 1-4 included herewith. For instance, other signal peptides which may be used in place of those disclosed above include: human growth hormone signal peptide (SEQ ID NOs: 168 and 169), murine immunoglobulin heavy chain variable region (VH 26-10) (SEQ ID NOs: 170 and 171), or human CD33 (SEQ ID NOs: 172 and 173).

Amongst other inventions, the present invention provides novel uses for the soluble receptors of the present invention. These soluble receptors can be based solely on IL-17RC (designated "IL-17RC," "soluble IL-17RC," or "sIL-17RC", all of which may be used herein interchangeably), or can be based on combining portions of IL-17RA with IL-17RC ("IL-17RC/IL-17RA," "hybrid RC/RA," "RC/RA," "IL-17RA/RC," or any variation thereof, for instance variant 1454, all of which may be used herein interchangeably). The present invention also provides soluble IL-17RC and IL-17RC/IL-17RA polypeptide fragments and fusion proteins, for use in human inflammatory and autoimmune diseases. The soluble receptors of the present invention can be used to block, inhibit, reduce, antagonize or neutralize the activity of either IL-17F or IL-17A, or both IL-17A and IL-17F in the treatment of inflammation and inflammatory diseases such as psoriasis, psoriatic arthritis, rheumatoid arthritis, endotoxemia, IBD, IBS, colitis, asthma, allograft rejection, immune mediated renal diseases, hepatobiliary diseases, multiple sclerosis, atherosclerosis, promotion of tumor growth, or degenerative joint disease and other inflammatory conditions disclosed herein.

An illustrative nucleotide sequence that encodes human IL-17RC ("IL-17RCx1") is provided by SEQ ID NO:1; the encoded polypeptide is shown in SEQ ID NO:2. IL-17RC functions as a receptor for both IL-17A (SEQ ID NOs:13 and 14) and IL-17F (SEQ ID NOs:15 and 16). IL-17RC can act as a monomer, a homodimer or a heterodimer. Preferably, IL-17RC acts as a homodimeric receptor for both IL-17A and/or IL-17F. As described in the present application, either the monomeric or the homodimeric receptor can comprise IL-17RC alone, or it may comprise portions of other IL-17 family receptors, such as IL-17RA ("IL-17RC/IL-17RA"). As such, the present invention encompasses soluble receptors that comprise portions of IL-17RC in combination with IL-17RA, IL-17RE or any other IL-17 family receptor. IL-17RC can also act as a heterodimeric receptor subunit for a IL-17-related cytokine. For instance, IL-17RC may form a heterodimer with IL-17RA or another IL-17-like receptor. IL-17RC is disclosed in commonly owned U.S. patent application Ser. No. 10/458,647, and commonly owned WIPO publication WO 01/04304, both of which are incorporated herein in their entirety by reference. Analysis of a human cDNA clone encoding IL-17RC (SEQ ID NO:1) revealed an open reading frame encoding 692 amino acids (SEQ ID NO:2) comprising a putative signal sequence of approximately 20 amino acid residues (amino acid residues 1 to 20 of SEQ ID NO:2), an extracellular ligand-binding domain of approximately 431 amino acid residues (amino acid residues 21-452 of SEQ ID NO:2; SEQ ID NO:3), a transmembrane domain of approximately 20 amino acid residues (amino acid residues 453-473 of SEQ ID NO:2), and an intracellular domain of approximately 203 amino acid residues (amino acid residues 474 to 677 of SEQ ID NO:2). Furthermore, a ligand binding domain is represented by SEQ ID NO:22.

Yet another illustrative nucleotide sequence that encodes a variant human IL-17RC, designated as "IL-17RCx4" is provided by SEQ ID NO:165, the encoded polypeptide is shown in SEQ ID NO:166. The predicted signal peptides is from residues 1-60 of SEQ ID NO:165 and 1-20 of SEQ ID NO:166; the extracellular domain from residues 61-1401 of SEQ ID NO:165 and 21-467 of SEQ ID NO:166; the transmembrane domain is from residues 1402-1464 of SEQ ID NO:165 and 468-488 of SEQ ID NO:166; and the intracellular domain is from residues 1465-2121 of SEQ ID NO:165 and 489-707 of SEQ ID NO:166.

Yet another illustrative nucleotide sequence that encodes a variant human IL-17RC, designated as "IL-17RC-1" is provided by SEQ ID NO:4, the encoded polypeptide is shown in SEQ ID NO:5. IL-17RC-1 is disclosed in commonly owned U.S. patent application Ser. No. 10/458,647, and commonly owned WIPO publication WO 01/04304, both of which are incorporated herein in their entirety by reference. Sequence analysis revealed that IL-17RC-1 is a truncated form of receptor polypeptide. That is, IL-17RC-1 lacks amino acid residues 1-113 of SEQ ID NO:2. SEQ ID NO:10 presents an amino acid sequence of a IL-17RC-1 polypeptide that includes the N-terminal portion of IL-17RC.

A comparison of the IL-17RC and IL-17RC-1 amino acid sequences also indicated that the two polypeptides represent alternatively spliced variants. The amino acid sequence of IL-17RC includes a 17 amino acid segment (amino acid residues 339 to 355 of SEQ ID NO:2), which IL-17RC-1 lacks, while IL-17RC lacks, following amino acid 479, a 13 amino acid segment found in IL-17RC-1 (amino acid residues 350 to 362 of SEQ ID NO:5). A polypeptide that contains both amino acid segments is provided by SEQ ID NO:11, whereas SEQ ID NO:12 presents the amino acid sequence of a polypeptide that lacks both 13 and 17 amino acid segments.

Yet another illustrative nucleotide sequence that encodes a variant human IL-17RC, designated as "IL-17RC-6" is provided by SEQ ID NO:23, the encoded polypeptide is shown in SEQ ID NO:24. IL-17RC-6 contains a 25 amino acid residue deletion as compared to IL-17RC as embodied in SEQ ID NO:2. Specifically, IL-17RC-6 does not contain amino acid residue 94 to amino acid residue 118 of SEQ ID NO:2. Analysis of a human cDNA clone encoding IL-17RC-6 (SEQ ID NO:23) revealed an extracellular ligand-binding domain of approximately 427 amino acid residues (amino acid residues 1-427 of SEQ ID NO:24), a transmembrane domain of approximately 20 amino acid residues (amino acid residues 428-448 of SEQ ID NO:24), and an intracellular domain of approximately 218 amino acid residues (amino acid residues 449 to 667 of SEQ ID NO:24).

An illustrative nucleotide sequence that encodes a variant murine IL-17RC is provided by SEQ ID NO:25; the encoded polypeptide is shown in SEQ ID NO:26. Murine IL-17RC functions as a receptor for both murine IL-17A (SEQ ID NOs:17 and 18) and murine IL-17F (SEQ ID NOs:19 and 20). Analysis of a murine cDNA clone encoding IL-17RC (SEQ ID NO:25) revealed an extracellular ligand-binding domain of approximately 449 amino acid residues SEQ ID NO:27). Furthermore, a ligand binding domain is represented by SEQ ID NO:28.

Yet another illustrative nucleotide sequence that encodes a variant murine IL-17RC is provided by SEQ ID NO:29; the encoded polypeptide is shown in SEQ ID NO:30.

The IL-17RC gene resides in chromosome 3p25-3p24. As discussed below, this region is associated with various disorders and diseases.

Northern analyses indicate that there is strong expression of the IL-17RC gene in thyroid, adrenal gland, prostate, and liver tissues, and less expression in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow. These observations show that IL-17RC sequences can be used differentiate between various tissues.

As described below, the present invention provides isolated polypeptides comprising an amino acid sequence that is at least 70%, at least 80%, or at least 90%, or greater than 95%, such as 96%, 97%, 98%, or greater than 99% or more identical to a reference amino acid sequence of 21-692 of SEQ ID NO:2, wherein the isolated polypeptide specifically binds with an antibody that specifically binds with a polypeptide comprising the amino acid sequence of SEQ ID NO:2. The present invention also provides isolated polypeptides comprising an amino acid sequence that is at least 70%, at least 80%, or at least 90% identical to a reference amino acid sequence selected from the group consisting of: (a) amino acid residues 21 to 452 of SEQ ID NO:2, (b) amino acid residues 21 to 435 of SEQ ID NO:10, (c) amino acid residues 21 to 677 of SEQ ID NO:2, and (d) amino acid residues 1 to 692 of SEQ ID NO:2, wherein the isolated polypeptide specifically binds with an antibody that specifically binds with a polypeptide consisting of either the amino acid sequence of SEQ ID NO:2, or the amino acid sequence of SEQ ID NO:10. Illustrative polypeptides include a polypeptide comprising the amino acid sequence of SEQ ID NO:2, SEQ ID NO:10, SEQ ID NO:11, or SEQ ID NO:12.

The present invention also provides isolated polypeptides comprising an extracellular domain, wherein the extracellular domain comprises either amino acid residues 21 to 452 of the amino acid sequence of SEQ ID NO:2 or amino acid residues 21 to 435 of the amino acid sequence of SEQ ID NO:10. Such polypeptides may further comprise a transmembrane domain that resides in a carboxyl-terminal position relative to the extracellular domain, wherein the transmembrane domain comprises amino acid residues 453 to 473 of SEQ ID NO:2. These polypeptides may also comprise an intracellular domain that resides in a carboxyl-terminal position relative to the transmembrane domain, wherein the intracellular domain comprises either amino acid residues 474 to 677 of SEQ ID NO:2, or amino acid residues 457 to 673 of SEQ ID NO:10, and optionally, a signal secretory sequence that resides in an amino-terminal position relative to the extracellular domain, wherein the signal secretory sequence comprises amino acid residues 1 to 20 of the amino acid sequence of SEQ ID NO:2.

The present invention also includes variant IL-17RC polypeptides, wherein the amino acid sequence of the variant polypeptide shares an identity with the amino acid sequence of SEQ ID NO:2 selected from the group consisting of at least 70% identity, at least 80% identity, at least 90% identity, at least 95% identity, or greater than 95% identity, and wherein any difference between the amino acid sequence of the variant polypeptide and the amino acid sequence of SEQ ID NO:2 is due to one or more conservative amino acid substitutions.

Moreover, the present invention also provides isolated polypeptides as disclosed above that bind IL-17F (e.g., human IL-17F polypeptide sequence as shown in SEQ ID NO:16). The human IL-17F polynucleotide sequence is shown in SEQ ID NO:15. The mouse IL-17F polynucleotide sequence is shown in SEQ ID NO:19, and corresponding polyepeptide is shown in SEQ ID NO:20. The present invention also provides isolated polypeptides as disclosed above that bind IL-17A (e.g., human IL-17A polypeptide sequence as shown in SEQ ID NO:14). The human IL-17A polynucleotide sequence is shown in SEQ ID NO:13. The mouse IL-17A polynucleotide sequence is shown in SEQ ID NO:17, and corresponding polyepeptide is shown in SEQ ID NO:18.

The present invention also provides isolated polypeptides and epitopes comprising at least 15 contiguous amino acid residues of an amino acid sequence of SEQ ID NO:2 or 3. Illustrative polypeptides include polypeptides that either comprise, or consist of SEQ ID NO:2 or 3, an antigenic epitope thereof, or a functional IL-17A or IL-17F binding fragment thereof. Moreover, the present invention also provides isolated polypeptides as disclosed above that bind to, block, inhibit, reduce, antagonize or neutralize the activity of IL-17F or IL-17A.

The present invention also includes variant IL-17RC polypeptides, wherein the amino acid sequence of the variant polypeptide shares an identity with the amino acid residues of SEQ ID NO:2 selected from the group consisting of at least 70% identity, at least 80% identity, at least 90% identity, at least 95% identity, or greater than 95% identity, such as 96%, 97%, 98%, or greater than 99% or more identity, and wherein any difference between the amino acid sequence of the variant polypeptide and the corresponding amino acid sequence of SEQ ID NO:2 is due to one or more conservative amino acid substitutions. Such conservative amino acid substitutions are described herein. Moreover, the present invention also provides isolated polypeptides as disclosed above that bind to, block, inhibit, reduce, antagonize or neutralize the activity of IL-17F or IL-17A.

The present invention further provides pharmaceutical compositions comprising a pharmaceutically acceptable carrier and at least one of such an expression vector or recombinant virus comprising such expression vectors. The present invention further includes pharmaceutical compositions, comprising a pharmaceutically acceptable carrier and a polypeptide or antibody described herein.

The present invention also provides fusion proteins, comprising a IL-17RC polypeptide and an immunoglobulin moiety. In such fusion proteins, the immunoglobulin moiety may be an immunoglobulin heavy chain constant region, such as a human $F_c$ fragment. The present invention further includes isolated nucleic acid molecules that encode such fusion proteins.

These and other aspects of the invention will become evident upon reference to the following detailed description. In addition, various references are identified below and are incorporated by reference in their entirety.

B) Definitions

In the description that follows, a number of terms are used extensively. The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "complement of a nucleic acid molecule" refers to a nucleic acid molecule having a complementary nucleotide sequence and reverse orientation as compared to a reference nucleotide sequence. For example, the sequence 5' ATGCACGGG 3' is complementary to 5' CCCGTGCAT 3'.

The term "degenerate nucleotide sequence" denotes a sequence of nucleotides that includes one or more degenerate codons as compared to a reference nucleic acid molecule that encodes a polypeptide. Degenerate codons contain different triplets of nucleotides, but encode the same amino acid residue (i.e., GAU and GAC triplets each encode Asp).

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a particular species is smaller than the complete DNA molecule of a chromosome from that species.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand. The term "cDNA" also refers to a clone of a cDNA molecule synthesized from an RNA template.

A "promoter" is a nucleotide sequence that directs the transcription of a structural gene. Typically, a promoter is located in the 5' non-coding region of a gene, proximal to the transcriptional start site of a structural gene. Sequence elements within promoters that function in the initiation of transcription are often characterized by consensus nucleotide sequences. These promoter elements include RNA polymerase binding sites, TATA sequences, CAAT sequences, differentiation-specific elements (DSEs; McGehee et al., *Mol. Endocrinol.* 7:551 (1993)), cyclic AMP response elements (CREs), serum response elements (SREs; Treisman, *Seminars in Cancer Biol.* 1:47 (1990)), glucocorticoid response elements (GREs), and binding sites for other transcription factors, such as CRE/ATF (O'Reilly et al., *J. Biol. Chem.* 267:19938 (1992)), AP2 (Ye et al., *J. Biol. Chem.* 269:25728 (1994)), SP1, cAMP response element binding protein (CREB; Loeken, *Gene Expr.* 3:253 (1993)) and octamer factors (see, in general, Watson et al., eds., *Molecular Biology of the Gene*, 4th ed. (The Benjamin/Cummings Publishing Company, Inc. 1987), and Lemaigre and Rousseau, *Biochem. J.* 303:1 (1994)). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance the activity or confer tissue specific activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

An "enhancer" is a type of regulatory element that can increase the efficiency of transcription, regardless of the distance or orientation of the enhancer relative to the start site of transcription.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) so long as that host DNA is combined with non-host DNA (i.e., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A "polypeptide" is a polymer of amino acid residues joined by peptide bonds, whether produced naturally or synthetically. Polypeptides of less than about 10 amino acid residues are commonly referred to as "peptides."

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

A peptide or polypeptide encoded by a non-host DNA molecule is a "heterologous" peptide or polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector. In the present context, an example of a recombinant host is a cell that produces IL-17RC from an expression vector. In contrast, IL-17RC can be produced by a cell that is a "natural source" of IL-17RC, and that lacks an expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a IL-17RC polypeptide fused with a polypeptide that binds an affinity matrix. Such a fusion protein provides a means to isolate large quantities of IL-17RC using affinity chromatography.

The term "receptor" denotes a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

A "soluble receptor" is a receptor polypeptide that is not bound to a cell membrane. Soluble receptors are most commonly ligand-binding receptor polypeptides that lack transmembrane and cytoplasmic domains, and other linkage to the cell membrane such as via glycophosphoinositol (gpi).

Soluble receptors can comprise additional amino acid residues, such as affinity tags that provide for purification of the polypeptide or provide sites for attachment of the polypeptide to a substrate, or immunoglobulin constant region sequences. Many cell-surface receptors have naturally occurring, soluble counterparts that are produced by proteolysis or translated from alternatively spliced mRNAs. Soluble receptors can be monomeric, homodimeric, heterodimeric, or multimeric, with multimeric receptors generally not comprising more than 9 subunits, preferably not comprising more than 6 subunits, and most preferably not comprising more than 3 subunits. Receptor polypeptides are said to be substantially free of transmembrane and intracellular polypeptide segments when they lack sufficient portions of these segments to provide membrane anchoring or signal transduction, respectively. Soluble receptors of cytokine receptors generally comprise the extracellular cytokine binding domain free of a transmembrane domain and intracellular domain. For example, representative soluble receptors include soluble receptors for IL-17RA as shown in SEQ ID NOs: 167 (polynucleotide) and 21 (polypeptide). It is well within the level of one of skill in the art to delineate what sequences of a known cytokine receptor sequence comprise the extracellular cytokine binding domain free of a transmembrane domain and intracellular domain. Moreover, one of skill in the art using the genetic code can readily determine polynucleotides that encode such soluble receptor polypeptides.

The term "secretory signal sequence" denotes a DNA sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, such as 96%, 97%, or 98% or more pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "expression" refers to the biosynthesis of a gene product. For example, in the case of a structural gene, expression involves transcription of the structural gene into mRNA and the translation of mRNA into one or more polypeptides.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a polypeptide encoded by a splice variant of an mRNA transcribed from a gene.

As used herein, the term "immunomodulator" includes cytokines, stem cell growth factors, lymphotoxins, co-stimulatory molecules, hematopoietic factors, and the like, and synthetic analogs of these molecules.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of less than $10^9$ $M^{-1}$.

An "anti-idiotype antibody" is an antibody that binds with the variable region domain of an immunoglobulin. In the present context, an anti-idiotype antibody binds with the variable region of an anti-IL-17RC antibody, and thus, an anti-idiotype antibody mimics an epitope of IL-17RC.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. For example, an anti-IL-17RC monoclonal antibody fragment binds with an epitope of IL-17RC.

The term "antibody fragment" also includes a synthetic or a genetically engineered polypeptide that binds to a specific antigen, such as polypeptides consisting of the light chain variable region, "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain. Construction of humanized antibodies for therapeutic use in humans that are derived from murine antibodies, such as those that bind to or neutralize a human protein, is within the skill of one in the art.

As used herein, a "therapeutic agent" is a molecule or atom which is conjugated to an antibody moiety to produce a conjugate which is useful for therapy. Examples of therapeutic agents include drugs, toxins, immunomodulators, chelators, boron compounds, photoactive agents or dyes, and radioisotopes.

A "detectable label" is a molecule or atom which can be conjugated to an antibody moiety to produce a molecule useful for diagnosis. Examples of detectable labels include chelators, photoactive agents, radioisotopes, fluorescent agents, paramagnetic ions, or other marker moieties.

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075 (1985); Nilsson et al., *Methods Enzymol.* 198:3 (1991)), glutathione S transferase (Smith and Johnson, *Gene* 67:31 (1988)), Glu-Glu affinity tag (Grussenmeyer et al., *Proc. Natl. Acad. Sci. USA* 82:7952 (1985)), substance P, FLAG peptide (Hopp et al., *Biotechnology* 6:1204 (1988)), streptavidin binding peptide, or other antigenic epitope or binding domain. See generally Ford et al., *Protein Expression and Purification* 2:95 (1991). DNA molecules encoding affinity tags are available from commercial suppliers (e.g., Pharmacia Biotech, Piscataway, N.J.).

A "naked antibody" is an entire antibody, as opposed to an antibody fragment, which is not conjugated with a therapeutic agent. Naked antibodies include both polyclonal and monoclonal antibodies, as well as certain recombinant antibodies, such as chimeric and humanized antibodies.

As used herein, the term "antibody component" includes both an entire antibody and an antibody fragment.

An "immunoconjugate" is a conjugate of an antibody component with a therapeutic agent or a detectable label.

As used herein, the term "antibody fusion protein" refers to a recombinant molecule that comprises an antibody component and a IL-17RC polypeptide component. Examples of an antibody fusion protein include a protein that comprises a IL-17RC extracellular domain, and either an Fc domain or an antigen-binding region.

A "target polypeptide" or a "target peptide" is an amino acid sequence that comprises at least one epitope, and that is expressed on a target cell, such as a tumor cell, or a cell that carries an infectious agent antigen. T cells recognize peptide epitopes presented by a major histocompatibility complex molecule to a target polypeptide or target peptide and typically lyse the target cell or recruit other immune cells to the site of the target cell, thereby killing the target cell.

An "antigenic peptide" is a peptide which will bind a major histocompatibility complex molecule to form an MHC-peptide complex which is recognized by a T cell, thereby inducing a cytotoxic lymphocyte response upon presentation to the T cell. Thus, antigenic peptides are capable of binding to an appropriate major histocompatibility complex molecule and inducing a cytotoxic T cells response, such as cell lysis or specific cytokine release against the target cell which binds or expresses the antigen. The antigenic peptide can be bound in the context of a class I or class II major histocompatibility complex molecule, on an antigen presenting cell or on a target cell.

In eukaryotes, RNA polymerase II catalyzes the transcription of a structural gene to produce mRNA. A nucleic acid molecule can be designed to contain an RNA polymerase II template in which the RNA transcript has a sequence that is complementary to that of a specific mRNA. The RNA transcript is termed an "anti-sense RNA" and a nucleic acid molecule that encodes the anti-sense RNA is termed an "anti-sense gene." Anti-sense RNA molecules are capable of binding to mRNA molecules, resulting in an inhibition of mRNA translation.

An "anti-sense oligonucleotide specific for IL-17RC" or a "IL-17RC anti-sense oligonucleotide" is an oligonucleotide having a sequence (a) capable of forming a stable triplex with a portion of the IL-17RC gene, or (b) capable of forming a stable duplex with a portion of an mRNA transcript of the IL-17RC gene.

A "ribozyme" is a nucleic acid molecule that contains a catalytic center. The term includes RNA enzymes, self-splicing RNAs, self-cleaving RNAs, and nucleic acid molecules that perform these catalytic functions. A nucleic acid molecule that encodes a ribozyme is termed a "ribozyme gene."

An "external guide sequence" is a nucleic acid molecule that directs the endogenous ribozyme, RNase P, to a particular species of intracellular mRNA, resulting in the cleavage of the mRNA by RNase P. A nucleic acid molecule that encodes an external guide sequence is termed an "external guide sequence gene."

The term "variant IL-17RC gene" refers to nucleic acid molecules that encode a polypeptide having an amino acid sequence that is a modification of SEQ ID NO:2. Such variants include naturally-occurring polymorphisms of IL-17RC genes, as well as synthetic genes that contain conservative amino acid substitutions of the amino acid sequence of SEQ ID NO:2. Additional variant forms of IL-17RC genes are nucleic acid molecules that contain insertions or deletions of the nucleotide sequences described herein. A variant IL-17RC gene can be identified, for example, by determining whether the gene hybridizes with a nucleic acid molecule having the nucleotide sequence of SEQ ID NO:1 OR SEQ ID NO:4, or its complement, under stringent conditions.

Alternatively, variant IL-17RC genes can be identified by sequence comparison. Two amino acid sequences have "100% amino acid sequence identity" if the amino acid residues of the two amino acid sequences are the same when aligned for maximal correspondence. Similarly, two nucleotide sequences have "100% nucleotide sequence identity" if the nucleotide residues of the two nucleotide sequences are the same when aligned for maximal correspondence. Sequence comparisons can be performed using standard software programs such as those included in the LASERGENE bioinformatics computing suite, which is produced by DNASTAR (Madison, Wis.). Other methods for comparing two nucleotide or amino acid sequences by determining optimal alignment are well-known to those of skill in the art (see, for example, Peruski and Peruski, *The Internet and the New Biology: Tools for Genomic and Molecular Research* (ASM Press, Inc. 1997), Wu et al. (eds.), "Information Superhighway and Computer Databases of Nucleic Acids and Proteins," in *Methods in Gene Biotechnology*, pages 123-151 (CRC Press, Inc. 1997), and Bishop (ed.), *Guide to Human Genome Computing*, 2nd Edition (Academic Press, Inc. 1998)). Particular methods for determining sequence identity are described below.

Regardless of the particular method used to identify a variant IL-17RC gene or variant IL-17RC polypeptide, a variant gene or polypeptide encoded by a variant gene may be functionally characterized the ability to bind specifically to an anti-IL-17RC antibody. A variant IL-17RC gene or variant IL-17RC polypeptide may also be functionally characterized the ability to bind to its ligand, for example, IL-17A and/or IL-17F, using a biological or biochemical assay described herein.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "ortholog" denotes a polypeptide or protein obtained from one species that is the functional counterpart of a polypeptide or protein from a different species. Sequence differences among orthologs are the result of specification.

"Paralogs" are distinct but structurally related proteins made by an organism. Paralogs are believed to arise through gene duplication. For example, α-globin, β-globin, and myoglobin are paralogs of each other.

The present invention includes functional fragments of IL-17RC genes. Within the context of this invention, a "functional fragment" of a IL-17RC gene refers to a nucleic acid molecule that encodes a portion of a IL-17RC polypeptide which is a domain described herein or at least specifically binds with an anti-IL-17RC antibody.

Due to the imprecision of standard analytical methods, molecular weights and lengths of polymers are understood to be approximate values. When such a value is expressed as "about" X or "approximately" X, the stated value of X will be understood to be accurate to ±10%.

C) Production of IL-17RA and IL-17RC Polynucleotides or Genes

Nucleic acid molecules encoding a human IL-17RA or IL-17RC gene or polynucleotides encoding any of the soluble polypeptides of the present invention can be obtained by screening a human cDNA or genomic library using polynucleotide probes based upon SEQ ID NO:1, SEQ ID NO:4. These techniques are standard and well-established, and may be accomplished using cloning kits available by commercial suppliers. See, for example, Ausubel et al. (eds.), *Short Protocols in Molecular Biology, 3rd Edition*, John Wiley & Sons 1995; Wu et al., *Methods in Gene Biotechnology, CRC Press, Inc.* 1997; Aviv and Leder, *Proc. Nat'l Acad. Sci. USA* 69:1408 (1972); Huynh et al., "Constructing and Screening cDNA Libraries in λgt10 and λgt11," in *DNA Cloning: A Practical Approach Vol. I*, Glover (ed.), page 49 (IRL Press, 1985); Wu (1997) at pages 47-52.

Nucleic acid molecules that encode a human IL-17RA or IL-17RC gene can also be obtained using the polymerase chain reaction (PCR) with oligonucleotide primers having nucleotide sequences that are based upon the nucleotide sequences of the IL-17RA or IL-17RC gene or cDNA. General methods for screening libraries with PCR are provided by, for example, Yu et al., "Use of the Polymerase Chain Reaction to Screen Phage Libraries," in *Methods in Molecular Biology, Vol. 15: PCR Protocols: Current Methods and Applications*, White (ed.), Humana Press, Inc., 1993. Moreover, techniques for using PCR to isolate related genes are described by, for example, Preston, "Use of Degenerate Oligonucleotide Primers and the Polymerase Chain Reaction to Clone Gene Family Members," in *Methods in Molecular Biology, Vol. 15: PCR Protocols: Current Methods and Applications*, White (ed.), Humana Press, Inc. 1993. As an alternative, an IL-17RA or IL-17RC gene can be obtained by synthesizing nucleic acid molecules using mutually priming long oligonucleotides and the nucleotide sequences described herein (see, for example, Ausubel (1995)). Established techniques using the polymerase chain reaction provide the ability to synthesize DNA molecules at least two kilobases in length (Adang et al., *Plant Molec. Biol.* 21:1131 (1993), Bambot et al., *PCR Methods and Applications* 2:266 (1993), Dillon et al., "Use of the Polymerase Chain Reaction for the Rapid Construction of Synthetic Genes," in *Methods in Molecular Biology, Vol. 15: PCR Protocols: Current Methods and Applications*, White (ed.), pages 263-268, (Humana Press, Inc. 1993), and Holowachuk et al., *PCR Methods Appl.* 4:299 (1995)). For reviews on polynucleotide synthesis, see, for example, Glick and Pasternak, *Molecular Biotechnology,* *Principles and Applications of Recombinant DNA* (ASM Press 1994), Itakura et al., *Annu. Rev. Biochem.* 53:323 (1984), and Climie et al., *Proc. Nat'l Acad. Sci. USA* 87:633 (1990).

D) Production of IL-17RA or IL-17RC Gene Variants

The present invention provides a variety of nucleic acid molecules, including DNA and RNA molecules, that encode the IL-17RA or IL-17RC polypeptides disclosed herein. Those skilled in the art will readily recognize that, in view of the degeneracy of the genetic code, considerable sequence variation is possible among these polynucleotide molecules. Moreover, the present invention also provides isolated soluble monomeric, homodimeric, heterodimeric and multimeric receptor polypeptides that comprise at least a portion of IL-17RC that is substantially homologous to the receptor polypeptide of SEQ ID NO:2. Thus, the present invention contemplates IL-17RA or IL-17RC polypeptide-encoding nucleic acid molecules comprising degenerate nucleotides of SEQ ID NO:1 or SEQ ID NO:4, and their RNA equivalents.

Those skilled in the art will readily recognize that, in view of the degeneracy of the genetic code, considerable sequence variation is possible among these polynucleotide molecules. SEQ ID NO:7 is a degenerate nucleotide sequence that encompasses all nucleic acid molecules that encode the IL-17RC polypeptide of SEQ ID NO:2. Those skilled in the art will recognize that the degenerate sequence of SEQ ID NO:7 also provides all RNA sequences encoding SEQ ID NO:2, by substituting U for T. Thus, the present invention contemplates IL-17RC polypeptide-encoding nucleic acid molecules comprising nucleotide 154 to nucleotide 2229 of SEQ ID NO:1, and their RNA equivalents. Similarly, the IL-17RC-1 degenerate sequence of SEQ ID NO:6 also provides all RNA sequences encoding SEQ ID NO:5, by substituting U for T.

Table 4 sets forth the one-letter codes to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 4

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons, encompassing all possible codons for a given amino acid, are set forth in Table 5.

TABLE 5

| Amino Acid | One Letter Code | Codons | | | | | Degenerate Codon |
|---|---|---|---|---|---|---|---|
| Cys | C | TGC | TGT | | | | TGY |
| Ser | S | AGC | AGT | TCA | TCC | TCG TCT | WSN |
| Thr | T | ACA | ACC | ACG | ACT | | ACN |
| Pro | P | CCA | CCC | CCG | CCT | | CCN |
| Ala | A | GCA | GCC | GCG | GCT | | GCN |
| Gly | G | GGA | GGC | GGG | GGT | | GGN |
| Asn | N | AAC | AAT | | | | AAY |
| Asp | D | GAC | GAT | | | | GAY |
| Glu | E | GAA | GAG | | | | GAR |
| Gln | Q | CAA | CAG | | | | CAR |
| His | H | CAC | CAT | | | | CAY |
| Arg | R | AGA | AGG | CGA | CGC | CGG CGT | MGN |
| Lys | K | AAA | AAG | | | | AAR |
| Met | M | ATG | | | | | ATG |
| Ile | I | ATA | ATC | ATT | | | ATH |
| Leu | L | CTA | CTC | CTG | CTT | TTA TTG | YTN |
| Val | V | GTA | GTC | GTG | GTT | | GTN |
| Phe | F | TTC | TTT | | | | TTY |
| Tyr | Y | TAC | TAT | | | | TAY |
| Trp | W | TGG | | | | | TGG |
| Ter | . | TAA | TAG | TGA | | | TRR |
| Asn\|Asp | B | | | | | | RAY |
| Glu\|Gln | Z | | | | | | SAR |
| Any | X | | | | | | NNN |

One of ordinary skill in the art will appreciate that some ambiguity is introduced in determining a degenerate codon, representative of all possible codons encoding an amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences of SEQ ID NO:6. Variant sequences can be readily tested for functionality as described herein.

Different species can exhibit "preferential codon usage." In general, see, Grantham et al., *Nucl. Acids Res.* 8:1893 (1980), Haas et al. *Curr. Biol.* 6:315 (1996), Wain-Hobson et al., *Gene* 13:355 (1981), Grosjean and Fiers, *Gene* 18:199 (1982), Holm, *Nuc. Acids Res.* 14:3075 (1986), Ikemura, *J. Mol. Biol.* 158:573 (1982), Sharp and Matassi, *Curr. Opin. Genet. Dev.* 4:851 (1994), Kane, *Curr. Opin. Biotechnol.* 6:494 (1995), and Makrides, *Microbiol. Rev.* 60:512 (1996). As used herein, the term "preferential codon usage" or "preferential codons" is a term of art referring to protein translation codons that are most frequently used in cells of a certain species, thus favoring one or a few representatives of the possible codons encoding each amino acid (See Table 5). For example, the amino acid threonine (Thr) may be encoded by ACA, ACC, ACG, or ACT, but in mammalian cells ACC is the most commonly used codon; in other species, for example, insect cells, yeast, viruses or bacteria, different Thr codons may be preferential. Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequences disclosed herein serve as a template for optimizing expression of polynucleotides in various cell types and species commonly used in the art and disclosed herein. Sequences containing preferential codons can be tested and optimized for expression in various species, and tested for functionality as disclosed herein.

An IL-17RA or IL-17RC-encoding cDNA can be isolated by a variety of methods, such as by probing with a complete or partial human cDNA or with one or more sets of degenerate probes based on the disclosed sequences. A cDNA can also be cloned using the polymerase chain reaction with primers designed from the representative human IL-17RA or IL-17RC sequences disclosed herein. In addition, a cDNA library can be used to transform or transfect host cells, and expression of the cDNA of interest can be detected with an antibody to IL-17RA or IL-17RC polypeptide.

Those skilled in the art will recognize that the sequence disclosed in SEQ ID NO:1 represents a single allele of human IL-17RC, and that allelic variation and alternative splicing are expected to occur. Allelic variants of this sequence can be cloned by probing cDNA or genomic libraries from different individuals according to standard procedures. Allelic variants of the nucleotide sequences disclosed herein, including those containing silent mutations and those in which mutations result in amino acid sequence changes, are within the scope of the present invention, as are proteins which are allelic variants of the amino acid sequences disclosed herein. cDNA molecules generated from alternatively spliced mRNAs, which retain the properties of the IL-17RC polypeptide are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Using the methods discussed above, one of ordinary skill in the art can prepare a variety of polypeptides encoding a soluble receptor that comprises a portion of an IL-17RC receptor subunit that is substantially homologous to either SEQ ID NO:1 or SEQ ID NO:4, or that encodes all of or a fragment of SEQ ID NO:2 or SEQ ID NO:5, or allelic variants thereof and retain the ligand-binding properties of the wild-type IL-17RC receptor. Such polypeptides may also include additional polypeptide segments as generally disclosed herein.

Within certain embodiments of the invention, the isolated nucleic acid molecules can hybridize under stringent conditions to nucleic acid molecules comprising nucleotide sequences disclosed herein. For example, such nucleic acid molecules can hybridize under stringent conditions to nucleic acid molecules comprising the nucleotide sequence of SEQ ID NO:1 OR SEQ ID NO:4, or to nucleic acid molecules comprising a nucleotide sequence complementary to SEQ ID NO:1 OR SEQ ID NO:4, or fragments thereof.

In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Following hybridization, the nucleic acid molecules can be washed to remove non-hybridized nucleic acid molecules under stringent conditions, or under highly stringent conditions. See, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and *Primer Premier* 4.0 (Premier Biosoft International; Palo Alto, Calif.), as well as sites on the Internet, are available tools for analyzing a given sequence and calculating $T_m$ based on user-defined criteria. It is well within the abilities of one skilled in the art to adapt hybridization and wash conditions for use with a particular polynucleotide hybrid.

The present invention also provides for isolated IL-17RA or IL-17RC polypeptides that have a substantially similar sequence identity to the polypeptides of SEQ ID NO:2 (IL-17RC) and SEQ ID NO:21 (IL-17RA), or their orthologs. The term "substantially similar sequence identity" is used herein to denote polypeptides having at least 70%, at least 80%, at least 90%, at least 95%, such as 96%, 97%, 98%, or greater than 95% sequence identity to the sequences shown in SEQ ID NO:2, or their orthologs. For example, variant and orthologous IL-17RA or IL-17RC receptors can be used to generate an immune response and raise cross-reactive antibodies to human IL-17RA or IL-17RC. Such antibodies can be humanized, and modified as described herein, and used therapeutically to treat psoriasis, psoriatic arthritis, IBD, IBS, colitis, endotoxemia as well as in other therapeutic applications described herein.

The present invention also contemplates IL-17RA or IL-17RC or IL-17RC/IL-17RA variant nucleic acid molecules that can be identified using two criteria: a determination of the similarity between the encoded polypeptide with any amino acid sequence as described herein, such as the amino acid sequence of SEQ ID NO:2 (IL-17RC), SEQ ID NO:21 (IL-17RA) or SEQ ID NOs:158 and 183 (IL-17RC/IL-17RA), and a hybridization assay. Such variants include nucleic acid molecules (1) that remain hybridized with a nucleic acid molecule having a nucleotide sequence as described herein, such as the nucleotide sequence of SEQ ID NO:1 or SEQ ID NO:4 for IL-17RC (or its full-length complement) or SEQ ID NO:157 for IL-17RC/IL-17RA (or its full-length complement) under stringent washing conditions, in which the wash stringency is equivalent to 0.5×-2× SSC with 0.1% SDS at 55-65° C., and (2) that encode a polypeptide having at least 70%, at least 80%, at least 90%, at least 95%, or greater than 95% such as 96%, 97%, 98%, or 99%, sequence identity to an amino acid sequence as described herein, such as the amino acid sequence of SEQ ID NO:2 and SEQ ID NO:158. Alternatively, IL-17RC variants can be characterized as nucleic acid molecules (1) that remain hybridized with a nucleic acid molecule as described herein, such as the nucleotide sequence of SEQ ID NO:1 OR SEQ ID NO:4 (or its full length complement) or of SEQ ID NO:157 (or its full-length complement) under highly stringent washing conditions, in which the wash stringency is equivalent to 0.1×-0.2×SSC with 0.1% SDS at 50-65° C., and (2) that encode a polypeptide having at least 70%, at least 80%, at least 90%, at least 95% or greater than 95%, such as 96%, 97%, 98%, or 99% or greater, sequence identity to an amino acid sequence as described herein, such as the amino acid sequence of SEQ ID NO:2 and SEQ ID NO:158.

The present invention provides, for example, an isolated polypeptide comprising an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and at least 99.5% sequence identity with amino acid residues 200-458 of SEQ ID NO:158 (which includes exons 8-16 of IL-17RC), or amino acid residues 33-458 of SEQ ID NO:158 (which includes exons 1-6 of IL-17A and 8-16 of IL-17RC), or amino acid residues 1-458 of SEQ ID NO:158, or amino acid residues 33-690 of SEQ ID NO:158 or amino acid residues 1-690 of SEQ ID NO:158, wherein the polypeptide binds IL-17A and/or IL-17F. The polypeptides can also be used to bind, block, reduce, antagonize or neutralize IL-17A and/or IL-17F in the treatment of psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease.

The present invention provides for an isolated nucleic acid molecule encoding a polypeptide wherein the encoded polypeptide comprises an amino acid sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% sequence identity with amino acid residues 200-458 of SEQ ID NO:158 (which includes exons 8-16 of IL-17RC), amino acid residues 33-458 of SEQ ID NO:158 (which includes exons 1-6 of IL-17A and 8-16 of IL-17RC), or amino acid residues 1-458 of SEQ ID NO:158, or amino acid residues 33-690 of SEQ ID NO:158 or amino acid residues 1-690 of SEQ ID NO:158, wherein the polypeptide binds IL-17A and/or IL-17F. The polypeptides may also be used to bind, block, reduce, antagonize or neutralize IL-17A and/or IL-17F and for use in the treatment of psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease.

The present invention also provides an isolated nucleic acid molecule encoding a polypeptide, wherein the nucleic acid molecule hybridizes to nucleotides 598-1374 of SEQ ID NO:157 (or full length complement thereof), nucleotides 97-1374 of SEQ ID NO:157 (or full length complement thereof), nucleotides 1-1374 of SEQ ID NO:157 (or full length complement thereof), nucleotides 97-2070 of SEQ ID NO:157 (or full length complement thereof) or nucleotides 1-2070 of SEQ ID NO:157 (or full length complement thereof) under hybridization conditions of prehybridization for 1 hour at 62° C. in hybridization solution (5×SSC (1×SSC is 0.15 M sodium chloride and 0.015 M sodium citrate), 0.02% sodium dodecyl sulfate (SDS), 0.1% N-lauroylsarcosine, 1% Blocking Reagent) followed by two stringency washes with 2×SSC, 0.1% SDS for 5 minutes at room temperature and once with 0.5×SSC, 0.1% SDS for 15 minutes at 62° C., wherein the encoded polypeptide binds, blocks, reduces, antagonizes or neutralizes IL-17A and/or IL-17F. The encoded polypeptide can also be used to treat psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease.

In specific variations, the present invention provides an isolated polypeptide comprising amino acid residues 33-458 of SEQ ID NO:158 (residues 1-426 of SEQ ID NO:183), amino acid residues 33-689 of SEQ ID NO:158 (residues 1-657 of SEQ ID NO:183), or amino acid residues 33-690 of SEQ ID NO:158 (residues 1-658 of SEQ ID NO:183). Optionally, the polypeptide may further comprise an immunoglobulin moiety, such as an immunoglobulin heavy chain constant region. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 459-689 of SEQ ID NO:158 (residues 427-657 of SEQ ID NO:183) or amino acid residues 459-690 of SEQ ID NO:158 (residues 427-658 of SEQ ID NO:183). The polypeptide may optionally further comprise a secretory signal sequence, such as, for example, the human IL-17RA signal sequence (e.g., SEQ ID NOs:184 and 185), human IL-17RC signal sequence (e.g., amino acid residues 1-20 of SEQ ID NO:2), otPA pre-pro signal sequence (SEQ ID NO:178), human growth hormone signal sequence (SEQ ID NOs:168 and 169), or human CD33 signal sequence (SEQ ID NOs:172 and 173). The polypeptide can be expressed recombinantly in cultured cells, such as prokaryotic cells (e.g., *E. coli*) and eukaryotic cells (e.g., mammalian cells such as Chinese Hamster Ovary cells, and yeast cells such as *Saccharomyces cerevisiae* and *Pichia pastoris*).

The present invention also provides isolated nucleic acid molecules encoding a polypeptide comprising amino acid residues 33-458 of SEQ ID NO:158. The nucleic acid molecule can be, for instance, the nucleotide sequence shown as nucleotide residues 97-1374 of SEQ ID NO:157 (the nucleotide sequence of SEQ ID NO:182). Optionally, the encoded polypeptide may further comprise an immunoglobulin moiety, such as an immunoglobulin heavy chain constant region. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 459-689 of SEQ ID NO:158, or amino acid residues 459-690 of SEQ ID NO:158. The encoded polypeptide may optionally further comprise a secretory signal sequence, such as, for example, the human IL-17RA signal sequence (e.g., SEQ ID NOs:184 and 185), human IL-17RC signal sequence (e.g., amino acid residues 1-20 of SEQ ID NO:2), otPA pre-pro signal sequence (SEQ ID NO:178), human growth hormone signal sequence (SEQ ID NOs:168 and 169), or human CD33 signal sequence (SEQ ID NOs:172 and 173). The encoded polypeptide can be expressed recombinantly in cultured cells, such as prokaryotic cells (e.g., *E. coli*) and eukaryotic cells (e.g., mammalian cells such as Chinese Hamster Ovary cells, and yeast cells such as *Saccharomyces cerevisiae* and *Pichia pastoris*).

The present invention also provides expression vectors comprising the following operably linked elements: a) a transcription promoter; b) a DNA segment encoding a polypeptide wherein the encoded polypeptide comprises amino acid residues 33-458 of SEQ ID NO:158; and c) a transcription terminator. The encoded polypeptide may further comprise an immunoglobulin moiety. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 459-689 of SEQ ID NO:158, or amino acid residues 459-690 of SEQ ID NO:158. The encoded polypeptide may optionally further comprise a secretory signal sequence, such as, for example, the human IL-17RA signal sequence (e.g., SEQ ID NOs:184 and 185), human IL-17RC signal sequence (e.g., amino acid residues 1-20 of SEQ ID NO:2), otPA pre-pro signal sequence (SEQ ID NO:178), human growth hormone signal sequence (SEQ ID NOs:168 and 169), and human CD33 signal sequence (SEQ ID NOs:172 and 173). The encoded polypeptide can be expressed recombinantly in cultured cells, such as prokaryotic cells (e.g., *E. coli*) and eukaryotic cells (e.g., mammalian cells such as Chinese Hamster Ovary cells, and yeast cells such as *Saccharomyces cerevisiae* and *Pichia pastoris*). The present invention also provides a method of producing a polypeptide comprising culturing a cell into which has been introduced an expression vector as described herein, wherein the cell expresses the polypeptide encoded by the DNA segment, and recovering the expressed polypeptide.

The present invention also provides for a composition comprising a polypeptide comprising amino acid residues 33-458 of SEQ ID NO:158 and a pharmaceutically acceptable carrier. Optionally, the polypeptide may further comprise an immunoglobulin moiety, such as an immunoglobulin heavy chain constant region. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 459-689 of SEQ ID NO:158, or amino acid residues 459-690 of SEQ ID NO:158.

The present invention also provides for a method of treating a subject suffering from a disease comprising administering to the subject a polypeptide comprising amino acid residues 33-458 of SEQ ID NO:158, wherein the polypeptide binds, blocks, reduces, antagonizes or neutralizes IL-17A and/or IL-17F activity, and wherein the disease is selected from the group consisting of psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease. Optionally, the polypeptide may further comprise an immunoglublulin moiety, such as an immunoglobulin heavy chain constant region. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 459-689 of SEQ ID NO:158, or amino acid residues 459-690 of SEQ ID NO:158.

The present invention also provides for a method of treating a subject suffering from a disease comprising administering to the subject a composition comprising a polypeptide comprising amino acid residues 33-458 of SEQ ID NO:158, and a pharmaceutically acceptable carrier wherein the polypeptide binds, blocks, reduces, antagonizes or neutralizes IL-17A and/or IL-17F activity, and wherein the disease is selected from the group consisting of psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease. Optionally, the polypeptide may further comprise an immunogloblulin moiety, such as an immunoglobulin heavy chain constant region. The immunoglobulin heavy chain constant region, for example, can be from IgG1, IgG2, IgG3, IgG4, IgA, IgD, IgM, IgE or a derivative thereof. The immunoglobulin heavy chain constant region may be capable of mediating Antibody-Dependent Cell-mediated Cytotoxicity ("ADCC") and/or Complement Dependent Cytotoxicity ("CDC"). The immunoglobulin heavy chain constant region can be, for instance, Fc5, Fc10, amino acid residues 458-689 of SEQ ID NO:158, or amino acid residues 458-690 of SEQ ID NO:158.

The present invention also provides an antibody or antibody fragment that specifically binds to a polypeptide comprising amino acid residues 33-458 of SEQ ID NO:158, amino acid residues 33-689 of SEQ ID NO:158, and/or amino acid residues 33-690 of SEQ ID NO:158. The antibody can be an antibody selected from the group consisting of a polyclonal antibody, a murine monoclonal antibody, a humanized antibody derived from a murine monoclonal antibody, an antibody fragment, neutralizing antibody, and a human monoclonal antibody. The antibody fragment may optionally be a fragment selected from the group consisting of F(ab')$_2$, F(ab)$_2$, Fab', Fab, Fv, scFv, and minimal recognition unit. The present invention also provides for an anti-idiotype antibody that specifically binds to an antibody or antibody fragment as described herein.

The present invention also provides fusion proteins comprising amino acid residues 33-458 of SEQ ID NO:158 and an immunoglobulin moiety. The immunoglobulin moiety may optionally be an immunoglobulin heavy chain constant region, such as amino acid residues 459-689 of SEQ ID NO:158 or amino acid residues 459-690 of SEQ ID NO:158. The present invention also provides for an isolated nucleic acid molecule encoding a fusion protein as described herein, such as nucleotides 97-2067 of SEQ ID NO:158 (nucleotides 1-1971 of SEQ ID NO:182) or nucleotides 97-2070 of SEQ ID NO:158 (nucleotides 1-1974 of SEQ ID NO:182). The present invention also provides compositions comprising the fusion proteins as described herein and a pharmaceutically acceptable carrier. These compositions may be used to treat one or more of the various diseases as described herein.

Percent sequence identity is determined by conventional methods. See, e.g., Altschul et al., *Bull. Math. Bio.* 48:603 (1986), and Henikoff and Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 6 (amino acids are indicated by the standard one-letter codes). The percent identity is then calculated as: ([Total number of identical matches]/[length of the longer sequence plus the number of gaps introduced into the longer sequence in order to align the two sequences])(100).

TABLE 6

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | −1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative IL-17RC variant. The FASTA algorithm is described by Pearson and Lipman, Proc. Nat'l Acad. Sci. USA 85:2444 (1988), and by Pearson, Meth. Enzymol. 183:63 (1990). Briefly, FASTA first characterizes sequence similarity by identifying regions shared by the query sequence (e.g., SEQ ID NO:2 or SEQ ID NO:3) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, J. Mol. Biol. 48:444 (1970); Sellers, SIAM J. Appl. Math. 26:787 (1974)), which allows for amino acid insertions and deletions. Illustrative parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, Meth. Enzymol. 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as described above.

The present invention includes nucleic acid molecules that encode a polypeptide having a conservative amino acid change, compared with an amino acid sequence disclosed herein. For example, variants can be obtained that contain one or more amino acid substitutions of SEQ ID NO:2 or 21, in which an alkyl amino acid is substituted for an alkyl amino acid in a IL-17RA or IL-17RC amino acid sequence, an aromatic amino acid is substituted for an aromatic amino acid in a IL-17RA or IL-17RC amino acid sequence, a sulfur-containing amino acid is substituted for a sulfur-containing amino acid in a IL-17RA or IL-17RC amino acid sequence, a hydroxy-containing amino acid is substituted for a hydroxy-containing amino acid in a IL-17RA or IL-17RC amino acid sequence, an acidic amino acid is substituted for an acidic amino acid in a IL-17RA or IL-17RC amino acid sequence, a basic amino acid is substituted for a basic amino acid in a IL-17RA or IL-17RC amino acid sequence, or a dibasic monocarboxylic amino acid is substituted for a dibasic monocarboxylic amino acid in a IL-17RA or IL-17RC amino acid sequence. Among the common amino acids, for example, a "conservative amino acid substitution" is illustrated by a substitution among amino acids within each of the following groups: (1) glycine, alanine, valine, leucine, and isoleucine, (2) phenylalanine, tyrosine, and tryptophan, (3) serine and threonine, (4) aspartate and glutamate, (5) glutamine and asparagine, and (6) lysine, arginine and histidine. The BLOSUM62 table is an amino acid substitution matrix derived from about 2,000 local multiple alignments of protein sequence segments, representing highly conserved regions of more than 500 groups of related proteins (Henikoff and Henikoff, Proc. Nat'l Acad. Sci. USA 89:10915 (1992)). Accordingly, the BLOSUM62 substitution frequencies can be used to define conservative amino acid substitutions that may be introduced into the amino acid sequences of the present invention. Although it is possible to design amino acid substitutions based solely upon chemical properties (as discussed above), the language "conservative amino acid substitution" preferably refers to a substitution represented by a BLOSUM62 value of greater than −1. For example, an amino acid substitution is conservative if the substitution is characterized by a BLOSUM62 value of 0, 1, 2, or 3. According to this system, preferred conservative amino acid substitutions are characterized by a BLOSUM62 value of at least 1 (e.g., 1, 2 or 3), while more preferred conservative amino acid substitutions are characterized by a BLOSUM62 value of at least 2 (e.g., 2 or 3). Particular variants of IL-17RC are characterized by having at least 70%, at least 80%, at least 90%, at least 95% or greater than 95% such as 96%, 97%, 98%, or 99% or greater sequence identity to the corresponding amino acid sequence (e.g., SEQ ID NO:2 or 21), wherein the variation in amino acid sequence is due to one or more conservative amino acid substitutions.

Conservative amino acid changes in a IL-17RA or IL-17RC gene can be introduced, for example, by substituting nucleotides for the nucleotides recited in SEQ ID NO:1 or SEQ ID NO:4. Such "conservative amino acid" variants can be obtained by oligonucleotide-directed mutagenesis, linker-scanning mutagenesis, mutagenesis using the polymerase chain reaction, and the like (see Ausubel (1995); and McPherson (ed.), *Directed Mutagenesis: A Practical Approach* (IRL Press 1991)). A variant IL-17RC polypeptide can be identified by the ability to specifically bind anti-IL-17RC antibodies.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an *E. coli* S30 extract and commercially available enzymes and other reagents. Proteins are purified by chromatography. See, for example, Robertson et al., *J. Am. Chem. Soc.* 113:2722 (1991), Ellman et al., *Methods Enzymol.* 202:301 (1991), Chung et al., *Science* 259:806 (1993), and Chung et al., *Proc. Nat'l Acad. Sci. USA* 90:10145 (1993).

In a second method, translation is carried out in *Xenopus* oocytes by microinjection of mutated mRNA and chemically aminoacylated suppressor tRNAs (Turcatti et al., *J. Biol. Chem.* 271:19991 (1996)). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395 (1993)).

A limited number of non-conservative amino acids, amino acids that are not encoded by the genetic code, non-naturally occurring amino acids, and unnatural amino acids may be substituted for IL-17RA or IL-17RC amino acid residues.

Essential amino acids in the polypeptides of the present invention can be identified according to procedures known in the art, such as site-directed mutagenesis or alanine-scanning mutagenesis (Cunningham and Wells, *Science* 244:1081 (1989), Bass et al., *Proc. Nat'l Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological activity to identify amino acid residues that are critical to the activity of the molecule. See also, Hilton et al., *J. Biol. Chem.* 271:4699 (1996).

Although sequence analysis can be used to further define the IL-17RA or IL-17RC ligand binding region, amino acids that play a role in IL-17RA or IL-17RC binding activity (such as binding of IL-17RC to either Il-17A or IL-17F, and IL-17RA to IL-17A) can also be determined by physical analysis of structure, as determined by such techniques as nuclear magnetic resonance, crystallography, electron diffraction or photoaffinity labeling, in conjunction with mutation of putative contact site amino acids. See, e.g., de Vos et al., *Science* 255:306 (1992), Smith et al., *J. Mol. Biol.* 224:899 (1992), and Wlodaver et al., *FEBS Lett.* 309:59 (1992). Specifically, three domains were identified:

1) Domain 1 (SEQ ID NOs: 159 and 160) comprises exons 8-10 of IL-17RC. This corresponds to IL-17RCx1's amino acid residues 193-276 of (SEQ ID NO:2) and IL-17RCx4's amino acid residues 208-291 of (SEQ ID NO:166). 2) Domain 2 (SEQ ID NOs: 161 and 162) comprises exons 11-13 of IL-17RC. This corresponds to IL-17RCx1's amino acid residues 277-370 of (SEQ ID NO:2) and IL-17RCx4's amino acid residues 292-385 of (SEQ ID NO:166). 3) Domain 3 (SEQ ID NOs: 163 and 164) comprises exons 14-16 of IL-17RC. This corresponds to IL-17RCx1's amino acid residues 371-447 of (SEQ ID NO:2) and IL-17RCx4's amino acid residues 386-462 of (SEQ ID NO:166).

Multiple amino acid substitutions can be made and tested using known methods of mutagenesis and screening, such as those disclosed by Reidhaar-Olson and Sauer (*Science* 241:53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204, and region-directed mutagenesis (Derbyshire et al., *Gene* 46:145 (1986), and Ner et al., *DNA* 7:127, (1988)). Moreover, IL-17RC or IL-17RA labeled with biotin or FITC can be used for expression cloning of IL-17RC ligands.

Variants of the disclosed IL-17RC or IL-17RA nucleotide and polypeptide sequences can also be generated through DNA shuffling as disclosed by Stemmer, *Nature* 370:389 (1994), Stemmer, *Proc. Nat'l Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-IL-17RC or IL-17RA antibodies, can be recovered from the host cells and rapidly sequenced using modern equipment. These methods allow the rapid determination of the importance of individual amino acid residues in a polypeptide of interest, and can be applied to polypeptides of unknown structure.

The present invention also includes "functional fragments" of IL-17RC or IL-17RA polypeptides and nucleic acid molecules encoding such functional fragments. These functional fragments may either bind ligand or ligands (i.e. both IL-17A and IL-17F) singly or together. Routine deletion analyses of nucleic acid molecules can be performed to obtain functional fragments of a nucleic acid molecule that encodes a IL-17RC or IL-17RA polypeptide. As an illustration, DNA molecules having the nucleotide sequence of SEQ ID NO:1 or SEQ ID NO:4 can be digested with Bal31 nuclease to obtain a series of nested deletions. The fragments are then inserted into expression vectors in proper reading frame, and the expressed polypeptides are isolated and tested for the ability to bind anti-IL-17RC antibodies. One alternative to exonuclease digestion is to use oligonucleotide-directed mutagenesis to introduce deletions or stop codons to specify production of a desired fragment. Alternatively, particular fragments of a IL-17RC or IL-17RA gene can be synthesized using the polymerase chain reaction.

This general approach is exemplified by studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993), Content et al., "Expression and preliminary deletion analysis of the 42 kDa 2-5A synthetase induced by human interferon," in *Biological Interferon Systems, Proceedings of ISIR-TNO Meeting on Interferon Systems*, Cantell (ed.), pages 65-72 (Nijhoff 1987), Herschman, "The EGF Receptor," in *Control of Animal Cell Proliferation, Vol.* 1, Boynton et al., (eds.) pages 169-199 (Academic Press 1985), Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995), and Meisel et al., *Plant Molec. Biol.* 30:1 (1996).

The present invention also contemplates functional fragments of a IL-17RC or IL-17RA gene that have amino acid changes, compared with an amino acid sequence disclosed herein. A variant IL-17RC or IL-17RA gene can be identified on the basis of structure by determining the level of identity with disclosed nucleotide and amino acid sequences, as discussed above. An alternative approach to identifying a variant gene on the basis of structure is to determine whether a nucleic acid molecule encoding a potential variant IL-17RC or IL-17RA gene can hybridize to a nucleic acid molecule comprising a nucleotide sequence, such as SEQ ID NO:1 or SEQ ID NO:4.

The present invention also includes using functional fragments of IL-17RC or IL-17RA polypeptides, antigenic epitopes, epitope-bearing portions or ligand-binding portions of IL-17RC and/or IL-17RA polypeptides, and nucleic acid molecules that encode such functional fragments, antigenic epitopes, epitope-bearing portions or ligand-binding portions of IL-17RC and/or IL-17RA polypeptides. Such fragments are used to generate polypeptides for use in generating soluble receptors or binding molecules that bind, block, inhibit, reduce, antagonize or neutralize activity of IL-17A or IL-17F or both IL-17A and IL-17F. A "functional" IL-17RC or IL-17RC/IL-17RA polypeptide or fragment thereof as defined herein is characterized by its ability to block, inhibit, reduce, antagonize or neutralize IL-17A and/or IL-17F inflammatory, proliferative or differentiating activity, by its ability to induce or inhibit specialized cell functions, or by its ability to bind specifically to IL-17A and/or IL-17F. As previously described herein, both IL-17RA and IL-17RC is characterized by a unique cytokine receptor structure and domains as described herein. Thus, the present invention further contemplates using fusion proteins encompassing: (a) polypeptide molecules comprising one or more of the domains described above; and (b) functional fragments comprising one or more of these domains. The other polypeptide portion of the fusion protein may be contributed by another cytokine receptor, such as an IL-17-like receptor, IL-17RA, IL-17RE, IL-17RD, or by a non-native and/or an unrelated secretory signal peptide that facilitates secretion of the fusion protein.

The present invention also provides polypeptide fragments or peptides comprising an ligand-binding portion of a IL-17RC or IL-17RA polypeptide described herein. Such fragments or peptides may comprise a portion of either IL-17RC or IL-17RA that binds to its respective ligand (IL-17A and/or IL-17F).

For any IL-17RC or IL-17RA polypeptide, including variants and fusion proteins, one of ordinary skill in the art can readily generate a fully degenerate polynucleotide sequence encoding that variant using the information set forth in Tables 1 and 2 above. Moreover, those of skill in the art can use standard software to devise IL-17RC or IL-17RA variants based upon the nucleotide and amino acid sequences described herein.

E) Production of IL-17RC, IL-17RA and IL-17RC/IL-17RA Polypeptides

The polypeptides of the present invention, including full-length polypeptides; soluble monomeric, homodimeric, heterodimeric and multimeric receptors; full-length receptors; receptor fragments (e.g. ligand-binding fragments and antigenic epitopes), functional fragments, and fusion proteins, can be produced in recombinant host cells following conventional techniques. To express an IL-17RC, IL-17RA and IL-17RC/IL-17RA gene, a nucleic acid molecule encoding the polypeptide must be operably linked to regulatory sequences that control transcriptional expression in an expression vector and then, introduced into a host cell. In addition to transcriptional regulatory sequences, such as promoters and enhancers, expression vectors can include translational regulatory sequences and a marker gene which is suitable for selection of cells that carry the expression vector.

Expression vectors that are suitable for production of a foreign protein in eukaryotic cells typically contain (1) prokaryotic DNA elements coding for a bacterial replication origin and an antibiotic resistance marker to provide for the growth and selection of the expression vector in a bacterial host; (2) eukaryotic DNA elements that control initiation of transcription, such as a promoter; and (3) DNA elements that control the processing of transcripts, such as a transcription termination/polyadenylation sequence. As discussed above, expression vectors can also include nucleotide sequences encoding a secretory sequence that directs the heterologous polypeptide into the secretory pathway of a host cell. For example, an IL-17RC expression vector may comprise an IL-17RC, IL-17RA and IL-17RC/IL-17RA gene and a secretory sequence derived from any secreted gene.

IL-17RC, IL-17RA and IL-17RC/IL-17RA proteins of the present invention may be expressed in mammalian cells. Examples of suitable mammalian host cells include African green monkey kidney cells (Vero; ATCC CRL 1587), human embryonic kidney cells (293-HEK; ATCC CRL 1573), baby hamster kidney cells (BHK-21, BHK-570; ATCC CRL 8544, ATCC CRL 10314), canine kidney cells (MDCK; ATCC CCL 34), Chinese hamster ovary cells (CHO-K1; ATCC CCL61; CHO DG44 (Chasin et al., *Som. Cell. Molec. Genet.* 12:555, 1986)), rat pituitary cells (GH1; ATCC CCL82), HeLa S3 cells (ATCC CCL2.2), rat hepatoma cells (H-4-II-E; ATCC CRL 1548) SV40-transformed monkey kidney cells (COS-1; ATCC CRL 1650) and murine embryonic cells (NIH-3T3; ATCC CRL 1658).

For a mammalian host, the transcriptional and translational regulatory signals may be derived from mammalian viral sources, for example, adenovirus, bovine papilloma virus, simian virus, or the like, in which the regulatory signals are associated with a particular gene which has a high level of expression. Suitable transcriptional and translational regulatory sequences also can be obtained from mammalian genes, for example, actin, collagen, myosin, and metallothionein genes.

Transcriptional regulatory sequences include a promoter region sufficient to direct the initiation of RNA synthesis. Suitable eukaryotic promoters include the promoter of the mouse metallothionein I gene (Hamer et al., *J. Molec. Appl. Genet.* 1:273 (1982)), the TK promoter of Herpes virus (McKnight, *Cell* 31:355 (1982)), the SV40 early promoter (Benoist et al., *Nature* 290:304 (1981)), the Rous sarcoma virus promoter (Gorman et al., *Proc. Nat'l Acad. Sci. USA* 79:6777 (1982)), the cytomegalovirus promoter (Foecking et al., *Gene* 45:101 (1980)), and the mouse mammary tumor virus promoter (see, generally, Etcheverry, "Expression of Engineered Proteins in Mammalian Cell Culture," in *Protein Engineering: Principles and Practice*, Cleland et al. (eds.), pages 163-181 (John Wiley & Sons, Inc. 1996)).

Alternatively, a prokaryotic promoter, such as the bacteriophage T3 RNA polymerase promoter, can be used to control gene expression in mammalian cells if the prokaryotic promoter is regulated by a eukaryotic promoter (Zhou et al., *Mol. Cell. Biol.* 10:4529 (1990), and Kaufman et al., *Nucl. Acids Res.* 19:4485 (1991)).

In certain embodiments, a DNA sequence encoding an IL-17RC, IL-17RA and IL-17RC/IL-17RA soluble receptor polypeptide, or a fragment of IL-17RC, IL-17RA or IL-17RC/IL-17RA polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

An expression vector can be introduced into host cells using a variety of standard techniques including calcium phosphate transfection, liposome-mediated transfection, microprojectile-mediated delivery, electroporation, and the like. The transfected cells can be selected and propagated to provide recombinant host cells that comprise the expression vector stably integrated in the host cell genome. Techniques for introducing vectors into eukaryotic cells and techniques for selecting such stable transformants using a dominant selectable marker are described, for example, by Ausubel (1995) and by Murray (ed.), *Gene Transfer and Expression Protocols* (Humana Press 1991).

For example, one suitable selectable marker is a gene that provides resistance to the antibiotic neomycin. In this case, selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A suitable amplifiable selectable marker is dihydrofolate reductase (DHFR), which confers resistance to methotrexate. Other drug resistance genes (e.g., hygromycin resistance, multi-drug resistance, puromycin acetyltransferase) can also be used. Alternatively, markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

The polypeptides of the invention can also be produced by cultured mammalian cells using a viral delivery system. Exemplary viruses for this purpose include adenovirus, retroviruses, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161 (1994), and Douglas and Curiel, *Science & Medicine* 4:44 (1997)). Advantages of the adenovirus system include the accommodation of relatively large DNA inserts, the ability to grow to high-titer, the ability to infect a broad range of mammalian cell types, and flexibility that allows use with a large number of available vectors containing different promoters.

By deleting portions of the adenovirus genome, larger inserts (up to 7 kb) of heterologous DNA can be accommodated. These inserts can be incorporated into the viral DNA by direct ligation or by homologous recombination with a co-transfected plasmid. An option is to delete the essential E1 gene from the viral vector, which results in the inability to replicate unless the E1 gene is provided by the host cell. Adenovirus vector-infected human 293 cells (ATCC Nos. CRL-1573, 45504, 45505), for example, can be grown as adherent cells or in suspension culture at relatively high cell density to produce significant amounts of protein (see Garnier et al., *Cytotechnol.* 15:145 (1994)).

The polypeptides of the invention can also be expressed in other higher eukaryotic cells, such as avian, fungal, insect, yeast, or plant cells. The baculovirus system provides an efficient means to introduce cloned genes into insect cells. Suitable expression vectors are based upon the *Autographa californica* multiple nuclear polyhedrosis virus (AcMNPV), and contain well-known promoters such as *Drosophila* heat shock protein (hsp) 70 promoter, *Autographa californica* nuclear polyhedrosis virus immediate-early gene promoter (ie-1) and the delayed early 39K promoter, baculovirus p10 promoter, and the *Drosophila metallothionein* promoter. A second method of making recombinant baculovirus utilizes a transposon-based system described by Luckow (Luckow, et al., *J. Virol.* 67:4566 (1993)). This system, which utilizes transfer vectors, is sold in the BAC-to-BAC kit (Life Technologies, Rockville, Md.). This system utilizes a transfer vector, PFASTBAC (Life Technologies) containing a Tn7 transposon to move the DNA encoding a polypeptide into a baculovirus genome maintained in *E. coli* as a large plasmid called a "bacmid." See, Hill-Perkins and Possee, *J. Gen. Virol.* 71:971 (1990), Bonning, et al., *J. Gen. Virol.* 75:1551 (1994), and Chazenbalk, and Rapoport, *J. Biol. Chem.* 270:1543 (1995). In addition, transfer vectors can include an in-frame fusion with DNA encoding an epitope tag at the C- or N-terminus of the expressed the polypeptide, for example, a Glu-Glu epitope tag (Grussenmeyer et al., *Proc. Nat'l Acad. Sci.* 82:7952 (1985)). Using a technique known in the art, a transfer vector containing a gene encoding a polypeptide of the present invention is transformed into *E. coli*, and screened for bacmids which contain an interrupted lacZ gene indicative of recombinant baculovirus. The bacmid DNA containing the recombinant baculovirus genome is then isolated using common techniques.

The illustrative PFASTBAC vector can be modified to a considerable degree. For example, the polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins (see, for example, Hill-Perkins and Possee, *J. Gen. Virol.* 71:971 (1990), Bonning, et al., *J. Gen. Virol.* 75:1551 (1994), and Chazenbalk and Rapoport, *J. Biol. Chem.* 270: 1543 (1995). In such transfer vector constructs, a short or long version of the basic protein promoter can be used. Moreover, transfer vectors can be constructed which replace the native secretory signal sequences with secretory signal sequences derived from insect proteins. For example, a secretory signal sequence from Ecdysteroid Glucosyltransferase (EGT), honey bee Melittin (Invitrogen Corporation; Carlsbad, Calif.), or baculovirus gp67 (PharMingen: San Diego, Calif.) can be used in constructs to replace the native IL-17RC secretory signal sequence.

The recombinant virus or bacmid is used to transfect host cells. Suitable insect host cells include cell lines derived from IPLB-Sf-21, a *Spodoptera frugiperda* pupal ovarian cell line, such as Sf9 (ATCC CRL 1711), Sf21AE, and Sf21 (Invitrogen Corporation; San Diego, Calif.), as well as *Drosophila* Schneider-2 cells, and the HIGH FIVEO cell line (Invitrogen) derived from *Trichoplusia ni* (U.S. Pat. No. 5,300,435). Commercially available serum-free media can be used to grow and to maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. When recombinant virus is used, the cells are typically grown up from an inoculation density of approximately 2-5× $10^5$ cells to a density of 1-2×$10^6$ cells at which time a recombinant viral stock is added at a multiplicity of infection (MOI) of 0.1 to 10, more typically near 3.

Established techniques for producing recombinant proteins in baculovirus systems are provided by Bailey et al., "Manipulation of Baculovirus Vectors," in *Methods in Molecular Biology, Volume 7: Gene Transfer and Expression Protocols*, Murray (ed.), pages 147-168 (The Humana Press, Inc. 1991), by Patel et al., "The baculovirus expression system," in *DNA Cloning 2: Expression Systems, 2nd Edition*, Glover et al. (eds.), pages 205-244 (Oxford University Press 1995), by Ausubel (1995) at pages 16-37 to 16-57, by Richardson (ed.), *Baculovirus Expression Protocols* (The Humana Press, Inc. 1995), and by Lucknow, "Insect Cell Expression Technology," in *Protein Engineering: Principles and Practice*, Cleland et al. (eds.), pages 183-218 (John Wiley & Sons, Inc. 1996).

Fungal cells, including yeast cells, can also be used to express the genes described herein. Yeast species of particular interest in this regard include *Saccharomyces cerevisiae*, *Pichia pastoris*, and *Pichia methanolica*. Suitable promoters for expression in yeast include promoters from GAL1 (galactose), PGK (phosphoglycerate kinase), ADH (alcohol dehydrogenase), AOX1 (alcohol oxidase), HIS4 (histidinol dehydrogenase), and the like. Many yeast cloning vectors have been designed and are readily available. These vectors include YIp-based vectors, such as YIp5, YRp vectors, such as YRp17, YEp vectors such as YEp13 and YCp vectors, such as YCp19. Methods for transforming *S. cerevisiae* cells with exogenous DNA and producing recombinant polypeptides therefrom are disclosed by, for example, Kawasaki, U.S. Pat. No. 4,599,311, Kawasaki et al., U.S. Pat. No. 4,931,373, Brake, U.S. Pat. No. 4,870,008, Welch et al., U.S. Pat. No. 5,037,743, and Murray et al., U.S. Pat. No. 4,845,075. Transformed cells are selected by phenotype determined by the selectable marker, commonly drug resistance or the ability to grow in the absence of a particular nutrient (e.g., leucine). A suitable vector system for use in *Saccharomyces cerevisiae* is the POT1 vector system disclosed by Kawasaki et al. (U.S. Pat. No. 4,931,373), which allows transformed cells to be selected by growth in glucose-containing media. Additional suitable promoters and terminators for use in yeast include those from glycolytic enzyme genes (see, e.g., Kawasaki, U.S. Pat. No. 4,599,311, Kingsman et al., U.S. Pat. No. 4,615, 974, and Bitter, U.S. Pat. No. 4,977,092) and alcohol dehydrogenase genes. See also U.S. Pat. Nos. 4,990,446, 5,063, 154, 5,139,936, and 4,661,454.

Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459 (1986), and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

For example, the use of *Pichia methanolica* as host for the production of recombinant proteins is disclosed by Raymond, U.S. Pat. No. 5,716,808, Raymond, U.S. Pat. No. 5,736,383, Raymond et al., *Yeast* 14:11-23 (1998), and in international publication Nos. WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, the promoter and terminator in the plasmid can be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A suitable selectable marker for use in *Pichia methanolica* is a *P. methanolica* ADE2 gene, which encodes phosphoribosyl-5-aminoimidazole carboxylase (AIRC; EC 4.1.1.21), and which allows ade2 host cells to grow in the absence of adenine. For large-scale, industrial processes where it is desirable to minimize the use of methanol, host cells can be used in which both methanol utilization genes (AUG1 and AUG2) are deleted. For production of secreted proteins, host cells can be deficient in vacuolar protease genes (PEP4 and PRB1). Electroporation is used to facilitate the introduction of a plasmid containing DNA encoding a polypeptide of interest into *P. methanolica* cells. *P. methanolica* cells can be transformed by electroporation using an exponentially decaying, pulsed electric field having a field strength of from 2.5 to 4.5 kV/cm, preferably about 3.75 kV/cm, and a time constant (t) of from 1 to 40 milliseconds, most preferably about 20 milliseconds.

Expression vectors can also be introduced into plant protoplasts, intact plant tissues, or isolated plant cells. Methods for introducing expression vectors into plant tissue include the direct infection or co-cultivation of plant tissue with *Agrobacterium tumefaciens*, microprojectile-mediated delivery, DNA injection, electroporation, and the like. See, for example, Horsch et al., *Science* 227:1229 (1985), Klein et al., *Biotechnology* 10:268 (1992), and Mild et al., "Procedures for Introducing Foreign DNA into Plants," in *Methods in Plant Molecular Biology and Biotechnology*, Glick et al. (eds.), pages 67-88 (CRC Press, 1993).

Alternatively, genes encoding the polypeptides of the present invention can be expressed in prokaryotic host cells. Suitable promoters that can be used to express IL-17RC polypeptides in a prokaryotic host are well-known to those of skill in the art and include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus, Streptomyces* promoters, the int promoter of bacteriophage lambda, the bla promoter of pBR322, and the CAT promoter of the chloramphenicol acetyl transferase gene. Prokaryotic promoters have been reviewed by Glick, *J. Ind. Microbiol.* 1:277 (1987), Watson et al., *Molecular Biology of the Gene*, 4th Ed. (Benjamin Cummins 1987), and by Ausubel et al. (1995).

Suitable prokaryotic hosts include *E. coli* and *Bacillus subtilus*. Suitable strains of *E. coli* include BL21(DE3), BL21 (DE3)pLysS, BL21(DE3)pLysE, DH1, DH4I, DH5, DH5I, DH5IF', DH5IMCR, DH10B, DH10B/p3, DH11S, C600, HB101, JM101, JM105, JM109, JM110, K38, RR1, Y1088, Y1089, CSH18, ER1451, and ER1647 (see, for example, Brown (ed.), *Molecular Biology Labfax* (Academic Press 1991)). Suitable strains of *Bacillus subtilus* include BR151, YB886, MI119, MI120, and B170 (see, for example, Hardy, "*Bacillus* Cloning Methods," in *DNA Cloning: A Practical Approach*, Glover (ed.) (IRL Press 1985)).

When expressing a polypeptide of the present invention in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Methods for expressing proteins in prokaryotic hosts are well-known to those of skill in the art (see, for example, Williams et al., "Expression of foreign proteins in *E. coli* using plasmid vectors and purification of specific polyclonal antibodies," in *DNA Cloning 2: Expression Systems*, 2nd Edition, Glover et al. (eds.), page 15 (Oxford University Press 1995), Ward et al., "Genetic Manipulation and Expression of Antibodies," in *Monoclonal Antibodies: Principles and Applications*, page 137 (Wiley-Liss, Inc. 1995), and Georgiou, "Expression of Proteins in Bacteria," in *Protein Engineering: Principles and Practice*, Cleland et al. (eds.), page 101 (John Wiley & Sons, Inc. 1996)).

Standard methods for introducing expression vectors into bacterial, yeast, insect, and plant cells are provided, for example, by Ausubel (1995).

General methods for expressing and recovering foreign protein produced by a mammalian cell system are provided by, for example, Etcheverry, "Expression of Engineered Proteins in Mammalian Cell Culture," in *Protein Engineering: Principles and Practice*, Cleland et al. (eds.), pages 163 (Wiley-Liss, Inc. 1996). Standard techniques for recovering protein produced by a bacterial system is provided by, for example, Grisshammer et al., "Purification of over-produced proteins from *E. coli* cells," in *DNA Cloning 2: Expression Systems, 2nd Edition*, Glover et al. (eds.), pages 59-92 (Oxford University Press 1995). Established methods for isolating recombinant proteins from a baculovirus system are described by Richardson (ed.), *Baculovirus Expression Protocols* (The Humana Press, Inc. 1995).

As an alternative, polypeptides of the present invention can be synthesized by exclusive solid phase synthesis, partial solid phase methods, fragment condensation or classical solution synthesis. These synthesis methods are well-known to those of skill in the art (see, for example, Merrifield, *J. Am. Chem. Soc.* 85:2149 (1963), Stewart et al., "Solid Phase Peptide Synthesis" (2nd Edition), (Pierce Chemical Co. 1984), Bayer and Rapp, *Chem. Pept. Prot.* 3:3 (1986), Atherton et al., *Solid Phase Peptide Synthesis: A Practical Approach* (IRL Press 1989), Fields and Colowick, "Solid-Phase Peptide Synthesis," *Methods in Enzymology Volume* 289 (Academic Press 1997), and Lloyd-Williams et al., *Chemical Approaches to the Synthesis of Peptides and Proteins* (CRC Press, Inc. 1997)). Variations in total chemical synthesis strategies, such as "native chemical ligation" and "expressed protein ligation" are also standard (see, for example, Dawson et al., *Science* 266:776 (1994), Hackeng et al., *Proc. Nat'l Acad. Sci. USA* 94:7845 (1997), Dawson, *Methods Enzymol.* 287: 34 (1997), Muir et al, *Proc. Nat'l Acad. Sci. USA* 95:6705 (1998), and Severinov and Muir, *J. Biol. Chem.* 273:16205 (1998)).

Peptides and polypeptides of the present invention comprise at least six, at least nine, or at least 15 contiguous amino acid residues of SEQ ID NO:2, 5 or 21. As an illustration, polypeptides can comprise at least six, at least nine, or at least 15 contiguous amino acid residues of SEQ ID NO:2, 5 and/or 21. Within certain embodiments of the invention, the polypeptides comprise 20, 30, 40, 50, 100, or more contiguous residues of these amino acid sequences. Nucleic acid molecules encoding such peptides and polypeptides are useful as polymerase chain reaction primers and probes.

Moreover, the polypeptides and fragments thereof of the present invention can be expressed as monomers, homodimers, heterodimers, or multimers within higher eukaryotic cells. Such cells can be used to produce IL-17RC monomeric, homodimeric, heterodimeric and multimeric receptor polypeptides that comprise at least a portion of an IL-17RC polypeptide ("IL-17RC-comprising receptors" or "IL-17RC-comprising receptor polypeptides"), a portion of IL-17RC and IL-17RA together (as either a monomer, homodimer or heterodimer) or can be used as assay cells in screening systems. Within one aspect of the present invention, a polypeptide of the present invention comprising at least the ligand-binding portion of either the IL-17RC or IL-17RA extracellular domain is produced by a cultured cell, and the cell is used to screen for ligands for the receptor, including the natural ligand, IL-17F, as well as IL-17A, or even agonists and antagonists of the natural ligand. To summarize this approach, a cDNA or gene encoding the receptor is combined with other genetic elements required for its expression (e.g., a transcription promoter), and the resulting expression vector is inserted into a host cell. Cells that express the DNA and produce functional receptor are selected and used within a variety of screening systems. Each component of the monomeric, homodimeric, heterodimeric and multimeric receptor complex can be expressed in the same cell. Moreover, the components of the monomeric, homodimeric, heterodimeric and multimeric receptor complex can also be fused to a transmembrane domain or other membrane fusion moiety to allow complex assembly and screening of transfectants as described above.

To assay polyepeptides of the present invention, mammalian cells suitable for use in expressing IL-17RC and IL-17RC/IL-17RA receptors or other receptors known to bind IL-17A or IL-17F (e.g., cells expressing IL-17R) and transducing a receptor-mediated signal include cells that express other receptor subunits that may form a functional complex with IL-17RC. It is also preferred to use a cell from the same species as the receptor to be expressed. Within a preferred embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, *Cell* 41: 727-734, (1985)) which is an IL-3 dependent murine pre-B cell line. Other cell lines include BHK, COS-1 and CHO cells. Suitable host cells can be engineered to produce the necessary receptor subunits or other cellular component needed for the desired cellular response. This approach is advantageous because cell lines can be engineered to express receptor subunits from any species, thereby overcoming potential limitations arising from species specificity. Species orthologs of the human receptor cDNA can be cloned and used within cell lines from the same species, such as a mouse cDNA in the BaF3 cell line. Cell lines that are dependent upon one hematopoietic growth factor, such as GM-CSF or IL-3, can thus be engineered to become dependent upon another cytokine that acts through the IL-17RC or IL-17RA receptor, such as IL-17F or IL-17A.

Cells expressing functional receptor are used within screening assays. A variety of suitable assays are known in the art. These assays are based on the detection of a biological response in a target cell. One such assay is a cell proliferation assay. Cells are cultured in the presence or absence of a test compound, and cell proliferation is detected by, for example, measuring incorporation of tritiated thymidine or by colorimetric assay based on the metabolic breakdown of 3-(4,5-dimethylthiazol-2-yl)-2,5-diphenyl tetrazolium bromide (MTT) (Mosman, *J. Immunol. Meth.* 65: 55-63, (1983)). An alternative assay format uses cells that are further engineered to express a reporter gene. The reporter gene is linked to a promoter element that is responsive to the receptor-linked pathway, and the assay detects activation of transcription of the reporter gene. A preferred promoter element in this regard is a serum response element, or SRE. See, e.g., Shaw et al., *Cell* 56:563-572, (1989). A preferred such reporter gene is a luciferase gene (de Wet et al., *Mol. Cell. Biol.* 7:725, (1987)). Expression of the luciferase gene is detected by luminescence using methods known in the art (e.g., Baumgartner et al., *J. Biol. Chem.* 269:29094-29101, (1994); Schenborn and Goiffin, *Promega Notes* 41:11, 1993). Luciferase activity assay kits are commercially available from, for example, Promega Corp., Madison, Wis. Target cell lines of this type can be used to screen libraries of chemicals, cell-conditioned culture media, fungal broths, soil samples, water samples, and the like. For example, a bank of cell-conditioned media samples can be assayed on a target cell to identify cells that produce ligand. Positive cells are then used to produce a cDNA library in a mammalian expression vector, which is divided into pools, transfected into host cells, and expressed. Media samples from the transfected cells are then assayed, with subsequent division of pools, re-transfection, subculturing, and re-assay of positive cells to isolate a cloned cDNA encoding the ligand.

An additional screening approach provided by the present invention includes the use of hybrid receptor polypeptides. These hybrid polypeptides fall into two general classes. Within the first class, the intracellular domain of IL-17RC, is joined to the ligand-binding domain of a second receptor. A second class of hybrid receptor polypeptides comprise the extracellular (ligand-binding) domain of IL-17RC (SEQ ID NO:3) and IL-17RA (SEQ ID NO:21) with an intracellular domain of a second receptor, preferably a hematopoietic cytokine receptor, and a transmembrane domain. Such hybrid monomers, homodimers, heterodimers and multimers of the present invention receptors of this second class are expressed in cells known to be capable of responding to signals transduced by the second receptor. Together, these two classes of hybrid receptors enable the identification of a responsive cell type for the development of an assay for detecting IL-17F or IL-17A. Moreover, such cells can be used in the presence of IL-17F or IL-17A to assay the soluble receptor antagonists of the present invention in a competition-type assay. In such assay, a decrease in the proliferation or signal transduction activity of IL-17F or IL-17A in the presence of a soluble receptor of the present invention demonstrates antagonistic activity. Moreover IL-17RC-soluble receptor binding assays, an cell-based assays, can also be used to assess whether a soluble receptor binds, blocks, inhibits, reduces, antagonizes or neutralizes IL-17F or IL-17A activity.

The present invention provides for an expression vector comprising the following operably linked elements: a) a transcription promoter; b) a DNA segment encoding a polypeptide wherein the encoded polypeptide comprises an amino acid sequence having at least 95% sequence identity with amino acid residues 33-458 of SEQ ID NO:158, wherein the encoded polypeptide binds IL-17A and/or IL-17F; and c) a transcription terminator. The DNA segment may further encode a secretory signal sequence. The DNA segment may further encode an immunoglobulin moiety, e.g., an immunoglobulin heavy chain constant region, amino acid residues 459-690 of SEQ ID NO:158. The expression vector may optionally be introduced into a cultured cell, such as *E. coli*, Chinese hamster ovary cell, wherein the cell expresses the polypeptide encoded by the DNA segment. Another embodiment of the present invention is a method of producing a polypeptide comprising culturing a cell into which has been introduced an expression vector of claim 13, wherein the cell expresses the polypeptide encoded by the DNA segment; and recovering the expresses polypeptide.

The present invention also provides a composition comprising an isolated polypeptide an isolated polypeptide comprising an amino acid sequence having at least 95% sequence identity with amino acid residues 33-458 of SEQ ID NO:158; and a pharmaceutically acceptable carrier. The polypeptide may further comprises an immunoglobuline moiety (e.g., immunoglobulin heavy chain constant region, such as an Fc region from IgG1, IgG2, IgG3, IgG4, variants and mutants thereof; amino acid residues 1-232 of SEQ ID NO:175, and amino acid residues 459-690 of SEQ ID NO:158).

The present invention also provides a method of treating a subject suffering from a disease caused, maintained or exascerbated by IL-17A and/or IL-17F activity comprising administering to the subject a polypeptide comprising an amino acid sequence having at least 95% sequence identity with amino acid residues 33-458 of SEQ ID NO:158, wherein the polypeptide binds, blocks, reduces, antagonizes or neutralizes IL-17A and/or IL-17F, and wherein the disease is selected from the group consisting of psoriasis, atopic and contact dermatitis, IBD, IBS, colitis, endotoxemia, arthritis, rheumatoid arthritis, Lyme disease arthritis, psoriatic arthritis, adult respiratory disease (ARD), septic shock, multiple organ failure, inflammatory lung injury such as asthma, chronic obstructive pulmonary disease (COPD), airway hyper-responsiveness, chronic bronchitis, allergic asthma, bacterial pneumonia, psoriasis, eczema, and inflammatory bowel disease such as ulcerative colitis and Crohn's disease, *helicobacter pylori* infection, intraabdominal adhesions and/or abscesses as results of peritoneal inflammation (i.e. from infection, injury, etc.), systemic lupus erythematosus (SLE), lupus nephritis, Diabetes Type I, coronary artery disease, stroke, multiple sclerosis, systemic sclerosis, scleroderma, nephrotic syndrome, sepsis, organ allograft rejection, graft vs. host disease (GVHD), transplant rejection (e.g., kidney, lung, and heart), streptococcal cell wall (SCW)-induced arthritis, osteoarthritis, gingivitis/periodontitis, herpetic stromal keratitis, osteoporosis, neuritis, cancers including prostate, renal, colon, ovarian, cervical, leukemia, cancer angiogenesis (such as ovarian cancer, cervical cancer and prostate cancer), B cell lymphoma, T cell lymphoma, cystic fibrosis, restenosis and Kawasaki disease.

F) Production of IL-17RC, IL-17RA and IL-17RC/IL-17RA Fusion Proteins and Conjugates One general class of IL-17RC, IL-17RA and IL-17RC/IL-17RA analogs are variants having an amino acid sequence that is a mutation of the amino acid sequence disclosed herein. Another general class of IL-17RC, IL-17RA and IL-17RC/IL-17RA analogs is provided by anti-idiotype antibodies, and fragments thereof, as described below. Moreover, recombinant antibodies comprising anti-idiotype variable domains can be used as analogs (see, for example, Monfardini et al., *Proc. Assoc. Am. Physicians* 108:420 (1996)). Since the variable domains of anti-idiotype IL-17RC antibodies mimic IL-17RC, these domains can provide IL-17RC binding activity. Methods of producing anti-idiotypic catalytic antibodies are known to those of skill in the art (see, for example, Joron et al., *Ann. N Y Acad. Sci.* 672:216 (1992), Friboulet et al., *Appl. Biochem. Biotechnol.* 47:229 (1994), and Avalle et al., *Ann. N Y Acad. Sci.* 864:118 (1998)).

Another approach to identifying IL-17RC, IL-17RA and IL-17RC/IL-17RA analogs is provided by the use of combinatorial libraries. Methods for constructing and screening phage display and other combinatorial libraries are provided, for example, by Kay et al., *Phage Display of Peptides and Proteins* (Academic Press 1996), Verdine, U.S. Pat. No. 5,783,384, Kay, et. al., U.S. Pat. No. 5,747,334, and Kauffman et al., U.S. Pat. No. 5,723,323.

IL-17RC, IL-17RA and IL-17RC/IL-17RA polypeptides have both in vivo and in vitro uses. As an illustration, a soluble form of IL-17RC can be added to cell culture medium to inhibit the effects of the IL-17RC ligand (i.e. IL-17F, IL-17A or both) produced by the cultured cells.

Fusion proteins of IL-17RC, IL-17RA and IL-17RC/IL-17RA can be used to express and isolate the corresponding polypeptide. As described below, particular IL-17RC, IL-17RA and IL-17RC/IL-17RA fusion proteins also have uses in diagnosis and therapy. One type of fusion protein comprises a peptide that guides a IL-17RC polypeptide from a recombinant host cell. To direct a IL-17RC polypeptide into the secretory pathway of a eukaryotic host cell, a secretory signal sequence (also known as a signal peptide, a leader sequence, prepro sequence or pre sequence) is provided in the IL-17RC expression vector. While the secretory signal sequence may be derived from IL-17RC, a suitable signal sequence may also be derived from another secreted protein or synthesized de novo. The secretory signal sequence is operably linked to a IL-17RC-encoding sequence such that the two sequences are joined in the correct reading frame and positioned to direct the newly synthesized polypeptide into the secretory pathway of the host cell. Secretory signal sequences are commonly positioned 5' to the nucleotide sequence encoding the polypeptide of interest, although certain secretory signal sequences may be positioned elsewhere in the nucleotide sequence of interest (see, e.g., Welch et al., U.S. Pat. No. 5,037,743; Holland et al., U.S. Pat. No. 5,143,830).

Although the secretory signal sequence of IL-17RC, IL-17RA and IL-17RC/IL-17RA as produced by mammalian cells (e.g., tissue-type plasminogen activator signal sequence, as described, for example, in U.S. Pat. No. 5,641,655) is useful for expression of the corresponding polypeptide in recombinant mammalian hosts, a yeast signal sequence is preferred for expression in yeast cells. Examples of suitable yeast signal sequences are those derived from yeast mating phermone α-factor (encoded by the MFα1 gene), invertase (encoded by the SUC2 gene), or acid phosphatase (encoded by the PHO5 gene). See, for example, Romanos et al., "Expression of Cloned Genes in Yeast," in *DNA Cloning* 2: A Practical Approach, $2^{nd}$ Edition, Glover and Hames (eds.), pages 123-167 (Oxford University Press 1995).

The soluble receptor polypeptides of the present invention can be prepared by expressing a truncated DNA encoding the extracellular domain, for example, a polypeptide which contains all or a portion SEQ ID NO:3, or the corresponding region of a non-human receptor. It is preferred that the extracellular domain polypeptides be prepared in a form substantially free of transmembrane and intracellular polypeptide segments. To direct the export of the receptor domain from the host cell, the receptor DNA is linked to a second DNA segment encoding a secretory peptide, such as a t-PA secretory peptide. To facilitate purification of the secreted receptor domain, a C-terminal extension, such as a poly-histidine tag, substance P, Flag™ peptide (Hopp et al., *Biotechnology* 6:1204-1210, (1988); available from Eastman Kodak Co., New Haven, Conn.) or another polypeptide or protein for which an antibody or other specific binding agent is available, can be fused to the receptor polypeptide.

In an alternative approach, a receptor extracellular domain or portion thereof of IL-17RC, IL-17RA or IL-17RC/IL-17RA together can be expressed as a fusion with immunoglobulin heavy chain constant regions, typically an Fc fragment, which contains two constant region domains and a hinge region but lacks the variable region (See Sledziewski, A Z et al., U.S. Pat. Nos. 6,018,026 and 5,750,375). The soluble polypeptides of the present invention include such fusions. One such fusion is shown in SEQ ID NO:64. Such fusions are typically secreted as multimeric molecules wherein the Fc portions are disulfide bonded to each other and two receptor polypeptides are arrayed in closed proximity to each other. Fusions of this type can be used to affinity purify the cognate ligand from solution, as an in vitro assay tool, to block, inhibit or reduce signals in vitro by specifically titrating out ligand, and as antagonists in vivo by administering them parenterally to bind circulating ligand and clear it from the circulation. To purify ligand, an IL-17RC, IL-17RA and IL-17RC/IL-17RA-Ig chimera is added to a sample containing the ligand (e.g., cell-conditioned culture media or tissue extracts) under conditions that facilitate receptor-ligand binding (typically near-physiological temperature, pH, and ionic strength). The chimera-ligand complex is then separated by the mixture using protein A, which is immobilized on a solid support (e.g., insoluble resin beads). The ligand is then eluted using conventional chemical techniques, such as with a salt or pH gradient. In the alternative, the chimera itself can be bound to a solid support, with binding and elution carried out as above. The chimeras may be used in vivo to regulate inflammatory responses including acute phase responses such as serum amyloid A (SAA), C-reactive protein (CRP), and the like. Chimeras with high binding affinity are administered parenterally (e.g., by intramuscular, subcutaneous or intravenous injection). Circulating molecules bind ligand and are cleared from circulation by normal physiological processes. For use in assays, the chimeras are bound to a support via the $F_c$ region and used in an ELISA format.

To assist in isolating polypeptides of the present invention, an assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

Ligand-binding receptor polypeptides can also be used within other assay systems known in the art. Such systems include Scatchard analysis for determination of binding affinity (see Scatchard, *Ann. NY Acad. Sci.* 51: 660-72, 1949) and calorimetric assays (Cunningham et al., *Science* 253:545-48, 1991; Cunningham et al., *Science* 245:821-25, 1991).

The present invention further provides a variety of other polypeptide fusions and related multimeric proteins comprising one or more polypeptide fusions. For example, a soluble IL-17RC, IL-17RA or IL-17RC/IL-17RA receptor polypeptide can be prepared as a fusion to a dimerizing protein as disclosed in U.S. Pat. Nos. 5,155,027 and 5,567,584. Preferred dimerizing proteins in this regard include immunoglobulin constant region domains, e.g., IgGγ1, and the human κ light chain. Immunoglobulin-soluble fusions of the present invention can be expressed in genetically engineered cells to produce a variety of multimeric IL-17RC, IL-17RA or IL-17RC/IL-17RA receptor analogs. Auxiliary domains can be fused to soluble polypeptides of the present invention to target them to specific cells, tissues, or macromolecules (e.g., collagen, or cells expressing IL-17F or IL-17A). The polypeptides of the present invention can be fused to two or more moieties, such as an affinity tag for purification and a targeting domain. Polypeptide fusions can also comprise one or more cleavage sites, particularly between domains. (See Tuan et al., *Connective Tissue Research* 34:1-9, 1996.)

In bacterial cells, it is often desirable to express a heterologous protein as a fusion protein to decrease toxicity, increase stability, and to enhance recovery of the expressed protein. For example, IL-17RC (or any polypeptide of the present invention) can be expressed as a fusion protein comprising a glutathione S-transferase polypeptide. Glutathione S-transferase fusion proteins are typically soluble, and easily purifiable from *E. coli* lysates on immobilized glutathione columns. In similar approaches, a IL-17RC fusion protein comprising a maltose binding protein polypeptide can be isolated with an amylose resin column, while a fusion protein comprising the C-terminal end of a truncated Protein A gene can be purified using IgG-Sepharose. Established techniques for expressing a heterologous polypeptide as a fusion protein in a bacterial cell are described, for example, by Williams et al., "Expression of Foreign Proteins in *E. coli* Using Plasmid Vectors and Purification of Specific Polyclonal Antibodies," in *DNA Cloning* 2: A Practical Approach, $2^{nd}$ Edition, Glover and Hames (Eds.), pages 15-58 (Oxford University Press 1995). In addition, commercially available expression systems are available. For example, the PINPOINT Xa protein purification system (Promega Corporation; Madison, Wis.) provides a method for isolating a fusion protein comprising a polypeptide that becomes biotinylated during expression with a resin that comprises avidin.

Peptide tags that are useful for isolating heterologous polypeptides expressed by either prokaryotic or eukaryotic cells include polyHistidine tags (which have an affinity for nickel-chelating resin), c-myc tags, calmodulin binding protein (isolated with calmodulin affinity chromatography), substance P, the RYIRS tag (which binds with anti-RYIRS antibodies), the Glu-Glu tag, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

Another form of fusion protein comprises a polypeptide of the present invention and an immunoglobulin heavy chain constant region, typically an Fc fragment, which contains two or three constant region domains and a hinge region but lacks the variable region. As an illustration, Chang et al., U.S. Pat. No. 5,723,125, describe a fusion protein comprising a human interferon and a human immunoglobulin Fc fragment. The C-terminal of the interferon is linked to the N-terminal of the Fc fragment by a peptide linker moiety. An example of a peptide linker is a peptide comprising primarily a T cell inert sequence, which is immunologically inert. An exemplary peptide linker has the amino acid sequence: GGSGG SGGGG SGGGG S (SEQ ID NO:9). In this fusion protein, an illustrative Fc moiety is a human γ4 chain, which is stable in solution and has little or no complement activating activity. Accordingly, the present invention contemplates a IL-17RC or an IL-17RC/IL-17RA fusion protein that comprises a IL-17RC or an IL-17RC and IL-17RA moiety and a human Fc fragment, wherein the C-terminus of the IL-17RC moiety is attached to the N-terminus of the Fc fragment via a peptide linker, such as a peptide comprising at least a portion of the amino acid sequence of SEQ ID NO:2, 5 or 21. Both the IL-17RC and the IL-17RA moiety can be the extraclualr domain or any fragment thereof. For example, a fusion protein can comprise the amino acid of SEQ ID NO:3 and an Fc fragment (e.g., a human Fc fragment) (SEQ ID NO:64). Another example of such a fusion protein is Variant 1454 (SEQ ID NOs: 157 and 158) which includes exons 1-6 of human IL-17RA and 8-16 of human IL-17RCx1, fused to Fc5 (SEQ ID NOs: 179 and 180). Variant 1454 also has the native signal peptide from human IL-17RA. Fc10, or any equivalent known in the art, may also be used in place of Fc5.

In another variation, a fusion protein of the present invention comprises an IgG sequence, an IL-17RC, IL-17RA or IL-17RC/IL-17RA moiety covalently joined to the aminoterminal end of the IgG sequence, and a signal peptide that is covalently joined to the aminoterminal of the IL-17RC or IL-17RA moiety, wherein the IgG sequence consists of the following elements in the following order: a hinge region, a $CH_2$ domain, and a $CH_3$ domain. Accordingly, the IgG sequence lacks a $CH_1$ domain. These moieties should display a biological activity, as described herein, such as the ability to bind with IL-17A and/or IL-17F. This general approach to producing fusion proteins that comprise both antibody and nonantibody portions has been described by LaRochelle et al., EP 742830 (WO 95/21258).

Fusion proteins comprising a IL-17RC or IL-17RC/IL-17RA moiety and an Fc moiety can be used, for example, as an in vitro assay tool. For example, the presence of IL-F in a biological sample can be detected using a IL-17RC-immunoglobulin fusion protein, in which the IL-17RC moiety is used to bind the ligand, and a macromolecule, such as Protein A or anti-Fc antibody, is used to bind the fusion protein to a solid support. Such systems can be used to identify agonists and antagonists that interfere with the binding of a IL-17 family ligands, e.g., IL-17F or both IL-17A and IL-17F, to their receptor.

The present invention further provides a variety of other polypeptide fusions. For example, part or all of a domain(s) conferring a desired biological function (eg. Binding IL-17A) can be added to a portion of IL-17RC with the functionally equivalent domain(s) from another member of the cytokine receptor family (i.e. IL-17RA) to create a different molecule (i.e. IL-17RC/IL-17RA). Polypeptide fusions can be expressed in recombinant host cells to produce a variety of these fusion analogs. An IL-17RC, IL-17RA or IL-17RC/IL-17RA polypeptide can be fused to two or more moieties or domains, such as an affinity tag for purification and a targeting domain. Polypeptide fusions can also comprise one or more cleavage sites, particularly between domains. See, for example, Tuan et al., *Connective Tissue Research* 34:1 (1996).

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. General methods for enzymatic and chemical cleavage of fusion proteins are described, for example, by Ausubel (1995) at pages 16-19 to 16-25.

IL-17RC and/or IL-17RA binding domains can be further characterized by physical analysis of structure, as determined by such techniques as nuclear magnetic resonance, crystallography, electron diffraction or photoaffinity labeling, in conjunction with mutation of putative contact site amino acids of ligand agonists. See, e.g., de Vos et al., *Science* 255:306 (1992), Smith et al., *J. Mol. Biol.* 224:899 (1992), and Wlodaver et al., *FEBS Lett.* 309:59 (1992).

The present invention also contemplates chemically modified IL-17RC or IL-17RC/IL-17RA compositions, in which the polypeptide is linked with a polymer. Illustrative IL-17RC or IL-17RC/IL-17RA polypeptides are soluble polypeptides that lack a functional transmembrane domain, such as a polypeptide consisting of amino acid residues SEQ ID NO:3 or 21. Typically, the polymer is water soluble so that the conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, or mono-(C1-C10) alkoxy, or aryloxy derivatives thereof (see, for example, Harris, et al., U.S. Pat. No. 5,252,714). The polymer may be branched or unbranched. Moreover, a mixture of polymers can be used to produce IL-17RC or IL-17RC/IL-17RA conjugates.

The conjugates of the present invention used for therapy can comprise pharmaceutically acceptable water-soluble polymer moieties. Suitable water-soluble polymers include polyethylene glycol (PEG), monomethoxy-PEG, mono-(C1-C10)alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropylene oxide/ethylene oxide copolymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A IL-17RC conjugate can also comprise a mixture of such water-soluble polymers.

One example of a IL-17RC conjugate comprises a IL-17RC moiety (or an IL-17RC/IL-17RA moiety) and a polyalkyl oxide moiety attached to the N-terminus of the IL-17RC moiety. PEG is one suitable polyalkyl oxide. As an illustration, IL-17RC (or IL-17RC/IL-17RA) can be modified with PEG, a process known as "PEGylation." PEGylation of IL-17RC can be carried out by any of the PEGylation reactions known in the art (see, for example, EP 0 154 316, Delgado et al., *Critical Reviews in Therapeutic Drug Carrier Systems* 9:249 (1992), Duncan and Spreafico, *Clin. Pharmacokinet.* 27:290 (1994), and Francis et al., *Int J Hematol* 68:1 (1998)). For example, PEGylation can be performed by an acylation reaction or by an alkylation reaction with a reactive polyethylene glycol molecule. In an alternative approach, IL-17RC conjugates are formed by condensing activated PEG, in which a terminal hydroxy or amino group of PEG has been replaced by an activated linker (see, for example, Karasiewicz et al., U.S. Pat. No. 5,382,657).

PEGylation by acylation typically requires reacting an active ester derivative of PEG with a IL-17RC or IL-17RC/IL-17RA polypeptide. An example of an activated PEG ester is PEG esterified to N-hydroxysuccinimide. As used herein, the term "acylation" includes the following types of linkages between IL-17RC or IL-17RC/IL-17RA and a water soluble polymer: amide, carbamate, urethane, and the like. Methods for preparing PEGylated IL-17RC or IL-17RC/IL-17RA by acylation will typically comprise the steps of (a) reacting a IL-17RC or IL-17RC/IL-17RA polypeptide with PEG (such as a reactive ester of an aldehyde derivative of PEG) under conditions whereby one or more PEG groups attach to IL-17RC or IL-17RC/IL-17RA, and (b) obtaining the reaction product(s). Generally, the optimal reaction conditions for acylation reactions will be determined based upon known parameters and desired results. For example, the larger the ratio of PEG:IL-17RC (or PEG:IL-17RC/IL-17RA), the greater the percentage of polyPEGylated IL-17RC (or IL-17RC/IL-17RA) product.

The product of PEGylation by acylation is typically a polyPEGylated product, wherein the lysine ε-amino groups are PEGylated via an acyl linking group. An example of a connecting linkage is an amide. Typically, the resulting IL-17RC or IL-17RC/IL-17RA will be at least 95% mono-, di-, or tri-pegylated, although some species with higher degrees of PEGylation may be formed depending upon the reaction conditions. PEGylated species can be separated from unconjugated IL-17RC or IL-17RC/IL-17RA polypeptides using standard purification methods, such as dialysis, ultrafiltration, ion exchange chromatography, affinity chromatography, and the like.

PEGylation by alkylation generally involves reacting a terminal aldehyde derivative of PEG with IL-17RC or IL-17RC/IL-17RA in the presence of a reducing agent. PEG groups can be attached to the polypeptide via a —CH$_2$—NH group.

Derivatization via reductive alkylation to produce a monoPEGylated product takes advantage of the differential reactivity of different types of primary amino groups available for derivatization. Typically, the reaction is performed at a pH that allows one to take advantage of the pKa differences between the ε-amino groups of the lysine residues and the α-amino group of the N-terminal residue of the protein. By such selective derivatization, attachment of a water-soluble polymer that contains a reactive group such as an aldehyde, to a protein is controlled. The conjugation with the polymer occurs predominantly at the N-terminus of the protein without significant modification of other reactive groups such as the lysine side chain amino groups. The present invention provides a substantially homogenous preparation of IL-17RC or IL-17RC/IL-17RA monopolymer conjugates.

Reductive alkylation to produce a substantially homogenous population of monopolymer IL-17RC or IL-17RC/IL-17RA conjugate molecule can comprise the steps of: (a) reacting a IL-17RC or IL-17RC/IL-17RA polypeptide with a reactive PEG under reductive alkylation conditions at a pH suitable to permit selective modification of the α-amino group at the amino terminus of the IL-17RC or IL-17RC/IL-17RA, and (b) obtaining the reaction product(s). The reducing agent used for reductive alkylation should be stable in aqueous solution and able to reduce only the Schiff base formed in the initial process of reductive alkylation. Illustrative reducing agents include sodium borohydride, sodium cyanoborohydride, dimethylamine borane, trimethylamine borane, and pyridine borane.

For a substantially homogenous population of monopolymer IL-17RC or IL-17RC/IL-17RA conjugates, the reductive alkylation reaction conditions are those that permit the selective attachment of the water-soluble polymer moiety to the N-terminus of IL-17RC or IL-17RC/IL-17RA. Such reaction conditions generally provide for pKa differences between the lysine amino groups and the α-amino group at the N-terminus. The pH also affects the ratio of polymer to protein to be used. In general, if the pH is lower, a larger excess of polymer to protein will be desired because the less reactive the N-terminal α-group, the more polymer is needed to achieve optimal conditions. If the pH is higher, the polymer:IL-17RC (or polymer:IL-17RC/IL-17RA) need not be as large because more reactive groups are available. Typically, the pH will fall within the range of 3 to 9, or 3 to 6. This method can be employed for making IL-17RC or IL-17RC/IL-17RA-comprising homodimeric, heterodimeric or multimeric soluble receptor conjugates.

Another factor to consider is the molecular weight of the water-soluble polymer. Generally, the higher the molecular weight of the polymer, the fewer number of polymer molecules which may be attached to the protein. For PEGylation reactions, the typical molecular weight is about 2 kDa to about 100 kDa, about 5 kDa to about 50 kDa, or about 12 kDa to about 25 kDa. The molar ratio of water-soluble polymer to IL-17RC or IL-17RC/IL-17RA will generally be in the range of 1:1 to 100:1. Typically, the molar ratio of water-soluble polymer to IL-17RC or IL-17RC/IL-17RA will be 1:1 to 20:1 for polyPEGylation, and 1:1 to 5:1 for monoPEGylation.

General methods for producing conjugates comprising a polypeptide and water-soluble polymer moieties are known in the art. See, for example, Karasiewicz et al., U.S. Pat. No. 5,382,657, Greenwald et al., U.S. Pat. No. 5,738,846, Nieforth et al., *Clin. Pharmacol. Ther.* 59:636 (1996), Monkarsh et al., *Anal. Biochem.* 247:434 (1997)). This method can be employed for making IL-17RC-comprising homodimeric, heterodimeric or multimeric soluble receptor conjugates.

The present invention contemplates compositions comprising a peptide or polypeptide, such as a soluble receptor or antibody described herein. Such compositions can further comprise a carrier. The carrier can be a conventional organic or inorganic carrier. Examples of carriers include water, buffer solution, alcohol, propylene glycol, macrogol, sesame oil, corn oil, and the like.

G) Isolation of IL-17RC or IL-17RC/IL-17RA Polypeptides

The polypeptides of the present invention can be purified to at least about 80% purity, to at least about 90% purity, to at least about 95% purity, or greater than 95%, such as 96%, 97%, 98%, or greater than 99% purity with respect to contaminating macromolecules, particularly other proteins and nucleic acids, and free of infectious and pyrogenic agents. The polypeptides of the present invention may also be purified to a pharmaceutically pure state, which is greater than 99.9% pure. In certain preparations, purified polypeptide is substantially free of other polypeptides, particularly other polypeptides of animal origin.

Fractionation and/or conventional purification methods can be used to obtain preparations of IL-17RC or IL-17RC/IL-17RA purified from natural sources (e.g., human tissue sources), synthetic IL-17RC or IL-17RC/IL-17RA polypeptides, and recombinant IL-17RC or IL-17RC/IL-17RA polypeptides and fusion IL-17RC or IL-17RC/IL-17RA polypeptides purified from recombinant host cells. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are suitable. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in IL-17RC or IL-17RC/IL-17RA isolation and purification can be devised by those of skill in the art.

The polypeptides of the present invention can also be isolated by exploitation of particular properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1 (1985)). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (M. Deutscher, (ed.), *Meth. Enzymol.* 182:529 (1990)). Within additional embodiments of the invention, a fusion of the polypeptide of interest and an affinity tag (e.g., maltose-binding protein, an immunoglobulin domain) may be constructed to facilitate purification. Moreover, the ligand-binding properties of the soluble IL-17RC or IL-17RC/IL-17RA polypeptides of the present invention can be exploited for purification, for example, of IL-17RC-comprising soluble receptors; for example, by using affinity chromatography wherein IL-17F ligand is bound to a column and the IL-17RC-comprising receptor is bound and subsequently eluted using standard chromatography methods.

IL-17RC, IL-17RA or IL-17RC/IL-17RA polypeptides or fragments thereof may also be prepared through chemical synthesis, as described above. These polypeptides may be monomers or multimers; glycosylated or non-glycosylated; PEGylated or non-PEGylated; and may or may not include an initial methionine amino acid residue.

H) Production of Antibodies to IL-17RC or IL-17RC/IL-17RA Proteins

Antibodies to IL-17RC or IL-17RC/IL-17RA can be obtained, for example, using the product of a IL-17RC or IL-17RC/IL-17RA expression vector or IL-17RC or IL-17RC/IL-17RA isolated from a natural source as an antigen. Particularly useful anti-IL-17RC or IL-17RC/IL-17RA antibodies "bind specifically" with IL-17RC or IL-17RC/IL-17RA. Antibodies are considered to be specifically binding if the antibodies exhibit at least one of the following two properties: (1) antibodies bind to IL-17RC or IL-17RC/IL-17RA with a threshold level of binding activity, and (2) antibodies do not significantly cross-react with polypeptides related to IL-17RC or IL-17RC/IL-17RA.

With regard to the first characteristic, antibodies specifically bind if they bind to a IL-17RC or IL-17RC/IL-17RA polypeptide, peptide or epitope with a binding affinity ($K_a$) of $10^6 M^{-1}$ or greater, preferably $10^7 M^{-1}$ or greater, more preferably $10^8 M^{-1}$ or greater, and most preferably $10^9 M^{-1}$ or greater. The binding affinity of an antibody can be readily determined by one of ordinary skill in the art, for example, by Scatchard analysis (Scatchard, *Ann. NY Acad. Sci.* 51:660 (1949)). With regard to the second characteristic, antibodies do not significantly cross-react with related polypeptide molecules, for example, if they detect IL-17RC or IL-17RC/IL-17RA, but not presently known polypeptides using a standard Western blot analysis. Examples of known related polypeptides include known cytokine receptors.

Anti-IL-17RC or IL-17RC/IL-17RA antibodies can be produced using antigenic IL-17RC or IL-17RC/IL-17RA epitope-bearing peptides and polypeptides. Antigenic epitope-bearing peptides and polypeptides of the present invention contain a sequence of at least nine, or between 15 to about 30 amino acids contained within SEQ ID NO:2, SEQ ID NO:3, SEQ ID NO:5 or another amino acid sequence disclosed herein. However, peptides or polypeptides comprising a larger portion of an amino acid sequence of the invention, containing from 30 to 50 amino acids, or any length up to and including the entire amino acid sequence of a polypeptide of the invention, also are useful for inducing antibodies that bind with IL-17RC or IL-17RC/IL-17RA. It is desirable that the amino acid sequence of the epitope-bearing peptide is selected to provide substantial solubility in aqueous solvents (i.e., the sequence includes relatively hydrophilic residues, while hydrophobic residues are typically avoided). Moreover, amino acid sequences containing proline residues may be also be desirable for antibody production.

As an illustration, potential antigenic sites in IL-17RC were identified using the Jameson-Wolf method, Jameson and Wolf, *CABIOS* 4:181, (1988), as implemented by the PROTEAN program (version 3.14) of LASERGENE (DNASTAR; Madison, Wis.). Default parameters were used in this analysis.

The Jameson-Wolf method predicts potential antigenic determinants by combining six major subroutines for protein structural prediction. Briefly, the Hopp-Woods method, Hopp et al., *Proc. Nat'l Acad. Sci. USA* 78:3824 (1981), was first used to identify amino acid sequences representing areas of greatest local hydrophilicity (parameter: seven residues averaged). In the second step, Emini's method, Emini et al., *J. Virology* 55:836 (1985), was used to calculate surface probabilities (parameter: surface decision threshold (0.6)=1). Third, the Karplus-Schultz method, Karplus and Schultz, *Naturwissenschaften* 72:212 (1985), was used to predict backbone chain flexibility (parameter: flexibility threshold (0.2)=1). In the fourth and fifth steps of the analysis, secondary structure predictions were applied to the data using the methods of Chou-Fasman, Chou, "Prediction of Protein Structural Classes from Amino Acid Composition," in *Prediction of Protein Structure and the Principles of Protein Conformation*, Fasman (ed.), pages 549-586 (Plenum Press 1990), and Garnier-Robson, Garnier et al., *J. Mol. Biol.* 120: 97 (1978) (Chou-Fasman parameters: conformation table=64 proteins; α region threshold=103; β region threshold=105; Garnier-Robson parameters: α and β decision constants=0). In the sixth subroutine, flexibility parameters and hydropathy/solvent accessibility factors were combined to determine a surface contour value, designated as the "antigenic index."

Finally, a peak broadening function was applied to the antigenic index, which broadens major surface peaks by adding 20, 40, 60, or 80% of the respective peak value to account for additional free energy derived from the mobility of surface regions relative to interior regions. This calculation was not applied, however, to any major peak that resides in a helical region, since helical regions tend to be less flexible. Hopp/Woods hydrophilicity profiles can be used to determine regions that have the most antigenic potential within SEQ ID NO:3 (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. Moreover, IL-17RC antigenic epitopes within SEQ ID NO:3 as predicted by a Jameson-Wolf plot, e.g., using DNASTAR Protean program (DNASTAR, Inc., Madison, Wis.) serve as preferred antigenic epitopes, and can be determined by one of skill in the art. Such antigenic epitopes include (1) amino acid residue 73 to amino acid residue 82 of SEQ ID NO:3; (2) amino acid residue 95 to amino acid residue 104 of SEQ ID NO:3; (3) amino acid residue 111 to amino acid residue 119 of SEQ ID NO:3; (4) amino acid residue 179 to amino acid residue 186 of SEQ ID NO:3; (5) amino acid residue 200 to amino acid residue 205 of SEQ ID NO:3; (6) amino acid residue 229 to amino acid residue 236 of SEQ ID NO:3; (7) amino acid residue 264 to amino acid residue 268 of SEQ ID NO:3; and (8) amino acid residue 275 to amino acid residue 281 of SEQ ID NO:3. The present invention contemplates the use of any one of antigenic peptides X to Y to generate antibodies to IL-17RC or as a tool to screen or identify neutralizing monoclonal antibodies of the present invention. The present invention also contemplates polypeptides comprising at least one of antigenic peptides X to Y. The present invention contemplates the use of any antigenic peptides or epitopes described herein to generate antibodies to IL-17RC, as well as to identify and screen anti-IL-17RC monoclonal antibodies that are neutralizing, and that may bind, block, inhibit, reduce, antagonize or neutralize the activity of IL-17F and IL-17A (individually or together).

Moreover, suitable antigens also include the IL-17RC or IL-17RC/IL-17RA polypeptides comprising a IL-17RC or IL-17RC/IL-17RA cytokine binding, or extracellular domain disclosed above in combination with another cytokine extracellular domain, such as a class I or II cytokine receptor domain, such as those that may form soluble IL-17RC or IL-17RC/IL-17RA heterodimeric or multimeric polypeptides, and the like.

Polyclonal antibodies to recombinant IL-17RC or IL-17RC/IL-17RA protein or to IL-17RC or IL-17RC/IL-17RA isolated from natural sources can be prepared using methods well-known to those of skill in the art. See, for example, Green et al., "Production of Polyclonal Antisera," in *Immunochemical Protocols* (Manson, ed.), pages 1-5 (Humana Press 1992), and Williams et al., "Expression of foreign proteins in *E. coli* using plasmid vectors and purification of specific polyclonal antibodies," in *DNA Cloning 2: Expression Systems, 2nd Edition*, Glover et al. (eds.), page 15 (Oxford University Press 1995). The immunogenicity of a IL-17RC or IL-17RC/IL-17RA polypeptide can be increased through the use of an adjuvant, such as alum (aluminum hydroxide) or Freund's complete or incomplete adjuvant. Polypeptides useful for immunization also include fusion polypeptides, such as fusions of IL-17RC or IL-17RC/IL-17RA or a portion thereof with an immunoglobulin polypeptide or with maltose binding protein. The polypeptide immunogen may be a full-length molecule or a portion thereof. If the polypeptide portion is "hapten-like," such portion may be advantageously joined or linked to a macromolecular carrier (such as keyhole limpet hemocyanin (KLH), bovine serum albumin (BSA) or tetanus toxoid) for immunization.

Although polyclonal antibodies are typically raised in animals such as horses, cows, dogs, chicken, rats, mice, rabbits, guinea pigs, goats, or sheep, an anti-IL-17RC or IL-17RC/IL-17RA antibody of the present invention may also be derived from a subhuman primate antibody. General techniques for raising diagnostically and therapeutically useful antibodies in baboons may be found, for example, in Goldenberg et al., international patent publication No. WO 91/11465, and in Losman et al., *Int. J. Cancer* 46:310 (1990).

Alternatively, monoclonal anti-IL-17RC or IL-17RC/IL-17RA antibodies can be generated. Rodent monoclonal antibodies to specific antigens may be obtained by methods known to those skilled in the art (see, for example, Kohler et al., *Nature* 256:495 (1975), Coligan et al. (eds.), *Current Protocols in Immunology*, Vol. 1, pages 2.5.1-2.6.7 (John Wiley & Sons 1991) ["Coligan"], Picksley et al., "Production of monoclonal antibodies against proteins expressed in *E. coli*," in *DNA Cloning 2: Expression Systems, 2nd Edition*, Glover et al. (eds.), page 93 (Oxford University Press 1995)).

Briefly, monoclonal antibodies can be obtained by injecting mice with a composition comprising a IL-17RC or IL-17RC/IL-17RA gene product, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

In addition, an anti-IL-17RC or IL-17RC/IL-17RA antibody of the present invention may be derived from a human monoclonal antibody. Human monoclonal antibodies are obtained from transgenic mice that have been engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13 (1994), Lonberg et al., *Nature* 368:856 (1994), and Taylor et al., *Int. Immun.* 6:579 (1994).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see, for example, Coligan at pages 2.7.1-2.7.12 and pages 2.9.1-2.9.3; Baines et al., "Purification of Immunoglobulin G (IgG)," in *Methods in Molecular Biology*, Vol. 10, pages 79-104 (The Humana Press, Inc. 1992)).

For particular uses, it may be desirable to prepare fragments of anti-IL-17RC or IL-17RC/IL-17RA antibodies. Such antibody fragments can be obtained, for example, by proteolytic hydrolysis of the antibody. Antibody fragments can be obtained by pepsin or papain digestion of whole antibodies by conventional methods. As an illustration, antibody fragments can be produced by enzymatic cleavage of antibodies with pepsin to provide a 5S fragment denoted F(ab')$_2$. This fragment can be further cleaved using a thiol reducing agent to produce 3.5S Fab' monovalent fragments. Optionally, the cleavage reaction can be performed using a blocking group for the sulfhydryl groups that result from cleavage of disulfide linkages. As an alternative, an enzymatic cleavage using pepsin produces two monovalent Fab fragments and an Fc fragment directly. These methods are described, for example, by Goldenberg, U.S. Pat. No. 4,331,647, Nisonoff et al., *Arch Biochem. Biophys.* 89:230 (1960), Porter, *Biochem. J.* 73:119 (1959), Edelman et al., in *Methods in Enzymology Vol.* 1, page 422 (Academic Press 1967), and by Coligan at pages 2.8.1-2.8.10 and 2.10.-2.10.4.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

For example, Fv fragments comprise an association of $V_H$ and $V_L$ chains. This association can be noncovalent, as described by Inbar et al., *Proc. Nat'l Acad. Sci. USA* 69:2659 (1972). Alternatively, the variable chains can be linked by an intermolecular disulfide bond or cross-linked by chemicals such as glutaraldehyde (see, for example, Sandhu, *Crit. Rev. Biotech.* 12:437 (1992)).

The Fv fragments may comprise $V_H$ and $V_L$ chains which are connected by a peptide linker. These single-chain antigen binding proteins (scFv) are prepared by constructing a structural gene comprising DNA sequences encoding the $V_H$ and $V_L$ domains which are connected by an oligonucleotide. The structural gene is inserted into an expression vector which is subsequently introduced into a host cell, such as *E. coli*. The recombinant host cells synthesize a single polypeptide chain with a linker peptide bridging the two V domains. Methods for producing scFvs are described, for example, by Whitlow et al., *Methods: A Companion to Methods in Enzymology* 2:97 (1991) (also see, Bird et al., *Science* 242:423 (1988), Ladner et al., U.S. Pat. No. 4,946,778, Pack et al., *Bio/Technology* 11:1271 (1993), and Sandhu, supra).

As an illustration, a scFv can be obtained by exposing lymphocytes to IL-17RC or IL-17RC/IL-17RA polypeptide in vitro, and selecting antibody display libraries in phage or similar vectors (for instance, through use of immobilized or labeled IL-17RC or IL-17RC/IL-17RA protein or peptide). Genes encoding polypeptides having potential IL-17RC or IL-17RC/IL-17RA polypeptide binding domains can be obtained by screening random peptide libraries displayed on phage (phage display) or on bacteria, such as *E. coli*. Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. 5,223,409, Ladner et al., U.S. Pat. No. 4,946,778, Ladner et al., U.S. Pat. No. 5,403,484, Ladner et al., U.S. Pat. No. 5,571,698, and Kay et al., *Phage Display of Peptides and Proteins* (Academic Press, Inc. 1996)) and random peptide display libraries and kits for screening such libraries are available commercially, for instance from CLONTECH Laboratories, Inc. (Palo Alto, Calif.), Invitrogen Inc. (San Diego, Calif.), New England Biolabs, Inc. (Beverly, Mass.), and Pharmacia LKB Biotechnology Inc. (Piscataway, N.J.). Random peptide display libraries can be screened using the IL-17RC or IL-17RC/IL-17RA sequences disclosed herein to identify proteins which bind to IL-17RC or IL-17RC/IL-17RA.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106 (1991), Courtenay-Luck, "Genetic Manipulation of Monoclonal Antibodies," in *Monoclonal Antibodies: Production, Engineering and Clinical Application*, Ritter et al. (eds.), page 166 (Cambridge University Press 1995), and Ward et al., "Genetic Manipulation and Expression of Antibodies," in *Monoclonal Antibodies: Principles and Applications*, Birch et al., (eds.), page 137 (Wiley-Liss, Inc. 1995)).

Alternatively, an anti-IL-17RC or IL-17RC/IL-17RA antibody may be derived from a "humanized" monoclonal antibody. Humanized monoclonal antibodies are produced by transferring mouse complementary determining regions from heavy and light variable chains of the mouse immunoglobulin into a human variable domain. Typical residues of human antibodies are then substituted in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. USA* 86:3833 (1989). Techniques for producing humanized monoclonal antibodies are described, for example, by Jones et al., *Nature* 321:522 (1986), Carter et al., *Proc. Nat'l Acad. Sci. USA* 89:4285 (1992), Sandhu, *Crit. Rev. Biotech.* 12:437 (1992), Singer et al., *J. Immun.* 150:2844 (1993), Sudhir (ed.), *Antibody Engineering Protocols* (Humana Press, Inc. 1995), Kelley, "Engineering Therapeutic Antibodies," in *Protein Engineering Principles and Practice*, Cleland et al. (eds.), pages 399-434 (John Wiley & Sons, Inc. 1996), and by Queen et al., U.S. Pat. No. 5,693,762 (1997).

Moreover, anti-IL-17RC or IL-17RC/IL-17RA antibodies or antibody fragments of the present invention can be PEGylated using methods in the art and described herein.

Polyclonal anti-idiotype antibodies can be prepared by immunizing animals with anti-IL-17RC or IL-17RC/IL-17RA antibodies or antibody fragments, using standard techniques. See, for example, Green et al., "Production of Polyclonal Antisera," in *Methods In Molecular Biology: Immunochemical Protocols*, Manson (ed.), pages 1-12 (Humana Press 1992). Also, see Coligan at pages 2.4.1-2.4.7. Alternatively, monoclonal anti-idiotype antibodies can be prepared using anti-IL-17RC or IL-17RC/IL-17RA antibodies or antibody fragments as immunogens with the techniques, described above. As another alternative, humanized anti-idiotype antibodies or subhuman primate anti-idiotype antibodies can be prepared using the above-described techniques. Methods for producing anti-idiotype antibodies are described, for example, by Irie, U.S. Pat. No. 5,208,146, Greene, et. al., U.S. Pat. No. 5,637,677, and Varthakavi and Minocha, *J. Gen. Virol.* 77:1875 (1996).

An anti-IL-17RC or IL-17RC/IL-17RA antibody can be conjugated with a detectable label to form an anti-IL-17RC or IL-17RC/IL-17RA immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^3$H, $^{125}$I, $^{131}$I, $^{35}$S and $^{14}$C.

Anti-IL-17RC or IL-17RC/IL-17RA immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-IL-17RC or IL-17RC/IL-17RA immunoconjugates can be detectably labeled by coupling an antibody component to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-IL-17RC or IL-17RC/IL-17RA immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-IL-17RC or IL-17RC/IL-17RA immunoconjugates can be detectably labeled by linking an anti-IL-17RC or IL-17RC/IL-17RA antibody component to an enzyme. When the anti-IL-17RC or IL-17RC/IL-17RA-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-IL-17RC or IL-17RC/IL-17RA antibodies can be accomplished using standard techniques known to the art. Typical methodology in this regard is described by Kennedy et al., *Clin. Chim. Acta* 70:1 (1976), Schurs et al., *Clin. Chim. Acta* 81:1 (1977), Shih et al., *Intl J. Cancer* 46:1101 (1990), Stein et al., *Cancer Res.* 50:1330 (1990), and Coligan, supra.

Moreover, the convenience and versatility of immunochemical detection can be enhanced by using anti-IL-17RC or IL-17RC/IL-17RA antibodies that have been conjugated with avidin, streptavidin, and biotin (see, for example, Wilchek et al. (eds.), "Avidin-Biotin Technology," *Methods In Enzymology, Vol.* 184 (Academic Press 1990), and Bayer et al., "Immunochemical Applications of Avidin-Biotin Technology," in *Methods In Molecular Biology, Vol.* 10, Manson (ed.), pages 149-162 (The Humana Press, Inc. 1992).

Methods for performing immunoassays are well-established. See, for example, Cook and Self, "Monoclonal Antibodies in Diagnostic Immunoassays," in *Monoclonal Antibodies: Production, Engineering, and Clinical Application*, Ritter and Ladyman (eds.), pages 180-208, (Cambridge University Press, 1995), Perry, "The Role of Monoclonal Antibodies in the Advancement of Immunoassay Technology," in *Monoclonal Antibodies: Principles and Applications*, Birch and Lennox (eds.), pages 107-120 (Wiley-Liss, Inc. 1995), and Diamandis, *Immunoassay* (Academic Press, Inc. 1996).

The present invention also contemplates kits for performing an immunological diagnostic assay for IL-17RC or IL-17RC/IL-17RA gene expression. Such kits comprise at least one container comprising an anti-IL-17RC or IL-17RC/IL-17RA antibody, or antibody fragment. A kit may also comprise a second container comprising one or more reagents capable of indicating the presence of IL-17RC or IL-17RC/IL-17RA antibody or antibody fragments. Examples of such indicator reagents include detectable labels such as a radioactive label, a fluorescent label, a chemiluminescent label, an enzyme label, a bioluminescent label, colloidal gold, and the like. A kit may also comprise a means for conveying to the user that IL-17RC or IL-17RC/IL-17RA antibodies or antibody fragments are used to detect IL-17RC or IL-17RC/IL-17RA protein. For example, written instructions may state that the enclosed antibody or antibody fragment can be used to detect IL-17RC or IL-17RC/IL-17RA. The written material can be applied directly to a container, or the written material can be provided in the form of a packaging insert.

I) Therapeutic Uses of the IL-17RC or IL-17RC/IL-17RA Polypeptides of the Invention Amino acid sequences having soluble IL-17RC or IL-17RC/IL-17RA activity can be used to modulate the immune system by binding ligands IL-17A and IL-17F (either singly or together), and thus, preventing the binding of these ligands with endogenous IL-17RC and/or IL-17RA receptor. Such antagonists, such as soluble IL-17RC or IL-17RC/IL-17RA, can also be used to modulate the immune system by inhibiting the binding of IL-17A and/or IL-17F with the endogenous IL-17RC and/or IL-17RA receptor. Accordingly, the present invention includes the use of proteins, polypeptides, and peptides having IL-17RC or IL-17RC/IL-17RA activity (such as soluble IL-17RC or IL-17RC/IL-17RA polypeptides, IL-17RC or IL-17RA polypeptide fragments, IL-17RC or IL-17RC/IL-17RA analogs, and IL-17RC or IL-17RC/IL-17RA fusion proteins) to a subject which lacks an adequate amount of this polypeptide, or which produces an excess of IL-17A and/or IL-17F. The polypeptides of the present invention (e.g., soluble IL-17RC and/or IL-17RC/IL-17RA) can be also used to treat a subject which produces an excess of either IL-17A, IL-17F, IL-17RA or IL-17RC. Suitable subjects include mammals, such as humans. For example, such soluble polypeptides are useful in binding, blocking, inhibiting, reducing, antagonizing or neutralizing IL-17A and IL-17F (either singly or together), in the treatment of inflammation and inflammatory diseases such as psoriasis, psoriatic arthritis, rheumatoid arthritis, endotoxemia, IBD, IBS, colitis, asthma, allograft rejection, immune mediated renal diseases, hepatobiliary diseases, multiple sclerosis, atherosclerosis, promotion of tumor growth, or degenerative joint disease and other inflammatory conditions disclosed herein.

Within preferred embodiments, the soluble receptor comprises IL-17RC (SEQ ID NO:3) and is a monomer, homodimer, heterodimer, or multimer that binds to, blocks, inhibits, reduces, antagonizes or neutralizes IL-17F and IL-17A (individually or together) in vivo. Antibodies and binding polypeptides to such IL-17RC monomer, homodimer, heterodimer, or multimers also serve as antagonists of IL-17RC activity, and as IL-17A and IL-17F antagonists (singly or together), as described herein.

Within other preferred embodiments, the soluble receptor comprises portions both IL-17RC and IL-17RA. One such preferred embodiment is an IL-17 Variant 1454 (SEQ ID NOs: 157 and 158) which includes exons 1-6 of human IL-17RA and 8-16 of human IL-17RCx1, fused to Fc5 (SEQ ID NOs: 179 and 180). Variant 1454 also has the native signal peptide from human IL-17RA. Fc10, or any equivalent known in the art, may also be used in place of Fc5.

In addition, described herein are both polyclonal and monoclonal neutralizing anti-IL-17F antibodies bind to, block, inhibit, reduce, antagonize or neutralize IL-17F and IL-17A activity in cell based neutralization assays. Analysis of the tissue distribution of the mRNA corresponding IL-17RC cDNA showed that mRNA the IL-17RC gene is strongly expressed in thyroid, adrenal gland, prostate, and liver tissues, and expressed to a lesser extent in heart, small intestine, stomach, and trachea tissues. In particular, IL-17RC is consistently expressed in non-T cell peripheral blood cell lines, including monocytes, B-cells, and cells of the myeloid lineage. Also, IL-17RC mRNA is reliably expressed in cell lines derived from skin. Other cell lines that express IL-17RC are all 5 of the large intestine cell lines that were present on the array. In contrast, there is little or no expression in brain, placenta, lung, skeletal muscle, kidney, pancreas, spleen, thymus, testis, ovary, colon, peripheral blood leukocytes, spinal cord, lymph node, and bone marrow. The ligand to which IL-17RC binds (IL-17F and/or IL-17A) is implicated in inducing inflammatory response and contributing to inflammatory diseases, primarily via its ability to enhance production of inflammatory mediators, including IL-1β, IL-6 and TNF-α, as well as those mediators that are involved in the proliferation, maturation and chemotaxis of neutrophils (reviewed in Witowski et al., *Cell. Mol. Life. Sci.* 61:567-579 (2004)).

Thus, particular embodiments of the present invention are directed toward use of soluble IL-17RC and soluble IL-17RC/IL-17RA polypeptides as antagonists in inflammatory and immune diseases or conditions such as psoriasis, psoriatic arthritis, atopic dermatitis, inflammatory skin conditions, rheumatoid arthritis, IBD, IBS, Crohn's Disease, diverticulosis, asthma, pancreatitis, type I diabetes (IDDM), pancreatic cancer, pancreatitis, Graves Disease, colon and intestinal cancer, autoimmune disease, sepsis, organ or bone marrow transplant; inflammation due to endotoxemia, trauma, surgery or infection; amyloidosis; splenomegaly; graft versus host disease; and where inhibition of inflammation, immune suppression, reduction of proliferation of hematopoietic, immune, inflammatory or lymphoid cells, macrophages, T-cells (including Th1 and Th2 cells), suppression of immune response to a pathogen or antigen, or other instances where inhibition of IL-17F and/or IL-17A is desired.

Moreover, soluble IL-17RC and soluble IL-17RC/IL-17RA polypeptides are useful to:

(1) Block, inhibit, reduce, antagonize or neutralize signaling via IL-17RA or IL-17RC in the treatment of acute inflammation, inflammation as a result of trauma, tissue injury, surgery, sepsis or infection, and chronic inflammatory diseases such as asthma, inflammatory bowel disease (IBD), IBS, chronic colitis, splenomegaly, rheumatoid arthritis, recurrent acute inflammatory episodes (e.g., tuberculosis), and treatment of amyloidosis, and atherosclerosis, Castleman's Disease, asthma, and other diseases associated with the induction of acute-phase response.

(2) Block, inhibit, reduce, antagonize or neutralize signaling IL-17RA or IL-17RC in the treatment of autoimmune diseases such as IDDM, multiple sclerosis (MS), systemic Lupus erythematosus (SLE), myasthenia gravis, rheumatoid arthritis, IBS and IBD to prevent or inhibit signaling in immune cells (e.g. lymphocytes, monocytes, leukocytes). Blocking, inhibiting, reducing, or antagonizing signaling via IL-17RC and/or IL-17RA, using the polypeptides of the present invention, may also benefit diseases of the pancreas, kidney, pituitary and neuronal cells. IDDM, NIDDM, pancreatitis, and pancreatic carcinoma may benefit. IL-17RC and/or IL-17RA may serve as a target for treatment of cancer where an antagonist of the present invention inhibits cancer growth and targets immune-mediated killing. (Holliger P, and Hoogenboom, H: *Nature Biotech.* 16: 1015-1016, 1998). Soluble polypeptides of the present invention may also be useful to treat nephropathies such as glomerulosclerosis, membranous neuropathy, amyloidosis (which also affects the kidney among other tissues), renal arteriosclerosis, glomerulonephritis of various origins, fibroproliferative diseases of the kidney, as well as kidney dysfunction associated with SLE, IDDM, type II diabetes (NIDDM), renal tumors and other diseases.

(3) Agonize, enhance, increase or initiate signaling via IL-17RA or IL-17RC in the treatment of autoimmune diseases such as IDDM, MS, SLE, myasthenia gravis, rheumatoid arthritis, IBS and IBD. The soluble polypeptides of the present invention may signal lymphocytes or other immune cells to differentiate, alter proliferation, or change production of cytokines or cell surface proteins that ameliorate autoimmunity. Specifically, modulation of a T-helper cell response to an alternate pattern of cytokine secretion may deviate an autoimmune response to ameliorate disease (Smith J A et al., *J. Immunol.* 160:4841-4849, 1998). Similarly, agonistic soluble polypeptides may be used to signal, deplete and deviate immune cells involved in asthma, allergy and atopoic disease. Signaling via IL-17RC and/or IL-17RA may also benefit diseases of the pancreas, kidney, pituitary and neuronal cells. IDDM, NIDDM, pancreatitis, and pancreatic carcinoma may benefit.

Soluble IL-17RC or IL-17RC/IL-17RA polypeptides described herein can be used to bind, block, inhibit, reduce, antagonize or neutralize IL-17F or IL-17A activity, either singly or together, in the treatment of autoimmune disease, atopic disease, NIDDM, pancreatitis and kidney dysfunction as described above. A soluble form of IL-17RC or IL-17RC/IL-17RA may be used to promote an antibody response mediated by Th cells and/or to promote the production of IL-4 or other cytokines by lymphocytes or other immune cells.

The soluble polypeptides of the present invention are useful as antagonists of IL-17A and/or IL-17F. Such antagonistic effects can be achieved by direct neutralization or binding of IL-17A or IL-17F. In addition to antagonistic uses, the soluble receptors of the present invention can bind IL-17F or IL-17A and act as carrier proteins for the ligand, in order to transport it to different tissues, organs, and cells within the body. As such, the soluble receptors of the present invention can be fused or coupled to molecules, polypeptides or chemical moieties that direct the soluble-receptor-Ligand complex to a specific site, such as a tissue, specific immune cell, or tumor. For example, in acute infection or some cancers, benefit may result from induction of inflammation and local acute phase response proteins by the action of IL-17F. Thus, the soluble receptors of the present invention can be used to specifically direct the action of IL-17A or IL-17F. See, Cosman, D. *Cytokine* 5: 95-106, 1993; and Fernandez-Botran, R. *Exp. Opin. Invest. Drugs* 9:497-513, 2000.

Inflammation is a protective response by an organism to fend off an invading agent. Inflammation is a cascading event that involves many cellular and humoral mediators. On one hand, suppression of inflammatory responses can leave a host immunocompromised; however, if left unchecked, inflammation can lead to serious complications including chronic inflammatory diseases (e.g., psoriasis, arthritis, rheumatoid arthritis, multiple sclerosis, inflammatory bowel disease and the like), septic shock and multiple organ failure. Importantly, these diverse disease states share common inflammatory mediators. The collective diseases that are characterized by inflammation have a large impact on human morbidity and mortality. Therefore it is clear that anti-inflammatory proteins, such as the soluble polypeptides of the present invention could have crucial therapeutic potential for a vast number of human and animal diseases, from asthma and allergy to autoimmunity and septic shock.

1. Arthritis

Arthritis, including osteoarthritis, rheumatoid arthritis, arthritic joints as a result of injury, and the like, are common inflammatory conditions which would benefit from the therapeutic use of anti-inflammatory proteins, such as the soluble polypeptides of the present invention. For example, rheumatoid arthritis (RA) is a systemic disease that affects the entire body and is one of the most common forms of arthritis. It is characterized by the inflammation of the membrane lining the joint, which causes pain, stiffness, warmth, redness and swelling. Inflammatory cells release enzymes that may digest bone and cartilage. As a result of rheumatoid arthritis, the inflamed joint lining, the synovium, can invade and damage bone and cartilage leading to joint deterioration and severe pain amongst other physiologic effects. The involved joint can lose its shape and alignment, resulting in pain and loss of movement.

Rheumatoid arthritis (RA) is an immune-mediated disease particularly characterized by inflammation and subsequent tissue damage leading to severe disability and increased mortality. A variety of cytokines are produced locally in the rheumatoid joints. Numerous studies have demonstrated that IL-1 and TNF-alpha, two prototypic pro-inflammatory cytokines, play an important role in the mechanisms involved in synovial inflammation and in progressive joint destruction. Indeed, the administration of TNF-alpha and IL-1 inhibitors in patients with RA has led to a dramatic improvement of clinical and biological signs of inflammation and a reduction of radiological signs of bone erosion and cartilage destruction. However, despite these encouraging results, a significant percentage of patients do not respond to these agents, suggesting that other mediators are also involved in the pathophysiology of arthritis (Gabay, *Expert. Opin. Biol. Ther.* 2(2): 135-149, 2002). One of those mediators could be IL-17A or IL-17F, and as such a molecule that binds or inhibits IL-17F or IL-17A activity, such as soluble IL-17RC or IL-17RC/IL-17RA, could serve as a valuable therapeutic to reduce inflammation in rheumatoid arthritis, and other arthritic diseases.

There are several animal models for rheumatoid arthritis known in the art. For example, in the collagen-induced arthritis (CIA) model, mice develop chronic inflammatory arthritis that closely resembles human rheumatoid arthritis. Since CIA shares similar immunological and pathological features with RA, this makes it an ideal model for screening potential human anti-inflammatory compounds. The CIA model is a well-known model in mice that depends on both an immune response, and an inflammatory response, in order to occur. The immune response comprises the interaction of B-cells and CD4+ T-cells in response to collagen, which is given as antigen, and leads to the production of anti-collagen antibodies. The inflammatory phase is the result of tissue responses from mediators of inflammation, as a consequence of some of these antibodies cross-reacting to the mouse's native collagen and activating the complement cascade. An advantage in using the CIA model is that the basic mechanisms of pathogenesis are known. The relevant T-cell and B-cell epitopes on type II collagen have been identified, and various immunological (e.g., delayed-type hypersensitivity and anti-collagen antibody) and inflammatory (e.g., cytokines, chemokines, and matrix-degrading enzymes) parameters relating to immune-mediated arthritis have been determined, and can thus be used to assess test compound efficacy in the CIA model (Wooley, *Curr. Opin. Rheum.* 3:407-20, 1999; Williams et al., *Immunol.* 89:9784-788, 1992; Myers et al., *Life Sci.* 61:1861-78, 1997; and Wang et al., *Immunol.* 92:8955-959, 1995).

One group has shown that an anti-mouse IL-17 antibody reduces symptoms in a mouse CIA-model relative to control mice, thus showing conceptually that the soluble polypeptides of the present invention would be beneficial in treating human disease. The administration of a single mouse-IL-17-specific rat antisera reduced the symptoms of arthritis in the animals when introduced prophylactically or after symptoms of arthritis were already present in the model (Lubberts et al, *Arthritis Rheum.* 50:650-9, 2004). Therefore, IL-17RC-Fc or IL-17RC/IL-17RA-Fc can be used to neutralize IL-17A and/or IL-17F in the treatment of specific human diseases such as arthritis, psoriasis, psoriatic arthritis, endotoxemia, inflammatory bowel disease (IBD), IBS, colitis, and other inflammatory conditions disclosed herein.

The administration of the soluble polypeptides of the present invention, such as IL-17RC-Fc or other IL-17RC/IL-17RA soluble and fusion proteins to these CIA model mice is used to evaluate their use as an antagonist to IL-17F and IL-17A to ameliorate symptoms and alter the course of disease. Moreover, results showing inhibition or neutralization of IL-17F and/or IL-17A by the soluble polypeptides of the present invention would provide proof of concept that other IL-17A or Il-17F antagonists can also be used to ameliorate symptoms and alter the course of disease. Furthermore, since IL-17A and/or IL-17F induces production of IL-1β and TNF-α, both of which are implicated in the pathogenesis and progression of rheumatoid arthritis, the systemic or local administration of these soluble polypeptides can potentially suppress the inflammatory response in RA. By way of example and without limitation, the injection of 10-200 ug IL-17RC-Fc per mouse (one to seven times a week for up to but not limited to 4 weeks via s.c., i.p., or i.m route of administration) can significantly reduce the disease score (paw score, incident of inflammation, or disease). Depending on the initiation of IL-17RC-Fc administration (e.g. prior to or at the time of collagen immunization, or at any time point following the second collagen immunization, including those time points at which the disease has already progressed), IL-17RC can be efficacious in preventing rheumatoid arthritis, as well as preventing its progression. Other potential therapeutics include IL-17RC/IL-17RA polypeptides, and the like.

2. Endotoxemia

Endotoxemia is a severe condition commonly resulting from infectious agents such as bacteria and other infectious disease agents, sepsis, toxic shock syndrome, or in immunocompromised patients subjected to opportunistic infections, and the like. Therapeutically useful of anti-inflammatory proteins, such as the soluble polypeptides of the present invention could aid in preventing and treating endotoxemia in humans and animals. These soluble polypeptides could serve as a valuable therapeutic to reduce inflammation and pathological effects in endotoxemia.

Lipopolysaccharide (LPS) induced endotoxemia engages many of the proinflammatory mediators that produce pathological effects in the infectious diseases and LPS induced endotoxemia in rodents is a widely used and acceptable model for studying the pharmacological effects of potential pro-inflammatory or immunomodulating agents. LPS, produced in gram-negative bacteria, is a major causative agent in the pathogenesis of septic shock (Glausner et al., *Lancet* 338:732, 1991). A shock-like state can indeed be induced experimentally by a single injection of LPS into animals. Molecules produced by cells responding to LPS can target pathogens directly or indirectly. Although these biological responses protect the host against invading pathogens, they may also cause harm. Thus, massive stimulation of innate immunity, occurring as a result of severe Gram-negative bacterial infection, leads to excess production of cytokines and other molecules, and the development of a fatal syndrome, septic shock syndrome, which is characterized by fever, hypotension, disseminated intravascular coagulation, and multiple organ failure (Dumitru et al. *Cell* 103:1071-1083, 2000).

These toxic effects of LPS are mostly related to macrophage activation leading to the release of multiple inflammatory mediators. Among these mediators, TNF appears to play a crucial role, as indicated by the prevention of LPS toxicity by the administration of neutralizing anti-TNF antibodies (Beutler et al., *Science* 229:869, 1985). It is well established that 1 ug injection of *E. coli* LPS into a C57B1/6 mouse will result in significant increases in circulating IL-6, TNF-alpha, IL-1, and acute phase proteins (for example, SAA) approximately 2 hours post injection. The toxicity of LPS appears to be mediated by these cytokines as passive immunization against these mediators can result in decreased mortality (Beutler et al., *Science* 229:869, 1985). The potential immunointervention strategies for the prevention and/or treatment of septic shock include anti-TNF mAb, IL-1 receptor antagonist, LIF, IL-10, and G-CSF.

The administration of the soluble polypeptides of the present invention to these LPS-induced model may be used to evaluate the use of IL-17RC or IL-17RC/IL-17RA to ameliorate symptoms and alter the course of LPS-induced disease. Moreover, results showing inhibition of IL-17F or IL-17A by these soluble polypeptides would provide proof of concept that other such antagonists can also be used to ameliorate symptoms in the LPS-induced model and alter the course of disease. The model will show induction of IL-17F by LPS injection and the potential treatment of disease by the soluble polypeptides. Since LPS induces the production of pro-inflammatory factors possibly contributing to the pathology of endotoxemia, the neutralization of IL-17F activity or other pro-inflammatory factors by an antagonist soluble polypeptide can be used to reduce the symptoms of endotoxemia, such as seen in endotoxic shock.

3. Inflammatory Bowel Disease IBD

In the United States approximately 500,000 people suffer from Inflammatory Bowel Disease (IBD) which can affect either colon and rectum (Ulcerative colitis) or both, small and large intestine (Crohn's Disease). The pathogenesis of these diseases is unclear, but they involve chronic inflammation of the affected tissues. The soluble polypeptides of the present invention could serve as a valuable therapeutic to reduce inflammation and pathological effects in IBD, UC and related diseases.

Ulcerative colitis (UC) is an inflammatory disease of the large intestine, commonly called the colon, characterized by inflammation and ulceration of the mucosa or innermost lining of the colon. This inflammation causes the colon to empty frequently, resulting in diarrhea. Symptoms include loosening of the stool and associated abdominal cramping, fever and weight loss. Although the exact cause of UC is unknown, recent research suggests that the body's natural defenses are operating against proteins in the body which the body thinks are foreign (an "autoimmune reaction"). Perhaps because they resemble bacterial proteins in the gut, these proteins may either instigate or stimulate the inflammatory process that begins to destroy the lining of the colon. As the lining of the colon is destroyed, ulcers form releasing mucus, pus and blood. The disease usually begins in the rectal area and may eventually extend through the entire large bowel. Repeated episodes of inflammation lead to thickening of the wall of the intestine and rectum with scar tissue. Death of colon tissue or sepsis may occur with severe disease. The symptoms of ulcerative colitis vary in severity and their onset may be gradual or sudden. Attacks may be provoked by many factors, including respiratory infections or stress.

Although there is currently no cure for UC available, treatments are focused on suppressing the abnormal inflammatory process in the colon lining. Treatments including corticosteroids immunosuppressives (e.g., azathioprine, mercaptopurine, and methotrexate) and aminosalicytates are available to treat the disease. However, the long-term use of immunosuppressives such as corticosteroids and azathioprine can result in serious side effects including thinning of bones, cataracts, infection, and liver and bone marrow effects. In the patients in whom current therapies are not successful, surgery is an option. The surgery involves the removal of the entire colon and the rectum.

There are several animal models that can partially mimic chronic ulcerative colitis. The most widely used model is the 2,4,6-trinitrobenesulfonic acid/ethanol (TNBS) induced colitis model, which induces chronic inflammation and ulceration in the colon. When TNBS is introduced into the colon of susceptible mice via intra-rectal instillation, it induces T-cell mediated immune response in the colonic mucosa, in this case leading to a massive mucosal inflammation characterized by the dense infiltration of T-cells and macrophages throughout the entire wall of the large bowel. Moreover, this histopathologic picture is accompanies by the clinical picture of progressive weight loss (wasting), bloody diarrhea, rectal prolapse, and large bowel wall thickening (Neurath et al. *Intern. Rev. Immunol.* 19:51-62, 2000).

Another colitis model uses dextran sulfate sodium (DSS), which induces an acute colitis manifested by bloody diarrhea, weight loss, shortening of the colon and mucosal ulceration with neutrophil infiltration. DSS-induced colitis is characterized histologically by infiltration of inflammatory cells into the lamina propria, with lymphoid hyperplasia, focal crypt damage, and epithelial ulceration. These changes are thought to develop due to a toxic effect of DSS on the epithelium and by phagocytosis of lamina propria cells and production of TNF-alpha and IFN-gamma. Despite its common use, several issues regarding the mechanisms of DSS about the relevance to the human disease remain unresolved. DSS is regarded as a T cell-independent model because it is observed in T cell-deficient animals such as SCID mice.

The administration of the soluble polypeptides of the present invention to these TNBS or DSS models can be used to evaluate their use to ameliorate symptoms and alter the course of gastrointestinal disease. Moreover, the results showing inhibition or neutralization of IL-17F and/or IL-17A by these soluble polypeptides provide proof of concept that they (or similar molecules) can also be used to ameliorate symptoms in the colitis/IBD models and alter the course of disease.

4. Psoriasis

Psoriasis is a chronic skin condition that affects more than seven million Americans. Psoriasis occurs when new skin cells grow abnormally, resulting in inflamed, swollen, and scaly patches of skin where the old skin has not shed quickly enough. Plaque psoriasis, the most common form, is characterized by inflamed patches of skin ("lesions") topped with silvery white scales. Psoriasis may be limited to a few plaques or involve moderate to extensive areas of skin, appearing most commonly on the scalp, knees, elbows and trunk. Although it is highly visible, psoriasis is not a contagious disease. The pathogenesis of the diseases involves chronic inflammation of the affected tissues. The soluble polypeptides of the present invention could serve as a valuable therapeutic to reduce inflammation and pathological effects in psoriasis, other inflammatory skin diseases, skin and mucosal allergies, and related diseases.

Psoriasis is a T-cell mediated inflammatory disorder of the skin that can cause considerable discomfort. It is a disease for which there is no cure and affects people of all ages. Psoriasis affects approximately two percent of the populations of European and North America. Although individuals with mild psoriasis can often control their disease with topical agents, more than one million patients worldwide require ultraviolet or systemic immunosuppressive therapy. Unfortunately, the inconvenience and risks of ultraviolet radiation and the toxicities of many therapies limit their long-term use. Moreover, patients usually have recurrence of psoriasis, and in some cases rebound, shortly after stopping immunosuppressive therapy.

The soluble polypeptides of the present invention may also be used within diagnostic systems for the detection of circulating levels of IL-17F or IL-17A, and in the detection of IL-17F or IL-17A associated with acute phase inflammatory response. Within a related embodiment, the soluble polypeptides of the present invention can be used to detect circulating or locally-acting IL-17F or IL-17A polypeptides. Elevated or depressed levels of ligand or receptor polypeptides may be indicative of pathological conditions, including inflammation or cancer. IL-17F is known to induce associated acute phase inflammatory response. Moreover, detection of acute phase proteins or molecules such as IL-17A or IL-17F can be indicative of a chronic inflammatory condition in certain disease states (e.g., asthma, psoriasis, rheumatoid arthritis, colitis, IBD, IBS). Detection of such conditions serves to aid in disease diagnosis as well as help a physician in choosing proper therapy.

In addition to other disease models described herein, the activity of the soluble polypeptides of the present invention on inflammatory tissue derived from human psoriatic lesions can be measured in vivo using a severe combined immune deficient (SCID) mouse model. Several mouse models have been developed in which human cells are implanted into immunodeficient mice (collectively referred to as xenograft models); see, for example, Cattan A R, Douglas E, *Leuk. Res.* 18:513-22, 1994 and Flavell, D J, *Hematological Oncology* 14:67-82, 1996. As an in vivo xenograft model for psoriasis, human psoriatic skin tissue is implanted into the SCID mouse model, and challenged with an appropriate antagonist. Moreover, other psoriasis animal models in ther art may be used to evaluate IL-17A and IL-17F antagonists, such as human psoriatic skin grafts implanted into AGR129 mouse model, and challenged with an appropriate antagonist (e.g., see, Boyman, O. et al., *J. Exp. Med. Online publication* #20031482, 2004, incorporated hereing by reference). The soluble polypeptides of the present invention that bind, block, inhibit, reduce, antagonize or neutralize the activity of IL-17F or both IL-17A and IL-17F are preferred antagonists, as well as other IL-17A and IL-17F antagonists can be used in this model. Similarly, tissues or cells derived from human colitis, IBD, IBS, arthritis, or other inflammatory lesions can be used in the SCID model to assess the anti-inflammatory properties of the IL-17A and IL-17F antagonists described herein.

Therapies designed to abolish, retard, or reduce inflammation using the soluble polypeptides of the present invention can be tested by administration to SCID mice bearing human inflammatory tissue (e.g., psoriatic lesions and the like), or other models described herein. Efficacy of treatment is measured and statistically evaluated as increased anti-inflammatory effect within the treated population over time using methods well known in the art. Some exemplary methods include, but are not limited to measuring for example, in a psoriasis model, epidermal thickness, the number of inflammatory cells in the upper dermis, and the grades of parakeratosis. Such methods are known in the art and described herein. For example, see Zeigler, M. et al. *Lab Invest* 81:1253, 2001; Zollner, T. M. et al. *J. Clin. Invest.* 109:671, 2002; Yamanaka, N. et al. *Microbiol Immunol.* 45:507, 2001; Raychaudhuri, S. P. et al. *Br. J. Dermatol.* 144:931, 2001; Boehncke, W. H et al. *Arch. Dermatol. Res.* 291:104, 1999; Boehncke, W. H et al. *J. Invest. Dermatol.* 116:596, 2001; Nickoloff, B. J. et al. *Am. J. Pathol.* 146:580, 1995; Boehncke, W. H et al. *J. Cutan. Pathol.* 24:1, 1997; Sugai, J., M. et al. *J. Dermatol. Sci.* 17:85, 1998; and Villadsen L. S. et al. *J. Clin. Invest.* 112:1571, 2003. Inflammation may also be monitored over time using well-known methods such as flow cytometry (or PCR) to quantitate the number of inflammatory or lesional cells present in a sample, score (weight loss, diarrhea, rectal bleeding, colon length) for IBD, paw disease score and inflammation score for CIA RA model. For example, therapeutic strategies appropriate for testing in such a model include direct treatment using soluble IL-17RC or IL-17RC/IL-17RA, or other IL-17A and IL-17F antagonists (singly or together), or related conjugates or antagonists based on the disrupting interaction of IL-17RC and/or IL-17RA with their corresponding ligands.

Psoriasis is a chronic inflammatory skin disease that is associated with hyperplastic epidermal keratinocytes and infiltrating mononuclear cells, including $CD4^+$ memory T cells, neutrophils and macrophages (Christophers, *Int. Arch. Allergy Immunol.*, 110:199, 1996). It is currently believed that environmental antigens play a significant role in initiating and contributing to the pathology of the disease. However, it is the loss of tolerance to self-antigens that is thought to mediate the pathology of psoriasis. Dendritic cells and $CD4^+$ T cells are thought to play an important role in antigen presentation and recognition that mediate the immune response leading to the pathology. We have recently developed a model of psoriasis based on the CD4+CD45RB transfer model (Davenport et al., *Internat. Immunopharmacol.*, 2:653-672). The soluble polypeptides of the present invention are administered to the mice. Inhibition of disease scores (skin lesions, inflammatory cytokines) indicates the effectiveness of those soluble polypeptides in psoriasis.

5. Atopic Dermatitis.

AD is a common chronic inflammatory disease that is characterized by hyperactivated cytokines of the helper T cell subset 2 (Th2). Although the exact etiology of AD is unknown, multiple factors have been implicated, including hyperactive Th2 immune responses, autoimmunity, infection, allergens, and genetic predisposition. Key features of the disease include xerosis (dryness of the skin), pruritus (itchiness of the skin), conjunctivitis, inflammatory skin lesions, *Staphylococcus aureus* infection, elevated blood eosinophilia, elevation of serum IgE and IgG1, and chronic dermatitis with T cell, mast cell, macrophage and eosinophil infiltration. Colonization or infection with *S. aureus* has been recognized to exacerbate AD and perpetuate chronicity of this skin disease.

AD is often found in patients with asthma and allergic rhinitis, and is frequently the initial manifestation of allergic disease. About 20% of the population in Western countries suffer from these allergic diseases, and the incidence of AD in developed countries is rising for unknown reasons. AD typically begins in childhood and can often persist through adolescence into adulthood. Current treatments for AD include topical corticosteroids, oral cyclosporin A, non-corticosteroid immunosuppressants such as tacrolimus (FK506 in ointment form), and interferon-gamma. Despite the variety of treatments for AD, many patients' symptoms do not improve, or they have adverse reactions to medications, requiring the search for other, more effective therapeutic agents. The soluble polypeptides of the present invention can be used to neutralize IL-17F and IL-17A in the treatment of specific human diseases such as atoptic dermatitis, inflammatory skin conditions, and other inflammatory conditions disclosed herein.

6. Asthma

IL-17 plays an important role in allergen-induced T cell activation and neutrophilic influx in the airways. The receptor for IL-17 is expressed in the airways (Yao et al., *Immunity* 3:811 (1995)) and IL-17 mediated neutrophil recruitment in allergic asthma is largely induced by the chemoattractant IL-8, GRO-α and macrophage inflammatory protein-2 (MIP-2) produced by IL-17 stimulated human bronchial epithelial cells (HBECs) and human bronichial fibroblasts (Yao et al., *J Immunol* 155:5483 (1995)); Molet et al., *J Allergy Clin Immunol* 108:430 (2001)). IL-17 also stimulates HBECs to release IL-6, a neutrophil-activating factor (Fossiez et al., *J Exp Med* 183:2593 (1996), and Linden et al., *Int Arch Allergy Immunol* 126:179 (2001)) and has been shown to synergize with TNF-α to prolong the survival of human neutrophils in vitro (Laan et al., *Eur Respir J* 21:387 (2003)). Moreover, IL-17 is capable of amplifying the inflammatory responses in asthma by its ability to enhance the secretion of cytokines implicated in airway remodeling such as the profibrotic cytokines, IL-6 and IL-11 and inflammatory mediators granulocyte colony-stimulating factor (G-CSF) and granulocyte macrophage colony-stimulating factor (GM-CSF) (Molet et al., *J Allergy Clin Immunol* 108:430 (2001)).

Clinical evidence shows that acute, severe exacerbations of asthma are associated with recruitment and activation of neutrophils in the airways, thus IL-17 is likely to play a significant role in asthma. Patients with mild asthma display a detectable increase in the local concentration of free, soluble IL-17A protein (Molet et al., *J Allergy Clin Immunol* 108:430 (2001)) while healthy human volunteers with induced, severe airway inflammation due to the exposure to a swine confinement, display a pronounced increase in the concentration of free, soluble IL-17A protein in the bronchoalveolar space (Fossiez et al., *J Exp Med* 183:2593 (1996), and Linden et al., *Int Arch Allergy Immunol* 126:179 (2001)). Furthermore, IL-17 levels in sputum have correlated with individuals who have increased airway hyper-reactivity Barczyk et al., *Respir Med* 97:726 (2003).

In animal models of airway hyper-responsiveness, chronic inhalation of ovalbumin by sensitized mice resulted in bronchial eosinophilic inflammation and early induction of IL-17 mRNA expression in inflamed lung tissue, together with a bronchial neutrophilia. (Hellings et al., *Am J Respir Cell Mol Biol* 28:42 (2003).) Anti-IL-17 monoclonal antibodies strongly reduced bronchial neutrophilic influx but significantly enhanced IL-5 levels in both bronchoalveolar lavage fluid and serum, and aggravated allergen-induced bronchial eosinophilic influx, suggesting that IL-17A may be involved in determining the balance between neutrophil and eosinophil accumulation following antigen insult. (Id.)

Among the IL-17 family members, IL-17F is most closely related to IL-17A. The biological activities mediated by IL-17F are similar to those of IL-17A, where IL-17F stimulates production of IL-6, IL-8 and G-CSF. (Hurst et al., *J Immunol* 169:443 (2002).) IL-17F also induces production of IL-2, transforming growth factor (TGF)-β, and monocyte chemoattractant protein (MCP) in endothelial cells. (Starnes et al., *J Immunol* 167:4137 (2001).) Similarly, allergen challenge can increase local IL-17F in patients with allergic asthma. (Kawaguchi et al., *J Immunol* 167:4430 (2001).) Gene delivery of IL-17F in murine lung increases neutrophils in the bronchoalveolar space, while mucosal transfer of the IL-17F gene enhances the levels of Ag-induced pulmonary neutrophilia and airway responsiveness to methacholine. (Oda et al., *Am J Respir Crit. Care Med* 171:12 (2005).)

Apart from asthma, several chronic inflammatory airway diseases are characterized by neutrophil recruitment in the airways and IL-17 has been reported to play an important role in the pathogenesis of respiratory conditions such as chronic obstructive pulmonary disease (COPD), bacterial pneumonia and cystic fibrosis (Linden et al., *Eur Respir J* 15:973 (2000); Ye et al., *Am J Respir Cell Mol Biol* 25:335 (2001); Rahman et al., *Clin Immunol* 115:268 (2005)). An anti-IL-17A and/or anti-IL-17F therapeutic molecule could be demonstrated to be efficacious for chronic inflammatory airway disease in an in vitro model of inflammation. The ability of antagonists to IL-17F and/or IL-17A activity, such as IL-17RC soluble receptors and antibodies thereto including the anti-human-IL-17RC monoclonal and neutralizing antibodies of the present invention to inhibit IL-17A or and/or IL-17F-induced cytokine and chemokine production from cultured HBECs or bronchial fibroblasts could be used as a measure of efficacy for such antagonists in the prevention of the production of inflammatory mediators directly resulting from IL-17A and/or F stimulation. If the addition of antagonists, such as the soluble polypeptides of the present invention, to IL-17F and/or IL-17A activity, markedly reduces the production and expression of inflammatory mediators, it would be expected to be efficacious in inflammatory aspects associated with chronic airway inflammation.

7. Irritable Bowel Syndrome ("IBS")

Irritable bowel syndrome represents a disease characterized by abdominal pain or discomfort and an erratic bowel habit. IBS patients can be characterized into three main groups based on bowel habits: those with predominantly loose or frequent stools, those with predominantly hard or infrequent stools, and those with variable or normal stools (Talley et al., 2002). Altered intestinal motility, abnormalities in epithelial function, abnormal transit of stool and gas, and stress, may contribute to symptoms, while visceral hypersensitivity is a key feature in most patients. Genetic factors affecting pain-signaling and disturbances in central processing of afferent signals are postulated to predispose individuals to IBS following specific environmental exposures. Studies have also demonstrated that inflammatory responses in the colon may contribute to increased sensitivity of smooth muscle and enteric nerves and therefore perturb sensory-motor functions in the intestine (Collins et al., 2001). There is clinical overlap between IBS and IBD, with IBS-like symptoms frequently reported in patients before the diagnosis of IBD, and a higher than expected IBS symptoms in patients in remission from established IBD. Thus, these conditions may coexist with a higher than expected frequency, or may exist on a continuum, with IBS and IBD at different ends of the same spectrum. However, it should be noted that in most IBS patients, colonic biopsy specimens appear normal. Nevertheless, IBS significantly affects a very large number of individuals (U.S. prevalence in 2000, approximately 16 million individuals), resulting in a total cost burden of 1.7 billion dollars (year 2000). Thus, among the most prevalent and costly gastrointestinal diseases and disorders, IBS is second only to gastroesophageal reflux disease (GERD). Yet unlike GERD, treatment for IBS remains unsatisfactory (Talley et al., 2002; Farhadi et al., 2001; Collins et al., 2001), demonstrating that IBS clearly represents an unmet medical need.

Converging disease models have been proposed that postulate an enhanced responsiveness of neural, immune or neuroimmune circuits in the central nervous system (CNS) or in the gut to central (psychosocial) or peripheral (tissue irritation, inflammation, infection) perturbations of normal homeostasis (Talley et al., 2002). This enhanced responsiveness results in dysregulation of gut motility, epithelial function (immune, permeability), and visceral hypersensitivity, which in turn results in IBS symptoms.

There may be a role for a number of different molecules in the pathogenesis of IBS including a role for molecules that stimulate neurons and those that are involved in initiation of inflammatory process. A number of our in-house molecules are known to be linked to possible activity on neurons due to their direct expression by neurons or expression of their receptors on neurons, including IL-17D, IL-17B and IL-31. Moreover, a number of IL-17 family members and related molecules have been associated with inflammation in the gut, including IL-17A, IL-17F, IL-23 and IL-31.

Efficacy of inhibitors of these molecules could be tested in vivo in animal models of disease. Several animal models have been proposed that mimic key features of IBS and involve centrally targeted stimuli (stress) or peripherally targeted stimuli (infection, inflammation). Two examples of in vivo animal models that can be used to determine the effectiveness of inhibitors in the treatment of IBS are (i) models focusing on primary CNS-directed pathogeneisis of IBS (stress models), and (ii) models focusing on gut-directed inducers of stress (i.e. gut inflammation, infection or physical stress). It should be noted however, that events within the CNS or in the gastrointestinal (GI) tract do not occur in isolation and that symptoms of IBS most likely result from a complex interaction between signals from the CNS on the GI and vice versa.

J) Pharmaceutical Formulations

For pharmaceutical use, the soluble polypeptides of the present invention are formulated for parenteral, particularly intravenous or subcutaneous, delivery according to conventional methods. Intravenous administration will be by bolus injection, controlled release, e.g., using mini-pumps or other appropriate technology, or by infusion over a typical period of one to several hours. In general, pharmaceutical formulations will include a hematopoietic protein in combination with a pharmaceutically acceptable carrier, such as saline, buffered saline, 5% dextrose in water or the like. Formulations may further include one or more excipients, preservatives, solubilizers, buffering agents, albumin to prevent protein loss on vial surfaces, etc. When utilizing such a combination therapy, the cytokines may be combined in a single formulation or may be administered in separate formulations. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 mg/kg of patient weight per day, preferably 0.5-20 mg/kg per day, with the exact dose determined by the clinician according to accepted standards, taking into account the nature and severity of the condition to be treated, patient traits, etc. Determination of dose is within the level of ordinary skill in the art. The proteins will commonly be administered over a period of up to 28 days following chemotherapy or bone-marrow transplant or until a platelet count of >20,000/mm$^3$, preferably >50,000/mm$^3$, is achieved. More commonly, the proteins will be administered over one week or less, often over a period of one to three days. In general, a therapeutically effective amount of the soluble polypeptides of the present invention in an amount sufficient to produce a clinically significant increase in the proliferation and/or differentiation of lymphoid or myeloid progenitor cells, which will be manifested as an increase in circulating levels of mature cells (e.g. platelets or neutrophils). Treatment of platelet disorders will thus be continued until a platelet count of at least 20,000/mm$^3$, preferably 50,000/mm$^3$, is reached. The soluble polypeptides of the present invention can also be administered in combination with other cytokines such as IL-3, -6 and -11; stem cell factor; erythropoietin; G-CSF and GM-CSF. Within regimens of combination therapy, daily doses of other cytokines will in general be: EPO, 150 U/kg; GM-CSF, 5-15 lg/kg; IL-3, 1-5 lg/kg; and G-CSF, 1-25 lg/kg. Combination therapy with EPO, for example, is indicated in anemic patients with low EPO levels.

Generally, the dosage of administered soluble polypeptides will vary depending upon such factors as the patient's age, weight, height, sex, general medical condition and previous medical history. Typically, it is desirable to provide the recipient with a dosage of such soluble polypeptide which is in the range of from about 1 pg/kg to 10 mg/kg (amount of agent/body weight of patient), although a lower or higher dosage also may be administered as circumstances dictate.

Administration of the soluble polypeptides of the present invention to a subject can be intravenous, intraarterial, intraperitoneal, intramuscular, subcutaneous, intrapleural, intrathecal, by perfusion through a regional catheter, or by direct intralesional injection. When administering therapeutic proteins by injection, the administration may be by continuous infusion or by single or multiple boluses.

Additional routes of administration include oral, mucosal-membrane, pulmonary, and transcutaneous. Oral delivery is suitable for polyester microspheres, zein microspheres, proteinoid microspheres, polycyanoacrylate microspheres, and lipid-based systems (see, for example, DiBase and Morrel, "Oral Delivery of Microencapsulated Proteins," in *Protein Delivery: Physical Systems*, Sanders and Hendren (eds.), pages 255-288 (Plenum Press 1997)). The feasibility of an intranasal delivery is exemplified by such a mode of insulin administration (see, for example, Hinchcliffe and Ilium, *Adv. Drug Deliv. Rev.* 35:199 (1999)). Dry or liquid particles comprising soluble IL-17RC or anti-IL-17RC antibodies can be prepared and inhaled with the aid of dry-powder dispersers, liquid aerosol generators, or nebulizers (e.g., Pettit and Gombotz, *TIBTECH* 16:343 (1998); Patton et al., *Adv. Drug Deliv. Rev.* 35:235 (1999)). This approach is illustrated by the AERX diabetes management system, which is a hand-held electronic inhaler that delivers aerosolized insulin into the lungs. Studies have shown that proteins as large as 48,000 kDa have been delivered across skin at therapeutic concentrations with the aid of low-frequency ultrasound, which illustrates the feasibility of trascutaneous administration (Mitragotri et al., *Science* 269:850 (1995)). Transdermal delivery using electroporation provides another means to administer the soluble polypeptides of the present invention (Potts et al., *Pharm. Biotechnol.* 10:213 (1997)).

A pharmaceutical composition comprising the soluble polypeptides of the present invention can be formulated according to known methods to prepare pharmaceutically useful compositions, whereby the therapeutic proteins are combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. See, for example, Gennaro (ed.), *Remington's Pharmaceutical Sciences*, 19th Edition (Mack Publishing Company 1995).

For purposes of therapy, the soluble polypeptides of the present invention and a pharmaceutically acceptable carrier are administered to a patient in a therapeutically effective amount. A combination of a therapeutic molecule of the present invention and a pharmaceutically acceptable carrier is said to be administered in a "therapeutically effective amount" if the amount administered is physiologically significant. An agent is physiologically significant if its presence results in a detectable change in the physiology of a recipient patient. For example, an agent used to treat inflammation is physiologically significant if its presence alleviates the inflammatory response.

A pharmaceutical composition comprising a soluble polypeptide of the present invention can be furnished in liquid form, in an aerosol, or in solid form. Liquid forms, are illustrated by injectable solutions and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems*, Ranade and Hollinger (eds.), pages 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)).

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., *Japanese Patent* 04-244,018; Kato et al., *Biol. Pharm. Bull.* 16:960 (1993)). These formulations were prepared by mixing soybean phosphatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug*

*Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

Polypeptides and antibodies can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

The present invention also contemplates chemically modified polypeptides having IL-17A and/or IL-17F binding activity such as IL-17RC or IL-17RC/IL-17RA monomeric, homodimeric, heterodimeric or multimeric soluble receptors, which a polypeptide is linked with a polymer, as discussed above.

Other dosage forms can be devised by those skilled in the art, as shown, for example, by Ansel and Popovich, *Pharmaceutical Dosage Forms and Drug Delivery Systems*, 5$^{th}$ Edition (Lea & Febiger 1990), Gennaro (ed.), *Remington's Pharmaceutical Sciences*, 19$^{th}$ Edition (Mack Publishing Company 1995), and by Ranade and Hollinger, *Drug Delivery Systems* (CRC Press 1996).

As an illustration, pharmaceutical compositions may be supplied as a kit comprising a container that comprises one of the soluble polypeptides of the present invention. Therapeutic polypeptides can be provided in the form of an injectable solution for single or multiple doses, or as a sterile powder that will be reconstituted before injection. Alternatively, such a kit can include a dry-powder disperser, liquid aerosol generator, or nebulizer for administration of a therapeutic polypeptide. Such a kit may further comprise written information on indications and usage of the pharmaceutical composition. Moreover, such information may include a statement that the composition is contraindicated in patients with known hypersensitivity to IL-17RC or IL-17RA.

A pharmaceutical composition comprising soluble polypeptides of the present invention can be furnished in liquid form, in an aerosol, or in solid form. Liquid forms, are illustrated by injectable solutions, aerosols, droplets, topological solutions, and oral suspensions. Exemplary solid forms include capsules, tablets, and controlled-release forms. The latter form is illustrated by miniosmotic pumps and implants (Bremer et al., *Pharm. Biotechnol.* 10:239 (1997); Ranade, "Implants in Drug Delivery," in *Drug Delivery Systems, Ranade and Hollinger (eds.), pages* 95-123 (CRC Press 1995); Bremer et al., "Protein Delivery with Infusion Pumps," in *Protein Delivery: Physical Systems*, Sanders and Hendren (eds.), pages 239-254 (Plenum Press 1997); Yewey et al., "Delivery of Proteins from a Controlled Release Injectable Implant," in *Protein Delivery: Physical Systems*, Sanders and Hendren (eds.), pages 93-117 (Plenum Press 1997)). Other solid forms include creams, pastes, other topological applications, and the like.

Liposomes provide one means to deliver therapeutic polypeptides to a subject intravenously, intraperitoneally, intrathecally, intramuscularly, subcutaneously, or via oral administration, inhalation, or intranasal administration. Liposomes are microscopic vesicles that consist of one or more lipid bilayers surrounding aqueous compartments (see, generally, Bakker-Woudenberg et al., *Eur. J. Clin. Microbiol. Infect. Dis.* 12 (Suppl. 1):561 (1993), Kim, *Drugs* 46:618 (1993), and Ranade, "Site-Specific Drug Delivery Using Liposomes as Carriers," in *Drug Delivery Systems*, Ranade and Hollinger (eds.), pages 3-24 (CRC Press 1995)). Liposomes are similar in composition to cellular membranes and as a result, liposomes can be administered safely and are biodegradable. Depending on the method of preparation, liposomes may be unilamellar or multilamellar, and liposomes can vary in size with diameters ranging from 0.02 µm to greater than 10 µm. A variety of agents can be encapsulated in liposomes: hydrophobic agents partition in the bilayers and hydrophilic agents partition within the inner aqueous space(s) (see, for example, Machy et al., *Liposomes In Cell Biology And Pharmacology* (John Libbey 1987), and Ostro et al., *American J. Hosp. Pharm.* 46:1576 (1989)). Moreover, it is possible to control the therapeutic availability of the encapsulated agent by varying liposome size, the number of bilayers, lipid composition, as well as the charge and surface characteristics of the liposomes.

Liposomes can adsorb to virtually any type of cell and then slowly release the encapsulated agent. Alternatively, an absorbed liposome may be endocytosed by cells that are phagocytic. Endocytosis is followed by intralysosomal degradation of liposomal lipids and release of the encapsulated agents (Scherphof et al., *Ann. N.Y. Acad. Sci.* 446:368 (1985)). After intravenous administration, small liposomes (0.1 to 1.0 µm) are typically taken up by cells of the reticuloendothelial system, located principally in the liver and spleen, whereas liposomes larger than 3.0 µm are deposited in the lung. This preferential uptake of smaller liposomes by the cells of the reticuloendothelial system has been used to deliver chemotherapeutic agents to macrophages and to tumors of the liver.

The reticuloendothelial system can be circumvented by several methods including saturation with large doses of liposome particles, or selective macrophage inactivation by pharmacological means (Claassen et al., *Biochim. Biophys. Acta* 802:428 (1984)). In addition, incorporation of glycolipid- or polyethelene glycol-derivatized phospholipids into liposome membranes has been shown to result in a significantly reduced uptake by the reticuloendothelial system (Allen et al., *Biochim. Biophys. Acta* 1068:133 (1991); Allen et al., *Biochim. Biophys. Acta* 1150:9 (1993)).

Liposomes can also be prepared to target particular cells or organs by varying phospholipid composition or by inserting receptors or ligands into the liposomes. For example, liposomes, prepared with a high content of a nonionic surfactant, have been used to target the liver (Hayakawa et al., *Japanese Patent* 04-244,018; Kato et al., *Biol. Pharm. Bull.* 16:960 (1993)). These formulations were prepared by mixing soybean phospatidylcholine, α-tocopherol, and ethoxylated hydrogenated castor oil (HCO-60) in methanol, concentrating the mixture under vacuum, and then reconstituting the mixture with water. A liposomal formulation of dipalmitoylphosphatidylcholine (DPPC) with a soybean-derived sterylglucoside mixture (SG) and cholesterol (Ch) has also been shown to target the liver (Shimizu et al., *Biol. Pharm. Bull.* 20:881 (1997)).

Alternatively, various targeting ligands can be bound to the surface of the liposome, such as antibodies, antibody fragments, carbohydrates, vitamins, and transport proteins. For example, liposomes can be modified with branched type galactosyllipid derivatives to target asialoglycoprotein (galactose) receptors, which are exclusively expressed on the surface of liver cells (Kato and Sugiyama, *Crit. Rev. Ther. Drug Carrier Syst.* 14:287 (1997); Murahashi et al., *Biol. Pharm. Bull.* 20:259 (1997)). Similarly, Wu et al., *Hepatology* 27:772 (1998), have shown that labeling liposomes with asialofetuin led to a shortened liposome plasma half-life and greatly enhanced uptake of asialofetuin-labeled liposome by hepatocytes. On the other hand, hepatic accumulation of liposomes comprising branched type galactosyllipid derivatives can be inhibited by preinjection of asialofetuin (Murahashi et al., *Biol. Pharm. Bull.* 20:259 (1997)). Polyaconitylated human serum albumin liposomes provide another approach for targeting liposomes to liver cells (Kamps et al., *Proc. Nat'l Acad. Sci. USA* 94:11681 (1997)). Moreover, Geho, et al. U.S. Pat. No. 4,603,044, describe a hepatocyte-directed liposome vesicle delivery system, which has specificity for hepatobiliary receptors associated with the specialized metabolic cells of the liver.

In a more general approach to tissue targeting, target cells are prelabeled with biotinylated antibodies specific for a ligand expressed by the target cell (Harasym et al., *Adv. Drug Deliv. Rev.* 32:99 (1998)). After plasma elimination of free antibody, streptavidin-conjugated liposomes are administered. In another approach, targeting antibodies are directly attached to liposomes (Harasym et al., *Adv. Drug Deliv. Rev.* 32:99 (1998)).

The soluble polypeptides of the present invention can be encapsulated within liposomes using standard techniques of protein microencapsulation (see, for example, Anderson et al., *Infect. Immun.* 31:1099 (1981), Anderson et al., *Cancer Res.* 50:1853 (1990), and Cohen et al., *Biochim. Biophys. Acta* 1063:95 (1991), Alving et al. "Preparation and Use of Liposomes in Immunological Studies," in *Liposome Technology*, 2nd Edition, Vol. III, Gregoriadis (ed.), page 317 (CRC Press 1993), Wassef et al., *Meth. Enzymol.* 149:124 (1987)). As noted above, therapeutically useful liposomes may contain a variety of components. For example, liposomes may comprise lipid derivatives of poly(ethylene glycol) (Allen et al., *Biochim. Biophys. Acta* 1150:9 (1993)).

Degradable polymer microspheres have been designed to maintain high systemic levels of therapeutic proteins. Microspheres are prepared from degradable polymers such as poly (lactide-co-glycolide) (PLG), polyanhydrides, poly (ortho esters), nonbiodegradable ethylvinyl acetate polymers, in which proteins are entrapped in the polymer (Gombotz and Pettit, *Bioconjugate Chem.* 6:332 (1995); Ranade, "Role of Polymers in Drug Delivery," in *Drug Delivery Systems*, Ranade and Hollinger (eds.), pages 51-93 (CRC Press 1995); Roskos and Maskiewicz, "Degradable Controlled Release Systems Useful for Protein Delivery," in *Protein Delivery: Physical Systems*, Sanders and Hendren (eds.), pages 45-92 (Plenum Press 1997); Bartus et al., *Science* 281:1161 (1998); Putney and Burke, *Nature Biotechnology* 16:153 (1998); Putney, *Curr. Opin. Chem. Biol.* 2:548 (1998)). Polyethylene glycol (PEG)-coated nanospheres can also provide carriers for intravenous administration of therapeutic proteins (see, for example, Gref et al., *Pharm. Biotechnol.* 10:167 (1997)).

Other dosage forms can be devised by those skilled in the art, as shown, for example, by Ansel and Popovich, *Pharmaceutical Dosage Forms and Drug Delivery Systems*, 5th Edition (Lea & Febiger 1990), Gennaro (ed.), *Remington's Pharmaceutical Sciences*, 19th Edition (Mack Publishing Company 1995), and by Ranade and Hollinger, *Drug Delivery Systems* (CRC Press 1996).

The present invention contemplates compositions of the soluble polypeptides of the present invention, and methods and therapeutic uses comprising the same polypeptide described herein. Such compositions can further comprise a carrier. The carrier can be a conventional organic or inorganic carrier. Examples of carriers include water, buffer solution, alcohol, propylene glycol, macrogol, sesame oil, corn oil, and the like.

K) Production of Transgenic Mice

Transgenic mice can be engineered to over-express the either IL-17F, IL-17A, IL-17RA or the IL-17RC gene in all tissues or under the control of a tissue-specific or tissue-preferred regulatory element. These over-producers can be used to characterize the phenotype that results from over-expression, and the transgenic animals can serve as models for human disease caused by excess IL-17F, IL-17A, IL-17RA or IL-17RC. Transgenic mice that over-express any of these also provide model bioreactors for production of IL-17RA or IL-17RC, such as any of the soluble polypeptides of the present invention in milk or blood of larger animals. Methods for producing transgenic mice are well-known to those of skill in the art (see, for example, Jacob, "Expression and Knockout of Interferons in Transgenic Mice," in Overexpression and Knockout of Cytokines in Transgenic Mice, Jacob (ed.), pages 111-124 (Academic Press, Ltd. 1994), Monastersky and Rob1 (eds.), Strategies in Transgenic Animal Science (ASM Press 1995), and Abbud and Nilson, "Recombinant Protein Expression in Transgenic Mice," in Gene Expression Systems: Using Nature for the Art of Expression, Fernandez and Hoeffler (eds.), pages 367-397 (Academic Press, Inc. 1999)).

For example, a method for producing a transgenic mouse that expresses a IL-17RC gene can begin with adult, fertile males (studs) (B6C3f1, 2-8 months of age (Taconic Farms, Germantown, N.Y.)), vasectomized males (duds) (B6D2f1, 2-8 months, (Taconic Farms)), prepubescent fertile females (donors) (B6C3f1, 4-5 weeks, (Taconic Farms)) and adult fertile females (recipients) (B6D2f1, 2-4 months, (Taconic Farms)). The donors are acclimated for one week and then injected with approximately 8 IU/mouse of Pregnant Mare's Serum gonadotrophin (Sigma Chemical Company; St. Louis, Mo.) I.P., and 46-47 hours later, 8 IU/mouse of human Chorionic Gonadotropin (hCG (Sigma)) I.P. to induce superovulation. Donors are mated with studs subsequent to hormone injections. Ovulation generally occurs within 13 hours of hCG injection. Copulation is confirmed by the presence of a vaginal plug the morning following mating.

Fertilized eggs are collected under a surgical scope. The oviducts are collected and eggs are released into urinanalysis slides containing hyaluronidase (Sigma). Eggs are washed once in hyaluronidase, and twice in Whitten's W640 medium (described, for example, by Menino and O'Claray, *Biol.*

Reprod. 77:159 (1986), and Dienhart and Downs, Zygote 4:129 (1996)) that has been incubated with 5% $CO_2$, 5% $O_2$, and 90% $N_2$ at 37° C. The eggs are then stored in a 37° C./5% $CO_2$ incubator until microinjection.

Ten to twenty micrograms of plasmid DNA containing a IL-17RC encoding sequence is linearized, gel-purified, and resuspended in 10 mM Tris-HCl (pH 7.4), 0.25 mM EDTA (pH 8.0), at a final concentration of 5-10 nanograms per microliter for microinjection. For example, the IL-17RC encoding sequences can encode a polypeptide comprising amino acid residues 21 to 452 of SEQ ID NO:2.

Plasmid DNA is microinjected into harvested eggs contained in a drop of W640 medium overlaid by warm, CO2-equilibrated mineral oil. The DNA is drawn into an injection needle (pulled from a 0.75 mm ID, 1 mm OD borosilicate glass capillary), and injected into individual eggs. Each egg is penetrated with the injection needle, into one or both of the haploid pronuclei.

Picoliters of DNA are injected into the pronuclei, and the injection needle withdrawn without coming into contact with the nucleoli. The procedure is repeated until all the eggs are injected. Successfully microinjected eggs are transferred into an organ tissue-culture dish with pre-gassed W640 medium for storage overnight in a 37° C./5% $CO_2$ incubator.

The following day, two-cell embryos are transferred into pseudopregnant recipients. The recipients are identified by the presence of copulation plugs, after copulating with vasectomized duds. Recipients are anesthetized and shaved on the dorsal left side and transferred to a surgical microscope. A small incision is made in the skin and through the muscle wall in the middle of the abdominal area outlined by the ribcage, the saddle, and the hind leg, midway between knee and spleen. The reproductive organs are exteriorized onto a small surgical drape. The fat pad is stretched out over the surgical drape, and a baby serrefine (Roboz, Rockville, Md.) is attached to the fat pad and left hanging over the back of the mouse, preventing the organs from sliding back in.

With a fine transfer pipette containing mineral oil followed by alternating W640 and air bubbles, 12-17 healthy two-cell embryos from the previous day's injection are transferred into the recipient. The swollen ampulla is located and holding the oviduct between the ampulla and the bursa, a nick in the oviduct is made with a 28 g needle close to the bursa, making sure not to tear the ampulla or the bursa.

The pipette is transferred into the nick in the oviduct, and the embryos are blown in, allowing the first air bubble to escape the pipette. The fat pad is gently pushed into the peritoneum, and the reproductive organs allowed to slide in. The peritoneal wall is closed with one suture and the skin closed with a wound clip. The mice recuperate on a 37° C. slide warmer for a minimum of four hours.

The recipients are returned to cages in pairs, and allowed 19-21 days gestation. After birth, 19-21 days postpartum is allowed before weaning. The weanlings are sexed and placed into separate sex cages, and a 0.5 cm biopsy (used for genotyping) is snipped off the tail with clean scissors.

Genomic DNA is prepared from the tail snips using, for example, a Qiagen Dneasy kit following the manufacturer's instructions. Genomic DNA is analyzed by PCR using primers designed to amplify a IL-17RC gene or a selectable marker gene that was introduced in the same plasmid. After animals are confirmed to be transgenic, they are back-crossed into an inbred strain by placing a transgenic female with a wild-type male, or a transgenic male with one or two wild-type female(s). As pups are born and weaned, the sexes are separated, and their tails snipped for genotyping.

To check for expression of a transgene in a live animal, a partial hepatectomy is performed. A surgical prep is made of the upper abdomen directly below the zyphoid process. Using sterile technique, a small 1.5-2 cm incision is made below the sternum and the left lateral lobe of the liver exteriorized. Using 4-0 silk, a tie is made around the lower lobe securing it outside the body cavity. An atraumatic clamp is used to hold the tie while a second loop of absorbable Dexon (American Cyanamid; Wayne, N.J.) is placed proximal to the first tie. A distal cut is made from the Dexon tie and approximately 100 mg of the excised liver tissue is placed in a sterile petri dish. The excised liver section is transferred to a 14 ml polypropylene round bottom tube and snap frozen in liquid nitrogen and then stored on dry ice. The surgical site is closed with suture and wound clips, and the animal's cage placed on a 37° C. heating pad for 24 hours post operatively. The animal is checked daily post operatively and the wound clips removed 7-10 days after surgery. The expression level of IL-17RC mRNA is examined for each transgenic mouse using an RNA solution hybridization assay or polymerase chain reaction.

In addition to producing transgenic mice that over-express IL-17F, IL-17A, IL-17RA or IL-17RC, it is useful to engineer transgenic mice with either abnormally low or no expression of any of these genes. Such transgenic mice provide useful models for diseases associated with a lack of IL-17F, IL-17A, IL-17RA or IL-17RC. As discussed above, IL-17RC gene expression can be inhibited using anti-sense genes, ribozyme genes, or external guide sequence genes. For example, to produce transgenic mice that under-express the IL-17RC gene, such inhibitory sequences are targeted to IL-17RC mRNA. Methods for producing transgenic mice that have abnormally low expression of a particular gene are known to those in the art (see, for example, Wu et al., "Gene Underexpression in Cultured Cells and Animals by Antisense DNA and RNA Strategies," in Methods in Gene Biotechnology, pages 205-224 (CRC Press 1997)).

An alternative approach to producing transgenic mice that have little or no IL-17RC gene expression is to generate mice having at least one normal IL-17RC allele replaced by a nonfunctional IL-17RC gene. One method of designing a nonfunctional IL-17RC gene is to insert another gene, such as a selectable marker gene, within a nucleic acid molecule that encodes IL-17RC. Standard methods for producing these so-called "knockout mice" are known to those skilled in the art (see, for example, Jacob, "Expression and Knockout of Interferons in Transgenic Mice," in *Overexpression and Knockout of Cytokines in Transgenic Mice*, Jacob (ed.), pages 111-124 (Academic Press, Ltd. 1994), and Wu et al., "New Strategies for Gene Knockout," in *Methods in Gene Biotechnology*, pages 339-365 (CRC Press 1997)).

The invention is further illustrated by the following non-limiting examples.

Example 1

Expression of the IL-17RC Gene

Northern analyses were performed using Human Multiple Tissue Blots (Clontech Laboratories, Inc., Palo Alto, Calif.). Two probes were generated from gel purified PCR products. The first probe was made using ZC21798 (5' CGG CGT GGT GGT CTT GCT CTT 3'; SEQ ID NO:8) and ZC21808 (5' TCC CGT CCC CCG CCC CAG GTC 3'; SEQ ID NO:31) as primers. The probe was a radioactively labeled using the Multiprime labeling kit from Amersham (Arlington Heights, Ill.) according to the manufacturer's protocol. The probe was purified using a NucTrap push column (Stratagene, La Jolla, Calif.). ExpressHyb (Clontech) solution was used for the prehybridization and hybridization solutions for the northern blots. Hybridization took place overnight at 65° C. Following hybridization, the blots were washed for 30 minutes each in solutions that contained 0.1% SDS and SSC as follows: twice in 2×SSC at room temperature, three times in 0.1×SSC at 50° C., once in 0.1×SSC at 55° C., and once in 0.1×SSC at 65° C. The results demonstrated the IL-17RC gene is strongly expressed in thyroid, adrenal gland, prostate, and liver tissues, and expressed to a lesser extent in heart, small intestine, stomach, and trachea tissues. In contrast, there is little or no expression in brain, placenta, lung, skeletal muscle, kidney, pancreas, spleen, thymus, testis, ovary, colon, peripheral blood leukocytes, spinal cord, lymph node, and bone marrow.

Example 2

Distribution of mRNA in Cell Line Panels Using PCR

Total RNA was purified from resting and stimulated cell lines grown in-house and purified using a Qiagen (Valencia, Calif.) RNeasy kit according to the manufacturer's instructions, or an acid-phenol purification protocol (Chomczynski and Sacchi, *Analytical Biochemistry*, 162:156-9, 1987). The quality of the RNA was assessed by running an aliquot on an Agilent Bioanalyzer. If the RNA was significantly degraded, it was not used for subsequent creation of first strand cDNA. Presence of contaminating genomic DNA was assessed by a PCR assay on an aliquot of the RNA with zc41011 (5'CTCTCCATCCTTATCTTTCATCAAC 3'; SEQ ID NO:32) and zc41012 (5'CTCTCTGCTGGCTAAACAAAA-CAC 3'; SEQ ID NO:33), primers that amplify a single site of intergenic genomic DNA. The PCR conditions for the contaminating genomic DNA assay were as follows: 2.5 μl 10× buffer and 0.5 μl Advantage 2 cDNA polymerase mix (BD Biosciences Clontech, Palo Alto, Calif.), 2 ul 2.5 mM dNTP mix (Applied Biosystems, Foster City, Calif.), 2.5 μl 10× Rediload (Invitrogen, Carlsbad, Calif.), and 0.5 μl 20 uM zc41011 and zc41012, in a final volume of 25 ul. Cycling parameters were 94° C. 20", 40 cycles of 94° C. 20" 60° C. 1'20" and one cycle of 72° C. 7'. 10 μl of each reaction was subjected to agarose gel electrophoresis and gels were examined for presence of a PCR product from contaminating genomic DNA. If contaminating genomic DNA was observed, the total RNA was DNAsed using DNA-free reagents (Ambion, Inc, Austin, Tex.) according to the manufacturer's instructions, then retested as described above. Only RNAs which appeared to be free of contaminating genomic DNA were used for subsequent creation of first strand cDNA.

20 μg total RNA from 82 human cell lines were each brought to 98 μl with H2O, then split into two 49 ul aliquots, each containing 10 μg total RNA, and placed in two 96-well PCR plates. To each aliquot was added reagents for first strand cDNA synthesis (Invitrogen First Strand cDNA Synthesis System, Carlsbad, Calif.): 20 μl 25 mM MgCl2, 10 ul 10×RT buffer, 10 ul 0.1M DTT, 2 μl oligo dT, 2 μl RNAseOut. Then, to one aliquot from each cell line 2 μl Superscript II Reverse Transcriptase was added, and to the corresponding cell line aliquot 2 μl H$_2$O was added to make a minus Reverse Transcriptase negative control. All samples were incubated as follows: 25° C. 10', 42° C. 50', 70° C. 15'. Samples were arranged in deep well plates and diluted to 1.7 ml with H$_2$O. A Multipette (Saigan) robot was used to aliquot 16.5 μl into each well of a 96-well PCR plate multiple times, generating numerous one-use PCR panels of the cell lines, which were then sealed and stored at −20° C. Each well in these panels represents first strand cDNA from approximately 100 ng total RNA. The 82 cell lines are spread across two panels, array #118A and #118B. Quality of first strand cDNA on the panels was assessed by a multiplex PCR assay on one set of the panels using primers to two widely expressed, but only moderately abundant genes, CLTC (clathrin) and TFRC (transferrin receptor C). 0.5 μl each of Clathrin primers zc42901 (5'CTCATATTGCTCAACTGTGTGAAAAG 3'; SEQ ID NO:34), zc42902 (5'TAGAAGCCACCTGAACA-CAAATCTG3'; SEQ ID NO:35), and TFRC primers zc42599 (5' ATCTTGCGTTGTATGTTGAAAATCAATT3'; SEQ ID NO:36), zc42600 (5'TTCTCCACCAGGTAAACAAGTC-TAC3'; SEQ ID NO:37), were mixed with 2.5 μl 10× buffer and 0.5 μl Advantage 2 cDNA polymerase mix (BD Biosciences Clontech, Palo Alto, Calif.), 2 μl 2.5 mM dNTP mix (Applied Biosystems, Foster City, Calif.), 2.5 μl 10× Rediload (Invitrogen, Carlsbad, Calif.), and added to each well of a panel of array #118A and array #118B. Cycling parameters were as follows: 94° C. 20", 35 cycles of 94° C. 20", 67° C. 80", and one cycle of 72° C. 7'. 10 μl of each reaction was subjected to agarose gel electrophoresis and gels were scored for the presence of a robust PCR product for each gene specific to the +RT wells for each cell line.

Expression of mRNA in the human first strand cDNA panels for IL-17RC was assayed by PCR with sense oligo ZC42756 (5' ctctccaggcccaagtcgtgctct3'; SEQ ID NO:38) and antisense oligo ZC42757 (5' ttgtcctggggccctcgtgtctcc3'; SEQ ID NO:39) under these PCR conditions per sample: 2.5 μl 10× buffer and 0.5 μl advantage 2 cDNA polymerase mix (BD Biosciences Clontech, Palo Alto, Calif.), 2 μl 2.5 mM dNTP mix (Applied Biosystems,), 2.5 ul 10× Rediload (Invitrogen, Carlsbad, Calif.), and 0.5 μl 20 uM each sense and antisense primer. Cycling conditions were 94° C. 2', 35 cycles of 94° C. 1', 66° C. 30", 72° C. 1.5°, and one cycle of 72° C. 7'. 10 μl of each reaction was subjected to agarose gel electrophoresis and gels were scored for positive or negative expression of IL-17RC.

IL-17RC mRNA is widely expressed in many cell lines representing a broad spectrum of tissue and cell types. In particular, IL-17RC is consistently expressed in non-T cell peripheral blood cell lines, including monocytes, B-cells, and cells of the myeloid lineage. Also, IL-17RC mRNA is reliably expressed in cell lines derived from skin. Other cell lines that express IL-17RC are all 5 of the large intestine cell lines that were present on the array.

Example 3

Distribution of mRNA in Mouse Cell Line Panels Using RT PCR

Total RNA was purified from 60 resting and stimulated cell lines grown in-house and purified using a Qiagen (Valencia, Calif.) RNeasy kit according to the manufacturer's instructions, an acid-phenol purification protocol (Chomczynski and Sacchi, Analytical Biochemistry, 162:156-9, 1987), or a Trizol reagent protocol (Invitrogen, Carlsbad, Calif.).

5 μg of total RNA from each cell line was arranged in a deep well 96-well plate, 125 μl 3M NaOAc and 100 μl Pellet Paint (Novagen, Madison, Wis.)) were added to each well, then the final volume was adjusted to 1.25 ml with H$_2$O. A Multipette (Saigan) robot was used to aliquot 25 μl of the RNA mixture followed by 75 ul EtOH into each well of a 96-well PCR plate multiple times, generating numerous one-use RT PCR panels of the cell lines, which were then sealed and stored at −20° C. RT PCR screening was performed by first centrifuging a panel in a Qiagen (Valencia, Calif.)

96-well centrifuge for 10' at 6000 RPM. Supernatant was removed by inverting the plate onto absorbent paper. RNA pellets were washed with 100 µl 70% EtOH, followed by a 5' centrifugation at 6000 RPM. Supernatant was again removed and plates allowed to air-dry until the remaining EtOH was evaporated. RNA pellets were resuspended in 15 µl H20.

Expression of IL-17RC mRNA in the mouse cell line RNA panels was assayed by RT PCR with zc38910 (5' acgaagcccaggtaccagaaagag3'; SEQ ID NO:40) and zc38679 (5' aaaagcgccgcagccaagagtagg3'; SEQ ID NO:41) under these RT PCR conditions per sample: SuperScript One-Step PCR with Platinum Taq kit, Invitrogen, Carlsbad, Calif. Cycling conditions were: 1 cycle of 48° C. for 30 minutes, 94° C. for 2 minutes, followed by 35 cycles of 94° C. for 15 seconds, 55° C. for 30 seconds, 72° C. for 1.5 minutes, followed by 1 cycle of 72° C. for 7 minutes. 10 µl of each reaction was subjected to agarose gel electrophoresis and gels were scored for positive or negative expression of IL-17RC.

Murine IL-17RCmRNA is expressed in several mouse cell lines, notably in cell lines derived from bone marrow, including osteoblast, adipocyte, and preadipocyte cell lines. Also, mouse IL-17RC is mRNA is represented in several samples from the endocrine system, such as pancreas stromal cell lines, pancreas islet cell lines, and hypothalamus, salivary gland, and testis cell lines.

Example 4

Refolding and Purification pIL-17F Produced in *E. coli*

A) Inclusion Body Isolation and Extraction of pIL-17F

Following induction of protein expression in either batch ferment or shaker flask culture, the *E. coli* broth is centrifuged in 1 liter bottles @ 3000 RPM in a Sorvall swinging bucket rotor. Washing of the cell paste to remove any broth contaminants is performed with 50 mM Tris pH 8.0 containing 200 mM NaCl and 5 mM EDTA until the supernate is clear.

The cell pellets are then suspended in ice-cold lysis buffer (50 mM Tris pH 8.0; 5 mM EDTA; 200 mM NaCl, 10% sucrose (w/v); 5 mM DTT; 5 mM Benzamidine;) to 10-20 Optical Density units at 600 nm. This slurry is then subjected to 3 passes at 8500-9000 psi in a chilled APV 2000 Lab Homogenizer producing a disrupted cell lysate. The insoluble fraction (inclusion bodies) is recovered by centrifugation of the cell lysate at 20,000×G for 1 hour at 4° C.

The inclusion body pellet resulting from the 20,000×G spin is weighed and then re-suspended in wash buffer (50 mM Tris pH 8 containing 200 mM NaCl, 5 mM EDTA, 5 mM DTT, 5 mM Benzamidine) at 10 ml wash buffer per gram inclusion bodies. Complete dispersion is achieved by homogenizing with an OMNI international rotor stator generator. This suspension is centrifuged at 20,000×G for 30 minutes at 4° C. The wash cycle is repeated 3-5 times until the supernatant is clear.

The final washed pellet is solubilized in 7M Guanidine HCl in 40 mM Tris buffer at pH 8 containing 0.1M Sodium Sulfite and 0.02 M Sodium Tetrathionate. The extraction and sulfitolysis reaction is allowed to proceed with gentle stirring at 4° C. overnight. The resulting pinkish colored solution is centrifuged at 35,000×g for 1 hour at 4° C. and the clarified supernate, containing the soluble pIL-17F, is 0.45 µm filtered.

B) pIL-17F Refolding Procedure

The solubilized, sulfitolyzed pIL-17F is refolded by drop wise dilution into ice cold refolding buffer containing 55 mM MES, 10.56 mM NaCl, 0.44 mM KCl, 0.055% PEG (3400 K), 1.1 mM EDTA, 20% Glycerol, 0.5M Guanidine HCl, 0.75 M Arginine and the Glutathione redox pair at a 1:1 ratio (1 mM GSH: 1 mM GSSG). The pH of the refolding buffer is adjusted to 6.5 with HCl and the pIL-17F is added to a final concentration of 100 ug/ml. Once diluted, the mixture is allowed to stir slowly in the cold room for 72 hours.

C) Product Recovery & Purification

The refolded pIL-17F is concentrated 10× vs. a 10 kDa cutoff membrane on a lab scale TFF system. Next it is filtered using a 0.45 micron membrane and the pH is adjusted to 5.1 with the addition of Acetic acid. The pH-adjusted material is captured by cation exchange chromatography on a Pharmacia SP Fast Flow column equilibrated in 50 mM Acetate buffer, pH 5.1. The pIL-17F is loaded by inline proportioning at 1:5 with equilibration buffer at a flow rate of 190 cm/hr. This dilution lowers the ionic strength enabling efficient binding of the target to the matrix. After sample loading is complete, the column is washed to baseline absorbance with equilibration buffer. The column is washed with 0.4 M NaCl in 50 mM Acetate buffer at pH 5.1 and then the bound protein is eluted with a 5 CV gradient from 0.4 M to 1.5 M NaCl in 50 mM Acetate buffer at pH 5.1. The protein elutes at ~1M NaCl and is approximately 85% dimeric by SDS PAGE analysis of eluate fractions. The fractions containing pIL-17F are pooled and concentrated against a 10 kDa cutoff ultrafiltration membrane using an Amicon stirred cell in preparation for the final purification and buffer exchange by size exclusion chromatography.

D) Size Exclusion Buffer Exchange and Formulation

The concentrated cation pool (at a volume of 3-4% of CV) is injected at a flow rate of 30 cm/hr onto a Pharmacia Superdex 75 size exclusion column equilibrated in 50 mM Sodium Phosphate buffer containing 109 mM NaCl, pH 7.2. The symmetric eluate peak containing the product is diluted to a concentration of 1 mg/ml in 50 mM Sodium Phosphate buffer containing 109 mM NaCl, pH 7.2. Finally the pIL-17F is 0.2 micron sterile filtered, aliquoted and stored at −80° C. The final process yield is 20%.

Example 5

Construction of Mammalian Soluble IL-17RC Expression Construct

An expression construct containing human IL-17RC [L21-K451]-mFc1 (mouse BALB/c µ2a Fc) is constructed via overlap PCR and homologous recombination using a DNA fragment (SEQ ID NO:42) encoding a IL-17RC polypeptide (SEQ ID NO:43), a DNA fragment encoding mFc1 (SEQ ID NO:44), and the expression vector pZMP20. The fragments are generated by PCR amplification.

The PCR fragment encoding IL-17RC [L21-K451] contains a 5' overlap with the pZMP20 vector sequence in the optimized tissue plasminogen activator pre-pro secretion leader sequence coding region, the IL-17RC extracellular domain coding [L21-K451], and a 3' overlap with the mFc1 coding region. The PCR amplification reaction uses the 5' oligonucleotide [GTTTCGCTCAGCCAGGAAATCCATGCCGAGTTGAGACGCTTCCGTAGACTGGAG AGGCTTGTGGGCCT; SEQ ID NO:46], the 3' oligonucleotide [TGTGGGCCCTCTGGGCTCCTTGTGGATGTATTTGTC; SEQ ID NO:47], and a previously generated DNA clone of IL-17RC as the template.

The PCR fragment encoding mFc1 contains a 5' overlap with the IL-17RC sequence, the mFc1 coding region, and a 3' overlap with the pZMP20 vector in the poliovirus internal ribosome entry site region. The PCR amplification reaction uses the 5 oligonucleotide [GACAAATACATCCACAAG- GAGCCCAGAGGGCCCACA; SEQ ID NO:48], the 3' oligonucleotide [CAACCCCAGAGCTGTTTTAAGGCGCGCCTCTAGATTATTTACCCGGAGTCCGGGA; SEQ ID NO:49], and a previously generated DNA clone of mFc1 as the template.

The PCR amplification reaction conditions are as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixtures are run on a 1% agarose gel and the DNA fragments corresponding to the expected sizes are extracted from the gel using a QIAquick™ Gel Extraction Kit (Qiagen, Cat. No. 28704).

The two PCR fragments are joined by overlap PCR. Approximately 1 µl each of the two gel extracted fragments are combined in a PCR amplification reaction using the 5' oligonucleotide [GTTTCGCTCAGCCAGGAAATCCATGCCGAGTTGAGACGCTTCCGTAGACTGGAG AGGCTTGTGGGGCCT; SEQ ID NO: 46] and the 3' oligonucleotide [CAACCCCAGAGCTGTTTTAAGGCGCGCCTCTAGATTATTTACCCGGAGTCCGGG A; SEQ ID NO:49]. PCR conditions used are as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture is run on a 1% agarose gel and the DNA fragment corresponding to the size of the insert is extracted from the gel using a QIAquick™ Gel Extraction Kit (Qiagen, Cat. No. 28704).

Plasmid pZMP20 is a mammalian expression vector containing an expression cassette having the MPSV promoter, a BglII site for linearization prior to yeast recombination, an otPA signal peptide sequence, an internal ribosome entry element from poliovirus, the extracellular domain of CD8 truncated at the C-terminal end of the transmembrane domain; an E. coli origin of replication; a mammalian selectable marker expression unit comprising an SV40 promoter, enhancer and origin of replication, a DHFR gene, and the SV40 terminator; and URA3 and CEN-ARS sequences required for selection and replication in S. cerevisiae.

The plasmid pZMP20 is digested with BglII prior to recombination in yeast with the gel extracted IL-17RC[L21-K451]-mFc1 PCR fragment. 100 µl of competent yeast (S. cerevisiae) cells are combined with 10 µl of the IL-17RC [L21-K451]-mFc1 insert DNA and 100 ng of BglII digested pZMP20 vector, and the mix is transferred to a 0.2 cm electroporation cuvette. The yeast/DNA mixture is electropulsed using power supply (BioRad Laboratories, Hercules, Calif.) settings of 0.75 kV (5 kV/cm), ∞ ohms, and 25 µF. Six hundred µl of 1.2 M sorbitol is added to the cuvette, and the yeast is plated in 100 µl and 300 µl aliquots onto two URA-D plates and incubated at 30° C. After about 72 hours, the Ura+ yeast transformants from a single plate are resuspended in 1 ml H$_2$O and spun briefly to pellet the yeast cells. The cell pellet is resuspended in 0.5 ml of lysis buffer (2% Triton X-100, 1% SDS, 100 mM NaCl, 10 mM Tris, pH 8.0, 1 mM EDTA). The five hundred µl of the lysis mixture is added to an Eppendorf tube containing 250 µl acid-washed glass beads and 300 µl phenol-chloroform, is vortexed for 3 minutes, and spun for 5 minutes in an Eppendorf centrifuge at maximum speed. Three hundred µl of the aqueous phase is transferred to a fresh tube, and the DNA is precipitated with 600 µl ethanol, followed by centrifugation for 30 minutes at maximum speed. The tube is decanted and the pellet is washed with 1 mL of 70% ethanol. The tube is decanted and the DNA pellet is resuspended in 30 µl 10 mM Tris, pH 8.0, 1 mM EDTA.

Transformation of electrocompetent E. coli host cells (DH12S) is done using 5 µl of the yeast DNA preparation and 50 µl of E. coli cells. The cells are electropulsed at 2.0 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) is added and then the cells are plated in 50 µl and 200 µl aliquots on two LB AMP plates (LB broth (Lennox), 1.8% Bacto™ Agar (Difco), 100 mg/L Ampicillin).

The inserts of three DNA clones for the construct is subjected to sequence analysis and one clone containing the correct sequence is selected. Large scale plasmid DNA is isolated using a commercially available kit (QIAGEN Plasmid Mega Kit, Qiagen, Valencia, Calif.) according to manufacturer's instructions.

Example 6

Construction of Mammalian Soluble IL-17RC Expression Constructs that Express IL-17RC-CEE, IL-17RC-CHIS, and IL-17RC-CFLAG An expression construct containing human IL-17RC [L21-K451] with a C-terminal tag, either Glu-Glu (CEE), six His (CHIS), or FLAG (CFLAG), is constructed via PCR and homologous recombination using a DNA fragment encoding IL-17RC [L21-K451] (SEQ ID NO:42) and the expression vector pZMP20.

The PCR fragment encoding IL-17RCCEE contains a 5' overlap with the pZMP20 vector sequence in the optimized tissue plasminogen activator pre-pro secretion leader sequence coding region, the IL-17RC extracellular domain coding [L21-K451], the sequence of the Glu-Glu tag (Glu Glu Tyr Met Pro Met Glu; SEQ ID NO:53), and a 3' overlap with the pZMP20 vector in the poliovirus internal ribosome entry site region. The PCR amplification reaction uses the 5' oligonucleotide [GTTTCGCTCAGCCAGGAAATCCATGCCGAGTTGAGACGCTTCCGTAGACTGGAG AGGCTTGTGGGGCCT; SEQ ID NO:46], the 3' oligonucleotide [CAACCCCAGAGCTGTTTTAAGGCGCGCCTCTAGATTATTCCATGGGCATGTATTC TTCCTTGTGGATGTATTTGTC; SEQ ID NO:50], and a previously generated DNA clone of IL-17RC as the template.

The PCR amplification reaction condition is as follows: 1 cycle, 94° C., 5 minutes; 35 cycles, 94° C., 1 minute, followed by 55° C., 2 minutes, followed by 72° C., 3 minutes; 1 cycle, 72° C., 10 minutes. The PCR reaction mixture is run on a 1% agarose gel and the DNA fragment corresponding to the expected size is extracted from the gel using a QIAquick™ Gel Extraction Kit (Qiagen, Cat. No. 28704).

The plasmid pZMP20 is digested with BglII prior to recombination in yeast with the gel extracted IL-17RCCEE PCR fragment. One hundred µl of competent yeast (S. cerevisiae) cells are combined with 10 µl of the IL-17RCCEE insert DNA and 100 ng of BglII digested pZMP20 vector, and the mix is transferred to a 0.2 cm electroporation cuvette. The yeast/DNA mixture is electropulsed using power supply (BioRad Laboratories, Hercules, Calif.) settings of 0.75 kV (5 kV/cm), ∞ ohms, and 25 µF. Six hundred µl of 1.2 M sorbitol is added to the cuvette, and the yeast is plated in 100 µl and 300 µl aliquots onto two URA-D plates and incubated at 30° C. After about 72 hours, the Ura+ yeast transformants from a single plate are resuspended in 1 ml H2O and spun briefly to pellet the yeast cells. The cell pellet is resuspended in 0.5 ml of lysis buffer (2% Triton X-100, 1% SDS, 100 mM NaCl, 10 mM Tris, pH 8.0, 1 mM EDTA). The five hundred µl of the lysis mixture is added to an Eppendorf tube containing 250 µl acid-washed glass beads and 300 µl phenol-chloroform, is vortexed for 3 minutes, and spun for 5 minutes in an Eppendorf centrifuge at maximum speed. Three hundred μl of the aqueous phase is transferred to a fresh tube, and the DNA is precipitated with 600 μl ethanol, followed by centrifugation for 30 minutes at maximum speed. The tube is decanted and the pellet is washed with 1 mL of 70% ethanol. The tube is decanted and the DNA pellet is resuspended in 30 μl 10 mM Tris, pH 8.0, 1 mM EDTA.

Transformation of electrocompetent *E. coli* host cells (DH12S) is done using 5 μl of the yeast DNA preparation and 50 μl of *E. coli* cells. The cells are electropulsed at 2.0 kV, 25 μF., and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is added and then the cells are plated in 50 μl and 200 μl aliquots on two LB AMP plates (LB broth (Lennox), 1.8% Bacto™ Agar (Difco), 100 mg/L Ampicillin).

The inserts of three DNA clones for the construct is subjected to sequence analysis and one clone containing the correct sequence is selected. Large scale plasmid DNA is isolated using a commercially available kit (QIAGEN Plasmid Mega Kit, Qiagen, Valencia, Calif.) according to manufacturer's instructions.

The same process is used to prepare the IL-17RC with a C-terminal his tag, composed of Gly Ser Gly Gly His His His His His His (IL-17RCCHIS; SEQ ID NO:51) or the C-terminal FLAG tag, composed of Gly Ser Asp Tyr Lys Asp Asp Asp Asp Lys (IL-17RCCFLAG; SEQ ID NO:52). To prepare these constructs, instead of the 3' oligonucleotide of SEQ ID NO:50; the 3' oligonucleotide [CAACCCCAGAGCTGTTT-TAAGGCGCGCCTCTAGATTAGTGATGGT-GATGGTGAT GTCCACCAGATCCCTTGTGGATG-TATTTGTC; SEQ ID NO:54] is used to generate IL-17RCCHIS or the 3' oligonucleotide [CAACCCCA-GAGCTGTTTTAAGGCGCGCCTCTAGAT-TACTTATCATCATCATCCTT ATAATCGGATCCCT-TGTGGATGTATTTGTC; SEQ ID NO:55] is used to generate IL-17RCCFLAG.

Example 7

Transfection and Expression of Soluble IL-17RC Receptor Expression Constructs that Express the IL-17RC-mFc1 Fusion Protein, and the IL-17RC-CEE, IL-17RC-CHIS, and IL-17RC-CFLAG C-Terminal Tagged Proteins Three sets of 200 μg of each of the soluble IL-17RC fusion or tagged expression constructs are separately digested with 200 units of PvuI at 37° C. for three hours, precipitated with isopropyl alcohol, and centrifuged in a 1.5 mL microfuge tube. The supernatant is decanted off the pellet, and the pellet is washed with 1 mL of 70% ethanol and allowed to incubate for 5 minutes at room temperature. The tube is spun in a microfuge for 10 minutes at 14,000 RPM and the supernatant is decanted off the pellet. The pellet is then resuspended in 750 μl of CHO cell tissue culture medium in a sterile environment, allowed to incubate at 60° C. for 30 minutes, and is allowed to cool to room temperature. Approximately $5 \times 10^6$ CHO cells are pelleted in each of three tubes and are resuspended using the DNA-medium solution. The DNA/cell mixtures are placed in a 0.4 cm gap cuvette and electroporated using the following parameters; 950 μF, high capacitance, at 300 V. The contents of the cuvettes are then removed, pooled, and diluted to 25 mLs with CHO cell tissue culture medium and placed in a 125 mL shake flask. The flask is placed in an incubator on a shaker at 37° C., 6% $CO_2$ with shaking at 120 RPM.

The CHO cells are subjected to nutrient selection followed by step amplification to 200 nM methotrexate (MTX), and then to 1 μM MTX. Fusion or tagged protein expression is confirmed by Western blot, and the CHO cell pool is scaled-up for harvests for protein purification.

Example 8

Expression of Soluble IL-17RC

An expression plasmid containing IL-17RC_Tbx-C(Fc9) (SEQ ID NO:64) was constructed via homologous recombination using a DNA fragment of IL-17RC_Tbx and the expression vector pZMP40. The fragment was generated by PCR amplification using primers zc44531 and zc44545.

The PCR fragment IL-17RC_Tbx contains a partial IL-17RC extracellular domain coding region, which was made using a previously generated clone of IL-17RC as the template. The fragment includes a 5' overlap with the pZMP40 vector sequence in the otPA coding region, the IL-17RC segment (amino acid residue 21 to 451 of SEQ ID NO:2), a linker sequence, a thrombin cleavage site, and a 3' overlap with the pZMP40 vector in the Fc9 coding region. PCR conditions used were as follows: 1 cycle, 94° C., 5 minutes; 35 cycles, 94° C., 1 minute, followed by 55° C., 2 minutes, followed by 72° C., 3 minutes; 1 cycle, 72° C., 10 minutes.

The PCR reaction mixtures were run on a 1% agarose gel and a band corresponding to the sizes of the inserts were gel-extracted using a QIAquick™ Gel Extraction Kit (Qiagen, Cat. No. 28704).

Plasmid pZMP40 is a mammalian expression vector containing an expression cassette having the MPSV promoter, multiple restriction sites for insertion of coding sequences, an otPA signal peptide sequence, and the sequence for Fc9; an internal ribosome entry site (IRES) element from poliovirus, and the extracellular domain of CD8 truncated at the C-terminal end of the transmembrane domain; an *E. coli* origin of replication; a mammalian selectable marker expression unit comprising an SV40 promoter, enhancer and origin of replication, a DHFR gene, and the SV40 terminator; and URA3 and CEN-ARS sequences required for selection and replication in *S. cerevisiae*. It was constructed from pZMP21 (Patent Pub. No. US 2003/0232414 A1; deposited at the American Type Culture Collection and designated as ATCC# PTA-5266).

The plasmid pZMP40 was cut with BglII prior to recombination in yeast with the PCR fragment. One hundred microliters of competent yeast (*S. cerevisiae*) cells were independently combined with 10 μl of the insert DNA (SEQ ID NO:66) and 100 ng of cut pZMP40 vector, and the mix was transferred to a 0.2-cm electroporation cuvette. The yeast/DNA mixture was electropulsed using power supply (BioRad Laboratories, Hercules, Calif.) settings of 0.75 kV (5 kV/cm), ∞ ohms, and 25 μl. Six hundred 0 of 1.2 M sorbitol was added to the cuvette, and the yeast was plated in a 100-μl and 300 μl aliquot onto two URA-D plates and incubated at 30° C. After about 72 hours, the Ura+ yeast transformants from a single plate were resuspended in 1 ml $H_2O$ and spun briefly to pellet the yeast cells. The cell pellet was resuspended in 0.5 ml of lysis buffer (2% Triton X-100, 1% SDS, 100 mM NaCl, 10 mM Tris, pH 8.0, 1 mM EDTA). The five hundred microliters of the lysis mixture was added to an Eppendorf tube containing 250 μl acid-washed glass beads and 300 μl phenol-chloroform, was vortexed for 3 minutes, and spun for 5 minutes in an Eppendorf centrifuge at maximum speed. Three hundred microliters of the aqueous phase was transferred to a fresh tube, and the DNA was precipitated with 600 μl ethanol (EtOH), followed by centrifugation for 30 minutes at maximum speed. The tube was decanted and the pellet was washed with 1 mL of 70% ethanol. The tube was decanted and the DNA pellet was resuspended in 30 μl TE.

Transformation of electrocompetent *E. coli* host cells (DH12S) was done using 5 μl of the yeast DNA prep and 50 μl of cells. The cells were electropulsed at 2.0 kV, 25 μF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added and then the cells were plated in a 50 μl and a 200 μl aliquot on two LB AMP plates (LB broth (Lennox), 1.8% Bacto™ Agar (Difco), 100 mg/L Ampicillin).

The inserts of three clones for the construct was subjected to sequence analysis and one clone for each construct, containing the correct sequence, was selected. Larger scale plasmid DNA was isolated using a commercially available kit (QIAGEN Plasmid Mega Kit, Qiagen, Valencia, Calif.) according to manufacturer's instructions.

Three sets of 200 μg of the IL-17RC[L21-K451]_Tbx_C (Fc9) construct were then each digested with 200 units of Pvu I at 37° C. for three hours and then were precipitated with IPA and spun down in a 1.5 mL microfuge tube. The supernatant was decanted off the pellet, and the pellet was washed with 1 mL of 70% ethanol and allowed to incubate for 5 minutes at room temperature. The tube was spun in a microfuge for 10 minutes at 14,000 RPM and the supernatant was decanted off the pellet. The pellet was then resuspended in 750 μl of PF-CHO media in a sterile environment, allowed to incubate at 60° C. for 30 minutes, and was allowed to cool to room temperature. $5 \times 10^6$ APFDXB11 cells were spun down in each of three tubes and were resuspended using the DNA-media solution. The DNA/cell mixtures were placed in a 0.4 cm gap cuvette and electroporated using the following parameters: 950 μF, high capacitance, and 300 V. The contents of the cuvettes were then removed, pooled, and diluted to 25 mLs with PF-CHO media and placed in a 125 mL shake flask. The flask was placed in an incubator on a shaker at 37° C., 6% $CO_2$, and shaking at 120 RPM.

The cell line was subjected to nutrient selection followed by step amplification to 200 nM methotrexate (MTX), and then to 1 μM MTX. Expression was confirmed by western blot, and the cell line was scaled-up and protein purification followed.

Example 9

Purification of Soluble IL-17RC from CHO Cells

Conditioned media from CHO cells expressing IL-17RC-TbX-Fc9 (SEQ ID NO:64) was concentrated approximately 10-fold with a Pellicon-II tangential flow system against two Biomax 0.1 m2 30 kD molecular weight cutoff membrane cassettes (Millipore, Bedford, Mass.). The concentrated media was pH adjusted to 5.5 with glacial acetic acid, 0.2 μm sterile filtered then loaded onto a Protein G sepharose fast flow resin (Pharmacia, Piscataway, N.J.) via batch chromatography overnight at 4 C. Prior to loading the pH adjusted conditioned media, the Protein G resin was pre-equilibrated with, 5 column volumes (approximately 150 ml) of 25 mM sodium acetate, 150 mM NaCl, pH5.5. The ratio of filtered, pH adjusted conditioned media to resin was 33:1 (v/v).

The batched chromatography process was performed at ambient room temperature (approximately 21 C). The batched, pH adjusted, 0.22 μm filtered, conditioned media was poured into an empty 5.5×20.5 cm glass column (Bio-Rad, Hercules, Calif.) and packed via gravity. The column was washed with 10 column volumes (approximately 300 ml) of 25 mM sodium acetate, 150 mM NaCl, pH5.5. Bound protein was then pH eluted with 100 mM glycine, pH 2.7. 9.0 ml fractions were collected and immediately neutralized with 1.0 ml 2.0M Tris, pH 8.0. The collected fractions were analyzed via SDS-PAGE Coomassie staining. Fractions containing IL-17RC-Tbx-Fc9 were pooled and concentrated approximately 6-fold using a 5 kD molecular weight cutoff Biomax membrane spin concentrator (Millipore, Bedford, Mass.) according to the manufacturer's instructions.

The pooled, concentrated fractions were then dialyzed, at 4 C, extensively against 1× phosphate buffered saline, pH 7.3 (Sigma, St. Louis, Mo.) using a 7 kD molecular weight cutoff membrane Slide-A-Lyzer (Pierce, Rockford, Ill.). IL-17RC-TbX-Fc9 as formulated in 1× phosphate buffered saline, pH 7.3 was 0.22 μm sterile filtered prior to aliquoting and storage at −80° C.

Example 10

Binding of IL-17A and IL-17F to Human IL-17RC

A) Binding of Biotinylated Cytokines to Transfected Cells

Baby Hamster Kidney (BHK) cells that had been transfected with expression vectors encoding human IL-17 receptor (SEQ ID NO:21), human IL-17RC (SEQ ID NO:2), or both of these receptors are assessed for their ability to bind biotinylated human IL-17A and human IL-17F. Cells are harvested with versene, counted and diluted to 107 cells per ml in staining media (SM), which is HBSS plus 1 mg/ml bovine serum albumin (BSA), 10 mM Hepes, and 0.1% sodium azide (w/v). Biotinylated human IL-17A (SEQ ID NO:14) and human IL-17F (SEQ ID NO:16) are incubated with the cells on ice for 30 minutes at various concentrations. After 30 minutes, excess cytokine is washed away with SM and the cells are incubated with a 1:100 dilution of streptavidin conjugated to phycoerythrin (SA-PE) for 30 minutes on ice. Excess SA-PE is washed away and cells are analyzed by flow cytometry. The amount of cytokine binding was quantitated from the mean fluorescence intensity of the cytokine staining. From this analysis, we find that human IL-17A binds both the human IL-17R and IL-17RC to a similar extent. Also, human IL-17F binds IL-17RC to a similar level, but binds IL-17R detectably, but to a much lower level than was seen with IL-17A.

B) Binding of Biotinylated Cytokines to Human Peripheral Blood Mononuclear Cells Human peripheral blood mononuclear cells (PBMC) were prepared from whole blood by ficoll density gradient centrifugation. PBMC at 107 cells per ml were simultaneously incubated with biotinylated IL-17A or IL-17F at 1 μg/ml and fluorochrome conjugated antibodies to specific cell surface proteins that were designed to distinguish various white blood cell lineages. These markers include CD4, CD8, CD19, CD11b, CD56 and CD16. Excess antibody and cytokine are washed away, and specific cytokine binding is detected by incubating with SA-PE as described above. Samples were analyzed by flow cytometry and from this analysis, we find that human IL-17A binds to virtually all PBMC populations examined, but that human IL-17F does not detectably bind to any population.

C) Inhibition of Specific Binding of Biotinlyated Human IL-17A and IL-17F with Unlabeled Cytokine Binding studies are performed as discussed above, but excess unlabeled human IL-17A and IL-17F are included in the binding reaction. In studies with BHK cells, the amount of unlabeled cytokine was varied over a range of concentrations and we find that addition of unlabeled IL-17A competed for binding of both IL-17A and IL-17F to both IL-17RC and IL-17R. However, unlabeled IL-17F competed for binding of both IL-17A and IL-17F to IL-17RC, but it did not compete effectively for binding to IL-17R. This indicates that both IL-17A and IL-17F specifically bind to IL-17RC, and that they bind at a site that is either identical or overlaps significantly since they cross-compete for binding. Also, IL-17A competes for the relatively weak binding of IL-17F for IL-17R, indicating these two cytokines also bind to a similar region in the IL-17R, but IL-17F binds IL-17R with much reduced affinity relative to IL-17RC.

D) Inhibition of Specific Binding of Biotinylated Human IL-17A and IL-17F with Soluble IL-17RC and IL-17R Binding studies are performed as discussed above, except that a soluble form of IL-17RC or IL-17R are included in the binding reactions. These soluble receptors are fusion proteins derived from the extracellular domain of each receptor fused to the human IgG1 constant (Fc) region. We find that soluble IL-17RC inhibits binding of both human IL-17A and IL-17F to both IL-17R and IL-17RC transfected BHK cells. However, soluble IL-17R inhibits binding of IL-17A to either receptor, but does not effectively block binding of IL-17F to IL-17RC, consistent with the poor binding of IL-17F for the IL-17R.

Example 11

IL-17A and IL-17F Bind to IL-17RC

A) Binding Inhibition with Cold Ligand

BHK cells transfected with hIL-17RC (SEQ ID NO:2) and IL-17R (SEQ ID NO:21) were plated at 40,000 cells/well in a 24-well dish (Costar 3527) two days prior to assay. IL-17A (SEQ ID NO:14) and IL-17F(SEQ ID NO:16) that had been radiolabeled by the iodobead method were added independently to wells in triplicate at 10 ng/ml with a total of 250 ul/well in binding buffer (RPMI 1640 media (JRH 51502-500M) with 10 mg/ml bovine serum albumin (Gibco15260-037)). Cold competitors were added in 100 fold molar excess. Competitors tested included IL-17A, IL-17B, IL-17C, IL-17D, IL-17E, IL-17F and IL-21. Wells were incubated on ice for 1-hour followed by two washes with PBS (Invitrogen 20012-027) and one wash with a high salt solution (1.5M NaCL, 50 mM HEPES pH 7.4). Wells were extracted with 500 ul of 0.8M NaOH for 30 min. at room temperature and counts per minute were measured in a gamma counter (Packard Cobra II A5005).

The results indicated that 100× molar cold IL-17A and IL-17F were able to reduce binding of 125I IL-17A to BHK hIL-17RC by approximately 7 fold while IL-17B,C,D,E and IL-21 had no effect on binding. 100× molar cold IL-17A reduced the binding of 125I IL-17A to BHK IL-17R by approximately 4 fold while IL-17B,C,D,E,F and IL-21 had no effect on binding. 100× molar cold IL-17A and IL-17F reduced the binding of 125I IL-17F to BHK hIL-17RC by approximately 4 fold and 5 fold, respectively, while IL-17B, C,D,E and IL-21 had no effect on binding.

B) Binding Inhibition with Soluble Receptor:

Binding to hzytor14 (SEQ ID NO:2) and IL-17R (SEQ ID NO:21) transfected BHK cells was performed as in one, but 100 fold molar excess soluble hIL-17RCx1/Fc9 (Example 8) and soluble IL-17R/Fc (obtained from R&D; Ref. 177-IR) were used in place of cold ligand in the competition. Cells were washed, extracted and counted as in part one.

Soluble hIL-17RC/Fc inhibited binding of 125IL-17F to BHK hIL-17RC with an IC50 of 10× molar excess average from three experiments. Soluble hIL-17RC/Fc inhibition of 125I IL-17A on the same cell line gave an average IC50 of 20× molar excess and soluble IL-17R/Fc inhibition of 125I IL-17A gave an average IC50 of 20× molar excess.

C) Binding Saturation

Transfected BHK cells were plated into 24-well dishes as in one. Radiolabeled IL-17A and IL-17F were added starting at a concentration of 4 nM in eight 1:3 dilutions (to a concentration of 1.83 pM) in triplicate with a total of 250 µl/well in binding buffer. Separately, 100 fold molar excess of cold ligand was added at each dilution point. Cells were washed, extracted and counted as in one. Specific counts per minute were plotted against concentration of radiolabeled ligand added by subtracting the 100 fold excess counts from the uncompeted counts at each dilution point. These normalized data were plotted to generate saturation binding curves for each combination of radiolabeled ligand and transfected BHK cells. Table 7 shows the affinity values calculated from all three experiments.

TABLE 7

| 125I IL-17A + BHK hIL-17RC | 125I IL-17A + BHK IL-17R |
|---|---|
| 1. 180 pM | 1. 2.5 +/− 0.2 nM |
| 2. 200 pM | 2. 4.5 +/− 0.3 nM |
| 3. 370 pM | 3. 5.9 +/− 0.1 nM |
| 125I IL-17F + BHK hIL-17RC | 125I IL-17F + BHK IL-17R |
| 1. 50 pM | 1. Very low affinity |
| 2. 60 pM | 2. Very low affinity |
| 3. 80 pM | 3. Very low affinity |

One-site binding curve fits agreed most closely with IL-17A & IL-17F binding to IL-17R. Two-site binding curve fits agreed most closely with IL-17A and IL-17F binding to hIL-17RC. The high affinity binding site is the value shown above. The low affinity binding site had very low affinity and varied widely between the three experiments.

Example 12

Murine Nih3t3 Cells Respond to Human IL-17A and IL-17F

A) Cell Plating and kz142 Adenovirus Reporter Infection.

Nih3t3 cells, derived from mouse fibroblasts (described in ATCC) Nih3t3 were plated at 5000 cells/well in solid white, cell culture coated 96 well plates, (Cat. #3917. Costar) using DMEM/10% FBS, containing glutamine and amended with pyruvate and cultured overnight at 37° C. and 5% $CO_2$. On this second day, the plating media was removed and Kz142 adenovirus particles at a multiplicity of infection of 5000 particles/cell were prepared in DMEM/1% FBS, containing glutamine and amended with pyruvate and cultured overnight at 37° C. and 5% $CO_2$.

B) Luciferase Assay Measuring IL-17A and F Activation of kz142 Adenovirus Reporter Infected nih3t3 Cells.

Following the overnight incubation with the adenovirus particle reporter, human IL-17A and IL-17F Ligand treatments were prepared in serum free media amended to 0.28% BSA. The adenovirus particles and media were removed and the appropriate ligand doses were given in triplicates. Incubation at 37° C. and 5% $CO_2$ was continued for 4 hours, after which the media was removed, cells lysed for 15 minutes and mean fluorescence intensity (MFI) measured using the luciferase assay system and reagents. (Cat. #e1531 Promega. Madison, Wis.) and a Microplate luminometer. Activity was detected at concentrations ranging from 0.1-1000 ng/ml human IL-17A and IL-17F, generating EC50 values of about 50 ng/ml for both ligands. These data suggest that nih3t3 cells carry receptors to these ligands and that IL-17A and IL-17F activate the NF-κB/Ap-1 transcription factor.

Example 13

Murine Nih3t3 Cells Express Both IL-17RA and IL-17RC

RTPCR analysis of nih3t3 RNA demonstrated that these cells are positive for both IL-17 RA and IL-17RC, consistent with their NF-κB/Ap-1 response to human IL-17A and IL-17F mediation being mediated through one or both of these receptors.
RTPCR Details:
A) Murine IL-17RC PCR
First strand cDNA was prepared from total RNA isolated from nih3t3 cells using standard methods. PCR was applied using hot star polymerase and the manufacturer's recommendations (Qiagen, Valencia, Calif.) using sense primer, zc38910, 5' ACGAAGCCCAGGTACCAGAAAGAG 3' (SEQ ID NO:56) and antisense primer, zc 38679, 5' AAAAGCGCCGCAGCCAAGAGTAGG 3' (SEQ ID NO:57) and 35 cycles of amplification. Agarose gel electrophoresis revealed a single, robust amplicon of the expected, 850 bp size.
B) Murine IL-17RA PCR
First strand cDNA was prepared from total RNA isolated from nih3t3 cells using standard methods. PCR was applied using hot star polymerase and the manufacturer's recommendations (Qiagen, Valencia, Calif.) using sense primer, zc38520, 5' CGTAAGCGGTGGCGGTTTTC 3' (SEQ ID NO:58) and antisense primer, zc 38521, 5' TGGGCAGGGCACAGTCACAG 3' (SEQ ID NO:59) and 35 cycles of amplification. Agarose gel electrophoresis revealed a single, robust amplicon of the expected, 498 bp size.

Example 14

Creation of a Stable Nih3t3 Assay Clone Expressing the ap1/nfkb Transcription Factor The murine nih3t3 cell line described above was stably transfected with the kz142 ap1/nfkb reporter construct, containing a neomycin-selectible marker. The Neo resistant transfection pool was plated at clonal density. Clones were isolated using cloning rings and screened by luciferase assay using the human IL-17A ligand as an inducer. Clones with the highest mean fluorescence intensity (MFI) (via Ap-1/NF-κB luciferase) and the lowest background were selected. A stable transfectant cell line was selected and called nih3t3/kz142.8.

Example 15

Inhibition of Activation by Human IL-17A and IL-17F in Murine Nih3t3 Cells Using Soluble IL-17RC and IL-17RA/FC Chimeras Soluble forms of IL-17RC or IL-17RA were used as antagonists of human IL-17A and IL-17F activation of Ap-1/NF-κB elements in a luciferase assay. These soluble receptors are fusion proteins derived from the extracellular domain of each receptor fused to the human IgG1 constant (Fc) region. The soluble human IL-17R FC fusion protein was purchased. (recombinant human IL-17R/FC chimera, catalog number 177-1R-100, R&D Systems, Inc., Minneapolis, Mn.) The soluble human IL-17RC FC chimera (IL-17RCsR/FC9) was constructed as described above. We find that an excess IL-17RCsR/FC9 and human IL17RsR/FC chimera inhibit EC50 levels of both human IL-17A and IL-17F mediation of Ap-1/NF-κB activation of the murine nih3t3/kz142.8 assay cell line.

The IL-17RCsR/FC9 protein showed the greatest potency in antagonizing IL-17F activation and IL17RsR/FC chimera showed the greatest potency in antagonizing IL-17A activation.

Example 16

IL-17F mRNA is Upregulated in a Murine Model of Asthma

IL-17F mRNA levels were measured in a sensitization and airway challenge model in mice. Groups of mice, 8 to 10 wks of age, were sensitized by intraperitoneal injection of 10 ug of recombinant *Dermatophagoides pteronyssinus* allergen 1 (DerP1) (Indoor biotechnologies, Cardiff, UK) in 50% Imject Alum (Pierce) on days 0 and 7. Seven days later, mice were challenged on 3 consecutive days (days 14, 15 and 16) with 20 μg of DerP1 in 50 μl PBS. There were 4 mice representing this group. Negative controls included 5 mice given phosphate buffered saline (PBS) sensitization, followed by PBS challenge. In addition to 3 mice given DerP1 sensitization, followed by PBS challenge. Forty-eight hours following allergen, or control challenge whole lung tissue was harvested and total RNA was isolated.

First strand cDNA was prepared using identical amounts of total RNA from each subject. IL-17F PCR was applied using Qiagen hotstar polymerase (Qiagen, Valencia, Calif.) and the manufacturer's recommendations. The IL-17F PCR utilized 35 cycles of amplification with sense primer, zc46098, 5' ACTTGCCATTCTGAGGGAGGTAGC 3' (SEQ ID NO:60) and antisense primer, 46099, 5' CACAGGTGCAGC-CAACTTTTAGGA 3' (SEQ ID NO:61). In order to establish that the template quality was uniform amongst all subjects, Beta Actin PCR was applied to the same amount of each template used in the IL-17F amplification. B actin PCR included 25 cycles of PCR with sense primer, zc44779, 5' GTGGGCCGCTCTAGGCACCA 3' (SEQ ID NO:62) and antisense primer, zcc44776, 5' CGGTTGGCCTTAGGGT-TCAGGGGGG 3' (SEQ ID NO:63).

All 4 mice from the DerP1 sensitized, DerP1 challenged treatment group (the asthma simulation) showed robust IL-17F amplification. In contrast, weak IL-17F amplification was seen from the negative controls, including 3 of 3 subjects representing the DerP1 sensitized/PBS challenged treatment group and 5 of 5 subjects from the PBS sensitized/PBS challenged treatment group. B actin amplification was at least as robust for the negative controls as for the asthma-simulated subjects, demonstrating that the weak negative control IL-17F amplification was not due to template problems.

Example 17

COS Cell Transfection and Secretion Trap

A) Cos Cell Transfection and Secretion Trap Assays Show that IL-17RCsR/Fc9 and IL-17F is a Receptor/Ligand Pair A secretion trap assay was used to match the human IL-17RC (SEQ ID NO:2) to the human IL-17F (SEQ ID NO:16). The soluble IL-17RCsR/Fc9 fusion protein (Example 8) was used as a binding reagent in a secretion assay. SV40 on containing expression vectors containing cDNA of human IL-17B,C,D,E, and F was transiently transfected into COS cells. The binding of IL-17RCsR/Fc9 to transfected COS cells was carried out using the secretion trap assay described below. Positive binding of IL-17RCsR/Fc9 was only seen to human IL-17F. These results demonstrate the novel finding that human IL-17RC and IL-17F is a receptor/ligand pair.

B) COS Cell Transfections

The COS cell transfection was performed as follows: Mix 3 ul pooled DNA and 5 ul Lipofectamine™ in 92 μl serum free DMEM media (55 mg sodium pyruvate, 146 mg L-glutamine, 5 mg transferrin, 2.5 mg insulin, 1 μg selenium and 5 mg fetuin in 500 ml DMEM), incubate at room temperature for 30 minutes and then add 400 ul serum free DMEM media. Add this 500 ul mixture onto $1.5 \times 10^5$ COS cells/well plated on 12-well tissue culture plate and incubate for 5 hours at 37° C. Add 500 ul 20% FBS DMEM media (100 ml FBS, 55 mg sodium pyruvate and 146 mg L-glutamine in 500 ml DMEM) and incubate overnight.

C) Secretion Trap Assay

The secretion trap assay was performed as follows: Media was rinsed off cells with PBS and then fixed for 15 minutes with 1.8% Formaldehyde in PBS. Cells were then washed with TNT (0.1M Tris-HCL, 0.15M NaCl, and 0.05% Tween-20 in H2O), and permeated with 0.1% Triton-X in PBS for 15 minutes, and again washed with TNT. Cells were blocked for 1 hour with TNB (0.1M Tris-HCL, 0.15M NaCl and 0.5% Blocking Reagent (NEN Renaissance TSA-Direct Kit) in H2O), and washed again with TNT. The cells were incubated for 1 hour with 1 μg/ml human IL-17RCx1 sR/FC9 soluble receptor fusion protein Cells were then washed with TNT. Cells were incubated for another hour with 1:200 diluted goat-anti-human Ig-HRP (Fc specific). Again cells were washed with TNT.

Positive binding was detected with fluorescein tyramide reagent diluted 1:50 in dilution buffer (NEN kit) and incubated for 4-6 minutes, and washed with TNT. Cells were preserved with Vectashield Mounting Media (Vector Labs Burlingame, Calif.) diluted 1:5 in TNT. Cells were visualized using a FITC filter on fluorescent microscope.

Example 18

Generation of Murine Anti-Human IL-17RC Monoclonal Antibodies

A) Immunization for Generation of Anti-IL-17RC Antibodies

1. Soluble IL-17RC-muFc

Six to twelve week old intact or IL-17RC knockout mice are immunized by intraperitoneal injection with 25-50 ug of soluble human IL-17RC-muFc protein (Example 23) mixed 1:1 (v:v) with Ribi adjuvant (Sigma) on a biweekly schedule. Seven to ten days following the third immunization, blood samples were taken via retroorbital bleed, the serum harvested and evaluated for its ability to inhibit the binding of IL-17 or IL-17F to IL-17RC in neutralization assays (e.g., described herein) and to stain IL-17RC transfected versus untransfected 293 cells in a FACS staining assay. Mice continued to be immunized and blood samples taken and evaluated as described above until neutralization titers reached a plateau. At that time, mice with the highest neutralization titers were injected intravascularly with 25-50 μg of soluble IL-17RC-Fc protein in PBS. Three days later, the spleen and lymph nodes from these mice were harvested and used for hybridoma generation, for example using mouse myeloma (P3-X63-Ag8.653.3.12.11) cells or other appropriate cell lines in the art, using standard methods known in the art (see, e.g., Kearney, J. F. et al., *J. Immunol.* 123:1548-50, 1979; and Lane, R. D. *J Immunol Methods* 81:223-8, 1985).

2. Soluble IL-17RC, IL-17RC-CEE, IL-17RC-CHIS, IL-17RC-CFLAG

Six to twelve week old intact or IL-17RC knockout mice are immunized by intraperitoneal injection with 25-50 ug of soluble human IL-17RC-CEE, IL-17RC-CHIS, or IL-17RC-CFLAG mixed 1:1 (v:v) with Ribi adjuvant (Sigma) on a biweekly schedule. Seven to ten days following the third immunization, blood samples are taken via retroorbital bleed, the serum harvested and evaluated for its ability to inhibit the binding of IL-17 or IL-17F to IL-17RC in neutralization assays (e.g., described herein) and to stain IL-17RC transfected versus untransfected 293 cells in a FACS staining assay. Mice are continued to be immunized and blood samples taken and evaluated as described above until neutralization titers reached a plateau. At that time, mice with the highest neutralization titers are injected intravascularly with 25-50 ug of soluble IL-17RC, IL-17RC-CEE, zcytor-CHIS, or IL-17RC-CFLAG antigen protein in PBS. Three days later, the spleen and lymph nodes from these mice are harvested and used for hybridoma generation, for example using mouse myeloma (P3-X63-Ag8.653.3.12.11) cells or other appropriate cell lines in the art, using standard methods known in the art (e.g., see Kearney, J. F. et al., *J. Immunol.* 123:1548-50, 1979; and Lane, R. D. *J Immunol Methods* 81:223-8, 1985).

3. P815 Transfectants that Express the IL-17RC

Six to ten week old female DBA/2 mice are immunized by intraperitoneal injection of $1 \times 10^5$ live, transfected P815 cells, for example P815/IL-17RC cells (e.g., 0.5 ml at a cell density of $2 \times 10^5$ cells/ml). Prior to injection, the cells are maintained in the exponential growth phase. For injection the cells are harvested, washed three times with PBS and then resuspended in PBS to a density of $2 \times 10^5$ cells/ml. In this model, the mice develop an ascites tumor within 2-3 weeks and progress to death by 4-6 weeks unless an immune response to the transfected target antigen has been mounted. At three weeks mice with no apparent abdominal swelling (indicative of ascites) are re-immunized as above at 2-3 week intervals. Seven to ten days following the second immunization, blood samples are taken via retroorbital bleed, the serum harvested and evaluated for its ability to inhibit the binding of IL-17 or IL-17F to IL-17 or IL-17RC in neutralization assays (e.g., described herein) and to stain IL-17RC transfected versus untransfected 293 cells in a FACS staining assay. Mice continue to be immunized and blood samples taken and evaluated as described above until neutralization titers reach a plateau. At that time, the mice with the highest neutralization titers are injected intraperitonealy with $1 \times 10^5$ live, transfected P815 cells. Four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (see, e.g., Kearney, J. F. et al., supra.; and Lane, R. D. supra.).

An alternative to the above immunization scheme with live, transfected P815 cells involves intraperitoneal injection of $1-5 \times 10^6$ irradiated, transfected cells every 2-3 weeks. In this approach, no animals develop and die of ascites. Instead, animals are monitored for a neutralizing immune response to IL-17RC in their serum as outlined above, starting with a bleed after the second immunization. Once neutralization titers have reached a maximal level, the mice with highest titers are given a pre-fusion, intraperitoneal injection of $5 \times 10^6$ irradiated cells and four days later, the spleen and lymph nodes from these mice are harvested and used for hybridoma generation, for example using mouse myeloma (P3-X63-Ag8.653.3.12.11) cells or other appropriate cell lines in the art, using standard methods known in the art (see, e.g., Kearney, J. F. et al., supra.; and Lane, R. D. supra.).

B) Screening the Hybridoma Fusions for Antibodies that Bind IL-17RC and Inhibit the Binding of IL-17 or IL-17F to IL-17RC Three different primary screens are performed on the hybridoma supernatants at 8-10 days post-fusion. For the first assay, antibodies in supernatants were tested for their ability to bind to plate bound soluble human IL-17RC, IL-17RC-muFc, IL-17RC-CEE, IL-17RC-CHIS, or IL-17RC-CFLAG protein by ELISA using HRP-conjugated goat anti-mouse kappa and anti-lambda light chain second step reagents to identify bound mouse antibodies. To demonstrate specificity for the IL-17RC portion of the IL-17RC fusion proteins, positive supernatants in the initial assay were evaluated on an irrelevant protein fused to the same murine Fc region (mG2a), EE sequence, HIS sequence, or FLAG sequence. Antibody in those supernatants that bound to IL-17RC-fusion protein and not the irrelevant muFc or other proteins containing fusion protein sequence were deemed to be specific for IL-17RC. For the second assay, antibodies in all hybridoma supernatants were evaluated by ELISA for their ability to inhibit the binding of biotinylated human IL-17 or biotinylated human IL-17F to plate bound IL-17RC-muFc or IL-17RC-fusion proteins.

All supernatants containing antibodies that bound specifically to IL-17RC, whether they inhibited the binding of IL-17 or IL-17F to IL-17RC or not in the ELISA assay, were subsequently tested for their ability to inhibit the binding of IL-17 or IL-17F to IL-17RC transfected Baf3 or BHK cells or normal human bronchial epithelial cells. All supernatants that were neutralization positive in either the IL-17 or IL-17F inhibition assays or both the IL-17 and IL-17F inhibition assays were subsequently evaluated for their ability to stain IL-17RC transfected versus non-transfected Baf3 or BHK cells by FACS analysis. This analysis was designed to confirm that inhibition of IL-17 or IL-17F binding to IL-17RC, was indeed due to an antibody that specifically binds the IL-17RC receptor. Additionally, since the FACS analysis was performed with an anti-IgG second step reagent, specific FACS positive results indicate that the neutralizing antibody was likely to be of the IgG class. By these means, a master well was identified that bound IL-17RC in the plate bound ELISA, inhibited the binding of IL-17 or IL-17F to IL-17RC in the ELISA based inhibition assay, blocked the interaction of IL-17 and IL-17F with IL-17RC transfected Baf3 or BHK cells, respectively, and was strongly positive for the staining of IL-17RC transfected Baf3 or BHK cells with an anti-mouse IgG second step reagent.

The third assay consists of primary human bronchial epithelial cells which express IL-17RC and can be induced to secrete IL-8 or IL-6 in response to IL-17F treatment. The specific monoclonal antibody is assayed by its ability to inhibit the IL-17 or IL-17F stimulated IL-8 or IL-6 production by these cells. IL-8 and IL-6 production is assayed in response to IL-17 or IL-17F as described herein.

Alternatively, the monoclonal antibody; anti-IL-17RC, mediated inhibition of IL-17 or IL-17F induced luciferase production in NIH 3T3 or other IL-17RC containing cells can be used with or in place of one of the bioactivity neutralization assays noted above. The NF-κB mediated luciferase assay in NIH 3T3 cells is described herein.

C) Cloning Anti-IL-17RC Specific Antibody Producing Hybridomas

Hybridoma cell lines producing a specific anti-IL-17RC mAb that cross-neutralized the binding of IL-17 and IL-17F to appropriately transfected BaF3 or BHK cells are cloned by a standard low-density dilution (less than 1 cell per well) approach. Approximately 5-7 days after plating, the clones are screened by ELISA on, for example, plate bound human IL-17RC-muFc followed by a retest of positive wells by ELISA on irrelevant muFc containing fusion protein as described above. Selected clones, whose supernatants bind to IL-17RC-muFc and not the irrelevant muFc containing fusion protein, are further confirmed for specific antibody activity by repeating both neutralization assays as well as the FACS analysis. All selected IL-17RC antibody positive clones are cloned a minimum of two times to help insure clonality and to assess stability of antibody production. Further rounds of cloning are performed and screened as described until, preferably, at least 95% of the resulting clones were positive for neutralizing anti-IL-17RC antibody production.

D) Biochemical Characterization of the Molecule Recognized by Anti-IL-17RC mAbs

Biochemical confirmation that the target molecule, IL-17RC, recognized by the putative anti-IL-17RC mAbs is indeed IL-17RC are performed by standard immunoprecipitation followed by SDS-PAGE analysis or western blotting procedures, both employing soluble membrane preparations from IL-17RC transfected versus untransfected Baf3 or BHK cells. Moreover, soluble membrane preparations of non-transfected cell lines that express IL-17RC are used show that the mAbs recognize the native receptor chain as well as the transfected one. Alternatively, the mAbs are tested for their ability to specifically immunoprecipitate or western blot the soluble IL-17RC-muFc protein.

Example 19

Neutralization of Human IL-17RC by Sera from Mice Injected with P815 Cells Transfected with Human IL-17RC Using a cell based neutralization assay, serum from mice injected with live human IL-17RC transfected P815 cells (Example 17) is added as a serial dilution at 1%, 0.5%, 0.25%, 0.13%, 0.06%, 0.03%, 0.02%, and 0%. The assay plates are incubated at 37° C., 5% $CO_2$ for 4 days at which time Alamar Blue (Accumed, Chicago, Ill.) is added at 20 μl/well. Plates are again incubated at 37° C., 5% $CO_2$ for 16 hours. Results showed that serum from four of the animals could neutralize signaling of both huIL-17 and huIL-17F through human IL-17RC.

Results such as these provide additional evidence that effectively blocking IL-17RC by binding, blocking, inhibiting, reducing, antagonizing or neutralizing IL-17 or IL-17F activity (individually or together), for example via a neutralizing monoclonal antibody to IL-17RC of the present invention, could be advantageous in reducing the effects of IL-17 and IL-17F (alone or together) in vivo and may reduce IL-17 and/or IL-17F-induced inflammation, such as that seen in, for example in psoriasis, IBD, colitis, chronic obstructive pulmonary disease, cystic fibrosis or other inflammatory diseases induced by IL-17, and or IL-17F including IBD, arthritis, asthma, psoriatic arthritis, colitis, inflammatory skin conditions, and atopic dermatitis.

Example 20

Pharmacokinetics of an Anti-Human IL-17RC Monoclonal Antibody

The test monoclonal antibody, anti-human IL-17RC mAb, is provided in, for example, 3×3 mL aliquots at a concentration of approximately 1 mg/mL (determined by UV Absorbance at 280 nM) and was stored at −80° C. until use. The vehicle is 1×PBS (50 mM $NaPO_4$, 109 mM NaCl), pH 7.3. The mAb is thawed at room temperature before use and aliquots 1 and 2 are used as provided for the 100 μg IV and SC dosing groups, respectively. Half of aliquot 3 is diluted 1:2 in 1×PBS for the 50 μg SC dose group and the second half of aliquot 3 is diluted 1:10 in 1×PBS for the 10 μg SC dose group. Female SCID mice (n=96) are obtained from Charles River Labs. Animals are checked for health on arrival and group-housed (3 animals per cage). The mice are 12 weeks old with an average body weight of approximately 22 g at the beginning of the study.

A) Dosing Protocol

Female SCID mice (n=24/dose group) are randomly placed into four dosing groups (Table 8). Group 1 was administered the anti-human IL-17RC mAb via IV injection of approximately 93 μL in a tail vein and Groups 2, 3, and 4 are administered the mAb via SC injection of approximately 93 μL in the scruff of the neck.

B) Sample Collection

Prior to blood collection, mice were fully anesthetized with halothane or isofluorane. Blood samples were collected via cardiac stick for all time points except the 168 hr timepoint (collected via eye bleed and the same animals were bled again at the 504 hr timepoint via cardiac stick). Blood was collected into serum separator tubes and allowed to clot for 15 minutes. Samples were subsequently centrifuged for 3 minutes at 14,000 rpm. Following centrifugation, aliquots of 125-150 uL were dispensed into labeled eppendorf tubes and immediately stored at −80° C. until analysis.

TABLE 8

| Group # | Dose (ROA) | Animals | PK Timepoints |
|---|---|---|---|
| 1 | 100 μg (IV) | 3 mice/timepoint* | 0.25, 1, 4, 8, 24, 72, 168, 336 and 504 hr |
| 2 | 100 μg (SC) | 3 mice/timepoint* | 0.25, 1, 4, 8, 24, 72, 168, 336 and 504 hr |
| 3 | 50 μg (SC) | 3 mice/timepoint* | 0.25, 1, 4, 8, 24, 72, 168, 336 and 504 hr |
| 4 | 10 μg (SC) | 3 mice/timepoint* | 0.25, 1, 4, 8, 24, 72, 168, 336 and 504 hr |

*The same animals were used for the 168 and 504 hr timepoints.

C) Quantification of Serum Anti-human IL-17RC mAb Concentrations by ELISA

An Enzyme Linked Immunosorbant Assay (ELISA) is developed and qualified to analyze mouse serum samples from animals dosed with anti-IL-17RC mAb during pharmacokinetic studies. This assay is designed to take advantage of a commercially available secondary antibody and colorimetric detection using TMB. The dilutions used for the standard curve were modified to improve the definition of the linear portion of the standard curve. A standard curve in the range of 100 ng/mL to 0.231 ng/mL with 2-fold dilutions allows for quantitation of the mouse serum samples. QC samples are diluted to 1:100, 1:1000 and 1:10000 in 10% SCID mouse serum and back calculated from the standard curve.

D) Pharmacokinetic Analysis

Serum concentration versus time data are downloaded into WinNonlin Professional 4.0 software (Pharsight, Inc.; Cary, N.C.) for pharmacokinetic analysis. Noncompartmental analysis is used to determine pharmacokinetic parameters based on the mean data at each time point.

Example 21

Neutralization of IL-17A and IL-17F Activity by a Anti-Human IL-17RC Monoclonal Antibody Using a cell-based neutralization assay, a purified mouse anti-human IL-17RC monoclonal antibody is added as a serial dilution, for example, at 10 μg/ml, 5 μg/ml, 2.5 μg/ml, 1.25 μg/ml, 625 ng/ml, 313 ng/ml, 156 ng/ml and 78 ng/ml. The assay plates are incubated at 37° C., 5% $CO_2$ for 4 days at which time Alamar Blue (Accumed, Chicago, Ill.) is added at 20 W/well. Plates are again incubated at 37° C., 5% $CO_2$ for 16 hours. This assay is able to demonstrate that the purified anti-human IL-17RC monoclonal antibody is able neutralize signaling of both huIL-17 and huIL-17F through human IL-17RC. For highly effective antibodies, when used at approx. 10 μg/ml concentration, the antibody completely neutralizes proliferation induced by huIL-17 or huIL-17F, with the inhibition of proliferation decreasing in a dose dependent fashion at the lower concentrations. An isotype-matched negative control mouse mAb, tested at the concentrations described above, is expected to provide no inhibition of proliferation of either cytokine. These results are able to further demonstrate that monoclonal antibodies to IL-17RC could indeed antagonize the activity of the pro-inflammatory ligands, IL-17 and IL-17F at low concentrations.

Example 22

IL-17A Induces Elevated Levels of IFN-gamma and TNF-Alpha in Human Peripheral Blood Mononuclear Cells Human peripheral blood mononuclear cells (PBMC) are purified by ficoll density gradient centrifugation and then incubated overnight at 37° C. in media alone, 50 ng/ml anti-human CD3 antibody, or the combination of 50 ng/ml anti-human CD3 antibody plus 1 μg/ml anti-human CD28 antibody. Replicate cultures for each of these conditions are set up and are given no cytokine, 25 ng/ml human IL-17A, or 25 ng/ml human IL-17F. After 24-hour incubations, supernatants from each culture are harvested and assayed for cytokine content using B-D Bioscience's human Th1/Th2 Cytometric Bead Array (CBA). We found that cultures that had been stimulated with either anti-CD3 or anti-CD3 plus anti-CD28 and had been supplemented with IL-17A contained significantly elevated levels of IFN-gamma and TNF-alpha (3-5-fold elevation of each) over cultures with no cytokine added or those that received IL-17F. Cultures in which no anti-CD3 stimulation was added did not show significant changes in cytokine levels. In addition, IL-17A addition induced no significant changes in other cytokines assayed for with the CBA including IL-2, IL-4, IL-5, and IL-10. This data indicates that IL-17A, but not IL-17F, can augment the production of IFN-gamma and TNF-alpha in PBMC cultures stimulated with anti-CD3 or anti-CD3 plus anti-CD28.

Example 23

The Murine Surrogate Molecule, mIL-17RA-Fc Decreases Disease Incidence and Progression in Mouse Collagen Induced Arthritis (CIA) Model A) Mouse Collagen Induced Arthritis (CIA) Model The CIA model of arthritis is an appropriate and well-regarded model to evaluate therapeutic potential of drugs (such as IL-17RC and IL-17RA/RC proteins described herein) to treat human arthritis. In the CIA model, mRNA levels of murine IL-17A and IL-17F were found to be significantly elevated (10-20 fold increases; p<0.001) in the affected popliteal lymph nodes and paws of arthritic mice compared to levels found in lymph nodes and paws of mice without arthritis, further supporting its use as a model for diseases in which IL-17A and IL-17F play a role. The mIL-17RA-Fc protein is an appropriate surrogate to the IL-17RC and IL-17RA/RC proteins described herein, since mIL-17RA-Fc can both and neutralize murine IL-17A and IL-17F, which is a similar feature of human IL-17RC or IL-17RA/RC being able to bind human IL-17A and IL-17F.

Eight to ten-week old male DBA/1 J mice (Jackson Labs; ~25-30 g each) were used for these studies. On day-21, animals were given an intradermal tail injection of 100 uL of 1 mg/ml chick Type II collagen formulated in Complete Freund's Adjuvant (prepared by Chondrex, Redmond, Wash.), and three weeks later on Day 0 mice were given the same injection except prepared in Incomplete Freund's Adjuvant. Animals began to show symptoms of arthritis following the second collagen injection, with most animals developing inflammation within 1-2 weeks. The extent of disease was evaluated in each paw by using a caliper to measure paw thickness, and by assigning a clinical score (0-3) to each paw: 0=Normal, 0.5=Toe(s) inflamed, 1=Mild paw inflammation, 2=Moderate paw inflammation, and 3=Severe paw inflammation as detailed below.

B) Monitoring Disease

Incidence of disease in this model is typically 95-100%, and 0-2 non-responders (determined after 6 weeks of observation) are typically seen in a study using 40 animals. Note that as inflammation begins, a common transient occurrence of variable low-grade paw or toe inflammation can occur. For this reason, an animal is not considered to have established disease until marked, persistent paw swelling has developed.

All animals were observed daily to assess the status of the disease in their paws, which was done by assigning a qualitative clinical score to each of the paws. Every day, each animal had its 4 paws scored according to its state of clinical disease. To determine the clinical score, the paw is thought of as having 3 zones, the toes, the paw itself (manus or pes), and the wrist or ankle joint. The extent and severity of the inflammation relative to these zones was noted including: observation of each toe for swelling; torn nails or redness of toes; notation of any evidence of edema or redness in any of the paws; notation of any loss of fine anatomic demarcation of tendons or bones; evaluation of the wrist or ankle for any edema or redness; and notation if the inflammation extends proximally up the leg. A paw score of 1, 2, or 3 was based first on the overall impression of severity, and second on how many zones are involved. The scale used for clinical scoring is shown below.

C) Clinical Score
  0=Normal
  0.5=One or more toes involved, but only the toes are inflamed
  1=mild inflammation involving the paw (1 zone), and may include a toe or toes
  2=moderate inflammation in the paw and may include some of the toes and/or the wrist/ankle (2 zones)
  3=severe inflammation in the paw, wrist/ankle, and some or all of the toes (3 zones)

Treatments: Established disease was defined as a qualitative score of paw inflammation ranking 1 or more. Once established disease was present, the date was recorded, designated as that animal's first day with "established disease", and treatment started. Mice were treated with PBS, or one of the following doses of mIL-17RA-Fc (diluted in PBS to desired concentration) i.p. every other day for a total of 5 doses: 150 µg; 75 µg; 25 ug; 10 µg.

Blood was collected throughout the experimental period to monitor serum levels of anti-collagen antibodies, as well as serum immunoglobulin and cytokine levels. Animals were euthanized 48 hours following their last ($5^{th}$) treatment, which was ~11 days following disease onset. Blood was collected for serum, and all paws were collected into 10% NBF for histology. Serum was collected and frozen at −80° C. for immunoglobulin and cytokine assays. The average paw scores for groups of mice treated with mIL-17RA-Fc are show below in Table 9.

TABLE 9

Average paw score for groups of mice treated with mIL-17RA-Fc in CIA model.

| Treatment | Day 4 of treatment | Day 10 of treatment |
|---|---|---|
| PBS | 1.59 + 0.15 | 2.13 + 0.20 |
| 10 µg mIL-17RA-Fc | 0.89 + 0.16* | 1.49 + 0.14* |
| 20 µg mIL-17RA-Fc | 0.95 + 0.19* | 1.35 + 0.24* |
| 75 µg mIL-17RA-Fc | 0.86 + 0.13* | 1.18 + 0.12* |
| 150 µg mIL-17RA-Fc | 0.64 + 0.17* | 0.83 + 0.2* |

Note:
day 1 was first day of therapeutic treatments; treatments were administered every other day via i.p. injections. Data are shown as mean + SEM.
*average paw scores significantly different than PBS-treated group ($p < 0.05$)

There was a dose-dependent, significant reduction in clinical score severity of mice treated with mIL-17RA-Fc compared to PBS-treated mice. The mice treated with 10 ug mIL-17RA-Fc had the least amount of significant efficacy (i.e., only significant for 3 out of the 10 treatment days). When analyzed by repeated measures ANOVA, the trend over time was statistically different for mice treated with 10 and 25 ug mIL-17RA-Fc compared to PBS ($p<0.05$); trend over time for mice treated with 75 ug or 150 ug mIL-17RA-Fc was highly significant compared to PBS-treated mice ($p<0.001$). Mice treated with mIL-17RA-Fc also had a dose-dependent reduction in the number of affected paws. For all serum cytokines measured at termination (IL-$\beta$, -6, -10, -12, -15, -17, IP-10, GM-CSF, TNF-$\alpha$, MIP-1$\alpha$, MCP, KC, and RANTES), serum levels were increased in diseased animals compared to non-diseased, pre-bled animals. With mIL-17RA-Fc treatments, serum cytokine levels of IL-1$\beta$, -6, -10, -15, and MIP-1$\alpha$ were reduced compared to PBS-treated mice. The greatest and most significant reductions were seen in 150 µg mIL-17RA-Fc treated animals. There was also a dose-dependent increase in the serum levels of mIL-17RA-Fc, measured at the end of the experiment. Histological analyses demonstrated dose-dependent reductions in joint inflammation and joint destruction, with groups of mice treated with 75 µg mIL-17RA-Fc showing significant reductions at $p<0.01$ and groups treated with 150 µg mIL-17RA-Fc showing the greatest efficacy ($p<0.001$).

All diseased animals showed higher levels of anti-collagen Ab by ELISA in the serum compared to prebled animals. No significant differences were seen between the treatment groups.

In summary, these results indicate that a murine surrogate (e.g., mIL-17RA-Fc) of the human IL-17RC and IL-17RA/RC proteins described herein can reduce inflammation, as well as disease incidence and progression associated with this appropriate model of arthritis, thus indicating efficacy of human IL-17RC and IL-17RA/RC proteins for the treatment of human arthritis.

Example 24

Stable Over-Expression of IL-17RC in the Murine Assay Cell Line, Nih3t3/kz142.8 Expressing the ap1/nfkb Transcription Factor The murine nih3t3/kz142.8 assay cell line was transfected with a human IL-17RCx1 (SEQ ID NO:2) in an expression vector with a methotrexate resistance gene (dihydrofolate reductase, DHFR) This transfection was performed using a commercially available kit and the manufacturer's recommendations. (Mirus, Madison, Wis. Cat. #MIR218) Cells were placed in 1 µM mtx amended growth medium to select for the expression vector containing the human IL-17RCX1 transgene. After selection a human IL-17RCx1 transfection pool was generated, and called nih3t3/kz142.8/hcytor14×1.
A) Luciferase Assay Using the nih3t3/kz142.8 Assay Cell Line Since nih3t3/kz142.8 has a stable kz142 reporter, there is no need for adenovirus infection to add this reporter. Thus the luciferase assay protocol was shorted and done the following way:

1. Cell Plating nih3t3/kz142.8 cells were plated at 5000 cells/well in solid white, cell culture coated 96 well plates, (Cat. #3917. Costar) using DMEM/10% FBS, containing glutamine and amended with pyruvate and cultured overnight at 37° C. and 5% CO2. On this second day, the plating media was removed and exchanged for DMEM/1% FBS, containing glutamine and amended with pyruvate and cultured overnight at 37° C. and 5% $CO_2$.

2. Luciferase Assay Measuring IL-17A and F Activation of the Stable kz142 Reporter Following the overnight incubation in the 1% FBS, DMEM media, human IL-17A, and IL-17F ligand dilutions were made in serum free media, amended with BSA to a 0.28% level. After adding the ligand dilutions, cells were incubated at 37° C. and 5% $CO_2$ for 4 hours, after which the media was removed, cells lysed for 15 minutes and mean fluorescence intensity (MFI) measured using the luciferase assay system and reagents, (Cat. #e1531 Promega. Madison, Wis.) and a Microplate luminometer. Activity was detected for both ligands at concentrations ranging from 0.1-1000 ng/ml. The nih3t3/kz142.8/hcytor14×1 transfection pool showed similar activity for the murine IL-17A ligand as did the parental cell line (Example 14). However, the cytor14×1 transfectant pool showed an elevated responsiveness to human IL-17A and F treatments, even when these ligand concentrations were as low as 20 femptograms. The fact that the mIL-17A signaling is comparable to that in the parental cell line (example 14) suggests that there isn't a general, non-specific problem with human IL-17RC-expressing cells and that the murine IL-17A is probably signaling through the endogenous murine nih3t3 cell IL-17R or IL-17RC receptor. Thus, the fact that human IL-17A and IL-17F cause an elevation of MFI at such low ligand concentrations may indicate a specific hyper-responsiveness of the cells to those ligands, which is mediated through the over-expressed human IL-17RC receptor.

This result has significant clinical and biological ramifications and utility. For example, physiological situations could cause local up-regulation of the IL-17RC receptors which could then make these areas hyper-responsive to IL-17A and IL-17F, resulting in biological activation at much lower ligand concentrations than those suggested without IL-17RC over-expression. Thus, far lower soluble receptor levels may be sufficient to antagonize these hypothetically lower ligand concentrations, than previously thought or recognized by those in the field.

Example 25

Antagonists to IL-17F and IL-17A Activity Decrease Disease Incidence and Progression in an Inflammatory Bowel Disease (IBD) Model This model is designed to show that cultured intestinal tissue from patients with IBD produce higher levels of inflammatory mediators compared to tissue from healthy controls. This enhanced production of inflammatory mediators (including but not limited to IL-1β, IL-4, IL-5, IL-6, IL-8, IL-12, IL-13, IL-15, IL-17 A and F, IL-18, IL-23, TNF-α, IFN-γ, MIP family members, MCP-1, G- and GM-CSF, etc.) contributes to the symptoms and pathology associated with IBDs such as Crohn's disease (CD) and ulcerative colitis (UC) by way of their effect(s) on activating inflammatory pathways and downstream effector cells. These pathways and components then lead to tissue and cell damage/destruction observed in vivo. Therefore, this model can simulate this enhanced inflammatory mediator aspect of IBD. Furthermore, when intestinal tissue from healthy controls or from human intestinal epithelial cell (IEC) lines is cultured in the presence of these inflammatory components, inflammatory pathway signaling can be observed, as well as evidence of tissue and cell damage.

Therapeutics that would be efficacious in human IBD in vivo would work in the above ex vivo or IEC models by inhibiting and/or neutralizing the production and/or presence of inflammatory mediators.

In this model, human intestinal tissue is collected from patients with IBD or from healthy controls undergoing intestinal biopsy, re-sectioning or from post-mortem tissue collection, and processed using a modification of Alexakis et al. (*Gut* 53:85-90; 2004). Under aseptic conditions, samples are gently cleaned with copious amounts of PBS, followed by culturing of minced sections of tissue, in the presence of complete tissue culture media (plus antibiotics to prevent bacterial overgrowth). Samples from the same pool of minced tissue are treated with one of the following: vehicle (PBS); recombinant human (rh) IL-17A; rhIL-17F; or rhIL-17A+ rhIL-17F. In addition, these are treated with or without an antagonist of either IL-17A or IL-17F, alone or in combination (such as a soluble IL-17RC). This experimental protocol is followed for studies with human IEC lines, with the exception that cells are passaged from existing stocks. After varying times in culture (from 1 h to several days), supernatants are collected and analyzed for levels of inflammatory mediators, including those listed above. In samples from patients with IBD or in samples treated with rhIL-17A and/or F, levels of inflammatory cytokines and chemokines are elevated compared to untreated healthy control tissue samples. The addition of antagonists to IL-17F and/or IL-17A activity, such as IL-17RC soluble receptors and antibodies thereto including the anti-human-IL-17RC monoclonal and neutralizing antibodies of the present invention markedly reduces the production of inflammatory mediators, and thus, would expect to be efficacious in human IBD.

Example 26

Antagonists to IL-17F and IL-17A activity Decrease Disease Incidence and Progression in a Multiple Sclerosis (MS) Model Multiple sclerosis (MS) is a complex disease that is thought to be mediated by a number of factors, including the presence of lymphocytic and mononuclear cell inflammatory infiltrates and demyelination throughout the CNS. Microglia are macrophage-like cells that populate the central nervous system (CNS) and become activated upon injury or infection. Microglia have been implicated as playing critical roles in various CNS diseases including MS, and may be used to study mechanism(s) of initiation, progression, and therapy of the disease (Nagai et al. *Neurobiol Dis* 8:1057-1068; 2001; Olson et al. *J Neurosci Methods* 128:33-43; 2003). Immortalized human microglial cell lines and/or established human astroglia cell lines can, therefore, be used to study some of the effects of inflammatory mediators on these cell types and their potential for neutralization. Inflammatory mediators (including but not limited to IL-β, IL-6, IL-8, IL-12, IL-13, IL-15, IL-17 A and F, IL-18, IL-23, TNF-α, IFN-γ, MIP family members, RANTES, IP-10, MCP-1, G- and GM-CSF, etc.) can contribute to the symptoms and pathology associated with MS by way of their effect(s) on activating inflammatory pathways and downstream effector cells.

In order to evaluate the pro-inflammatory actions of IL-17A and IL-17F, and the ability of an antagonist to IL-17F and/or IL-17A activity, such as IL-17RC soluble receptors and antibodies thereto including the anti-human-IL-17RC monoclonal and neutralizing antibodies of the present invention to neutralize or decrease these effects, cultured glial cells are treated with one of the following: vehicle; rhIL-17A; rhIL-17F; rhIL-17A+IL-17F. In addition, these are treated with or without an antagonist of either IL-17A or IL-17F, alone or in combination (such as a soluble IL-17RC). After varying times in culture (from 1 h to several days), supernatants and cells are collected and analyzed for levels and/or expression of inflammatory mediators, including those listed above. Levels of inflammatory cytokines and chemokines are elevated in the presence of rhIL-17A and/or IL-17F compared to cultures treated with vehicle alone. The addition of antagonists to IL-17F and/or IL-17A activity, such as IL-17RC soluble receptors and antibodies thereto including the anti-human-IL-17RC monoclonal and neutralizing antibodies of the present invention markedly reduces the production and expression of inflammatory mediators, and thus, would expect to be efficacious in inflammatory aspects associated with human MS.

Example 27

Antagonists to IL-17F and IL-17A activity Decrease Disease Incidence and Progression in a Rheumatoid Arthritis (RA) and Osteoarthritis (OA) Model This model is designed to show that human synovial cultures (including synovial macrophages, synovial fibroblasts, and articular chondrocytes) and explants from patients with RA and OA produce higher levels of inflammatory mediators compared to cultures/explants from healthy controls. This enhanced production of inflammatory mediators (including but not limited to oncostatin M, IL-1β, IL-6, IL-8, IL-12, IL-15, IL-17A and F, IL-18, IL-23, TNF-α, IFN-γ, IP-10, RANTES, RANKL, MIP family members, MCP-1, G- and GM-CSF, nitric oxide, etc.) contributes to the symptoms and pathology associated with RA and OA by way of their effect(s) on activating inflammatory pathways and downstream effector cells. These pathways and components then lead to inflammatory infiltrates, cartilage and matrix loss/destruction, bone loss, and upregulation of prostaglandins and cyclooxygenases. Therefore, this model can simulate the destructive inflammatory aspects of RA and OA in in vitro and ex vivo experiments. Furthermore, when explants and synovial cultures from healthy controls are cultured in the presence of several of these inflammatory components (e.g. oncostatin M, TNF-α, IL-1β, IL-6, IL-17A and F, IL-15, etc.), inflammatory pathway signaling can be observed. Therapeutics that would be efficacious in human RA in vivo would work in the above in vitro and ex vivo models by inhibiting and/or neutralizing the production and/or presence of inflammatory mediators.

In this model, human synovial explants are collected from patients with RA, OA, or from healthy controls undergoing joint replacement or from post-mortem tissue collection, and processed using a modification of Wooley and Tetlow (*Arthritis Res* 2: 65-70, 2000) and van 't Hof et al (*Rheumatology* 39:1004-1008, 2000). Cultures of synovial fibroblasts, synovial macrophages and articular chondrocytes are also studied. Replicate samples are treated with one of the following: vehicle (PBS); recombinant human (rh) IL-17A; rhIL-17F; or rhIL-17A+rhIL-17F, and some samples contain various combinations of oncostatin M, TNF-α, IL-1β, IL-6, IL-17A, IL-17F, and IL-15. In addition, these are treated with or without an antagonist to IL-17F and/or IL-17A activity, such as IL-17RC soluble receptors and antibodies thereto including the anti-human-IL-17RC monoclonal and neutralizing antibodies of the present invention. After varying time of culture (from 1 h to several days), supernatants are collected and analyzed for levels of inflammatory mediators, including those listed above. In samples from patients with RA or OA, or in samples treated with rhIL-17A and/or F (either alone or in combination with other inflammatory cytokines), levels of inflammatory cytokines and chemokines are elevated compared to untreated healthy control explants or in untreated cell cultures. The addition of antagonists to IL-17F and/or IL-17A activity, such as IL-17RC soluble receptors and antibodies thereto including the anti-human-IL-17RC monoclonal and neutralizing antibodies of the present invention markedly reduces the production of inflammatory mediators, and thus, would expect to be efficacious in human RA and OA.

Example 28

IL-17A and IL-17F Functional Responses

NIH-3T3/KZ142 cells were stably transfected with human IL-17RCx1 (SEQ ID NO:1) and mouse IL-17RCx1 (SEQ ID NO:25). As described above, each line was treated for 7 and 15 minutes with a dose response of IL-17A, IL-17F, murine IL-17F, and appropriate controls. Both IL-17A and IL-17F gave a dose dependent response in phosphorylated IκB-α and p38 MAPK transcription factors when IL-17RCx1 (SEQ ID NO:1) was transfected, approximately 30% greater then the inherent signaling from the control line. IL-17A and IL-17F gave no increase in signaling when the murine IL-17RCx1 (SEQ ID NO:25) was transfected. Murine IL-17F gave no increase in signaling for either human or murine IL-17RCx1.

Example 29

IL-17A, IL-17F, IL-17RA and IL-17RC Expression in Murine Disease Models

Four murine models of disease (asthma, DSS colitis, atopic dermatitis and experimental allergic encephalomyelitis) were analyzed using know techniques for the expression of IL-17A, IL-17F, IL-17R and IL-17RC.

In the asthma model, IL-17A and IL-17F are expressed at very low to undetectable levels in lung, spleen, lung draining lymph nodes and lung infiltrating cells in diseased and non-diseased mice. IL-17RC message was found to be more highly expressed in lung compared to spleen and lymph node but was not regulated with disease. IL-17R was more highly expressed in spleen and lung draining lymph node compared to lung but was also not regulated with disease.

Contrary to the asthma model, IL-17A and IL-17F were highly up-regulated in diseased but not normal mice in the DSS-colitis model in both proximal and distal colon. Neither cytokine was significantly up-regulated in the mesenteric lymph node. Further, it was found that up-regulation of both cytokines in the context of acute DSS-induced colitis and not in chronic DSS-induced colitis. IL-17R was found to be prominently expressed in mesenteric lymph nodes as compared to proximal and distal colon, but was not regulated with disease. In contrast, IL-17RC was more highly expressed in proximal distal colon tissue compared to mesenteric lymph nodes. IL-17RC expression was also not regulated with disease.

In atopic dermatitis, IL-17A mRNA was not detectable. IL-17F was found to be expressed in both skin and skin-draining lymph nodes but did not appear to be significantly regulated with disease. IL-17R mRNA was more highly expressed in skin-draining lymph nodes as compared to skin but was not regulated with disease. IL-17RC was more highly expressed in skin compared to skin-draining lymph nodes but was also not regulated with disease.

In experimental allergic encephalomyelitis, both IL-17A and IL-17F appeared to up-regulated in spinal chord in diseased but not healthy mice. IL-17F may have been more highly expressed in lymph nodes compared to spinal cord but expression in the lymph nodes was not regulated with disease. However, overall levels of expression in these tissues was quite low. IL-17R was more highly expressed in lymph node tissue compared to brain and spinal cord. IL-17RC was not tested.

In short, IL-17A and IL-17F expression appears to be regulated with disease in the context of the DSS-induced colitis and experimental allergic encephalomyelitis models but apparently not for asthma or atopic dermatitis. IL-17R and IL-17RC expression does not appear to be regulated with disease but IL-17R expression appears to be enriched in lymphoid tissues while IL-17RC expression appears to be enriched in non-lymphoid tissues.

Example 30

IL-17RC is a Mediator of Activation to Both IL-17A and IL-17F

The murine nih3t3/kz142.8 assay cell line was transfected with a human IL-17RCX1 (SEQ ID NO:2) in an expression vector with a methotrexate resistance gene. (dihydrofolate reductase, DHFR) Human IL-17RA (SEQ ID NO:21) was similarly tranfected into this cell line. Transfections were performed using a commercially available kit and the manufacturer's recommendations. (Mirus, Madison, Wis. Cat. #MIR218) Cells were placed in 1 µM mtx amended growth medium to select for the expression vector containing the expression constructs. After selection transfection pools were generated, and called nih3t3/kz142.8/hcytor14×1 and nih3t3/kz142.8/IL-17R.
A) Luciferase Assay Using the nih3t3/kz142.8-Based Cell Lines.
Since nih3t3/kz142.8 based cell lines have stable ap1/nfkb reporters (kz142), there is no need for adenovirus infection to add this reporter. Thus the luciferase assay protocol was shorted and done the following way:

1. Cell Plating
Cells were plated at 5000 cells/well in solid white, cell culture coated 96 well plates, (Cat. #3917. Costar) using DMEM/10% FBS, containing glutamine and amended with pyruvate and cultured overnight at 37° C. and 5% $CO_2$. On this second day, the plating media was removed and exchanged for DMEM/1% FBS, containing glutamine and amended with pyruvate and cultured overnight at 37° C. and 5% $CO_2$.
2. Luciferase Assay Measuring IL-17A and F Activation of the Stable kz142 Reporter
Following the overnight incubation in the 1% fbs, DMEM media, human IL-17A, and IL-17F ligand dilutions were made in serum free media, amended with BSA to a 0.28% level. After adding the ligand dilutions, cells were incubated at 37° C. and 5% $CO_2$ for 4 hours, after which the media was removed, cells lysed for 15 minutes and mean fluorescence intensity (MFI) measured using the luciferase assay system and reagents, (Cat. #e1531 Promega. Madison, Wis.) and a Microplate luminometer. Activity was detected for both ligands at concentrations ranging from 0.1-100 ng/ml.

The EC50s discussed below are averages of at least 4 experiments. The nih3t3/kz142.8/hcytor14×1 transfection pool showed similar activity for the murine IL-17A ligand as did the parental cell line, with an EC50 of about 4 ng/ml (Example 14). The fact that the mIL-17A signaling in the hcytor14×1 recombinant line is comparable to that in the parental cell line (example 14) suggests that murine IL-17A is probably signaling through the endogenous murine nih3t3 cell IL-17RA or IL-17RC receptors and does not activate the cells through hcytor14×1. However, the hIL-17RCX1 transfectant pool showed an elevated responsiveness to human IL-17A treatment, with an EC50 of 0.41 ng/ml Vs 2.8 ng/ml (averages of 4 experiments) in the parental line (a 6.8 fold more potent EC50 in the recombinant line) In addition, the hIL-17RCX1 recombinant line had an enhanced responsiveness to hIL-17F, with an EC50 of 0.61 ng/ml in the recombinant line Vs 10 ng/ml in the parental line (a 17-fold more potent EC50 in the recombinant line). The increased potency to hIL-17A and F in the hIL-17RCX1 line is consistent with human IL-17RCX1 being a high affinity receptor for both human IL-17A and IL-17F. In contrast, the hIL-17RA recombinant line had enhanced sensitivity only to hIL-17A, with an EC50 of 0.6 ng/ml vs 2.8 ng/ml for the parental line. There was not an enhancement of the hIL-17F EC50 in the hIL-17RA recombinant line, with an IL-17F EC50 of 12.4 ng/ml vs 8.9 ng/ml in the parental line.

This result is significant because it specifically implicates hIL-17RCX1 as a mediator of activation to both hIL-17A and hIL-17F and suggests that hIL-17RA mediates signaling only to hIL-17A activation and not hIL-17F.

Example 31

Intravenous Administration of IL-17A and IL-17F

To determine the effect of i.v. delivery of murine or human IL-17A or IL-17F on complete blood counts (CBC) and serum cytokines/chemokines in BALB/c mice at various time points.

I.V. administration of 1 µg mIL-17A resulted in an approximate 2-fold increase in circulating neutrophils (by CBC) and approximate 10-fold increase in serum KC and MCP-1 (by Luminex) 1-2 h following administration; similar results in these chemokines were observed with 5 ug hIL-17A. Blood monocyte levels were also significantly increased in mice treated with 1 µg mIL-17A (showed the greatest increase), 5

μg hIL-17A or 5 μg hIL-17F at the 2 h timepoint. I.V. administration of m and hIL-17F resulted in marked increases in serum IL-15 (by Luminex) at the 1 and 2 h time points, and small increases in serum KC and MCP-1 at these same timepoints.

Example 32

Neutralization of Intravenous Administration IL-17A and IL-17F

To neutralize the i.v. IL-17A and IL-17F-mediated increases in cytokines and chemokines with i.p. soluble receptors (mIL-17RA:Fc for murine ligands; soluble human IL-17RC for human ligands), female BALB/c mice were administered by i.p. injection either PBS, 100 μg mIL-17RA-Fc, or 100 μg soluble human IL-17RC three hours prior to receiving by i.v. tail injection: PBS; 2 μg of either mIL-17A, mIL-17F, or 2 μg of both mIL-17A and mIL-17F (for mice that received mIL-17RA-Fc); or 2 μg of either hIL-17A, hIL-17F, or 2 μg of both hIL-17A and hIL-17F (for mice that received soluble human IL-17RC). Serum was collected 1 h following ligand administration and analyzed for a small number of serum cytokines and chemokines.

Mice pretreated with i.p. murine soluble receptor had significant reductions (~2-2.2 fold lower; p<0.05) in murine IL-17A-mediated increases in serum concentrations of IL-17A and KC(CXCL1) compared to mice treated with PBS+murine IL-17A. Mice pretreated with i.p. human IL-17RC-Fc had significant reductions (~2-fold lower; p<0.05) in human IL-17F-mediated increases in serum concentrations of IL-15; had significant reductions (~30% lower; p<0.05) in IL-17A-mediated increases in KC; had significant reductions (~25% lower; p<0.05) in human IL-17A+IL-17F-mediated increases in KC; and had significant reductions (~2-fold; p<0.05) in either human IL-17F or IL-17A+IL-17F mediated increases in IL-15.

Example 33

Plate Based Protein binding Assays of the Soluble IL-17RC and IL-17RC/IL-17RA Polypeptides The format of the Capture EIA is as follows: Coat the ELISA plate with Goat anti Human IgG at 1 μg/ml and incubate overnight at 4° C. Wash and block the plate with 200 μl per well 1% BSA for 1 hour at room temperature. Wash, add the soluble receptor variants (A1586F, A1587F) or IL17RCx1 (A1034F) dilution series (100 μg/ml through 0.10 μg/ml) to the plate and incubate for 1 hour at room temperature. Wash, add biotin labeled ligand @ 10:1 (IL17A) or 6:1 (IL17F) and incubate for 1 hour at room temperature. Wash, add Strept Avidin—Horse Radish Peroxidase @ 0.5 μg/mL and incubate for 1 hour at room temperature. Wash, add TMB substrate for 4 minutes. Stop the reaction by adding Stop Solution. (Note: All reagents volumes were 50 μl per well unless stated otherwise). A positive result would be high OD values, generally above 0.5. The results indicated that construct 1342 (SEQ ID NO:74) does not bind IL-17A and weakly binds IL-17F in this assay. Construct 1341 (SEQ ID NO:72) binds both IL-17A and IL-17F very strongly. IL-17RCx1 binds IL-17A and IL-17F.

The format of the Neutralization EIA is as follows: Coat the ELISA plate with soluble receptor (A1034F) at 1 μg/ml and incubate overnight at 4° C. Wash and block the plate with 200 μl per well 1% BSA for 1 hour at room temperature. While blocking, in a separate plate incubate the soluble receptor variants (A1586F, A1587F) dilution series (50 μg/ml through 0.05 μg/ml) with biotin labeled ligand @ 10:1 (IL17A) or 6:1 (IL17F) in equal volumes for 1 hour at room temperature. Wash the blocked plate, add the receptor-ligand complex to the blocked plate and incubate for 1 hour at room temperature. Wash, add Strept Avidin—Horse Radish Peroxidase @ 0.5 μg/mL and incubate for 1 hour at room temperature. Wash, add TMB substrate for 7 minutes. Stop the reaction by adding Stop Solution. (Note: All reagents volumes were 50 μl per well unless stated otherwise). A positive result would be low OD values, generally below 0.5. The results indicated that construct 1342 (SEQ ID NO:74) weakly neutralizes binding of IL17A to IL17RCx1 and strongly neutralizes binding of IL17F to IL17RCx1. Construct 1341 (SEQ ID NO:72) weakly neutralizes binding of IL17A to IL17RCx1 and weakly neutralizes binding of IL17F to IL17RCx1. Neutralization indicates that the variant protein is binding the biotinylated ligand.

Example 34

FACS Binding Assay Protocol

To assess the ability of the soluble IL-17RC and IL-17RC/IL-17RA polypeptides of the present invention to bind the ligands IL-17A and IL-17F, a Flow Cytometry-based competitive binding assay was utilized. Incubation of a BHK cell line stably transfected with full length IL17RCx4 in the presence of the ligands IL17A or IL17F, and the soluble receptor targeted to bind the ligands allows for detection and relative quantification of ligand bound to the cell surface (and therefore unbound by the soluble receptor). The biotinylation of the ligand allows for FACS detection using a secondary Streptavidin conjugated fluorophore. A reduction in cell bound ligand over a titration of the soluble receptor is recorded as a reduction in the mean fluorescence of the cells. Biotinylated ligands are individually pre-mixed at 1 ug/ml with titrating amounts of soluble receptor in staining media (HBSS+1% BSA+0.1% NaAzide+10 mM HEPES) in 100 ul volumes and incubated at RT for 15 minutes. A BHK cell line stably transfected with full length IL17RCx4 is prepared for ligand staining by resuspension with Versene (Invitrogen cat. 15040-066), equilibrating to 2×10e5 cells/100 ul, pelleting, and resuspension in the ligand/soluble receptor pre-mix. Stained cells are incubated at 4° for 30 minutes, washed 1× in staining media, and stained with Streptavidin-PE (BD Pharmingen cat. 554061) at a 1:100 ratio. Cells are incubated at 4° in the dark for 30 minutes, washed 2× in staining media, and re-suspended in a 1:1 ratio of staining media and Cytofix (BD Bioscience 554655). The BD LSRII Flow Cytometer or similar instrument is used for data collection and analysis. FIG. 5 depicts a standard graph. The graph was generated using the Prizm software program. The Y values represent the MFI normalized to maximum and minimum (100% and 0%) based on ligand only and no ligand/no soluble receptor control wells, and thus the percent binding of the ligand to the cells. The software calculates the IC50 for each curve.

Example 35

Inhibition of Specific Binding of Biotinylated Human IL-17A and IL17F with a Soluble IL-17RC/IL-17RA Polypeptide The binding assay used to determine the ability of the soluble IL-17RC and IL-17RC/IL-17RA polypeptides to bind IL-17A and IL17F is described herein. Binding studies are performed as discussed above, except that additional soluble polypeptides, such as SEQ ID NOs: 157 and 158 was included in the binding reaction. This soluble polypeptide inhibited binding of both human IL-17A and IL-17F to IL-17RC transfected BHK cells to the same extent as soluble human IL-17RCx1 Fc fusion protein (SEQ ID NO:64). The remainder of soluble polypeptides, including the soluble polypeptide of SEQ ID Nos: 157 and 158, are included in Table 10 below.

TABLE 10*

| Soluble Polypeptide | Variant | IC50-IL17A | Soluble Polypeptide | Variant | IC50-IL17F |
|---|---|---|---|---|---|
| IL17RA/RC | 1407 | 7 | IL17RC | 1390 | 9 |
| IL17RA/RC | 1407 | 9 | IL17RA/RC | 1454 | 18 |
| IL17RA/RC | 1454 | 4 | IL17RA/RC | 1454 | 31 |
| IL17RA/RC | 1454 | 17 | IL17RA/RC | 1454 | 95 |
| IL17RA/RC | 1454 | 20 | IL17RA/RC | 1407 | 33 |
| IL17RC | 1390 | 12 | IL17RA/RC | 1407 | 42 |
| IL17RA/RC | 1341 | 30 | IL17RC | 1210 | 31 |
| IL17RC | 1210 | 35 | IL17RC | 1210 | 61 |
| IL17RC | 1210 | 47 | IL17RC | 1210 | 67 |
| IL17RC | 1210 | 74 | IL17RA/RC | 1341 | 47 |
| IL17RC | 1459 | 126 | IL17RC | 1459 | 103 |
| IL17RC | 1342 | 217 | IL17RC | 1342 | 313 |

*Cell-based Competition Binding IC50 (ng/uL); ordering of Constructs from strongest binders to weakest based on IC50's for each ligand Example 36

Binding Affinity of the IL-17RC and IL-17RC/IL-17RA Soluble Polypeptides to IL-17A and IL-17F IL-17RCx1, IL-17RA and the soluble IL-17RC/IL-17RA soluble polypeptide (SEQ ID Nos: 157 and 158) were tested for binding affinity to both IL-17A and IL-17F as follows: Gt-anti-Hu IgG-Fc specific Antibody (Jackson #109-005-008) was diluted to 50 ug/ml in pH 5.0 Na Acetate and immobilized onto a CM5 Biacore chip. The protocol was optimized to capture receptor at a theoretical binding max. before injecting a concentration series of each ligand to observe association and dissociation. The soluble receptors and the IL-17RC/IL-17RA polypeptide were tested for binding of a concentration series of each ligand. The surface was regenerated with 2×30 sec. injections of pH 1.75 glycine between cycles. Data was evaluated using Biacore Evaluation software to define kinetic values and is shown in Table 11 below.

TABLE 11*

| ka (l/Ms) | kd (l/s) | KD (M) | Rmax (RU) | Chi$^2$ (RU$^2$) |
|---|---|---|---|---|
| Human IL17RCx1 Affinity for Human IL-17A May 2005 | | | | |
| 1.05E+06 | 4.90E−04 | 4.69E−10 | 9.02 | 0.424 |
| 1.24E+06 | 4.38E−04 | 3.52E−10 | 8.86 | 0.324 |
| Human IL17RCx1 Affinity for Human IL-17F May 2005 | | | | |
| 9.91E+05 | 4.31E−04 | 4.35E−10 | 7.22 | 0.378 |
| 1.11E+06 | 3.84E−04 | 3.46E−10 | 7.57 | 0.549 |
| Soluble IL-17RC/IL-17RA Polypeptide for Human IL-17A April 2006 | | | | |
| 1.42E+06 | 6.22E−05 | 4.39E−11 | 20.5 | 0.460 |
| 2.61E+06 | 9.95E−05 | 3.82E−11 | 18.3 | 0.888 |
| Soluble IL-17RC/IL-17RA Polypeptide for Human IL-17F April 2006 | | | | |
| 1.82E+06 | 2.61E−04 | 1.43E−10 | 10.2 | 0.495 |
| 2.49E+06 | 3.15E−04 | 1.26E−10 | 11.2 | 0.544 |
| Human IL-17RA Affinity for Human IL-17A June 2006 | | | | |
| 3.70E+05 | 8.65E−05 | 2.34E−10 | 29.5 | 0.249 |
| 2.89E+05 | 8.57E−05 | 2.96E−10 | 35.1 | 0.197 |
| Human IL-17RA Affinity for Human IL-17F July 2006 | | | | |
| 2.09E+04 | 5.56E−04 | 2.66E−08 | 20.3 | 0.071 |
| 2.55E+04 | 4.40E−04 | 1.72E−08 | 9.9 | 0.076 |

*Equilibrium and rate constants are shown and values fall within machine limits.
Chi2 refers to the sum of the square of the residuals between the binding curves and the evaluation fitting curves. The closer to 0, the more confidence we have in the data. This data is shown with good confidence.

These data demonstrates the binding of human IL-17A and human IL-17F to human IL-17RA and human IL-17RC. Specifically, human IL-17RC demonstrates similar binding affinity for both human IL-17A and human IL-17F with dissociation equilibrium constants (KD) in the 400 picomolar (pM) range. The soluble IL-17RC/IL-17RA polypeptide bound human IL-17A with slightly higher affinity, KD~40 pM, than human IL-17F, KD~140 pM. Human IL-17RA produced the largest discrepancy of ligand affinity with a 100-fold difference between human IL-17A, KD~300 pM, and human IL-17F, KD~30 nanomolar (nM), binding.

Example 37

Creation of Recombinant Human IL-17RA/NIH3T3/KZ142.8 and IL-17RCx4/NIH3T3/KZ142.8 Reporter Assay Cell Lines The murine NIH3T3/KZ142.8 reporter cell line described herein was used to create new assay cell lines, recombinant for either human IL-17RA (SEQ ID NO:21) or IL-17RCx4 (SEQ ID NO:166). This was accomplished by transfection of these cells with expression constructions containing each of these cDNAs. The expression vector utilized, pzmp11, which contains the dihydrofolate reductase gene. Thus transfectants were selected using 1 uM methotrexate amended growth medium to create stable pools. These assay cell lines were called hIL-17RA/NIH3T3/KZ142.8 and hIL-17RCX4/NIH3T3/KZ142.8.

Example 38

A Soluble IL-17RC/IL-17RA Polypeptide Antagonizes Human IL-17A Activation of Recombinant Human IL-17RA/NIH3T3/KZ142.8 Cells The efficacy of soluble IL-17RC/IL-17RA soluble polypeptide (SEQ ID Nos: 157 and 158) competition for human IL-17A activation of recombinant hIL-17RA/NIH3T3/KZ142.8 cells was measured as follows: Cell plating and preparation for a luciferase assay was the same as that described herein. The day of the assay, these cells were first given a triplicate 2 fold dose series of one volume of soluble receptors at 2 fold the final concentration including the soluble polypeptide above, IL-17RA and IL-17RC beginning at a 2 μg/ml, (which results in a 1 ug/ml final concentration once combined with the ligand). Next one volume of IL-17A was applied at 1 ng/ml, which is 2 fold the final concentration of 0.5 ng/ml which results from the receptor-ligands mixing together. The maximum activation was determined using a triplicate set which received 0.5 ng/ml of IL-17A without receptor. The basal activation was determined using a triplicate set which received only assay medium which contained neither ligand nor soluble receptor. Data analysis revealed IC50 for IL-17A activation of the above cell line by the soluble polypeptide was 1 ng/ml. There wasn't sufficient potency of soluble IL-17RA or IL-17RC to convincingly antagonize 0.5 ng/ml hIL-17A activation of this cell line with even the highest dose of 1 µg/ml soluble receptor.

Example 39

A Soluble IL-17RC/IL-17RA Polypeptide Antagonizes Human IL-17F Activation of Recombinant Human IL-17RA/NIH3T3/KZ142.8 Cells The efficacy of the soluble IL-17RC/IL-17RA polypeptide (SEQ ID Nos: 157 and 158) competition for human IL-17F activation of recombinant hIL-17RA/NIH3T3/KZ142.8 cells (described above) was measured as follows: Cell plating and preparation for a luciferase assay was the same as that described herein. The day of the assay, these cells were first given a triplicate 2 fold dose series of one volume of soluble polypeptide at 2 fold the final concentration including the soluble polypeptide above, IL-17RA and IL-17RC beginning at a 4 ug/ml, (which results in a 2 ug/ml final concentration once combined with the ligand). Next one volume of IL-17F was applied at 40 ng/ml, which is 2 fold the final concentration of 20 ng/ml which results from the receptor-ligands mixing together. The maximum activation was determined using a triplicate set which received 20 ng/ml of IL-17F without receptor. The basal activation was determined using a triplicate set which received only assay medium which contained neither ligand nor soluble receptor. Data analysis revealed IC50 for IL-17F activation of the above cell line by the IL-17RC/IL-17RA soluble polypeptide of 0.48 ug/ml. There wasn't sufficient potency of soluble IL-17RA or IL-17RC to show any antagonism of 20 ng/ml IL-17F activation of this cell line with even the highest dose of 2 ug/ml soluble receptor.

Example 40

A Soluble IL-17RC/IL-17RA Polypeptide Antagonizes Human IL-17F Activation of Recombinant Human IL-17RCx4/NIH3T3/KZ142.8 cells The efficacy of soluble IL-17RC/IL-17RA polypeptide (SEQ ID Nos: 157 and 158) competition for IL-17F activation of recombinant hIL-17RCX4/NIH3T3/KZ142.8 cells (described above) was measured as follows: Cell plating and preparation for a luciferase assay was the same as that described herein. The day of the assay, these cells were first given triplicate 5 fold serial doses of one volume of soluble receptors at 2 fold the final concentration including the above soluble polypeptide, IL-17RA and IL-17RC beginning at a 4 ug/ml. Next one volume of IL-17F lot A1275F was applied at 2 ng/ml, which is 2 fold the final concentration of 1 ng/ml which results from the receptor-ligands mixing together. The maximum activation was determined using a triplicate set which received 1 ng/ml of IL-17F without receptor. The basal activation was determined using a triplicate set which received only assay medium which contained neither ligand nor soluble receptor. Data analysis revealed IC50 for IL-17F activation of the soluble IL-17RC/IL-17RA polypeptide of 0.8 ug/ml, IL-17RC was bug/ml, and IL-17RA had no antagonism at any dose.

Example 41

Soluble IL-17RC/IL-17RA Polypeptide Neutralizes the Activity of Both Human IL-17A and IL-17F Induction of G-CSF, IL-6 and IL-8

Human small airway epithelial cells (SAEC) were treated with human IL-17A or with human IL-17F and 48 hr supernatants were collected. These supernatants were assayed and showed a dose-dependent induction of G-CSF, IL-6, and IL-8, as shown in Table 12 below:

TABLE 12

| SAEC treated with: | | Fold Induction in 48 hr supernatants | | |
|---|---|---|---|---|
| | | G-CSF | IL-6 | IL-8 |
| huIL-17A | 50 ng/ml | 26 | 13 | 8 |
| | 10 ng/ml | 24 | 14 | 6 |
| | 2 ng/ml | 14 | 8 | 3 |
| | 0.4 ng/ml | 13 | 8 | 3 |
| huIL-17F | 250 ng/ml | 15 | 11 | 4 |
| | 50 ng/ml | 10 | 8 | 3 |
| | 10 ng/ml | 8 | 8 | 2 |
| | 2 ng/ml | 4 | 5 | 2 |

SAEC were also treated with 0.01-10 ug/ml doses of soluble IL-17RC/IL-17RA polypeptide (SEQ ID Nos: 157 and 158) in combination with 10 ng/ml human IL-17A or 50 ng/ml human IL-17F (both ligand and soluble polypeptide were incubated together for 30 minutes at 37° C. before adding to cells), and 48 hr supernatants collected. As shown in Table 13 below, these supernatants showed decreased G-CSF, IL-6, and IL-8, demonstrating that the soluble IL-17RC/IL-17RA polypeptide was able to effectively neutralize the activity of both human IL-17A and human IL-17F induction of these cytokines. It is noted that IC50 values were not able to be determined for the neutralization of IL-6, because at the lowest dose (0.01 µg/ml) of the soluble IL-17RC/IL-17RA polypeptide tested, neutralization had only returned to approximately 50% of max.).

TABLE 13

| Soluble IL-17RA/RC receptor neutralizes activity of huIL-17A/F: | IC50 of IL-17RA/RC (ug/ml) |
|---|---|
| huIL-17A(10 ng/ml) induction of G-CSF | 0.14 |
| huIL-17F(50 ng/ml) induction of G-CSF | 1.20 |
| huIL-17A(10 ng/ml) induction of IL-8 | 0.03 |
| huIL-17F(50 ng/ml) induction of IL-8 | 0.57 |
| huIL-17A(10 ng/ml) induction of IL-6 | 94% neutralized at 10 ug/ml |
| | 49% neutralized at 0.01 ug/ml |
| huIL-17F(50 ng/ml) induction of IL-6 | 72% neutralized at 10 ug/ml |
| | 57% neutralized at 0.01 ug/ml |

Example 42

Efficacy of the Soluble IL-17RC and IL-17RC/IL-17RA Polypeptides in Human Multiple Sclerosis Samples Multiple sclerosis (MS) is a complex disease that is thought to be mediated by a number of factors, including the presence of lymphocytic and mononuclear cell inflammatory infiltrates and demyelination throughout the CNS. Microglia are macrophage-like cells that populate the central nervous system (CNS) and become activated upon injury or infection. Microglia and neuronal cells have both been implicated as playing critical roles in various CNS diseases including MS, and may be used to study mechanism(s) of initiation, progression, and therapy of the disease (Nagai et al., *Neurobiol Dis* 8:1057-1068; 2001; Olson et al., *J Neurosci Methods* 128:33-43; 2003; Giuliani et al., *J Neuroimmunol* 165: 83-91; 2005). Primary neuronal cell cultures, immortalized human microglial cell lines and/or established human astroglia cell lines can, therefore, be used to study some of the effects of inflammatory mediators on these cell types and their potential for neutralization. Inflammatory mediators (including but not limited to IL-1β, IL-6, IL-8, IL-12, IL-13, IL-15, IL-17 A and F, IL-18, IL-23, TNF-α, IFN-γ, MIP family members, RANTES, IP-10, MCP-1, G- and GM-CSF, etc.) can contribute to the symptoms and pathology associated with MS by way of their effect(s) on activating inflammatory pathways and downstream effector cells.

In order to evaluate the pro-inflammatory actions of IL-17A and IL-17F on these cells types, and the ability of the soluble polypeptides of the present invention, such as the soluble IL-17RC/IL-17RA polypeptide (SEQ ID NO:158) to neutralize or decrease these effects, cultured neuronal or glial cells are treated with one of the following: vehicle; rhIL-17A; rhIL-17F; rhIL-17A+IL-17F. In addition, these are treated with or without a soluble polypeptide of the present invention, such as the soluble IL-17RC/IL-17RA polypeptide (SEQ ID NO:158). In a separate set of cultures, circulating T cells isolated from human subjects and activated with anti-CD3, are added to the cultured neuronal and glial cells in the absence of exogenous IL-17A or IL17-F, thus providing a co-culture method of investigating the destructive effects of activated T cells on these cell types. The T cells are treated with or without a soluble polypeptide of the present invention, such as the soluble IL-17RC/IL-17RA polypeptide (SEQ ID NO:158). After varying times in culture (from 1 h to several days), supernatants and cells are collected and analyzed for levels and/or expression of inflammatory mediators, including those listed above, and also analyzed for cell survival. Levels of inflammatory cytokines and chemokines, and death of neuronal cells, are elevated in the presence of rhIL-17A and/or IL-17F compared to cultures treated with vehicle alone. The addition of a soluble polypeptide of the present invention, such as the soluble IL-17RC/IL-17RA polypeptide (SEQ ID NO:158) markedly reduces the production and expression of inflammatory mediators in these cultures, and increases cell survival in the neuronal cells.

Therefore, because these ex vivo experiments demonstrate that a soluble polypeptide of the present invention, such as the soluble IL-17RC/IL-17RA polypeptide (SEQ ID NO:158) can reduce the destructive and inflammatory actions that are associated with the pathobiology of human MS, treatment with such soluble polypeptides would be expected to be efficacious in reducing the inflammatory aspects, neuronal death, and/or demyelination associated with human MS.

Example 43

Efficacy of the Soluble IL-17RC and IL-17RC/IL-17RA Polypeptides in Human Rheumatoid Arthritis ("RA") and Osteoartritis ("OA") Samples These models are designed to show that human synovial cultures (including synovial macrophages, synovial fibroblasts, and articular chondrocytes) and explants from patients with RA and OA produce higher levels of inflammatory mediators compared to cultures/explants from healthy controls, which in turn can contribute to the degradation of extracellular matrix components (e.g. bone, cartilage, etc), which is a hallmark of these diseases. In addition, the co-culture models described below are designed to show that inflammatory mediators present in RA/OA synovial fluid and/or activated T cells can also result in greater inflammation and matrix degradation.

The enhanced production of inflammatory mediators (including but not limited to oncostatin M, IL-1β, IL-6, IL-8, IL-12, IL-15, IL-17 A and F, IL-18, IL-23, TNF-α, IFN-γ, IP-10, RANTES, RANKL, MIP family members, MCP-1, MMP-9, G- and GM-CSF, nitric oxide, etc.) contributes to the symptoms and pathology associated with RA and OA by way of their effect(s) on activating inflammatory pathways and downstream effector cells. These pathways and components then lead to inflammatory infiltrates, cartilage and matrix loss/destruction, bone loss, and upregulation of matrix metalloproteases, prostaglandins and cyclooxygenases. Therefore, these models can simulate the destructive inflammatory aspects of RA and OA in in vitro and ex vivo experiments. Furthermore, when explants and synovial cultures from healthy controls are cultured in the presence of exogenously added inflammatory components (e.g. oncostatin M, TNF-α, IL-1β, IL-6, IL-17A and F, IL-15, etc.), or alternatively, in the presence of synovial fluid from RA patients (which would contain inflammatory components endogenously), inflammatory and degradative pathway signaling can be observed. Therapeutics that would be efficacious in human RA in vivo would work in the above in vitro and ex vivo models by inhibiting and/or neutralizing the production and/or presence of inflammatory mediators.

In these models, human synovial explants are collected from patients with RA, OA, or from healthy controls undergoing joint replacement or from post-mortem tissue collection, and processed using a modification of Wooley and Tetlow (*Arthritis Res* 2: 65-70; 2000) and van 't H of et al (*Rheumatology* 39:1004-1008; 2000). Cultures of synovial fibroblasts, synovial macrophages and articular chondrocytes are also studied. Replicate samples are treated with one of the following: vehicle (PBS); recombinant human (rh) IL-17A; rhIL-17F; or rhIL-17A+rhIL-17F, and some samples contain various combinations of oncostatin M, TNF-α, IL-1β, IL-6, IL-17A, IL-17F, and IL-15. A separate set of samples are treated with activated human T cells, or synovial fluid from healthy controls or patients with RA or OA. In addition, all of these samples are treated with or without a soluble polypeptide of the present invention, such as a soluble IL-17RC polypeptide or a soluble IL-17RC/IL-17RA polypeptide (SEQ ID NO:158). After varying time of culture (from 1 h to several days), supernatants and cells are collected and analyzed for levels of inflammatory mediators and cartilage/bone/matrix biomarkers, including those listed above. In samples from patients with RA or OA, or in samples treated with RA/OA synovial fluid, activated T cells, rhIL-17A and/or rhIL-17F (either alone or in combination with other inflammatory cytokines), levels of inflammatory cytokines and chemokines and cartilage/bone/matrix degradative markers are elevated compared to untreated healthy control explants or in untreated cell cultures. The addition of a soluble polypeptide of the present invention markedly reduces the production of inflammatory and cartilage/bone/matrix degradative mediators, and thus, would expect to be efficacious in human RA and OA.

Example 44

Efficacy of the Soluble IL-17RC and IL-17RC/IL-17RA Polypeptides in Human Inflammatory Bowel Disease ("IBD") Samples Via Mucosal Biopsy Cultures This model is designed to show that cultured intestinal tissue from patients with IBD produce higher levels of inflammatory mediators compared to tissue from healthy controls. This enhanced production of inflammatory mediators (including but not limited to IL-1β, IL-4, IL-5, IL-6, IL-8, IL-12, IL-13, IL-15, IL-17 A and F, IL-18, IL-23, TNF-α, IFN-γ, MIP family members, MCP-1, G- and GM-CSF, etc.) contributes to the symptoms and pathology associated with IBD such as Crohn's disease (CD) and ulcerative colitis (UC) by way of their effect(s) on activating inflammatory pathways and downstream effector cells. These pathways and components then lead to tissue and cell damage/destruction observed in vivo. Therefore, this model can simulate this enhanced inflammatory mediator aspect of IBD. Furthermore, when intestinal tissue from healthy controls or from human intestinal epithelial cell (IEC) lines is cultured in the presence of these inflammatory components, inflammatory pathway signaling can be observed, as well as evidence of tissue and cell damage.

Therapeutics that would be efficacious in human IBD in vivo would work in the above ex vivo or IEC models by inhibiting and/or neutralizing the production and/or presence of inflammatory mediators.

In this model, human intestinal tissue is collected from patients with IBD or from healthy controls undergoing intestinal biopsy, re-sectioning or from post-mortem tissue collection, and processed using a modification of Alexakis et al. (*Gut* 53:85-90, 2004). Under aseptic conditions, samples are gently cleaned with copious amounts of PBS, followed by culturing of minced sections of tissue, in the presence of complete tissue culture media (plus antibiotics to prevent bacterial overgrowth). Samples from the same pool of minced tissue are treated with one of the following: vehicle (PBS); recombinant human (rh) IL-17A; rhIL-17F; or rhIL-17A+ rhIL-17F. In addition, these are treated with or without a soluble polypeptide of the present invention, such as a soluble IL-17RC polypeptide or a soluble IL-17RC/IL-17RA polypeptide (SEQ ID NO:158). This experimental protocol is followed for studies with human IEC lines, with the exception that cells are passaged from existing stocks. After varying times in culture (from 1 h to several days), supernatants are collected and analyzed for levels of inflammatory mediators, including those listed above. In samples from patients with IBD or in samples treated with rhIL-17A and/or F, levels of inflammatory cytokines and chemokines are elevated compared to untreated healthy control tissue samples. The addition of a soluble polypeptide of the present invention markedly reduces the production of inflammatory mediators, and thus, would expect to be efficacious in human IBD.

An additional arm of this study can include comparisons of the production of inflammatory mediators from tissue biopsies of IBD patients undergoing effective treatment, and those either not currently taking medications or considered non-responders to treatment.

Example 45

Efficacy of the Soluble IL-17RC and IL-17RC/IL-17RA Polypeptides in Human IBD Samples via Epithelial Barrier Function Maintenance of epithelial barrier integrity is a critical factor in the preservation of a healthy gastrointestinal tract. Experimental evidence suggests that leakiness of the epithelial barrier in the gut may contribute to the development of IBD. Immune cells located in the intestinal lamina propria generally interact with intestinal epithelial cells via cell to cell contact or production of soluble factors to maintain immune surveillance and contribute to epithelial barrier integrity. However, prolonged or dysregulated immune-mediated inflammation may contribute to defects in epithelial barrier cell integrity and function. The following study is designed to measure the direct effect(s) of T cell-derived IL-17A and/or IL-17F on epithelial barrier integrity.

In this example, intestinal epithelial cell lines, like Caco-2 cells, are differentiated on semipermeable membranes and co-cultured on the basolateral side with either T cells or monocytes derived from biopsies from IBD patients or normal individuals. Epithlelial monolayer integrity is monitored over time using assessment of transepithelial electrical resistance or resistance of the monolayer to dye diffusion. Decreases in transepithial resistance of monolayers in co-cultures would suggest a disruption in the monolayer induced by the activity of the T cells or monocytes in the co-culture. Inhibitors of IL-17A and IL-17F such as the soluble polypeptides of the present invention, such as a soluble IL-17RC polypeptide or a soluble IL-17RC/IL-17RA polypeptide (SEQ ID NO:158) could be used to determine the relative contribution of IL-17A and IL-17F to the disruption of the epithelial monolayer and test whether inhibitors of IL-17A and IL-17F would be effective in maintaining epithelial barrier integrity. Prevention of epithelial monolayer disruption induced by activated T cells by such molecules would suggest that the soluble IL-17RC and IL-17RC/IL-17RA polypeptides of the present invention may be effective for the therapeutic treatment of IBD in humans.

Co-culture systems could also be generated using monolayers formed by primary epithelium from IBD patients to determine whether these cells are more sensitive to IL-17A and IL-17F compared to epithelial cells derived from healthy individuals. If so, these data would suggest that inhibiting IL-17A and IL-17F would be a suitable strategy for the therapeutic treatment of IBD.

Example 46

Effects of IL-17A and IL-17F on Lamina PropPria T cells and Monocytes/Macrophages from Normal and Human IBD Samples Dysregulated or sustained immune-mediated inflammation may contribute to the symptoms and pathology associated with IBD by way of tissue damage or permanent skewing to inappropriate or prolonged immune responses. This model can determine the potential down-stream consequences of exposure of disease-associated T cells and monocytes to IL-17A and IL-17F which may be present in the immediate environmental cytokine mileu of the intestinal tissue.

Therapeutics that would be efficacious in human IBD in vivo would work in the above ex vivo models by inhibiting and/or neutralizing the production and/or presence of inflammatory mediators (including but not limited to IL-1β, IL-4, IL-5, IL-6, IL-8, IL-12, IL-13, IL-15, IL-17 A and F, IL-18, IL-23, TNF-α, IFN-γ, MIP family members, MCP-1, G- and GM-CSF, etc.).

In this model, T cells and monocytes/macrophages are isolated from biopsy samples by carefully mincing biopsies with scissors in HBSS, treating with collagense and Dispase II and incubating for 1 hr at 37° C. in a shaker. The cell suspension is filtered through nylon mesh to remove debris and cell clumps and washed multiple times in HBSS. T cells and macrophage/monocytes can be isolated using direct cell sorting or bead-depletion/enrichment protocols. Isolated cells are incubated in the presence of IL-17A and IL-17F. This induces the production of inflammatory mediators by T cells and monocytes/macrophages or results in skewing subsequent T cell responses to highly pro-inflammatory responses. Comparisons between the types of inflammatory mediators produced by cells from IBD patients and those from cells of normal individuals can be made and might suggest that T cells and monocyte/macrophages from IBD patients produce a more pro-inflammatory profile in the presence of IL-17A and IL-17F. The addition of a soluble polypeptide of the present invention, such as a soluble IL-17RC polypeptide or a soluble IL-17RC/IL-17RA polypeptide (SEQ ID NO:158) to neutralize the production of downstream inflammatory mediators induced by IL-17A and IL-17F suggests that such soluble IL-17RC and IL-17RC/IL-17RA polypeptides may be efficacious in the therapeutic treatment of patients with IBD.

Example 47

Efficacy of the Soluble IL-17RC and IL-17RC/IL-17RA Polypeptides in Irritable Bowel Syndrome ("IBS"): CNS-Directed Pathogenesis A model focusing on primary CNS-directed pathogenesis of IBS which employs stress stimuli to induce symptoms characteristic of IBS. The neonatal psychosocial stress model mimics some clinical features associated with IBS patients including visceral hyperalgesia, diarrhea and stress-sensitivity. Daily separation of the litter from their mothers for 180 minutes each day during postnatal days 4-18 will result in an alteration of maternal behaviour and significantly reduce times of the licking/grooming behaviour. The stress on the neonates results in permanent changes in the CNS resulting in altered stress-induced visceral and somatic pain sensitivity. Colonic motor function in response to stress is enhanced in these animals and preliminary data shows evidence of increased intestinal permeability (Mayer et al., 2002). Treatment with a soluble polypeptide of the present invention, such as a soluble IL-17RC polypeptide or a soluble IL-17RC/IL-17RA polypeptide (SEQ ID NO:158) and subsequent analysis of colonic motor function, epithelial permeability and response to stress stimuli could determine efficacy in this animal model of IBS. Decreases in the incidence of symptoms following treatment with these inhibitors would suggest potential efficacy in the treatment of IBS.

Example 48

Efficacy of the Soluble IL-17RC and IL-17RC/IL-17RA Polypeptides in Irritable Bowel Syndrome ("IBS"): Primary Gut-Directed Inducers of Stress This is a model focusing on primary gut-directed inducers of stress (ie. gut inflammation, infection or physical stress). Animal studies have indicated that low-grade inflammation or immune activation may be a basis for altered motility, and/or afferent and epithelial function of the gut (Mayer et al., 2002). In this model, daily colon irritation is produced in neonatal animals (days 8-21) in the form of daily intracolonic injection of mustard oil. Mustard oil is a neural stimulant and has been shown to induce visceral hyperalgesia following intracolonic administration. This model mimics key features of the IBS including visceral hypersensitivity and alteration in bowel habits. Animals also present with diarrhea or constipation, a key feature of IBS patients (Mayer et al., 2002; Kimball et al., 2005). A soluble polypeptide of the present invention, such as a soluble IL-17RC polypeptide or a soluble IL-17RC/IL-17RA polypeptide (SEQ ID NO:158) could be delivered to determine changes in the development of symptoms associated with this model. Decreases in the incidence or magnitude of visceral hypersensitivity and altered gut motility following therapeutic treatment with our inhibitors would suggest a potential for these molecules to be efficacious in the treatment of IBS.

Example 49

Designing a Scalable Protein Production Process for a Soluble IL-17A and IL-17F Antagonist In designing strategies focused on developing a scaleable protein production process for a soluble form of IL-17RC, many difficulties were encountered with identifying an expression system that allowed high level protein concentrations in the conditioned media. Western blot analysis demonstrated low levels of protein secretion with protein accumulating in the cell. In the discovery of the soluble polypeptides of the present invention, more than seventy different expression constructs were designed, generated, and tested for expression in either BHK cells, CHO cells, or HEK 293 cells. Several were tested in more than one host cell lines. Variations of tested soluble IL-17RC expression cassette included:
1) Alternative signal sequences such as: a) native; b) otPA; c) mouse immunoglobulin heavy chain variable region; d) human growth hormone; e) mouse IL17RA.
2) Two different naturally occurring splice variants (IL-17RCx1, SEQ ID NO:2; and IL-17RCx4, SEQ ID NO:166).
3) Addition of linker sequences between the IL-17RC extracellular domain (ECD) and the Fc portion, such as: a) no linker; b) a 9 amino acid linker based on GlyGlyGlySer; and c) a 20 amino acid linker based on GlyGlyGlySer.
4) His tagged monomeric forms.
5) Both amino- and carboxyl-terminal Fc fusion proteins.
6) Removal of N-linked carbohydrate attachment sites.
7) Gln for Asn amino acid substitutions.
8) Hybrid fusion proteins between IL17RA and IL17RC All of the soluble IL-17RC variant expression constructs were tested for protein expression by transient transfection in HEK 293 cells. Western blot analysis was used to detect protein secreted into the conditioned medium compared to protein retained in the cell by sampling cell lysates. Most of the constructs expressed protein secreted into the conditioned medium that was barely detectable by Western Blot. Additionally, the signal was greater from the cell lysate sample in comparison to the conditioned media sample indicating an inability for the protein to be efficiently secreted. Those expression constructs that resulted in the highest signals in the conditioned media were used to transfect stable CHO cell pools. Protein titers were measured from the stable CHO pools and where possible, purified protein was analyzed for IL-17A and IL-17F binding in a cell based competition binding assay. The following table shows protein expression results from the highest expressing constructs in CHO cell stable pools. Where absolute protein concentration measurements were below the level of detection, the protein titer is indicated as <0.5 mg/mL.

IL-17RC and IL-17RC/RA protein expression constructs number designation, brief description of exons included, protein titer from stably transfected CHO cell pools, and IL17A and IL17F binding ability. Not all the sequences of the variants included in Table 14 were included herewith.

TABLE 14

| Description | Protein Titer (mg/L) | Binding |
|---|---|---|
| x1 splice variant IL17RC exons 1-6, exons 8-16 (Variant 1210) | 3.0 | Ability to Block IL17A and IL17F |
| X4 splice variant IL17RC exons 1-16 | <0.5 | Unable to obtain enough sample |
| IL17RC exons 1-6 | <0.5 | Inactive |
| IL17RC exons 8-13 | 1.6 | Inactive |
| IL17RC exons 7-16 (Variant S10) | <0.5 | Ability to Block IL17A and IL17F |
| IL17RA exons 1-10 IL17RC exons 8-16 (Variant 1407) | 32.5 | Ability to Block IL17A and IL17F |
| IL17RA exons 1-6 IL17RC exons 8-16 IL17RA exons 7-10 | <0.5 | Inactive |
| IL17RA exons 1-3 IL17RC exons 4-16 | <0.5 | Unable to obtain enough sample |
| IL17RA exons 1 IL17RC exons 2-16 | <0.5 | Unable to obtain enough sample |
| IL17RA exons 1-6 IL17RC exons 8-16 (Variant 1454) | 19 | Ability to Block IL17A and IL17F |

Example 50

Determination of Amino Terminal Sequence of IL-17RA/RC-Fc5

Protein Expression: An expression construct containing DNA encoding IL17RA/RC-Fc5 (SEQ ID NO:157, encoding the amino acid sequence of SEQ ID NO:158) was used to transfect CHO DXB-11 cells. IL17RA/RC-Fc5 protein was purified from conditioned media harvests by Protein A affinity chromatography followed by size exclusion chromatography.

N-terminal Amino Acid Sequence Analysis: Standard automated N-terminal polypeptide sequencing (Edman degradation) was performed using reagents from Applied Biosystems. N-terminal sequence analysis was performed on a Model 494 Protein Sequencer System (Applied Biosystems, Inc., Foster City, Calif.). Data analysis was performed with SequencePro Protein Sequencing Analysis Software, version 2.0 (Applied Biosystems). Sample preparation included loading 100 picomoles (pmol) of the sample onto a precycled filter.

N-terminal sequence analysis of the IL-17RA/RC-Fc5 samples (lots A1672F, A1774F, and A1776F) yielded a sequence starting at L33 (Leucine).

Example 51

Treatment of Oxazalone Colitis with the Murine Surrogate Molecule, Soluble Murine IL-17RA-Fc The following oxazalone colitis studies were performed in female C57BL/10 mice (~20 g). Mice are sensitized with cutaneous oxazolone (3% in 100% ethanol) on day −5, followed by intra-rectal challenge with 1.25% oxazolone in 50% ethanol on day 0. Mice develop acute colitis over the next 2-3 days. They are typically euthanized and tissues harvested on day 2.

Two independent oxazalone colitis studies were performed to determine if soluble murine (m) IL-17RA-Fc treatment can show efficacy in a murine oxazolone-induced colitis that resembles human ulcerative colitis. The mIL-17RA-Fc protein is an appropriate surrogate to the IL-17RC and IL-17RA/RC proteins described herein, since mIL-17RA-Fc can both and neutralize murine IL-17A and IL-17F, which is a similar feature of human IL-17RC and IL-17RA/RC being able to bind human IL-17A and IL-17F.

Results from the first study indicated that treatment with mIL-17RA-Fc resulted in a significant ($p<0.05$), ~2-fold reduction in disease index score (includes weight loss, stool consistency and blood in stool) versus oxazalone-mice treated with PBS. Treatments were administered daily as 100 µg, i.p. from either day −6 or day −1 of the oxazalone colitis model to day 1. The group of mice treated with mIL-17RA-Fc also had fewer improved histology scores and less severe colitis-induced colon shortening compared to oxazalone colitis mice treated with PBS.

In the second study, mice were treated daily with PBS or mIL-17RA-Fc (100 µg, i.p.) from day −6 to day 1 of the model, and included appropriate oxazalone-vehicle controls (ethanol only). In addition, groups of mice were included that were allowed to recover from colitis for 7 days following the challenge, to evaluate whether mIL-17RA-Fc may affect this phase of the model. Results indicated that there was a significant ~3-fold reduction ($p<0.05$) in disease index score with soluble murine IL-17RA-Fc1 treatment administered daily from day −6 to day 1 of the model. The incidence of noticeable lesions at day 2 was reduced in oxazalone mice (37.5% of mice) treated with mIL-17RA-Fc1 compared to oxazalone PBS-treated mice (75% of mice). In addition, there were improvements in histology scores and less severe ($p<0.05$) colitis-induced colon shortening in mice treated with mIL-17RA-Fc compared to oxazalone colitis mice treated with PBS. There were no differences in the 7-day recovery groups, as all mice had recovered by this time point. In colon cultures (colon piece incubated for 24 h at 37 degrees C.) obtained from oxazalone mice at Day 2 of the model, all inflammatory cytokines/chemokines evaluated were elevated compared to vehicle (ethanol) mice. Treatment with mIL-17RA-Fc in oxazalone mice resulted in lower colonic production of IL-17A, IL-17F, TNF-α, IL-1β, IL-4, IL-12, GM-CSF, and IFN-γ compared to levels in PBS-treated oxazolone mice. Concentrations of colonic IL-17A and IL-17F were significantly correlated with each other ($R=0.93$; $p<0.000001$). Concentrations of IL-17A and IL-17F were significantly correlated with levels of TNF-α ($R=0.91$ and 0.95; $p<0.0000001$), IL-1β ($R=0.64$ for both; $p<0.01$); IFN-γ ($R=0.71$ and 0.72; $p<0.01$), and IL-6 ($R=0.57$ for both; $p<0.05$). Disease index scores were correlated with colonic production of IL-17A ($R=0.70$; $p<0.01$), IL-17F ($R=0.72$; $p<0.01$), TNF-α ($R=0.76$; $p<0.001$), IL-4 ($R=0.59$; $p<0.05$); IL-1β ($R=0.50$; $p<0.05$); and IFN-γ ($R=0.52$; $p<0.05$)

In summary, treatment with a surrogate (e.g., mIL-17RA-Fc) to human IL-17RC and IL-17RA/RC proteins described herein reduces colitis disease symptoms, reduces colonic production of inflammatory cytokines, and improves pathology. These results indicate that the use of human IL-17-RC or IL-17RA/RC proteins as described herein is efficacious in the treatment of human IBD.

Example 52

Effect of Mouse IL-17F Overexpression in Murine Models of Disease

Transgenic mice overexpressing IL-17F gene under the control of a hematopoietic cell-specific promoter (the EuLck promoter) were produced using methods as substantially described herein (see *Production of Transgenic Mice*, Section (K), supra).

Ratio of serum IL-17A to IL-17F in IL-17F transgenic mice is similar to humans: Mice that overexpressed murine IL-17F on the EuLck promoter were found to have markedly elevated serum levels of IL-17F (approximately 2 ng/mL) compared to levels found in wild-type mice (levels non-detectable), as measured by an in-house developed Luminex-based assay. Serum levels of IL-17A were approximately 10-fold lower than IL-17F levels in the IL-17F transgenic mice (~0.2 ng/mL). Thus, the ratio of IL-17A:F in the transgenic mice was ~1:10. In wildtype mice, there was only detectable serum IL-17A (~0.1 ng/mL). This observation of markedly higher (e.g., 10-fold) IL-17F serum levels than IL-17A levels is what is typically observed in humans with autoimmune diseases, thus supporting the use of IL-17F transgenic mice to study the role of IL-17F in mouse models of human disease, such as multiple sclerosis and arthritis.

Experimental allergic encephalomyelitis (EAE) studies: Two independent studies were performed to evaluate the effect of IL-17F overexpression in a mouse model of human multiple sclerosis, specifically murine experimental allergic encephalomyelitis (EAE). Female C57BL/6 wild-type littermate control mice or EuLck IL-17F transgenic mice on the C57BL/6 background (~20-22 g each) were immunized with MOG35-55/Ribi (Study 1) or MOG35-55/CFA (Study 2) adjuvant on day 0, followed by i.v. pertussis toxin on day 2. Mice were weighed and scored daily for clinical symptoms of disease (e.g., tail and limb paralysis). Results from both studies indicated that IL-17F transgenic mice had a significant ($p<0.05$) increase in disease onset and severity compared to wild-type mice. In Study #1, transgenic mice had an earlier peak of disease that averaged a 36% higher disease severity score than wild-type mice. In Study #2, the IL-17F transgenic mice had disease severity scores that were 50-70% higher than wild-type littermate control mice.

Collagen induced arthritis (CIA) studies: Two independent studies were performed to evaluate the effect of IL-17F overexpression in a mouse model of human rheumatoid arthritis, specifically murine collagen induced arthritis (CIA). Male C57BL/6 wild-type littermate control mice or EuLck IL-17F transgenic mice on the C57BL/6 background (~23-28 g each) were immunized, via tail injections, with chick Type II collagen in CFA, followed by chick Type II collagen in IFA three weeks later. Mice were scored daily for clinical symptoms (i.e., paw swelling) of disease. Results from both studies indicated that IL-17F transgenic mice had a significant ($p<0.05$) increase (~2.5-3-fold) in disease onset and severity compared to wild-type littermate control mice.

Example 53

Pharmacokinetics of Murine IL-17RA-Fc, Human IL-17RC-Fc, and Human IL-17RA/RC-Fc Three independent pharmacokinetic studies were performed with various soluble IL-17 receptors, including the murine surrogate (mIL-17RA-Fc) to the human soluble IL-17RC and IL-17RA/RC receptors. For these studies, female C57BL/6 mice were obtained from Charles River Labs. Animals were checked for health on arrival and group-housed (5 animals per cage). The mice were 10-12 weeks old with an average body weight of approximately 20 g at the beginning of the study.

A) Dosing Protocol

For each of the three studies, mice (n=24/dose group) were randomly placed into a designated group for a specified route of administration: intravenous (i.v.), intraperitoneal (i.p.) or subcutaneous (s.c.; at scruff of neck). Each group of mice was administered the appropriate protein via the assigned route of administration in a volume of 100 µL.

B) Sample Collection

Prior to blood collection at various time points (from 0.25 to 336 hours), mice were fully anesthetized with halothane or isofluorane. Blood samples were collected via cardiac stick for all time points. Blood was collected into serum separator tubes and allowed to clot for 15 minutes. Samples were subsequently centrifuged for 3 minutes at 14,000 rpm. Following centrifugation, aliquots of 125-150 uL were dispensed into labeled eppendorf tubes and immediately stored at −80° C. until analysis.

C) Results

Murine IL-17RA-Fc pharmacokinetic study: Half-life for i.v. administration was 61 h; 70 h for i.p. administration; and 69 h for s.c. dosing. I.P. dosing was 100% bioavailable; s.c. was 67%. The volume of distribution was 6.7, 8.7, and 10.3 mL for i.v., i.p. and s.c. routes, respectively. The longest time point for data collection was 120 h post-dosing; serum levels of mIL-17RA-Fc1 had not returned to basal levels by this time. Subsequent pharmacokinetic studies (summarized below) were carried out to 336 h.

Human IL-17RC-Fc pharmacokinetic study: Half-life for i.v. administration was 72 h; 64 h for i.p. administration; and 54 h for s.c. dosing. I.P. and s.c. dosing were 100% bioavailable. The volume of distribution was 2.7, 2.4, and 2.2 mL for i.v., i.p. and s.c. routes, respectively.

Human IL-17RA/RC-Fc (variant 1454) pharmacokinetic study: Half-life for i.v. administration was 46 h; 49 h for i.p. administration; and 52 h for s.c. dosing. I.P. dosing was 100% bioavailable; s.c. was 69%. The volume of distribution was 1.7, 2.2, and 3.5 mL for i.v., i.p. and s.c. routes, respectively.

Example 54

Therapeutic Efficacy of the Murine Surrogate Molecule, mIL-17RA-Fc, in the Treatment of Graft Verus Host Disease (GVHD)

Graft-vs-host disease (GVHD) is a complication that is observed after stem cell or bone marrow transplant, or following transfusions of blood or blood components, most commonly in immunocompromised patients. Although most common following allogeneic transplant, GVHD also occurs with lower frequency following syngeneic and autologous transplant. GVHD can occur in immunocompetent patients who receive blood from a donor who is homozygous for an HLA haplotype for which the patient is heterozygous. The condition results from the engraftment of immunocompetent donor lymphocytes contained in the transplant, which become activated and proliferate in response to host antigens. These infection-fighting cells then attack tissues in the host's body. GVHD is traditionally categorized as acute when it occurs within the first 100 days after transplantation and chronic if it occurs more than 100 days after transplantation. Tissues typically involved include the liver, gastrointestinal tract, and skin; significant inflammation can occur.

The incidence of GVHD increases with increasing degree of mismatch between donor and recipient HLA antigens, increasing donor age, and increasing patient age. Estimates of occurrence range from 20% to 70%, depending on these and other parameters. However, the disease may be underdiagnosed and underreported.

Symptoms of acute GVHD include rash, yellow skin and eyes due to elevated concentrations of bilirubin, and diarrhea. Acute GVHD is graded on a scale of 1 to 4; grade 4 is the most severe. Chronic GVHD may develop de novo or by progression from acute GVHD. Symptoms vary more widely than those of acute GVHD and are similar to various autoimmune disorders. Some symptoms include dry eyes, dry mouth, rash, ulcers of the skin and mouth, joint contractures (inability to move joints easily), abnormal test results of blood obtained from the liver, stiffening of the lungs (difficulty in breathing), inflammation in the eyes, difficulty in swallowing, muscle weakness, or a white film in the mouth. Other symptoms of GVHD include tissue damage (including gut, skin, liver and, in severe cases, lung and kidney) and sepsis-like symptoms caused by increased levels of circulating inflammatory cytokines ("cytokine storm"). In some severe instances, GVHD can be fatal.

First-line treatment of GVHD includes steroid (e.g., methylprednisolone) therapy. Chronic GVHD is treated with a combination of steroids and cyclosporin A. Side effects of steroid immunosuppression include increased rates of infection and secondary malignancies, which can be fatal. Current treatments may also interfere with the graft-versus-tumor activity of transplanted donor cells. In view of these serious side effects, more selective therapeutic agents are needed.

IL-17RC and IL-17RA/RC proteins described herein are expected to be efficacious in GVHD and/or transplantation. It has been reported that IL-17A (and most likely, IL-17F) levels are elevated in serum and urine of patients and animal models of transplant rejection. Therefore, neutralization of IL-17A and IL-17F with soluble human IL-17RC or IL-17RA/RC proteins would result in better outcome(s) of GVHD and/or organ transplantation.

Efficacy of a murine surrogate (mIL-17RA-Fc) to human IL-17RC and IL-17RA/RC proteins were evaluated in a mouse model of acute GVHD (Durie et al., *J. Clin. Invest.* 94:1333-1338, 1994). Parental mice (C57BL/6; n=12) were euthanized, and their spleens were collected. The pooled spleens were smashed using two glass slides to dissociate splenic cells. Lysis buffer was added to the splenocyte suspension to remove red blood cells. The cells were washed in RPMI 1640 (10% FBS) medium and resuspended in an appropriate amount of PBS to make a cell concentration of 300 million cells/ml. Recipient mice (C57BL/6×DBA/2 F1) were divided into treatment groups (PBS or mIL-17RA-Fc). Murine IL-17RA-Fc treatments were administered by intraperitoneal injection (150 µg per injection) every other day beginning on day −1 and continuing until day 15. On day 0, 80 million donor splenic lymphocytes from B6 mice were injected intravenously into recipient mice (C57BL/6×DBA/2 F1 (BDF1); n=10 per group) mice. Mice were monitored 3 times a week for changes in body weight (a hallmark sign of worsening disease in this model) and any signs of moribundity. Mice that lost >20% of their initial body weight were euthanized. Otherwise, mice were sacrificed 12-18 days after the cell transfer, and spleen and blood collected.

Spleens were stained for T- and B-cell markers, including MHC class I markers ($H2^b$ and $H2^d$) to look at donor/recipient cell ratio (acute GVHD spleen cells are mostly donor cells). Sera were collected to measure serum level of IgG1, IgG2a, and IgE by ELISA, and cytokine and chemokine levels using a commercially available kit (Luminex Corporation, Austin, Tex.).

Figure 6:
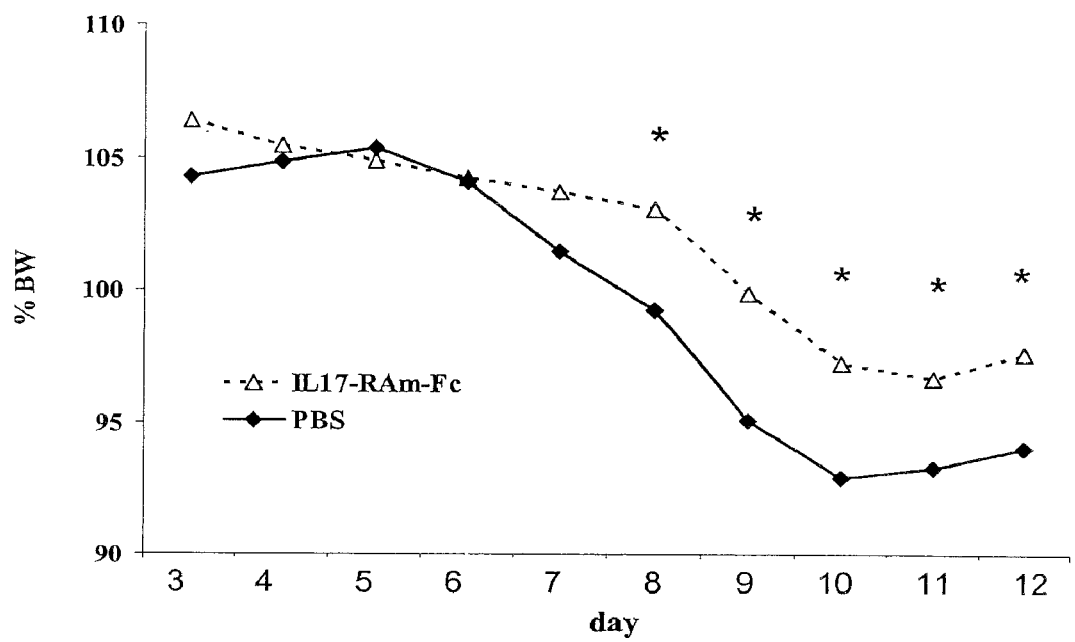
FIG. 6 shows efficacy of mIL-17RA-Fc treatment in a mouse model of Graft-versus-host disease (GVHD). Recipient mice (C57BL/6×DBA/2 F1) were divided into treatment groups (PBS or mIL-17RA-Fc). Murine IL-17RA-Fc treatments were administered by intraperitoneal injection (150 µg per injection) every other day beginning on day −1 and continuing until day 15. On day 0, 80 million donor splenic lymphocytes from B6 mice were injected intravenously into recipient mice (C57BL/6×DBA/2 F1 (BDF1); n=10 per group) mice. Mice were monitored 3 times a week for changes in body weight, a hallmark sign of worsening disease in this model. Body weight loss in the IL-17RA-Fc treatment group (open triangles) was not severe, and there was significantly less body weight loss ($p<0.05$) than in PBS controls (solid diamonds).

Results of two independent studies showed a correlation of the animal model with development of acute GVHD. There was a loss of host (BDF1) spleen cells and decreased numbers of donor (C57BL/6) Treg cells in PBS controls. In the treated animals, mIL-17RA-Fc treatment maintained host spleen cells, CD4+ T cells, and Treg cells. No treatment prevented the activation or expansion of donor (C57BL/6) conventional CD4+ T cells. All groups had similar numbers of donor conventional CD4+ T cells, and GITR (glucocorticoid-induced tumor necrosis factor receptor family-related gene) was upregulated by donor conventional CD4+ T cells. In both studies, body weight loss in IL-17RA-Fc treatment groups was not severe and there was significantly less body weight loss in both studies ($p<0.05$) than in PBS controls (Study #2; see FIG. 6). IL-17RA-Fc treatment did not prevent splenomegaly on the basis of spleen:body weight ratio, but treatments did reduce the disease-mediated increase in spleen cell numbers in Study #2, compared to PBS-treated controls (2-fold lower numbers; $p<0.01$). In Study #1, mice treated with mIL-17RA-Fc had significantly higher serum concentrations of IL-10 (~2-fold higher; $p<0.05$) compared to PBS-treated controls (IL-10 is thought to be primarily an anti-inflammatory cytokine). In Study #2, mice treated with mIL-17RA-Fc had significantly lower serum concentrations of TNF-α and IFN-γ. In both studies, mIL-17RA-Fc treatment resulted in a significantly lower percentage of host granulocytes (~2.5-fold lower; $p<0.001$).

In summary, treatment with the murine surrogate (mIL-17RA-Fc) of IL-17RC and IL-17RA/RC proteins described herein resulted in therapeutic efficacy in a murine model of GVHD. These results indicate that the use of human IL-17RC and IL-17RA/RC proteins as described herein is efficacious in the treatment of GVHD and transplant rejection.

Example 55

IL17A-CH6/IL17F-CEE Heterodimer Expression in 293F

Two expression plasmids, encoding IL17A-CH6 (nucleotide and amino acid sequences shown in SEQ ID NOs:186 and 187, respectively) and IL17F-CEE (nucleotide and amino acid sequences shown in SEQ ID NOs:188 and 189, respectively), were each constructed in vector pZMP45 via homologous recombination in yeast.

The IL17A-CH6 fragment was created with PCR, using a previously generated plasmid containing IL17A as template, the forward primer zc57312 to create a 5' overlap in pZMP45, and reverse primer zc48893 to create a Serine-Glycine linker, the 6× Histidine tag, and a 3' overlap in pZMP45. The IL17F-CEE fragment was created with PCR, using a previously generated plasmid containing IL17F as the template, the forward primer zc57314 to create a 5' overlap in pZMP45, and reverse primer zc58978 to create a Serine-Glycine linker, the EE tag (EEYMPME; SEQ ID NO:190), and a 3' overlap in pZMP45. The PCR conditions, using Platinum® PCR Super-Mix High Fidelity (Invitrogen, Cat. #12532-016), were as follows: 1 cycle 94° C. for 2 min; 30 cycles 94° C. for 30 sec., 55° C. for 30 sec, 68° C. for 45 sec; then hold at 4° C. The PCR reaction mixtures were then run on a 1% agarose gel with 1×TAE. The correct bands were excised and purified using Qiagen's gel purification kit (Qiagen, catalog #28704).

Plasmid pZMP45 is a mammalian expression vector containing an expression cassette having the CMV promoter, Intron A, multiple restriction sites for insertion of coding sequences, and an otPA signal peptide sequence, the SV40 terminator, an *E. coli* origin of replication, and URA3 and CEN-ARS sequences required for selection and replication in *S. cerevisiae*.

100 µL of electrocompetent yeast cells (*S. cerevisiae*) were combined with 100 of purified DNA from above, mixed with 100 ng of BglII-cut pZMP45 plasmid, and transferred to a 0.2 cm electroporation cuvette. The yeast-DNA mixture was electropulsed at 0.75 kV (5 kV/cm), ∞ ohms, 25 µF. To each cuvette was added 1 ml of 1.2M sorbitol, and the yeast were plated onto a URA-DS plate and incubated at 30° C. After about 72 hours, approximately 50 µL packed yeast cells taken from the Ura+ yeast transformants of a single plate was resuspended in 100 µL of lysis buffer (2% Triton X-100, 1% SDS, 100 mM NaCl, 10 mM Tris, pH 8.0, 1 mM EDTA), 100 µL of Qiagen P1 buffer from a Qiagen miniprep kit (Qiagen, Valencia, Calif., catalog #27104), and 20 U of Zymolyase (Zymo Research, Orange, Calif., catalog #1001). This mixture was incubated for 30 minutes at 37° C., and the remainder of the Qiagen miniprep protocol was performed, starting with the addition of reagent P2. The DNA was eluted with 40 µL EB reagent.

Fifteen µL electrocompetent E. coli cells (DH12S, Invitrogen, Carlsbad, Calif.) were transformed with 2 µL yeast DNA in a 0.2 cm electroporation cuvette. The cells were electropulsed at 1.75 kV, 25 µF, and 400 ohms. Following electroporation, 1 ml SOC (2% Bacto Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was added to the cuvette. This solution was plated on two LB AMP plates (LB broth (Lennox), 1.8% Bacto Agar (Difco), 100 mg/L Ampicillin), one with 200 µL of transformants, the second with 100 µL.

Individual clones were picked from the transformation plates, and were sequenced to identify one clone containing the correct expression construct for IL17A-CH6 and one for IL17F-CEE. Larger scale plasmid DNA was isolated using the Invitrogen mega prep kit (Invitrogen, Carlsbad, Calif., catalog #457009) according to manufacturer's instructions.

Transfection into 293F Cells

To test for expression of the IL17A CH6-IL17F CEE heterodimer, 293F cells were transiently transfected using Lipofectamine-2000 (Invitrogen, Carlsbad, Calif., catalog #11668-019) and OptiMEM (Invitrogen, Carlsbad, Calif., catalog #31985-070) and grown in a 12-well plate. IL17A was previously determined to be the less expressed protein of the two, so a DNA ratio of 3 parts IL17A CH6 to 1 part IL17F CEE was used for the transfection. 2 µg plasmid DNA and one million cells were used for the transfection. After 96 hours, medium was harvested and prepared for a Western blot assay.

Invitrogen materials and protocols were used for the Western blot with anti-6× histidine (R&D Systems, Minneapolis, Minn., catalog #MAB050H) as the detection antibody for IL17A CH6, and with an in-house mouse mAb as the detection antibody for IL17F CEE, and Jackson HRP-goat anti mouse IgG (H+ L) (catalog #115-035-003)+BD Parm. HRP-anti mouse IgG2a (R19-15) (catalog #553391) as the secondary antibodies. Significant expression was observed, so a large scale transfection was done for protein acquisition.

Example 56

Purification of Single Chain Human IL17A:IL17F Heterodimer from CHO DXB11 Cell Culture Expression Recombinant human IL17A:IL17F heterodimer protein (zcyto40f2 v.2) was produced from expression of a single chain construct in CHO DXB11 cells and cell culture in a WAVE apparatus. The construct was comprised of sequences for Human IL17A at the N-terminus with IL17F at the C-terminus (construct 1789; C-His tagged) linked with a $(G_4S)_3$ linker. A His tag was added to the C-terminus to effect efficient product capture. Approximately 10 L of conditioned media were harvested and sterile filtered using a 0.2 µm filter. The media was adjusted to pH 5.0 with addition of acetic acid while stirring. At this point a significant precipitation process occurred and the pH adjusted media was again filtered through a two stage 0.8 to 0.2 micron filter (Pall Corporation).

Cation Exchange Chromatography

The adjusted media was then loaded, at 10 ml/min, to a pre equilibrated Cation exchange column, 16 mL bed volume; 2 cm. dia. (SP Fast Flow resin, GE Healthcare) using an AKTA™ explorer Chromatography platform (GE Healthcare). The equilibration buffer was pH 5.0, 0.02 M Acetic acid, 0.1M NaCl. Upon completing the sample load, the column was washed for 20 column volumes with equilibration buffer, at which point a stable UV @ 280 nm baseline was obtained.

The bound protein fraction was eluted at a flow rate of 20 ml/minute, collecting 5 ml fractions while forming a 20 column volume gradient between equilibration buffer and elution buffer; 0.02, Acetic acid, 1.0M NaCl, pH 5.0. Fractions were analyzed by SDS-PAGE Coomassie and Western Blot formats. A dense distinct band at 38 k Da was observed in the first (main peak) of two eluate peaks observed during the gradient elution. The main peak transport domain; fractions #20-48 inclusive, exhibited specific anti-His tag staining, the entire breadth of Western blot stainable fractions was pooled and moved forward in the process.

IMAC Chromatography (Metal Chelation Affinity Step)

A 5 mL H isTrap IMAC column (GE Healthcare) was equilibrated with 20 column volumes of buffer; 0.5 M NaCl, 50 mM NaPhos; 25 mM Imidazole at pH 7.5. The cation exchange pool, 144 ml, was adjusted for IMAC chromatography with addition of sufficient solid reagent to bring the concentration to 25 mM Imidazole. An equimolar mix of mono and dibasic Sodium phosphate solutions (0.5 M each) was added to bring the phosphate buffering to 20 mM, at which point the pH was adjusted to 7.5 with addition of 2 N NaOH.

The adjusted cation exchange pool is now ready to load to the H isTrap IMAC column. The loading flow rate was 4 ml/min. Upon completing the sample load, the IMAC column was washed with 40 column volumes of equilibration Buffer prior to step elution with 0.4 M NaCl, 400 mM Imidazole pH 7.5 buffer. Soon after switching to the elution buffer, a substantial peak eluted from the column.

This material was pooled and concentrated to 3 ml for injection to the final process step, size exclusion chromatography.

Size Exclusion Chromatography Process

The concentrate from the IMAC step was injected to a pre-equilibrated Superdex 200 (GE Healthcare; 16/60; 120 ml) SEC column flowing at 1.5 ml/min in mobile phase composed of 35 mM Sodium Phosphate Buffer; 109 mM NaCl, pH 7.3. Fractions of 1.5 ml were collected. Some early, low level eluting materials precede a mostly symmetric peak eluting at 0.7 column volumes. Fractions directly preceding and within this main peak were analyzed by SDS-PAGE with Coomassie staining. A pool of fractions was made to deliver the highest purity product, some fractions containing product were excluded due to co-elution with undesirable contaminants.

Analysis of Purified Single Chain Human IL17A:IL17F Heterodimer

Recombinant, single chain Human IL17A:IL17F heterodimer, was analyzed by SDS-PAGE (10% BisTris, Invitrogen, Carlsbad, Calif.) with 0.1% Coomassie R250 staining for protein and after transfer to nitrocellulose, by immunoblotting with Anti-His-HRP. The purified proteins were electrophoresed using an Invitrogen Novex's Xcell II mini-cell, and transferred to nitrocellulose (0.2 mm; Invitrogen, Carlsbad, Calif.) at ambient temperature at 600 mA for 45 minutes in a buffer containing 25 mM Tris base, 200 mM glycine, and 20% methanol. The filters were then blocked with 10% nonfat dry milk in 50 mM Tris, 150 mM NaCl, 5 mM EDTA, 0.05% Igepal (TBS) for 15 minutes at room temperature. The nitrocellulose was quickly rinsed, and the specific HRP conjugated antibody (1:2500) was added. The blots were incubated overnight at 4° C., with gentle shaking. Following the incubation, the blots were washed three times for 15 minutes each in TBS, and then quickly rinsed in $H_2O$. The blots were developed using commercially available chemiluminescent substrate reagents (Roche LumiLight), and the signal was captured using Lumi-Imager's Lumi Analyst 3.0 software (Boehringer Mannheim GmbH, Germany.) Non-reducing Coomassie staining analysis revealed a dimeric product as a doublet, with the lower member predominating.

SDS-PAGE with Coomassie staining analysis for reduced and non-reduced product revealed a doublet of disproportionate intensities at the apparent electrophoretic mobility for dimeric polypeptide chain. The upper band of the doublet being the predominant form observed. Reducing SDS-PAGE and Western blot data exhibited a negligible amount of lower molecular weight species. N-terminal sequence analysis was run on 100 pmol of product. The results indicated a single N-terminus recovered at a repetitive yield of 57.9 pmol with the N-terminal residue being G24, the start of Human IL17A sequence. Amino acid composition data conformed to the theoretical composition. Analytical size exclusion analysis indicated 99+% purity of the product.

Example 57

Measurement of Binding Affinity of IL-17RA/RC-Fc5 to the IL-17A/F Heterodimer Antigen Via Surface Plasmon Resonance (Biacore)

This study was performed to evaluate the binding affinity of IL-17RA/RC-Fc5 (variant 1454) to the IL-17A/F 2 chain heterodimer.

Affinity Determination

Kinetic rate constants, equilibrium association constants, and equilibrium dissociation constants were measured for the interaction of IL-17RA/RC-Fc5 with the IL-17A/F heterodimer antigen via surface plasmon resonance. The association rate constant ($k_a$ ($M^{-1}s^{-1}$)) is a value that reflects the rate of the antigen-receptor complex formation. The dissociation rate constant ($k_d$ ($s^{-1}$)) is a value that reflects the stability of this complex. Equilibrium binding affinity is typically expressed as either an equilibrium dissociation constant ($K_D$ (M)) or an equilibrium association constant ($K_A$ ($M^{-1}$)). $K_D$ is obtained by dividing the dissociation rate constant by the association rate constant ($k_d/k_a$), while $K_A$ is obtained by dividing the association rate constant by the dissociation rate constant ($k_a/k_d$). Antagonists with similar $K_D$ (or a similar $K_A$) can have widely variable association and dissociation rate constants. Consequently, measuring the $k_a$ and $k_d$ as well as the $K_A$ or $K_D$ helps to more uniquely describe the affinity of the receptor-antigen interaction.

Materials and Methods

An experiment was completed to measure the binding affinity of the purified IL-17RA/RC-Fc5 receptor to the human recombinant IL-17A/F heterodimer. The binding kinetics and affinity study was performed on a Biacore T100™ system (GE Healthcare, Piscataway, N.J.). Methods for the Biacore T100™ were programmed using Biacore T100™ Control Software, v 1.1.1. Since the IL-17RA/RC-Fc5 receptor contained a human Fc domain, goat anti-human IgG Fc-gamma (Jackson ImmunoResearch, West Grove, Pa.) was used as a capture antibody for these studies. The capture antibody was covalently immobilized to a CM4 sensor chip using a mixture of 0.4 M EDC [N-ethyl-N'-(3-diethylaminopropyl) carbodiimide] and 0.1 M NHS(N-hydroxysuccinimide) to a density of approximately 4000 RU. After immobilization of the antibody, the remaining active sites on the flow cell were blocked with 1 M ethanolamine. The IL-17RA/RC-Fc5 receptor was captured onto one flow cell of the CM4 chip at an approximate density of 90-100 RU. Capture of the receptor to the immobilized surface was performed at a flow rate of 10 μL/min. The Biacore instrument measures the mass of protein bound to the sensor chip surface, and thus, capture of the soluble receptor was verified for each analysis cycle.

For binding studies with the IL-17A/F heterodimer (IL17A-CH6/IL17F-CEE 2 chain heteromdimer as described in Example 55, supra), serial 1:3 dilutions of antigen from 33 nM-0.015 nM were injected over the surface and allowed to specifically bind to the IL-17RA/RC-FC5 receptor captured on the sensor chip. Duplicate injections of each IL-17A/F antigen concentration were performed with an association time of 7 minutes and a dissociation time of 15 minutes. Kinetic binding studies were performed with a flow rate of 30 μL/min. All binding experiments were performed at 25° C. in a buffer of 10 mM HEPES, 150 mM NaCl, 3 mM EDTA, 0.05% Surfactant P20 (GE Healthcare, Piscataway, N.J.), 1 mg/mL bovine serum albumin (Proliant Biologicals, Boone, Iowa), pH 7.4.

Between analysis cycles, the flow cell was washed with 20 mM hydrochloric acid to regenerate the surface. This wash step removed the captured IL-17RA/RC-Fc5 receptor from the immobilized antibody surface, and allowed for the subsequent binding of the next test sample. Data was compiled using the Biacore T100™ Evaluation software (version 1.1.1). Data was processed by subtracting reference flow cell and blank injections. Baseline stability was assessed to ensure that the regeneration step provided a consistent binding surface throughout the sequence of injections. Duplicate injection curves were checked for reproducibility. The IL-17A/F heterodimer has two potential binding partners (IL-17A and IL-17F) for the IL-17RA/RC-Fc5 receptor. If only one portion of the heterodimer binds to the receptor, a simple 1:1 binding model would be appropriate and the curves should fit well to this model. However, if both the IL-17A and IL-17F portions of the heterodimer bind to the receptor, the bivalent binding model would be appropriate and the curves should fit this model. The binding curves were globally fit to both the 1:1 and bivalent analyte binding models.

Results

The IL-17RA/RC-Fc5 receptor was characterized for its binding affinity for the human IL-17A/F heterodimer antigen. Association rate constants ($k_a$ ($M^{-1}s^{-1}$)) and dissociation rate constants ($k_d$ ($s^{-1}$)) were measured. While the resulting binding curves did not fit the 1:1 binding model, the data fit well to the bivalent analyte model. This result is consistent with both portions (IL-17A and IL-17F) of the IL-17A/F heterodimer binding to the soluble receptor. The bivalent analyte binding model measures two values for both $k_a$ ($k_{a1}$ and $k_{a2}$) and for $k_d$ ($k_{d1}$ and $k_{d2}$). The first set of values ($k_{a1}$ and $k_{d1}$) describes the monovalent kinetics of the interaction. The affinity reported for these samples was derived from these values, and is designated $K_{a1}$ and $K_{A1}$. The second set of values ($k_{a1}$ and $k_{d2}$) refers to the avidity of the interaction and was not reported. The measured binding kinetics were 5E+05

(M$^{-1}$s$^{-1}$) for k$_{a1}$ and 2E-03 (s$^{-1}$) for k$_{d1}$, resulting in a calculated K$_{a1}$ of 4E-9 (M) [K$_{A1}$ of 2E+8 (M$^{-1}$)]. These values are comparable to the results obtained with the IL17A/A and the IL17F/F homodimers.

TABLE 15

Binding Affinity for IL-17A/F Heterodimer

| Antigen | k$_{a1}$ (M$^{-1}$s$^{-1}$) | k$_{d1}$ (s$^{-1}$) | K$_{D1}$ (M) | K$_{A1}$ (M$^{-1}$) |
|---|---|---|---|---|
| IL-17A/F Heterodimer | 5.E+05 | 2.E-03 | 4.E-9 | 2.E+8 |

Example 58

IL17A/F Heterodimer Activity and Neutralization by IL-17RA/RC-Fc5

IL17A/F heterodimer constructs (zcyto40f2v.1-2chain and zcyto40f2-single chain) were tested for activity and IL-17RA/RC-Fc5 neutralization. The IL-17RC activity assay utilizes the NIH-3T3 cell line transfected with the KZ170 reporter construct for detection of NFκB mediated detection of IL-17A and IL-17F signaling in a luciferase reporter assay. Both heterodimer constructs showed a dose-dependent response in this assay, with EC50 values of 15.19 nM and 20.59 nM for the 2-chain and single chain constructs, respectively. IL-17A and IL-17F homodimers also showed dose dependent responses, with EC50 values of 2.026 nM and 17.31 nM, respectively.

IL-17A/F heterodimer constructs were also tested in a neutralization assay utilizing the NIH-3T3/KZ170 luciferase reporter cell-based assay. The soluble receptor IL-17RA/RC-Fc5 (variant 1454) was titrated with a constant concentration of ligand and tested in the reporter bioassay. Both heterodimer constructs were neutralized in a dose dependent manner by the IL-17RA/RC-Fc5 soluble receptor, with IC50 values of 3.169 nM and 13.34 nM for the 2-chain and single chain constructs, respectively. IL-17A and IL-17F homodimers were also neutralized in a dose dependent manner, with IC50 values of 0.1673 nM and 0.8735 nM, respectively.

From the foregoing, it will be appreciated that, although specific embodiments of the invention have been described herein for purposes of illustration, various modifications may be made without deviating from the spirit and scope of the invention. All publications, patents, and patent applications cited herein are hereby incorporated by reference in their entireties for all purposes.

What is claimed is:

1. A method of reducing inflammation in a subject, the method comprising administering an effective amount of an isolated polypeptide to the subject, wherein the polypeptide comprises an amino acid sequence having at least 95% sequence identity with amino acid residues 33-458 of SEQ ID NO:158, wherein the polypeptide is capable of binding IL-17A and/or IL-17F, and wherein the inflammation in the subject is reduced.

2. A method of treating an inflammatory disease in a subject, the method comprising administering an effective amount of an isolated polypeptide to the subject, wherein the polypeptide comprises an amino acid sequence having at least 95% sequence identity with amino acid residues 33-458 of SEQ ID NO:158, and wherein the polypeptide is capable of binding IL-17A and/or IL-17F.

3. The method of claim 1 or 2, further comprising an immunoglobulin moiety.

4. The method of claim 3, wherein the immunoglobulin moiety is an immunoglobulin heavy chain constant region.

5. The method of claim 3, wherein the polypeptide comprises an amino acid sequence having at least 95% sequence identity with amino residues 33-690 of SEQ ID NO:158.

6. The method of claim 3, wherein the immunoglobulin moiety comprises amino acid residues 459-689 or 459-690 of SEQ ID NO:158.

7. The method of claim 3, wherein the immunoglobulin moiety comprises amino acid residues 1-232 of SEQ ID NO:175.

8. The method of claim 1 or 2, wherein the polypeptide further comprises PEGylation.

9. The method of claim 1 or 2, wherein the polypeptide comprises amino acid residues 33-458 of SEQ ID NO:158.

10. The method of claim 9, wherein the polypeptide further comprises an immunoglobulin moiety.

11. The method of claim 10, wherein the immunoglobulin moiety is an immunoglobulin heavy chain constant region.

12. The method of claim 10, wherein the polypeptide comprises amino acid residues 33-689 of SEQ ID NO:158.

13. The method of claim 10, wherein the polypeptide comprises amino acid residues 33-690 of SEQ ID NO:158.

14. The method of claim 2, wherein the disease is selected from the group consisting of psoriasis, psoriatic arthritis, rheumatoid arthritis, osteoarthritis, Lyme disease arthritis, streptococcal cell wall (SCW)-induced arthritis, ulcerative colitis, Crohn's disease, irritable bowel syndrome (IBS), diverticulosis, pancreatitis, type I diabetes (IDDM), Graves Disease, atopic dermatitis, contact dermatitis, an immune-mediated renal disease, multiple sclerosis (MS), systemic sclerosis, scleroderma, nephrotic syndrome, sepsis, systemic lupus erythematosus (SLE), myasthenia gravis, glomerulosclerosis, membranous neuropathy, renal arteriosclerosis, glomemlonephritis, amyloidosis, Castleman's Disease, splenomegaly, transplant rejection, graft-versus-host disease (GVHD), atherosclerosis, endotoxemia, toxic shock syndrome, septic shock, inflammatory lung injury, asthma, adult respiratory disease (ARD), chronic obstructive pulmonary disease (COPD), cystic fibrosis, allergic asthma, allergic rhinitis, airway hyper-responsiveness, chronic bronchitis, eczema, intraabdominal adhesions and/or abscesses as a result of peritoneal inflammation, lupus nephritis, stroke, gingivitis/periodontitis, herpetic stromal keratitis, osteoporosis, neuritis, restenosis, and Kawasaki disease.

* * * * *

UNITED STATES PATENT AND TRADEMARK OFFICE
CERTIFICATE OF CORRECTION

| | | |
|---|---|---|
| PATENT NO. | : 8,242,072 B2 | Page 1 of 1 |
| APPLICATION NO. | : 13/293384 | |
| DATED | : August 14, 2012 | |
| INVENTOR(S) | : Steven D. Levin et al. | |

It is certified that error appears in the above-identified patent and that said Letters Patent is hereby corrected as shown below:

Title Page, Item (62):

Please change the first item under Related U.S. Application Data from "Division of application No. 12/828,041, filed on Jun. 30, 2010" to --Continuation of application No. 12/828,041, filed on Jun. 30, 2010--.

Signed and Sealed this
Twenty-third Day of October, 2012

David J. Kappos
*Director of the United States Patent and Trademark Office*